United States Patent
Bailey et al.

(10) Patent No.: US 12,084,496 B2
(45) Date of Patent: Sep. 10, 2024

(54) ANTI-ROR ANTIBODY CONSTRUCTS

(71) Applicant: EXELIXIS, INC., Alameda, CA (US)

(72) Inventors: Lucas Bailey, Madison, WI (US);
Qufei Li, Middleton, WI (US);
Malgorzata Agnieszka Nocula-Lugowska, Brighton, MA (US);
Bryan Glaser, Fitchburg, WI (US)

(73) Assignee: EXELIXIS, INC., Alameda, CA (US)

( * ) Notice: Subject to any disclaimer, the term of this patent is extended or adjusted under 35 U.S.C. 154(b) by 399 days.

(21) Appl. No.: 17/048,549

(22) PCT Filed: Apr. 18, 2019

(86) PCT No.: PCT/US2019/028051
§ 371 (c)(1),
(2) Date: Oct. 16, 2020

(87) PCT Pub. No.: WO2019/204564
PCT Pub. Date: Oct. 24, 2019

(65) Prior Publication Data
US 2021/0155692 A1  May 27, 2021

Related U.S. Application Data

(60) Provisional application No. 62/659,635, filed on Apr. 18, 2018.

(51) Int. Cl.
| | | |
|---|---|---|
| *C07K 16/28* | (2006.01) | |
| *A61K 39/00* | (2006.01) | |
| *A61K 45/06* | (2006.01) | |
| *A61P 35/00* | (2006.01) | |
| *C07K 16/46* | (2006.01) | |

(52) U.S. Cl.
CPC .......... *C07K 16/2803* (2013.01); *A61K 45/06* (2013.01); *A61P 35/00* (2018.01); *C07K 16/468* (2013.01); *A61K 2039/505* (2013.01)

(58) Field of Classification Search
CPC .............. C07K 16/2803; C07K 16/468; C07K 2317/24; C07K 2317/77; C07K 2317/94; C07K 16/2809; C07K 16/2818; C07K 16/2878; C07K 2317/31; C07K 2317/35; C07K 2317/522; C07K 2317/526; C07K 2317/55; C07K 2317/92; C07K 2317/524; A61K 45/06; A61K 2039/505; A61P 35/00
See application file for complete search history.

(56) References Cited

U.S. PATENT DOCUMENTS

| | | |
|---|---|---|
| 7,985,783 B2 | 7/2011 | Carrico et al. |
| 9,228,023 B2 | 1/2016 | Rohlff et al. |
| 2006/0193852 A1 | 8/2006 | Dorken et al. |
| 2017/0198045 A1 | 7/2017 | Johnson et al. |
| 2017/0210799 A1 | 7/2017 | Anderson et al. |
| 2017/0233472 A1 | 8/2017 | Barat et al. |
| 2017/0306044 A1 | 10/2017 | Vu et al. |
| 2018/0016354 A1 | 1/2018 | Wozniak-Knopp et al. |
| 2018/0118811 A1 | 5/2018 | Bailey et al. |
| 2021/0207126 A1 | 7/2021 | Luo et al. |
| 2024/0043502 A1 | 2/2024 | Bailey et al. |

FOREIGN PATENT DOCUMENTS

| | | | |
|---|---|---|---|
| JP | | 2017536341 A | 12/2017 |
| JP | | 2018503380 A | 2/2018 |
| WO | WO | 2011079902 A2 | 7/2011 |
| WO | WO | 2011079902 A3 | 7/2011 |
| WO | WO | 2012075158 A1 | 6/2012 |
| WO | WO | 2014031174 A1 | 2/2014 |
| WO | WO | 2014167022 A1 | 10/2014 |
| WO | WO | 2016055592 A1 | 4/2016 |
| WO | WO | 2016055593 A1 | 4/2016 |
| WO | WO | 2016094873 A2 | 6/2016 |
| WO | WO | 2016094873 A3 | 6/2016 |
| WO | WO | 2016115559 A1 | 7/2016 |
| WO | WO | 2016142768 A1 | 9/2016 |
| WO | WO | 2016187220 A2 | 11/2016 |
| WO | WO | 2016187220 A3 | 11/2016 |
| WO | WO | 2017053469 A2 | 3/2017 |
| WO | WO | 2017053469 A3 | 3/2017 |
| WO | WO | 2017127499 A1 | 7/2017 |
| WO | WO | 2017127702 A1 | 7/2017 |
| WO | WO | 2018075692 A2 | 4/2018 |
| WO | WO | 2018075692 A3 | 4/2018 |

OTHER PUBLICATIONS

Hellmann et al. (2018) Novel Antibody Drug Conjugates Targeting Tumor-Associated Receptor Tyrosine Kinase ROR2 by Functional Screening of Fully Human Antibody Libraries Using Transpo-mAb Display on Progenitor B Cells. Front. Immunol. 9:2490. (Year: 2018).*

Bacac et al., 2016, "A Novel Carcinoembryonic Antigen T-Cell Bispecific Antibody (CEA TCB) for the Treatment of Solid Tumors," Clin. Cancer Res., 22(13):3286-3297.

Bainbridge et al., 2014, "Evolutionary divergence in the catalytic activity of the CAM-1, ROR1 and ROR2 kinase domains," PLoS One, 9(7):e102695 (10 pages).

Balakrishnan et al., 2017, "Analysis of ROR1 Protein Expression in Human Cancer and Normal Tissues," Clin. Cancer Res., 23(12):3061-3071 (Epub 2016).

Barat et al., 2016, "Development of a Humanized ROR1 × CD3 Bispecific DART® Molecule for the Treatment of Solid and Liquid Tumors," Proceedings of the 107th Annual Meeting of the American Association for Cancer Research (AACR), Apr. 16-20, 2016, New Orleans, LA, Poster 1489 (6 pages).

Berger et al., 2015, "Safety of targeting ROR1 in primates with chimeric antigen receptor-modified T cells, " Cancer Immunol. Res., 3(2):206-216 (Epub 2014).

(Continued)

*Primary Examiner* — Brad Duffy
(74) *Attorney, Agent, or Firm* — JONES DAY

(57) ABSTRACT

Anti-ROR antibody constructs, pharmaceutical compositions comprising the constructs, and methods of use thereof are presented.

34 Claims, 111 Drawing Sheets

Specification includes a Sequence Listing.

(56) References Cited

OTHER PUBLICATIONS

Billiard et al., 2005, "The orphan receptor tyrosine kinase Ror2 modulates canonical Wnt signaling in osteoblastic cells," Mol. Endocrinol., 19(1):90-101 (Epub 2004).
Borcherding et al., 2014, "ROR1, an embryonic protein with an emerging role in cancer biology," Protein Cell, 5(7):496-502.
Chang et al., 2015, "Expression of ROR1, pAkt, and pCREB in gastric adenocarcinoma," Ann. Diagn. Pathol., 19(5):330-334.
Choi et al., 2015, "Pre-clinical Specificity and Safety of UC-961, a First-In-Class Monoclonal Antibody Targeting ROR1," Clin. Lymphoma Myeloma. Leuk., 15 Suppl(0):S167-S169 (author manuscript) (7 pages).
Choi et al., 2015, "Pre-clinical Specificity and Safety of UC-961, a First-In-Class Monoclonal Antibody Targeting ROR1," Clin. Lymphoma Myeloma. Leuk., 15 Suppl(0):S167-S169.
Chuprakov et al., 2021, "Tandem-Cleavage Linkers Improve the In Vivo Stability and Tolerability of Antibody-Drug Conjugates," Bioconjug. Chem., 32(4):746-754.
Correnti et al., 2018, "Simultaneous multiple interaction T-cell engaging (SMITE) bispecific antibodies overcome bispecific T-cell engager (BiTE) resistance via CD28 co-stimulation," Leukemia, 32(5):1239-1243 (author manuscript) and supplemental materials (15 pages).
Cui et al., 2013, "Targeting ROR1 inhibits epithelial-mesenchymal transition and metastasis," Cancer Res., 73(12):3649-3660 (author manuscript) (19 pages).
Cui et al., 2013, "Targeting RORI inhibits epithelial-mesenchymal transition and metastasis," Cancer Res., 73(12):3649-3660.
Gentile et al., 2011, "Ror1 is a pseudokinase that is crucial for Met-driven tumorigenesis," Cancer Res., 71(8):3132-3141.
Gohil et al., 2017, "An ROR1 bi-specific T-cell engager provides effective targeting and cytotoxicity against a range of solid tumors," Oncoimmunology, 6(7):e1326437 (11 pages).
Henry et al., 2015, "Targeting the ROR1 and ROR2 receptors in epithelial ovarian cancer inhibits cell migration and invasion," Oncotarget, 6(37):40310-40326.
Henry et al., 2017, "Distinct Patterns of Stromal and Tumor Expression of ROR1 and ROR2 in Histological Subtypes of Epithelial Ovarian Cancer," Transl. Oncol., 10(3):346-356 (author manuscript) (11 pages).
Henry et al., 2017, "Distinct Patterns of Stromal and Tumor Expression of ROR1 and ROR2 in Histological Subtypes of Epithelial Ovarian Cancer," Transl. Oncol., 10(3):346-356.
Inestrosa et al., 2013, "Chapter 4: Wnt Signaling Roles on the Structure and Function of the Central Synapses: Involvement in Alzheimer's Disease," in Trends in Cell Signaling Pathways in Neuronal Fate Decision, InTech, pp. 115-139.
International Searching Authority, International Search Report and Written Opinion for International Patent Application No. PCT/US2019/028051 (Pub No. WO 2019204564) mailed Aug. 9, 2019 (12 pages).
Karvonen et al., 2017, "Targeting ROR1 identifies new treatment strategies in hematological cancers," Biochem. Soc. Trans., 45(2):457-464.
Kolb et al., 2016, "ROR1 is an Intriguing Target for Cancer Therapy," Mol. Enzy. Drug Targ., 2(1:4) (3 pages).
Masiakowski et al., 1992, "A novel family of cell surface receptors with tyrosine kinase-like domain," J. Biol. Chem., 267(36):26181-26190.
Nerreter et al., 2017, "ROR2 is a novel target for CAR T cells in breast cancer," Database Accession No. 618608084, Sep. 1, 2017, Abstract (2 pages).
Niesen et al., 2007, "The use of differential scanning fluorimetry to detect ligand interactions that promote protein stability," Nat. Protoc., 2(9):2212-2221.

O'Connell et al., 2013, "Hypoxia induces phenotypic plasticity and therapy resistance in melanoma via the tyrosine kinase receptors ROR1 and ROR2," Cancer Discov., 3(12):1378-1393 (author manuscript) (45 pages).
O'Connell et al., 2013, "Hypoxia induces phenotypic plasticity and therapy resistance in melanoma via the tyrosine kinase receptors ROR1 and ROR2," Cancer Discov., 3(12):1378-1393.
Paganoni et al., 2010, "Ror1-Ror2 complexes modulate synapse formation in hippocampal neurons," Neuroscience, 165(4):1261-1274 (Epub 2009).
Peng et al., 2017, "Mining Naïve Rabbit Antibody Repertoires by Phage Display for Monoclonal Antibodies of Therapeutic Utility," J. Mol. Biol., 429(19):2954-2973.
Qi et al., 2018, "Potent and selective antitumor activity of a T cell-engaging bispecific antibody targeting a membrane-proximal epitope of ROR1," Proc. Natl. Acad. Sci. USA, 115(24):E5467-E5476 (author manuscript) (57 pages).
Qi et al., 2018, "Potent and selective antitumor activity of a T cell-engaging bispecific antibody targeting a membrane-proximal epitope of ROR1," Proc. Natl. Acad. Sci. USA, 115(24):E5467-E5476.
Rabuka et al., 2012, "Site-specific chemical protein conjugation using genetically encoded aldehyde tags," Nat. Protoc,, 7(6):1052-1067.
Rasmussen et al., 2013, "Receptor tyrosine kinase-like orphan receptor 2 (Ror2) expression creates a poised state of Wnt signaling in renal cancer," J. Biol. Chem., 288(36):26301-26310.
Rebagay et al., 2012, "ROR1 and ROR2 in Human Malignancies: Potentials for Targeted Therapy," Front. Oncol., 2:34 (8 pages).
Rhoden et al., 2016, "A Modeling and Experimental Investigation of the Effects of Antigen Density, Binding Affinity, and Antigen Expression Ratio on Bispecific Antibody Binding to Cell Surface Targets," J. Biol. Chem., 291(21):11337-11347.
Sanchez-Solana et al., 2012, "Mouse resistin modulates adipogenesis and glucose uptake in 3T3-L1 preadipocytes through the ROR1 receptor," Mol. Endocrinol., 26(1):110-127 (Epub 2011).
Seckinger et al., 2017, "Target Expression, Generation, Preclinical Activity, and Pharmacokinetics of the BCMA-T Cell Bispecific Antibody EM801 for Multiple Myeloma Treatment," Cancer Cell, 31(3):396-410 and Supplemental Information (31 pages).
Seckinger et al., 2017, "Target Expression, Generation, Preclinical Activity, and Pharmacokinetics of the BCMA-T Cell Bispecific Antibody EM801 for Multiple Myeloma Treatment," Cancer Cell, 31(3):396-410 and Supplemental Information (author manuscript) (31 pages).
Smith et al., 2015, "A novel, native-format bispecific antibody triggering T-cell killing of B-cells is robustly active in mouse tumor models and cynomolgus monkeys," Sci. Rep., 5:17943 (12 pages).
Sun et al., 2015, "Up-regulation of ROR2 is associated with unfavorable prognosis and tumor progression in cervical cancer," Int. J. Clin. Exp. Pathol., 8(1):856-861.
Wada et al., 2013, "Selective modulation of Wnt ligands and their receptors in adipose tissue by chronic hyperadiponectinemia," PLoS One, 8(7):e67712 (11 pages).
Yamaguichi et al., 2016, "ROR1 sustains caveolae and survival signalling as a scaffold of cavin-1 and caveolin-1," Nat. Commun., 7:10060 (13 pages).
Zhang et al., 2012, "ROR1 is expressed in human breast cancer and associated with enhanced tumor-cell growth," PLoS One, 7(3):e31127 (12 pages).
Zhang et al., 2012, "The onco-embryonic antigen ROR1 is expressed by a variety of human cancers," Am. J. Pathol., 181(6):1903-1910.
Zhang et al., 2014, "Ovarian cancer stem cells express ROR1, which can be targeted for anti-cancer-stem-cell therapy," Proc. Natl. Acad. Sci. USA, 111(48):17266-17271.
Zhou et al., 2017, "ROR1 expression as a biomarker for predicting prognosis in patients with colorectal cancerm," Oncotarget, 8(20):32864-32872.

\* cited by examiner

| valency | 2 | 2 | 3 | 3 | 3 | 3 | 3 | 3 | 3 |
|---|---|---|---|---|---|---|---|---|---|
| # specificities | 1 | 2 | 2 | 2 | 2 | 2 | 3 | 3 | 1 |
| Exemplary Specificity Allocation (left x right) | (A) x (A) | (A) x (B)<br>(A₁) x (A₂) | 2(A-B) x 1(A) | 2(A-A) x 1(B) | 1(A) x 2(B-A) | 1(A) x 2(B-B) | 2(A-B) x 1(C)<br>2(A-B) x 1(A₂) | 1(A) x 2(B-C)<br>1(A₁) x 2(A₂-B) | 2(A) x 1(A) |
| name | Monoclonal antibody (mAb) | Bispecific 1x1 B-Body™ | Bispecific 2x1 B-Body™ | Bispecific 2x1 B-Body™ | Bispecific 1x2 B-Body™ | Bispecific 1x2 B-Body™ | Trispecific 2x1 B-Body™ | Trispecific 1x2 B-Body™ | Monospecific 2x1 B-Body™ |

Letter = Unique Target Protein
Subscript = Unique Epitope (as needed)

● Binding Specificity #1
◐ Binding Specificity #2
● Binding Specificity #3

FIG. 2

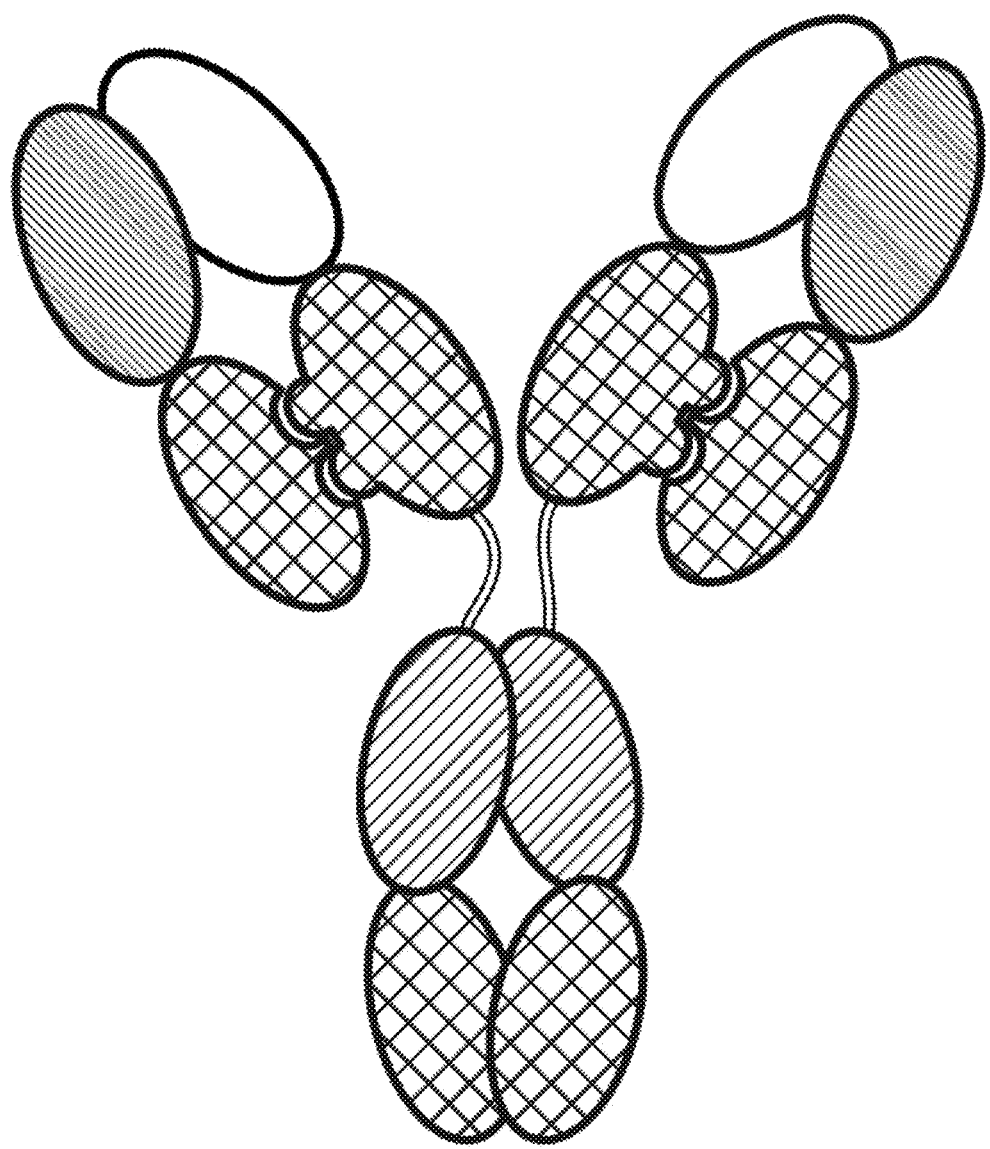
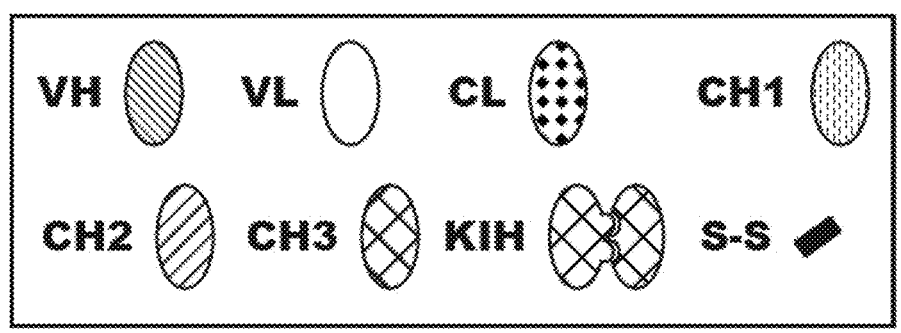
FIG. 4

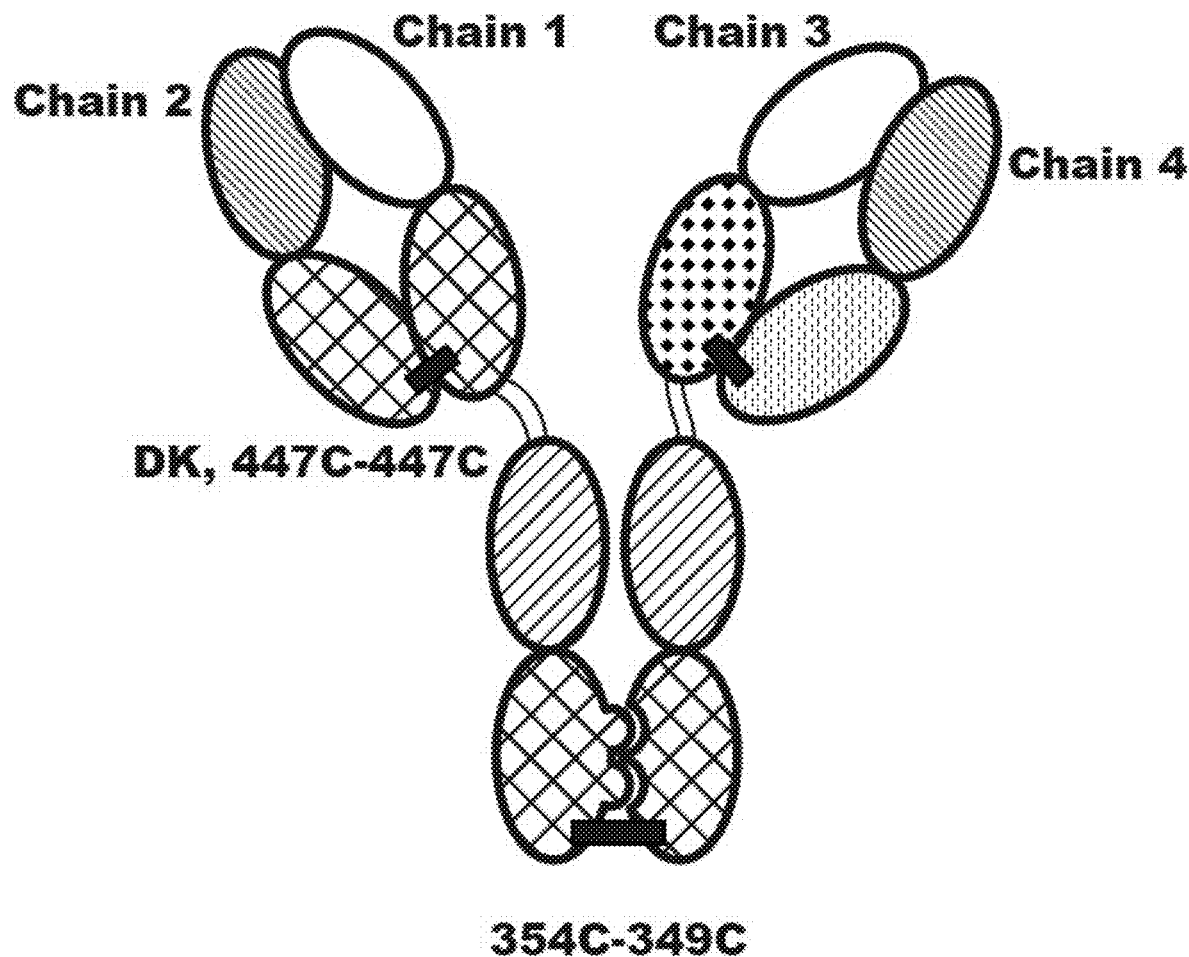
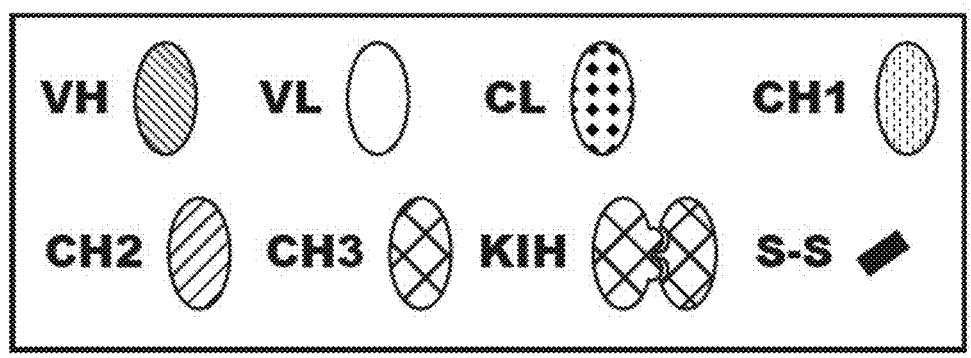
FIG. 6

*Data from Schaefer et al. (Proc Natl Acad Sci USA. 2011 Jul 5;108(27):11187-92)

L: Ladder
1: B-Body "BC1" Supernatant
2: Flow Through from Affinity Resin 1
3: Eluate from Affinity Resin 1
4: Peak Eluate from Cation Exchange 5: B-Body "BC1" Supernatant
6: Flow Through from Protein A Resin
7: Eluate from Protein A Resin
8: Eluate 1 from Cation Exchange
9: Eluate 2 from Cation Exchange
10: Eluate3 from Cation Exchange

BC1 B-Body™ SDS-PAGE  CrossMab SDS-PAGE*

*Data from Schaefer et al. (Proc Natl Acad Sci U S A. 2011 Jul 5;108(27):11187-92)

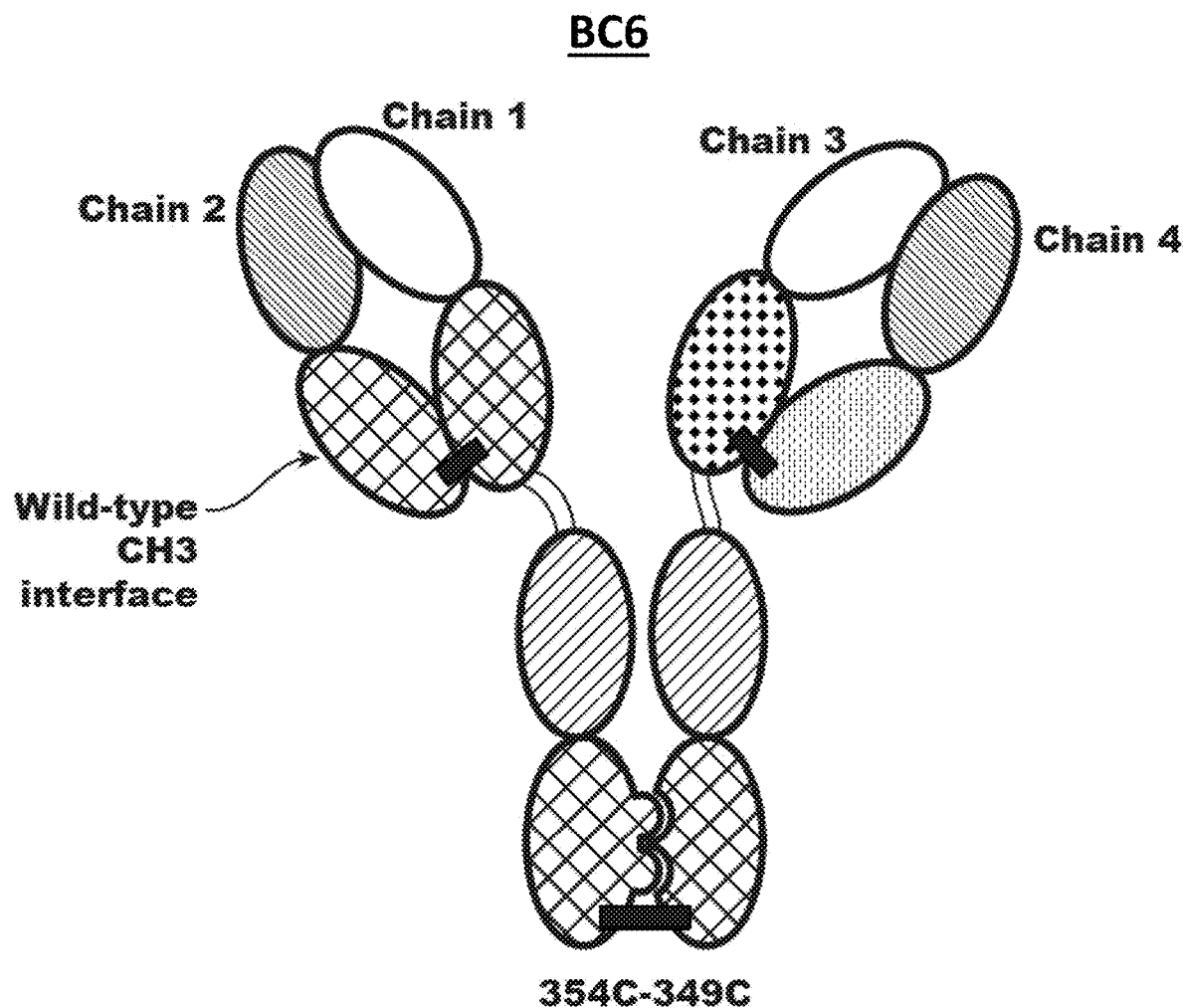
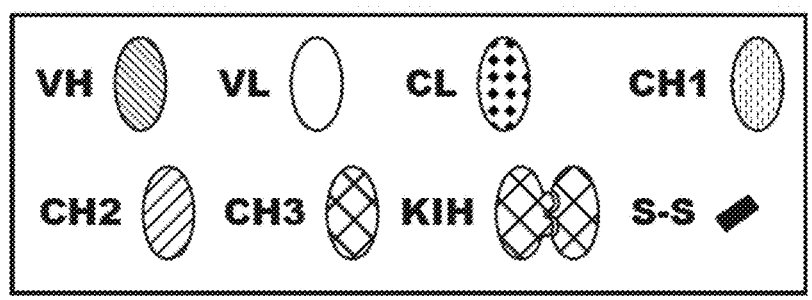
FIG. 14

L: Ladder
1: BC6 CH1 eluate 4/25
2: BC6 CH1 eluate 4/5
3: BC6 MonoS peak C12
4: BC6 MonoS peak D9

L: Ladder
1: BC28: 349C-354C
2: BC29: 351C-351C
3: BC30: 354C-349C
4: BC31: 394C-394C
5: BC32: 407C-407C L: Ladder
1: BC1 (2X1) CH1 eluate
2: BC1 CH1 eluate 3: BC1 (2X1) supernatant from Expi 293
4: BC1 (2X1) flow through after protein A
5: BC1 (2X1) protein A eluate
6: BC1 (2X1) flow through after CH1 resin
7: BC1 (2X1) CH1 eluate

CTLA4-4 x Nivo x CTLA4-4 (1x2)

L: Ladder
1: BC1 (1x1)
2: BC1 (1x1) + DTT
3: BC1 (2X1)
4: BC1 (2X1) + DTT
5: CTLA4 x Nivo x CTLA4 (1x2)
6: CTLA4 x Nivo x CTLA4 (1x2) + DTT
7: BC22 (1X1X1a)
8: BC22 (1X1X1a) + DTT

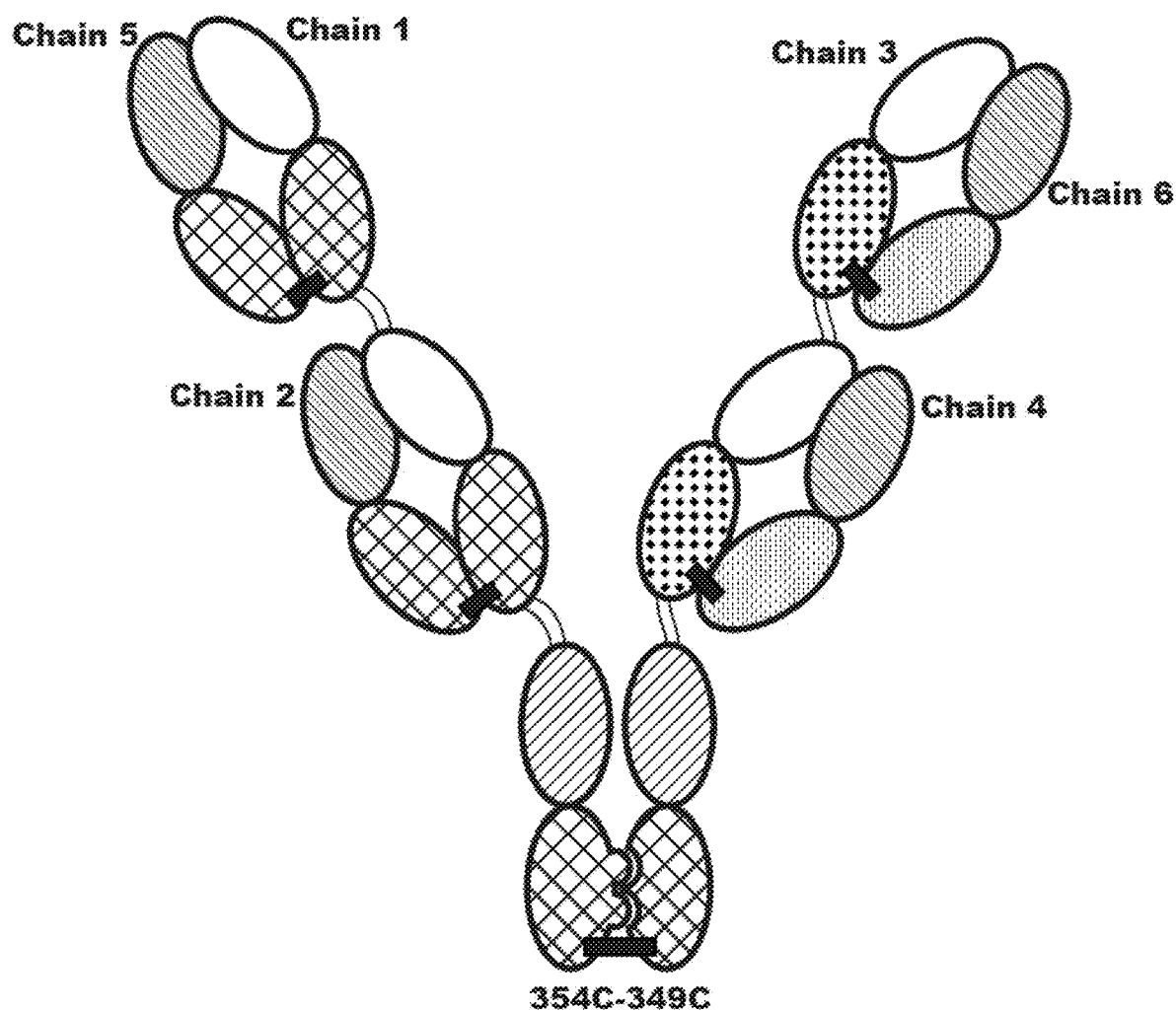
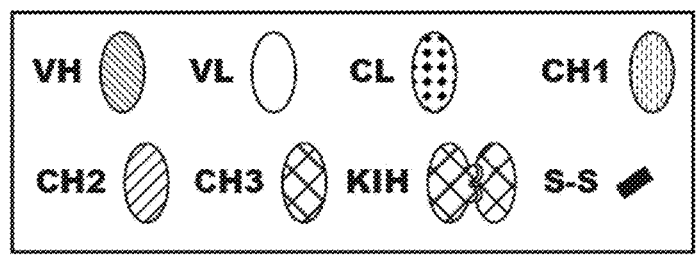
FIG. 35

L: Ladder
1: BC21 (2X1), CH1 eluate
2: BC21 (2X1), pk 1 after IEX
3: BC21 (2X1), pk2 after IEX
4: BC12 (1X2), CH1 eluate
5: BC12 (1X2), pk 1 after IEX
6: BC12 (1X2), pk 2 after IEX
7: BC22 (2X2), CH1 eluate
8: BC22 (2X2), pk 1 after IEX
9: BC22 (2X2), pk 2 after IEX

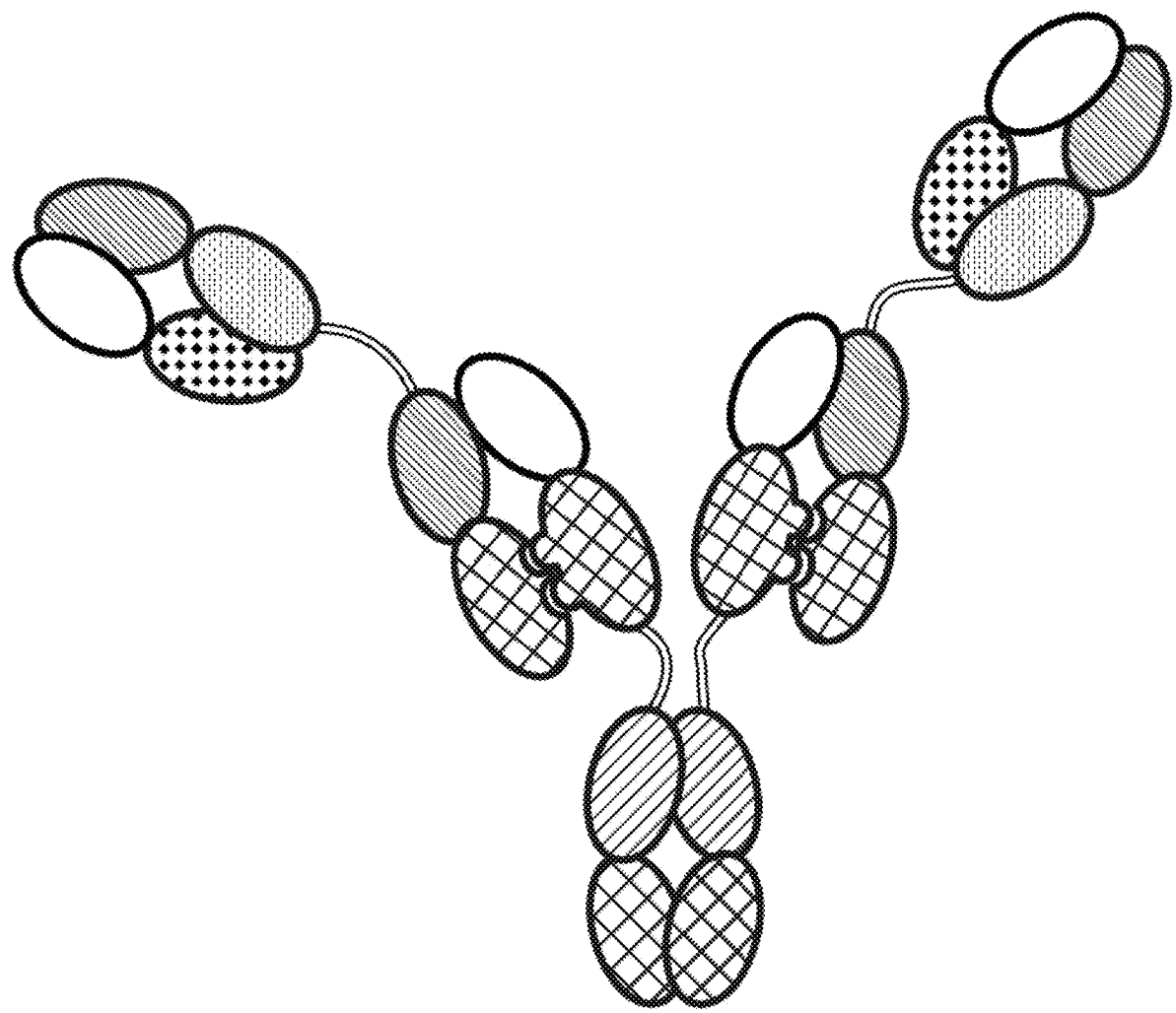
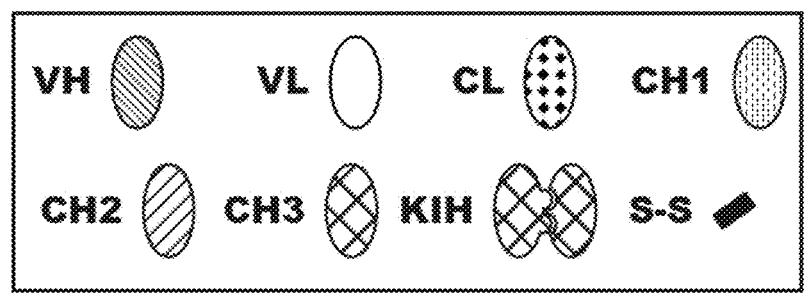
FIG. 37

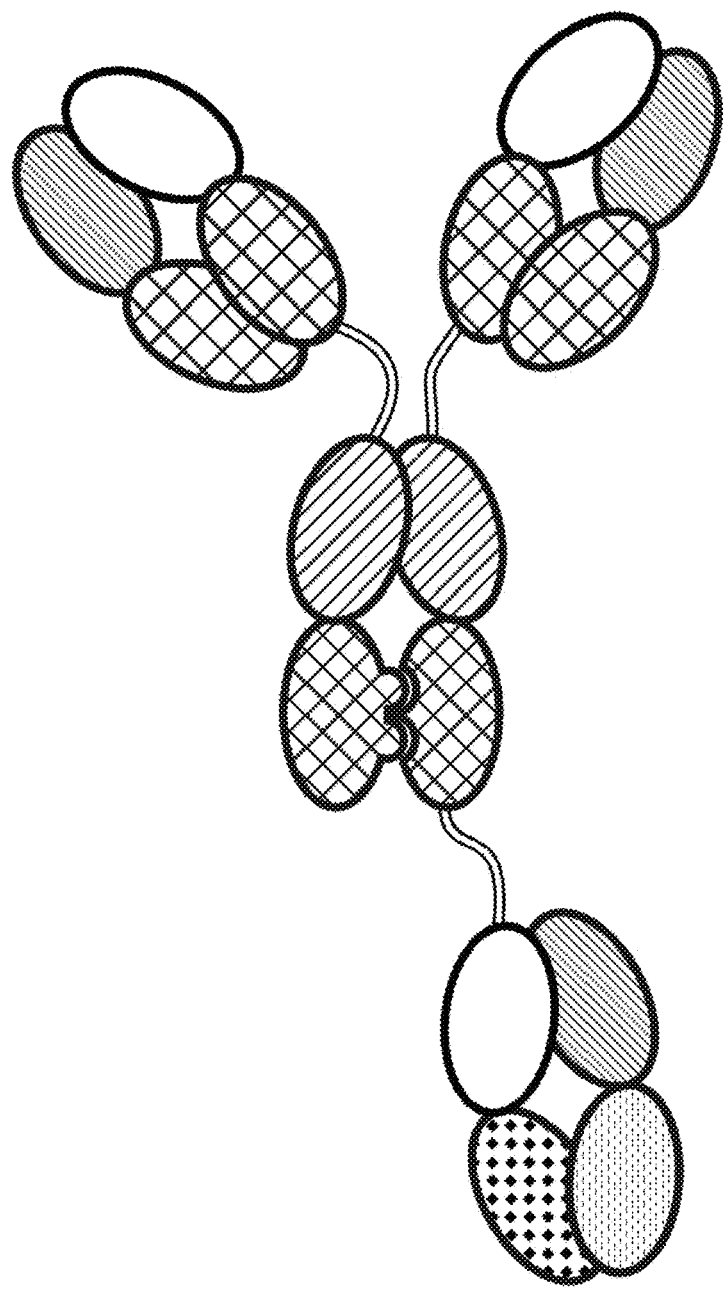
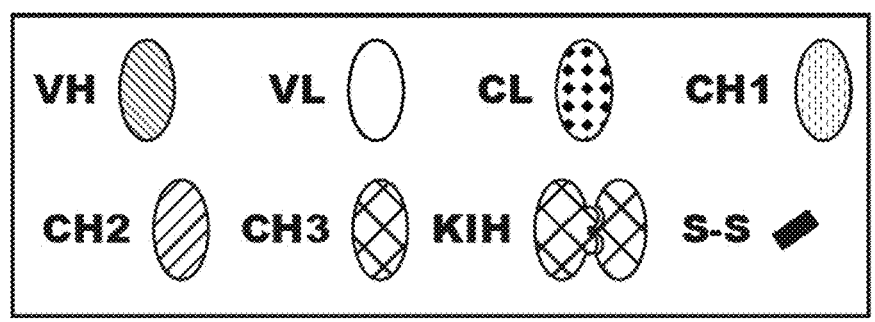
FIG. 43

L: Ladder
1: BC1 (1x1)
2: BC1 (1x1) + DTT
3: BC28 (1x1)
4: BC28 (1x1) + DTT
5: BC44 (1x1)
6: BC44 (1x1) + DTT
7: BC28 (1x2)
8: BC28 (1x2) + DTT
9: BC28 (1x1x1a)
10: BC28 (1x1x1a) + DTT

ANTI-ROR ANTIBODY CONSTRUCTS

1. CROSS-REFERENCE TO RELATED APPLICATIONS

This application is a U.S. National Stage Application under 35 U.S.C. § 371 of International Patent Application No. PCT/US2019/028051, filed Apr. 18, 2019, which claims the benefit of U.S. Provisional Patent Application No. 62/659,635, filed Apr. 18, 2018, the disclosure of each of which is incorporated by reference herein in its entirety.

2. SEQUENCE LISTING

This application incorporates by reference a Substitute Sequence Listing submitted with this application as an ASCII text file, entitled "14529-001-999_SUB_SEQ_LIS-TING.txt", created on Feb. 5, 2023, and is 336,%1 bytes in size.

3. BACKGROUND

The design and therapeutic use of multispecific antibodies—antibody-derived proteins engineered to recognize multiple targets—is an area of intensive research. Multispecific antibodies offer the promise of greater therapeutic control than is routinely provided by monospecific monoclonal antibodies. For example, multispecific antibodies can be engineered to provide greater target specificity than monospecific antibodies, reducing the off-target effects associated with many antibody therapies, particularly antibody-based immunotherapies. Multispecific antibodies also offer the promise of therapeutic strategies that are not possible with monospecific antibodies, such as synergistic targeting of multiple cell receptors, especially in immunotherapy. One such immunotherapy is the use of bispecific antibodies to recruit and redirect T cells to target and kill specific tumor cell populations through bispecific engagement of a T cell marker and a tumor cell marker. For example, the targeting of B cell lymphoma using CD3×CD19 bispecific antibodies, such as by the CD3×CD19 BiTE blinatumomab (Blincyto), is described in U.S. Pub. No. 2006/0193852.

There is, therefore, a need for improved multispecific antibodies that specifically bind to distinct cell populations, including tumor cell populations, with improvements including increased affinity or avidity, reduced off-target binding, and/or reduced unintended immune activation.

Various tumors can demonstrate cell-surface expression of tyrosine-protein kinase transmembrane receptor (ROR) antigens, as described in greater detail in Gentile, el al. (*Cancer Res;* 71(8) Apr. 15, 2011), Rebagay, et al. (*Front. Oncol.,* 18 Apr. 2012). Zhang, et al. (*American Journal of Pathology,* Vol. 181, No. 6, December 2012), Henry, el al. (*Oncotarget,* Vol. 6, No. 37 2015), Zhang, et al. (*PLoS ONE* 7(3): e31127), and Bainbridge, et al. (*PLoS ONE* 9(7): e102695.), each herein incorporated by reference in their entirety. In addition, ROR expression may not be expressed, or only demonstrate limited expression, in normal, i.e. non-cancerous, tissue as described in Balakrishnan et al. (*Clin Cancer Res.* 2017 Jun. 15; 23(12): 3061-3071), herein incorporated in its entirety. Thus ROR antigens can be used as a tumor-specific marker in certain tumors. Examples of tumors and cancers with demonstrated ROR expression include, but are not limited to, pancreatic cancer, ovarian cancer, breast cancer, lung cancer, gastric cancer, melanoma, Ewing sarcoma, chronic lymphocytic leukemia, mantle cell lymphoma, and B-ALL, as described in Gohil et al. (*Onco-immunology.* 2017; 6(7): e1326437), herein incorporated in its entirety. Other cancers include, but are not limited to, hematological cancer, prostate cancer, colon cancer, renal cancer, and uterine cancer. Use of ROR multispecific antibodies, formatted in various antibody platforms, to target tumors is described in Gohil, et al., international application WO 2017/053469, international application WO 2014/167022, U.S. Pub. No. 2017/0198045, international application WO 2016/094873, international application WO 2017/127499, and international application WO 2016/142768, each of which is herein incorporated by reference in its entirety.

ROR antigen binding molecules thus have therapeutic potential in treatment of cancer. Multispecific ROR binding molecules that bind T cell surface antigens in addition to a ROR antigen have potential to provide T cell redirected killing of ROR-expressing cancer cells.

There is, therefore, a need for ROR antigen binding molecules, including multispecific ROR antigen binding molecules. There is also a need for ROR antigen binding molecules that have improvements including increased affinity or avidity, reduced off-target binding, and/or reduced unintended immune activation. There is a particular need for a multispecific ROR antigen binding molecule that has improved manufacturability, and is readily purified.

4. SUMMARY

In a first aspect, antigen binding molecules are provided. In every embodiment, the antigen binding molecule includes at least an antigen binding site specific for a ROR antigen; the binding molecules are therefore termed ROR antigen binding molecules.

Described herein are tyrosine-protein kinase transmembrane receptor (ROR) antigen binding molecules comprising: A) a CDR1, a CDR2, and a CDR3 amino acid sequences of a light chain variable region (VL) from a ROR antigen binding site, wherein the CDR1. CDR2, and CDR3 VL sequences are selected from Table 6; and B) comprises a CDR1, a CDR2, and a CDR3 amino acid sequences of a heavy chain variable region (VH) from the ROR antigen binding site, wherein the CDR1, CDR2, and CDR3 VH sequences are selected from Table 6, wherein the ROR antigen binding site is a first antigen binding site and is specific for (i) ROR1 and ROR2, (ii) ROR1, or (iii) ROR2. In certain aspects, the ROR antigen binding molecule further comprises a second antigen binding site. In certain aspects, the second antigen binding site is the same as the first antigen binding site. In certain aspects, the second antigen binding site is specific for a second antigen different from the ROR antigen of the first antigen binding site. In certain aspects, the second antigen is a CD3 antigen.

Described herein are tyrosine-protein kinase transmembrane receptor (ROR) antigen binding molecules comprising: a first and a second polypeptide chain, wherein: (a) the first polypeptide chain comprises a domain A, a domain B, a domain D, and a domain E, wherein the domains are arranged, from N-terminus to C-terminus, in a A-B-D-E orientation, and wherein domain A has a VL amino acid sequence, domain B has a CH3 amino acid sequence, domain D has a CH2 amino acid sequence, domain E has a constant region domain amino acid sequence; (b) the second polypeptide chain comprises a domain F and a domain G, wherein the domains are arranged, from N-terminus to C-terminus, in a F-G orientation, and wherein domain F has a VH amino acid sequence and domain G has a CH3 amino acid sequence; and (c) the first and the second polypeptides are associated through an interaction between the A and the F domains and an interaction between the B and the G domains to form the ROR antigen binding molecule, wherein the interaction between the A domain and the F domain form a first antigen binding site specific for a ROR antigen.

In certain aspects, the ROR antigen is ROR1. In certain aspects, the ROR antigen is ROR2. In certain aspects, the ROR antigen is ROR1 and ROR2. In certain aspects, the ROR antigen is a domain selected from the group consisting of: a ROR1 Frizzle domain, ROR2 Frizzle domain, a ROR1 Ig-like domain, a ROR2 Ig-like domain, a ROR1 Kringle domain, and a ROR2 Kringle domain. In certain aspects, the ROR antigen comprises a human ROR antigen.

In certain aspects, Domain A comprises a CDR1, a CDR2, and a CDR3 amino acid sequences of a specific light chain variable region (VL) from a specific ROR antigen binding site, wherein the CDR1, CDR2, and CDR3 VL sequences are selected from Table 6, and Domain F comprises a CDR1, a CDR2, and a CDR3 amino acid sequences of a specific heavy chain variable region (VH) from the specific ROR antigen binding site, wherein the CDR1, CDR2, and CDR3 VH sequences are selected from Table 6. In certain aspects, the specific ROR antigen binding site is 12A-10, 12A-10 D54E Y55Q, or 12A-27 from Table 6.

In certain aspects, Domain A comprises a VL having one or two amino acid mutations as compared with a VL sequence of the antibody in Table 6, wherein the one or two amino acid mutations are in one or more CDR regions in the VL. In certain aspects, Domain F comprises a VH having one or two amino acid mutations as compared with a VH sequence of the antibody in Table 6, wherein the one or two amino acid mutations are in one or more CDR regions in the VH. In certain aspects, Domain A comprises a VL having the VL sequence of 12A-10 with one or more mutations in one or more CDR regions. In certain aspects, Domain A comprises a VL having the VL sequence of 12A-27 with one or more mutations in one or more CDR regions. In certain aspects, Domain F comprises a VL having the VL sequence of 12A-10 with one or more mutations in one or more CDR regions. In certain aspects, Domain F comprises a VL having the VL sequence of 12A-27 with one or more mutations in one or more CDR regions.

In certain aspects, the amino acid sequences of the B domain and the G domain are identical, wherein the sequence is an endogenous CH3 sequence.

In certain aspects, the amino acid sequences of the B domain and the G domain are different and separately comprise respectively orthogonal modifications in an endogenous CH3 sequence, wherein the B domain interacts with the G domain, and wherein neither the B domain nor the G domain significantly interacts with a CH3 domain lacking the orthogonal modification.

In certain aspects, the orthogonal modifications of the B domain and the G domain comprise mutations that generate engineered disulfide bridges between the B domain and the G domain. In certain aspects, the mutations of the B domain and the G domain that generate engineered disulfide bridges are a S354C mutation in one of the B domain and G domain, and a 349C in the other domain.

In certain aspects, the orthogonal modifications of the B domain and the G domain comprise knob-in-hole mutations. In certain aspects, the knob-in hole mutations are a T366W mutation in one of the B domain and G domain, and a T366S, L368A, and aY407V mutation in the other domain.

In certain aspects, the orthogonal modifications of the B domain and the G domain comprise charge-pair mutations.

In certain aspects, the charge-pair mutations are a T366K mutation in one of the B domain and G domain, and a L351D mutation in the other domain.

In certain aspects, the E domain has a CH3 amino acid sequence.

In certain aspects, the amino acid sequences of the E domain and the K domain are identical, wherein the sequence is an endogenous CH3 sequence.

In certain aspects, the amino acid sequences of the E domain and the K domain are different. In certain aspects, the different sequences separately comprise respectively orthogonal modifications in an endogenous CH3 sequence, wherein the E domain interacts with the K domain, and wherein neither the E domain nor the K domain significantly interacts with a CH3 domain lacking the orthogonal modification.

In certain aspects, the orthogonal modifications comprise mutations that generate engineered disulfide bridges between the E domain and the K domain. In certain aspects, the mutations that generate engineered disulfide bridges are a S354C mutation in one of the E domain and the K domain, and a 349C in the other domain.

In certain aspects, the orthogonal modifications in the E domain and the K domain comprise knob-in-hole mutations. In certain aspects, the knob-in hole mutations are a T366W mutation in one of the E domain or the K domain and a T366S, L368A, and aY407V mutation in the other domain.

In certain aspects, the orthogonal modifications in the E domain and the K domain comprise charge-pair mutations. In certain aspects, the charge-pair mutations are a T366K mutation in one of the E domain or the K domain and a corresponding L351D mutation in the other domain.

In certain aspects, the amino acid sequences of the E domain and the K domain are endogenous sequences of two different antibody domains, the domains selected to have a specific interaction that promotes the specific association between the first and the third polypeptides. In certain aspects, the two different amino acid sequences are a CH1 sequence and a CL sequence.

In certain aspects, the sequence that forms the junction between the A domain and the B domain is IKRTPREP (SEQ ID NO:57) or IKRTVREP (SEQ ID NO:58).

In certain aspects, the sequence that forms the junction between the F domain and the G domain is SSASPREP (SEQ ID NO:63).

In certain aspects, at least one CH3 amino acid sequence has a C-terminal tripeptide insertion connecting the CH3 amino acid sequence to a hinge amino acid sequence, wherein the tripeptide insertion is selected from the group consisting of PGK, KSC, and GEC.

In certain aspects, the sequences are human sequences.

In certain aspects, at least one CH3 amino acid sequence is an IgG sequence. In certain aspects, the IgG sequences are IgG1 sequences.

In certain aspects, at least one CH3 amino acid sequence has one or more isoallotype mutations. In certain aspects, the isoallotype mutations are D356E and L358M.

In certain aspects, the CL amino acid sequence is a Ckappa sequence.

In certain aspects, the CH2 sequences have one or more engineered mutations that reduce Fc effector function. In certain aspects, the one or more engineered mutations are at position L234, L235, and P329. In certain aspects, the one or more engineered mutations are L234A, L235A, and P329G. In certain aspects, the one or more engineered mutations are L234A. L235A, and P329K.

Also described herein are tyrosine-protein kinase transmembrane receptor (ROR) antigen binding molecules comprising: a first, second, third, and fourth polypeptide chain, wherein: (a) the first polypeptide chain comprises a domain A, a domain B, a domain D, and a domain E, wherein the domains are arranged, from N-terminus to C-terminus, in a A-B-D-E orientation, and domain A has a VL amino acid sequence, domain B has a CH3 amino acid sequence, domain D has a CH2 amino acid sequence, and domain E has a constant region domain amino acid sequence; (b) the second polypeptide chain comprises a domain F and a domain G, wherein the domains are arranged, from N-terminus to C-terminus, in a F-G orientation, and wherein domain F has a VH amino acid sequence and domain G has a CH3 amino acid sequence; (c) the third polypeptide chain comprises a domain H, a domain I, a domain J, and a domain K, wherein the domains are arranged, from N-terminus to C-terminus, in a H-I-J-K orientation, and w % herein domain H has a variable region domain amino acid sequence, domain I has a constant region domain amino acid sequence, domain J has a CH2 amino acid sequence, and K has a constant region domain amino acid sequence; (d) the fourth polypeptide chain comprises a domain L and a domain M, w % herein the domains are arranged, from N-terminus to C-terminus, in a L-M orientation, and wherein domain L has a variable region domain amino acid sequence and domain M has a constant region domain amino acid sequence; (e) the first and the second polypeptides are associated through an interaction between the A and the F domains and an interaction between the B and the G domains; (f) the third and the fourth polypeptides are associated through an interaction between the H and the L domains and an interaction between the I and the M domains; and (g) the first and the third polypeptides are associated through an interaction between the D and the J domains and an interaction between the E and the K domains to form the ROR antigen binding molecule, wherein the interaction between the A domain and the F domain form a first antigen binding site, the interaction between the H domain and the L domain form a second antigen binding site, and wherein the first antigen binding site, the second antigen binding site, or the first and the second antigen binding site are specific for a ROR antigen.

In certain aspects, the first antigen binding site is specific for the ROR antigen. In certain aspects, the second antigen binding site is specific for the ROR antigen. In certain aspects, the first and the second antigen binding site is specific for the ROR antigen.

In certain aspects, the ROR antigen is ROR1. In certain aspects, the ROR antigen is ROR2. In certain aspects, the ROR antigen is ROR1 and ROR2. In certain aspects, the ROR antigen is a domain selected from the group consisting of: a ROR1 Frizzle domain, ROR2 Frizzle domain, a ROR1 Ig-like domain, a ROR2 Ig-like domain, a ROR1 Kringle domain, and a ROR2 Kringle domain. In certain aspects, the ROR antigen comprises a human ROR antigen.

In certain aspects, Domain A comprises a CDR1, a CDR2, and a CDR3 amino acid sequences of a specific light chain variable region (VL) from a specific ROR antigen binding site, wherein the CDR1, CDR2, and CDR3 VL sequences are selected from Table 6, and Domain F comprises a CDR1, a CDR2, and a CDR3 amino acid sequences of a specific heavy chain variable region (VH) from the specific ROR antigen binding site, wherein the CDR1, CDR2, and CDR3 VH sequences are selected from Table 6. In certain aspects, the specific ROR antigen binding site is 12A-10, 12A-10 D54E Y55Q or 12A-27 from Table 6.

In certain aspects, Domain A comprises a VL having one or two amino acid mutations as compared with a VL sequence of the antibody in Table 6, wherein the one or two amino acid mutations are in one or more CDR regions in the VL. In certain aspects, Domain F comprises a VH having one or two amino acid mutations as compared with a VH sequence of the antibody in Table 6, wherein the one or two amino acid mutations are in one or more CDR regions in the VH. In certain aspects, Domain A comprises a VL having the VL sequence of 12A-10 with one or more mutations in one or more CDR regions. In certain aspects, Domain A comprises a VL having the VL sequence of 12A-27 with one or more mutations in one or more CDR regions. In certain aspects, Domain F comprises a VL having the VL sequence of 12A-10 with one or more mutations in one or more CDR regions. In certain aspects, Domain F comprises a VL having the VL sequence of 12A-27 with one or more mutations in one or more CDR regions.

In certain aspects, the second antigen binding site comprises: A) within the third polypeptide chain a specific light chain variable region (VL) amino acid sequence selected from the group consisting of: SEQ ID NO:69 and SEQ ID NO:73; and B) within the fourth polypeptide chain a specific heavy chain variable region (VH) amino acid sequence selected from the group consisting of: SEQ ID NO:68, SEQ ID NO:70, SEQ ID NO:71, and SEQ ID NO:72.

In certain aspects, the second antigen binding site comprises: A) within the fourth polypeptide chain a specific light chain variable region (VL) amino acid sequence selected from the group consisting of: SEQ ID NO:69 and SEQ ID NO:73; and B) within the third polypeptide chain a specific heavy chain variable region (VH) amino acid sequence selected from the group consisting of: SEQ ID NO:68, SEQ ID NO:70, SEQ ID NO:71, and SEQ ID NO:72.

In certain aspects, the amino acid sequences of the B domain and the G domain are identical, wherein the sequence is an endogenous CH3 sequence.

In certain aspects, the amino acid sequences of the B domain and the G domain are different and separately comprise respectively orthogonal modifications in an endogenous CH3 sequence, wherein the B domain interacts with the G domain, and wherein neither the B domain nor the G domain significantly interacts with a CH3 domain lacking the orthogonal modification.

In certain aspects, the orthogonal modifications of the B domain and the G domain comprise mutations that generate engineered disulfide bridges between the B domain and the G domain. In certain aspects, the mutations of the B domain and the G domain that generate engineered disulfide bridges are a S354C mutation in one of the B domain and G domain, and a 349C in the other domain.

In certain aspects, the orthogonal modifications of the B domain and the G domain comprise knob-in-hole mutations. In certain aspects, the knob-in hole mutations are a T366W mutation in one of the B domain and G domain, and a T366S, L368A, and aY407V mutation in the other domain.

In certain aspects, the orthogonal modifications of the B domain and the G domain comprise charge-pair mutations. In certain aspects, the charge-pair mutations are a T366K mutation in one of the B domain and G domain, and a L351D mutation in the other domain.

In certain aspects, the E domain has a CH3 amino acid sequence.

In certain aspects, the amino acid sequences of the E domain and the K domain are identical, wherein the sequence is an endogenous CH3 sequence.

In certain aspects, the amino acid sequences of the E domain and the K domain are different. In certain aspects, the different sequences separately comprise respectively orthogonal modifications in an endogenous CH3 sequence, wherein the E domain interacts with the K domain, and wherein neither the E domain nor the K domain significantly interacts with a CH3 domain lacking the orthogonal modification.

In certain aspects, the orthogonal modifications comprise mutations that generate engineered disulfide bridges between the E domain and the K domain. In certain aspects, the mutations that generate engineered disulfide bridges are a S354C mutation in one of the E domain and the K domain, and a 349C in the other domain.

In certain aspects, the orthogonal modifications in the E domain and the K domain comprise knob-in-hole mutations. In certain aspects, the knob-in hole mutations are a T366W mutation in one of the E domain or the K domain and a T366S. L368A, and aY407V mutation in the other domain.

In certain aspects, the orthogonal modifications in the E domain and the K domain comprise charge-pair mutations. In certain aspects, the charge-pair mutations are a T366K mutation in one of the E domain or the K domain and a corresponding L351D mutation in the other domain.

In certain aspects, the amino acid sequences of the E domain and the K domain are endogenous sequences of two different antibody domains, the domains selected to have a specific interaction that promotes the specific association between the first and the third polypeptides. In certain aspects, the two different amino acid sequences are a CH1 sequence and a CL sequence.

In certain aspects, domain I has a CL sequence and domain M has a CH1 sequence.

In certain aspects, domain H has a VL sequence and domain L has a VH sequence.

In certain aspects, domain H has a VL amino acid sequence; domain I has a CL amino acid sequence; domain K has a CH3 amino acid sequence; domain L has a VH amino acid sequence; and domain M has a CH1 amino acid sequence.

In certain aspects, the ROR antigen binding molecule further comprises: a fifth polypeptide chain, wherein: (a) the first polypeptide chain further comprises a domain N and a domain 0, wherein the domains are arranged, from N-terminus to C-terminus, in a N-O-A-B-D-E orientation, and wherein domain N has a variable region domain amino acid sequence, domain O has a constant region domain amino acid sequence; (b) the ROR antigen binding molecule further comprises a fifth polypeptide chain, comprising: a domain P and a domain Q, wherein the domains are arranged, from N-terminus to C-terminus, in a P-Q orientation, and wherein domain P has a variable region domain amino acid sequence and domain Q has a constant region domain amino acid sequence; and (c) the first and the fifth polypeptides are associated through an interaction between the N and the P domains and an interaction between the O and the Q domains to form the ROR antigen binding molecule.

In certain aspects, (a) the amino acid sequences of domain N and domain A are identical, the amino acid sequences of domain H is different from the sequence of domain N and domain A, the amino acid sequences of domain O and domain B are identical, the amino acid sequences of domain I is different from the sequence of domain O and domain B, the amino acid sequences of domain P and domain F are identical, the amino acid sequences of domain L is different from the sequence of domain P and domain F, the amino acid sequences of domain Q and domain G are identical, the amino acid sequences of domain M is different from the sequence of domain Q and domain G; and (b) wherein the interaction between the A domain and the F domain form a first antigen binding site specific for a first antigen, the interaction between the H domain and the L domain form a second antigen binding site specific for a second antigen, and the interaction between the N domain and the P domain form a third antigen binding site specific for the first antigen. In certain aspects, the first antigen is the ROR antigen. In certain aspects, the second antigen is a CD3 antigen.

In certain aspects, (a) the amino acid sequences of domain N, domain A, and domain H are different, the amino acid sequences of domain O, domain B. and domain I are different, the amino acid sequences of domain P, domain F, and domain L are different, and the amino acid sequences of domain Q, domain G, and domain M are different; (b) the interaction between the A domain and the F domain form a first antigen binding site specific for a first antigen, the interaction between the H domain and the L domain form a second antigen binding site specific for a second antigen, and the domain N and domain P form a third antigen binding site specific for a third antigen, and (c) the first, the second, or the third antigen is the ROR antigen.

In certain aspects, the ROR antigen binding molecule further comprises: a sixth polypeptide chain, wherein: (a) the third polypeptide chain further comprises a domain R and a domain S, wherein the domains are arranged, from N-terminus to C-terminus, in a R-S-H-I-J-K orientation, and wherein domain R has a variable region domain amino acid sequence and domain S has a constant domain amino acid sequence; (b) the ROR antigen binding molecule further comprises a sixth polypeptide chain, comprising: a domain T and a domain U, wherein the domains are arranged, from N-terminus to C-terminus, in a T-U orientation, and wherein domain T has a variable region domain amino acid sequence and domain U has a constant domain amino acid sequence; and (c) the third and the sixth polypeptides are associated through an interaction between the R and the T domains and an interaction between the S and the U domains to form the ROR antigen binding molecule.

In certain aspects: (a) the amino acid sequences of domain R and domain A are identical, the amino acid sequences of domain H is different from the sequence of domain R and domain A, the amino acid sequences of domain S and domain B are identical, the amino acid sequences of domain I is different from the sequence of domain S and domain B, the amino acid sequences of domain T and domain F are identical, the amino acid sequences of domain L is different from the sequence of domain T and domain F, the amino acid sequences of domain U and domain G are identical, the amino acid sequences of domain M is different from the sequence of domain U and domain G and (b) the interaction between the A domain and the F domain form a first antigen binding site specific for a first antigen, the interaction between the H domain and the L domain form a second antigen binding site specific for a second antigen; and the interaction between the R domain and the T domain form a third antigen binding site specific for the first antigen. In certain aspects, the first antigen is the ROR antigen. In certain aspects, the second antigen is a CD3 antigen.

In certain aspects, (a) the amino acid sequences of domain R and domain H are identical, the amino acid sequences of domain A is different from the sequence of domain R and domain H, the amino acid sequences of domain S and domain I are identical, the amino acid sequences of domain B is different from the sequence of domain S and domain I, the amino acid sequences of domain T and domain L are identical, the amino acid sequences of domain F is different from the sequence of domain T and domain L, the amino acid sequences of domain U and domain M are identical, the amino acid sequences of domain G is different from the sequence of domain U and domain M, and (b) the interaction between the A domain and the F domain form a first antigen binding site specific for a first antigen, the interaction between the H domain and the L domain form a second antigen binding site specific for a second antigen, and the interaction between the R domain and the T domain form a third antigen binding site specific for the second antigen. In certain aspects, the second antigen is the ROR antigen. In certain aspects, the first antigen is a CD3 antigen.

In certain aspects, (a) the amino acid sequences of domain R, domain A, and domain H are different, the amino acid sequences of domain S, domain B, and domain I are different, the amino acid sequences of domain T, domain F, and domain L are different, and the amino acid sequences of domain U, domain G. and domain M are different; (b) the interaction between the A domain and the F domain form a first antigen binding site specific for a first antigen, the interaction between the H domain and the L domain form a second antigen binding site specific for a second antigen, and the interaction between the R domain and the T domain form a third antigen binding site specific for a third antigen; and (c) the first, the second, or the third antigen is the ROR antigen.

In certain aspects, the ROR antigen binding molecule further comprises: a fifth and a sixth polypeptide chain, wherein: (a) the first polypeptide chain further comprises a domain N and a domain O, wherein the domains are arranged, from N-terminus to C-terminus, in a N-O-A-B-D-E orientation; (b) the third polypeptide chain further comprises a domain R and a domain S, wherein the domains are arranged, from N-terminus to C-terminus, in a R-S-H-I-J-K orientation; (c) the ROR antigen binding molecule further comprises a fifth and a sixth polypeptide chain, wherein: the fifth polypeptide chain comprises a domain P and a domain Q, wherein the domains are arranged, from N-terminus to C-terminus, in a P-Q orientation, and the sixth polypeptide chain comprises a domain T and a domain U, wherein the domains are arranged, from N-terminus to C-terminus, in a T-U orientation; and (d) the first and the fifth polypeptides are associated through an interaction between the N and the P domains and an interaction between the O and the Q domains, and the third and the sixth polypeptides are associated through an interaction between the R and the T domains and an interaction between the S and the U domains to form the ROR antigen binding molecule.

In certain aspects, (a) the amino acid sequences of domain N and domain A are identical, the amino acid sequences of domain H and domain R are identical, the amino acid sequences of domain O and domain B are identical, the amino acid sequences of domain I and domain S are identical, the amino acid sequences of domain P and domain F are identical, the amino acid sequences of domain L and domain T are identical, the amino acid sequences of domain Q and domain G are identical, the amino acid sequences of domain M and domain U are identical; and (b) wherein the interaction between the A domain and the F domain form a first antigen binding site specific for a first antigen, the domain N and domain P form a second antigen binding site specific for the first antigen, the interaction between the H domain and the L domain form a third antigen binding site specific for a second antigen, and the interaction between the R domain and the T domain form a fourth antigen binding site specific for the second antigen.

In certain aspects, (a) the amino acid sequences of domain H and domain A are identical, the amino acid sequences of domain N and domain R are identical, the amino acid sequences of domain I and domain B are identical, the amino acid sequences of domain O and domain S are identical, the amino acid sequences of domain L and domain F are identical, the amino acid sequences of domain P and domain T are identical, the amino acid sequences of domain M and domain G are identical, the amino acid sequences of domain Q and domain U are identical; and (b) wherein the interaction between the A domain and the F domain form a first antigen binding site specific for a first antigen, the domain N and domain P form a second antigen binding site specific for a second antigen, the interaction between the H domain and the L domain form a third antigen binding site specific for the first antigen, and the interaction between the R domain and the T domain form a fourth antigen binding site specific for the second antigen.

In certain aspects, the sequence that forms the junction between the A domain and the B domain is IKRTPREP (SEQ ID NO:57) or IKRTVREP (SEQ ID NO:58).

In certain aspects, the sequence that forms the junction between the F domain and the G domain is SSASPREP (SEQ ID NO:63).

In certain aspects, at least one CH3 amino acid sequence has a C-terminal tripeptide insertion connecting the CH3 amino acid sequence to a hinge amino acid sequence, wherein the tripeptide insertion is selected from the group consisting of PGK, KSC, and GEC.

In certain aspects, the sequences are human sequences.

In certain aspects, at least one CH3 amino acid sequence is an IgG sequence. In certain aspects, the IgG sequences are IgG1 sequences.

In certain aspects, at least one CH3 amino acid sequence has one or more isoallotype mutations. In certain aspects, the isoallotype mutations are D356E and L358M.

In certain aspects, the CL amino acid sequence is a Ckappa sequence.

In certain aspects, the CH2 sequences have one or more engineered mutations that reduce Fc effector function. In certain aspects, the one or more engineered mutations are at position L234, L235, and P329. In certain aspects, the one or more engineered mutations are L234A, L235A, and P329G. In certain aspects, the one or more engineered mutations are L234A, L235A, and P329K.

Also described herein are tyrosine-protein kinase transmembrane receptor (ROR) antigen binding molecules comprising: a first antigen binding site specific for a ROR antigen, wherein the first antigen binding site comprises: A) a CDR1, a CDR2, and a CDR3 amino acid sequences of a specific light chain variable region (VL) from a specific ROR antigen binding site, wherein the CDR1, CDR2, and CDR3 VL sequences are selected from Table 6; and B) comprises a CDR1, a CDR2, and a CDR3 amino acid sequences of a specific heavy chain variable region (VH) from the specific ROR antigen binding site, wherein the CDR1. CDR2, and CDR3 VH sequences are selected from Table 6.

In certain aspects, the first antigen binding site comprises a VL having one or two amino acid mutations as compared with a VL sequence of the antibody in Table 6, wherein the one or two amino acid mutations are in one or more CDR regions in the VL. In certain aspects, the first antigen binding site comprises a VH having one or two amino acid mutations as compared with a VH sequence of the antibody in Table 6, wherein the one or two amino acid mutations are in one or more CDR regions in the VH.

In certain aspects, the first antigen binding site is specific for ROR1. In certain aspects, the first antigen binding site is specific for ROR2. In certain aspects, the first antigen binding site is specific for ROR1 and ROR2. In certain aspects, the ROR antigen is a domain selected from the group consisting of: a ROR1 Frizzle domain, ROR2 Frizzle domain, a ROR1 Ig-like domain, a ROR2 Ig-like domain, a ROR1 Kringle domain, and a ROR2 Kringle domain. In certain aspects, the ROR antigen comprises a human ROR antigen.

In certain aspects, the ROR antigen binding molecule further comprises a second antigen binding site. In certain aspects, the second antigen binding site is specific for the ROR antigen. In certain aspects, the second antigen binding site is specific for a second antigen different from the ROR antigen. In certain aspects, the second antigen is a CD3 antigen. In certain aspects, the antigen binding site is specific for an epitope of the CD3 antigen. In certain aspects, the second antigen binding site comprises: A) a specific light chain variable region (VL) amino acid sequence selected from the group consisting of: SEQ ID NO:69 and SEQ ID NO:73; and B) a specific heavy chain variable region (VH) amino acid sequence selected from the group consisting of: SEQ ID NO:68, SEQ ID NO:70, SEQ ID NO:71, and SEQ ID NO:72. In certain aspects, the second antigen binding site comprises: A) a specific light chain variable region (VL) amino acid sequence selected from the group consisting of: SEQ ID NO:69 and SEQ ID NO:73; and B) a specific heavy chain variable region (VH) amino acid sequence selected from the group consisting of: SEQ ID NO:68, SEQ ID NO:70, SEQ ID NO:71, and SEQ ID NO:72.

In certain aspects, the ROR antigen binding molecule comprises an antibody format selected from the group consisting of: full-length antibodies, Fab fragments, Fvs, scFvs, tandem scFvs, Diabodies, scDiabodies, DARTs, tandAbs, and minibodies. In certain aspects, the ROR antigen binding molecule comprises; a first and a second polypeptide chain, wherein: (a) the first polypeptide chain comprises a domain A, a domain B, a domain D, and a domain E, wherein the domains are arranged, from N-terminus to C-terminus, in a A-B-D-E orientation, wherein domain A has a variable region domain amino acid sequence, and wherein domain B, domain D. and domain E have a constant region domain amino acid sequence; (b) the second polypeptide chain comprises a domain F and a domain G, wherein the domains are arranged, from N-terminus to C-terminus, in a F-G orientation, and wherein domain F has a variable region domain amino acid sequence and domain G has a constant region domain amino acid sequence c) the first and the second polypeptides are associated through an interaction between the A and the F domain and an interaction between the B domain and the G domain to form the ROR antigen binding molecule, and wherein the interaction between the A domain and the F domain form a first antigen binding site.

In certain aspects, the ROR antigen binding molecule further comprises: a third and a fourth polypeptide chain, wherein: (a) the third polypeptide chain comprises a domain H, a domain I, a domain J, and a domain K, wherein the domains are arranged, from N-terminus to C-terminus, in a H-I-J-K orientation, and wherein domain H has a variable region domain amino acid sequence, and domains I, J, and K have a constant region domain amino acid sequence; (b) the fourth polypeptide chain comprises a domain L and a domain M, wherein the domains are arranged, from N-terminus to C-terminus, in a L-M orientation, and wherein domain L has a variable region domain amino acid sequence and domain M has a constant region amino acid sequence; (c) the third and the fourth polypeptides are associated through an interaction between the H and the L domains and an interaction between the I and the M domains; and (d) the first and the third polypeptides are associated through an interaction between the D domain and the J domain and an interaction between the E domain and the K domain to form the ROR antigen binding molecule, and wherein the interaction between the H domain and the L domain form a second antigen binding site. In certain aspects, the first antigen binding site is specific for the ROR antigen. In certain aspects, the second antigen binding site is specific for CD3.

In certain aspects, domain B and domain G have a CH3 amino acid sequence.

In certain aspects, the amino acid sequences of the B domain and the G domain are identical, wherein the sequence is an endogenous CH3 sequence.

In certain aspects, the amino acid sequences of the B domain and the G domain are different and separately comprise respectively orthogonal modifications in an endogenous CH3 sequence, wherein the B domain interacts with the G domain, and wherein neither the B domain nor the G domain significantly interacts with a CH3 domain lacking the orthogonal modification.

In certain aspects, the orthogonal modifications of the B domain and the G domain comprise mutations that generate engineered disulfide bridges between the B domain and the G domain. In certain aspects, the mutations of the B domain and the G domain that generate engineered disulfide bridges are a S354C mutation in one of the B domain and G domain, and a 349C in the other domain.

In certain aspects, the orthogonal modifications of the B domain and the G domain comprise knob-in-hole mutations. In certain aspects, the knob-in hole mutations of the B domain and the G domain are a T366W mutation in one of the B domain and G domain, and a T366S, L368A, and aY407V mutation in the other domain.

In certain aspects, the orthogonal modifications of the B domain and the G domain comprise charge-pair mutations. In certain aspects, the charge-pair mutations of the B domain and the G domain are a T366K mutation in one of the B domain and G domain, and a L351 D mutation in the other domain.

In certain aspects, domain B and domain G have an IgM CH2 amino acid sequence or an IgE CH2 amino acid sequence. In certain aspects, the IgM CH2 amino acid sequence or the IgE CH2 amino acid sequence comprise orthogonal modifications.

In certain aspects, domain I has a CL sequence and domain M has a CH1 sequence. In certain aspects, domain I has a CH1 sequence and domain M has a CL sequence. In certain aspects, the CH1 sequence and the CL sequence each comprise one or more orthogonal modifications, wherein a domain having the CH1 sequence does not significantly interact with a domain having a CL sequence lacking the orthogonal modification.

In certain aspects, the orthogonal modifications comprise mutations that generate engineered disulfide bridges between the at least one CH1 domain and a CL domain, the mutations selected from the group consisting of: an engineered cysteine at position 138 of the CH1 sequence and position 116 of the CL sequence; an engineered cysteine at position 128 of the CH1 sequence and position 119 of the CL sequence, and an engineered cysteine at position 129 of the CH1 sequence and position 210 of the CL sequence.

In certain aspects, the orthogonal modifications comprise mutations that generate engineered disulfide bridges between the at least one CH1 domain and a CL domain, wherein the mutations comprise and engineered cysteines at position 128 of the CH1 sequence and position 118 of a CL Kappa sequence.

In certain aspects, the orthogonal modifications comprise mutations that generate engineered disulfide bridges between the at least one CH1 domain and a CL domain, the mutations selected from the group consisting of: a F118C mutation in the CL sequence with a corresponding A141C in the CH1 sequence; a F118C mutation in the CL sequence with a corresponding L128C in the CH1 sequence; and a S162C mutations in the CL sequence with a corresponding P171C mutation in the CH1 sequence.

In certain aspects, the orthogonal modifications comprise charge-pair mutations between the at least one CH1 domain and a CL domain, the charge-pair mutations selected from the group consisting of: a F118S mutation in the CL sequence with a corresponding A141L in the CH1 sequence; a F118A mutation in the CL sequence with a corresponding A141L in the CH1 sequence; a F118V mutation in the CL sequence with a corresponding A141L in the CH1 sequence; and a T129R mutation in the CL sequence with a corresponding K147D in the CH1 sequence.

In certain aspects, the orthogonal modifications comprise charge-pair mutations between the at least one CH1 domain and a CL domain, the charge-pair mutations selected from the group consisting of: a N138K mutation in the CL sequence with a corresponding G166D in the CH1 sequence, and a N138D mutation in the CL sequence with a corresponding G166K in the CH1 sequence.

In certain aspects, domain A has a VL amino acid sequence and domain F has a VH amino acid sequence. In certain aspects, domain A has a VH amino acid sequence and domain F has a VL amino acid sequence.

In certain aspects, domain H has a VL amino acid sequence and domain L has a VH amino acid sequence. In certain aspects, domain H has a VH amino acid sequence and domain L has a VL amino acid sequence.

In certain aspects, domain D and domain J have a CH2 amino acid sequence.

In certain aspects, the E domain has a CH3 amino acid sequence.

In certain aspects, the amino acid sequences of the E domain and the K domain are identical, wherein the sequence is an endogenous CH3 sequence.

In certain aspects, the amino acid sequences of the E domain and the K domain are different. In certain aspects, the different sequences separately comprise respectively orthogonal modifications in an endogenous CH3 sequence, wherein the E domain interacts with the K domain, and wherein neither the E domain nor the K domain significantly interacts with a CH3 domain lacking the orthogonal modification.

In certain aspects, the orthogonal modifications comprise mutations that generate engineered disulfide bridges between the E domain and the K domain. In certain aspects, the mutations that generate engineered disulfide bridges are a S354C mutation in one of the E domain and the K domain, and a 349C in the other domain. In certain aspects, the orthogonal modifications in the E domain and the K domain comprise knob-in-hole mutations. In certain aspects, the knob-in hole mutations are a T366W mutation in one of the E domain or the K domain and a T366S, L368A, and aY407V mutation in the other domain. In certain aspects, the orthogonal modifications in the E domain and the K domain comprise charge-pair mutations. In certain aspects, the charge-pair mutations are a T366K mutation in one of the E domain or the K domain and a corresponding L351D mutation in the other domain.

In certain aspects, the amino acid sequences of the E domain and the K domain are endogenous sequences of two different antibody domains, the domains selected to have a specific interaction that promotes the specific association between the first and the third polypeptides. In certain aspects, the two different amino acid sequences are a CH1 sequence and a CL sequence.

In certain aspects, the ROR antigen binding molecule further comprises a third antigen binding site. In certain aspects, the third antigen binding site is specific for a ROR antigen. In certain aspects, the first antigen binding site and the third antigen binding site are specific for the same ROR antigen. In certain aspects, the first antigen binding site and the third antigen binding site are specific for different ROR antigens.

In certain aspects. ROR antigen binding molecule comprises a fifth polypeptide chain, wherein (a) the first polypeptide chain further comprises a domain N and a domain O, wherein the domains are arranged, from N-terminus to C-terminus, in a N-O-A-B-D-E orientation, and wherein domain N has a variable region domain amino acid sequence, domain O has a constant region amino acid sequence; (b) the fifth polypeptide chain comprises a domain P and a domain Q, wherein the domains are arranged, from N-terminus to C-terminus, in a P-Q orientation, and wherein domain P has a variable region domain amino acid sequence and domain Q has a constant region amino acid sequence; and (c) the first and the fifth polypeptides are associated through an interaction between the N and the P domains and an interaction between the O and the Q domains to form the ROR antigen binding molecule.

In certain aspects, (a) the amino acid sequences of domain N and domain A are identical, the amino acid sequences of domain H is different from the sequence of domain N and domain A, the amino acid sequences of domain O and domain B are identical, the amino acid sequences of domain I is different from the sequence of domain O and domain B, the amino acid sequences of domain P and domain F are identical, the amino acid sequences of domain L is different from the sequence of domain P and domain F, the amino acid sequences of domain Q and domain G are identical, the amino acid sequences of domain M is different from the sequence of domain Q and domain G; and (b) wherein the interaction between the A domain and the F domain form a first antigen binding site specific for a first antigen, the interaction between the H domain and the L domain form a second antigen binding site specific for a second antigen, and the interaction between the N domain and the P domain form a third antigen binding site specific for the first antigen. In certain aspects, the first antigen is a ROR antigen. In certain aspects, the second antigen is a CD3 antigen.

In certain aspects, (a) the amino acid sequences of domain N, domain A, and domain H are different, the amino acid sequences of domain O, domain B, and domain I are different, the amino acid sequences of domain P, domain F, and domain L are different, and the amino acid sequences of domain Q, domain G, and domain M are different; and (b) the interaction between the A domain and the F domain form a first antigen binding site specific for a first antigen, the interaction between the H domain and the L domain form a second antigen binding site specific for a second antigen, and the interaction between the N domain and the P domain form a third antigen binding site specific for a third antigen.

In certain aspects, the ROR antigen binding molecule comprises a sixth polypeptide chain, wherein: (a) the third polypeptide chain further comprises a domain R and a domain S, wherein the domains are arranged, from N-terminus to C-terminus, in a R-S-H-I-J-K orientation, and wherein domain R has a variable region amino acid sequence and domain S has a constant domain amino acid sequence; (b) the sixth polypeptide chain comprises: a domain T and a domain U, wherein the domains are arranged, from N-terminus to C-terminus, in a T-U orientation, and wherein domain T has a variable region amino acid sequence and domain U has a constant domain amino acid sequence; and (c) the third and the sixth poly peptides are associated through an interaction between the R and the T domains and an interaction between the S and the U domains to form the ROR antigen binding molecule.

In certain aspects, (a) the amino acid sequences of domain R and domain A are identical, the amino acid sequences of domain H is different from the sequence of domain R and domain A, the amino acid sequences of domain S and domain B are identical, the amino acid sequences of domain I is different from the sequence of domain S and domain B, the amino acid sequences of domain T and domain F are identical, the amino acid sequences of domain L is different from the sequence of domain T and domain F, the amino acid sequences of domain U and domain G are identical, the amino acid sequences of domain M is different from the sequence of domain U and domain G, and (b) the interaction between the A domain and the F domain form a first antigen binding site specific for a first antigen, the interaction between the H domain and the L domain form a second antigen binding site specific for a second antigen, and the interaction between the R domain and the T domain form a third antigen binding site specific for the first antigen. In certain aspects, the first antigen is a ROR antigen. In certain aspects, the second antigen is a CD3 antigen.

In certain aspects, (a) the amino acid sequences of domain R and domain H are identical, the amino acid sequences of domain A is different from the sequence of domain R and domain H, the amino acid sequences of domain S and domain I are identical, the amino acid sequences of domain B is different from the sequence of domain S and domain I, the amino acid sequences of domain T and domain L are identical, the amino acid sequences of domain F is different from the sequence of domain T and domain L, the amino acid sequences of domain U and domain M are identical, the amino acid sequences of domain G is different from the sequence of domain U and domain M, and (b) the interaction between the A domain and the F domain form a first antigen binding site specific for a first antigen, the interaction between the H domain and the L domain form a second antigen binding site specific for a second antigen, and the interaction between the R domain and the T domain form a third antigen binding site specific for the second antigen. In certain aspects, the second antigen is a ROR antigen. In certain aspects, the first antigen is a CD3 antigen.

In certain aspects. (a) the amino acid sequences of domain R, domain A. and domain H are different, the amino acid sequences of domain S, domain B. and domain I are different, the amino acid sequences of domain T, domain F, and domain L are different, and the amino acid sequences of domain U, domain G, and domain M are different; and (b) the interaction between the A domain and the F domain form a first antigen binding site specific for a first antigen, the interaction between the H domain and the L domain form a second antigen binding site specific for a second antigen, and the interaction between the R domain and the T domain form a third antigen binding site specific for a third antigen.

Also described herein are purified ROR antigen binding molecules, the purified ROR antigen binding molecules comprising any of the ROR antigen binding molecule described herein. In certain aspects, the purified ROR antigen binding molecules are purified by a purification method comprising a CH1 affinity purification step. In certain aspects, the purification method is a single-step purification method.

Also described herein are pharmaceutical compositions comprising any of the ROR antigen binding molecules described herein and a pharmaceutically acceptable diluent.

Also described herein are methods for treating a subject with cancer, the methods comprising administering a therapeutically effective amount of any of the pharmaceutical compositions described herein. In certain aspects, the cancer is selected from the group consisting of: pancreatic cancer, ovarian cancer, breast cancer, lung cancer, gastric cancer, melanoma. Ewing sarcoma, chronic lymphocytic leukemia, mantle cell lymphoma, B-ALL, hematological cancer, prostate cancer, colon cancer, renal cancer, and uterine cancer.

5. BRIEF DESCRIPTION OF THE DRAWINGS

FIG. 1 shows an alignment of the CH3-CH3 IgG1 dimer pair with CH1-$C_L$. The quaternary structures align with an RMSD of ~1.6 Å$^2$.

FIG. 2 presents schematic architectures, with respective naming conventions, for various binding molecules (also called antibody constructs) described herein.

FIG. 3 presents a higher resolution schematic of polypeptide chains and their domains, with respective naming conventions, for the bivalent 1×1 antibody constructs described herein.

FIG. 4 shows the architecture of an exemplary bivalent, monospecific, construct.

FIG. 5 shows data from a biolayer interferometry (BLI) experiment, described in Example 1, in which a bivalent monospecific binding molecule having the architecture illustrated in FIG. 4 [polypeptide 1: VL-CH3(Knob)-CH2-CH3/ polypeptide 2: VH-CH3(Hole)] was assayed. The antigen binding site was specific for TNFα. The BLI response from binding molecule immobilization and TNFα binding to the immobilized construct demonstrates robust, specific, bivalent binding to the antigen. The data are consistent with a molecule having a high percentage of intended pairing of polypeptide 1 and polypeptide 2.

FIG. 6 illustrates features of an exemplary bivalent 1×1 bispecific binding molecule, "BC1".

FIG. 7A shows size exclusion chromatography (SEC) analysis of "BC1", demonstrating that a single-step CH1 affinity purification step (CaptureSelect™ CH1 affinity resin) yields a single, monodisperse peak via gel filtration in which >98% is unaggregated bivalent protein. FIG. 7B shows comparative literature data of SEC analysis of a CrossMab bivalent antibody construct [data from Schaefer et a. (*Proc Natl Acad Sci USA*. 2011 Jul. 5; 108(27):11187-92)].

Figure 10A:
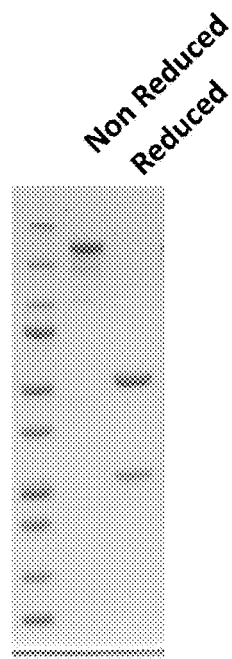
Figure 10B:
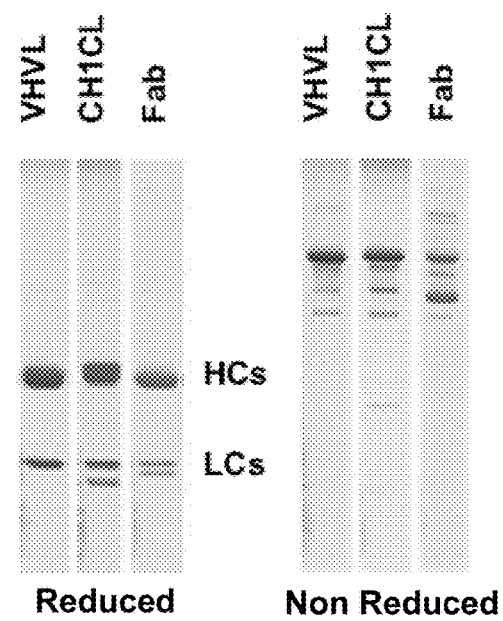

FIGS. 10A and 10B compare SDS-PAGE gels of "BC1" after single-step CH1-affinity purification under both non-reducing and reducing conditions (FIG. 10A) with SDS-PAGE gels of a CrossMab bispecific antibody under non-reducing and reducing conditions as published in the referenced literature (FIG. 10B).

Figure 11A:
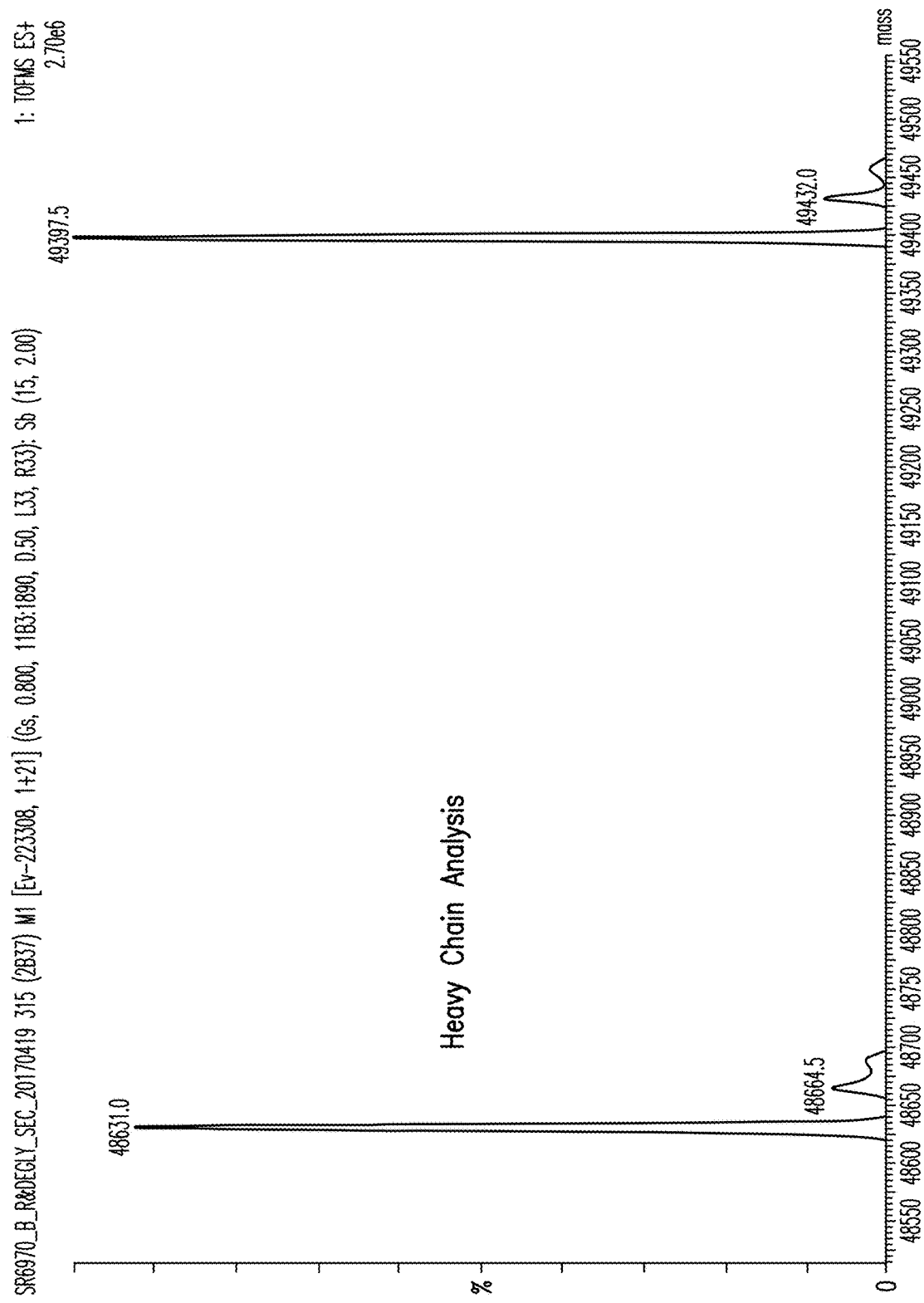

FIGS. 11A and 113 show mass spectrometry analysis of "BC1", demonstrating two distinct heavy chains (FIG. 11A) and two distinct light chains (FIG. 11B) under reducing conditions.

Figure 12:
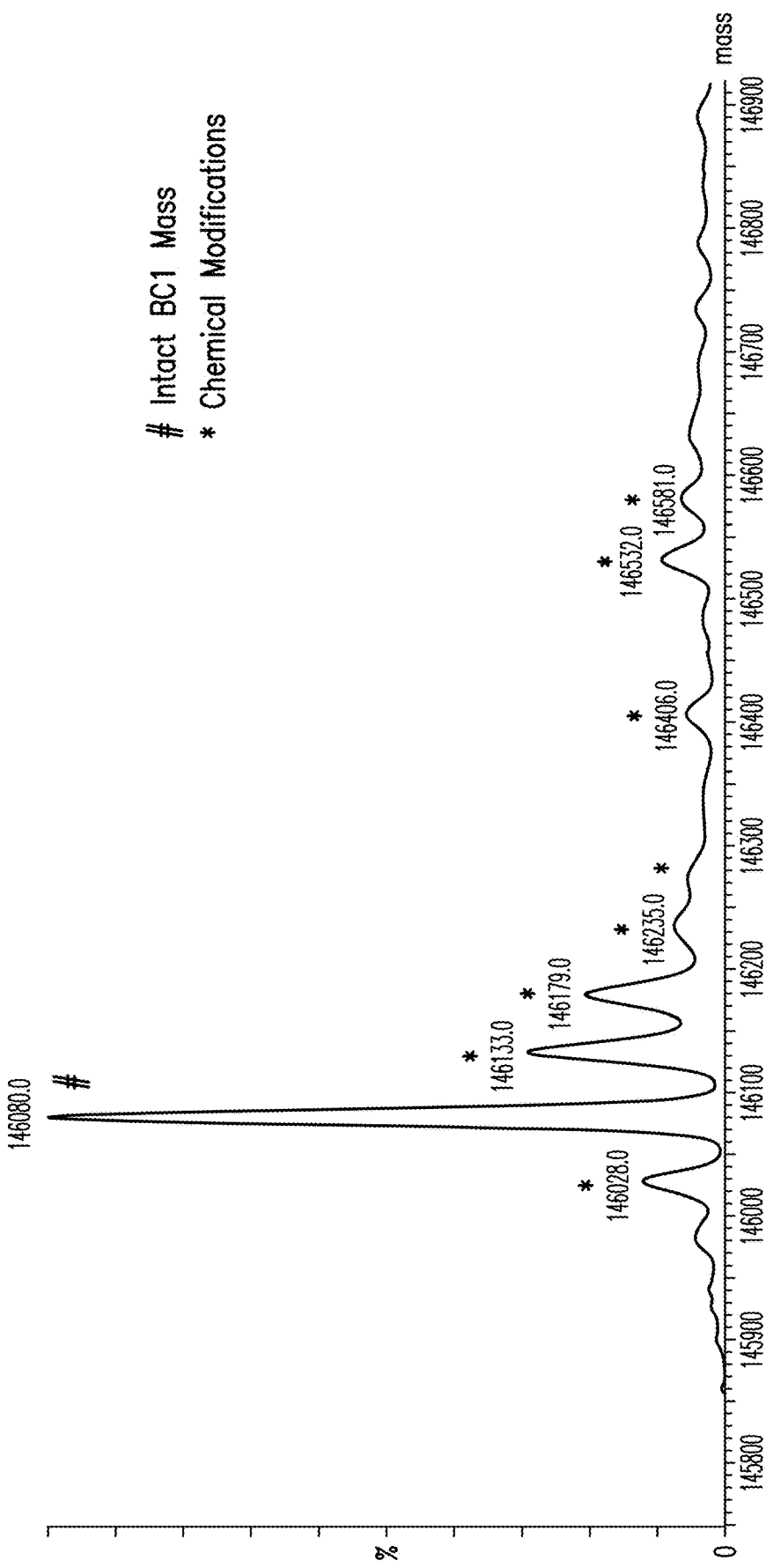

FIG. 12 presents a mass spectrometry analysis of purified "BC1" under non-reducing conditions, confirming the absence of incomplete pairing after purification.

Figure 13:
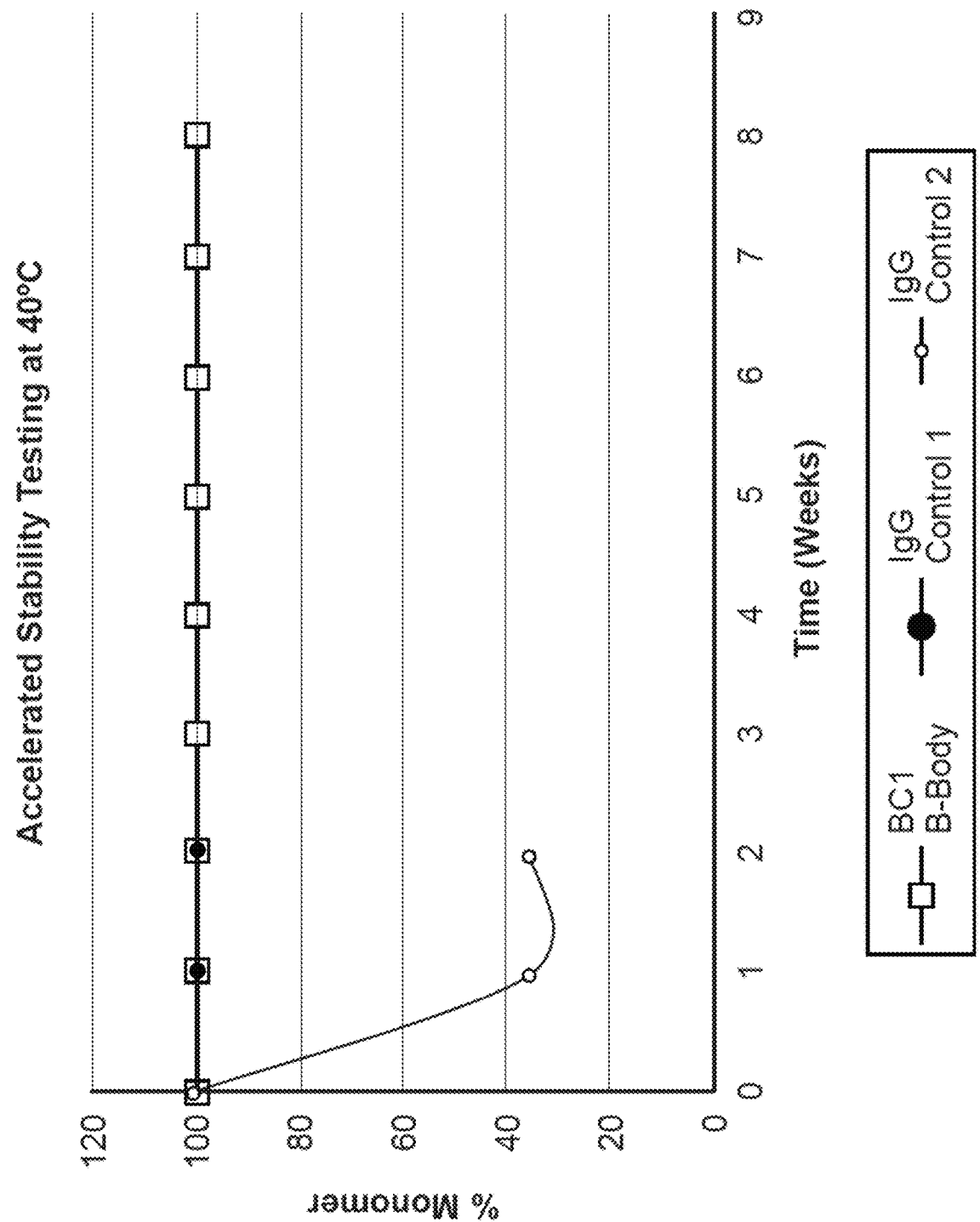

FIG. 13 presents accelerated stability testing data demonstrating stability of "BC1" over 8 weeks at 40° C., compared to two IgG control antibodies.

FIG. 14 illustrates features of an exemplary bivalent lxi bispecific binding molecule, "BC6", further described in Example 3.

Figure 15A:
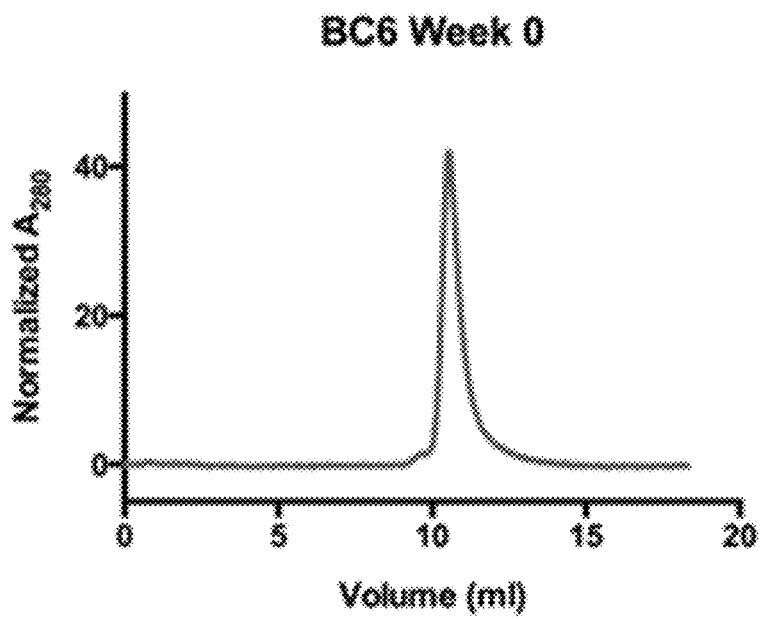
Figure 15B:
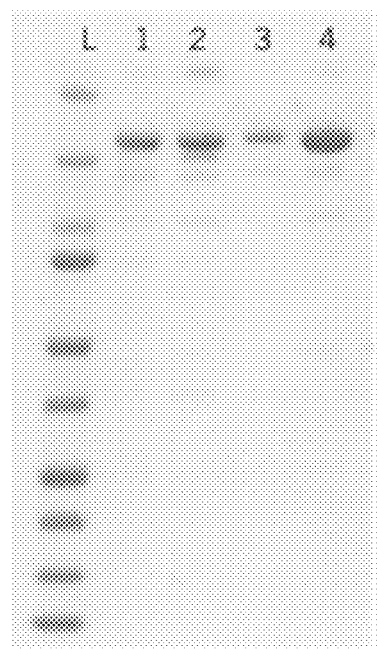

FIG. 15A presents size exclusion chromatography (SEC) analysis of "BC6" following one-step purification using the CaptureSelect™ CH1 affinity resin, demonstrating that the single step CH1 affinity purification yields a single monodisperse peak and the absence of non-covalent aggregates. FIG. 15B shows a SDS-PAGE gel of "BC6" under non-reducing conditions.

Figure 16:
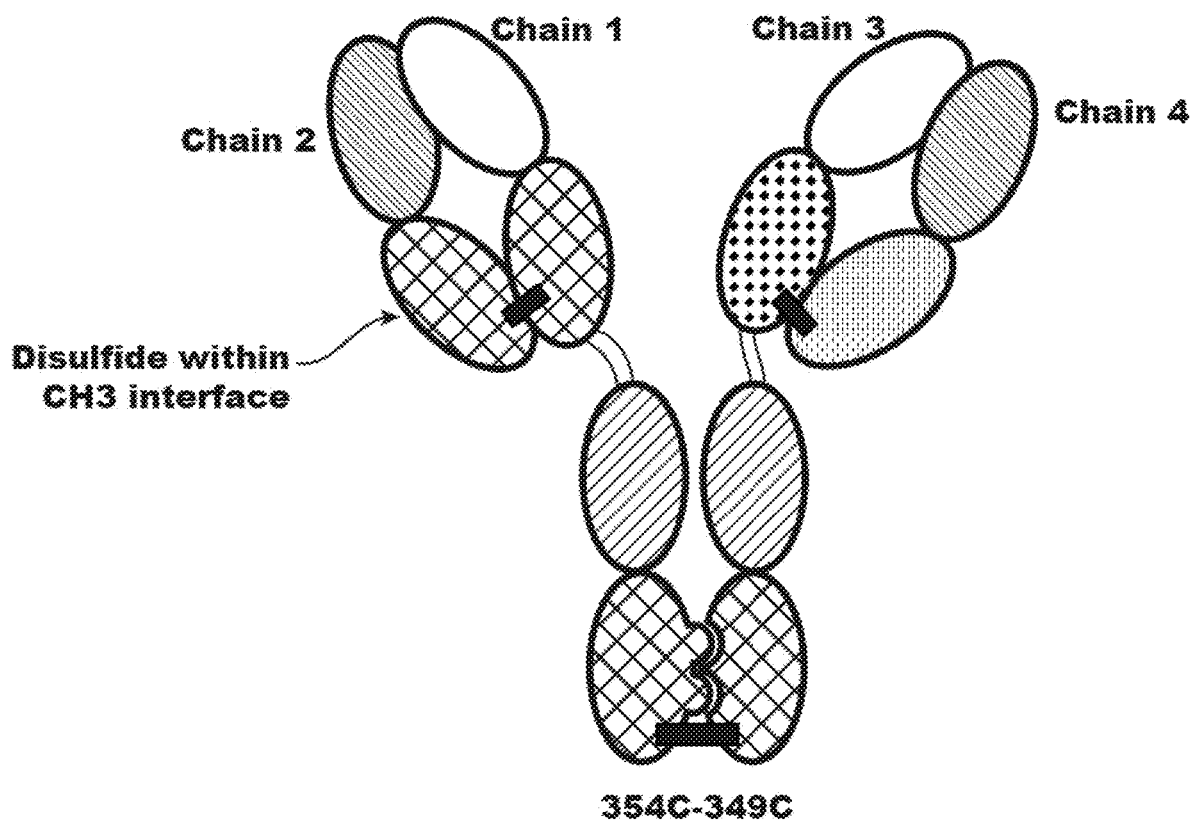

FIG. 16 illustrates features of an exemplary bivalent bispecific binding molecule, "BC28", further described in Example 4.

Figure 17:
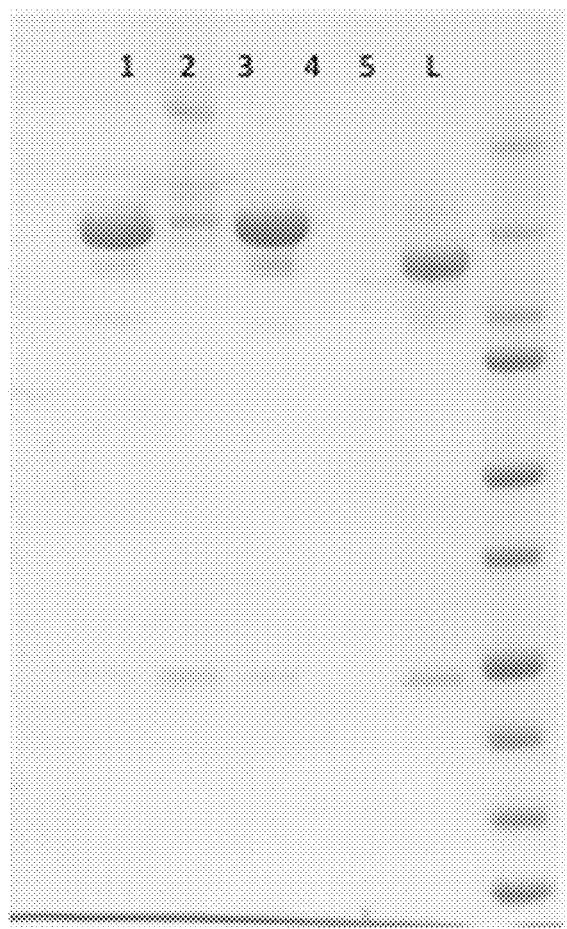

FIG. 17 shows SDS-PAGE analysis under non-reducing conditions following single-step CH1 affinity purification of "BC28", "BC29", "BC30", "BC31", and "BC32".

Figure 18:
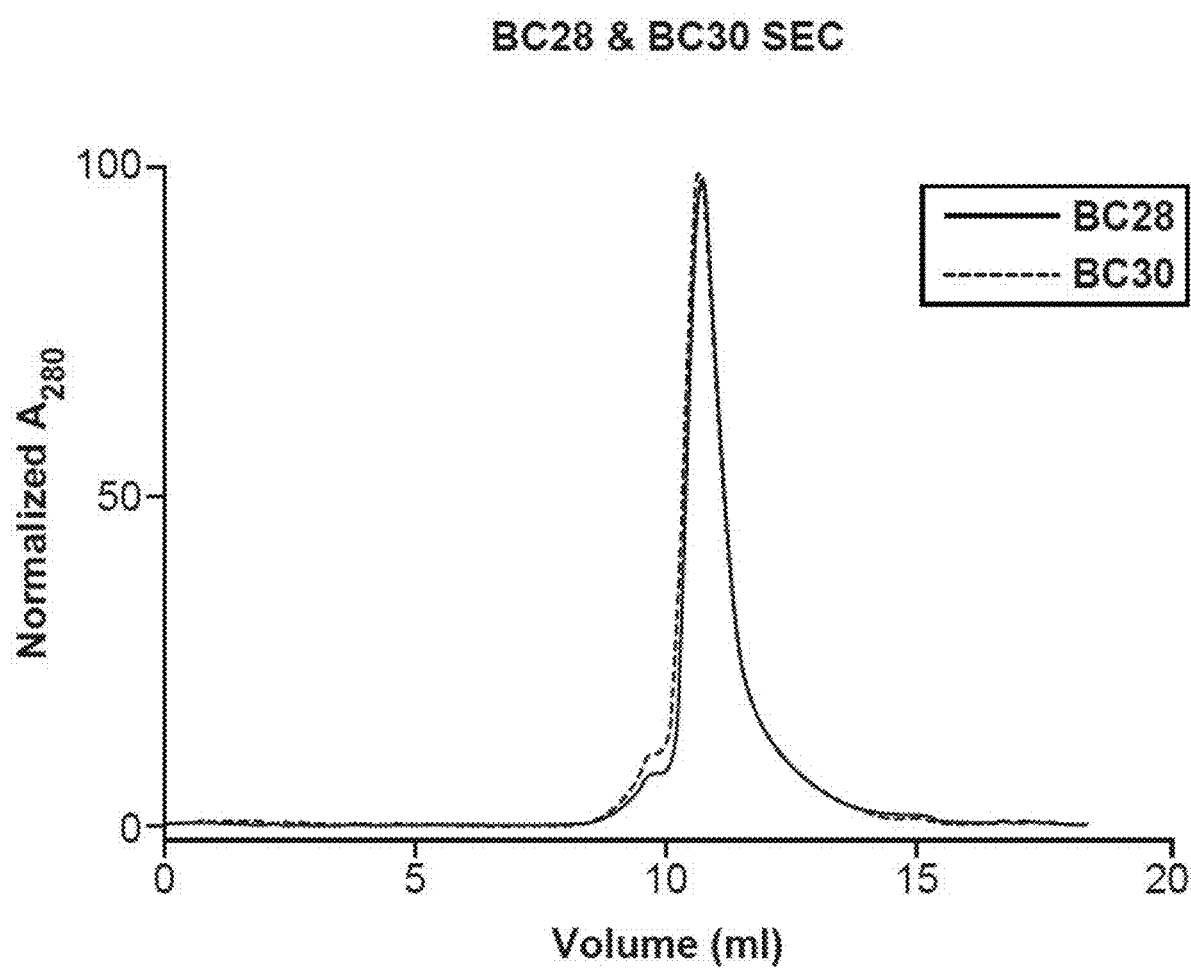

FIG. 18 shows SEC analysis of "BC28" and "BC30", each following one-step purification using the CaptureSelect™ CH1 affinity resin.

Figure 19:
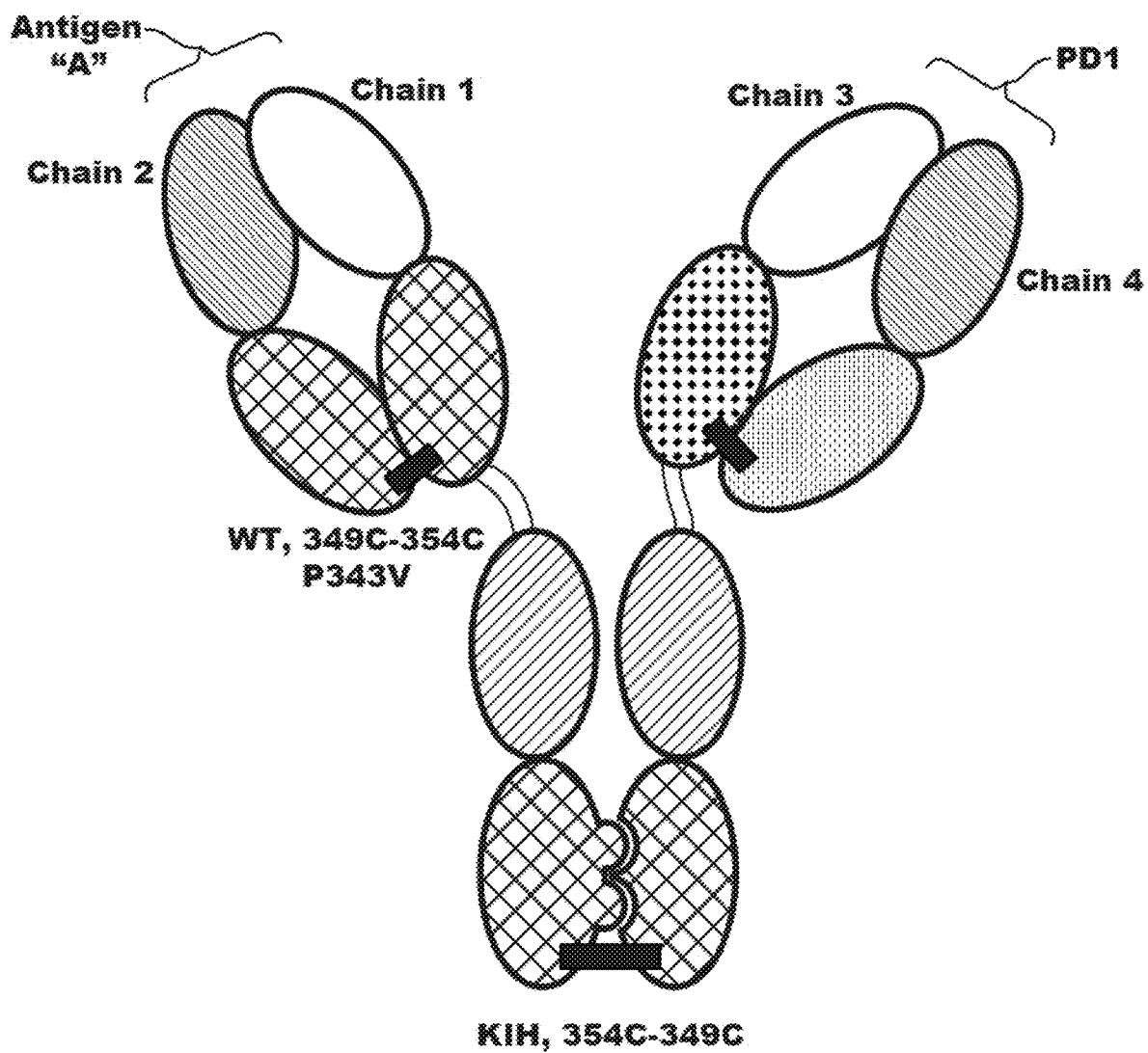

FIG. 19 illustrates features of an exemplary bivalent bispecific binding molecule, "BC44", further described in Example 5.

Figure 20A:
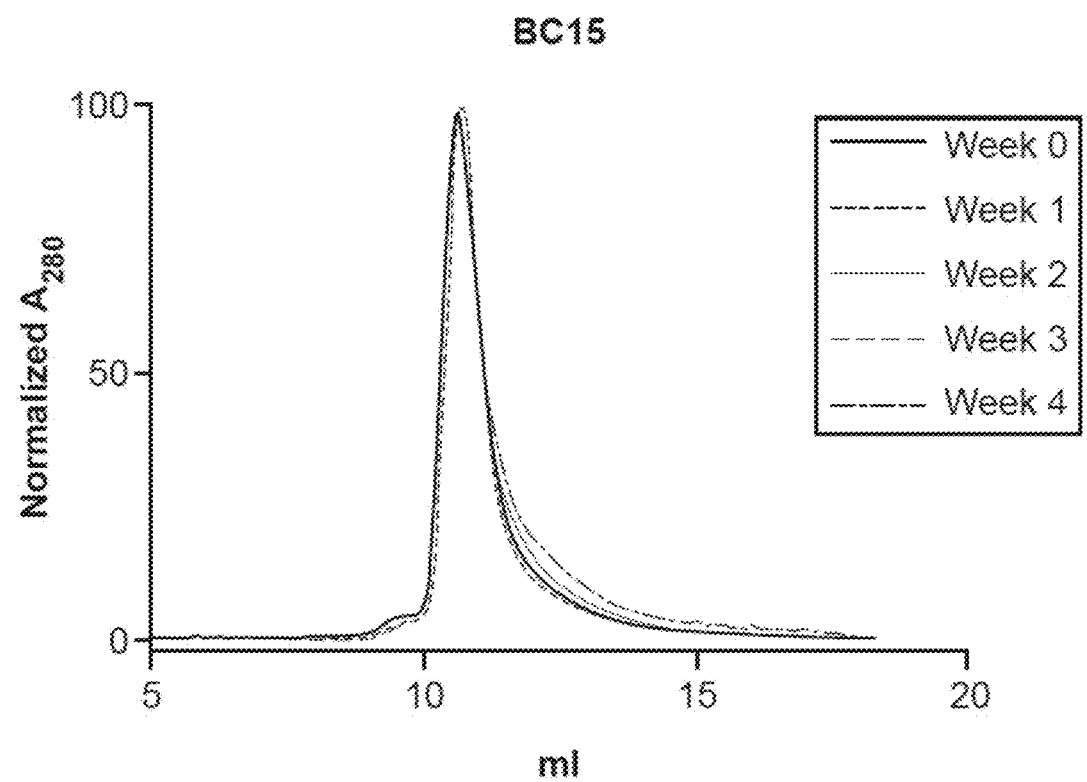
Figure 20B:
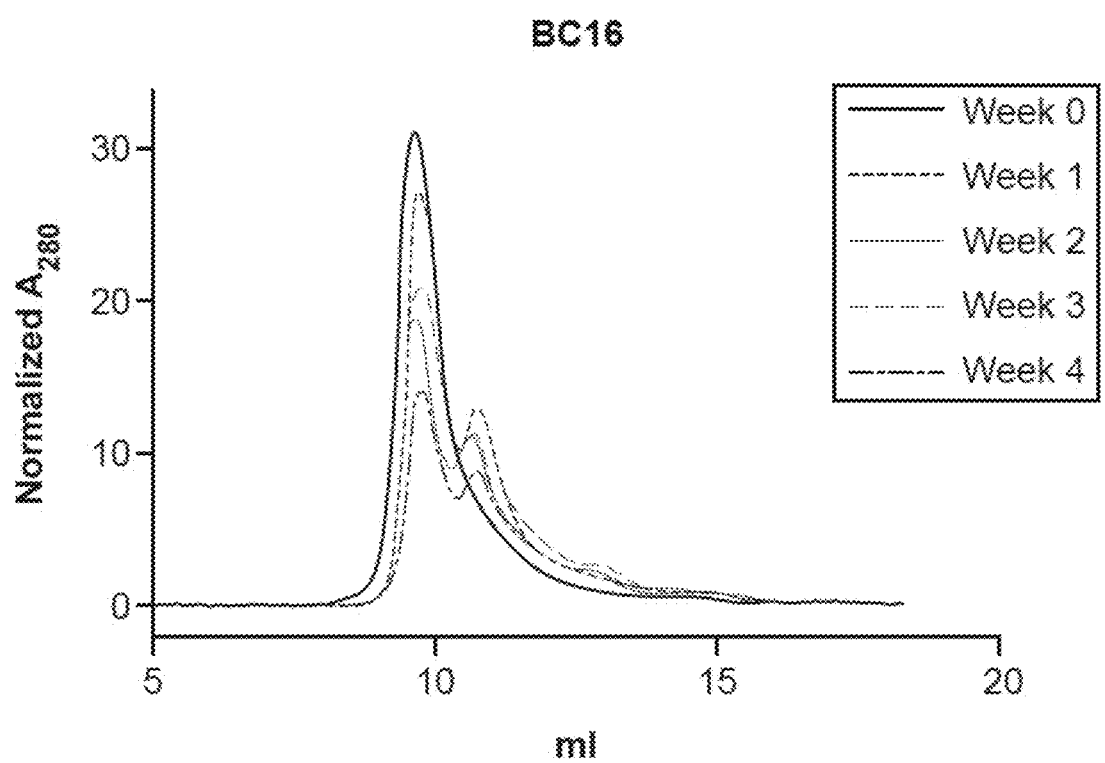

FIGS. 20A and 20B show size exclusion chromatography (SEC) data of two bivalent binding molecules. "BC15" and "BC16", respectively, under accelerated stability testing conditions. "BC15" and "BC16" have different variable region-CH3 junctions.

Figure 21:
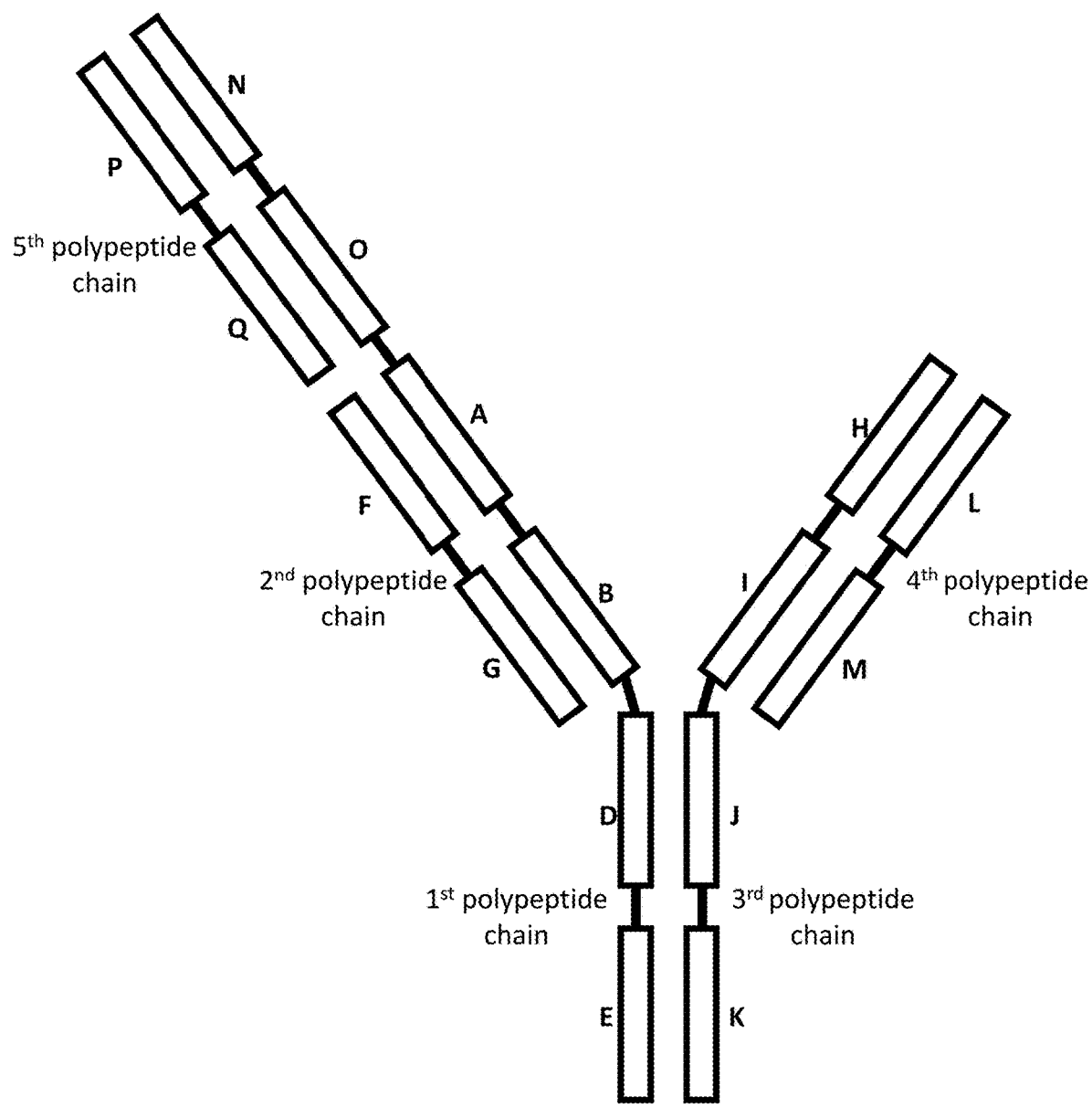

FIG. 21 presents a schematic of five polypeptide chains and their domains, with respective naming conventions, for the trivalent 2×1 antibody constructs described herein, wherein according to the naming convention, chain 5 is named "5$^{th}$ polypeptide chain" in the schematic.

Figure 22:
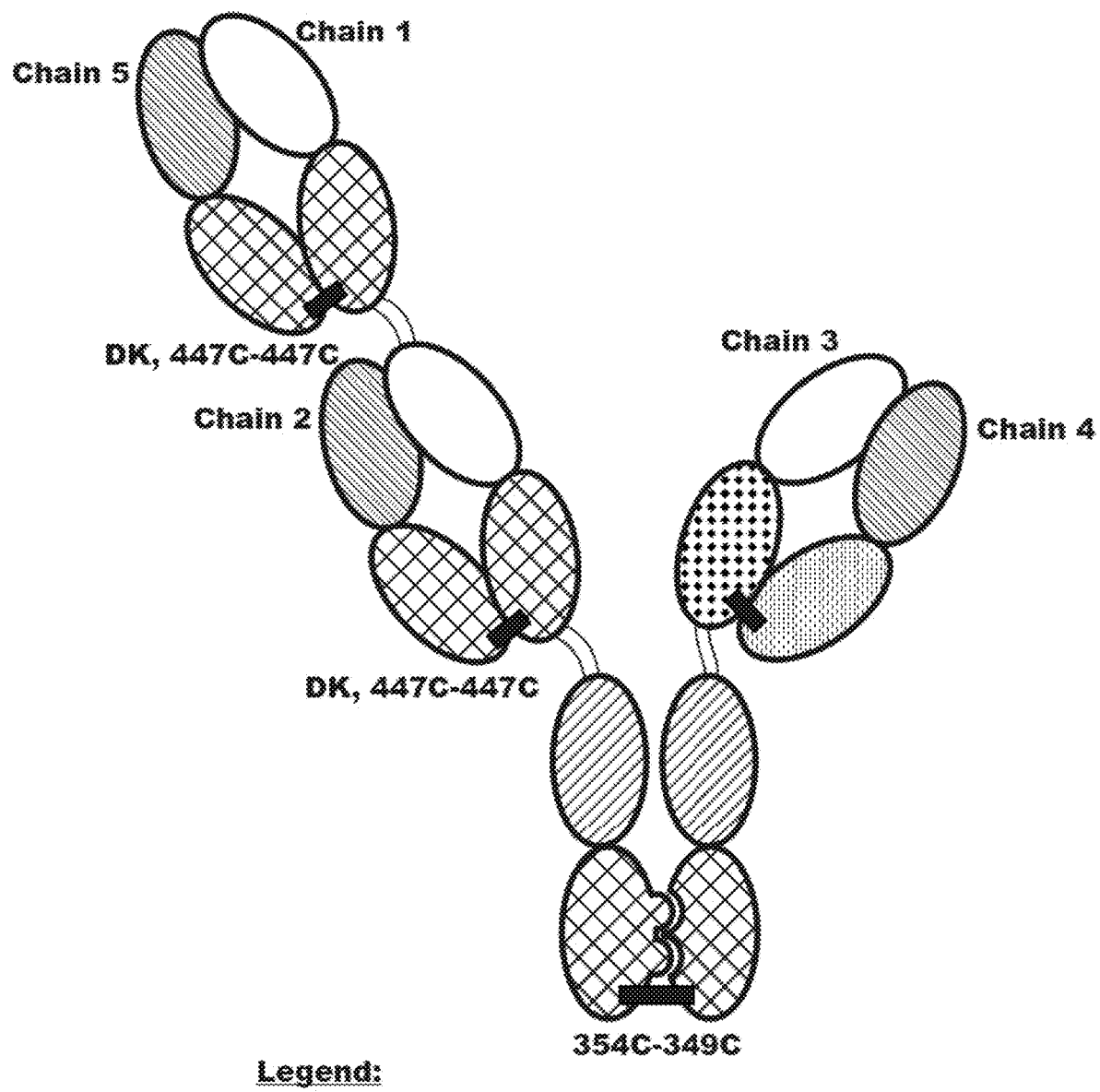

FIG. 22 illustrates features of an exemplary trivalent 2×1 bispecific binding molecule. "BC1-2×1", further described in Example 7.

Figure 23:
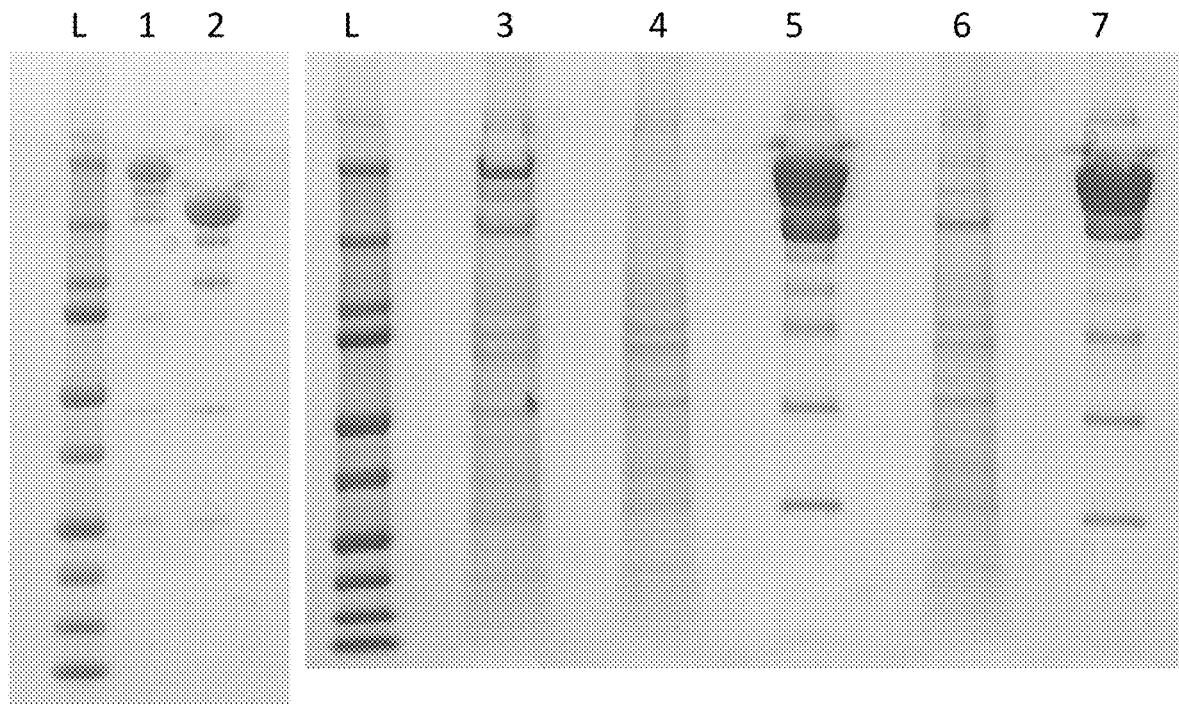

FIG. 23 shows non-reducing SDS-PAGE of "BC1" and "BC1-2×1" protein expressed using the ThermoFisher Expi293 transient transfection system, at various stages of purification.

Figure 24:
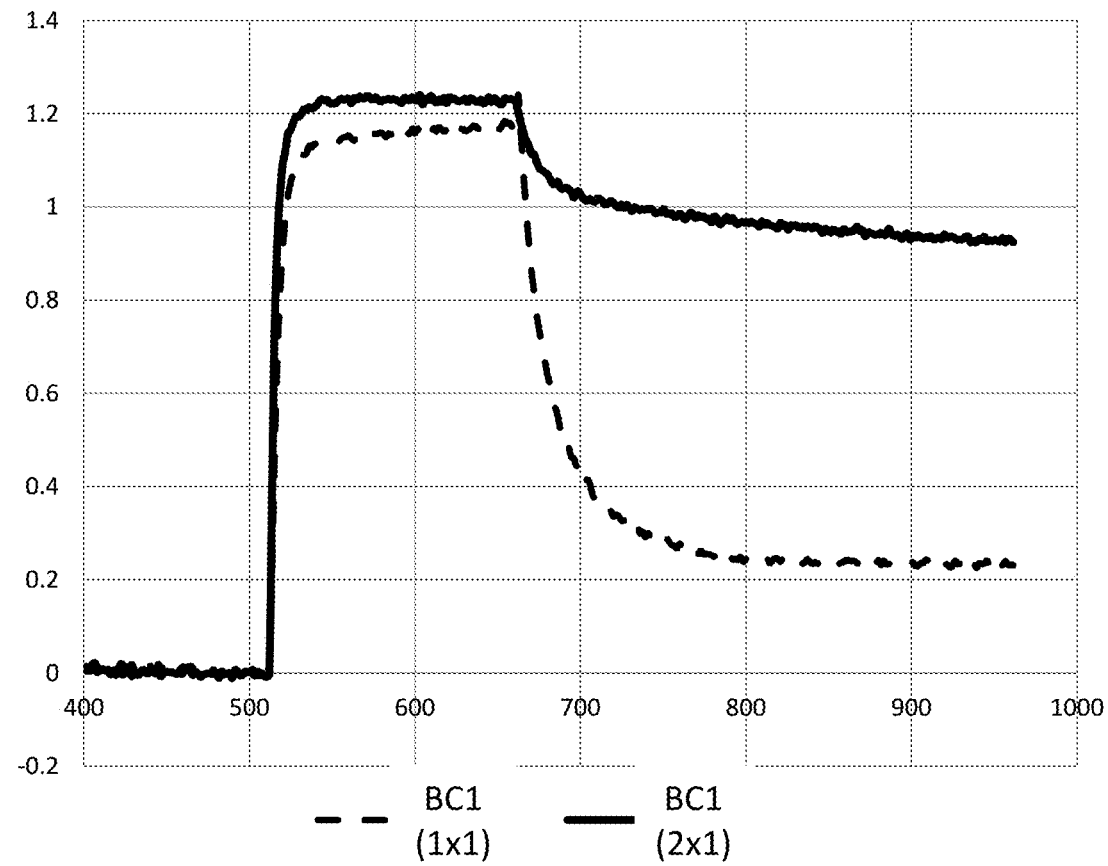

FIG. 24 compares the avidity of the bivalent 1×1 construct "BC1" to the avidity of the trivalent 2×1 construct "BC1-2×1" using an Octet (Pall ForteBio) biolayer interferometry analysis.

Figure 25:
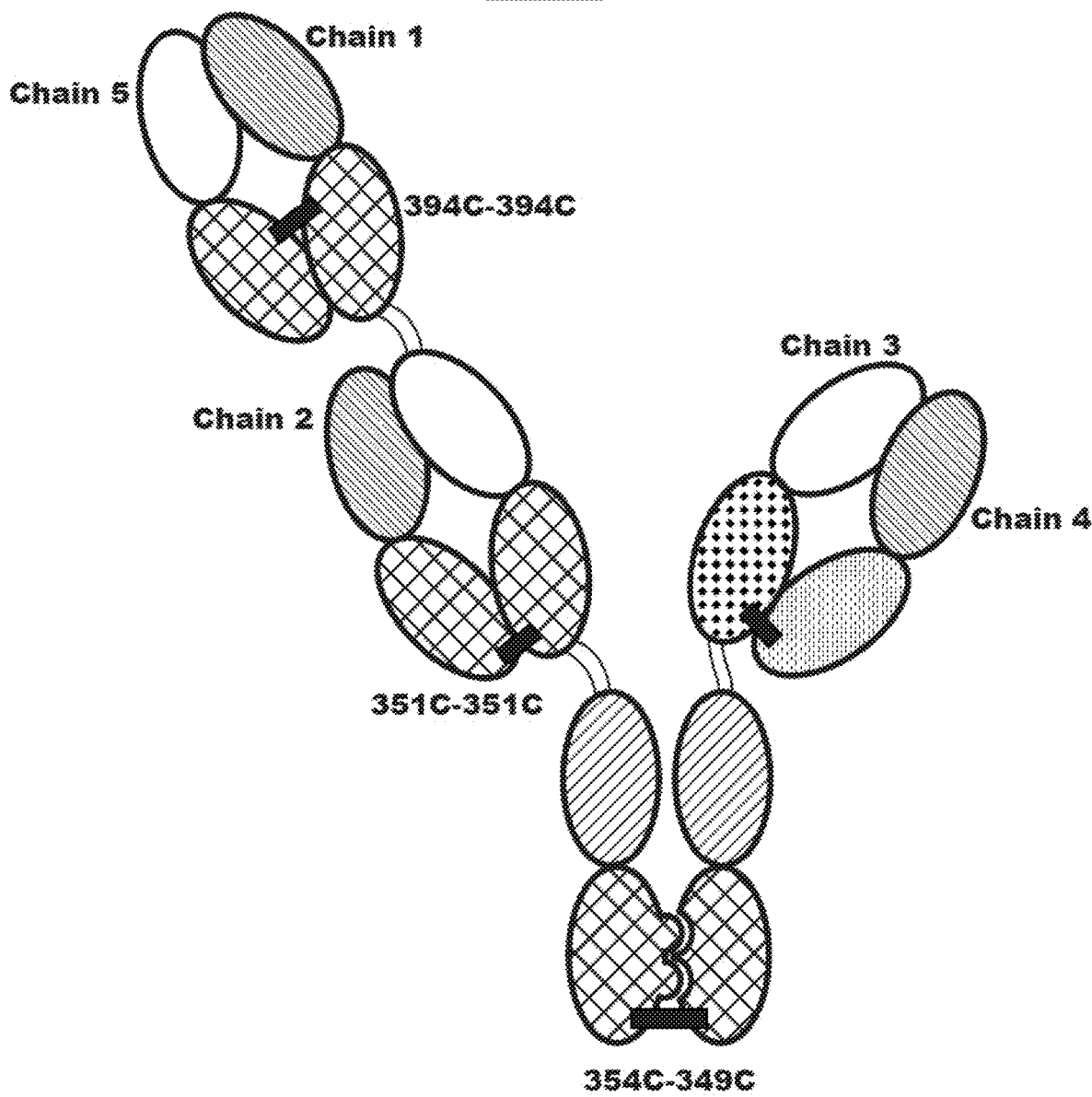

FIG. 25 illustrates salient features of a trivalent 2×1 construct, "TB111."

Figure 26:
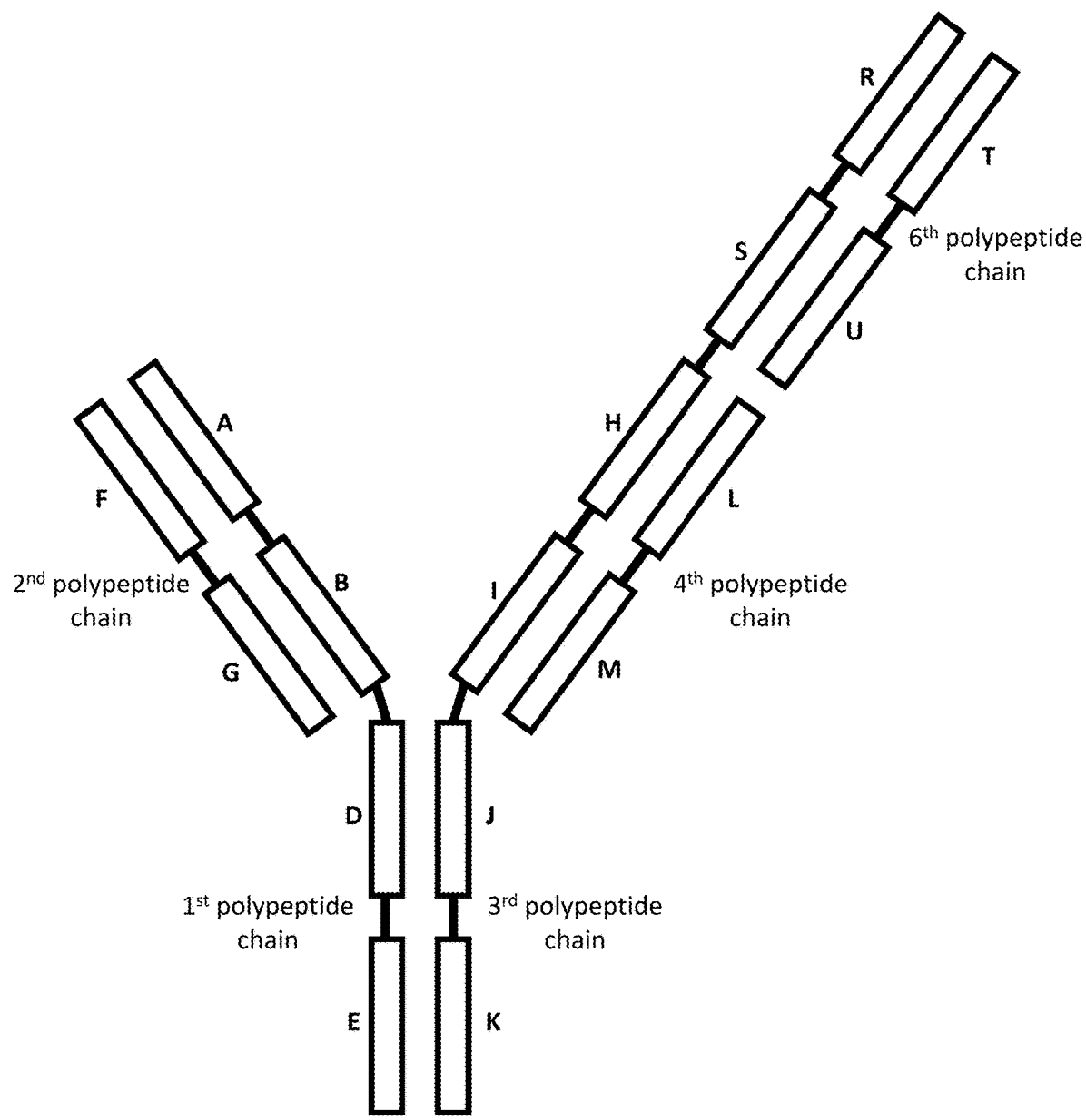

FIG. 26 presents a schematic of five polypeptide chains and their domains, with respective naming conventions, for the trivalent 1×2 antibody constructs described herein, wherein according to the naming convention, chain 5 is named "6$^{th}$ polypeptide chain" in the schematic.

Figure 27:
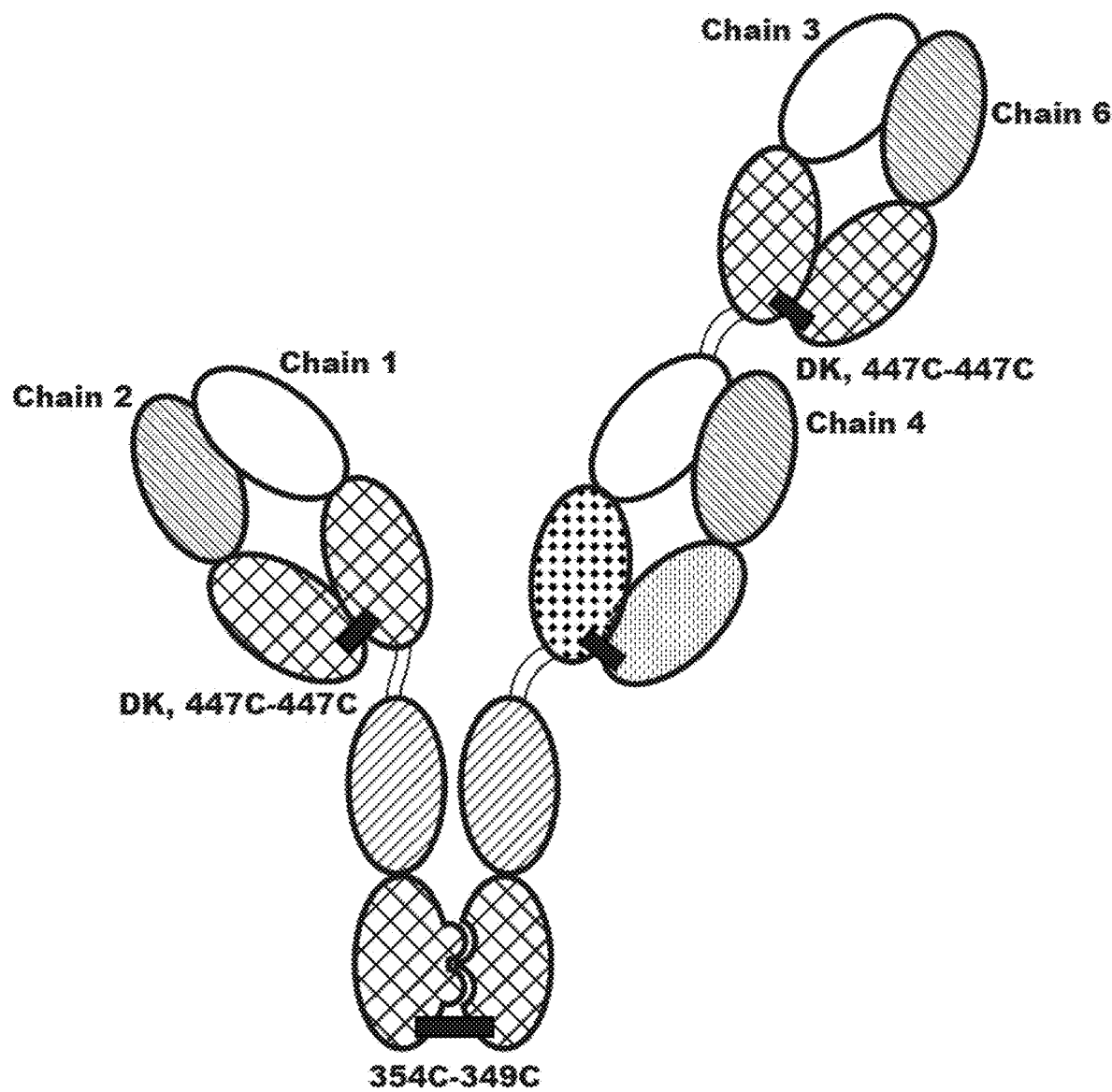

FIG. 27 illustrates features of an exemplary trivalent 1×2 construct "CTLA4-4× Nivo×CTLA4-4", further described in Example 10.

Figure 28:
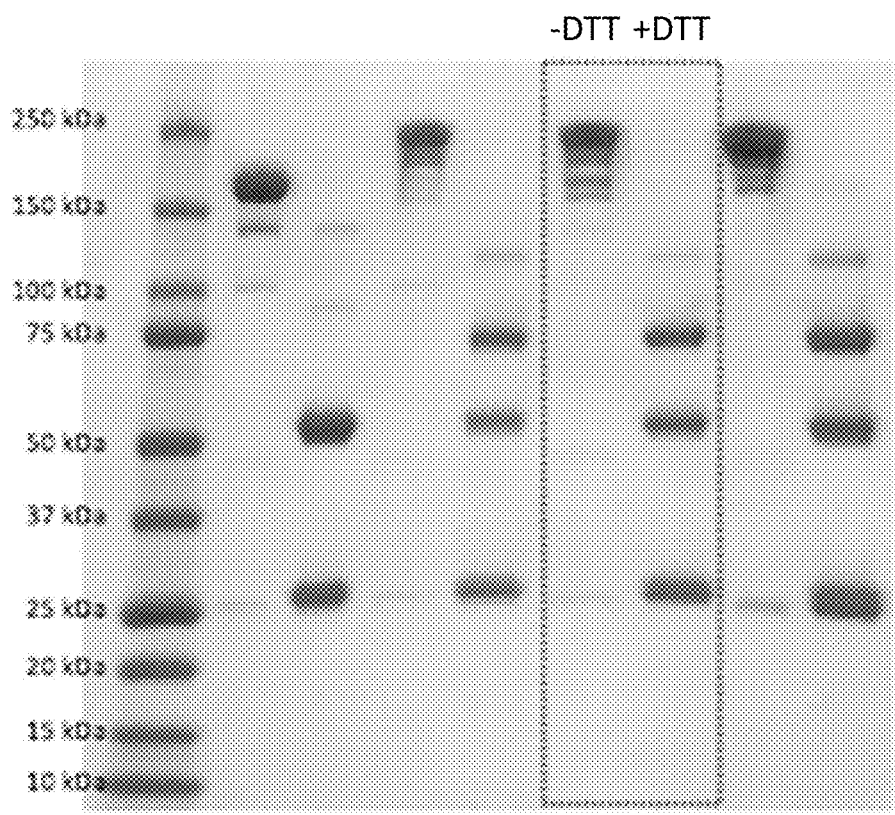

FIG. 28 is a SDS-PAGE gel in which the lanes showing the trivalent 1×2 construct "CTLA4-4×Nivo×CTLA4-4" construct under non-reducing ("−DTT") and reducing ("+DTT") conditions have been boxed.

Figure 29:
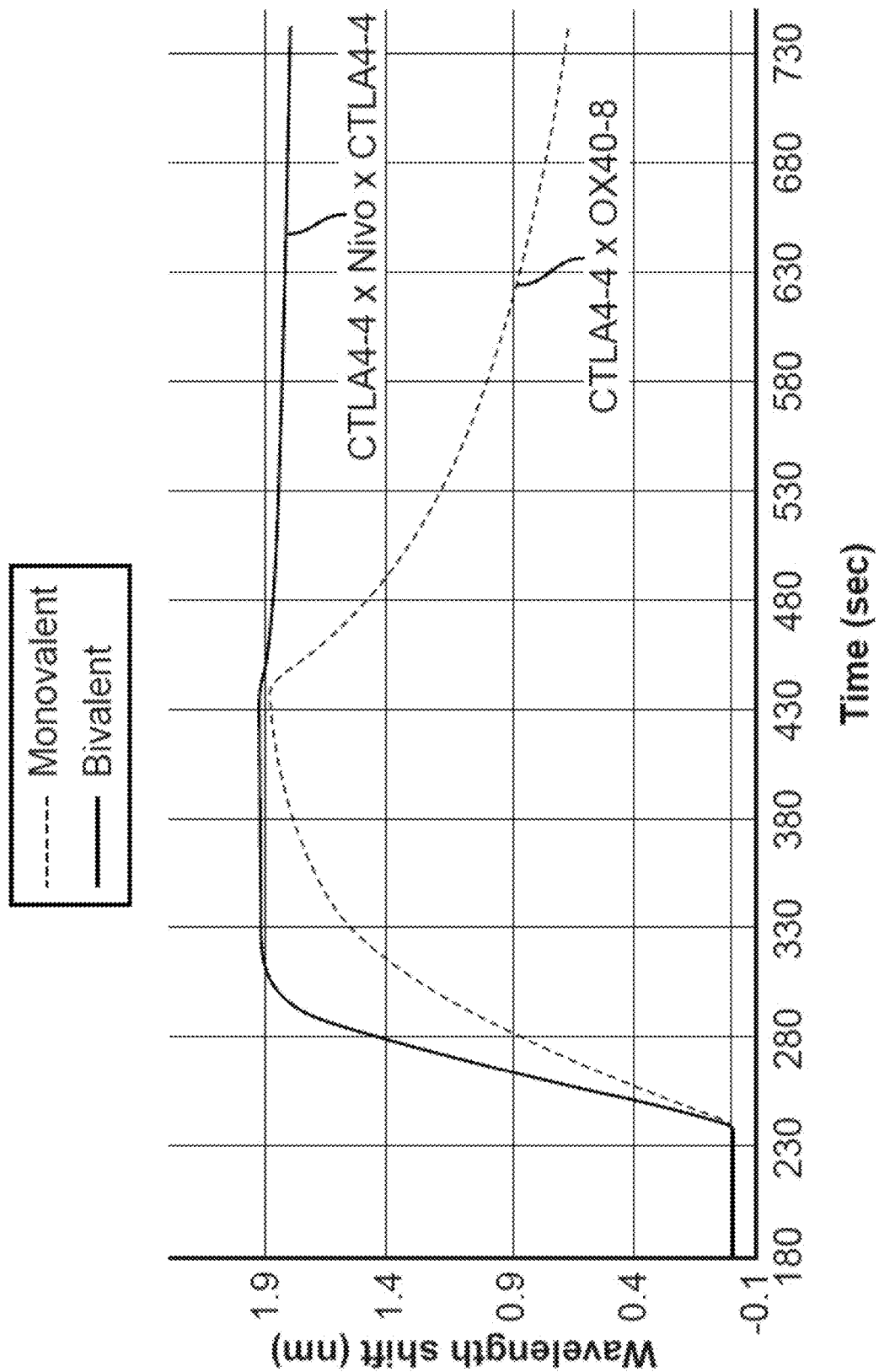

FIG. 29 shows a comparison of antigen binding between two antibodies; bivalent 1×1 construct "CTLA44×OX40-8" and the trivalent 1×2 construct "CTLA44×Nivo×CTLA4-4." "CTLA4-4×OX40-8" binds to CTLA4 monovalently, while "CTLA4-4×Nivo×CTLA4-4" binds to CTLA4 bivalently.

Figure 30:
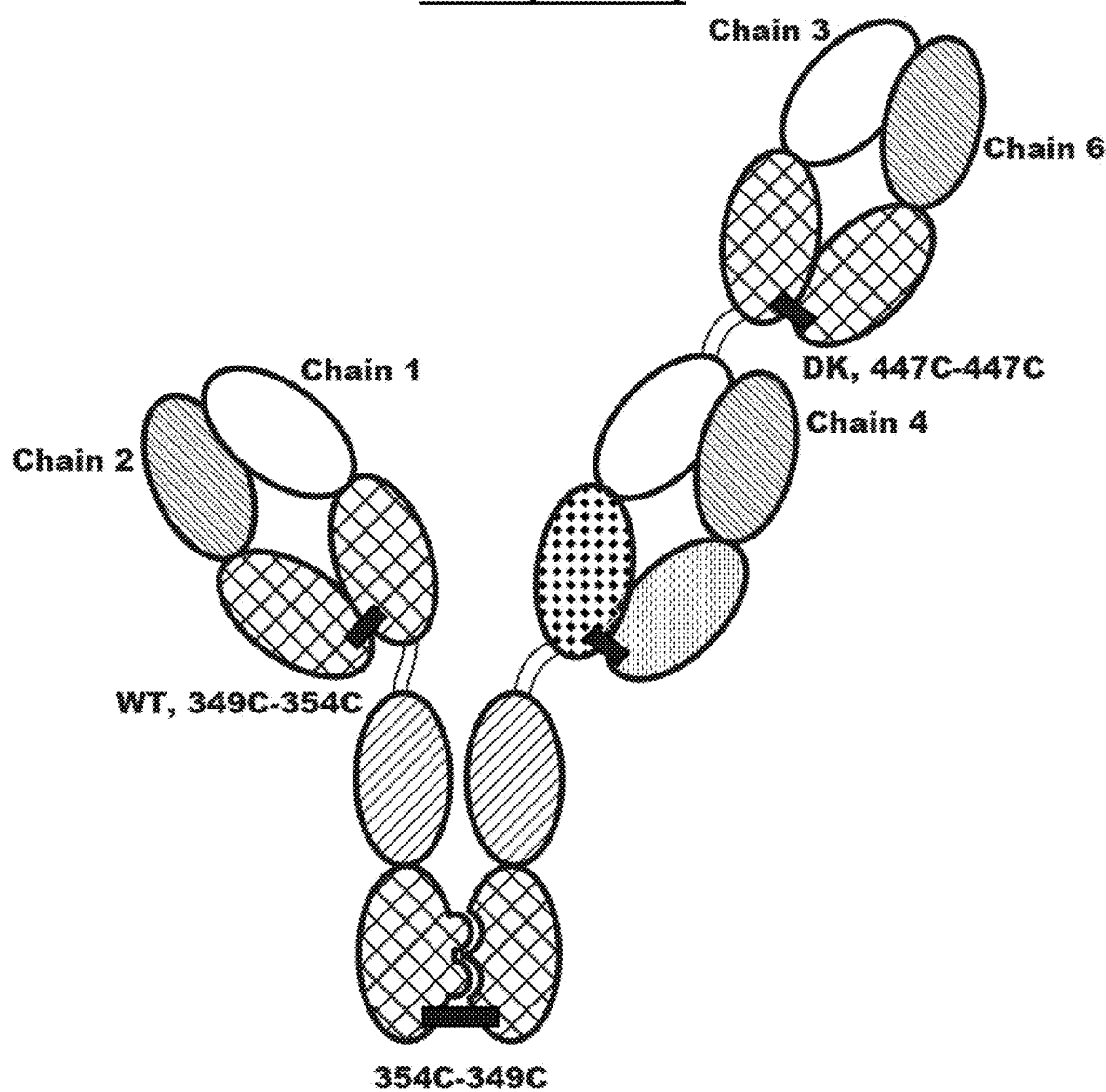

FIG. 30 illustrates features of an exemplary trivalent 1×2 trispecific construct, "BC28-1×1×1a", further described in Example 11.

Figure 31:
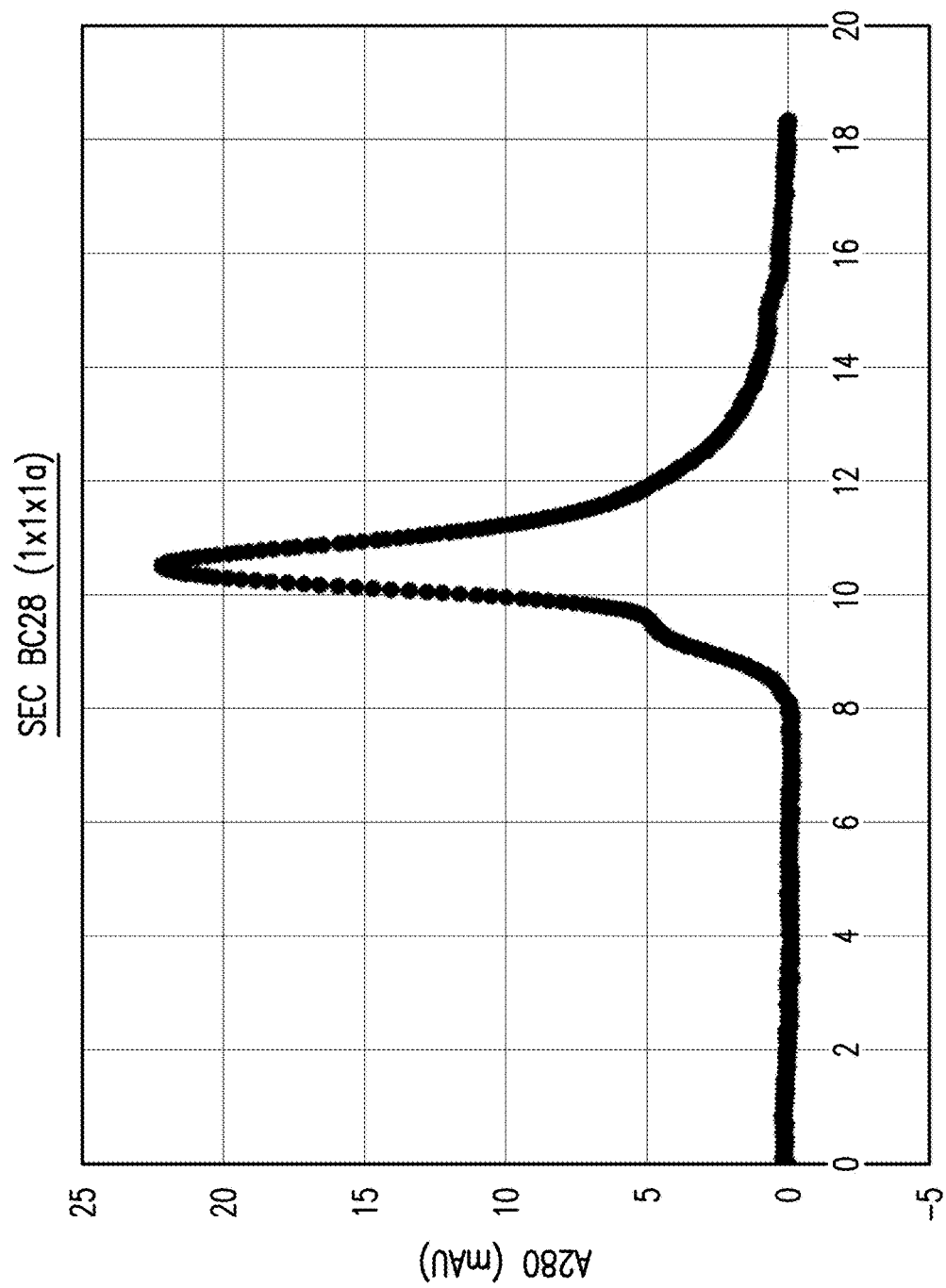

FIG. 31 shows size exclusion chromatography of "BC28-1×1×1a" following transient expression and single step CH1 affinity resin purification, demonstrating a single well-defined peak.

Figure 32:
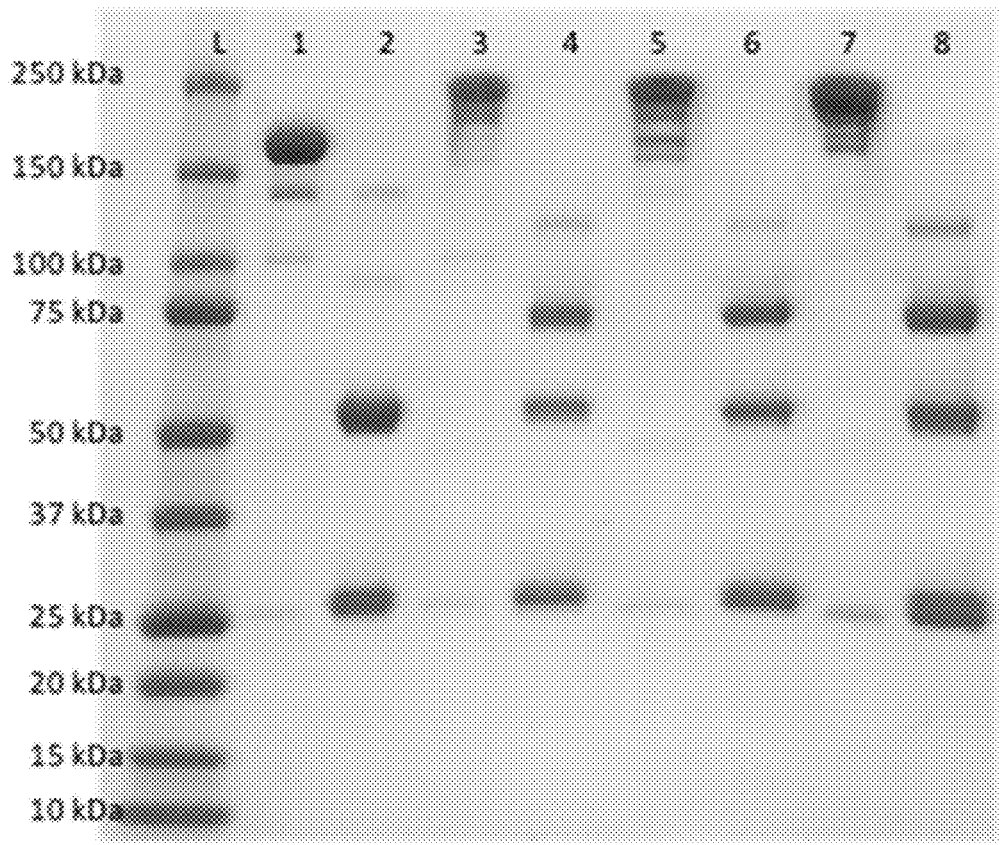

FIG. 32 shows SDS-PAGE results with bivalent and trivalent constructs, each after transient expression and one-step purification using the CaptureSelect™ CH1 affinity resin, under non-reducing and reducing conditions, as further described in Example 12.

Figure 33A:
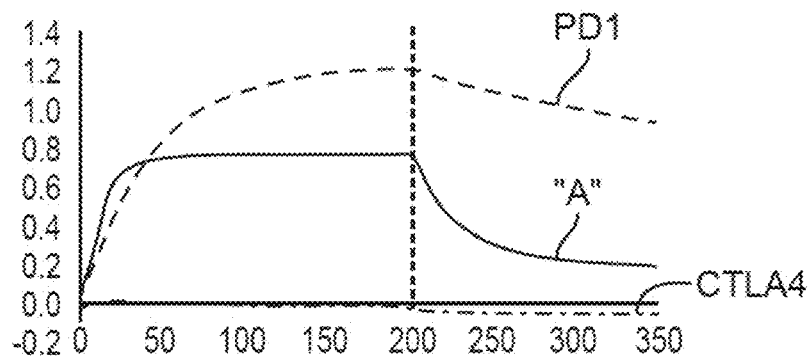
Figure 33B:
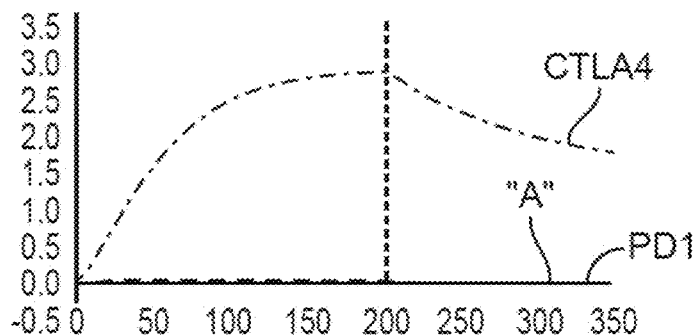
Figure 33C:
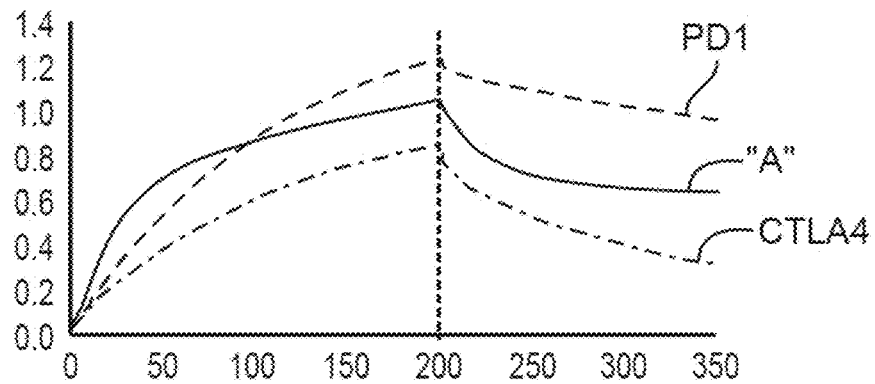

FIGS. 33A-33C show Octet binding analyses to 3 antigens: PD1, Antigen "A", and CTLA4. As further described in Example 13, FIG. 33A shows binding of "BC1" to PD1 and Antigen "A"; FIG. 33B shows binding of a bivalent bispecific construct "CTLA4-4×OX40-8" to CTLA4, Antigen "A", and PD1; FIG. 33C shows binding of trivalent trispecific "BC28-1×1×1a" to PD1, Antigen "A", and CTLA4.

Figure 34:
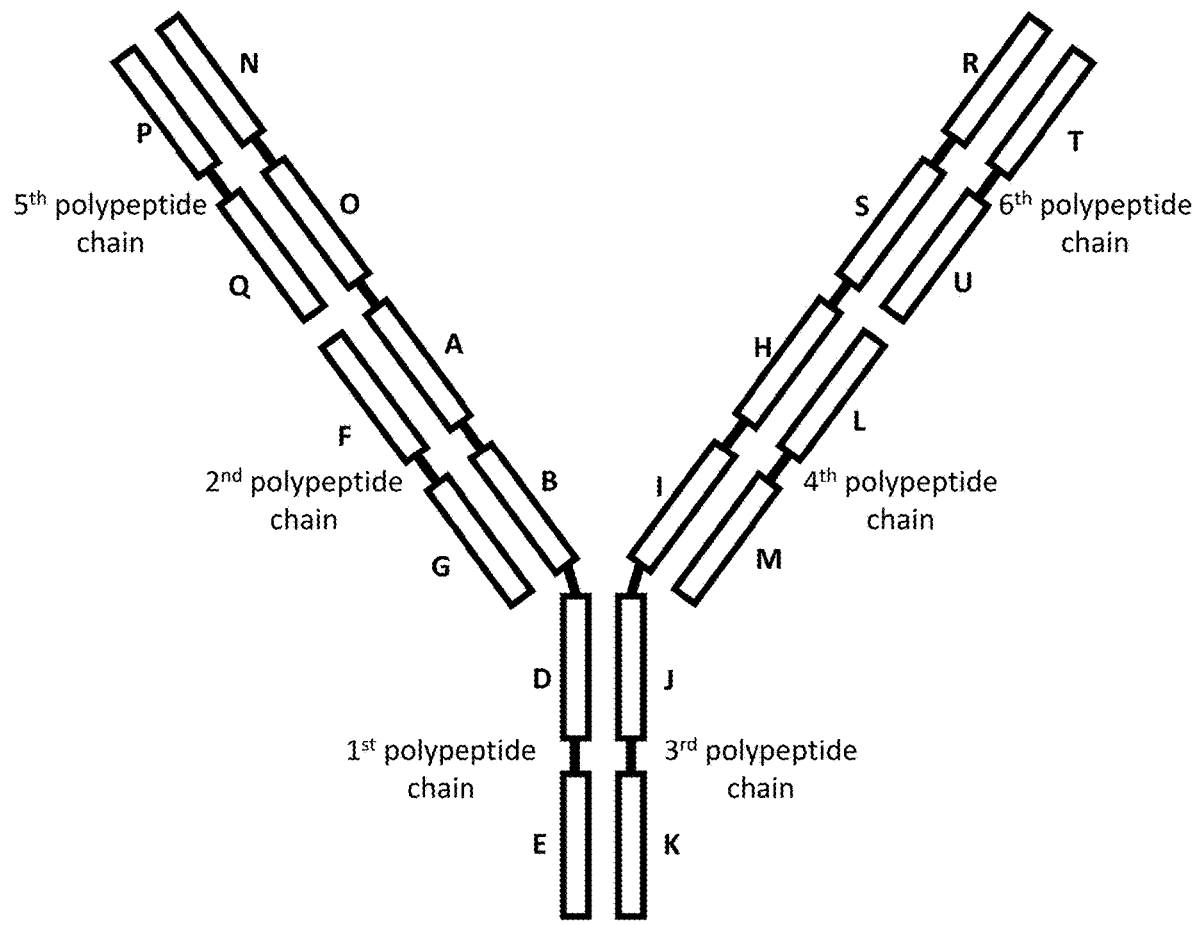

FIG. 34 presents a schematic of six polypeptide chains and their domains, with respective naming conventions, for certain tetravalent 2×2 constructs described herein.

FIG. 35 illustrates certain salient features of the exemplary tetravalent 2×2 construct, "BC22-2×2" further described in Example 14.

Figure 36:
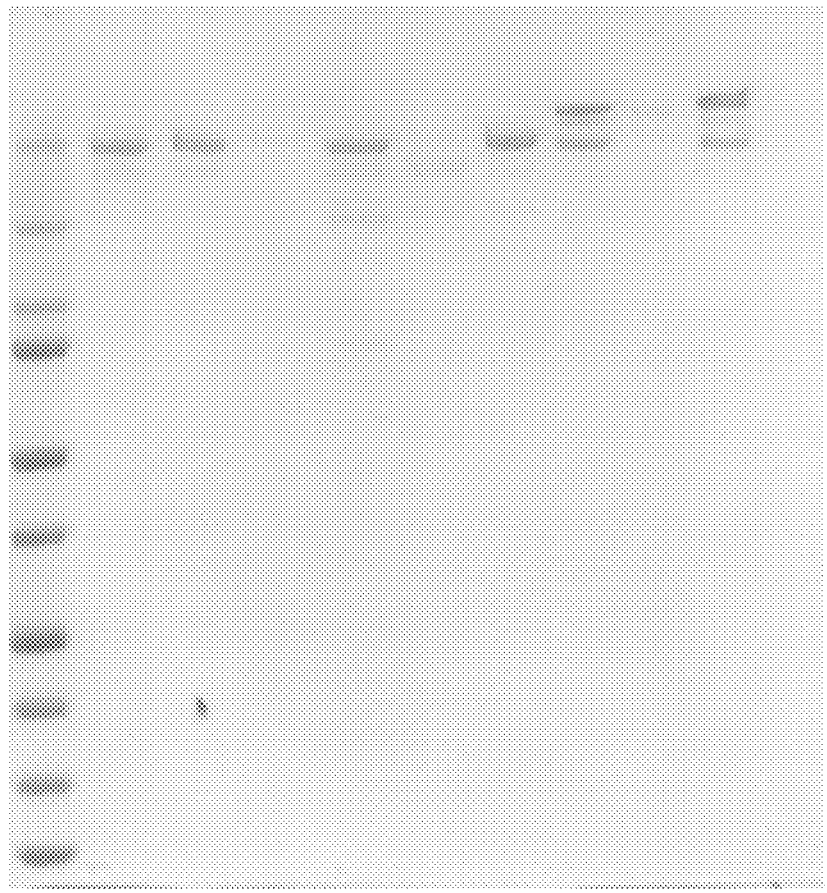

FIG. 36 is a non-reducing SDS-PAGE gel comparing the 2×2 tetravalent "BC22-2×2" construct to a 1×2 trivalent construct "BC12-1×2" and a 2×1 trivalent construct "BC21-2×1" at different stages of purification.

FIG. 37 provides architecture for an exemplary tetravalent 2×2 construct.

Figure 38:
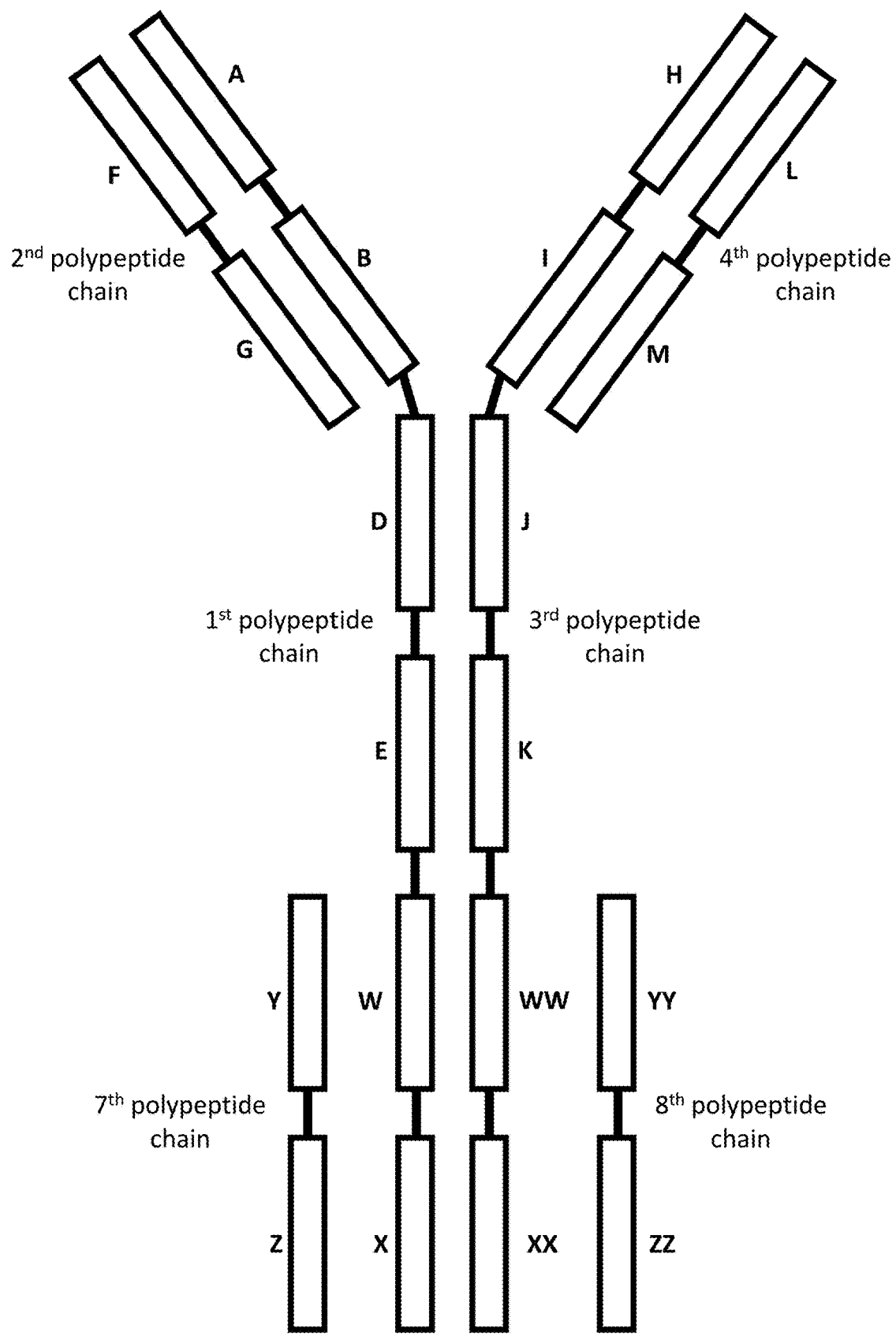

FIG. 38 presents a schematic of six polypeptide chains and their domains, with respective naming conventions, for certain tetravalent constructs described herein, wherein according to the naming convention, chain 5 is named "7$^{th}$ polypeptide chain" and chain 6 is named "8$^{th}$ polypeptide chain" in the schematic.

Figure 39:
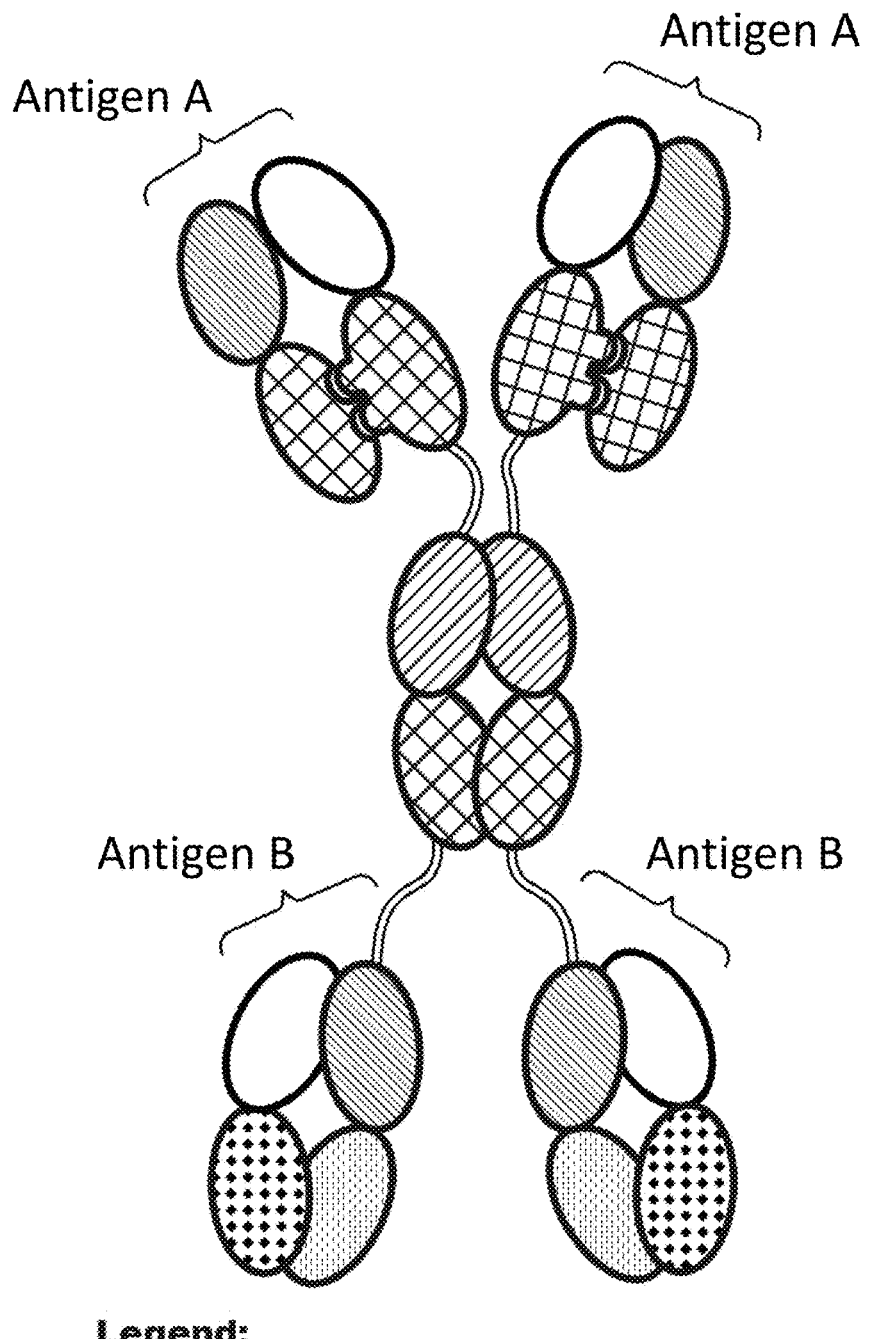

FIG. 39 provides exemplary architecture of a bispecific tetravalent construct.

Figure 40:
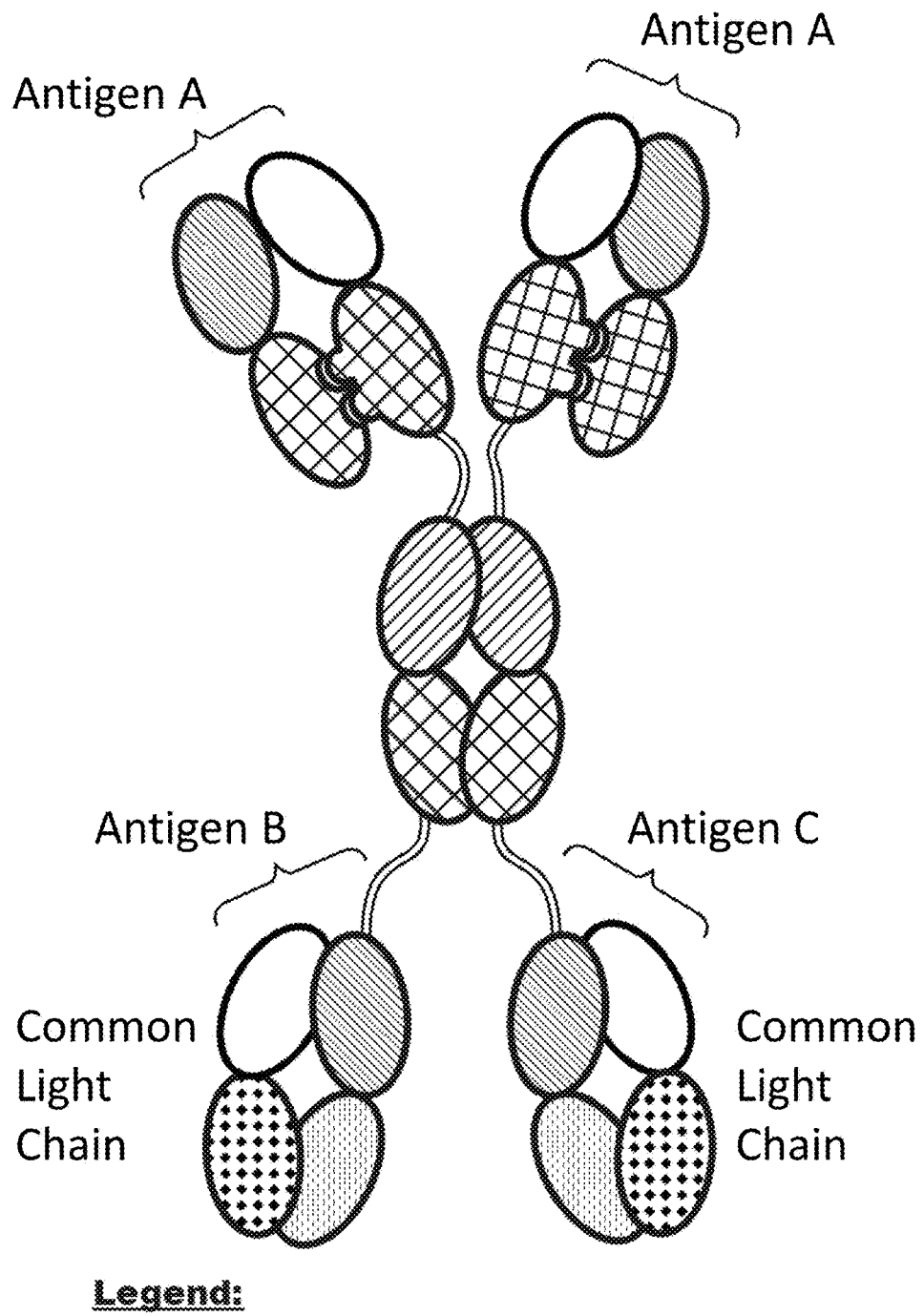

FIG. 40 provides exemplary architecture for a trispecific tetravalent construct utilizing a common light chain strategy.

Figure 41:
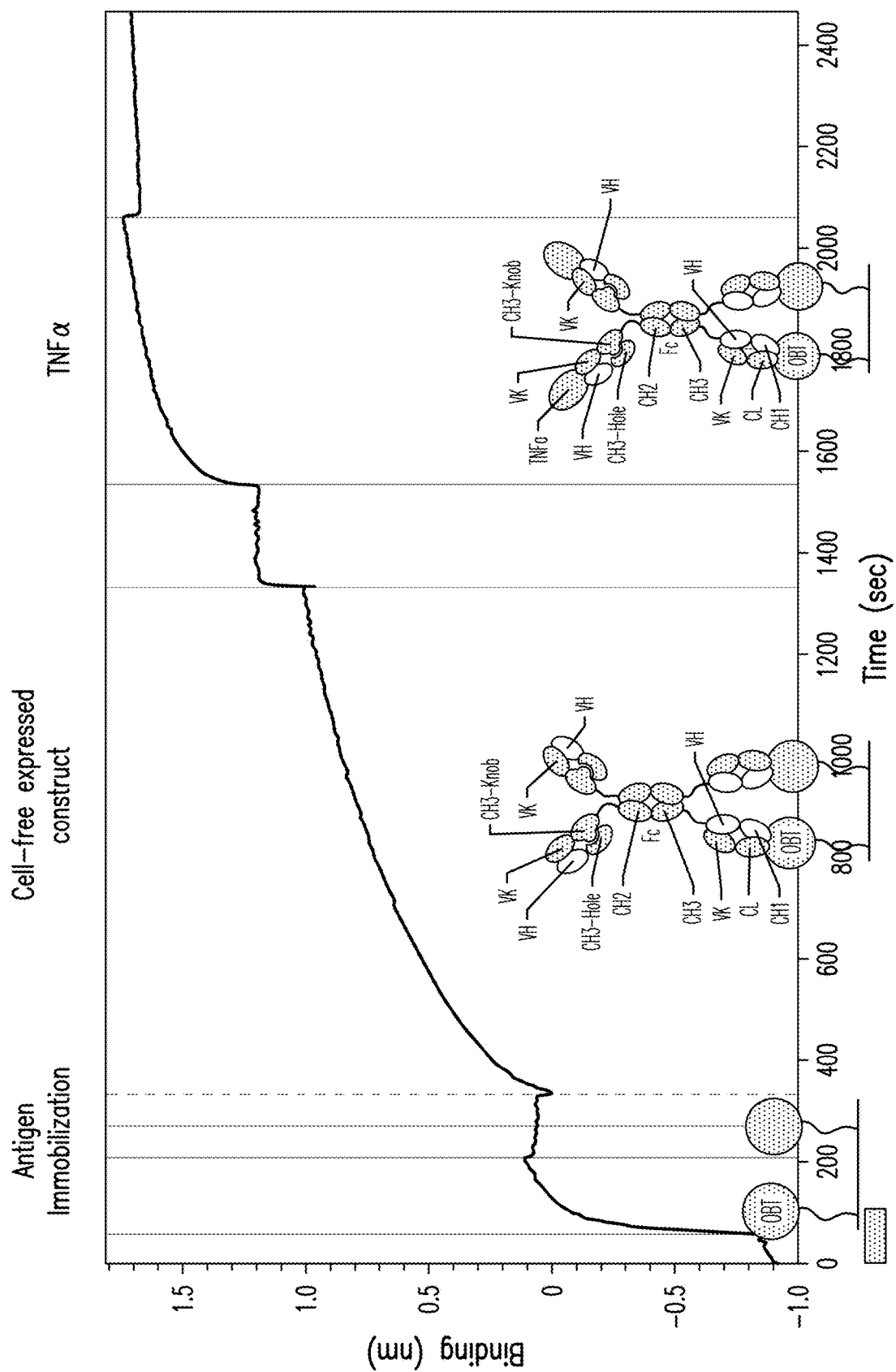

FIG. 41 shows bispecific antigen engagement by the tetravalent construct schematized in FIG. 39, demonstrating that this construct was capable of simultaneous engagement. The biolayer interferometry (BLI) response from B-Body immobilization and TNFα binding to the immobilized construct are consistent with a molecule with a high percentage of intended chain pairing.

Figure 42:
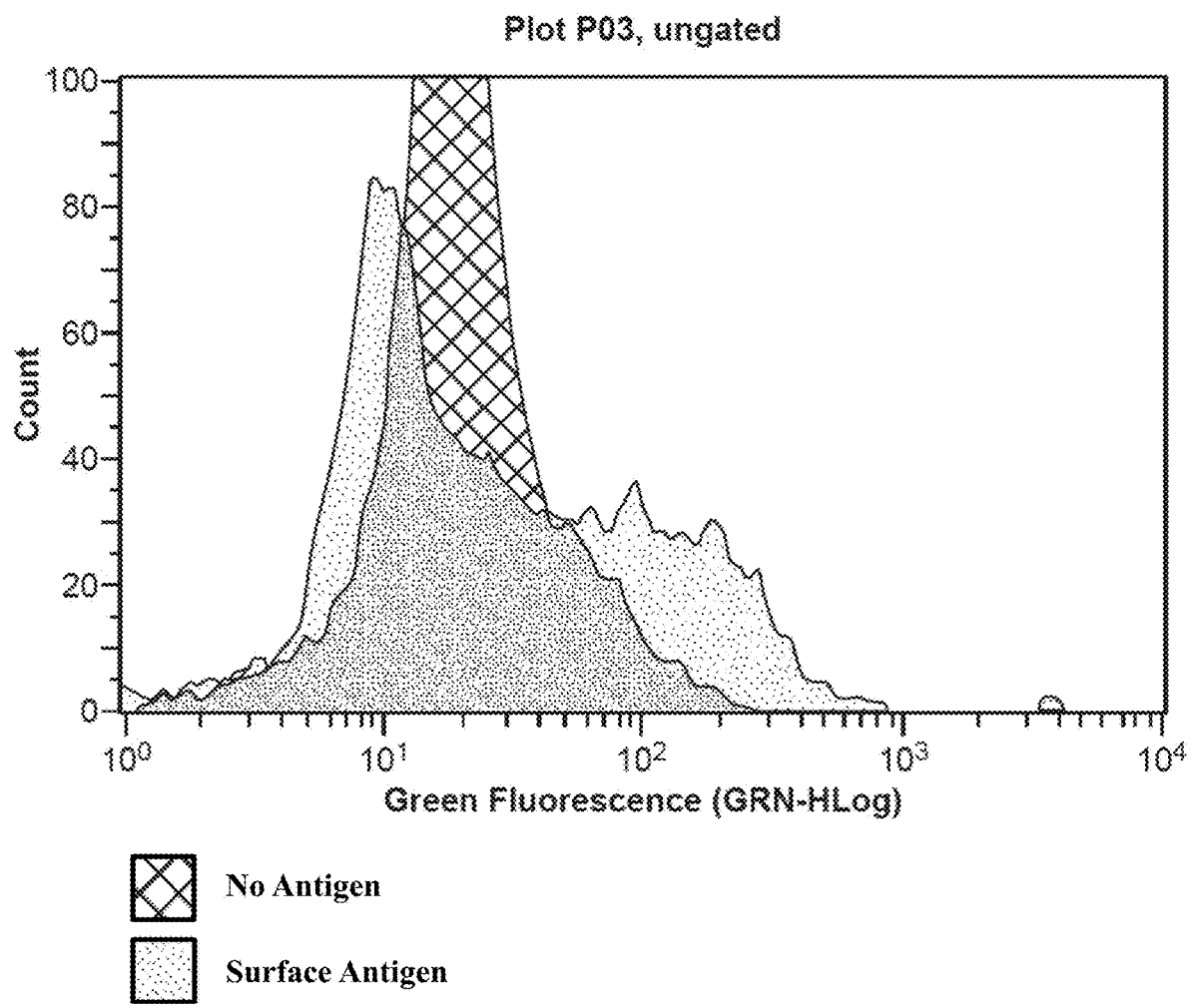

FIG. 42 provides flow cytometry analysis of B-Body binding to cell-surface antigen. Cross-hatched signal indicates cells without antigen; dotted signal indicates transiently transfected cells with surface antigen.

FIG. 43 provides exemplary architecture of a trivalent construct.

Figure 44:
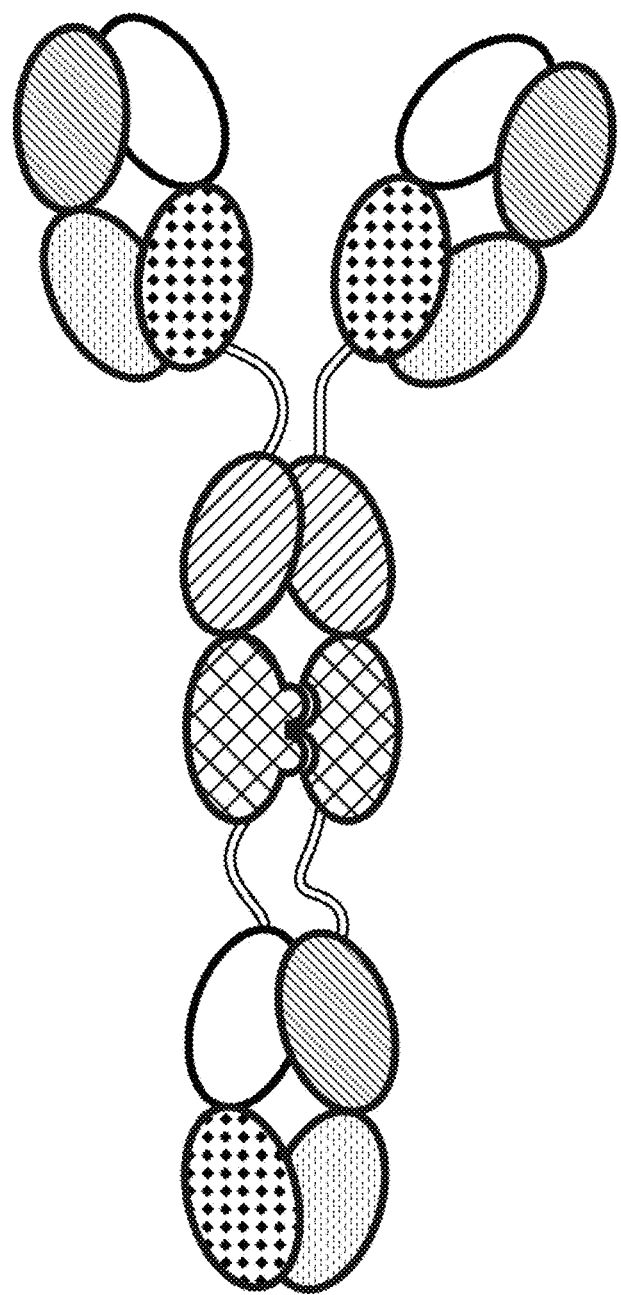

FIG. 44 provides exemplary architecture of a trivalent construct.

Figure 45:
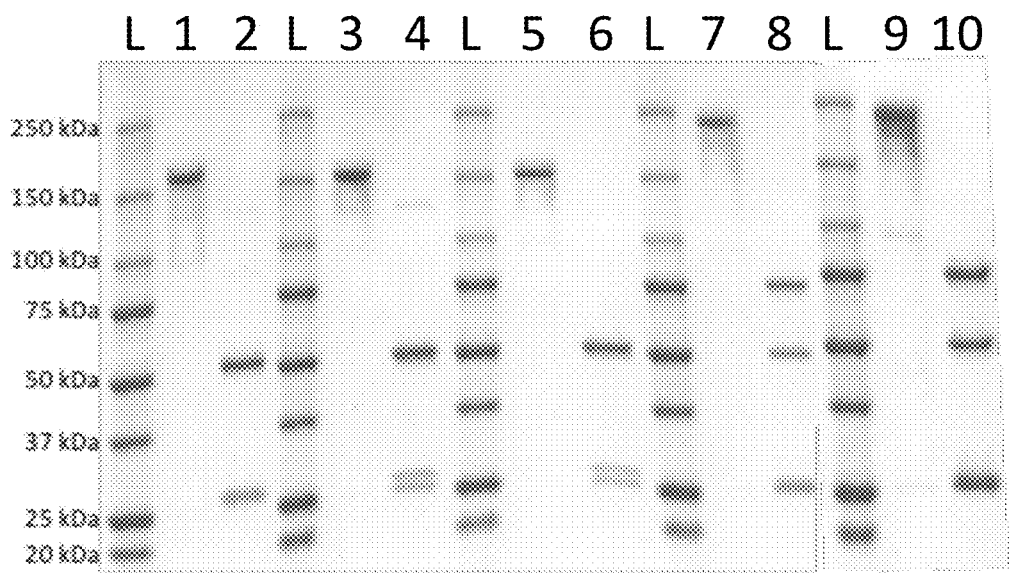

FIG. 45 shows SDS-PAGE results with bivalent and trivalent constructs, each after transient expression and one-step purification using the CaptureSelect™ CH1 affinity resin, under non-reducing and reducing conditions, as further described in Example 17.

Figure 46:
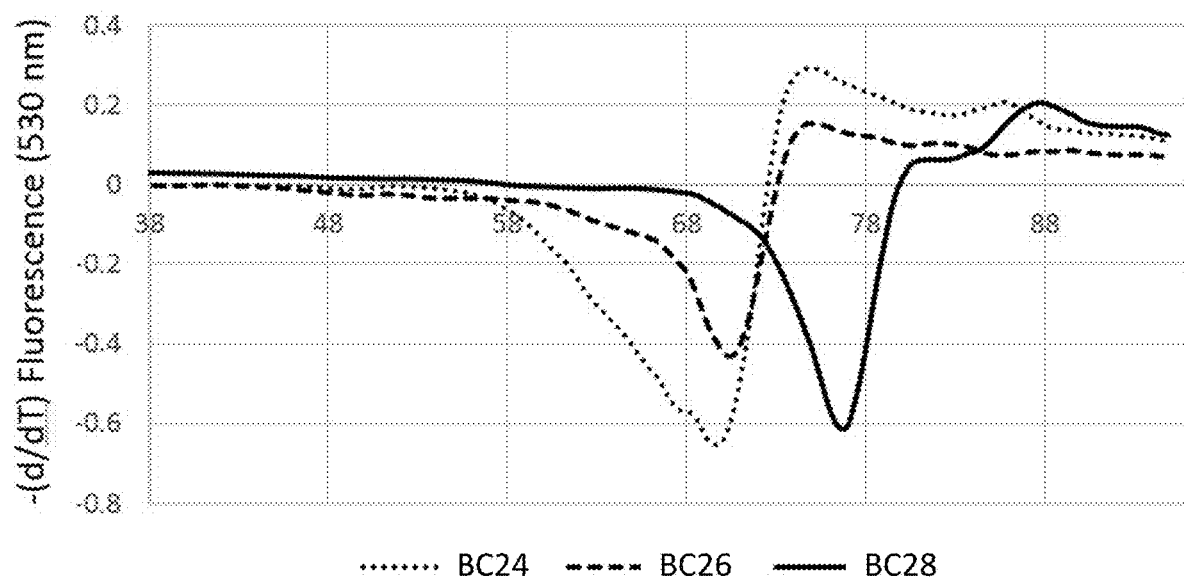

FIG. 46 shows differences in the thermal transitions for "BC24jv", "BC26jv", and "BC28jv" measured to assess pairing stability of junctional variants.

Figure 47:
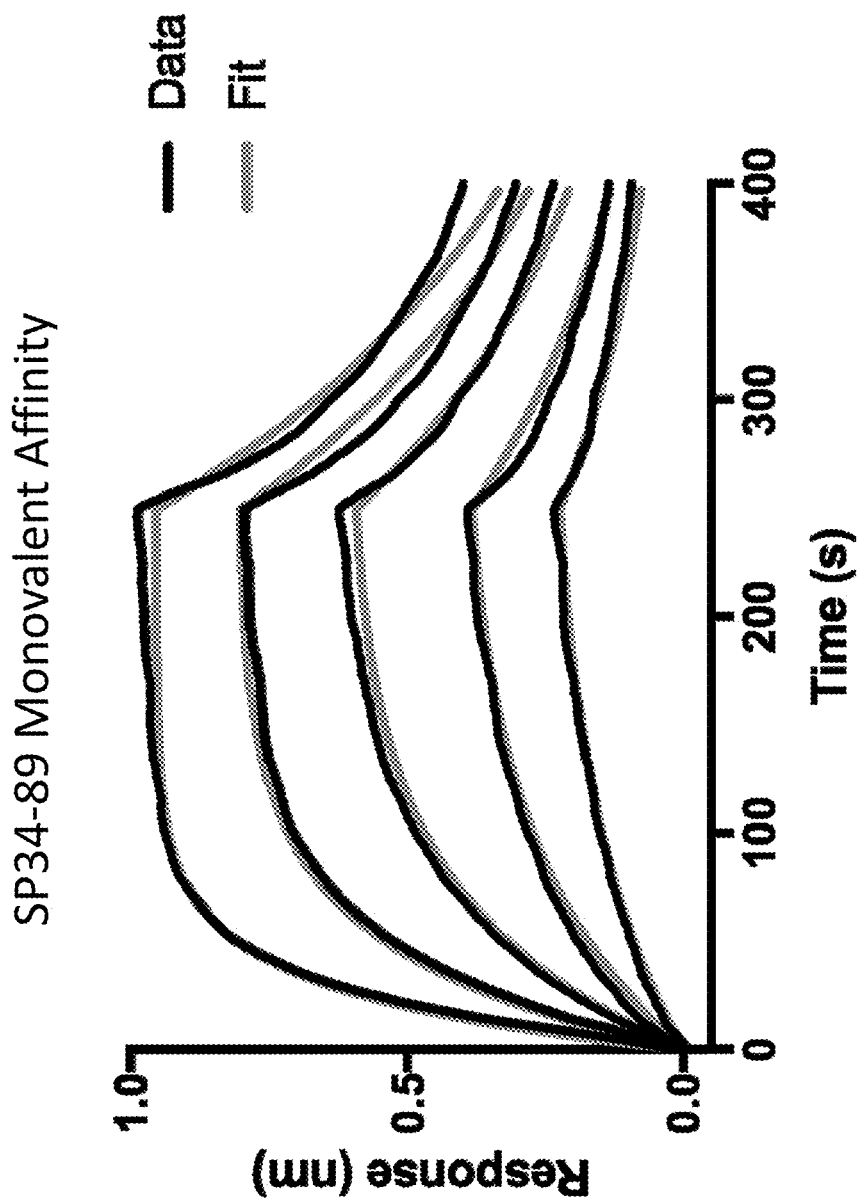

FIG. 47 demonstrates Octet (Pall ForteBio) biolayer interferometry analysis of a two-fold serial dilution (200-12.5 nM) used to determine binding affinity to CD3 for a non-mutagenized SP34-89 monovalent B-Body.

Figure 48A:
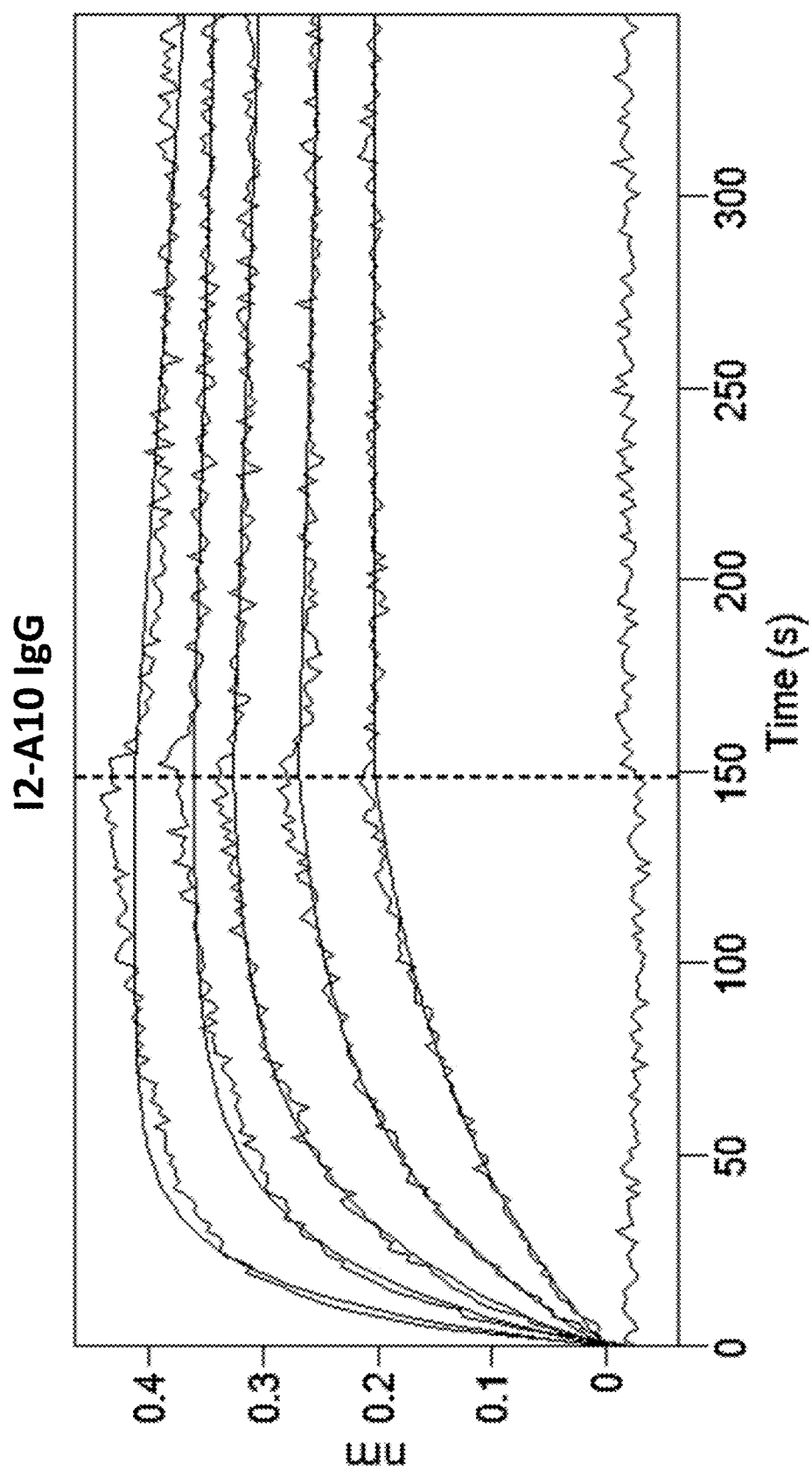
Figure 48B:
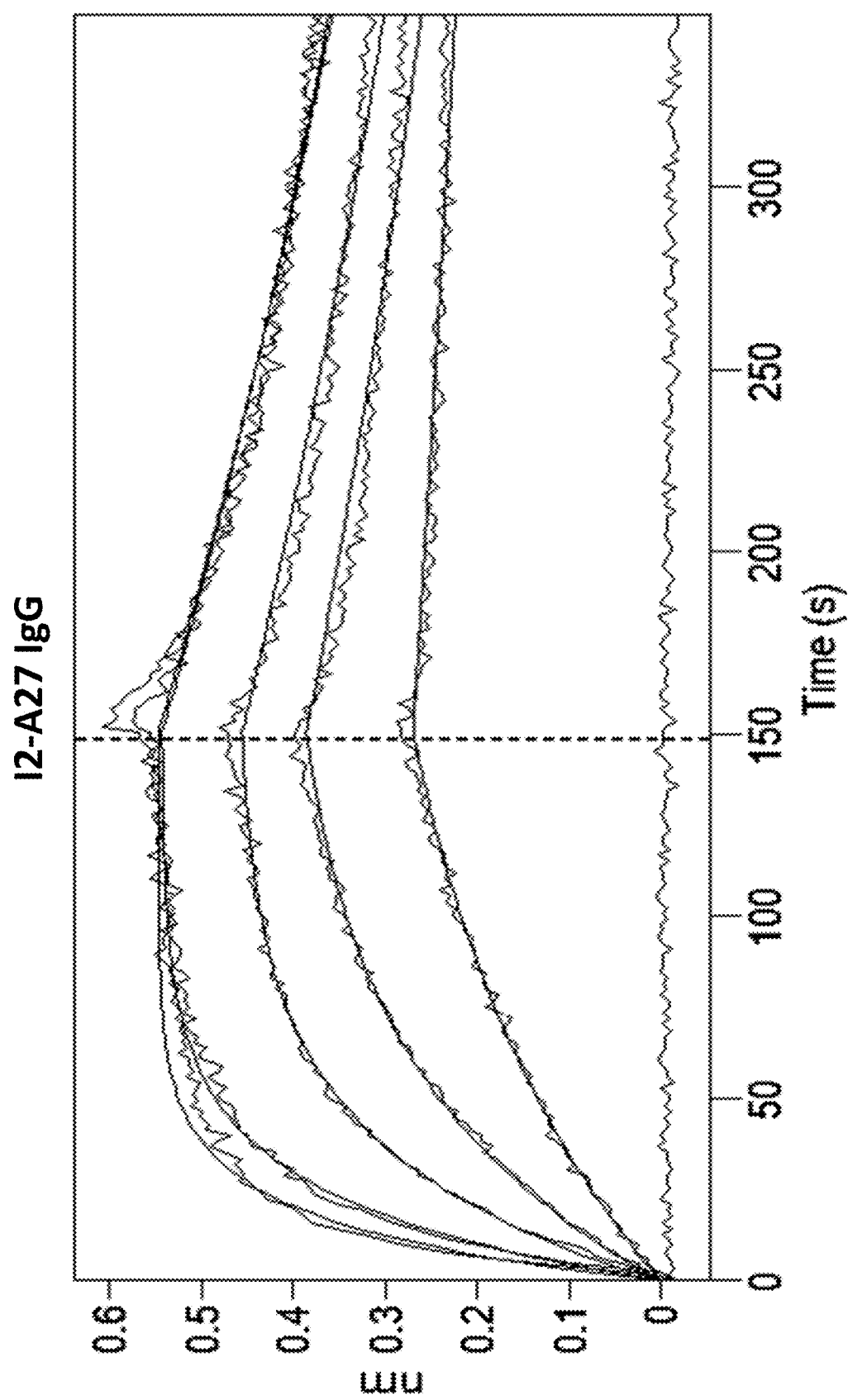

FIGS. 48A-48B demonstrate Octet (Pall ForteBio) biolayer interferometry analysis of a two-fold serial dilution (200-12.5 nM) used to determine binding affinity to ROR1 for two ROR antigen binding site candidates (FIG. 48A clone 12-A10; FIG. 48B clone 12-A27).

Figure 49:
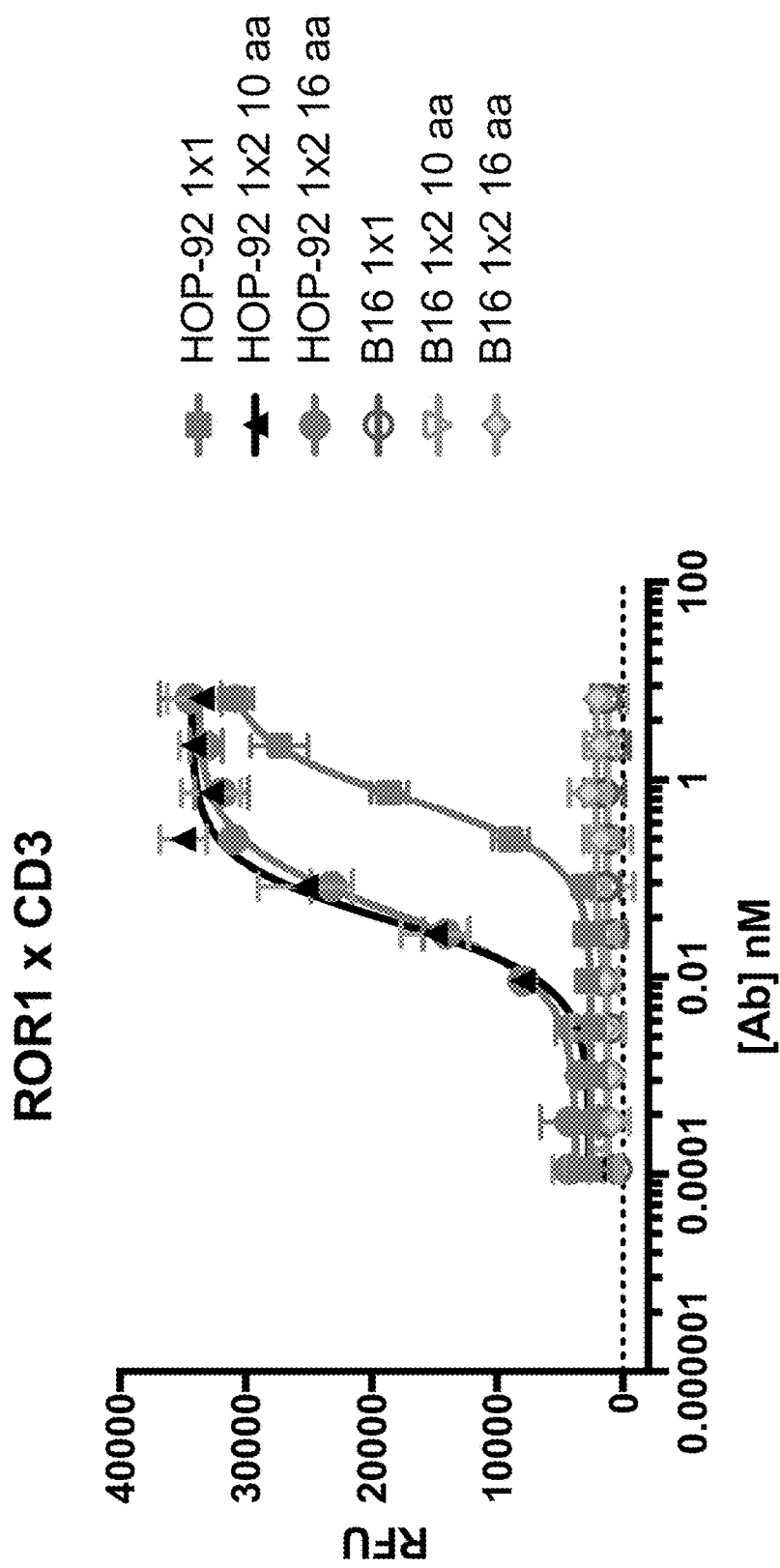

FIG. 49 shows that ROR×CD3 bispecific 1×1 and 1×2 B-bodies resulted in activation of reporter T cells when mixed with ROR1 expressing tumor lines (HOP-92), but no activation w % ben mixed with tumor lines that do not express ROR1 (B16).

Figure 50:
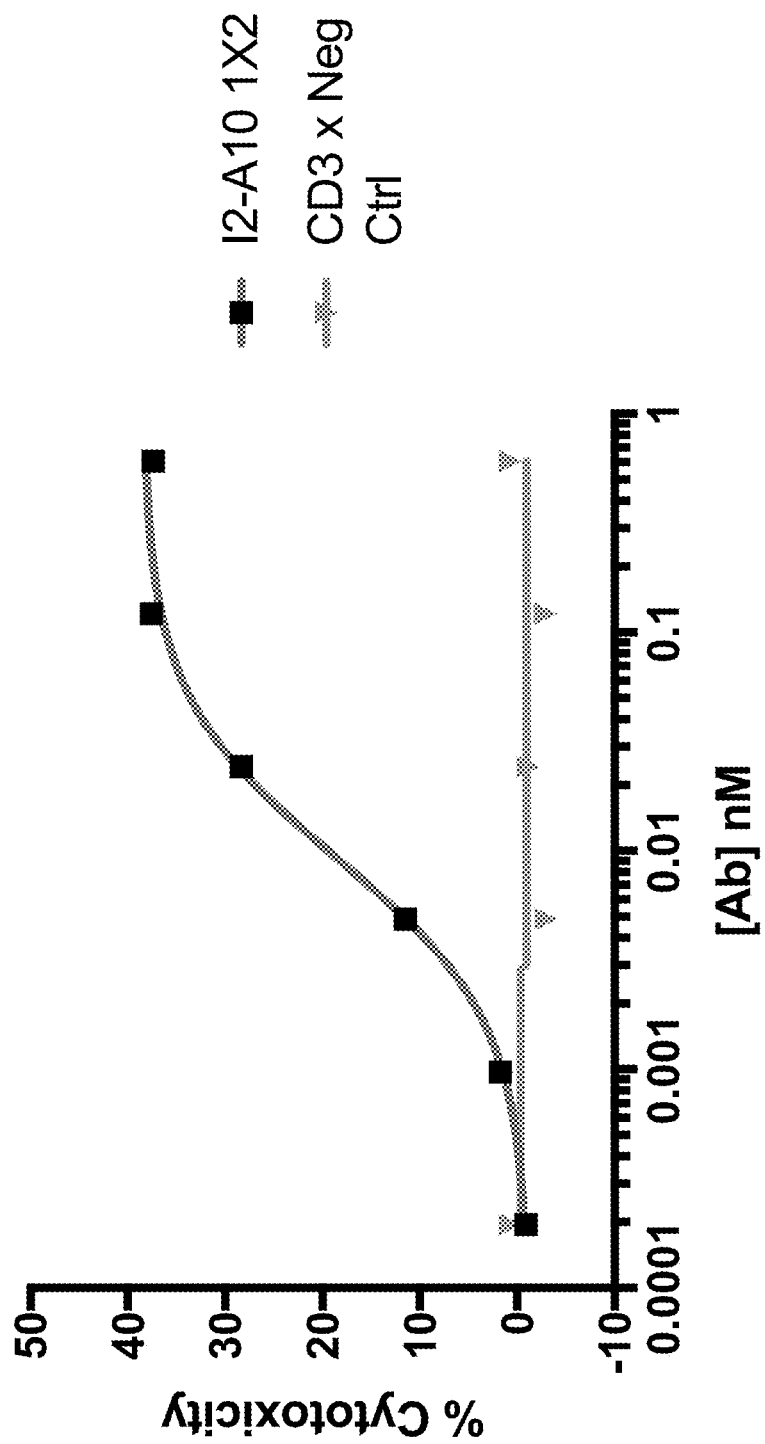
Figure 51A:
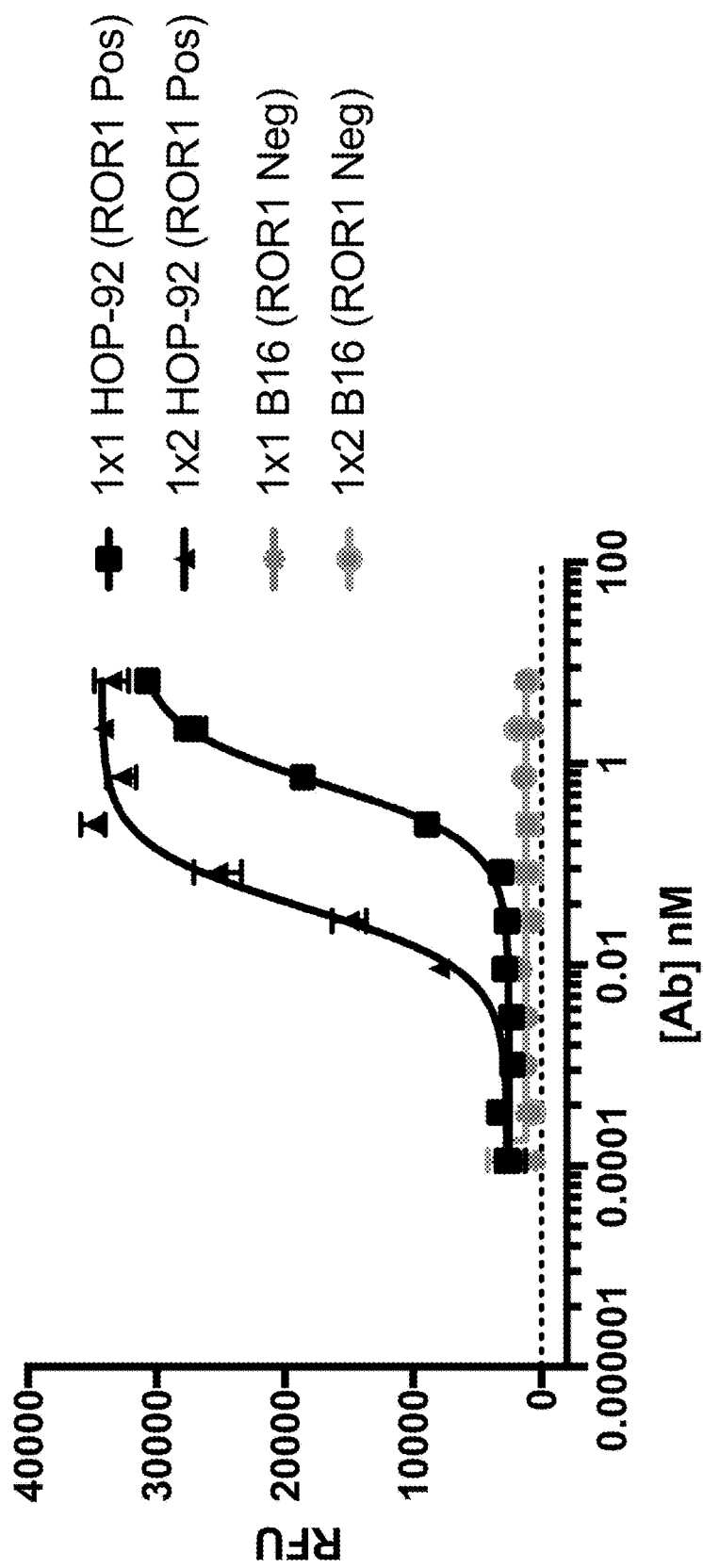
Figure 51B:
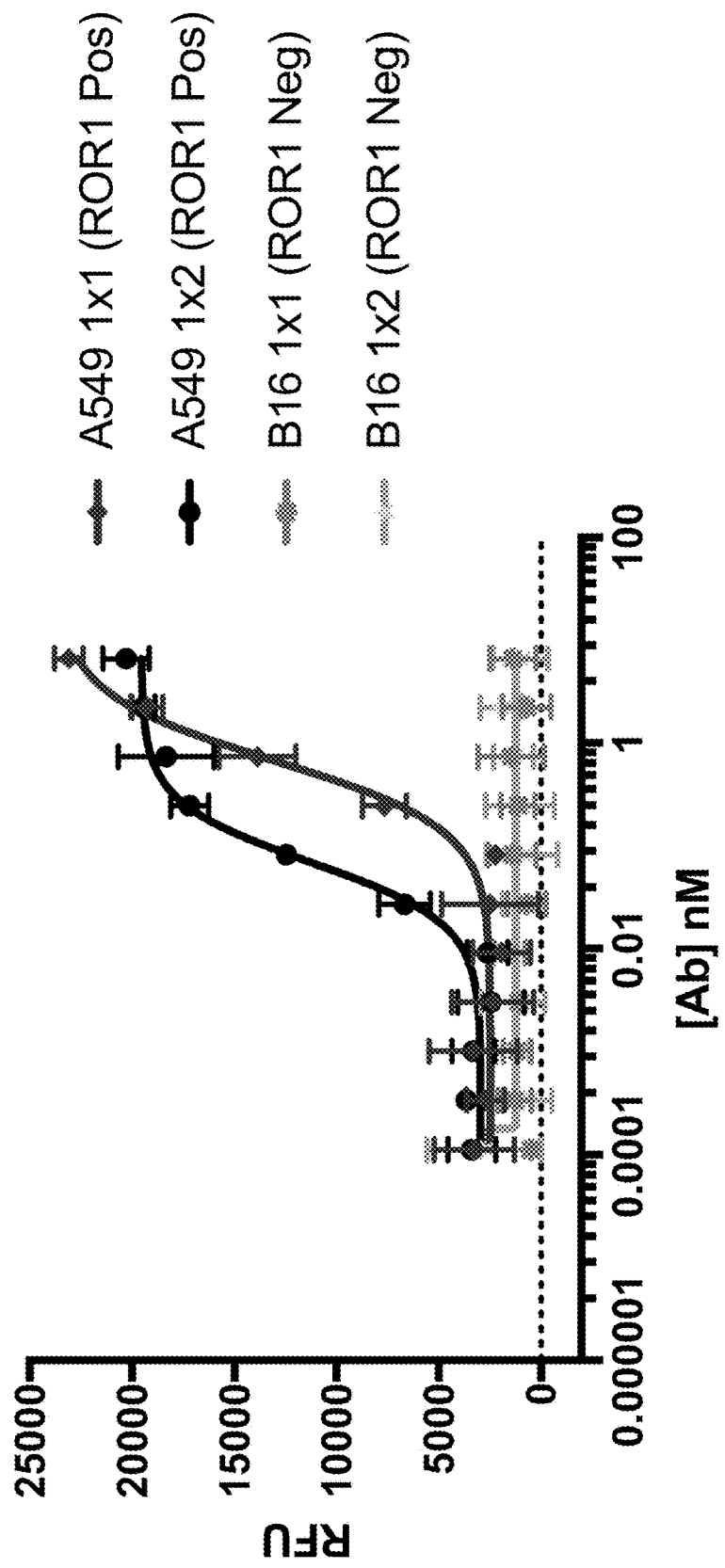
Figure 51C:
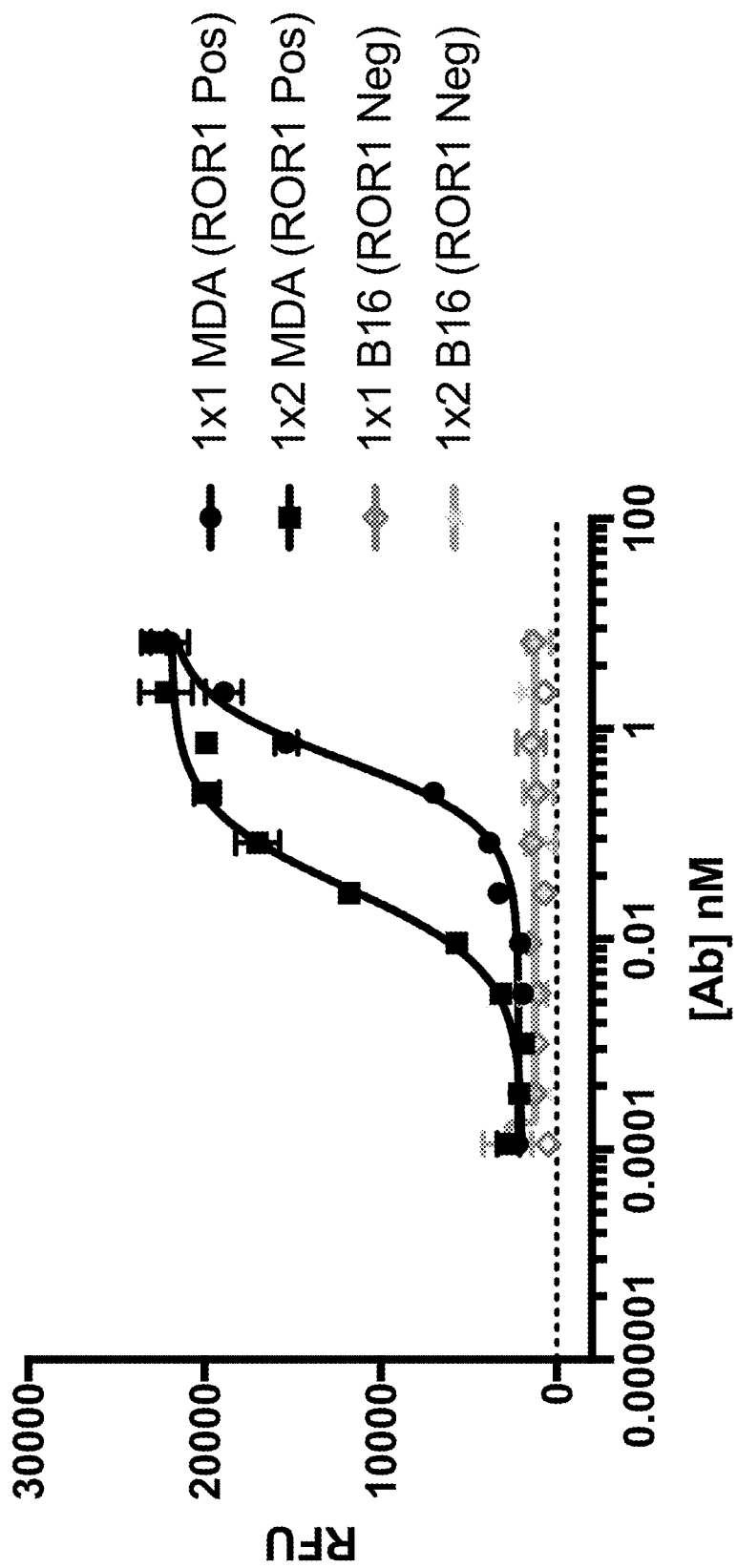
Figure 51D:
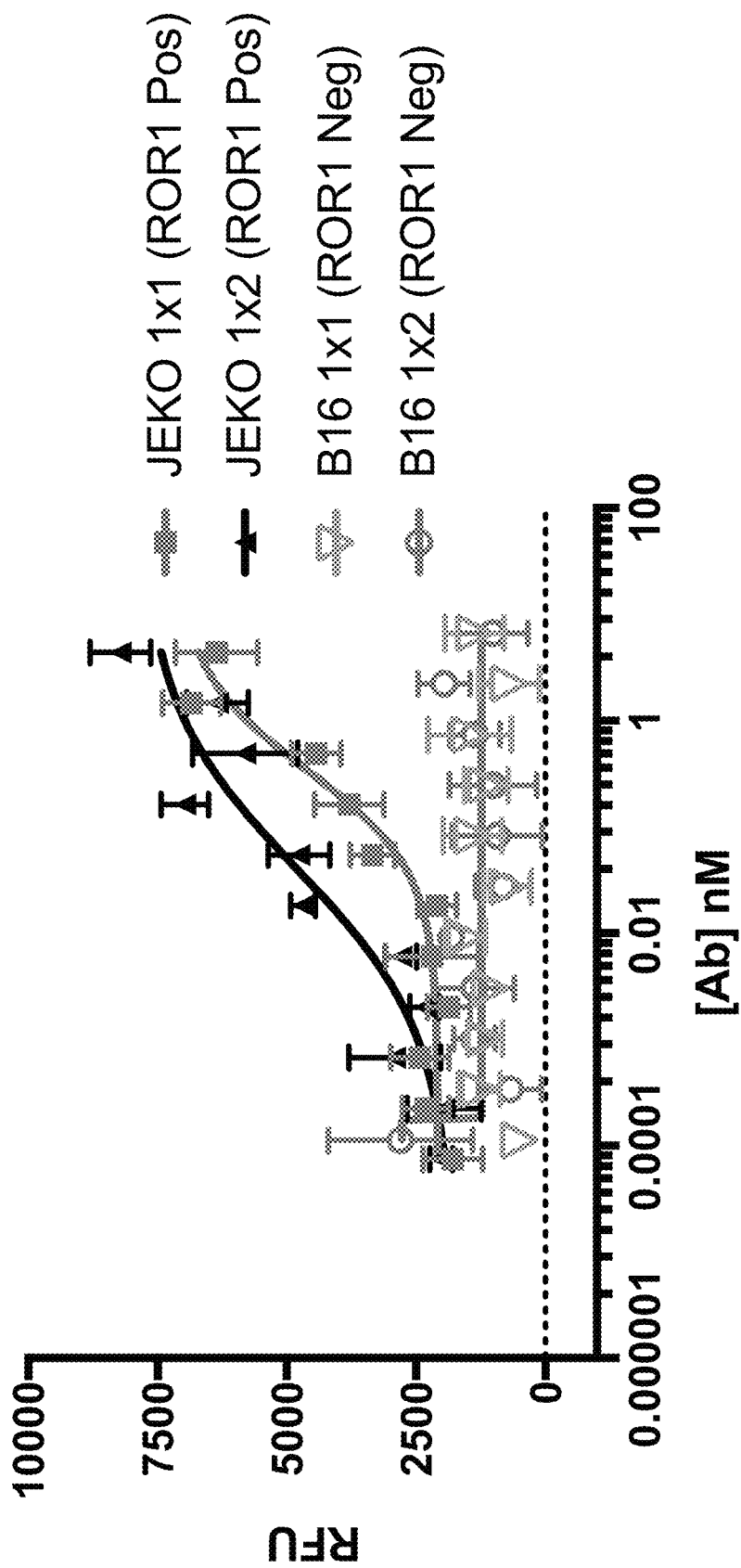
Figure 51E:
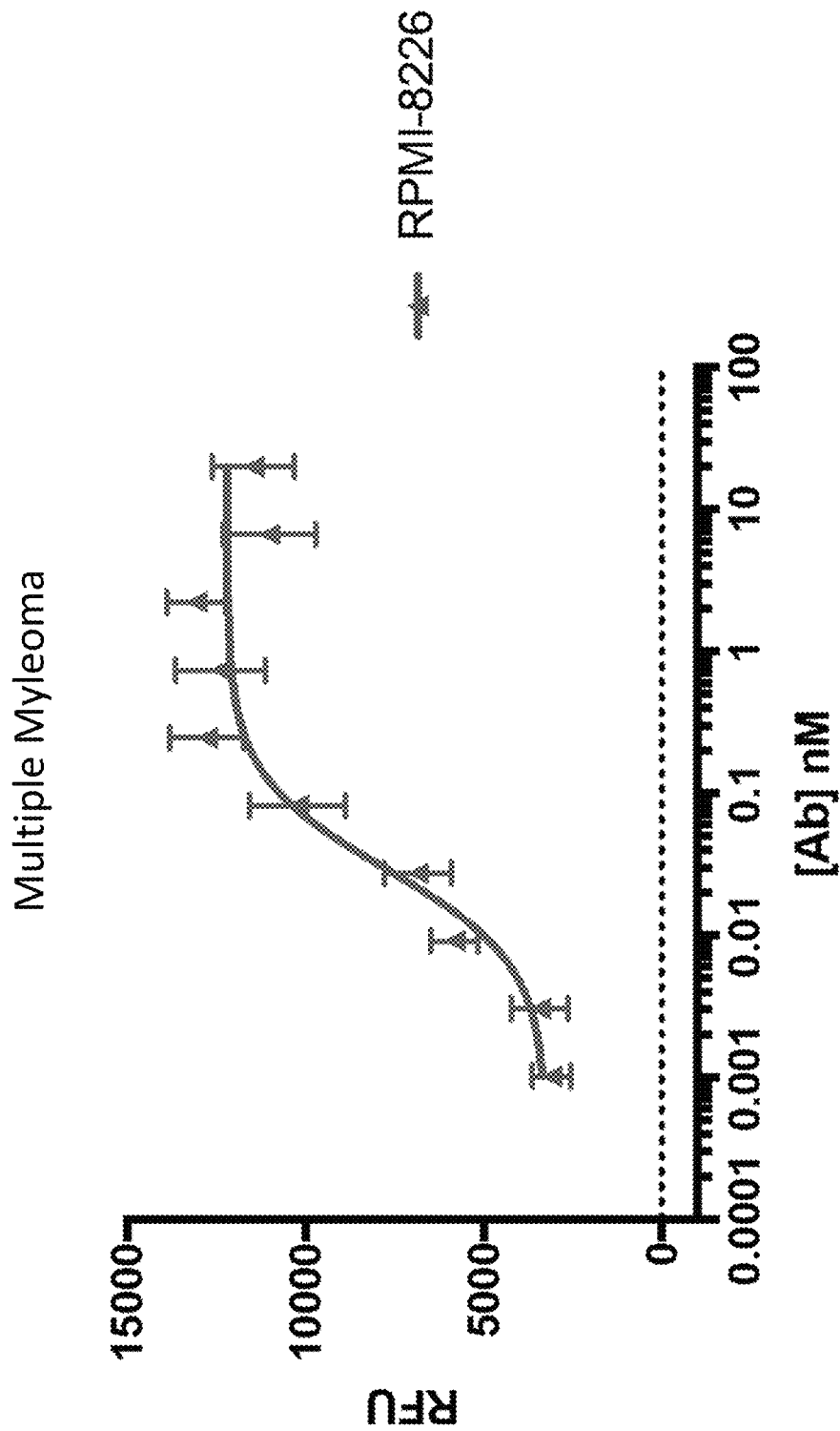

FIG. 50 shows the ROR×CD3 bispecific 12A-10 1×2 B-body resulted in cytotoxic T cell mediated killing when mixed with ROR1 expressing tumor lines (MDA-MD-231), but did not result in cytotoxicity when a CD3 bispecific B-body having an irrelevant tumor ABS (e.g., a tumor antigen not expressed in MDA-MD-231) was added to the mixture.

FIGS. 51A-51E show that the ROR×CD3 bispecific 12A-3 1xi and 1×2 B-bodies resulted in activation of the reporter T cells when mixed with ROR expressing tumor lines HOP-92 (FIG. 51A), A549 (FIG. 51B), MDA-MD-231 (FIG. 51C), JeKo-1 (FIG. 51D), and RPMI-8226 (FIG. 51E), but no activation when mixed with tumor lines that do not express ROR1 (B16).

Figure 52:
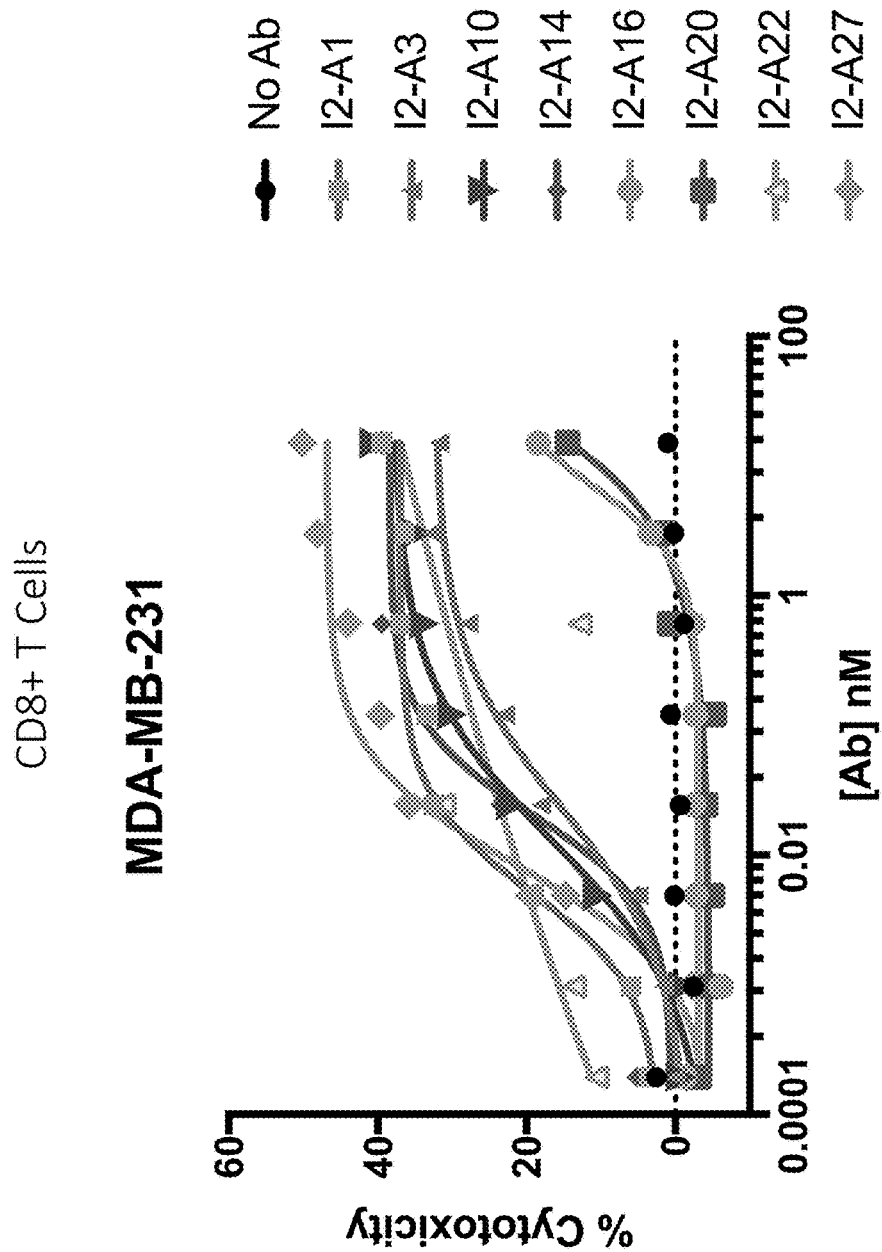

FIG. 52 shows that the ROR×CD3 bispecific 1×2 B-bodies 12A-1, 12A-3, 12A-10, 12A-14, 12A-22, and 12A-27 resulted in cytotoxic T cell mediated killing when mixed with ROR1 expressing tumor lines (MDA-MD-231), but 1×2 B-bodies 12A-16 and 12A-22 did not result in potent cytotoxicity.

Figure 53A:
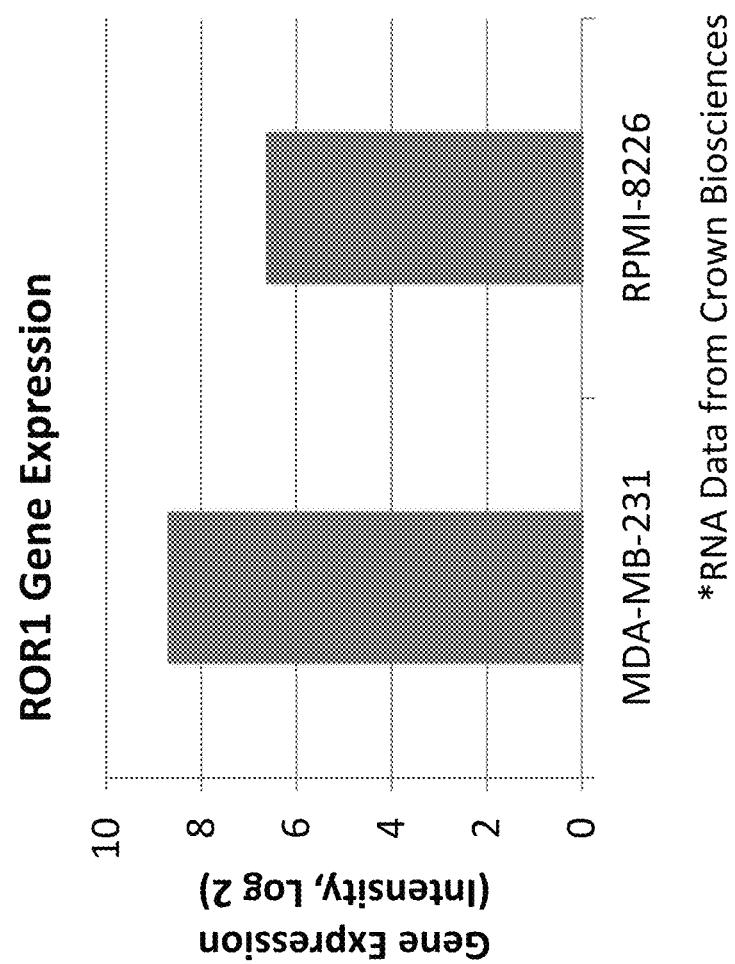
Figure 53C:
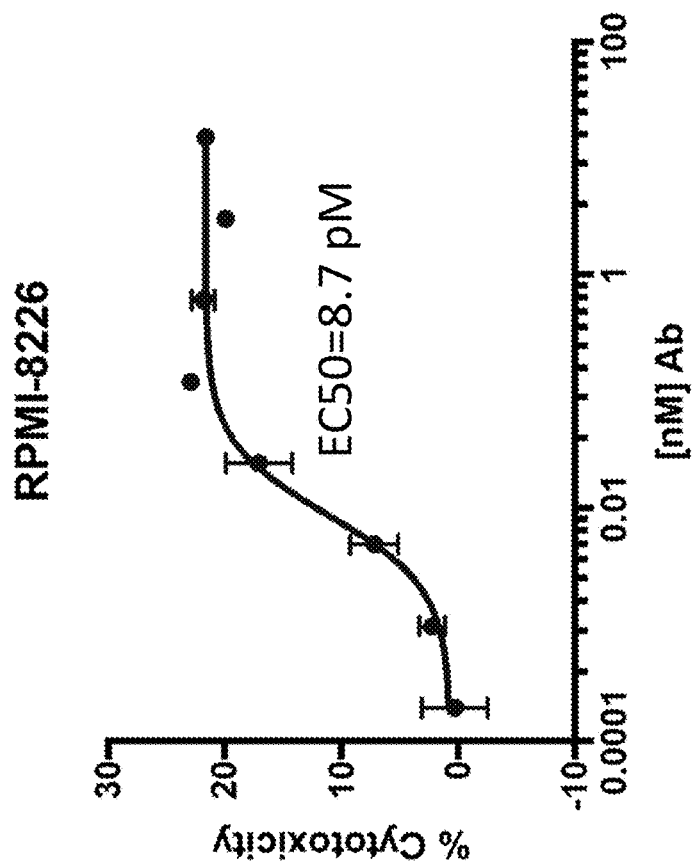
Figure 53B:
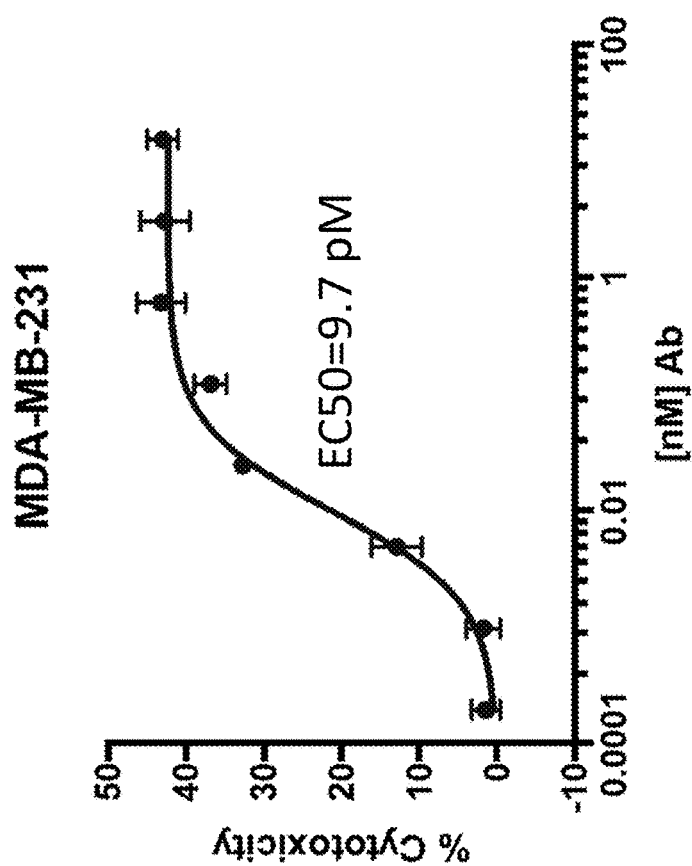

FIG. 53A illustrates published ROR1 expression data for the MDA-MD-231 and RPMI-8226 tumor lines FIG. 53B and FIG. 53C demonstrate that the cytotoxicity efficacy correlates with ROR1 in MDA-MD-231 and RPMI-8226 tumor cell lines.

Figure 54A:
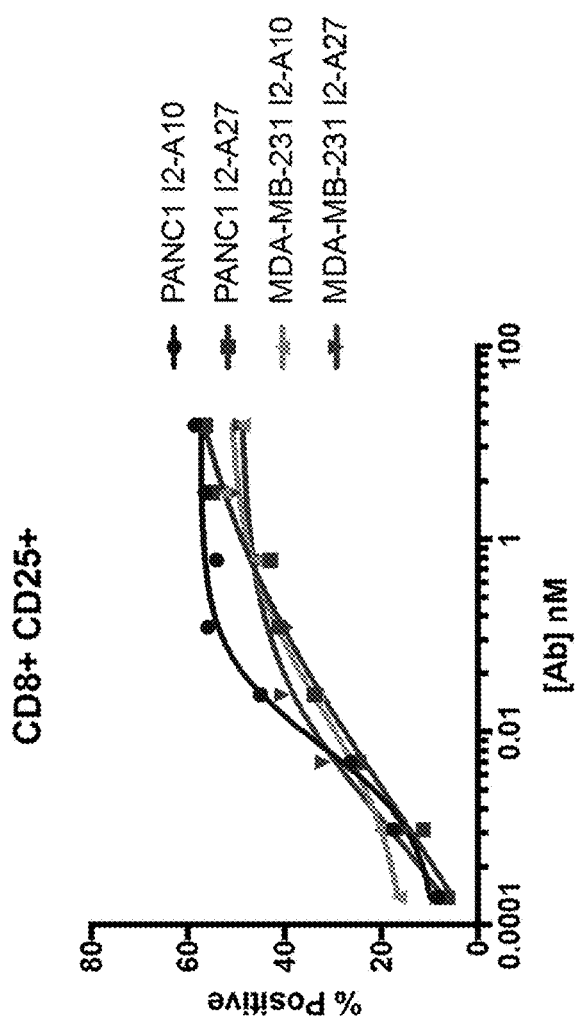
Figure 54B:
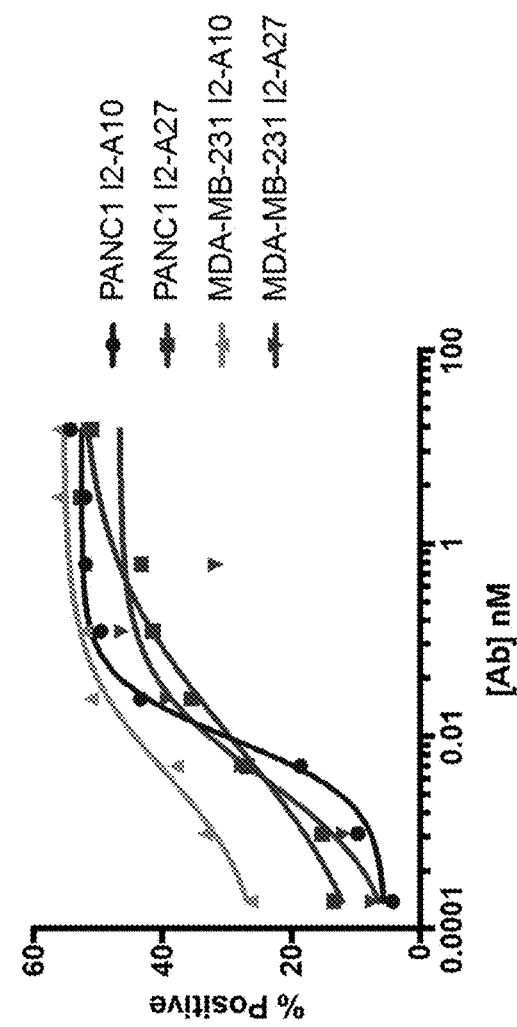
Figure 54C:
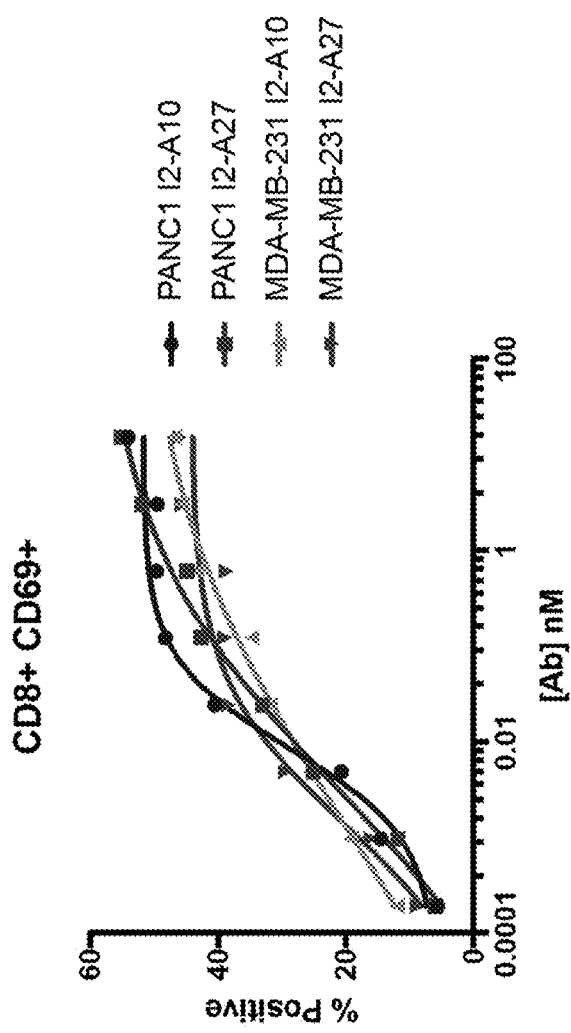
Figure 54D:
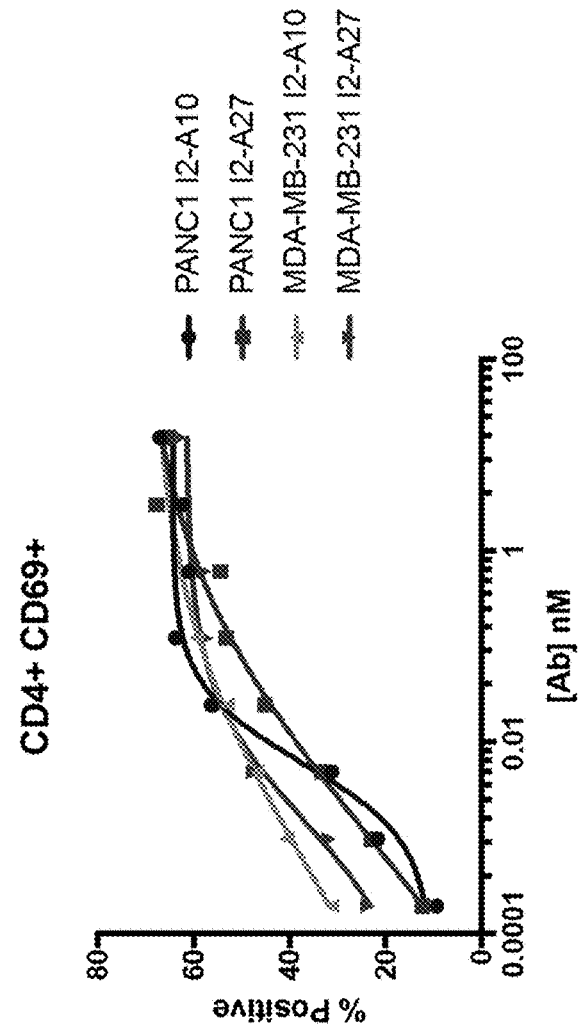
Figure 54E:
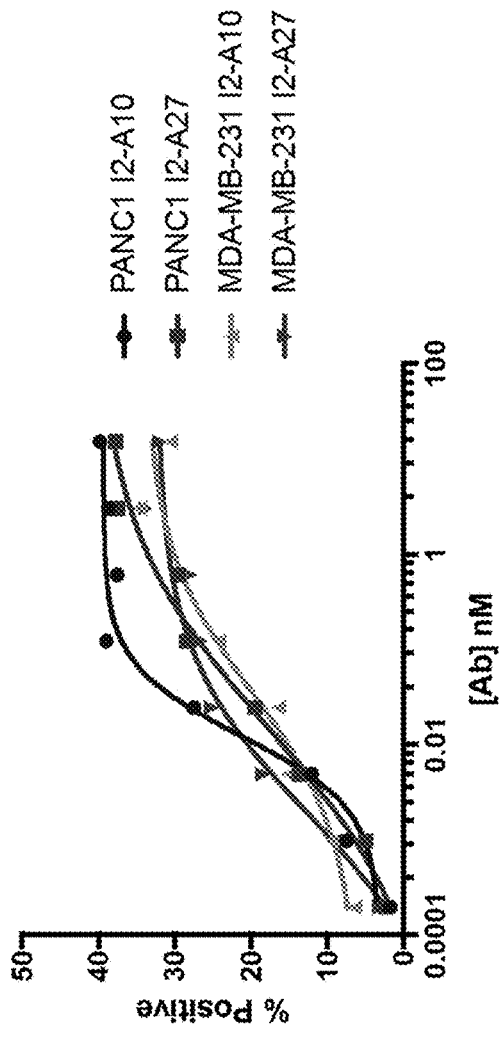
Figure 54F:
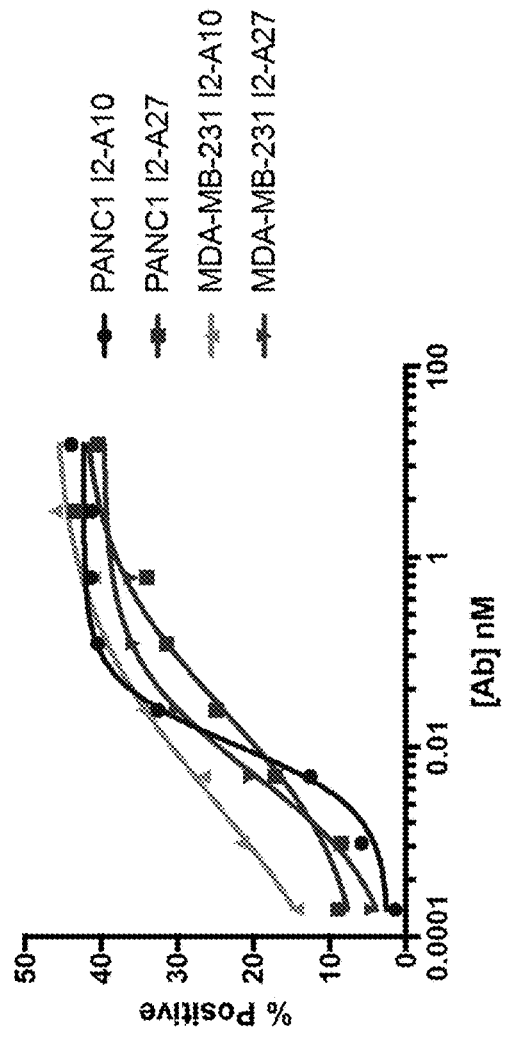

FIGS. 54A-54F show that 12A-10 and 12A-27 B-bodies activated CD8+ T cells in a PBMC population as determined by quantifying CD25 (FIG. 54A), CD69 (FIG. 54C), and both CD25 and CD69 (FIG. 54E), as well as activated CD4+ T cells in a PBMC population as determined by quantifying CD25 (FIG. 54B), CD69 (FIG. 54D), and both CD25 and CD69 (FIG. 54F).

Figure 55:
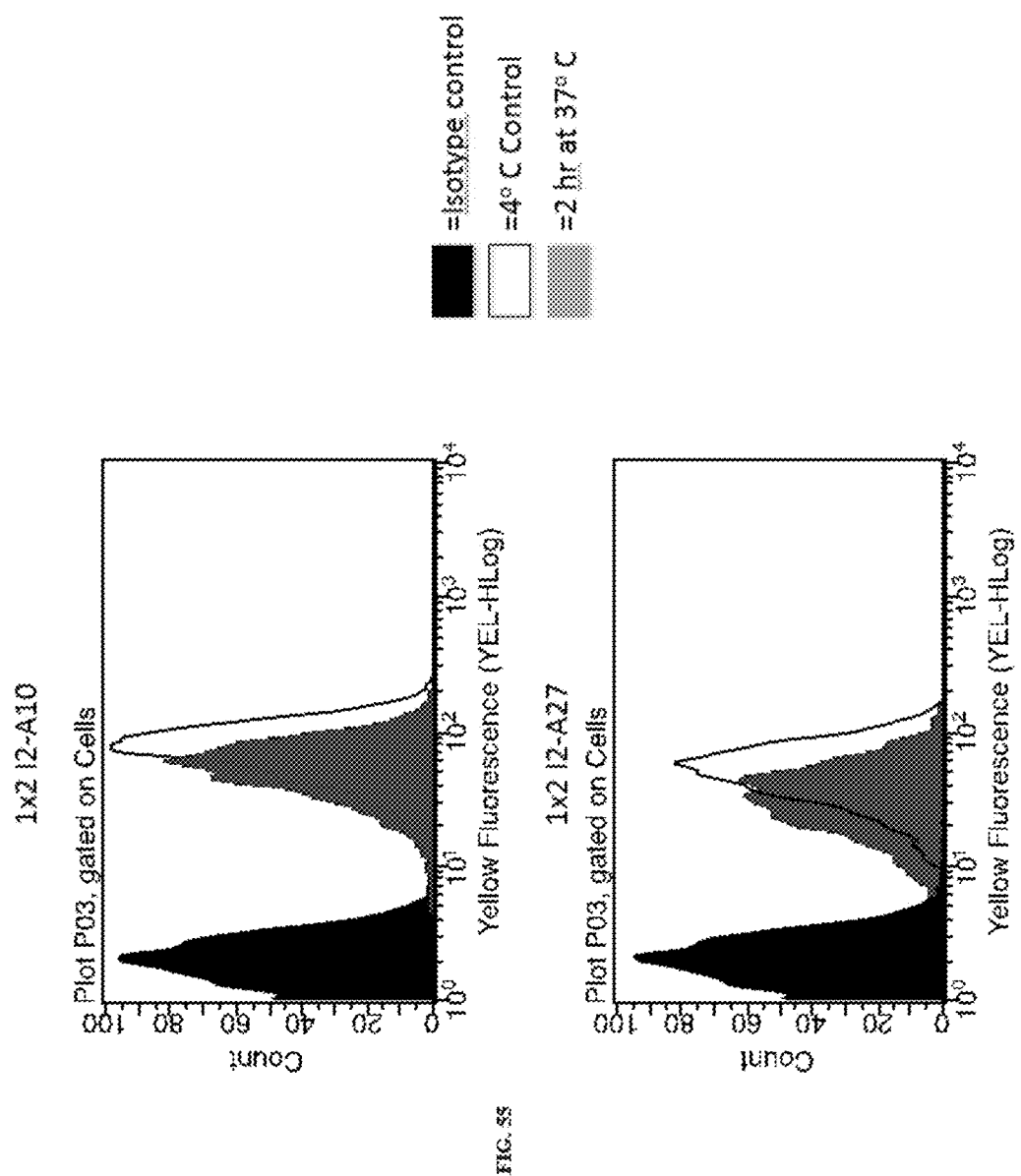

FIG. 55 shows that 26% and 36% of candidates 12A-10 (top panel) and 12A-27 (bottom panel) were internalized following a 2 hour incubation with MDA-MB-231 cells, respectively.

Figure 56:
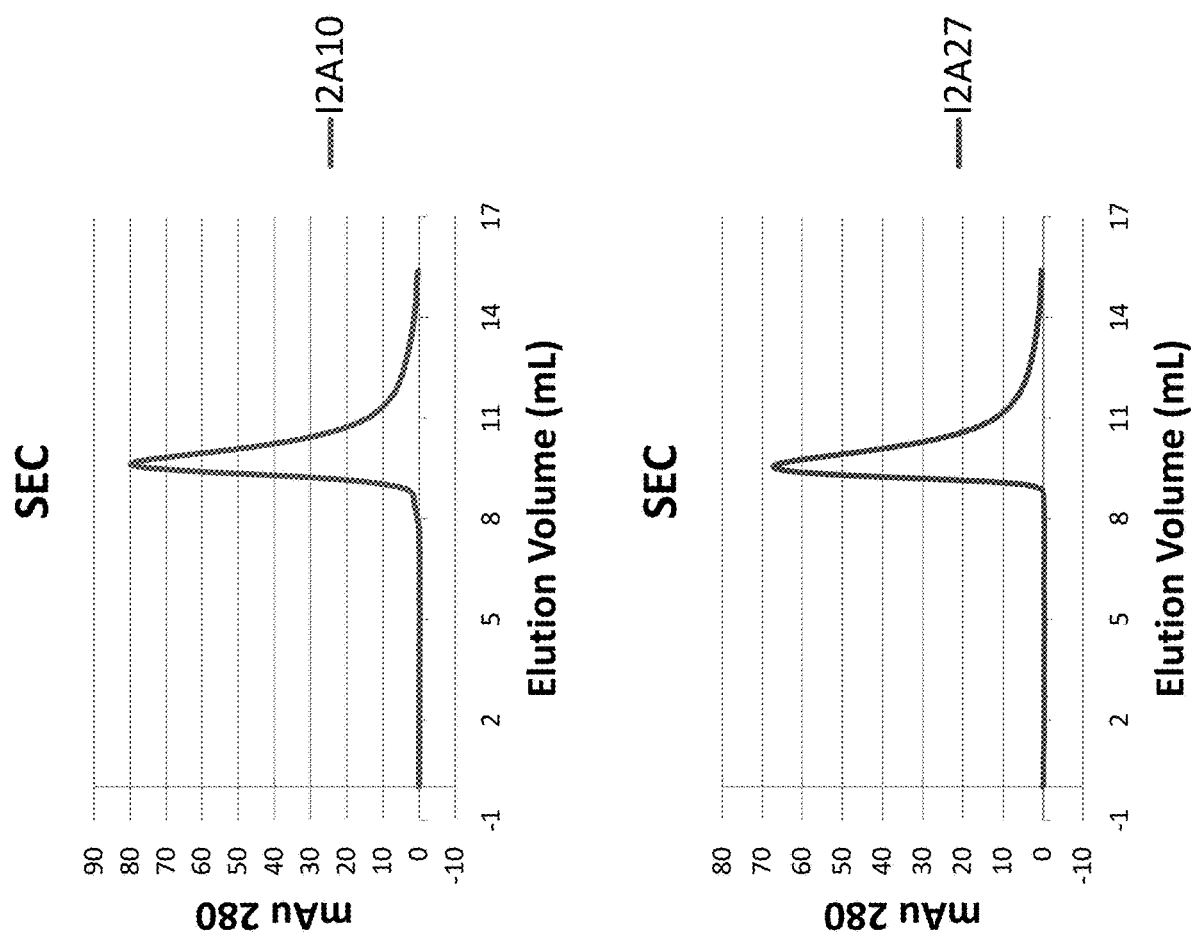

FIG. 56 shows size exclusion chromatography (SEC) analysis, demonstrating that a single-step CH1 affinity purification step yields single, monodisperse peaks via gel filtration in which >98% is unaggregated protein for 1×2 B-body candidates 12A-10 (top panel) and 12A-27 (bottom panel).

Figures 57A, 57B:
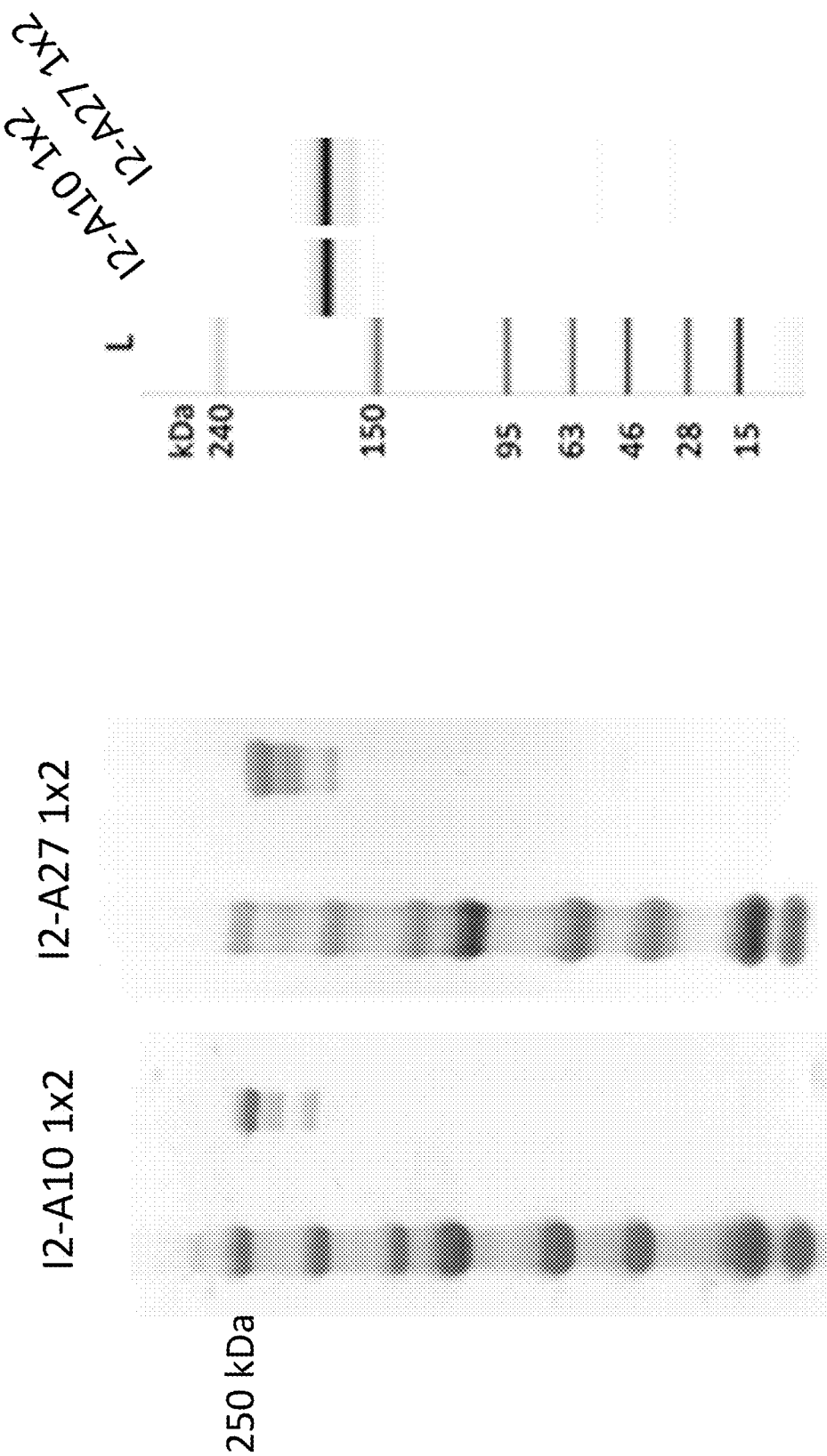

FIG. 57A shows non-reducing SDS-PAGE gels of 1×2 B-body candidates 12A-10 (left panel) and 12A-27 (right panel), demonstrating a major band of fully assembled constructs (high-migrating 250 kDa band).

FIG. 57B shows Bioanalyzer (Agilent) analysis of non-reduced samples for 1×2 B-body candidates 12A-10 and 12A-27 demonstrating a major band of fully assembled constructs.

Figure 58:
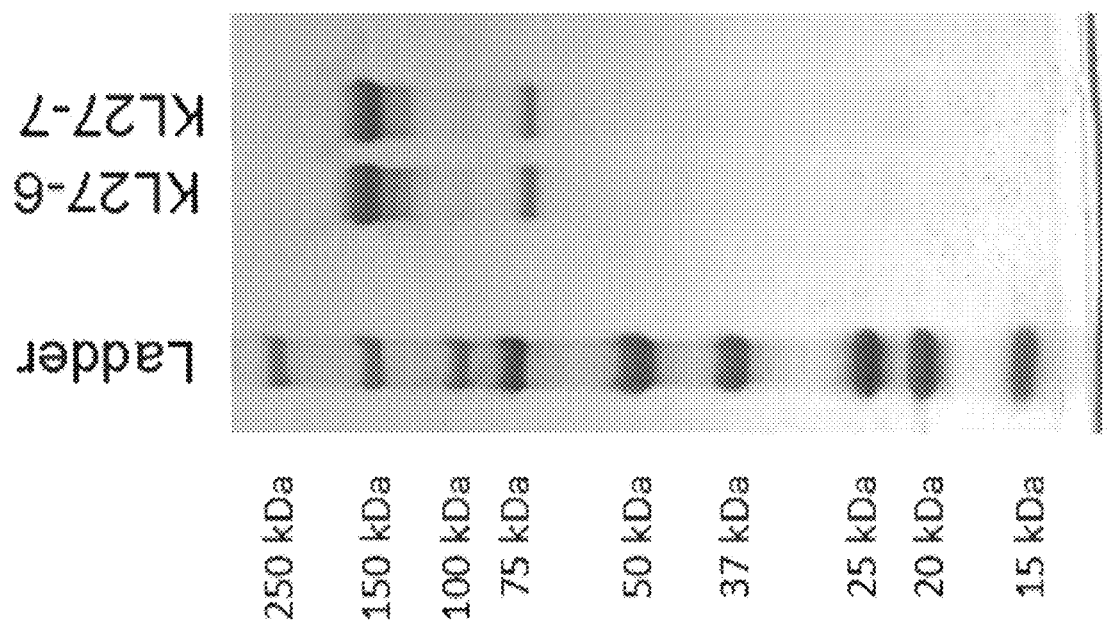

FIG. 58 shows SDS-PAGE analysis of bispecific antibodies comprising standard knob-hole orthogonal mutations introduced into CH3 domains found in their native positions within the Fc portion of the bispecific antibody that have been purified using a single-step CH1 affinity purification step (CaptureSelect™ CH1 affinity resin).

Figure 59A:
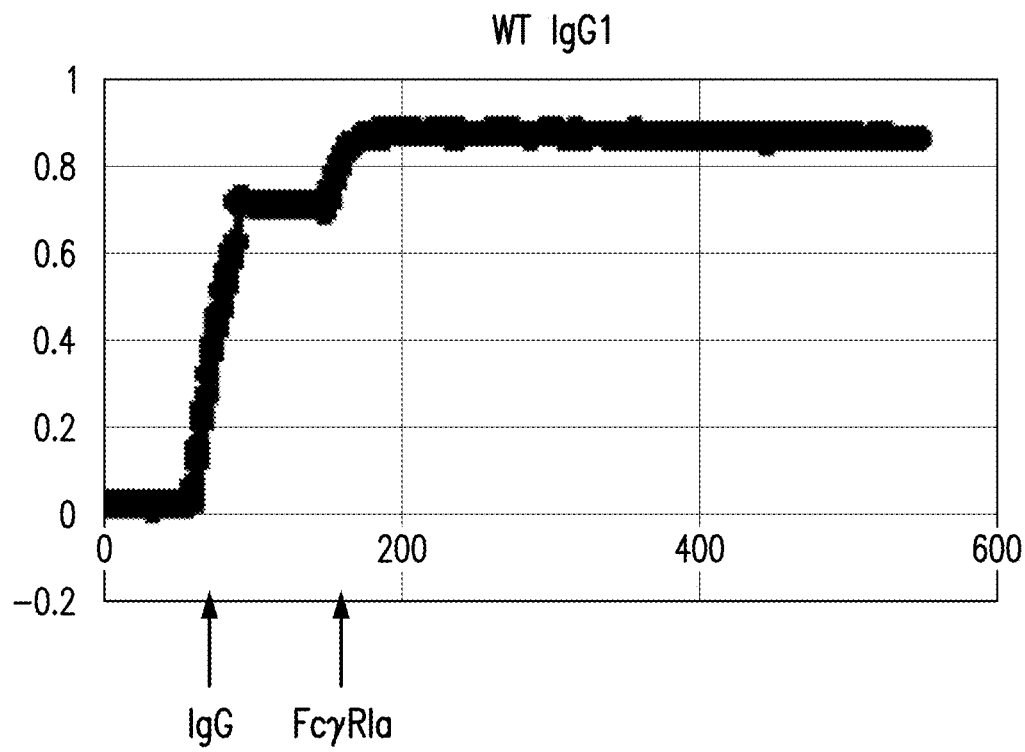
Figure 59B:
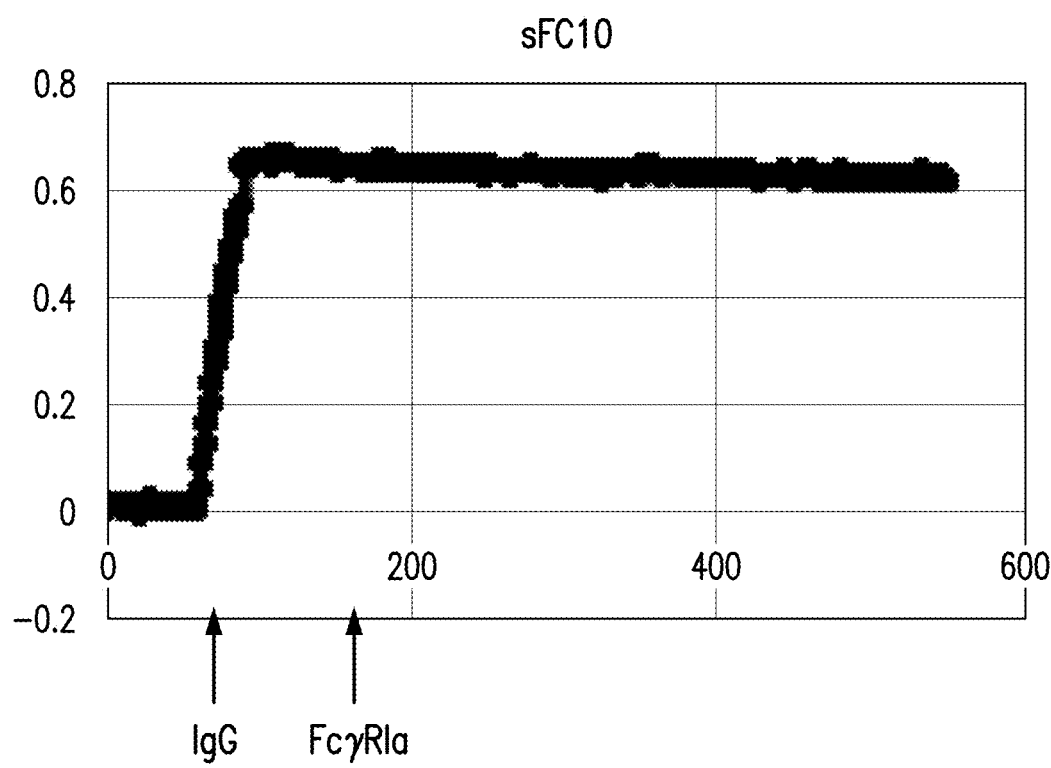

FIGS. 59A-59B show Octet (Pall ForteBio) biolayer interferometry analysis demonstrating FcγRIa binding to trastuzumab (FIG. 59A "WT IgG1"), but not sFc10 (FIG. 59B).

Figure 60:
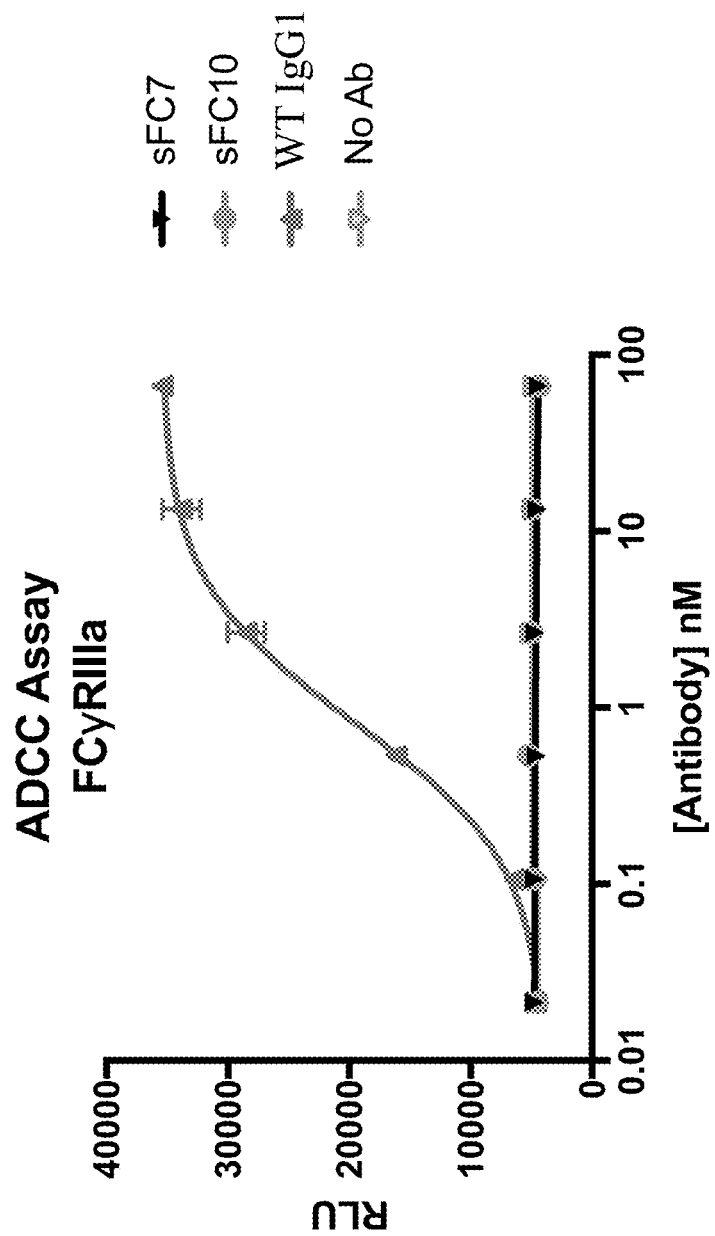

FIG. 60 shows killing by trastuzumab (Herceptin, "WT-IgG1") but not by sFc7 or sFc10 in an ADCC assay.

Figure 61:
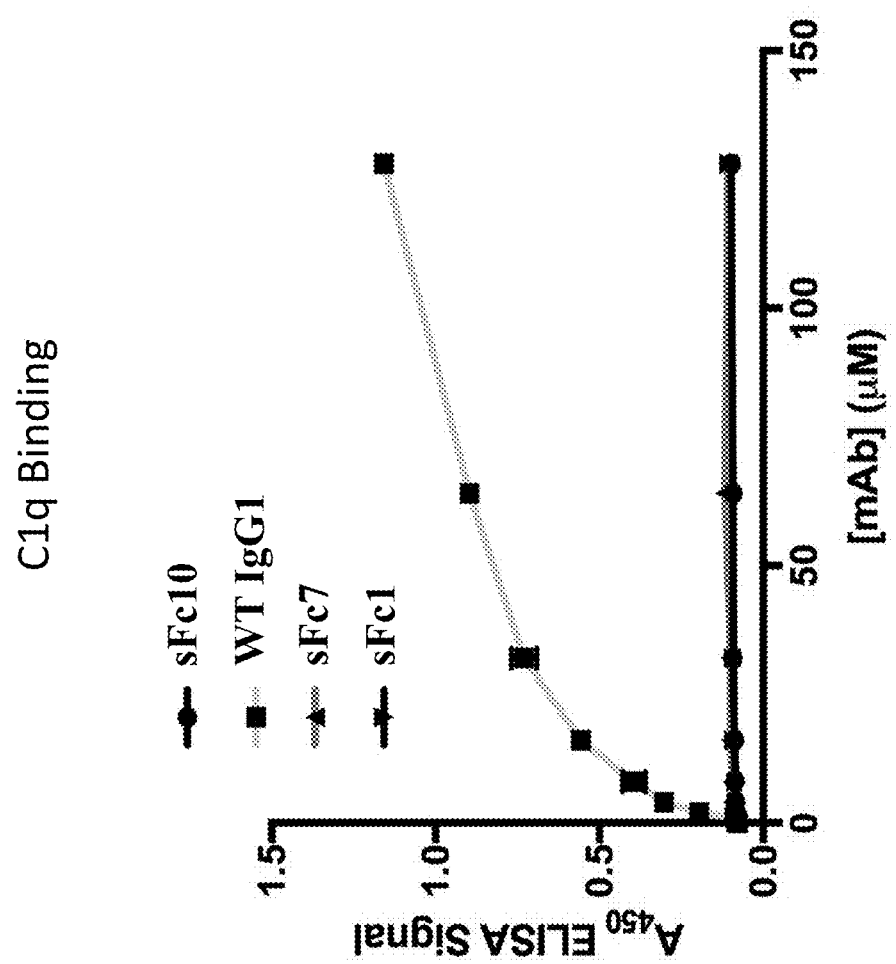

FIG. 61 shows C1q binding by trastuzumab (Herceptin, "WT-IgG1") but not by sFc1, sFc7, or sFc10 in a C1q ELISA.

Figures 62A, 62B, 62C:
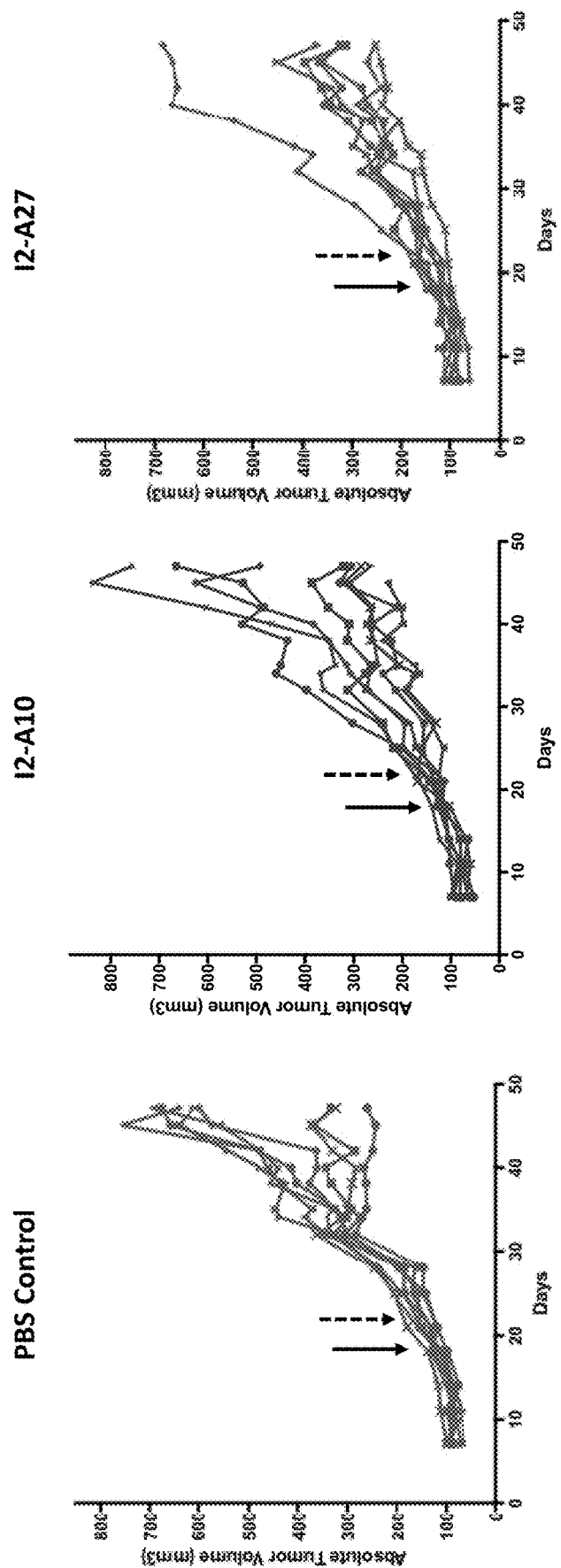

FIGS. 62A-62C show tumor volume monitored for mice engrafted with tumor cells, humanized with PBMCs (left solid arrow), then subsequently treated IV (right dashed arrow) with PBS (FIG. 62A), 1×2 B-body candidate 12-A10 (FIG. 62B), or 1×2 B-body candidate 12-A27 (FIG. 62C).

Figure 63:
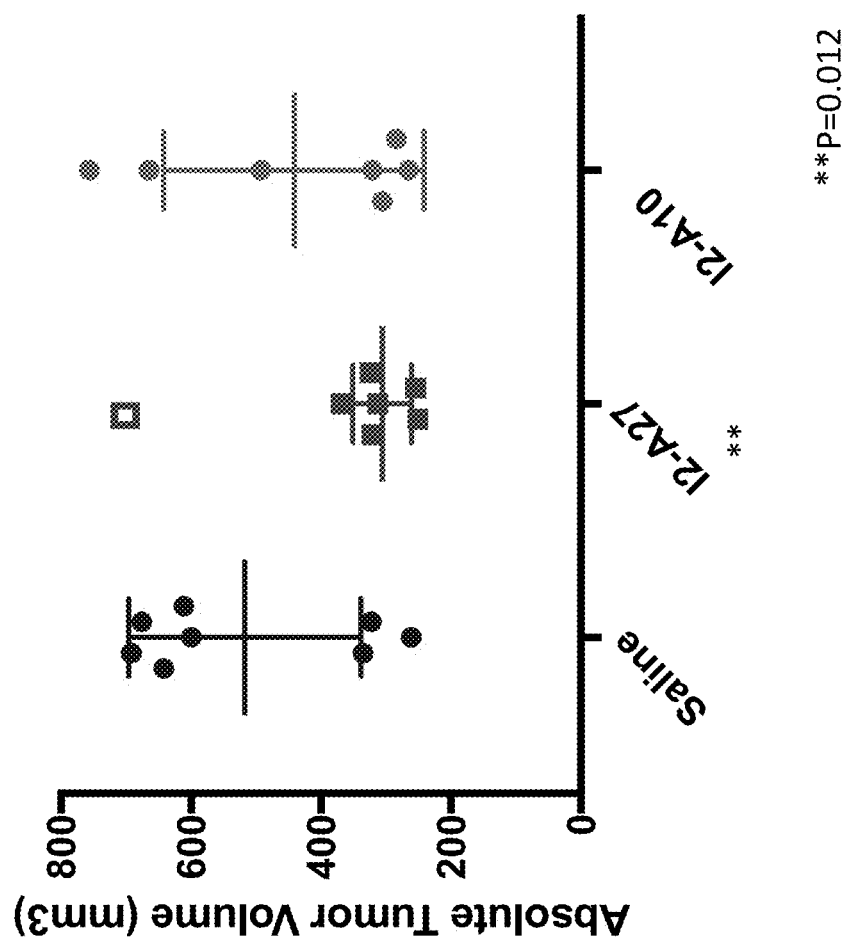

FIG. 63 shows tumor volume at the conclusion of the study for each of the mice, with mean and standard deviation for each group shown. The open square for the 12-A27 group was removed from the analysis due to probable non-humanization by PMBCs.

Figure 64A:
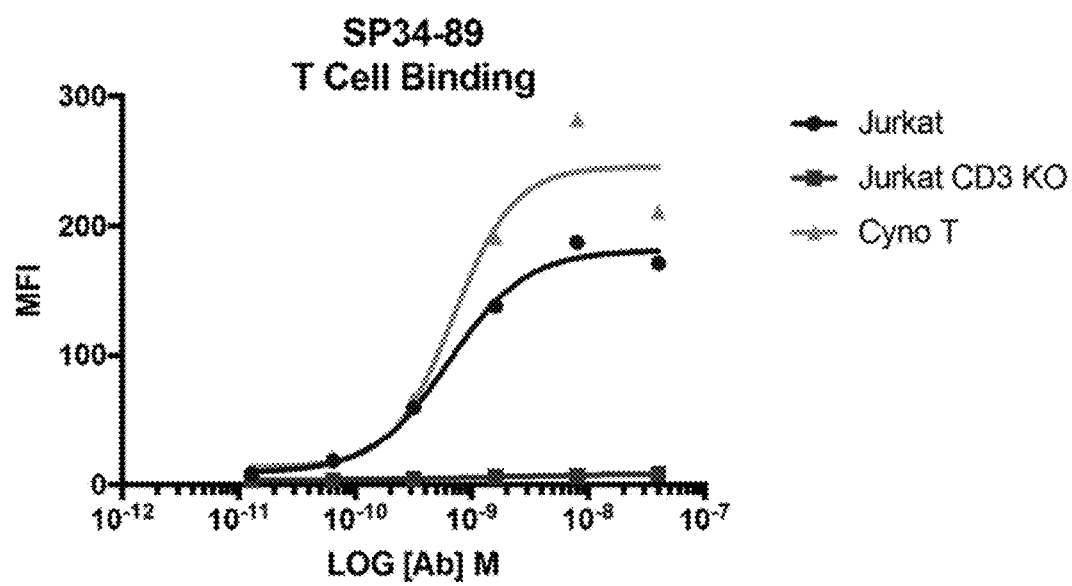
Figure 64B:
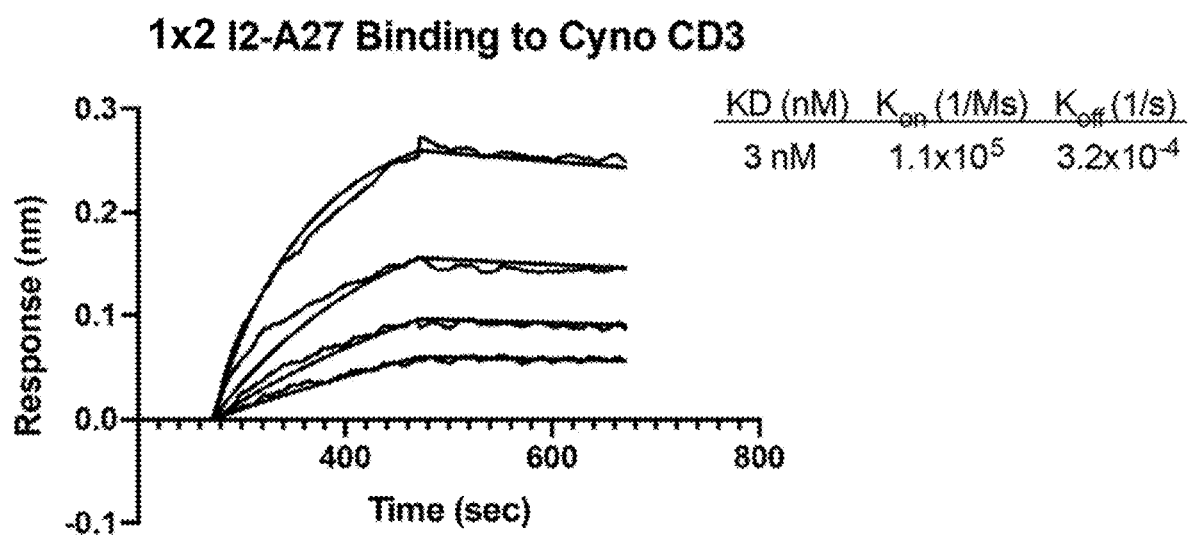

FIG. 64A shows binding of SP34-89 to Jurkat and cynomolgus T cells. FIG. 64B shows binding of an 12-A27 1×2 B-body™ bispecific antibody to cynomolgus CD3 delta and epsilon heterodimer.

Figure 65A:
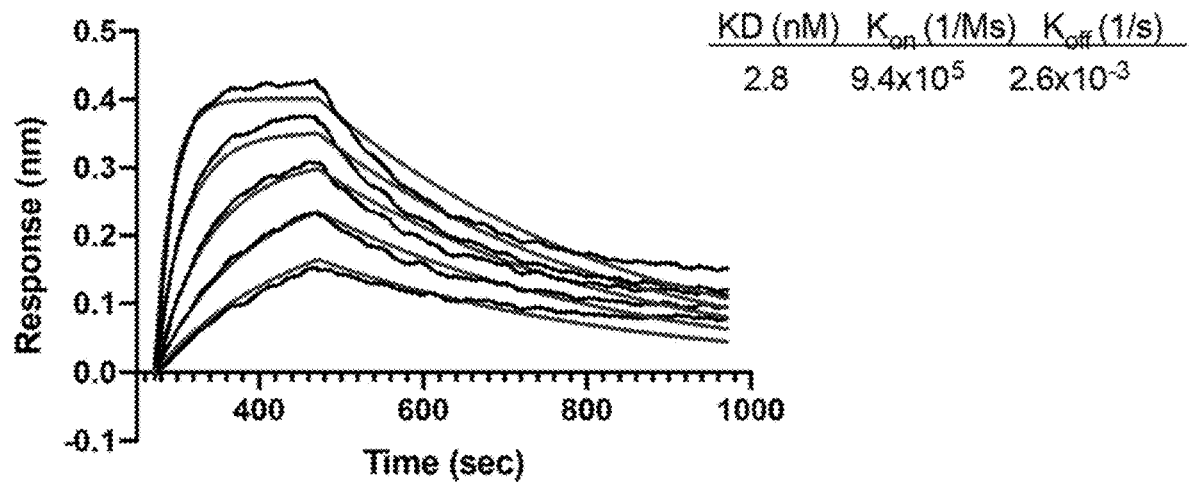
Figure 65B:
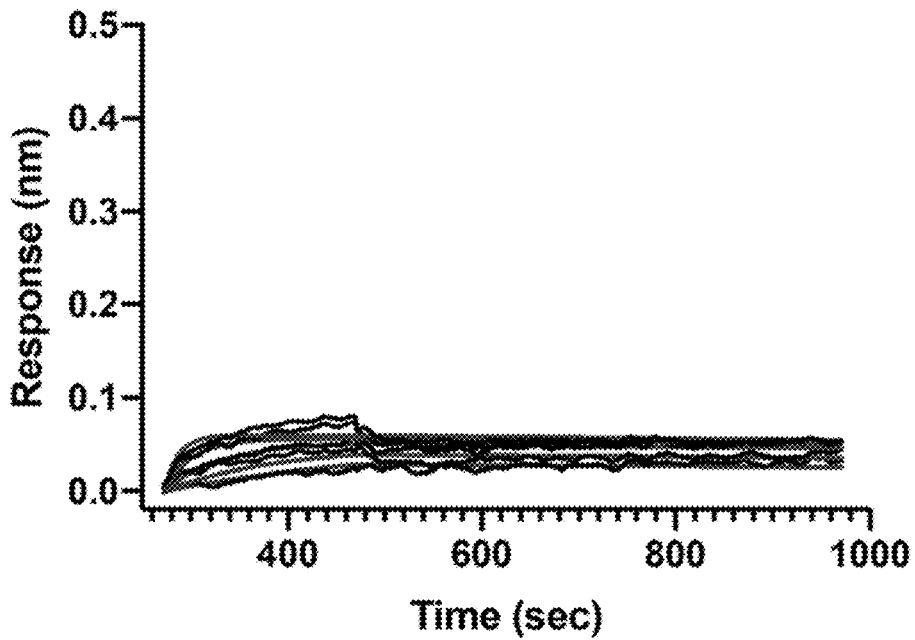
Figure 65C:
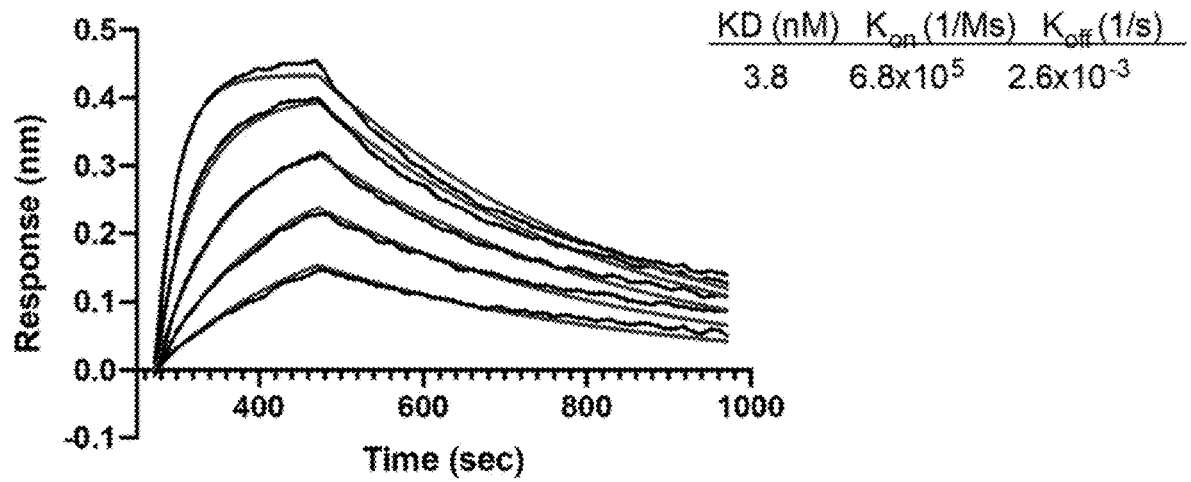

FIG. 65A shows binding of an 12-A27 IgG antibody to ROR1 in a monovalent binding assay. FIG. 65B shows minimal binding of an 12-A27 IgG antibody to ROR2. FIG. 65C shows binding of an 12-A27 1×2 B-body™ to ROR1 in a monovalent binding assay.

Figure 65D:
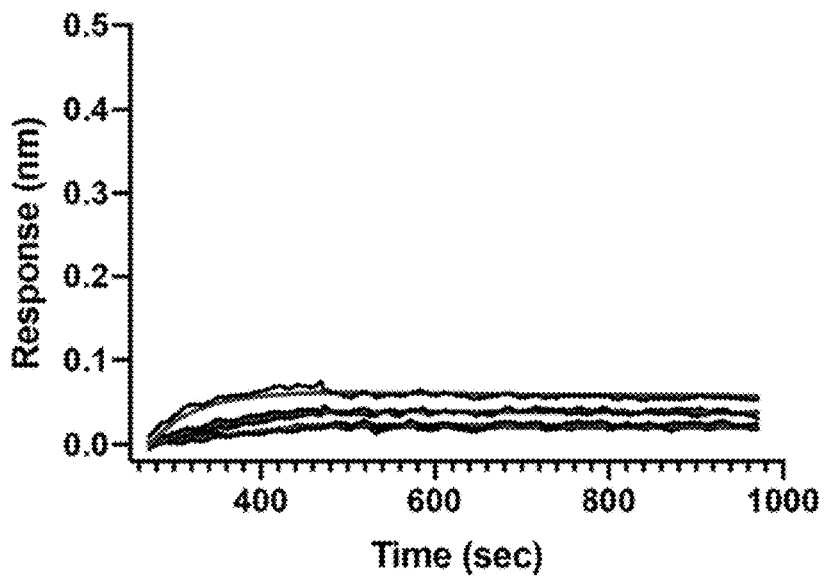
Figure 65E:
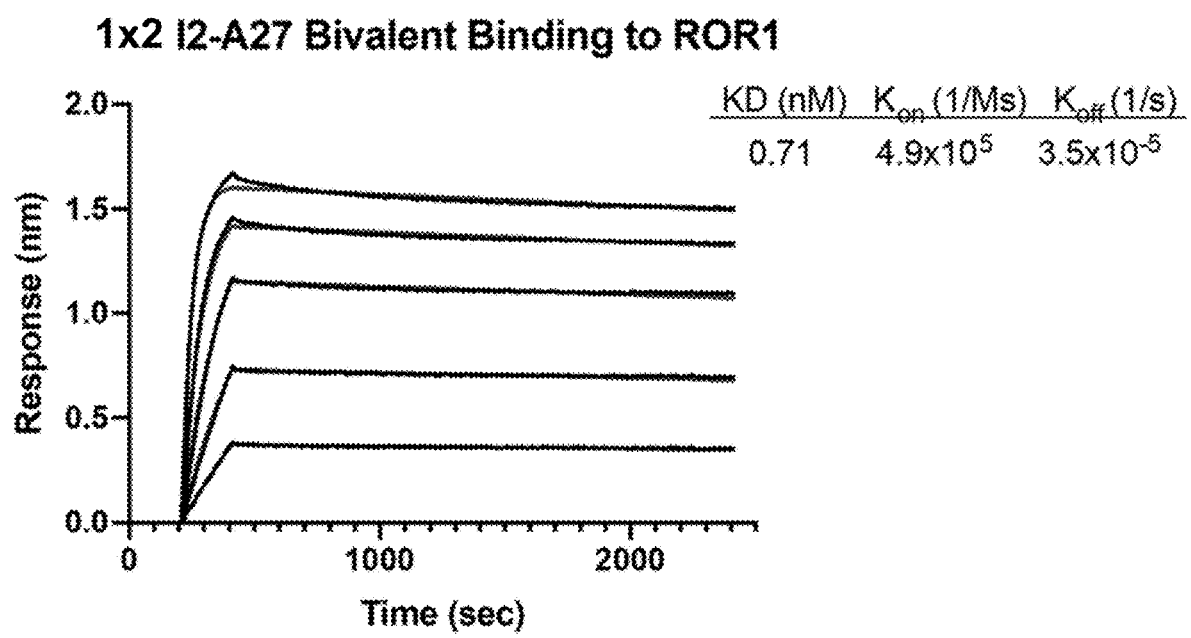

FIG. 65D shows minimal binding of an 12-A27 1×2 B-body™ to ROR2. FIG. 65E shows binding of an 12-A27 1×2 B-body™ to ROR1 in a bivalent binding assay.

Figure 66A:
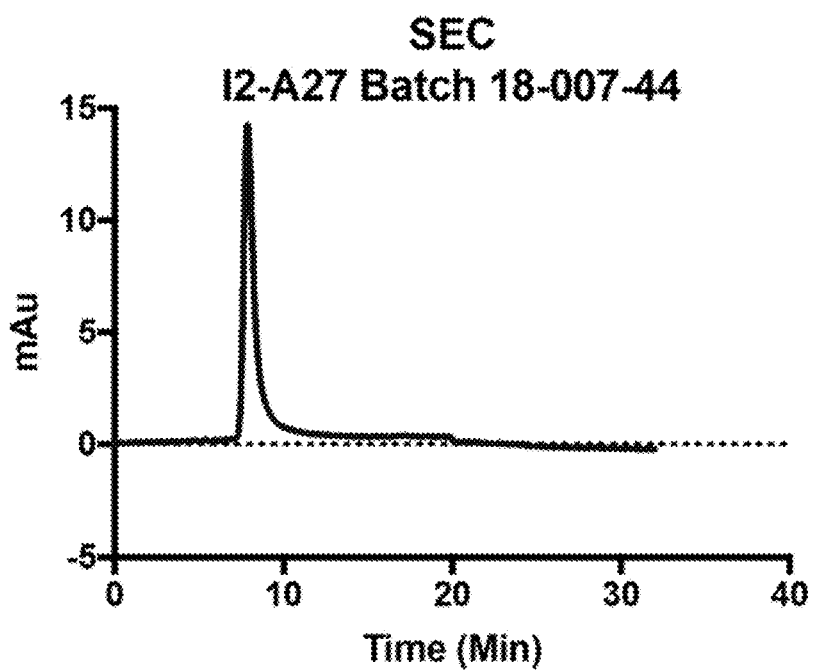
Figure 66B:
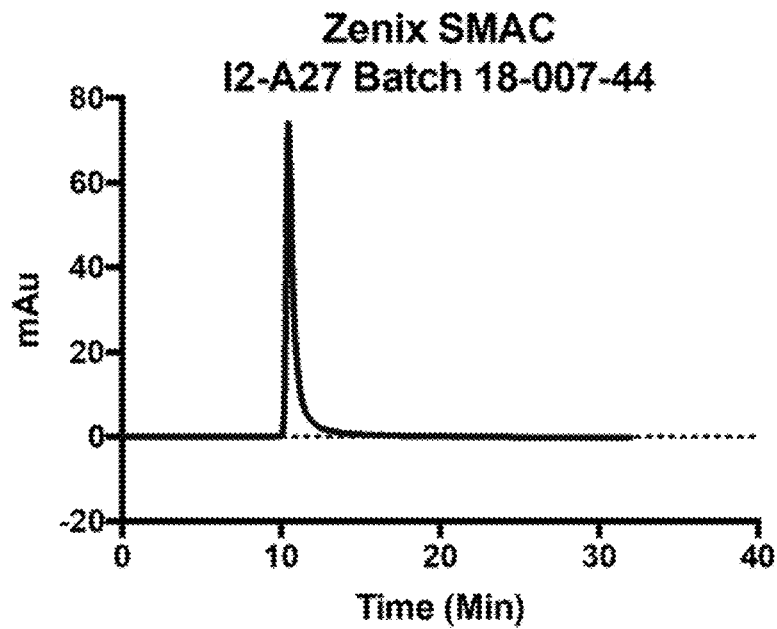
Figure 66C:
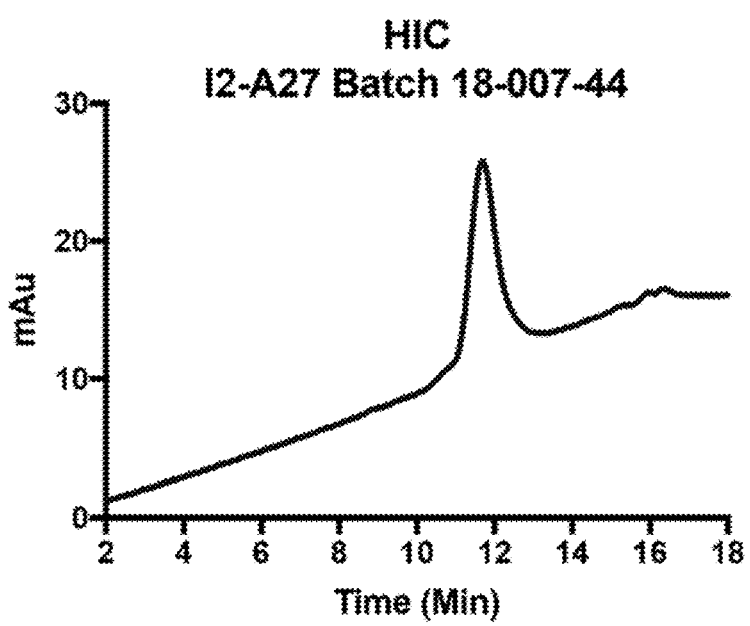

FIG. 66A shows SEC analysis of an 12-A27 1×2 B-body™. FIG. 66B shows SMAC analysis of an 12-A27 1×2 B-body™. FIG. 66C shows HIC analysis of an 12-A27 1×2 B-body™.

Figure 67A:
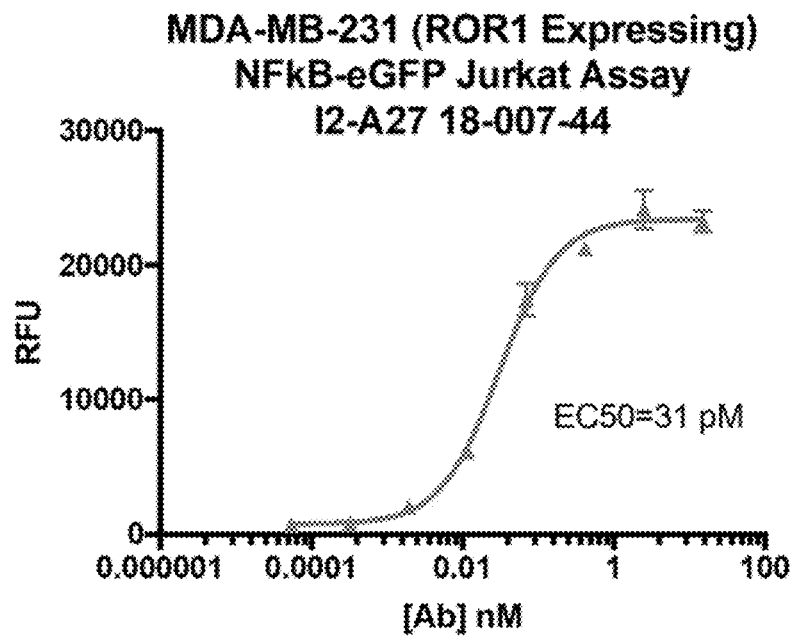
Figure 67B:
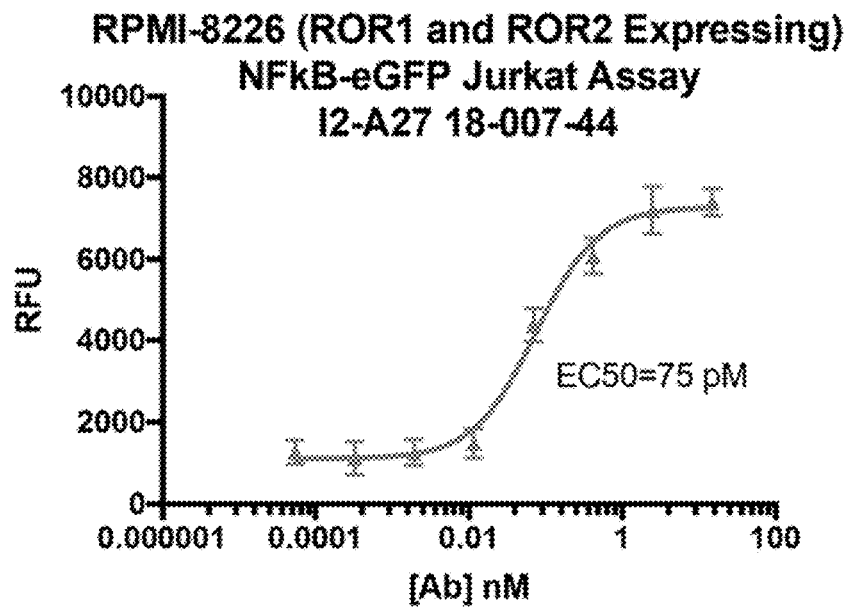
Figure 67C:
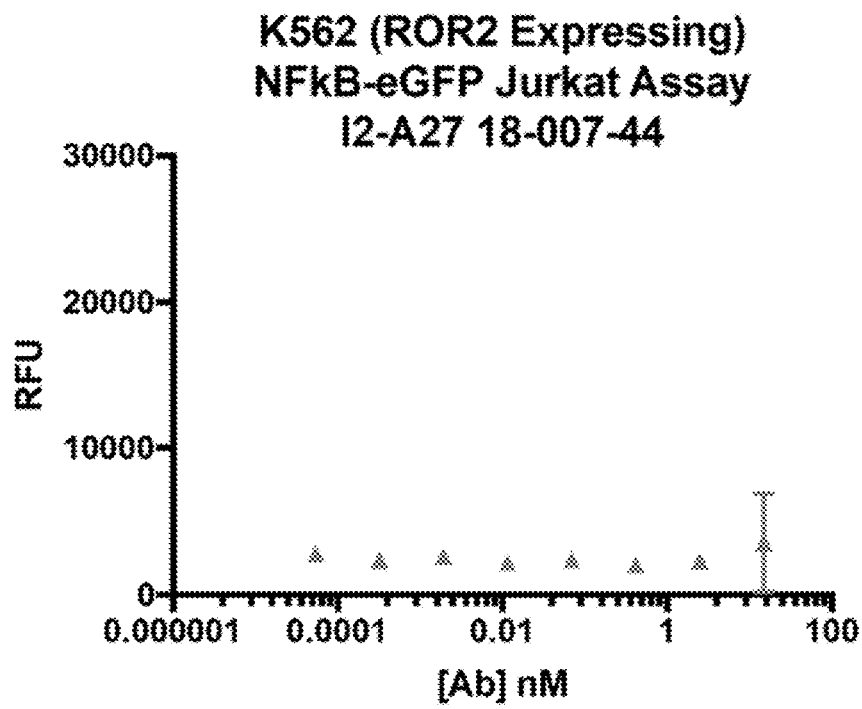

FIG. 67A shows activity of an 12-A27 1×2 B-body™ in a Jurkat assay with MDA-MB-231 (ROR1 expressing) cells. FIG. 67B shows activity of an 12-A27 1×2 B-body™ in a Jurkat assay with RPMI-8226 (ROR1 and ROR2 expressing) cells. FIG. 67C shows inactivity of an 12-A27 1×2 B-body™ in a Jurkat assay with K562 (ROR2 expressing) cells.

Figure 67D:
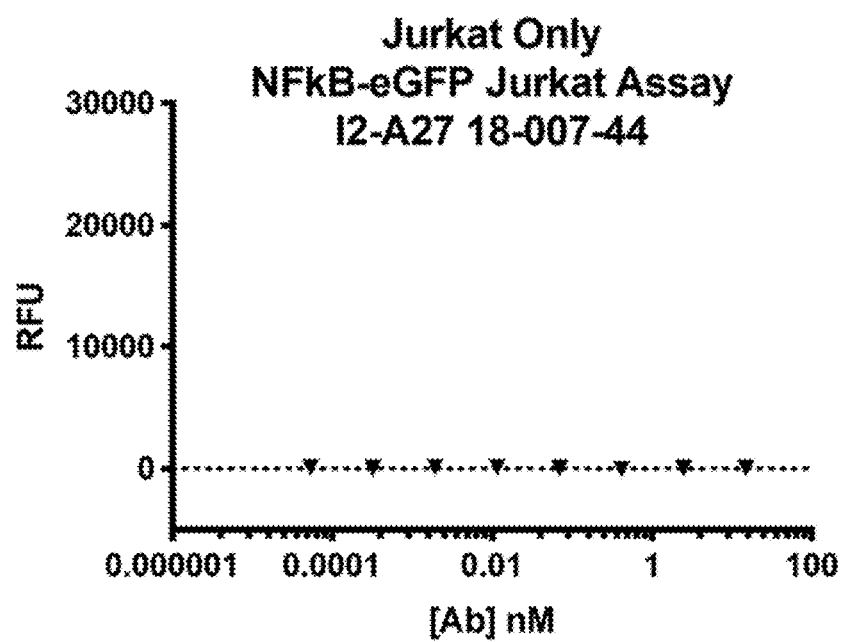

FIG. 67D shows inactivity of an 12-A27 1×2 B-body™ in a Jurkat assay in the absence of a target cell line.

Figure 68A:
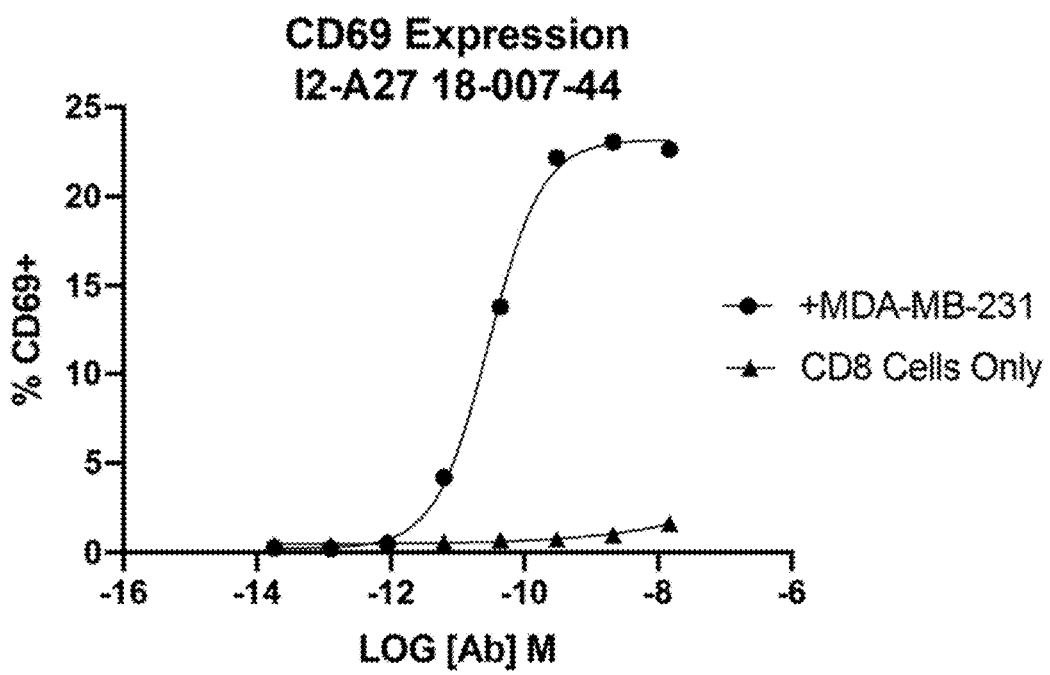
Figure 68B:
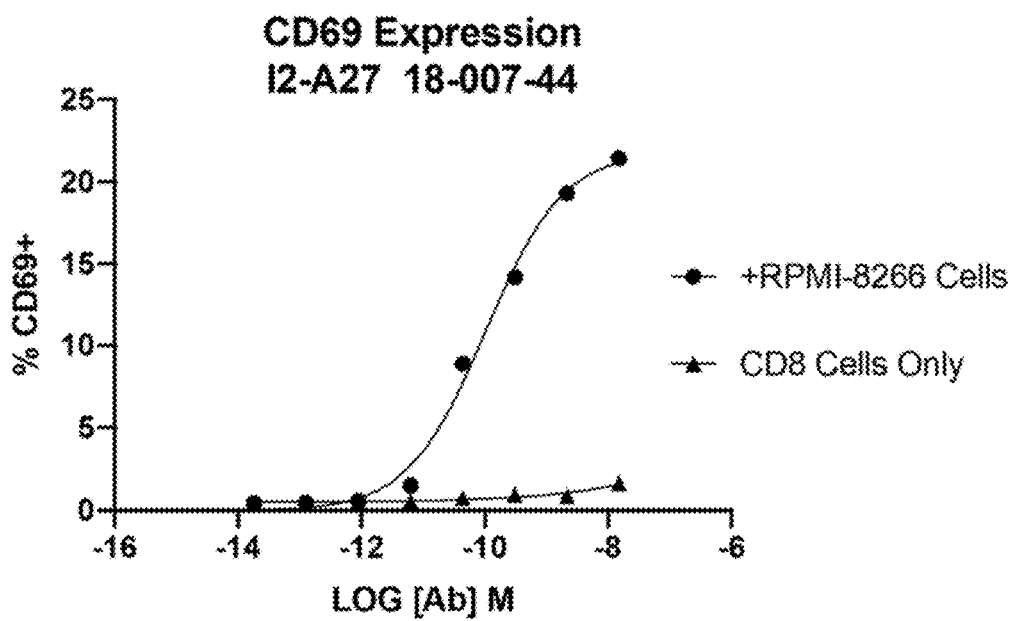

FIG. 68A shows CD69 expression with various concentrations of an 12-A27 1×2 B-body™ and ROR1 expressing MDA-MB-231 cells. FIG. 68B shows CD69 expression with various concentrations of an 12-A27 1×2 B-body™ and ROR1 expressing RPMI-8226 cells.

Figure 68C:
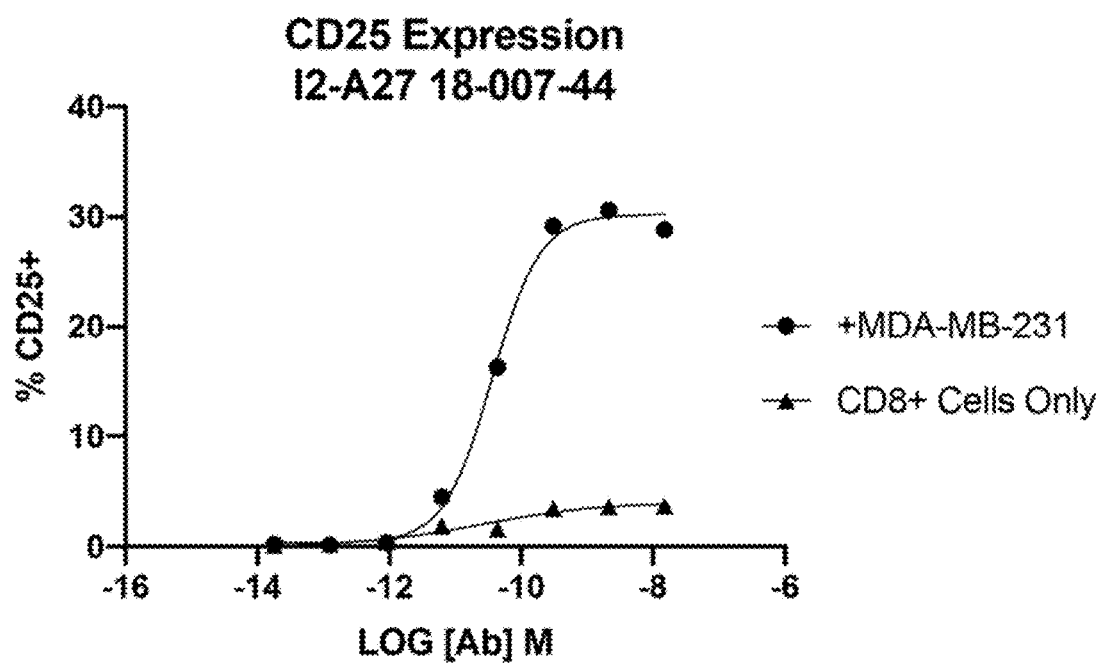
Figure 68D:
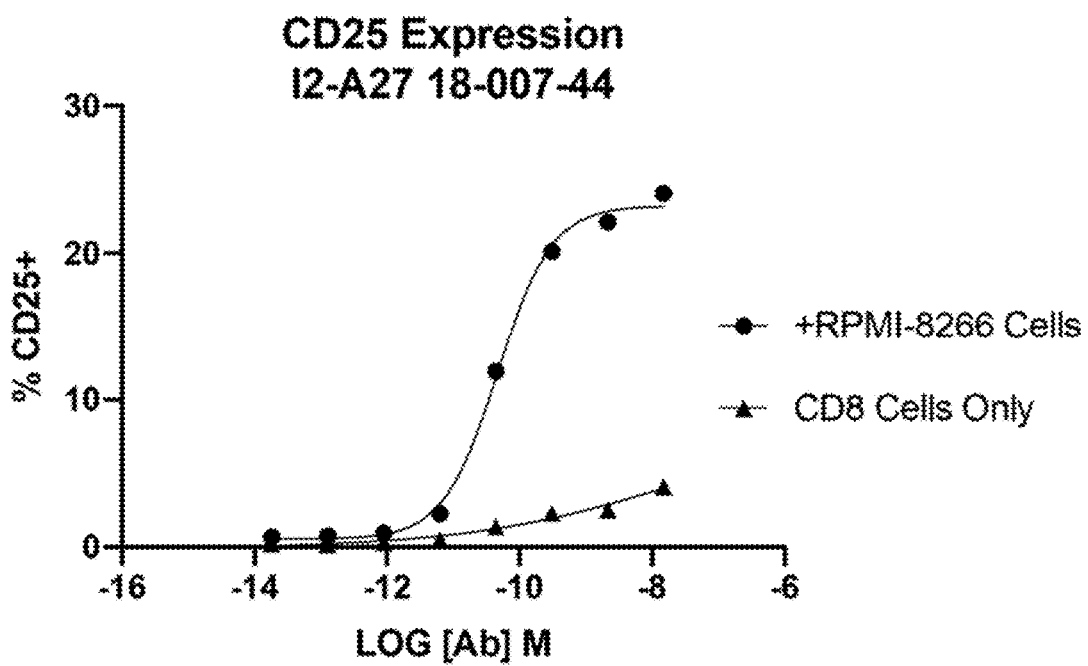

FIG. 68C shows CD25 expression with various concentrations of an 12-A27 1×2 B-body™ and ROR1 expressing MDA-MB-231 cells. FIG. 68D shows CD25 expression with various concentrations of an 12-A27 1×2 B-body™ and ROR1 expressing RPMI-8226 cells.

Figure 69A:
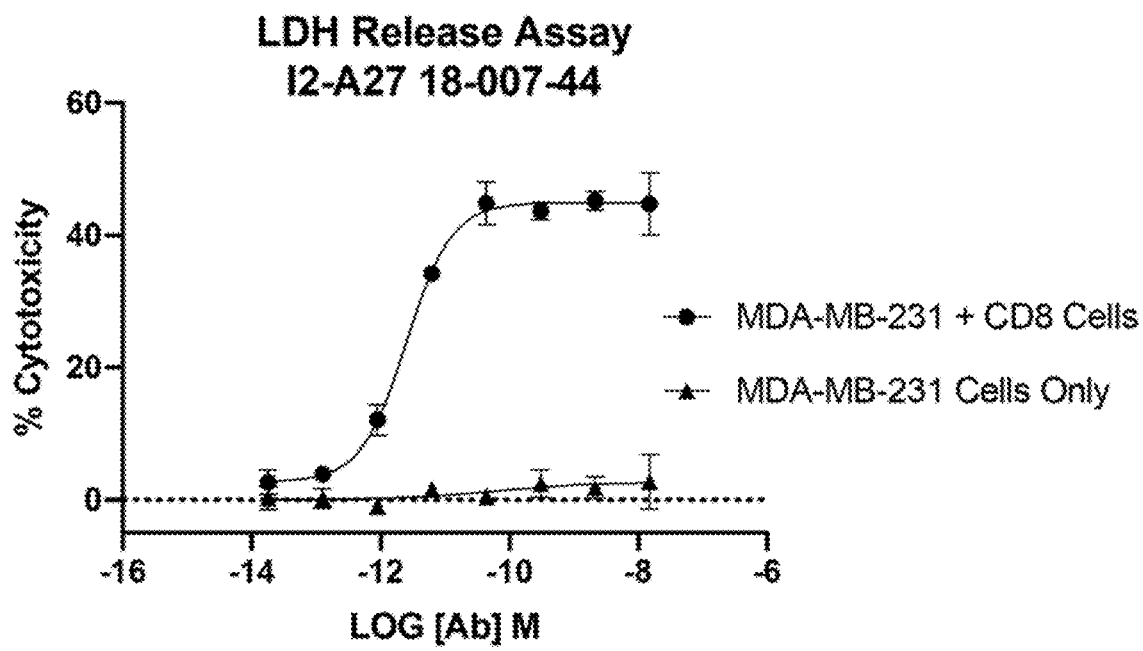
Figure 69B:
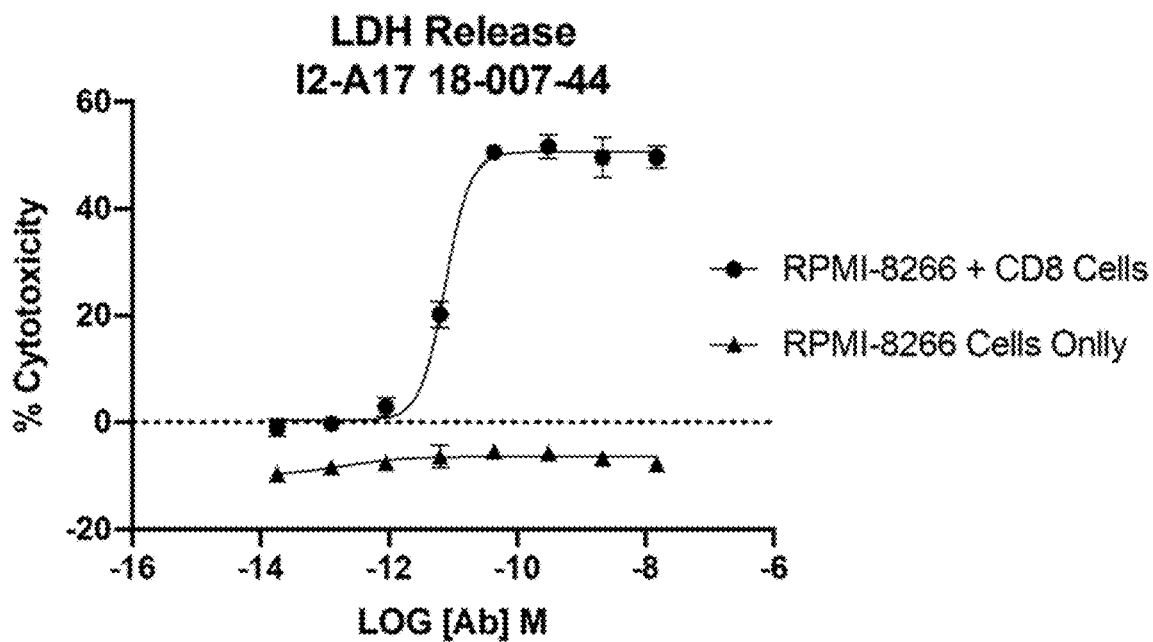

FIG. 69A shows LDH release with various concentrations of an 12-A27 1×2 B-body™ and ROR1 expressing MDA-MB-231 cells. FIG. 69B shows LDH release with various concentrations of an 12-A27 1×2 B-body™ and ROR1 expressing RPMI-8226 cells.

Figure 70A:
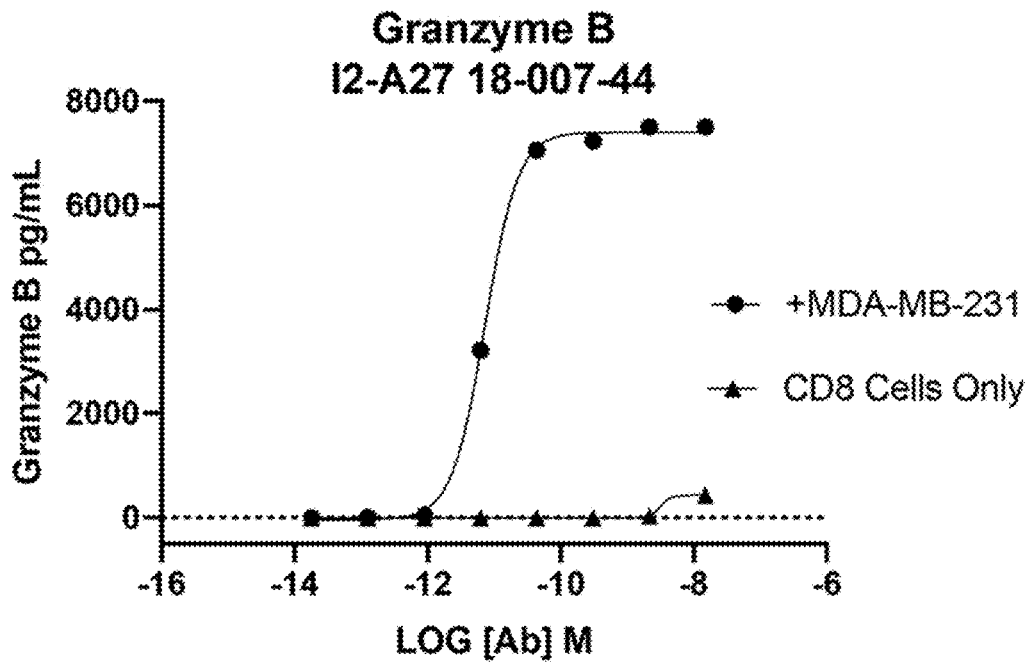
Figure 70B:
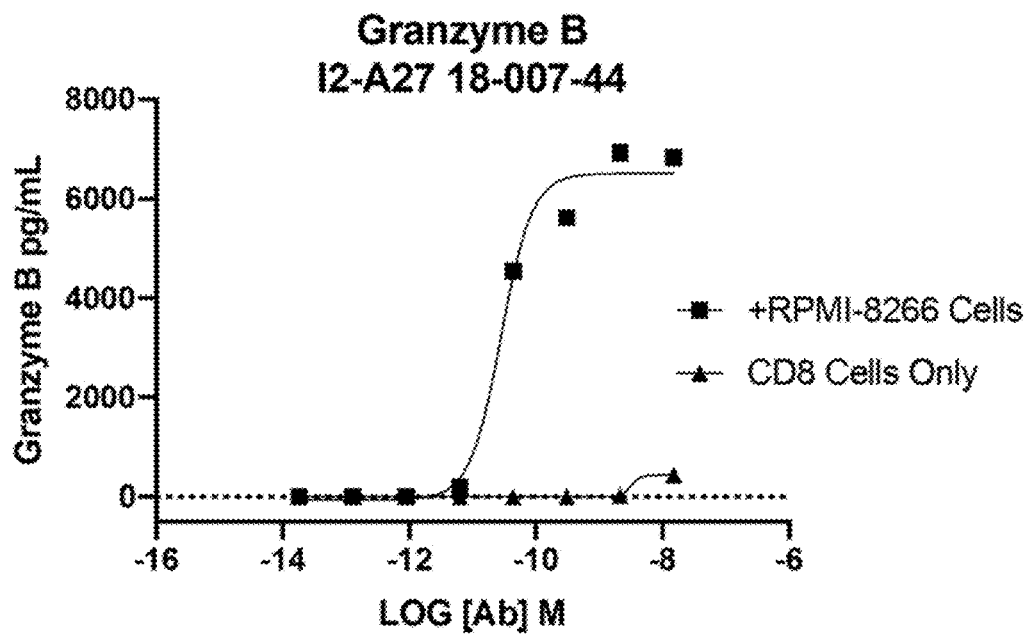

FIG. 70A shows Granzyme B with various concentrations of an 12-A27 1×2 B-body™ and ROR1 expressing MDA-MB-231 cells. FIG. 70B shows Granzyme B with various concentrations of an 12-A27 1×2 B-body-™ and ROR1 expressing RPMI-8226 cells.

Figure 70C:
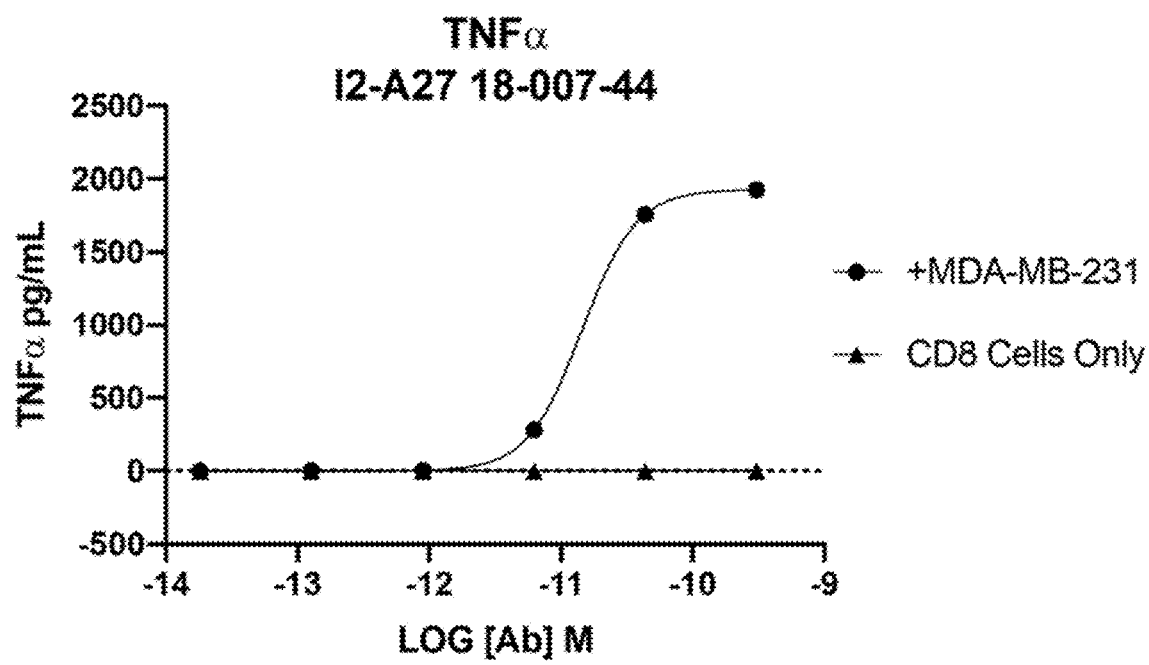
Figure 70D:
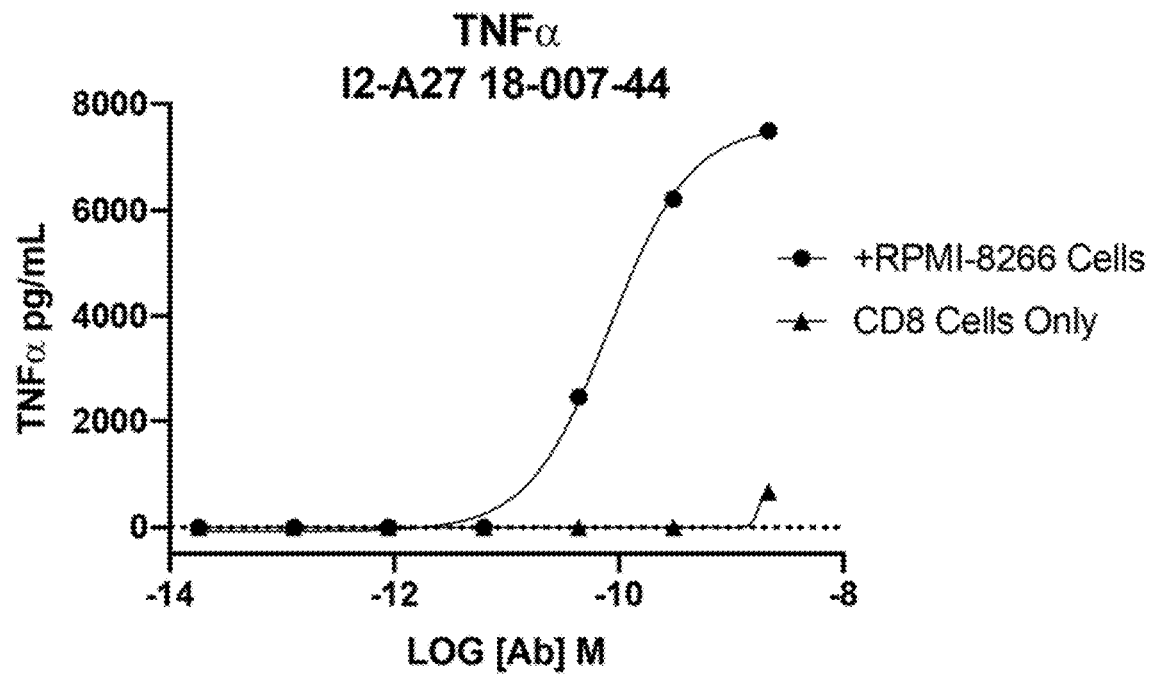
Figure 70E:
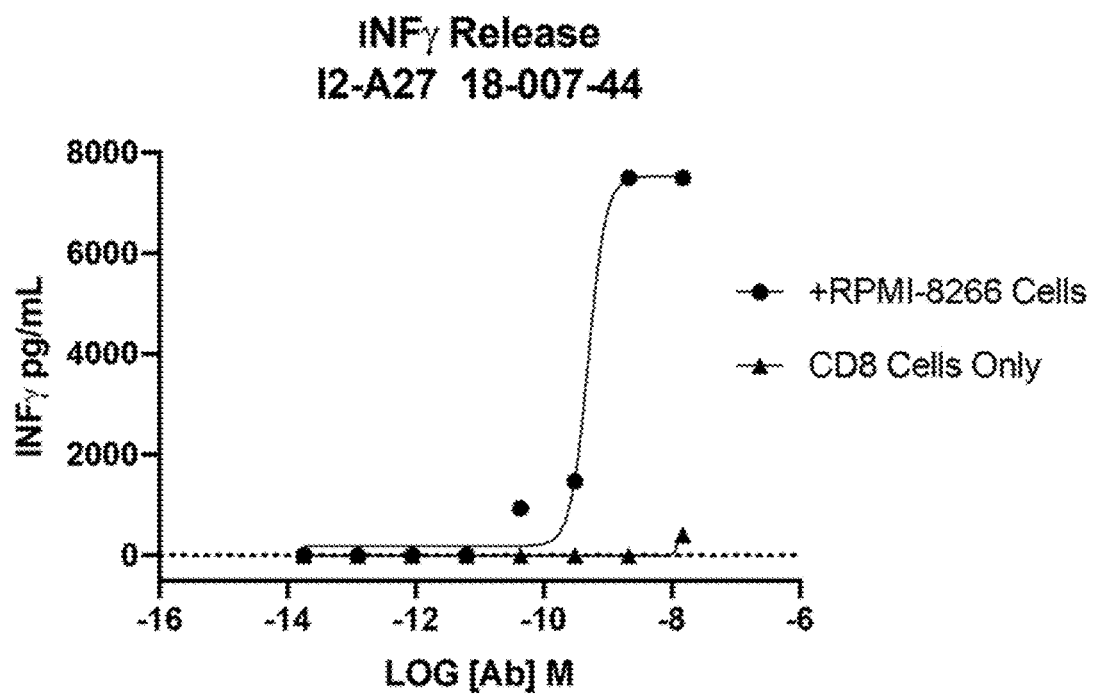
Figure 70F:
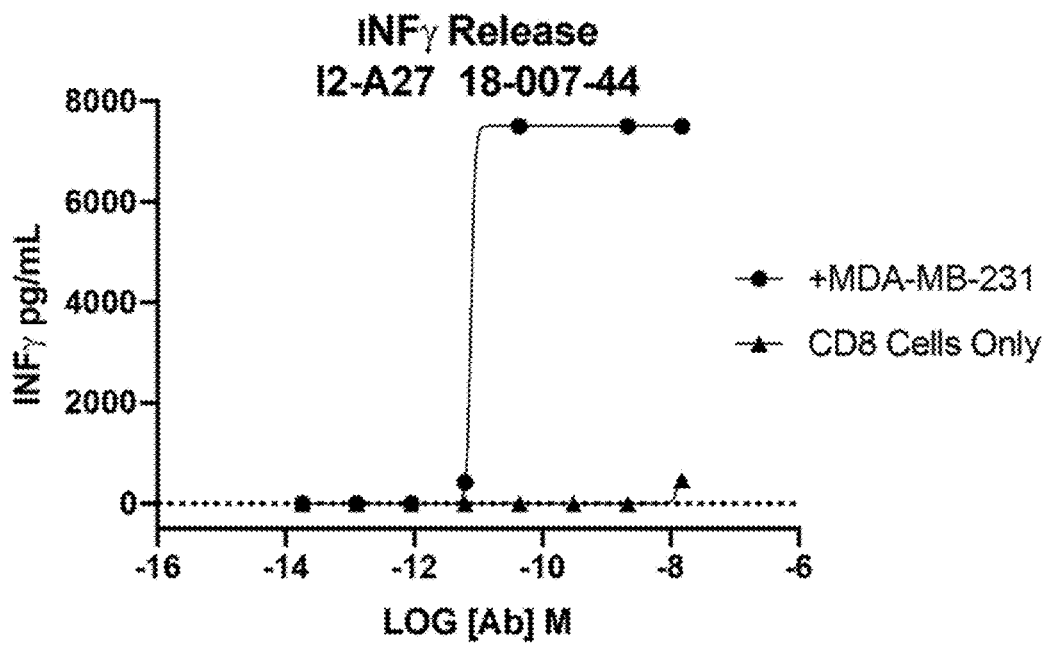

FIG. 70C shows TNFα secretion with various concentrations of an 12-A27 1×2 B-body™ and ROR1 expressing MDA-MB-231 cells. FIG. 70D shows TNFα secretion with various concentrations of an 12-A27 1×2 B-body™ and ROR1 expressing RPMI-8226 cells. FIG. 70E shows IFNγ release with various concentrations of an 12-A27 1×2 B-body™ and ROR1 expressing MDA-MB-231 cells. FIG. 70F shows IFNγ release with various concentrations of an 12-A27 1×2 B-body™ and ROR1 expressing RPMI-8226 cells.

Figure 71A:
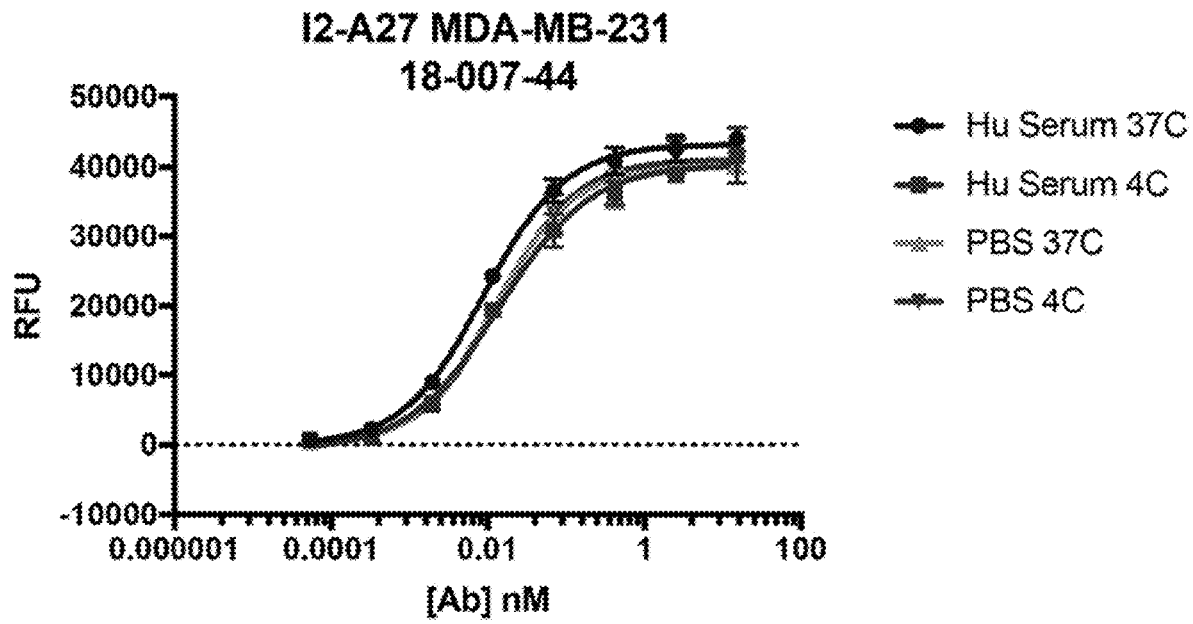
Figure 71B:
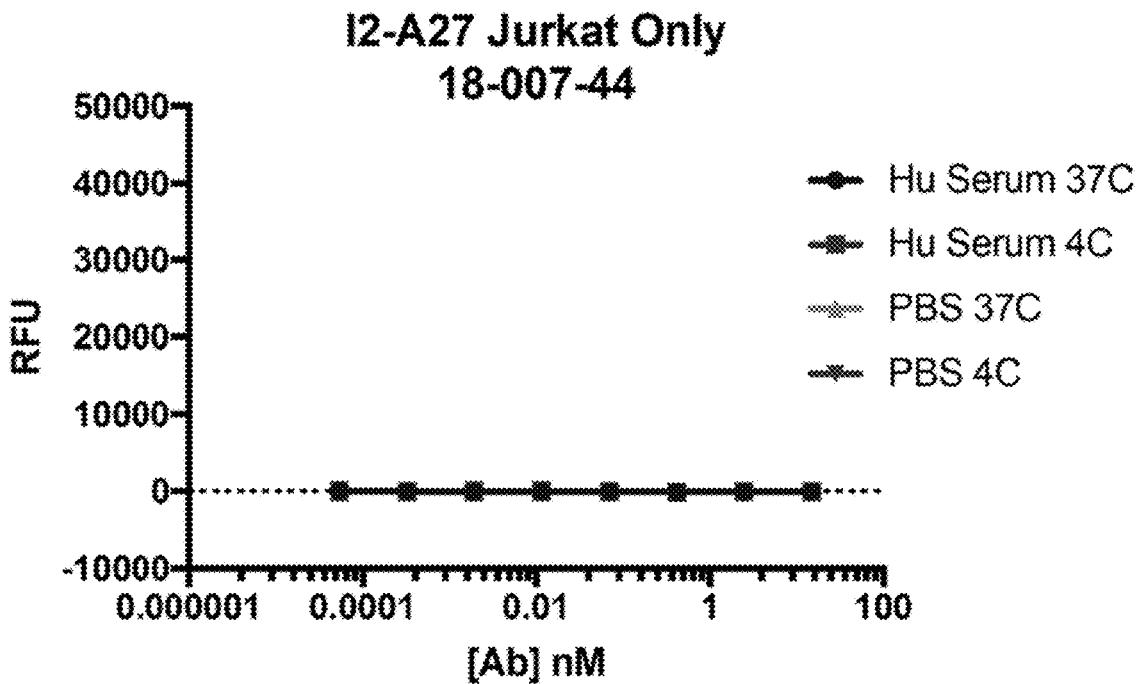

FIG. 71A shows activity for 12-A27 1×2 B-body™ samples stored in human serum at 4° C. or 37° C. for 1 week. FIG. 71B shows inactivity of samples in a Jurkat assay in the absence of ROR1 expressing cells.

Figure 72:
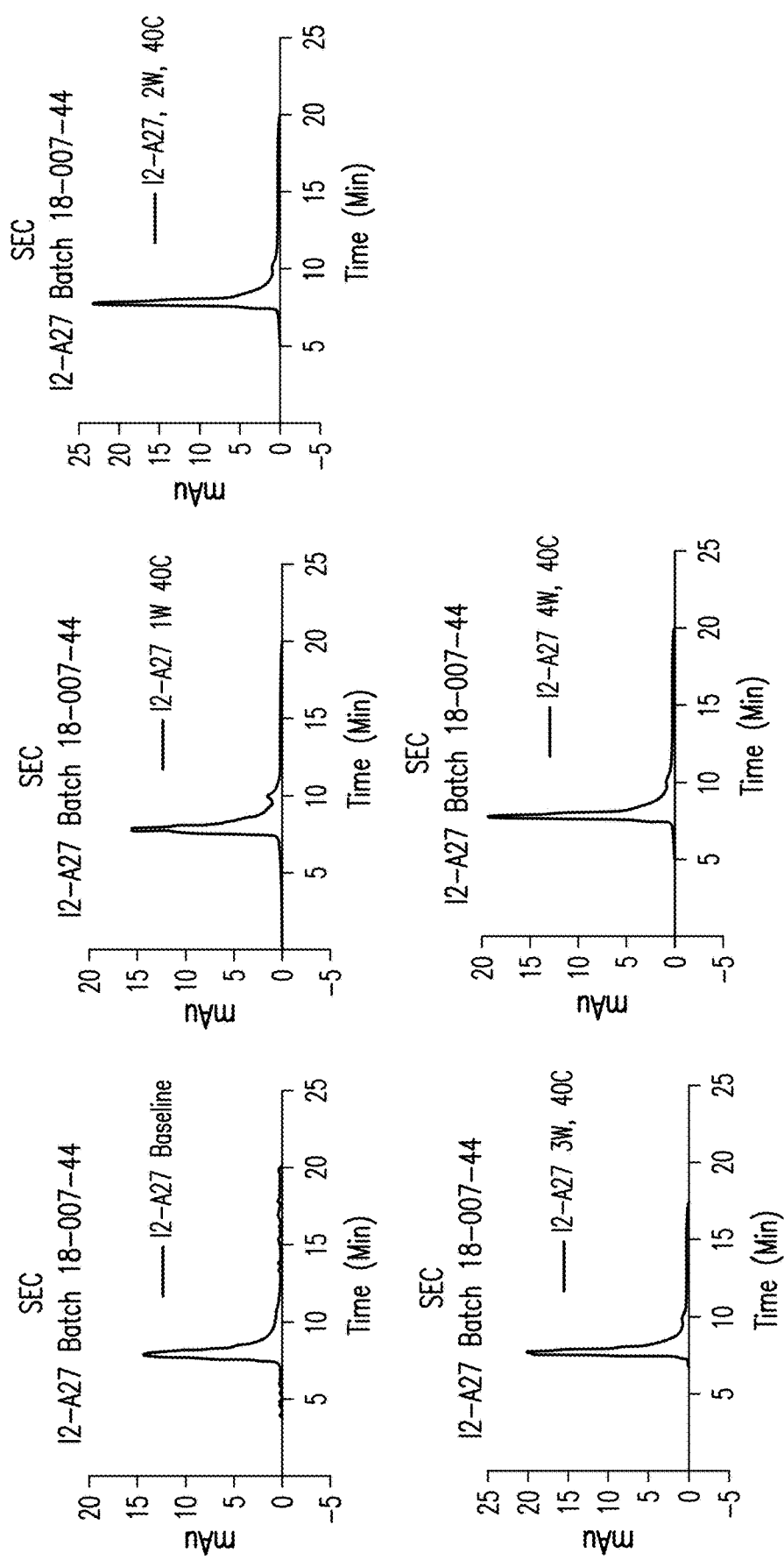

FIG. 72 shows stability assays of 12-A27 1×2 B-body™ samples under accelerated conditions.

Figure 73:
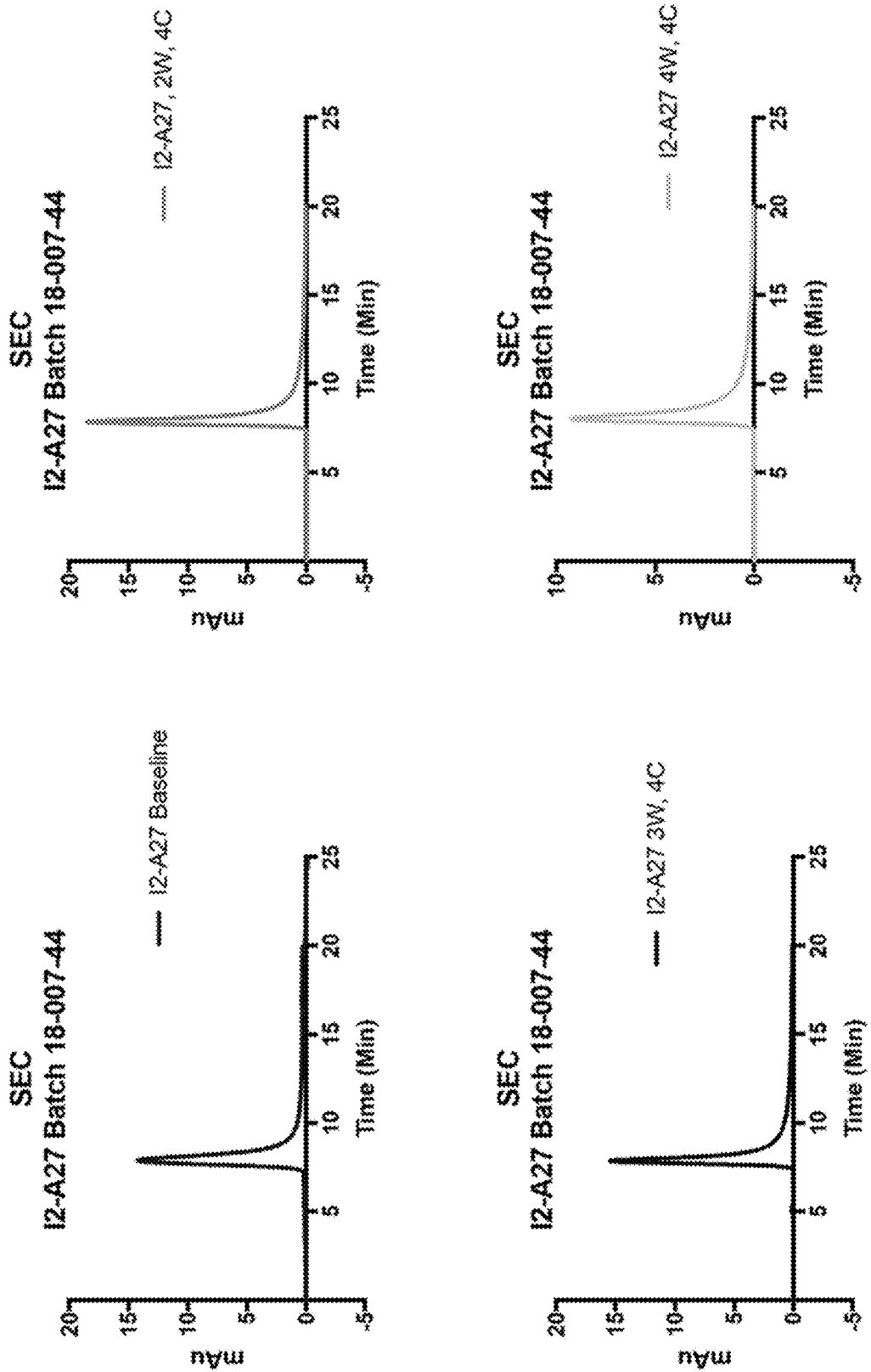

FIG. 73 shows stability assays of 12-A27 1×2 B-body™ samples under real time conditions.

Figure 74:
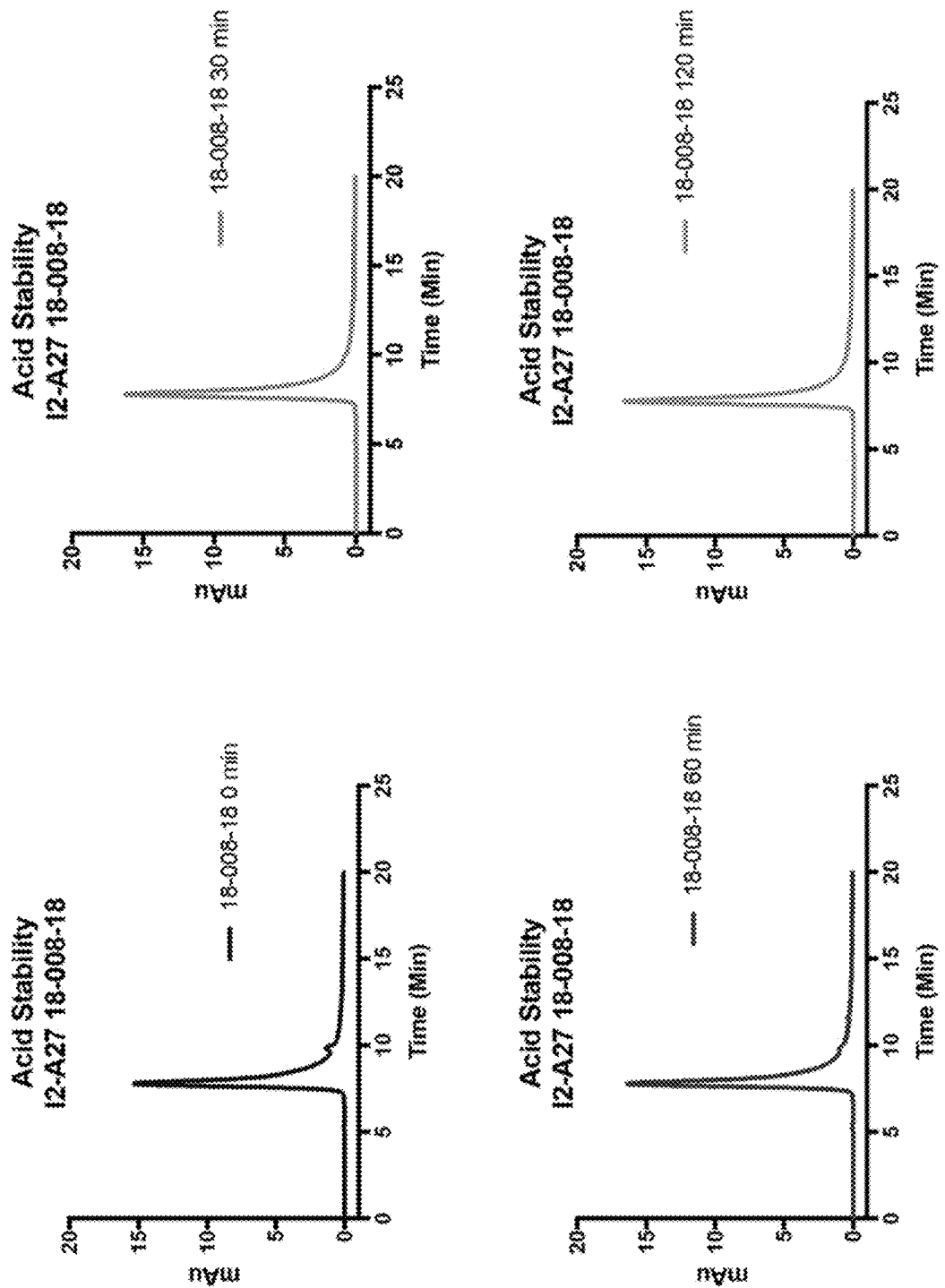

FIG. 74 shows acid stability assays of an 12-A27 1×2 B-body™.

Figure 75:
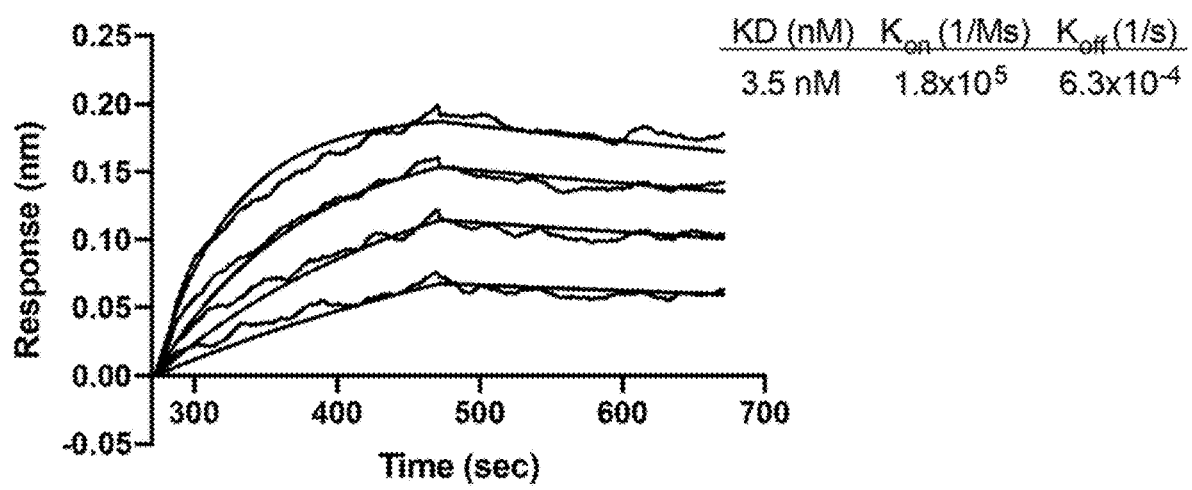

FIG. 75 shows binding of an 12-A10 D54E Y55Q 1×2 B-body™ to cynomolgus CD3 delta and epsilon heterodimer.

Figure 76A:
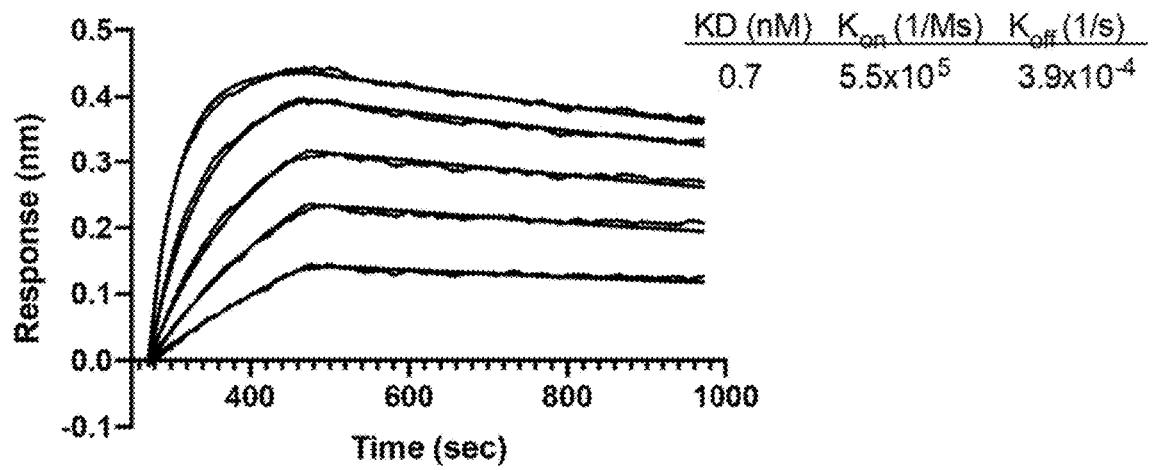
Figure 76B:
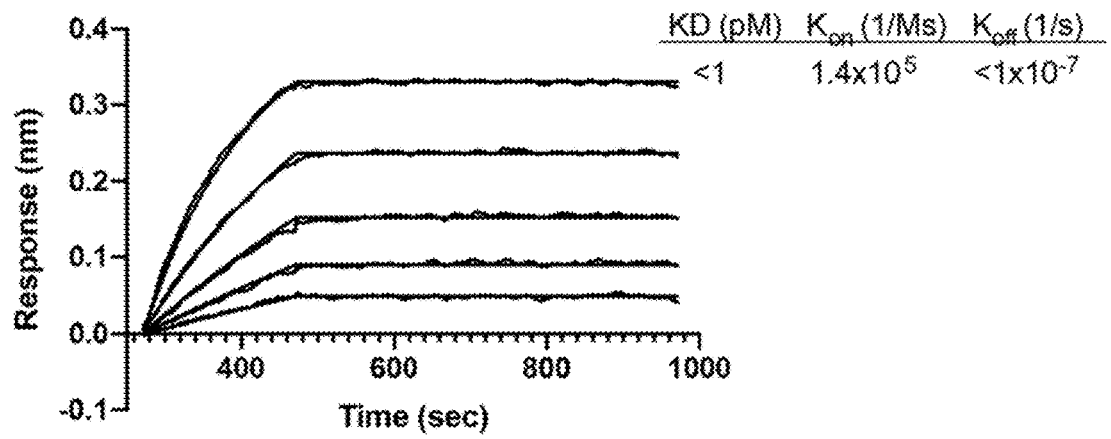
Figure 76C:
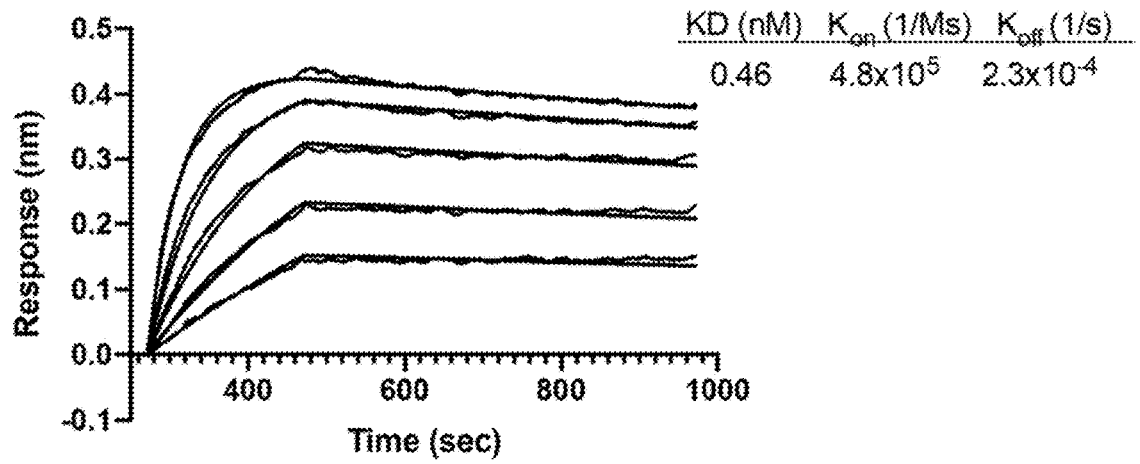
Figure 76D:
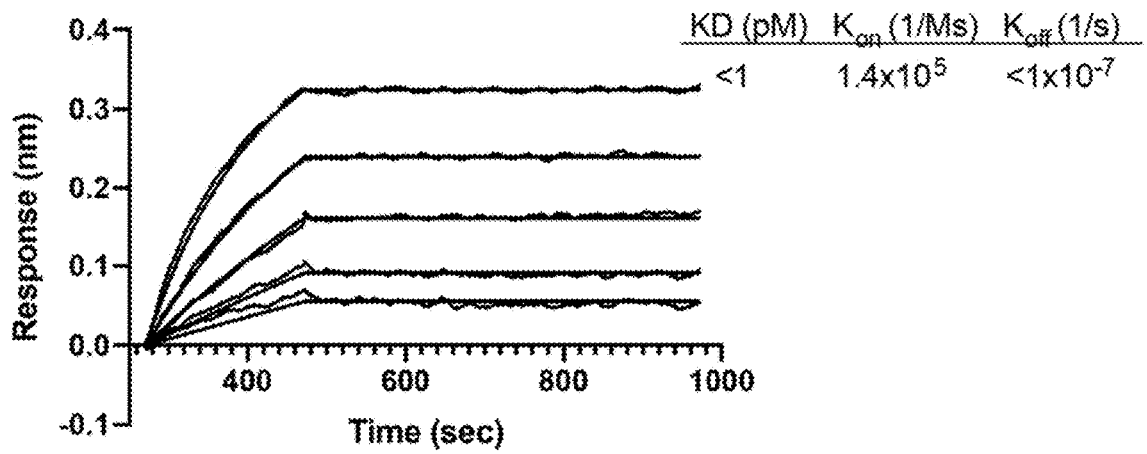
Figure 76E:
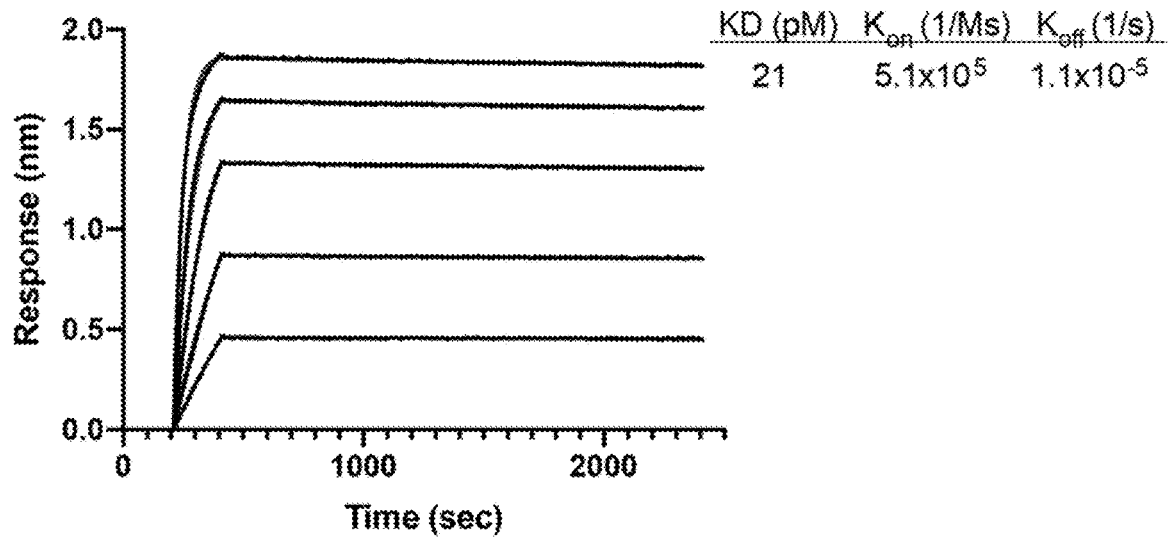
Figure 76F:
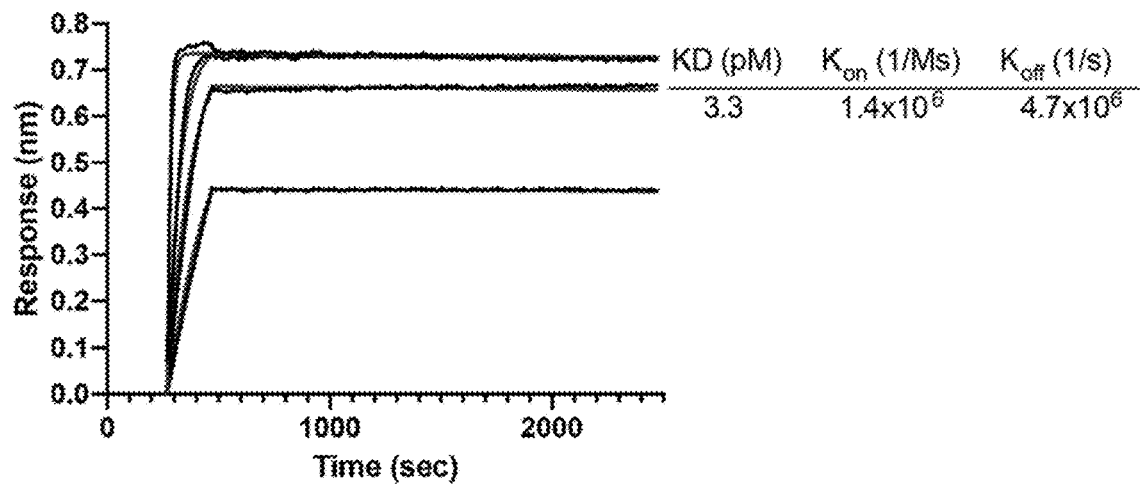

FIG. 76A shows binding of an 12-A10 D54E Y55Q IgG antibody to ROR1 in an monovalent binding assay. FIG. 76B shows binding of an 12-A10 D54E Y55Q IgG to ROR2 in a monovalent binding assay. FIG. 76C shows binding of an 12-A10 D54E Y55Q 1×2 B-body™ to ROR1 in a monovalent binding assay. FIG. 76D shows binding of an 12-A10 D54E Y55Q 1×2 B-body™ to ROR2 in a monovalent binding assay. FIG. 76E shows binding of an 12-A10 D54E Y55Q 1×2 B-body™ to ROR1 in a bivalent binding assay. FIG. 76F shows binding of an 12-A10 D54E Y55Q 1×2 B-body™ to ROR2 in a bivalent binding assay.

Figure 77:
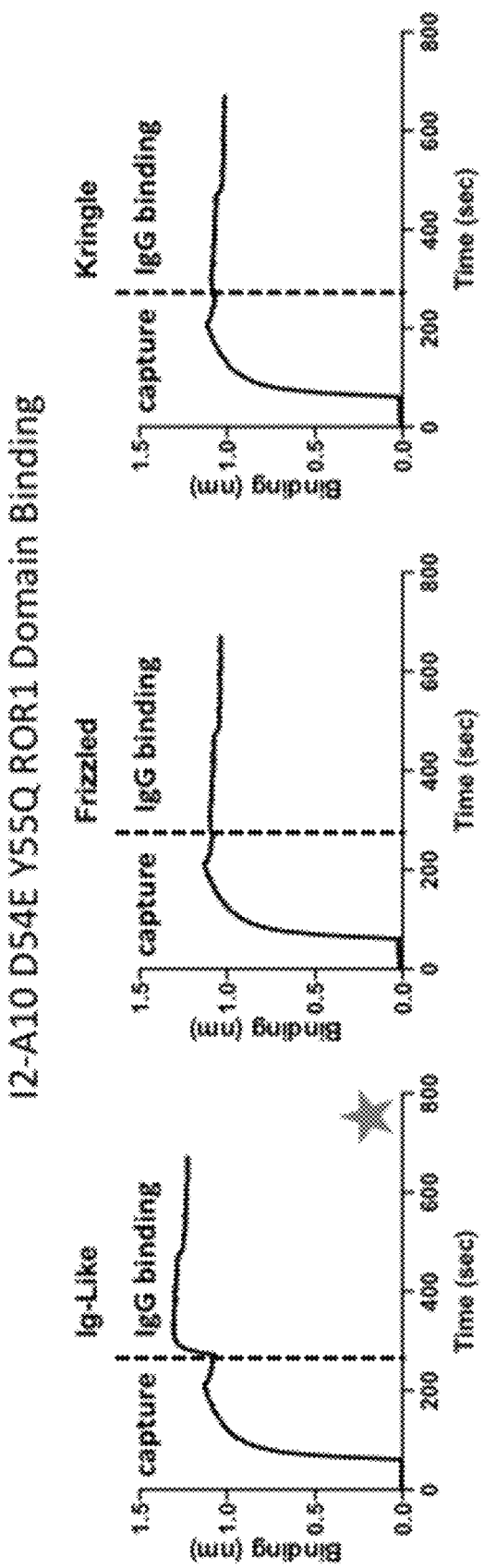

FIG. 77 shows binding of an 12-A10 D54E Y55Q 1×2 B-body™ to Ig-like domain of ROR.

Figure 78A:
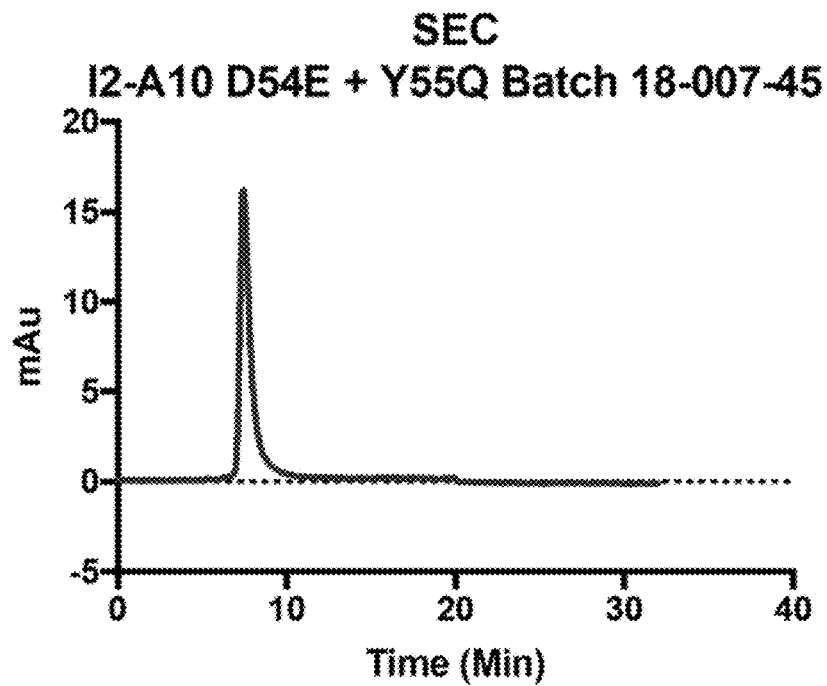
Figure 78B:
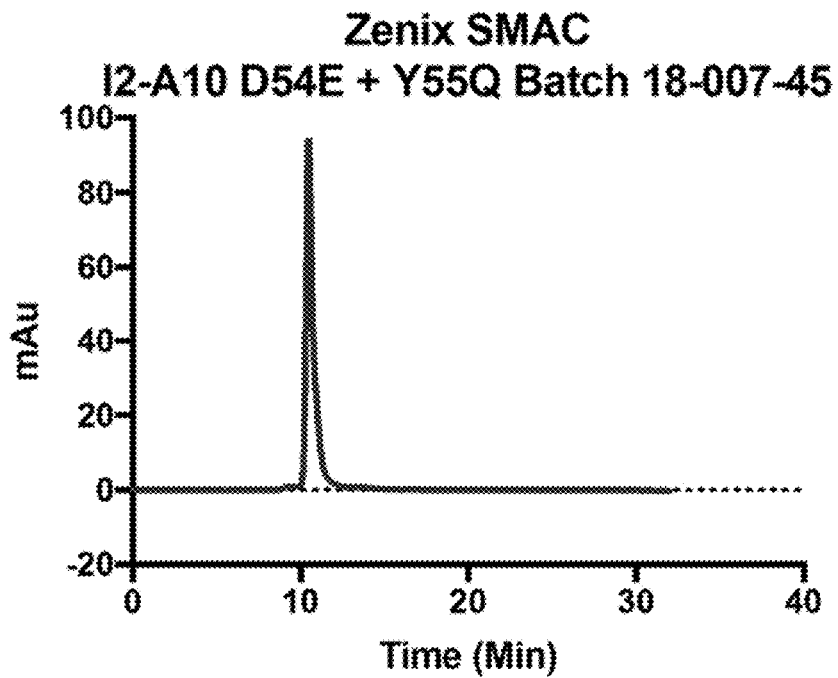
Figure 78C:
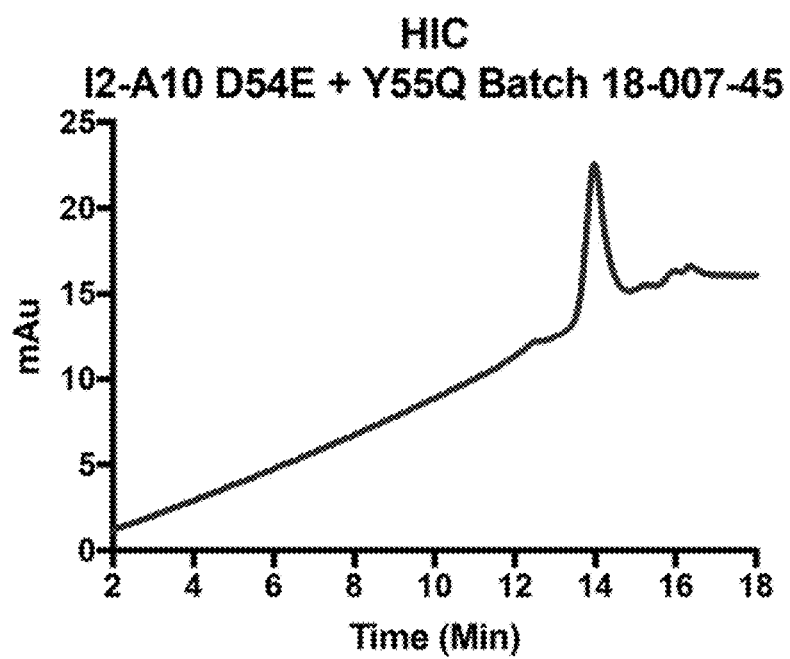

FIG. 78A shows SEC analysis of an 12-A10 D54E Y55Q 1×2 B-body™. FIG. 78B shows SMAC analysis of an 12-A10 D54E Y55Q 1×2 B-body™. FIG. 78C shows HIC analysis of an 12-A10 D54E Y55Q 1×2 B-body™.

Figure 79A:
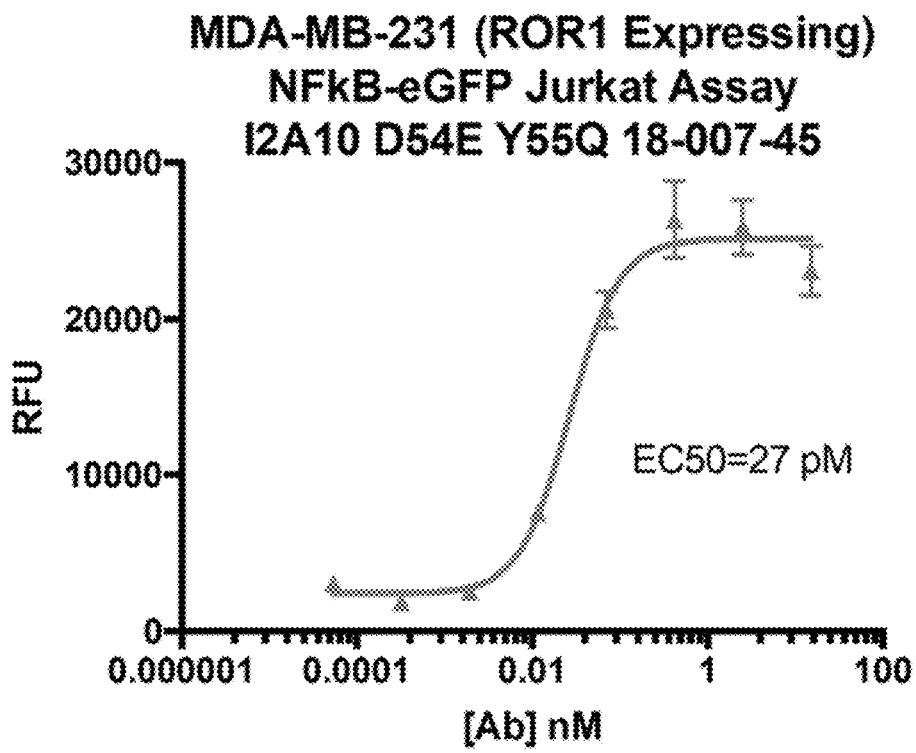
Figure 79B:
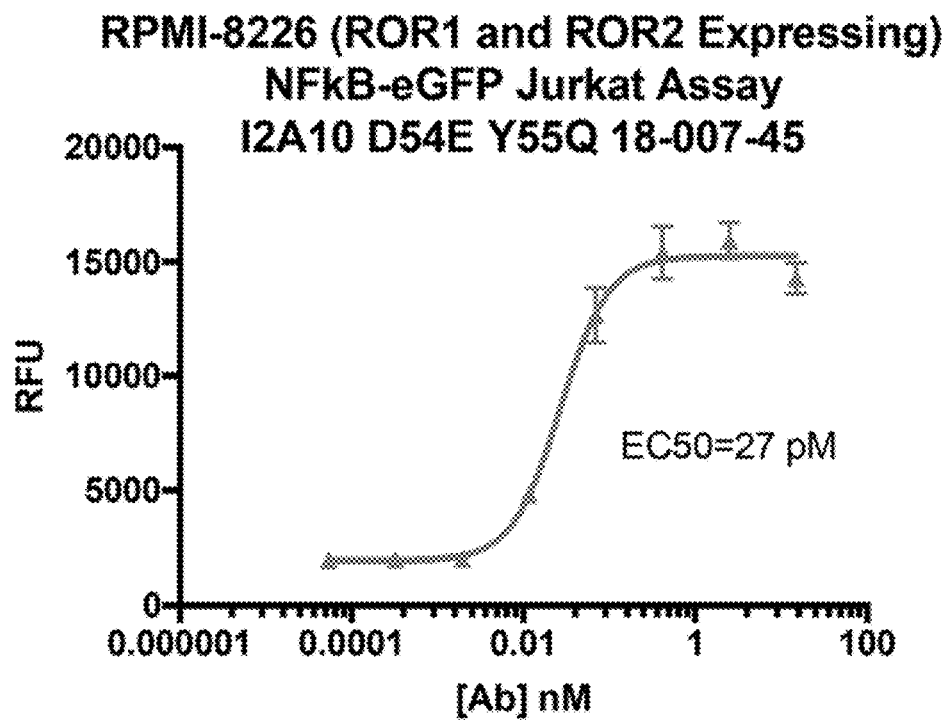

FIG. 79A shows activity of an 12-A10 D54E Y55Q 1×2 B-body™ in Jurkat assay with MDA-MB-231 (ROR1 expressing) cells. FIG. 79B shows activity of an 12-A10 D54E Y55Q 1×2 B-body™ in a Jurkat assay with RPMI-8226 (ROR1 and ROR2 expressing) cells.

Figure 79C:
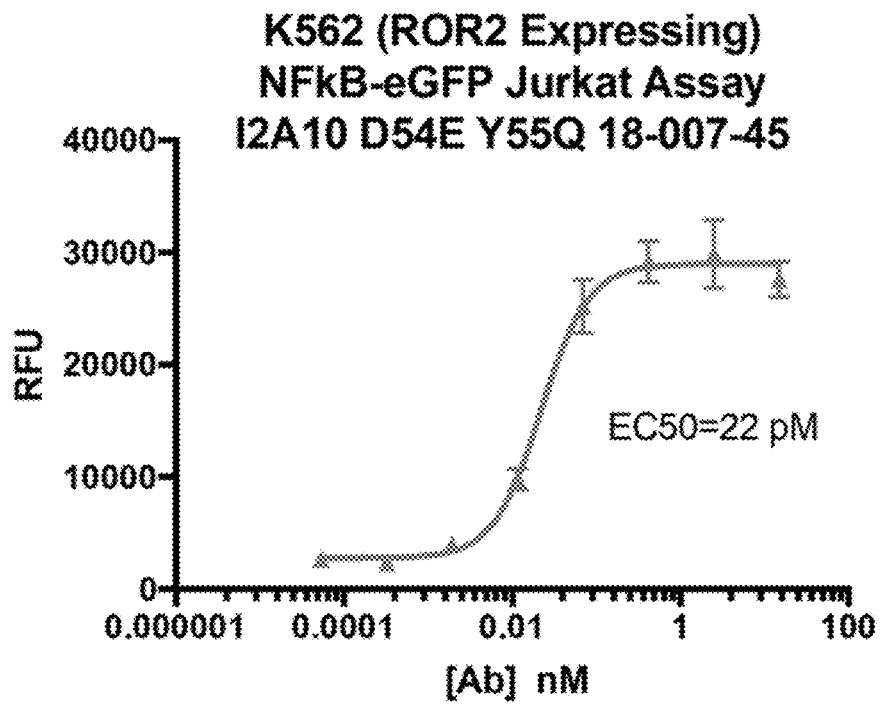
Figure 79D:
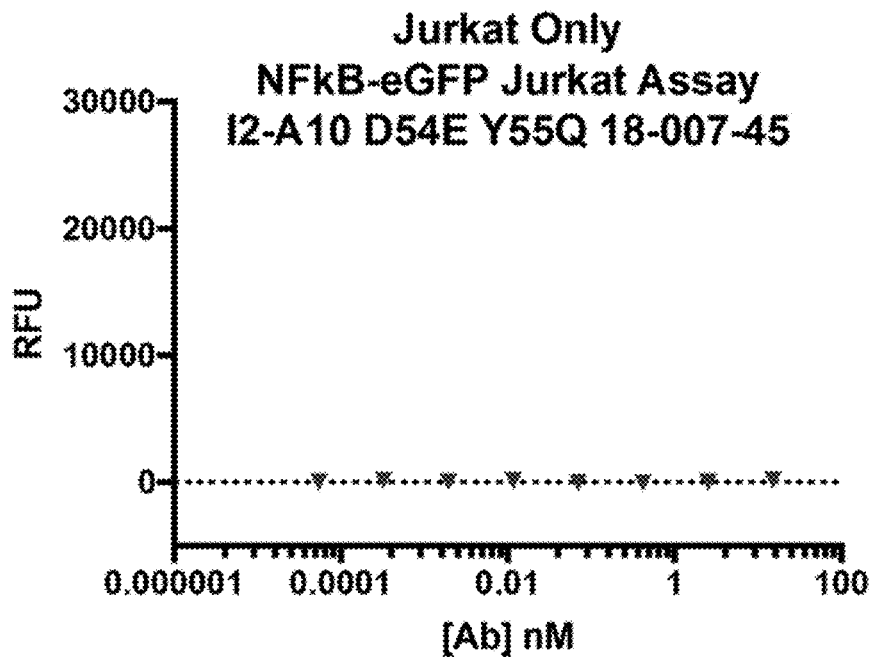

FIG. 79C shows activity of an 12-A10 D54E Y55Q 1×2 B-body™ with K562 (ROR2 expressing) cells. FIG. 79D shows inactivity of an 12-A10 D54E Y55Q 1×2 B-body™ in a Jurkat assay in the absence of a target cell line.

Figure 80A:
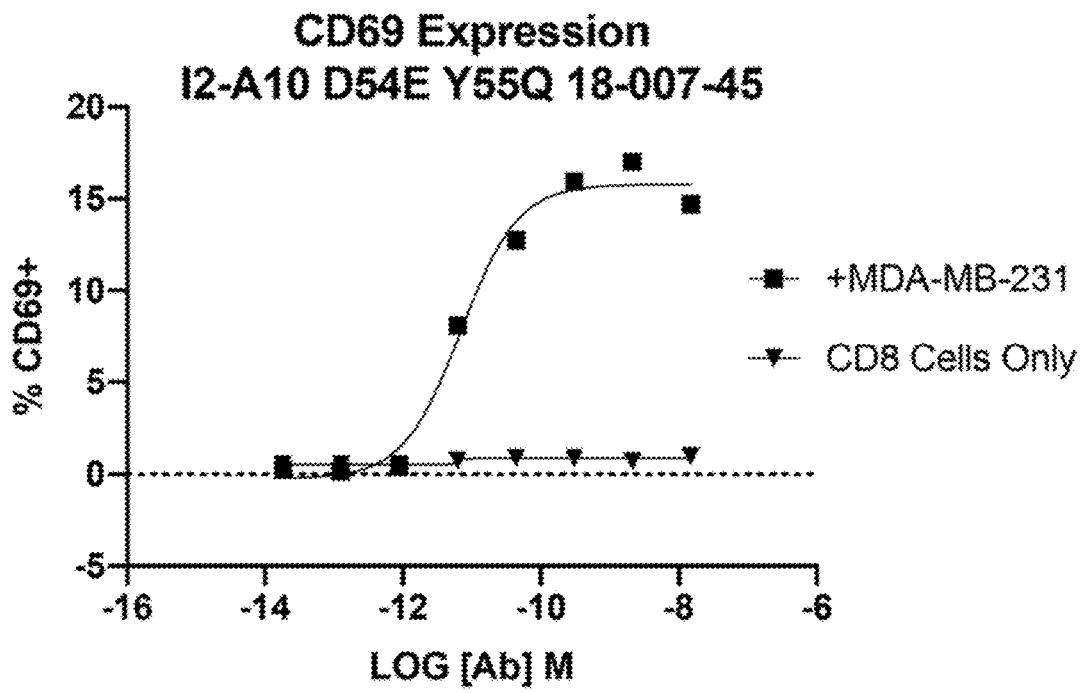
Figure 80B:
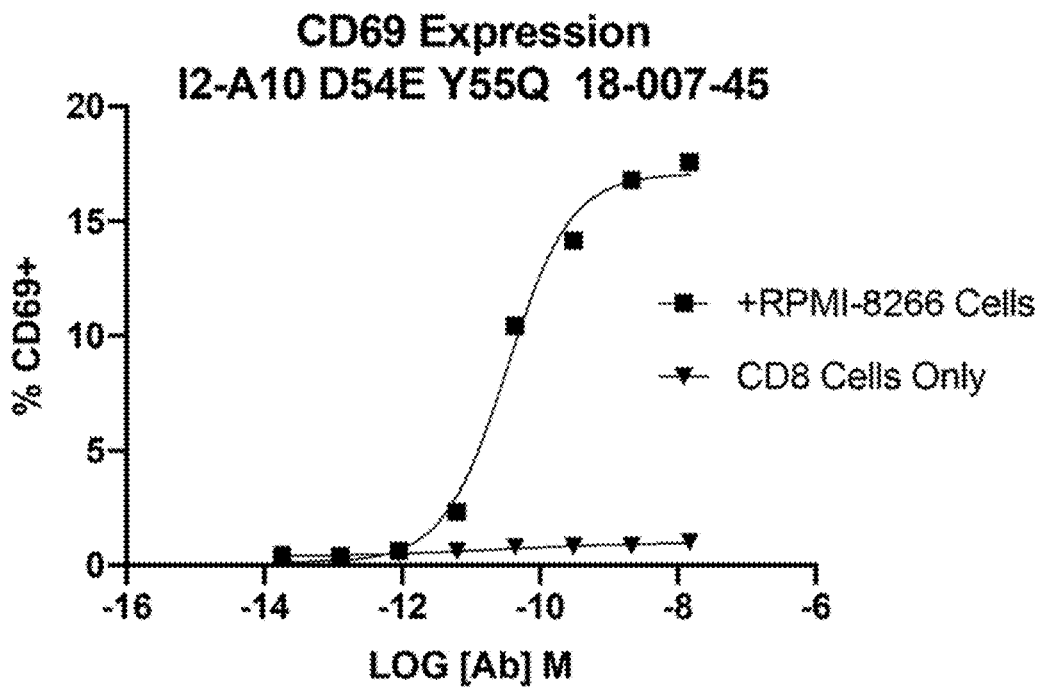
Figure 80C:
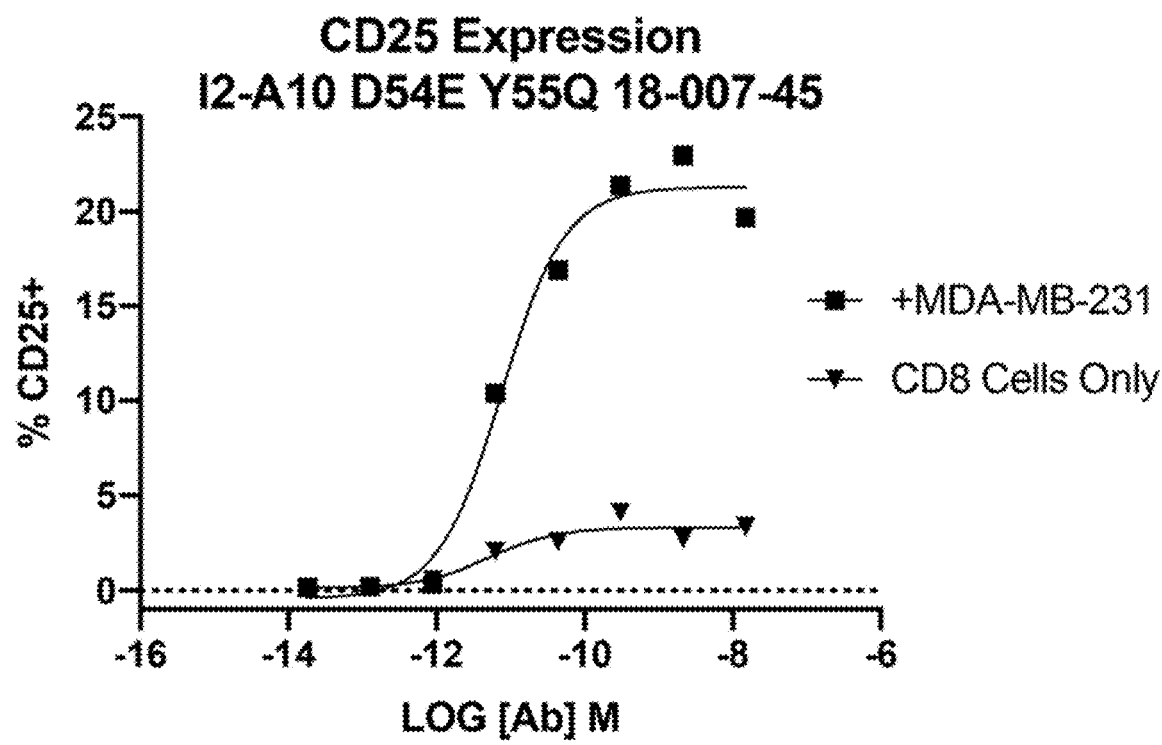
Figure 80D:
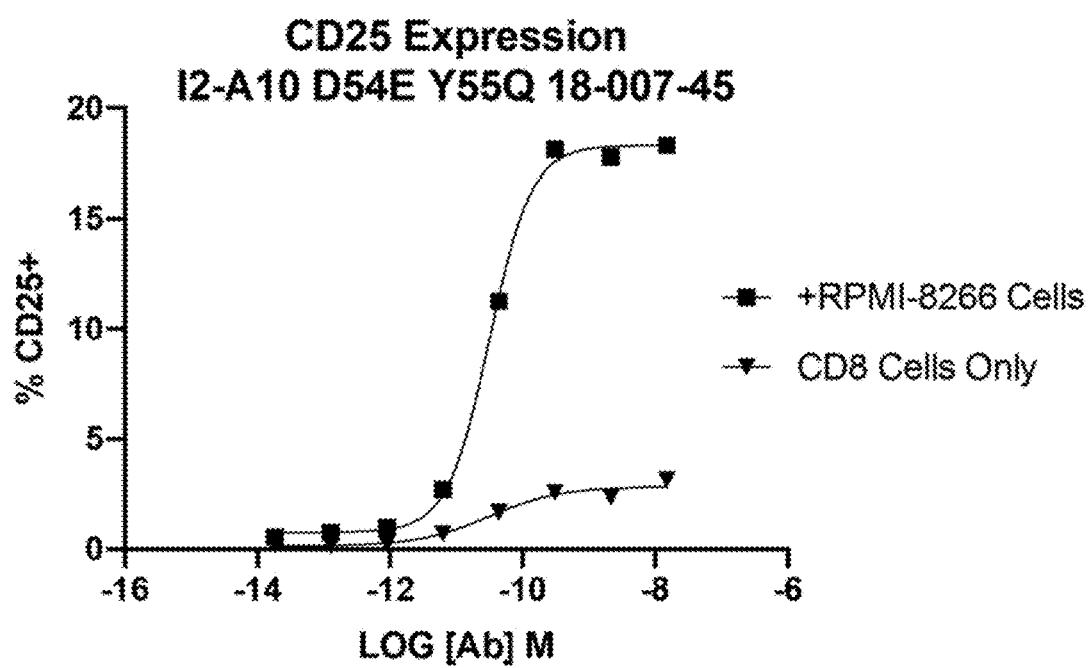

FIG. 80A shows CD69 expression with various concentrations of an 12-A10 D54E Y55Q 1×2 B-body™ and ROR1 expressing MDA-MB-231 cells. FIG. 80B shows CD69 expression with various concentrations of an 12-A10 D54E Y55Q 1×2 B-body™ and ROR1 and ROR2 expressing RPMI-8226 cells. FIG. 80C shows CD25 expression with various concentrations of an 12-A10 D54E Y55Q 1×2 B-body™ and ROR1 expressing MDA-MB-231 cells. FIG. 80D shows CD25 expression with various concentrations of an 12-A10 D54E Y55Q 1×2 B-body™ and ROR1 and ROR2 expressing RPMI-8226 cells.

Figure 81A:
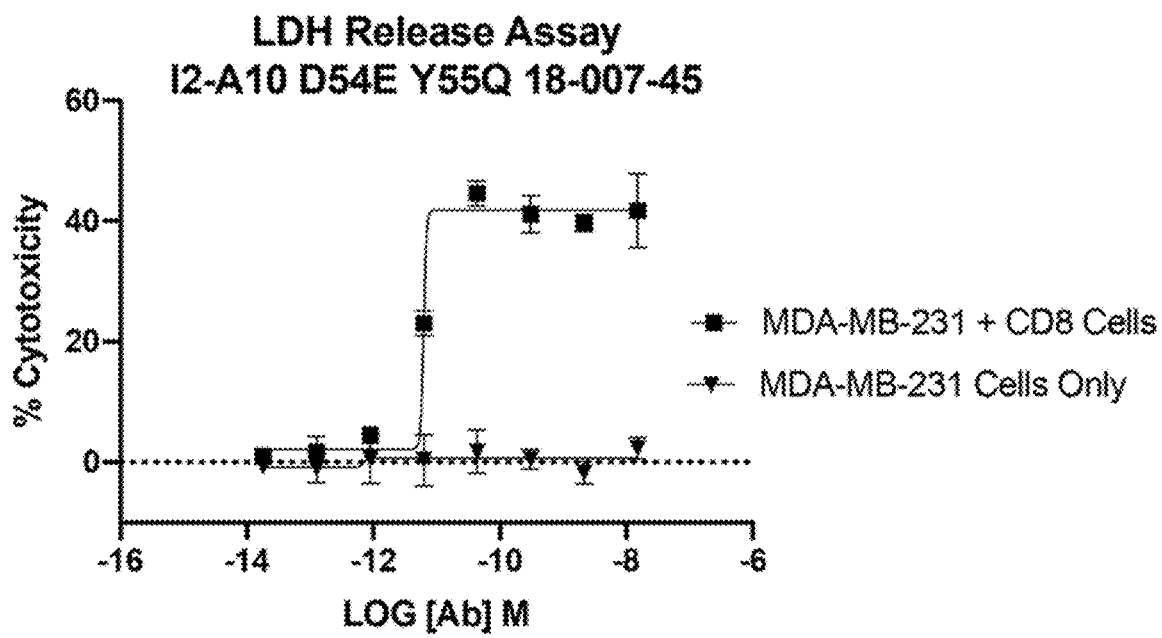
Figure 81B:
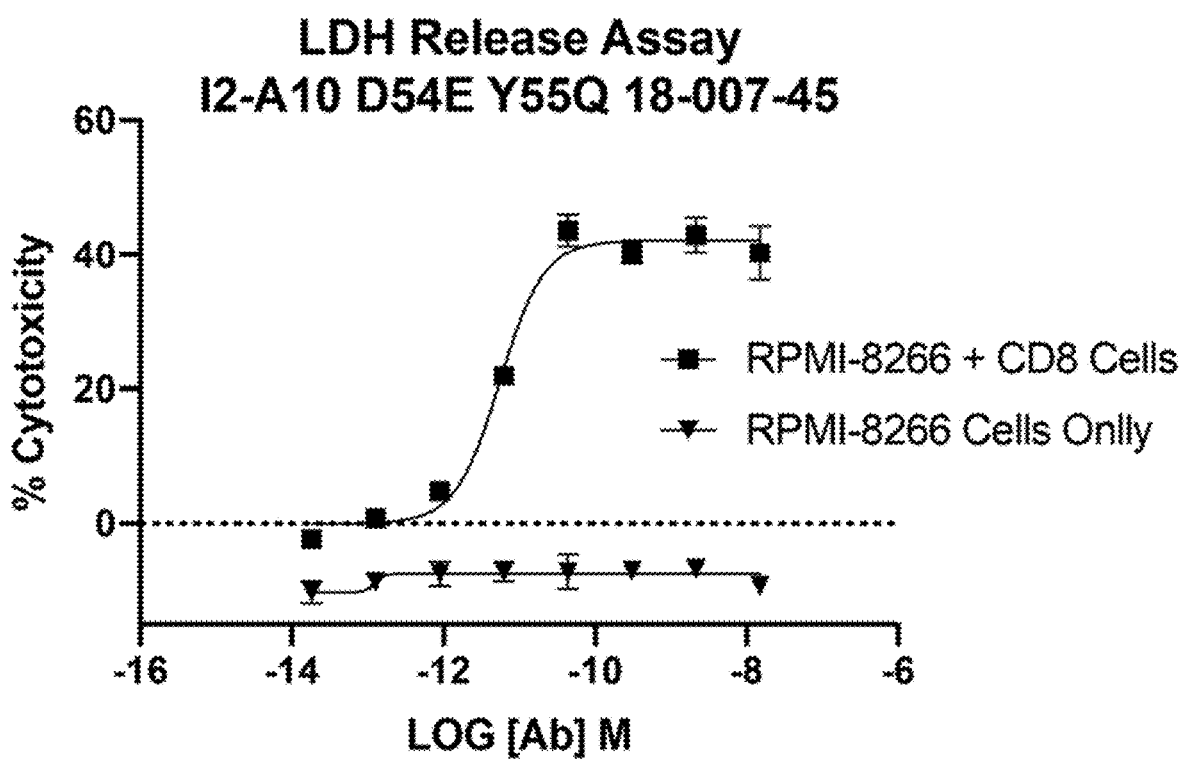

FIG. 81A shows LDH release with various concentrations of an 12-A10 D54E Y55Q 1×2 B-body™ and ROR1 expressing MDA-MB-231 cells. FIG. 81B shows LDH release with various concentrations of an 12-A10 D54E Y55Q 1×2 B-body™ and ROR1 and ROR2 expressing RPMI-8226 cells.

Figure 82A:
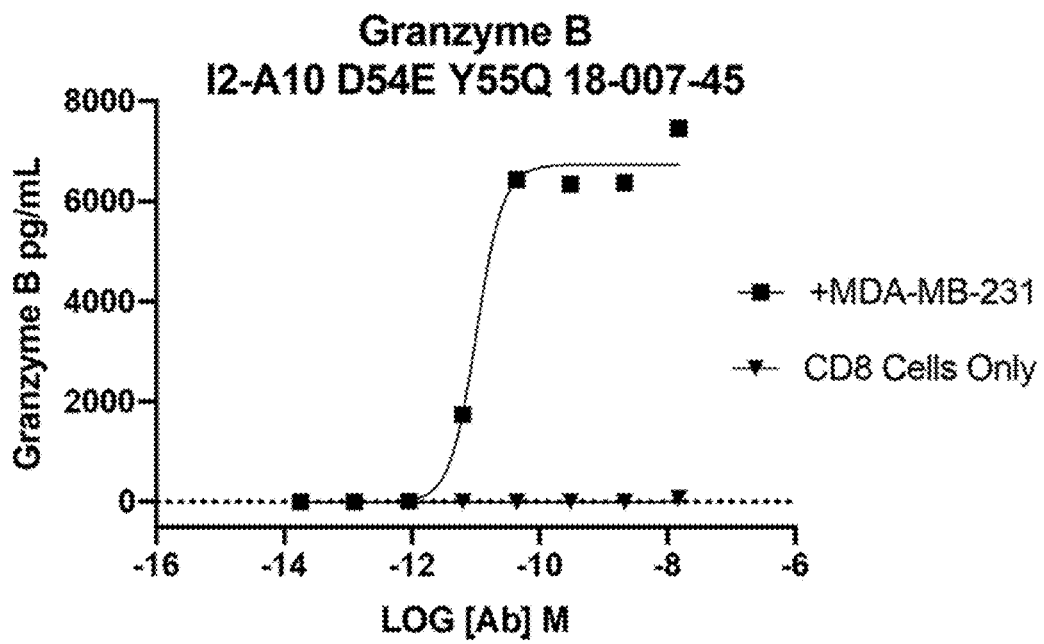
Figure 82B:
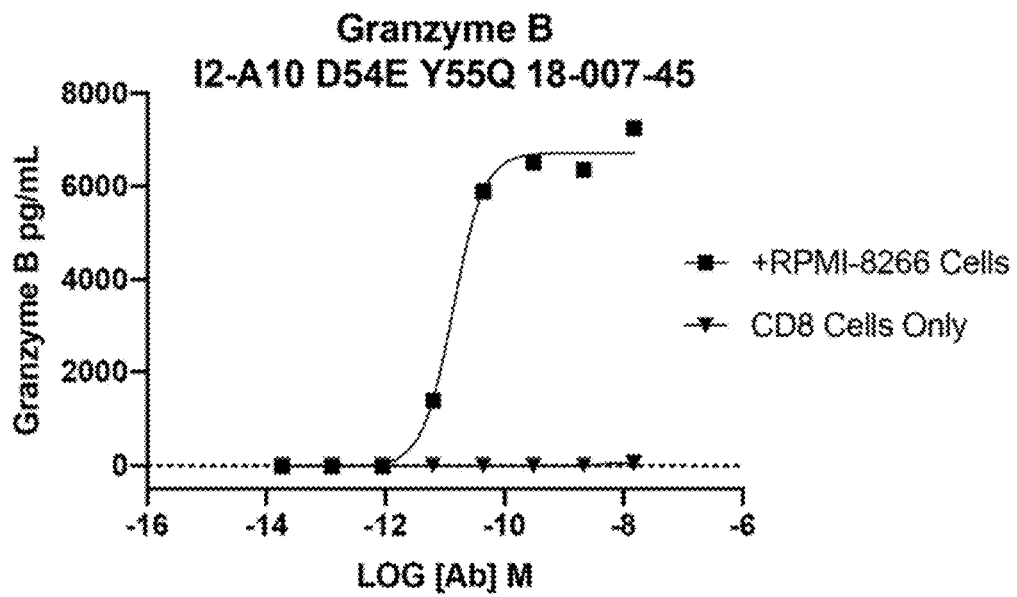
Figure 82C:
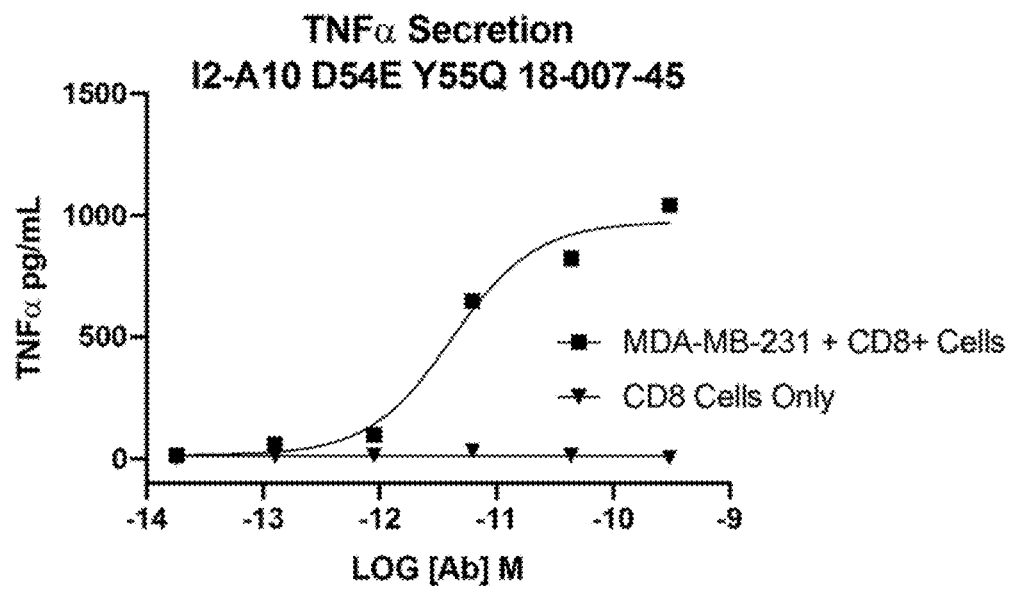
Figure 82D:
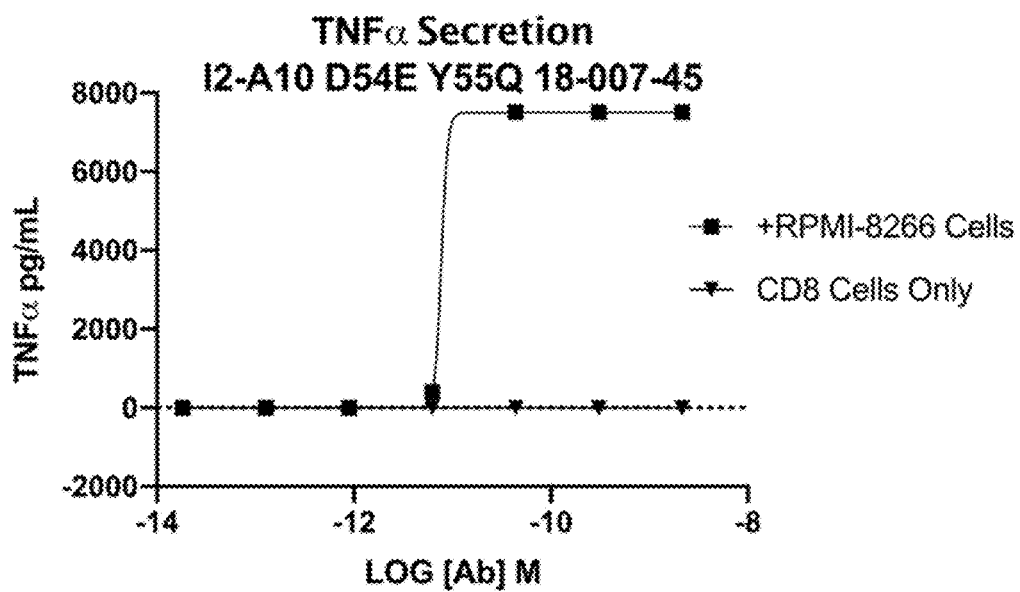
Figure 82E:
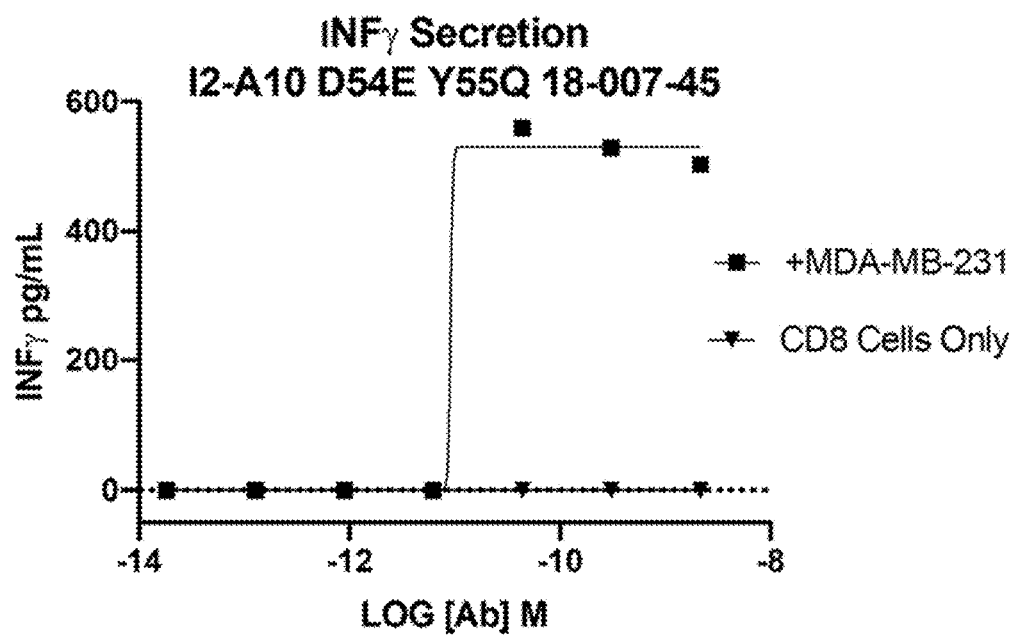
Figure 82F:
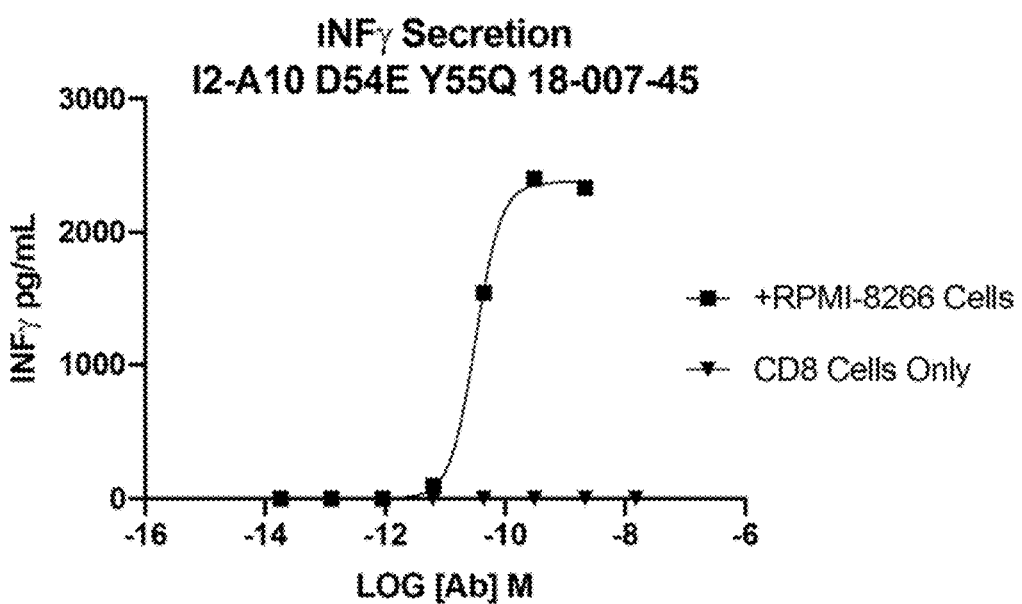

FIG. 82A shows Granzyme B with various concentrations of an 12-A10 D54E Y55Q 1×2 B-body™ and ROR1 expressing MDA-MB-231 cells. FIG. 82B shows Granzyme B with various concentrations of an 12-A10 D54E Y55Q 1×2 B-body™ and ROR1 and ROR2 expressing RPMI-8226 cells. FIG. 82C shows TNFα secretion with various concentrations of an 12-A10 D54E Y55Q 1×2 B-body and ROR1 expressing MDA-MB-231 cells. FIG. 82D shows TNFα secretion with various concentrations of an 12-A10 D54E Y55Q 1×2 B-body™ and ROR1 and ROR2 expressing RPMI-8226 cells. FIG. 82E shows IFNγ secretion with various concentrations of an 12-A10 D54E Y55Q 1×2 B-body™ and ROR1 expressing MDA-MB-231 cells. FIG. 82F shows IFNγ secretion with various concentrations of an 12-A10 D54E Y55Q 1×2 B-body™ and ROR1 and ROR2 expressing RPMI-8226 cells.

Figure 83A:
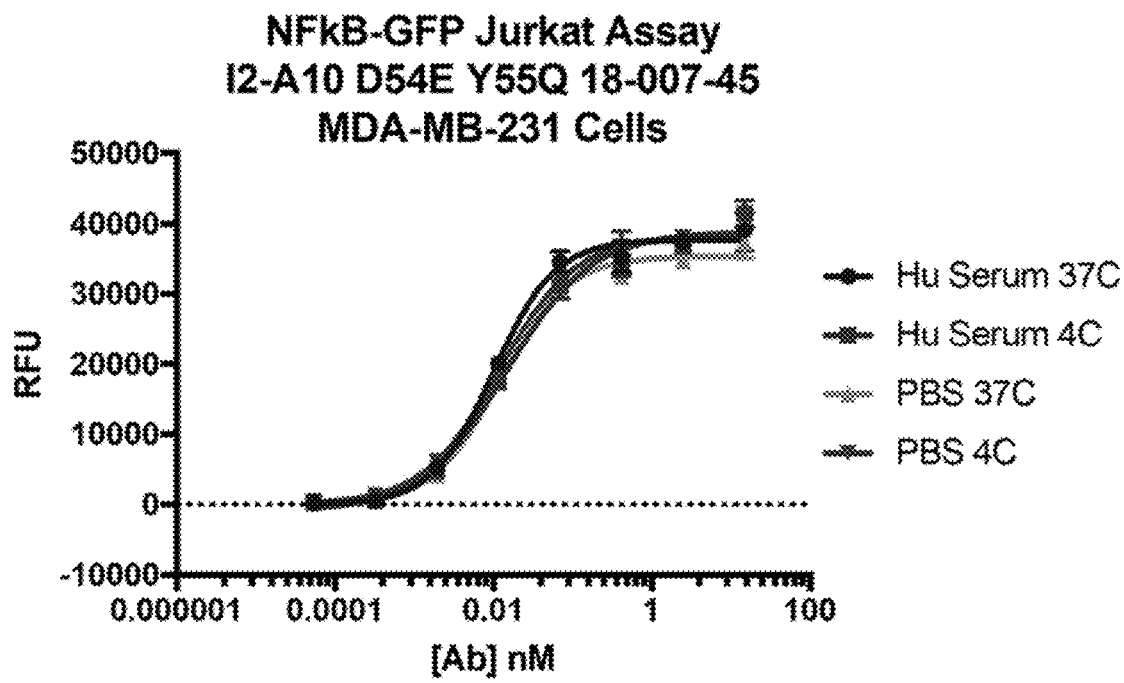
Figure 83B:
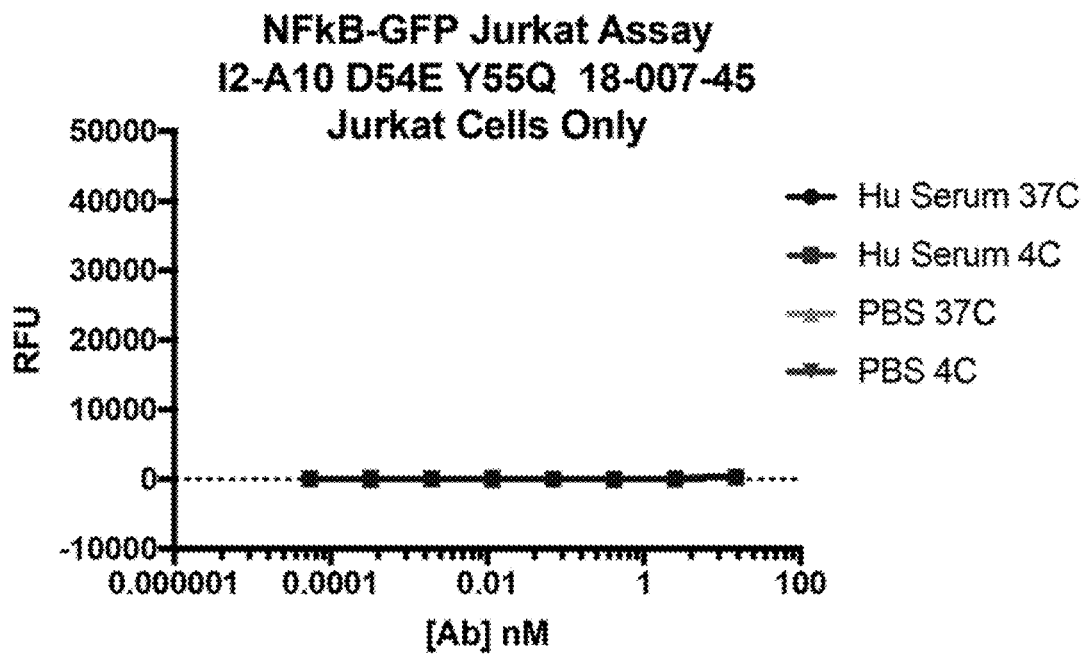

FIG. 83A shows activity of an 12-A10 D54E Y55Q 1×2 B-body™ samples stored in human serum at 4° C. or 37° C. for 1 week. FIG. 83B shows inactivity of samples in a Jurkat assay in the absence of ROR1 expressing cells.

Figure 84:
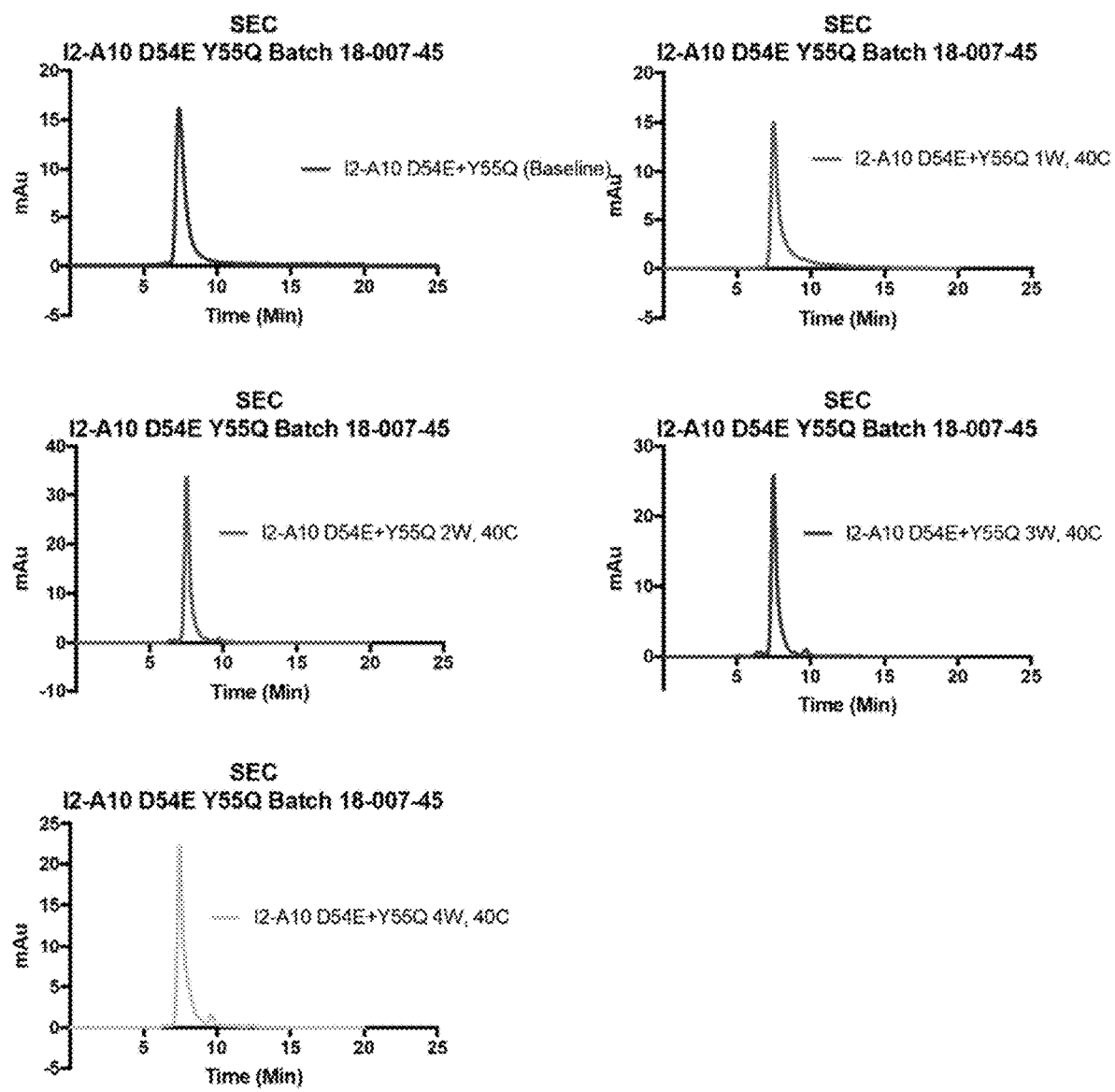

FIG. 84 shows stability assays of 12-A10 D54E Y55Q 1×2 B-body™ samples under accelerated conditions.

Figure 85:
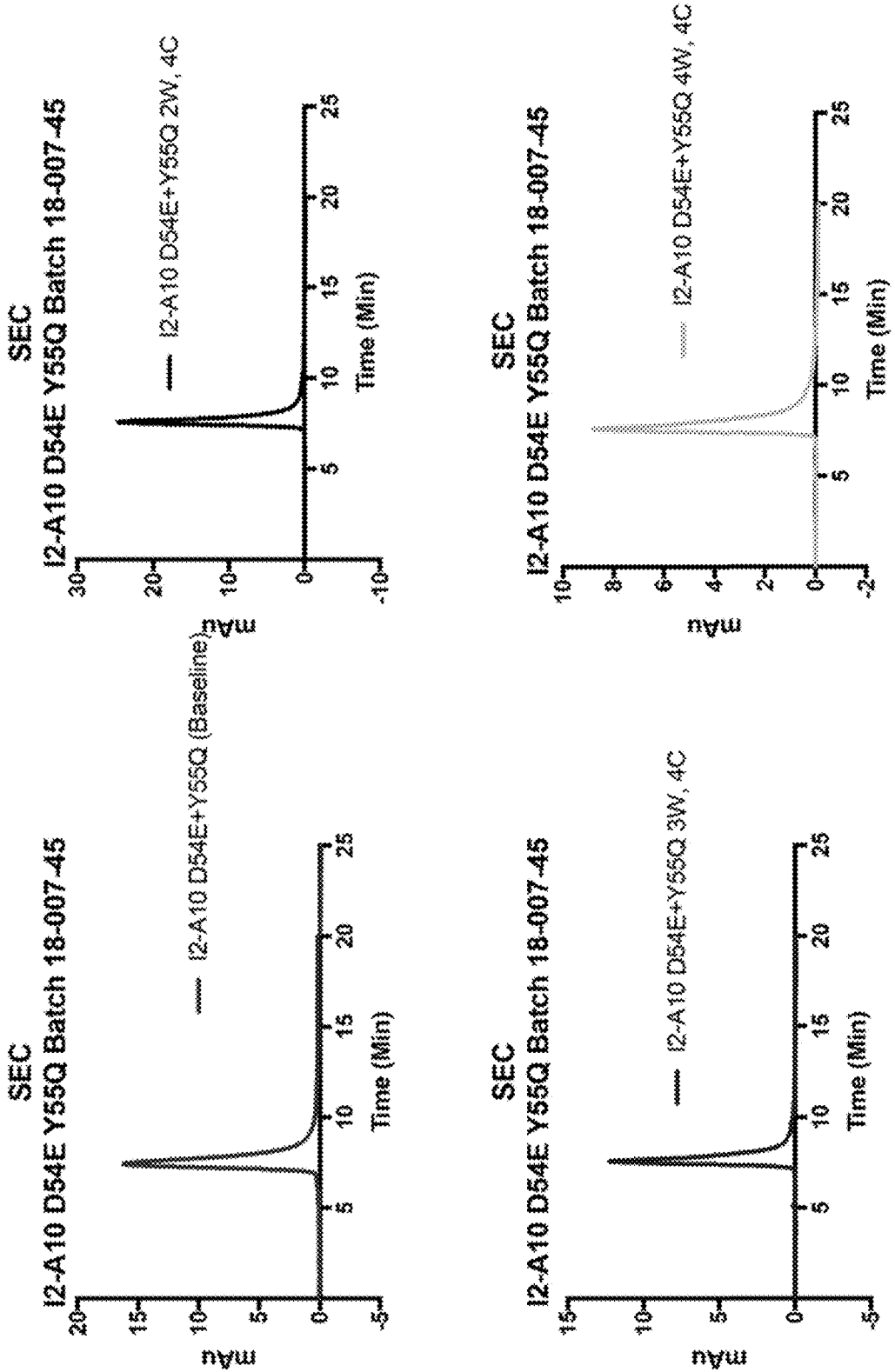

FIG. 85 shows stability assays of 12-A10 D54E Y55Q 1×2 B-body™ samples under real time conditions.

Figure 86:
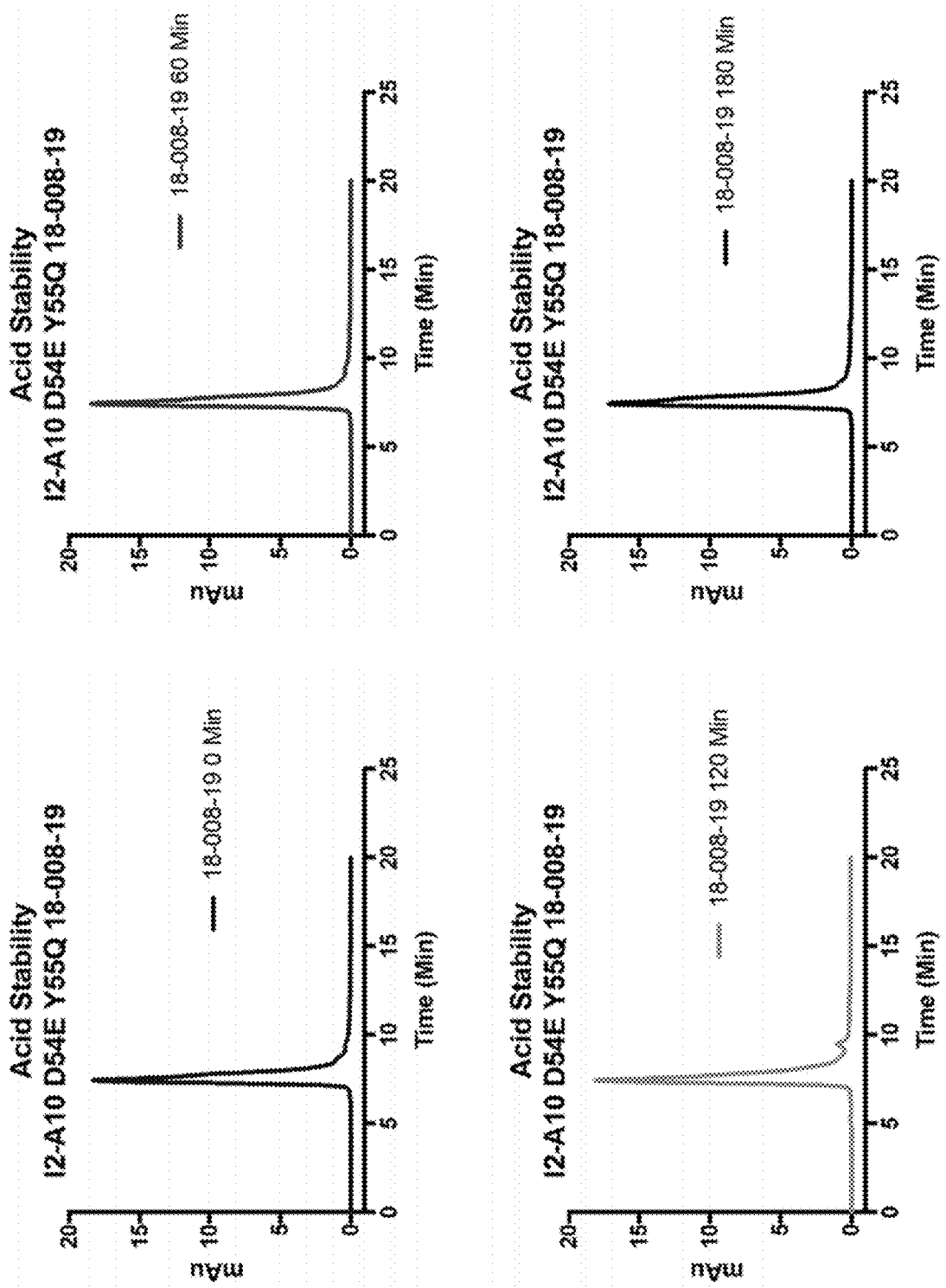

FIG. 86 shows acid stability assays of an 12-A10 D54E Y55Q 1×2 B-body™.

Figure 87:
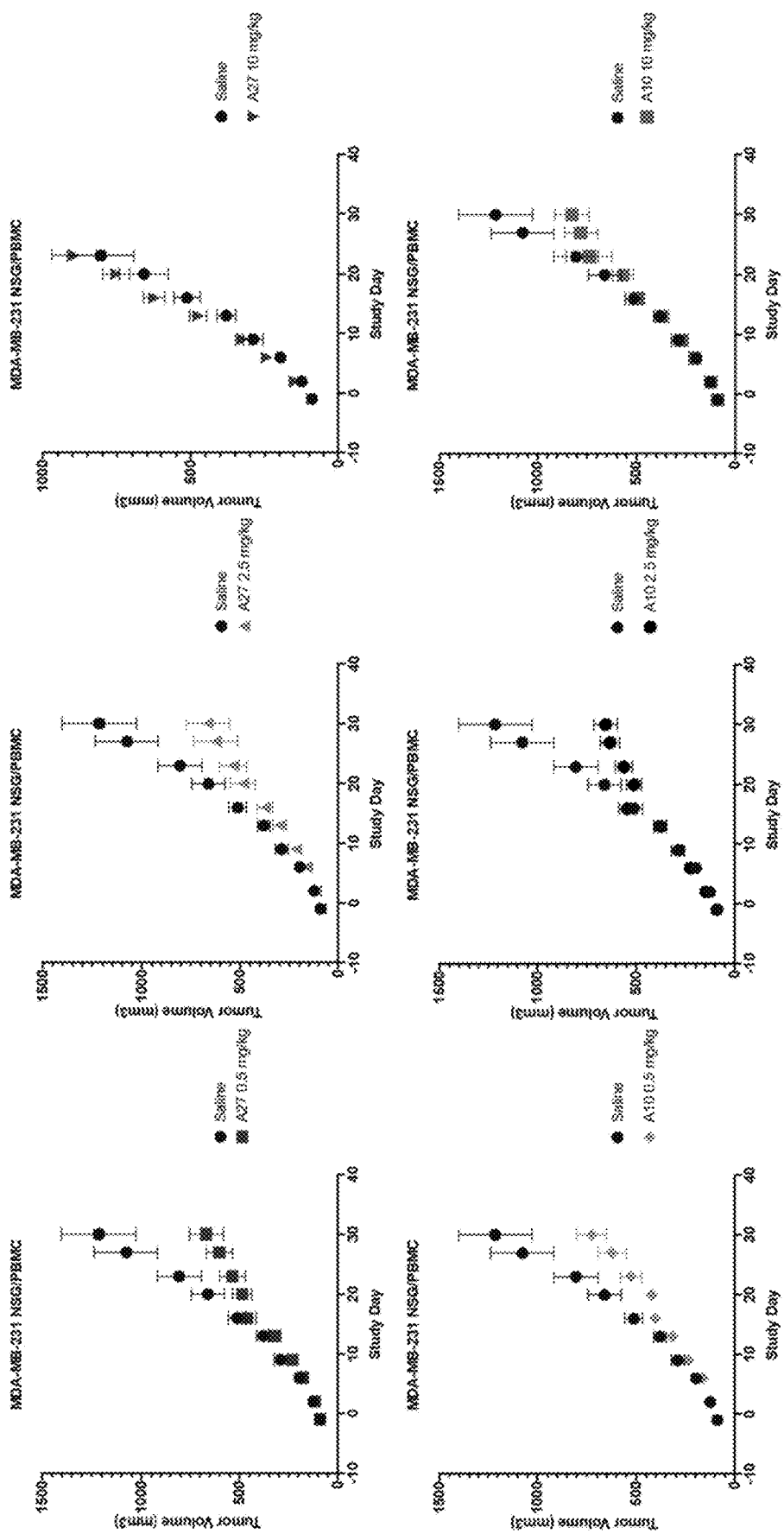

FIG. 87 shows in vivo efficacy of an 12-27 1×2 B-body™ and an 12-A10 D54E Y55Q 1×2 B-body™ to reduce tumor volume (mm) in a mouse model of cancer.

Figure 88:
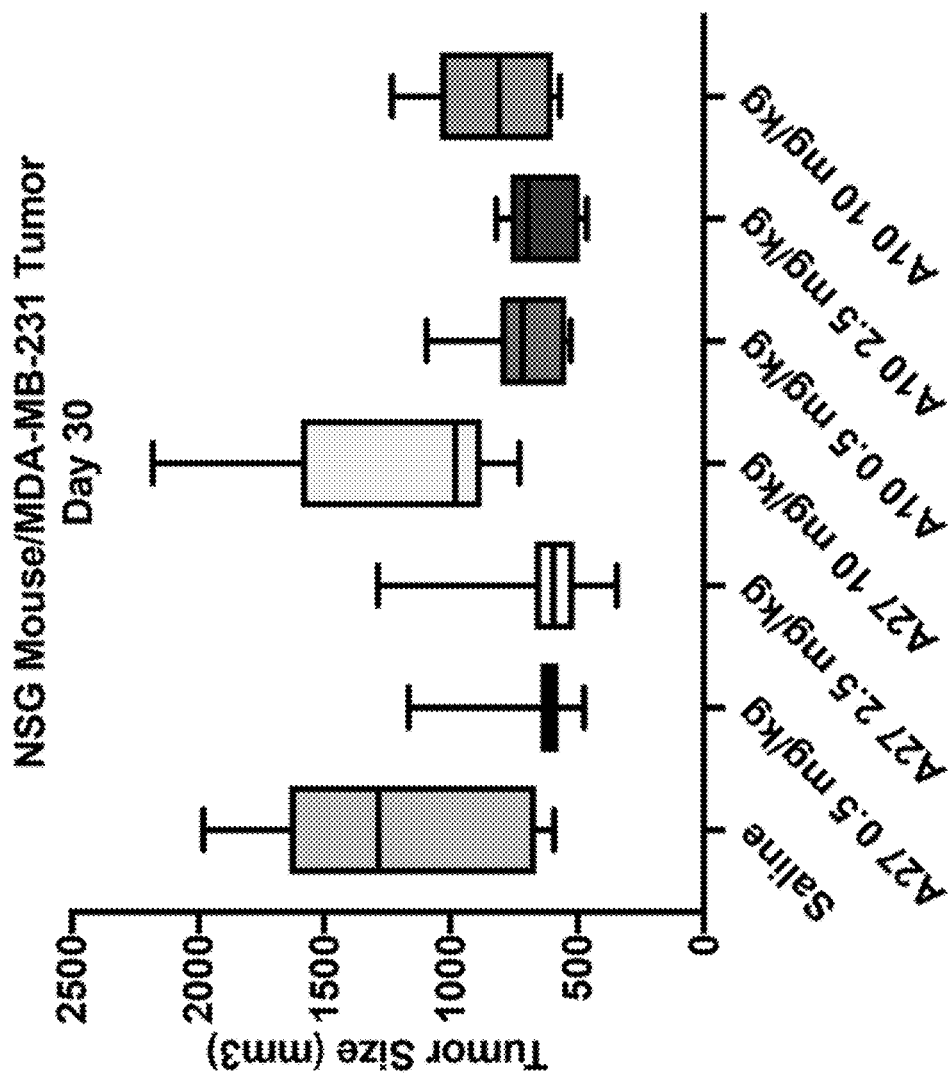

FIG. 88 shows in vivo efficacy of multiple doses of an 12-27 1×2 B-body™ and an 12-A10 D54E Y55Q 1×2 B-body™ to reduce tumor size (mm$^3$) in a mouse model of cancer.

The figures depict various embodiments of the present invention for purposes of illustration only. One skilled in the art will readily recognize from the following discussion that alternative embodiments of the structures and methods illustrated herein may be employed without departing from the principles of the invention described herein.

6. DETAILED DESCRIPTION

6.1. Definitions

Unless defined otherwise, all technical and scientific terms used herein have the meaning commonly understood by a person skilled in the art to which this invention belongs. As used herein, the following terms have the meanings ascribed to them below.

By "antigen binding site" is meant a region of a ROR binding molecule that specifically recognizes or binds to a given antigen or epitope.

Figure 1:
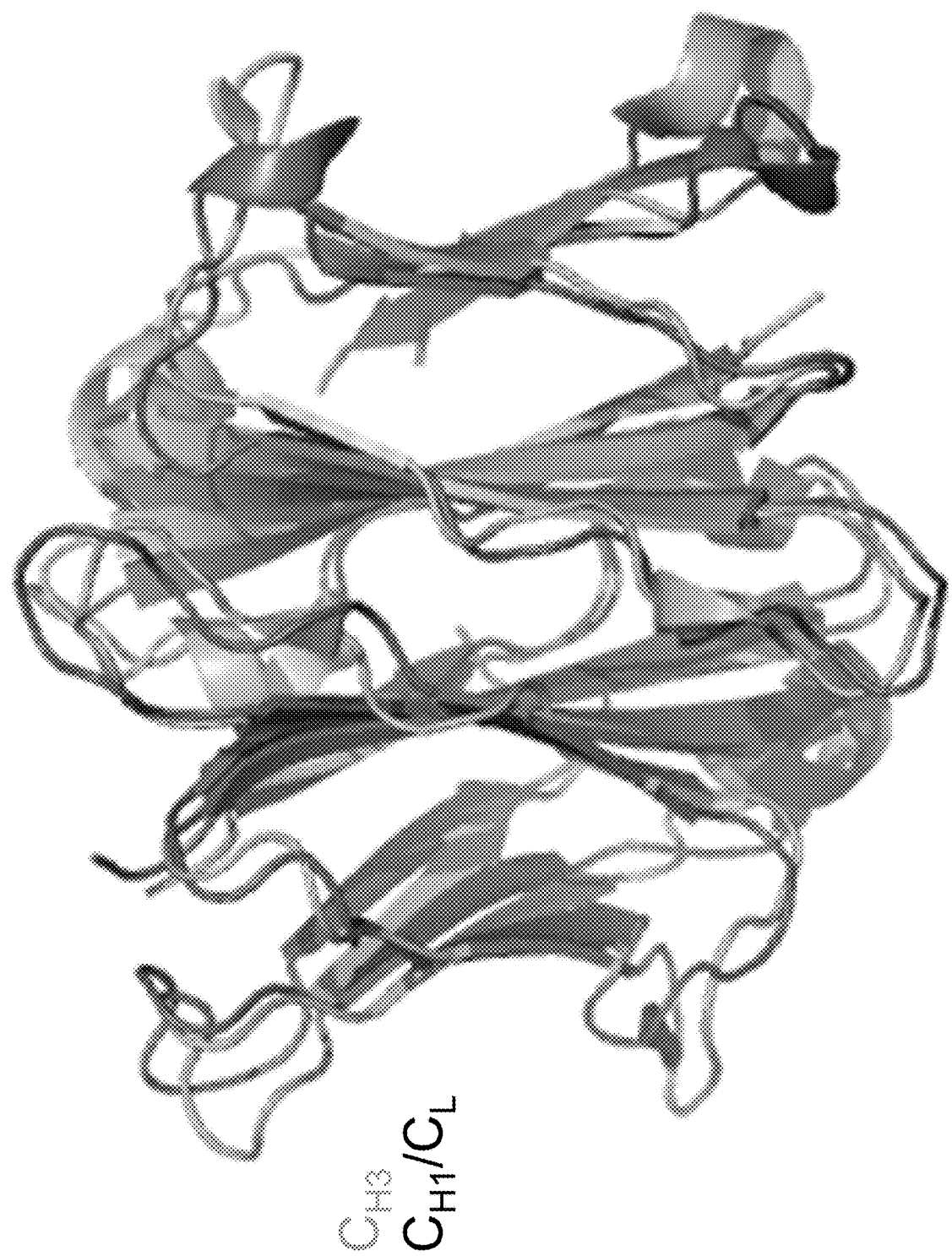
Figure 3:
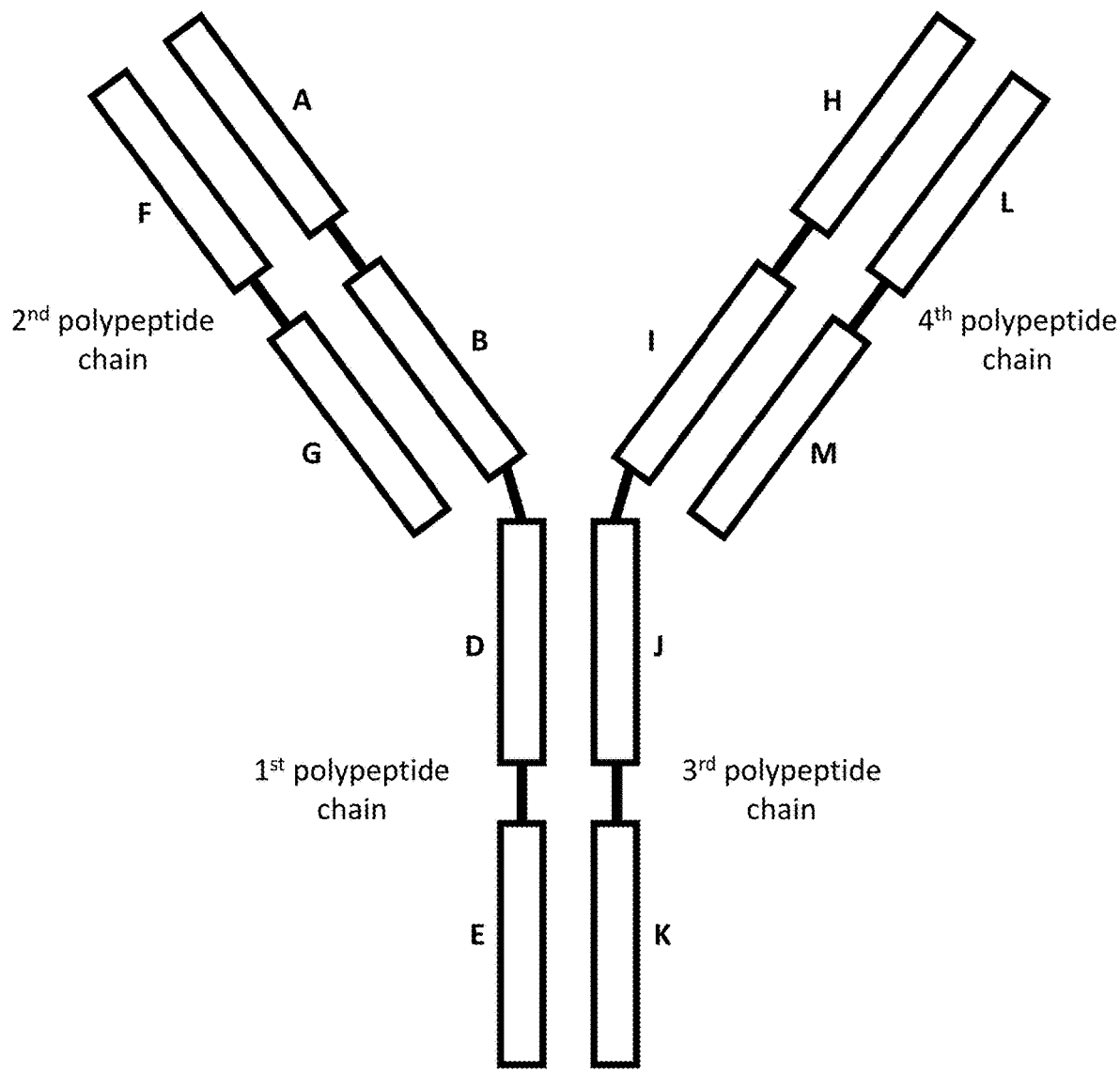

"B-Body," as used herein and with reference to FIG. 3, refers to binding molecules comprising the features of a first and a second polypeptide chain, wherein: (a) the first polypeptide chain comprises a domain A, a domain B, a domain D, and a domain E, wherein the domains are arranged, from N-terminus to C-terminus, in a A-B-D-E orientation, and wherein domain A has a VL amino acid sequence, domain B has a CH3 amino acid sequence, domain D has a CH2 amino acid sequence, and domain E has a constant region domain amino acid sequence; (b) the second polypeptide chain comprises a domain F and a domain G, wherein the domains are arranged, from N-terminus to C-terminus, in a F-G orientation, and wherein domain F has a VH amino acid sequence and domain G has a CH3 amino acid sequence; and (c) the first and the second polypeptides are associated through an interaction between the A and the F domains and an interaction between the B and the G domains to form the binding molecule. B-bodies are described in more detail in International Patent Application No. PCT/US2017/057268, herein incorporated by reference in its entirety.

As used herein, the terms "treat" or "treatment" refer to both therapeutic treatment and prophylactic or preventative measures, wherein the object is to prevent or slow down (lessen) an undesired physiological change or disorder, such as the progression of multiple sclerosis, arthritis, or cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, and so on.

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease. A therapeutically effective amount can be a "prophylactically effective amount" as prophylaxis can be considered therapy.

6.2. Other Interpretational Conventions

Unless otherwise specified, all references to sequences herein are to amino acid sequences.

Unless otherwise specified, antibody constant region residue numbering is according to the Eu index as described at wmv.imgt.org/IMGTScientificChart/Numbering/Hu-_IGHGnber.html #refs (accessed Aug. 22, 2017) and in Edelman et al., *Proc. Natl. Acad. USA*, 63:78-85 (1969),
which are hereby incorporated by reference in their entireties, and identifies the residue according to its location in an endogenous constant region sequence regardless of the residue's physical location within a chain of the ROR binding molecules described herein. By "endogenous sequence" or "native sequence" is meant any sequence, including both nucleic acid and amino acid sequences, which originates from an organism, tissue, or cell and has not been artificially modified or mutated.

Polypeptide chain numbers (e.g., a "first" polypeptide chains, a "second" polypeptide chain. etc. or polypeptide "chain 1," "chain 2." etc.) are used herein as a unique identifier for specific polypeptide chains that form a binding molecule and is not intended to connote order or quantity of the different polypeptide chains within the binding molecule.

In this disclosure, "comprises," "comprising," "containing," "having," "includes," "including," and linguistic variants thereof have the meaning ascribed to them in U.S. Patent law, permitting the presence of additional components beyond those explicitly recited.

Ranges provided herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless specifically stated or apparent from context, as used herein the term "or" is understood to be inclusive. Unless specifically stated or apparent from context, as used herein, the terms "a", "an", and "the" are understood to be singular or plural.

Unless specifically stated or otherwise apparent from context, as used herein the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

6.3. ROR Antigen Binding Molecules

In a first aspect, antigen binding molecules are provided. In every embodiment, the antigen binding molecule includes at least a first antigen binding site specific for a ROR antigen; the binding molecules are therefore termed ROR antigen binding molecules.

The ROR binding molecules described herein bind specifically to ROR antigens.

As used herein, "ROR antigens" refer to members of the tyrosine-protein kinase transmembrane receptor (ROR) family, including members ROR1 and ROR2. In certain embodiments, the ROR binding molecule has antigen binding sites that specifically bind to ROR1 only. In other embodiments, the ROR binding molecule has antigen binding sites that specifically bind to ROR2 only. In still other embodiments, the ROR binding molecule has antigen binding sites that are cross-reactive and specifically bind to both ROR1 and ROR2.

ROR1 and ROR2 proteins typically consist of at least four protein domains: three extracellular domains—Ig-like, FZ, and Kringle domains—as well as the intracellular Protein Kinase domain. In some embodiments, the ROR binding molecule has antigen binding sites that specifically bind to the extracellular portion of the ROR antigen. In certain embodiments, the ROR binding molecule has antigen binding sites that specifically bind to the Ig-like domain. In other embodiments, the ROR binding molecule has antigen binding sites that specifically bind to the FZ domain. In still other embodiments, the ROR binding molecule has antigen binding sites that specifically bind to the Kringle domain. In particular embodiments, the ROR binding molecule has antigen binding sites that specifically bind to at least a portion of a single ROR domain. In particular embodiments, the ROR binding molecule has antigen binding sites that specifically bind to at least a portion of more than one ROR domain, such as the junction between a first and a second ROR domain. The ROR domains can refer to ROR1 domains or ROR2 domains.

In specific embodiments, the ROR antigen is human. UniProt accession #Q01973 describes a canonical human ROR1 protein, including its sequences and domain features, and is hereby incorporated by reference in its entirety. SEQ ID NO:94 provides the full-length ROR1 protein sequence. With reference to the full-length sequence from the N-terminus to C-terminus, the Ig-Like domain is defined as amino acids 42-147, the FZ domain as amino acids 165-299, and the Kringle domain as amino acids 312-391. UniProt accession #Q01974 describes a canonical human ROR2 protein, including its sequences and domain features, and is hereby incorporated by reference in its entirety. SEQ ID NO:95 provides the full-length ROR2 protein sequence. With reference to the full-length sequence from the N-terminus to C-terminus, the Ig-Like domain is defined as amino acids 55-145, the FZ domain as amino acids 169-303, and the Kringle domain as amino acids 316-394.

Various tumors can demonstrate cell-surface expression of ROR antigens, as described in greater detail in Gentile, et al. (*Cancer Res;* 71(8) Apr. 15, 2011), Rebagay, et al. (*Front. Oncol.,* 18 Apr. 2012), Zhang, et al. (*American Journal of Pathology*, Vol. 181, No. 6, December 2012), Henry, et al. (*Oncotarget*, Vol. 6, No. 37 2015), Zhang, et al. (*PLoS ONE* 7(3): e31127), and Bainbridge, et al. (*PLoS ONE* 9(7): e102695.), each herein incorporated by reference in their entirety. In addition. ROR expression may not be expressed, or only demonstrate limited expression, in normal, i.e. non-cancerous, tissue as described in Balakrishnan et al. (*Clin Cancer Res.* 2017 Jun. 15; 23(12): 3061-3071), herein incorporated in its entirety. Thus ROR antigens can be used as a tumor-specific marker in certain tumors. Examples of tumors and cancers with demonstrated ROR expression include, but are not limited to, pancreatic cancer, ovarian cancer, breast cancer, lung cancer, gastric cancer, melanoma. Ewing sarcoma, chronic lymphocytic leukemia, mantle cell lymphoma, and B-ALL, as described in Gohil et al. (*Oncoimmunology.* 2017; 6(7): e1326437), herein incorporated in its entirety. Other cancers include, but are not limited to, hematological cancer, prostate cancer, colon cancer, renal cancer, and uterine cancer.

In various embodiments, the ROR binding molecule additionally binds specifically to at least one antigen additional to a ROR antigen.

In a specific embodiment, the ROR binding molecule is a bispecific bivalent molecule. In another embodiment, the ROR binding molecule is a bispecific trivalent molecule. In particular embodiments, the ROR binding molecule has antigen binding sites that specifically bind the ROR antigen and a T cell surface expressed molecule. In a specific embodiment, the ROR binding molecule has antigen binding sites that specifically bind the ROR antigen and the T cell surface expressed protein CD3. Without wishing to be bound by theory, the ROR binding molecule that specifically binds the ROR antigen and the T cell surface expressed molecule (i.e., CD3) can direct T cell mediated killing (cytotoxicity) of cells expressing the ROR antigen through redirecting T cells to the ROR expressing cells (i.e., target cells). T cell mediated killing using bispecific anti-CD3 molecules is described in detail in U.S. Pub. No. 2006/0193852, herein incorporated by reference in its entirety. In some embodiments, the T cell surface expressed molecule is selected from any molecule capable of redirecting T cells to a target cell.

With reference to FIG. 3, in a series of embodiments, the ROR binding molecules comprise a first and a second polypeptide chain, wherein: (a) the first polypeptide chain comprises a domain A, a domain B, a domain D, and a domain E, wherein the domains are arranged, from N-terminus to C-terminus, in a A-B-D-E orientation, wherein domain A has a variable region domain amino acid sequence, and wherein domain B, domain D. and domain E have a constant region domain amino acid sequence; (b) the second polypeptide chain comprises a domain F and a domain G, wherein the domains are arranged, from N-terminus to C-terminus, in a F-G orientation, and wherein domain F has a variable region domain amino acid sequence and domain G has a constant region domain amino acid sequence; (c) the third polypeptide chain comprises a domain H, a domain I, a domain J, and a domain K, wherein the domains are arranged, from N-terminus to C-terminus, in a H-I-J-K orientation, and wherein domain H has a variable region domain amino acid sequence, domain I has a CL amino acid sequence, and domains J and K have a constant region domain amino acid sequence; (d) the fourth polypeptide chain comprises a domain L and a domain M, wherein the domains are arranged, from N-terminus to C-terminus, in a L-M orientation, and wherein domain L has a variable region domain amino acid sequence, and wherein the fourth polypeptide chain comprises the CH1 domains and domain M is the CH1 domain, or portion thereof; (e) the first and the second polypeptides are associated through an interaction between the A and the F domains and an interaction between the B and the G domains; (f) the third and the fourth polypeptides are associated through an interaction between the H and the L domains and an interaction between the I and the M domains; (g) the first and the third polypeptides are associated through an interaction between the D and the J domains and an interaction between the E and the K domains to form the ROR binding molecule.

In a series of embodiments, (a) the first polypeptide chain comprises a domain A, a domain B, a domain D. and a domain E, wherein the domains are arranged, from N-terminus to C-terminus, in a A-B-D-E orientation, wherein domain A has a variable region domain amino acid sequence, and wherein domain B, domain D. and domain E have a constant region domain amino acid sequence; (b) the second polypeptide chain comprises a domain F and a domain G, wherein the domains are arranged, from N-terminus to C-terminus, in a F-G orientation, and wherein domain F has a variable region domain amino acid sequence and domain G has a constant region domain amino acid sequence; (c) the third polypeptide chain comprises a domain H, a domain I, a domain J, and a domain K, wherein the domains are arranged, from N-terminus to C-terminus, in a H-I-J-K orientation, and wherein the third polypeptide chain comprises the CH1 domain and domain I is the CH1 domain, or portion thereof, domain H has a variable region domain amino acid sequence, and domains J and K have a constant region domain amino acid sequence; (d) the fourth polypeptide chain comprises a domain L and a domain M, wherein the domains are arranged, from N-terminus to C-terminus, in a L-M orientation, and wherein domain L has a variable region domain amino acid sequence, and wherein domain M has a CL amino acid sequence; (e) the first and the second polypeptides are associated through an interaction between the A and the F domains and an interaction between the B and the G domains; (f) the third and the fourth polypeptides are associated through an interaction between the H and the L domains and an interaction between the I and the M domains; (g) the first and the third polypeptides are associated through an interaction between the D and the J domains and an interaction between the E and the K domains to form the ROR binding molecule.

6.3.1. Domain a (Variable Region)

In the ROR binding molecules, domain A has a variable region domain amino acid sequence. Variable region domain amino acid sequences, as described herein, are variable region domain amino acid sequences of an antibody including VL and VH antibody domain sequences. VL and VH sequences are described in greater detail below in Sections 6.3.1.1 and 6.3.1.4, respectively. In a preferred embodiment, domain A has a VL antibody domain sequence and domain F has a VH antibody domain sequence.

6.3.1.1. VL Regions

The VL amino acid sequences useful in the ROR binding molecules described herein are antibody light chain variable domain sequences. In a typical arrangement in both natural antibodies and the antibody constructs described herein, a specific VL amino acid sequence associates with a specific VH amino acid sequence to form an antigen-binding site. In various embodiments, the VL amino acid sequences are mammalian sequences, including human sequences, synthesized sequences, or combinations of human, non-human mammalian, mammalian, and/or synthesized sequences, as described in further detail below in Sections 6.3.1.2 and 6.3.1.3.

In various embodiments, VL amino acid sequences are mutated sequences of naturally occurring sequences. In certain embodiments, the VL amino acid sequences are lambda (λ) light chain variable domain sequences. In certain embodiments, the VL amino acid sequences are kappa (κ) light chain variable domain sequences. In a preferred embodiment, the VL amino acid sequences are kappa (κ) light chain variable domain sequences.

In the ROR binding molecules described herein, the C-terminus of domain A is connected to the N-terminus of domain B. In certain embodiments, domain A has a VL amino acid sequence that is mutated at its C-terminus at the junction between domain A and domain B, as described in greater detail below in Section 6.3.19.1 and in Example 6.

6.3.1.2. Complementarity Determining Regions

The VL amino acid sequences comprise highly variable sequences termed "complementarity determining regions" (CDRs), typically three CDRs (CDR1, CD2, and CDR3). In a variety of embodiments, the CDRs are mammalian sequences, including, but not limited to, mouse, rat, hamster, rabbit, camel, donkey, goat, and human sequences. In a preferred embodiment, the CDRs are human sequences. In various embodiments, the CDRs are naturally occurring sequences. In various embodiments, the CDRs are naturally occurring sequences that have been mutated to alter the binding affinity of the antigen-binding site for a particular antigen or epitope. In certain embodiments, the naturally occurring CDRs have been mutated in an in vivo host through affinity maturation and somatic hypermutation. In certain embodiments, the CDRs have been mutated in vitro through methods including, but not limited to PCR-mutagenesis and chemical mutagenesis. In various embodiments, the CDRs are synthesized sequences including, but not limited to, CDRs obtained from random sequence CDR libraries and rationally designed CDR libraries.

6.3.1.3. Framework Regions and CDR Grafting

The VL amino acid sequences comprise "framework region" (FR) sequences. FRs are generally conserved sequence regions that act as a scaffold for interspersed CDRs (see Section 6.3.1.2), typically in a FRI-CDR1-FR2-CDR2-FR3-CDR3-FR4 arrangement (from N-terminus to C-terminus). In a variety of embodiments, the FRs are mammalian sequences, including, but not limited to mouse, rat, hamster, rabbit, camel, donkey, goat, and human sequences. In a preferred embodiment, the FRs are human sequences. In various embodiments, the FRs are naturally occurring sequences. In various embodiments, the FRs are synthesized sequences including, but not limited, rationally designed sequences.

In a variety of embodiments, the FRs and the CDRs are both from the same naturally occurring variable domain sequence. In a variety of embodiments, the FRs and the CDRs are from different variable domain sequences, wherein the CDRs are grafted onto the FR scaffold with the CDRs providing specificity for a particular antigen. In certain embodiments, the grafted CDRs are all derived from the same naturally occurring variable domain sequence. In certain embodiments, the grafted CDRs are derived from different variable domain sequences. In certain embodiments, the grafted CDRs are synthesized sequences including, but not limited to, CDRs obtained from random sequence CDR libraries and rationally designed CDR libraries. In certain embodiments, the grafted CDRs and the FRs are from the same species. In certain embodiments, the grafted CDRs and the FRs are from different species. In a preferred grafted CDR embodiment, an antibody is "humanized", wherein the grafted CDRs are non-human mammalian sequences including, but not limited to, mouse, rat, hamster, rabbit, camel, donkey, and goat sequences, and the FRs are human sequences. Humanized antibodies are discussed in more detail in U.S. Pat. No. 6,407,213, the entirety of which is hereby incorporated by reference for all it teaches. In various embodiments, portions or specific sequences of FRs from one species are used to replace portions or specific sequences of another species' FRs.

6.3.1.4. VH Regions

The VH amino acid sequences in the ROR binding molecules described herein are antibody heavy chain variable domain sequences. In a typical antibody arrangement in both nature and in the ROR binding molecules described herein, a specific VH amino acid sequence associates with a specific VL amino acid sequence to form an antigen-binding site. In various embodiments, VH amino acid sequences are mammalian sequences, including human sequences, synthesized sequences, or combinations of non-human mammalian, mammalian, and/or synthesized sequences, as described in further detail above in Sections 6.3.1.2 and 6.3.1.3. In various embodiments, VH amino acid sequences are mutated sequences of naturally occurring sequences.

6.3.2. Domain B (Constant Region)

In the ROR binding molecules, Domain B has a constant region domain sequence. Constant region domain amino acid sequences, as described herein, are sequences of a constant region domain of an antibody.

In a variety of embodiments, the constant region sequences are mammalian sequences, including, but not limited to, mouse, rat, hamster, rabbit, camel, donkey, goat, and human sequences. In a preferred embodiment, the constant region sequences are human sequences. In certain embodiments, the constant region sequences are from an antibody light chain. In particular embodiments, the constant region sequences are from a lambda or kappa light chain. In certain embodiments, the constant region sequences are from an antibody heavy chain. In particular embodiments, the constant region sequences are an antibody heavy chain sequence that is an IgA1, IgA2, IgD, IgE, IgG1, IgG2, IgG3, IgG4, or IgM isotype. In a specific embodiment, the constant region sequences are from an IgG isotype. In a preferred embodiment, the constant region sequences are from an IgG1 isotype. In preferred specific embodiments, the constant region sequence is a CH3 sequence. CH3 sequences are described in greater detail below in Section 6.3.2.1. In other preferred embodiments, the constant region sequence is an orthologous CH2 sequence. Orthologous CH2 sequences are described in greater detail below in Section 6.3.2.2.

In particular embodiments, the constant region sequence has been mutated to include one or more orthogonal mutations. In a preferred embodiment, domain B has a constant region sequence that is a CH3 sequence comprising knob-hole (synonymously, "knob-in-hole," "KIH") orthogonal mutations, as described in greater detail below in Section 6.3.14.2, and either a S354C or a Y349C mutation that forms an engineered disulfide bridge with a CH3 domain containing an orthogonal mutation, as described in in greater detail below in Section 6.3.14.1. In some preferred embodiments, the knob-hole orthogonal mutation is a T366W mutation.

6.3.2.1. CH3 Regions

CH3 amino acid sequences, as described herein, are sequences of the C-terminal domain of an antibody heavy chain.

In a variety of embodiments, the CH3 sequences are mammalian sequences, including, but not limited to, mouse, rat, hamster, rabbit, camel, donkey, goat, and human sequences. In a preferred embodiment, the CH3 sequences are human sequences. In certain embodiments, the CH3 sequences are from an IgA1, IgA2, IgD, IgE, IgM, IgG1, IgG2, IgG3, IgG4 isotype or CH4 sequences from an IgE or IgM isotype. In a specific embodiment, the CH3 sequences are from an IgG isotype. In a preferred embodiment, the CH3 sequences are from an IgG1 isotype.

In certain embodiments, the CH3 sequences are endogenous sequences. In particular embodiments, the CH3 sequence is UniProt accession number P01857 amino acids 224-330. In various embodiments, a CH3 sequence is a segment of an endogenous CH3 sequence. In particular embodiments, a CH3 sequence has an endogenous CH3 sequence that lacks the N-terminal amino acids G224 and Q225. In particular embodiments, a CH3 sequence has an endogenous CH3 sequence that lacks the C-terminal amino acids P328, G329, and K330. In particular embodiments, a CH3 sequence has an endogenous CH3 sequence that lacks both the N-terminal amino acids G224 and Q225 and the C-terminal amino acids P328, G329, and K330. In preferred embodiments, a ROR binding molecule has multiple domains that have CH3 sequences, wherein a CH3 sequence can refer to both a full endogenous CH3 sequence as well as a CH3 sequence that lacks N-terminal amino acids, C-terminal amino acids, or both.

In certain embodiments, the CH3 sequences are endogenous sequences that have one or more mutations. In particular embodiments, the mutations are one or more orthogonal mutations that are introduced into an endogenous CH3 sequence to guide specific pairing of specific CH3 sequences, as described in more detail below in Sections 6.3.14.1-6.3.14.3.

In certain embodiments, the CH3 sequences are engineered to reduce immunogenicity of the antibody by replacing specific amino acids of one allotype with those of another allotype and referred to herein as isoallotype mutations, as described in more detail in Stickler et al. (Genes Immun. 2011 April; 12(3): 213-221), which is herein incorporated by reference for all that it teaches. In particular embodiments, specific amino acids of the G1m1 allotype are replaced. In a preferred embodiment, isoallotype mutations D356E and L358M are made in the CH3 sequence.

In a preferred embodiment, domain B has a human IgG1 CH3 amino acid sequence with the following mutational changes: P343V; Y349C; and a tripeptide insertion, 445P, 446G, 447K. In other preferred embodiments, domain B has a human IgG1 CH3 sequence with the following mutational changes: T366K; and a tripeptide insertion, 445K, 446S, 447C. In still other preferred embodiments, domain B has a human IgG1 CH3 sequence with the following mutational changes: Y349C and a tripeptide insertion, 445P, 446G, 447K.

In certain embodiments, domain B has a human IgG1 CH3 sequence with a 447C mutation incorporated into an otherwise endogenous CH3 sequence.

In the ROR binding molecules described herein, the N-terminus of domain B is connected to the C-terminus of domain A. In certain embodiments, domain B has a CH3 amino acid sequence that is mutated at its N-terminus at the junction between domain A and domain B, as described in greater detail below in Section 6.3.19.1 and Example 6.

In the ROR binding molecules, the C-terminus of domain B is connected to the N-terminus of domain D. In certain embodiments, domain B has a CH3 amino acid sequence that is extended at the C-terminus at the junction between domain B and domain D, as described in greater detail below in Section 6.3.19.3.

6.3.2.2. Orthologous CH2 Regions

CH2 amino acid sequences, as described herein, are sequences of the third domain of an antibody heavy chain, with reference from the N-terminus to C-terminus. CH2 amino acid sequences, in general, are discussed in more detail below in section 6.3.3. In a series of embodiments, a ROR binding molecule has more than one paired set of CH2 domains that have CH2 sequences, wherein a first set has CH2 amino acid sequences from a first isotype and one or more orthologous sets of CH2 amino acid sequences from another isotype. The orthologous CH2 amino acid sequences, as described herein, are able to interact with CH2 amino acid sequences from a shared isotype, but not significantly interact with the CH2 amino acid sequences from another isotype present in the ROR binding molecule. In particular embodiments, all sets of CH2 amino acid sequences are from the same species. In preferred embodiments, all sets of CH2 amino acid sequences are human amino acid sequences. In other embodiments, the sets of CH2 amino acid sequences are from different species. In particular embodiments, the first set of CH2 amino acid sequences is from the same isotype as the other non-CH2 domains in the ROR binding molecule. In a specific embodiment, the first set has CH2 amino acid sequences from an IgG isotype and the one or more orthologous sets have CH2 amino acid sequences from an IgM or IgE isotype. In certain embodiments, one or more of the sets of CH2 amino acid sequences are endogenous CH2 sequences. In other embodiments, one or more of the sets of CH2 amino acid sequences are endogenous CH2 sequences that have one or more mutations. In particular embodiments, the one or more mutations are orthogonal knob-hole mutations, orthogonal charge-pair mutations, or orthogonal hydrophobic mutations. Orthologous CH2 amino acid sequences useful for the ROR binding molecules are described in more detail in international PCT applications WO2017/011342 and WO2017/106462, herein incorporated by reference in their entirety.

6.3.3. Domain D (Constant Region)

In the ROR binding molecules described herein, domain D has a constant region amino acid sequence. Constant region amino acid sequences are described in more detail in Section 6.3.2.

In a preferred series of embodiments, domain D has a CH2 amino acid sequence. CH2 amino acid sequences, as described herein, are CH2 amino acid sequences of the third domain of a native antibody heavy chain, with reference from the N-terminus to C-terminus. In a variety of embodiments, the CH2 sequences are mammalian sequences, including but not limited to mouse, rat, hamster, rabbit, camel, donkey, goat, and human sequences. In a preferred embodiment, the CH2 sequences are human sequences. In certain embodiments, the CH2 sequences are from an IgA1, IgA2, IgD. IgE, IgG1, IgG2, IgG3, IgG4, or IgM isotype. In a preferred embodiment, the CH2 sequences are from an IgG1 isotype.

In certain embodiments, the CH2 sequences are endogenous sequences. In particular embodiments, the sequence is UniProt accession number P01857 amino acids 111-223. In a preferred embodiment, the CH2 sequences have an N-terminal hinge region peptide that connects the N-terminal variable domain-constant domain segment to the CH2 domain, as discussed in more detail below in Section 6.3.19.3.

In the ROR binding molecules, the N-terminus of domain D is connected to the C-terminus of domain B. In certain embodiments, domain B has a CH3 amino acid sequence that is extended at the C-terminus at the junction between domain D and domain B, as described in greater detail below in Section 6.3.19.3.

6.3.4. Domain E (Constant Region)

In the ROR binding molecules, domain E has a constant region domain amino acid sequence. Constant region amino acid sequences are described in more detail in Section 6.3.2.

In certain embodiments, the constant region sequence is a CH3 sequence. CH3 sequences are described in greater detail above in Section 6.3.2.1. In particular embodiments, the constant region sequence has been mutated to include one or more orthogonal mutations. In a preferred embodiment, domain E has a constant region sequence that is a CH3 sequence comprising knob-hole (synonymously, "knob-in-hole," "KIH") orthogonal mutations, as described in greater detail below in Section 6.3.14.2, and either a S354C or a Y349C mutation that forms an engineered disulfide bridge with a CH3 domain containing an orthogonal mutation, as described in in greater detail below in Section 6.3.14.1. In some preferred embodiments, the knob-hole orthogonal mutation is a T366W mutation.

In certain embodiments, the constant region domain sequence is a CH1 sequence. In particular embodiments, the CH1 amino acid sequence of domain E is the only CH1 amino acid sequence in the ROR binding molecule. In certain embodiments, the N-terminus of the CH1 domain is connected to the C-terminus of a CH2 domain, as described in greater detail below in 6.3.19.5. In certain embodiments, the constant region sequence is a CL sequence. In certain embodiments, the N-terminus of the CL domain is connected to the C-terminus of a CH2 domain, as described in greater detail below in 6.3.19.5. CH1 and CL sequences are described in further detail in Section 6.3.8.1.

6.3.5. Domain F (Variable Region)

In the ROR binding molecules, domain F has a variable region domain amino acid sequence. Variable region domain amino acid sequences, as discussed in greater detail in Section 6.3.1, are variable region domain amino acid sequences of an antibody including VL and VH antibody domain sequences. VL and VH sequences are described in greater detail above in Sections 6.3.1.1 and 6.3.1.4, respectively. In a preferred embodiment, domain F has a VH antibody domain sequence.

6.3.6. Domain G (Constant Region)

In the ROR binding molecules, domain G has a constant region amino acid sequence. Constant region amino acid sequences are described in more detail in Section 6.3.2.

In preferred specific embodiments, the constant region sequence is a CH3 sequence. CH3 sequences are described in greater detail below in Section 6.3.2.1. In other preferred embodiments, the constant region sequence is an orthologous CH2 sequence. Orthologous CH2 sequences are described in greater detail below in Section 6.3.2.2.

In certain preferred embodiments, domain G has a human IgG1 CH3 sequence with the following mutational changes: S354C; and a tripeptide insertion, 445P, 446G, 447K. In some preferred embodiments, domain G has a human IgG1 CH3 sequence with the following mutational changes: S354C; and 445P, 446G, 447K tripeptide insertion. In some preferred embodiments, domain G has a human IgG1 CH3 sequence with the following changes: L351D, and a tripeptide insertion of 445G, 446E, 447C.

6.3.7. Domain H (Variable Region)

In the ROR binding molecules, domain L has a variable region domain amino acid sequence. Variable region domain amino acid sequences, as discussed in greater detail in Section 6.3.1, are variable region domain amino acid sequences of an antibody including VL and VH antibody domain sequences. VL and VH sequences are described in greater detail above in Sections 6.3.1.1, and 6.3.1.4, respectively. In a preferred embodiment, domain H has a VL antibody domain sequence.

6.3.8. Domain I (Constant Region)

In the ROR binding molecules, domain I has a constant region domain amino acid sequence. Constant region domain amino acid sequences are described in greater detail above in Section 6.3.2. In a series of preferred embodiments of the ROR binding molecules, domain I has a CL amino acid sequence. In another series of embodiments, domain I has a CH1 amino acid sequence. CH1 and CL amino acid sequences are described in further detail in Section 6.3.8.1.

6.3.8.1. CH1 and CL Regions

CH1 amino acid sequences, as described herein, are sequences of the second domain of an antibody heavy chain, with reference from the N-terminus to C-terminus. In certain embodiments, the CH1 sequences are endogenous sequences. In a variety of embodiments, the CH1 sequences are mammalian sequences, including, but not limited to mouse, rat, hamster, rabbit, camel, donkey, goat, and human sequences. In a preferred embodiment, the CH1 sequences are human sequences. In certain embodiments, the CH1 sequences are from an IgA1, IgA2, IgD, IgE, IgG1, IgG2, IgG3, IgG4, or IgM isotype. In a preferred embodiment, the CH1 sequences are from an IgG1 isotype. In preferred embodiments, the CH1 sequence is UniProt accession number P01857 amino acids 1-98.

The CL amino acid sequences useful in the ROR binding molecules described herein are antibody light chain constant domain sequences. In certain embodiments, the CL sequences are endogenous sequences. In a variety of embodiments, the CL sequences are mammalian sequences, including, but not limited to mouse, rat, hamster, rabbit, camel, donkey, goat, and human sequences. In a preferred embodiment. CL sequences are human sequences.

In certain embodiments, the CL amino acid sequences are lambda (λ) light chain constant domain sequences. In particular embodiments, the CL amino acid sequences are human lambda light chain constant domain sequences. In preferred embodiments, the lambda (λ) light chain sequence is UniProt accession number P0CG04.

In certain embodiments, the CL amino acid sequences are kappa (κ) light chain constant domain sequences. In a preferred embodiment, the CL amino acid sequences are human kappa (κ) light chain constant domain sequences. In a preferred embodiment, the kappa light chain sequence is UniProt accession number P01834.

In certain embodiments, the CH1 sequence and the CL sequences are both endogenous sequences. In certain embodiments, the CH1 sequence and the CL sequences separately comprise respectively orthogonal modifications in endogenous CH1 and CL sequences, as discussed below in greater detail in Section 6.3.8.2. It is to be understood that orthogonal mutations in the CH1 sequence do not eliminate the specific binding interaction between the CH1 binding reagent and the CH1 domain. However, in some embodiments, the orthogonal mutations may reduce, though not eliminate, the specific binding interaction. CH1 and CL sequences can also be portions thereof, either of an endogenous or modified sequence, such that a domain having the CH1 sequence, or portion thereof, can associate with a domain having the CH1 sequence, or portion thereof. Furthermore, the ROR binding molecule having a portion of the CH1 sequences described above can be bound by the CH1 binding reagent.

Without wishing to be bound by theory, the CH1 domain is also unique in that it's folding is typically the rate limiting step in the secretion of IgG (Feige et al. *Mol Cell.* 2009 Jun 12:34(5):569-79; herein incorporated by reference in its entirety). Thus, purifying the ROR binding molecules based on the rate limiting component of CH1 comprising polypeptide chains can provide a means to purify complete complexes from incomplete chains, e.g., purifying complexes having a limiting CH1 domain from complexes only having one or more non-CH1 comprising chains.

While the CH1 limiting expression may be a benefit in some aspects, as discussed, there is the potential for CH1 to limit overall expression of the complete ROR binding molecules. Thus, in certain embodiments, the expression of the polypeptide chain comprising the CH1 sequence(s) is adjusted to improve the efficiency of the ROR binding molecules forming complete complexes. In an illustrative example, the ratio of a plasmid vector constructed to express the polypeptide chain comprising the CH1 sequence(s) can be increased relative to the plasmid vectors constructed to express the other polypeptide chains. In another illustrative example, the polypeptide chain comprising the CH1 sequence(s) when compared to the polypeptide chain comprising the CL sequence(s) can be the smaller of the two polypeptide chains. In another specific embodiment, the expression of the polypeptide chain comprising the CH1 sequence(s) can be adjusted by controlling which polypeptide chain has the CH1 sequence(s). For example, engineering the ROR binding molecule such that the CH1 domain is present in a two-domain polypeptide chain (e.g., the $4^{th}$ polypeptide chain described herein), instead of the CH1 sequence's native position in a four-domain polypeptide chain (e.g., the $3^{rd}$ polypeptide chain described herein), can be used to control the expression of the polypeptide chain comprising the CH1 sequence(s). However, in other aspects, a relative expression level of CH1 containing chains that is too high compared to the other chains can result in incomplete complexes the have the CH1 chain, but not each of the other chains. Thus, in certain embodiments, the expression of the polypeptide chain comprising the CH1 sequence(s) is adjusted to both reduce the formation incomplete complexes without the CH1 containing chain, and to reduce the formation incomplete complexes with the CH1 containing chain but without the other chains present in a complete complex.

6.3.8.2. CH1 and CL Orthogonal Modifications

In certain embodiments, the CH1 sequence and the CL sequences separately comprise respectively orthogonal modifications in endogenous CH1 and CL sequences.

Orthogonal mutations, in general, are described in more detail below in Sections 6.3.14.1-6.3.14.3.

In particular embodiments, the orthogonal modifications in endogenous CH1 and CL sequences are an engineered disulfide bridge selected from engineered cysteines at position 138 of the CH1 sequence and position 116 of the CL sequence, at position 128 of the CH1 sequence and position 119 of the CL sequence, or at position 129 of the CH1 sequence and position 210 of the CL sequence, as numbered and discussed in more detail in U.S. Pat. Nos. 8,053,562 and 9,527,927, each incorporated herein by reference in its entirety. In a preferred embodiment, the engineered cysteines are at position 128 of the CH1 sequence and position 118 of the CL Kappa sequence, as numbered by the Eu index.

In a series of preferred embodiments, the mutations that provide non-endogenous cysteine amino acids are a F118C mutation in the CL sequence with a corresponding A141C in the CH1 sequence, or a F118C mutation in the CL sequence with a corresponding L128C in the CH1 sequence, or a S162C mutations in the CL sequence with a corresponding P171C mutation in the CH1 sequence, as numbered by the Eu index.

In a variety of embodiments, the orthogonal mutations in the CL sequence and the CH1 sequence are charge-pair mutations. In specific embodiments the charge-pair mutations are a F118S, F118A or F118V mutation in the CL sequence with a corresponding A141L in the CH1 sequence, or a T129R mutation in the CL sequence with a corresponding K147D in the CH1 sequence, as numbered by the Eu index and described in greater detail in Bonisch et al. (*Protein Engineering, Design & Selection,* 2017, pp. 1-12), herein incorporated by reference for all that it teaches. In a series of preferred embodiments the charge-pair mutations are a N138K mutation in the CL sequence with a corresponding G166D in the CH1 sequence, or a N138D mutation in the CL sequence with a corresponding G166K in the CH1 sequence, as numbered by the Eu index.

6.3.9. Domain J (CH2)

In the ROR binding molecules, domain J has a CH2 amino acid sequence. CH2 amino acid sequences are described in greater detail above in Section 6.3.3. In a preferred embodiment, the CH2 amino acid sequence has an N-terminal hinge region that connects domain J to domain I, as described in more detail below in Section 6.3.19.4.

In the ROR binding molecules, the C-terminus of domain J is connected to the N-terminus of domain K. In particular embodiments, domain J is connected to the N-terminus of domain K that has a CH1 amino acid sequence or CL amino acid sequence, as described in further detail below in Section 6.3.19.5.

6.3.10. Domain K (Constant Region)

In the ROR binding molecules, domain K has a constant region domain amino acid sequence. Constant region domain amino acid sequences are described in greater detail above in Section 6.3.2. In a preferred embodiment, domain K has a constant region sequence that is a CH3 sequence comprising knob-hole orthogonal mutations, as described in greater detail below in Section 6.3.14.2; isoallotype mutations, as described in more detail above in 6.3.2.1; and either a S354C or a Y349C mutation that forms an engineered disulfide bridge with a CH3 domain containing an orthogonal mutation, as described in in greater detail below in Section 6.3.14.1. In some preferred embodiments, the knob-hole orthogonal mutations combined with isoallotype mutations are the following mutational changes: D356E, L358M, T366S, L368A, and Y407V.

In certain embodiments, the constant region domain sequence is a CH1 sequence. In particular embodiments, the CH1 amino acid sequence of domain K is the only CH1 amino acid sequence in the ROR binding molecule. In certain embodiments, the N-terminus of the CH1 domain is connected to the C-terminus of a CH2 domain, as described in greater detail below in 6.3.19.5. In certain embodiments, the constant region sequence is a CL sequence. In certain embodiments, the N-terminus of the CL domain is connected to the C-terminus of a CH2 domain, as described in greater detail below in 6.3.19.5. CH1 and CL sequences are described in further detail in Section 6.3.8.1.

6.3.11. Domain L (Variable Region)

In the ROR binding molecules, domain L has a variable region domain amino acid sequence. Variable region domain amino acid sequences, as discussed in greater detail in Section 6.3.1, are variable region domain amino acid sequences of an antibody including VL and VH antibody domain sequences. VL and VH sequences are described in greater detail above in Sections 6.3.1.1 and 6.3.1.4, respectively. In a preferred embodiment, domain L has a VH antibody domain sequence.

6.3.12. Domain M (Constant Region)

In the ROR binding molecules, domain M has a constant region domain amino acid sequence. Constant region domain amino acid sequences are described in greater detail above in Section 6.3.2. In a series of preferred embodiments of the ROR binding molecules, domain I has a CH1 amino acid sequence. In another series of preferred embodiments, domain I has a CL amino acid sequence. CH1 and CL amino acid sequences are described in further detail in Section 6.3.8.1.

6.3.13. Pairing of Domains A & F

In the ROR binding molecules, a domain A VL or VH amino acid sequence and a cognate domain F VL or VH amino acid sequence are associated and form an antigen binding site (ABS). The A:F antigen binding site (ABS) is capable of specifically binding an epitope of an antigen. Antigen binding by an ABS is described in greater detail below in Section 6.3.13.1.

In a variety of multivalent embodiments, the ABS formed by domains A and F (A:F) is identical in sequence to one or more other ABSs within the ROR binding molecule and therefore has the same recognition specificity as the one or more other sequence-identical ABSs within the ROR binding molecule.

In a variety of multivalent embodiments, the A:F ABS is non-identical in sequence to one or more other ABSs within the ROR binding molecule. In certain embodiments, the A:F ABS has a recognition specificity different from that of one or more other sequence-non-identical ABSs in the ROR binding molecule. In particular embodiments, the A:F ABS recognizes a different antigen from that recognized by at least one other sequence-non-identical ABS in the ROR binding molecule. In particular embodiments, the A:F ABS recognizes a different epitope of an antigen that is also recognized by at least one other sequence-non-identical ABS in the ROR binding molecule. In these embodiments, the ABS formed by domains A and F recognizes an epitope of antigen, wherein one or more other ABSs within the ROR binding molecule recognizes the same antigen but not the same epitope.

6.3.13.1. Binding of Antigen by ABS

An ABS, and the ROR binding molecule comprising such ABS, is said to "recognize" the epitope (or more generally, the antigen) to which the ABS specifically binds, and the epitope (or more generally, the antigen) is said to be the "recognition specificity" or "binding specificity" of the ABS.

The ABS is said to bind to its specific antigen or epitope with a particular affinity. As described herein, "affinity" refers to the strength of interaction of non-covalent intermolecular forces between one molecule and another. The affinity, i.e. the strength of the interaction, can be expressed as a dissociation equilibrium constant ($K_D$), wherein a lower $K_D$ value refers to a stronger interaction between molecules.

$K_D$ values of antibody constructs are measured by methods well known in the art including, but not limited to, bio-layer interferometry (e.g. Octet/FORTEBIO®), surface plasmon resonance (SPR) technology (e.g. Biacore®), and cell binding assays. For purposes herein, affinities are dissociation equilibrium constants measured by bio-layer interferometry using Octet/FORTEBIO*.

"Specific binding," as used herein, refers to an affinity between an ABS and its cognate antigen or epitope in which the $K_D$ value is below $10^{-6}$ M, $10^{-7}$ M, $10^{-8}$ M, $10^{-9}$ M, or $10^{-10}$ M.

The number of ABSs in a ROR binding molecule as described herein defines the "valency" of the ROR binding molecule, as schematized in FIG. 2. A ROR binding molecule having a single ABS is "monovalent". A ROR binding molecule having a plurality of ABSs is said to be "multivalent". A multivalent ROR binding molecule having two ABSs is "bivalent." A multivalent ROR binding molecule having three ABSs is "trivalent." A multivalent ROR binding molecule having four ABSs is "tetravalent."

In various multivalent embodiments, all of the plurality of ABSs have the same recognition specificity. As schematized in FIG. 2, such a ROR binding molecule is a "monospecific" "multivalent" binding construct. In other multivalent embodiments, at least two of the plurality of ABSs have different recognition specificities. Such ROR binding molecules are multivalent and "multispecific". In multivalent embodiments in which the ABSs collectively have two recognition specificities, the ROR binding molecule is "bispecific." In multivalent embodiments in which the ABSs collectively have three recognition specificities, the ROR binding molecule is "trispecific."

In multivalent embodiments in which the ABSs collectively have a plurality of recognition specificities for different epitopes present on the same antigen, the ROR binding molecule is "multiparatopic." Multivalent embodiments in which the ABSs collectively recognize two epitopes on the same antigen are "biparatopic."

In various multivalent embodiments, multivalency of the ROR binding molecule improves the avidity of the ROR binding molecule for a specific target. As described herein, "avidity" refers to the overall strength of interaction between two or more molecules, e.g. a multivalent ROR binding molecule for a specific target, wherein the avidity is the cumulative strength of interaction provided by the affinities of multiple ABSs. Avidity can be measured by the same methods as those used to determine affinity, as described above. In certain embodiments, the avidity of a ROR binding molecule for a specific target is such that the interaction is a specific binding interaction, wherein the avidity between two molecules has a $K_D$ value below $10^{-6}$ M, $10^{-7}$ M, $10^{-8}$ M, $10^{-9}$ M, or $10^{-10}$ M. In certain embodiments, the avidity of a ROR binding molecule for a specific target has a $K_D$ value such that the interaction is a specific binding interaction, wherein the one or more affinities of individual ABSs do not have has a $K_D$ value that qualifies as specifically binding their respective antigens or epitopes on their own. In certain embodiments, the avidity is the cumulative strength of interaction provided by the affinities of multiple ABSs for separate antigens on a shared specific target or complex, such as separate antigens found on an individual cell. In certain embodiments, the avidity is the cumulative strength of interaction provided by the affinities of multiple ABSs for separate epitopes on a shared individual antigen.

6.3.14. Pairing of Domains B & G

In the ROR binding molecules described herein, a domain B constant region amino acid sequence and a domain G constant region amino acid sequence are associated. Constant region domain amino acid sequences are described in greater detail above in Section 6.3.2.

In a series of preferred embodiments, domain B and domain G have CH3 amino acid sequences. CH3 sequences are described in greater detail above in Section 6.3.2.1. In various embodiments, the amino acid sequences of the B and the G domains are identical. In certain of these embodiments, the sequence is an endogenous CH3 sequence.

In a variety of embodiments, the amino acid sequences of the B and the G domains are different, and separately comprise respectively orthogonal modifications in an endogenous CH3 sequence, wherein the B domain interacts with the G domain, and wherein neither the B domain nor the G domain significantly interacts with a CH3 domain lacking the orthogonal modification.

"Orthogonal modifications" or synonymously "orthogonal mutations" as described herein are one or more engineered mutations in an amino acid sequence of an antibody domain that increase the affinity of binding of a first domain having orthogonal modification for a second domain having a complementary orthogonal modification. In certain embodiments, the orthogonal modifications decrease the affinity of a domain having the orthogonal modifications for a domain lacking the complementary orthogonal modifications. In certain embodiments, orthogonal modifications are mutations in an endogenous antibody domain sequence. In a variety of embodiments, orthogonal modifications are modifications of the N-terminus or C-terminus of an endogenous antibody domain sequence including, but not limited to, amino acid additions or deletions. In particular embodiments, orthogonal modifications include, but are not limited to, engineered disulfide bridges, knob-in-hole mutations, and charge-pair mutations, as described in greater detail below in Sections 6.3.14.1-6.3.14.3. In particular embodiments, orthogonal modifications include a combination of orthogonal modifications selected from, but not limited to, engineered disulfide bridges, knob-in-hole mutations, and charge-pair mutations. In particular embodiments, the orthogonal modifications can be combined with amino acid substitutions that reduce immunogenicity, such as isoallotype mutations, as described in greater detail above in Section 6.3.2.1.

6.3.14.1. Orthogonal Engineered Disulfide Bridges

In a variety of embodiments, the orthogonal modifications comprise mutations that generate engineered disulfide bridges between a first and a second domain. As described herein, "engineered disulfide bridges" are mutations that provide non-endogenous cysteine amino acids in two or more domains such that a non-native disulfide bond forms when the two or more domains associate. Engineered disulfide bridges are described in greater detail in Merchant et al. (*Nature Biotech* (1998) 16:677-681), the entirety of which is hereby incorporated by reference for all it teaches. In certain embodiments, engineered disulfide bridges improve orthogonal association between specific domains. In a particular embodiment, the mutations that generate engineered disulfide bridges are a K392C mutation in one of a first or second CH3 domains, and a D399C in the other CH3 domain. In a preferred embodiment, the mutations that generate engineered disulfide bridges are a S354C mutation in one of a first or second CH3 domains, and a Y349C in the other CH3 domain. In another preferred embodiment, the mutations that generate engineered disulfide bridges are a 447C mutation in both the first and second CH3 domains that are provided by extension of the C-terminus of a CH3 domain incorporating a KSC tripeptide sequence.

6.3.14.2. Orthogonal Knob-Hole Mutations

In a variety of embodiments, orthogonal modifications comprise knob-hole (synonymously, knob-in-hole) mutations. As described herein, knob-hole mutations are mutations that change the steric features of a first domain's surface such that the first domain will preferentially associate with a second domain having complementary steric mutations relative to association with domains without the complementary steric mutations. Knob-hole mutations are described in greater detail in U.S. Pat. Nos. 5,821,333 and 8,216,805, each of which is incorporated herein in its entirety. In various embodiments, knob-hole mutations are combined with engineered disulfide bridges, as described in greater detail in Merchant et al. (*Nature Biotech* (1998) 16:677-681)), incorporated herein by reference in its entirety. In various embodiments, knob-hole mutations, isoallotype mutations, and engineered disulfide mutations are combined.

In certain embodiments, the knob-in-hole mutations are a T366Y mutation in a first domain, and a Y407T mutation in a second domain. In certain embodiments, the knob-in-hole mutations are a F405A in a first domain, and a T394W in a second domain. In certain embodiments, the knob-in-hole mutations are a T366Y mutation and a F405A in a first domain, and a T394W and a Y407T in a second domain. In certain embodiments, the knob-in-hole mutations are a T366W mutation in a first domain, and a Y407A in a second domain. In certain embodiments, the combined knob-in-hole mutations and engineered disulfide mutations are a S354C and T366W mutations in a first domain, and a Y349C, T366S, L368A, and aY407V mutation in a second domain. In a preferred embodiment, the combined knob-in-hole mutations, isoallotype mutations, and engineered disulfide mutations are a S354C and T366W mutations in a first domain, and a Y349C, D356E, L358M, T366S, L368A, and aY407V mutation in a second domain.

6.3.14.3. Orthogonal Charge-Pair Mutations

In a variety of embodiments, orthogonal modifications are charge-pair mutations. As used herein, charge-pair mutations are mutations that affect the charge of an amino acid in a domain's surface such that the domain will preferentially associate with a second domain having complementary charge-pair mutations relative to association with domains without the complementary charge-pair mutations. In certain embodiments, charge-pair mutations improve orthogonal association between specific domains. Charge-pair mutations are described in greater detail in U.S. Pat. Nos. 8,592,562, 9,248,182, and 9,358,286, each of which is incorporated by reference herein for all they teach. In certain embodiments, charge-pair mutations improve stability between specific domains. In a preferred embodiment, the charge-pair mutations are a T366K mutation in a first domain, and a L351 D mutation in the other domain.

6.3.15. Pairing of Domains E & K

In various embodiments, the E domain has a CH3 amino acid sequence.

In various embodiments, the K domain has a CH3 amino acid sequence.

In a variety of embodiments, the amino acid sequences of the E and K domains are identical, wherein the sequence is an endogenous CH3 sequence.

In a variety of embodiments, the sequences of the E and K domains are different. In a variety of embodiments, the different sequences separately comprise respectively orthogonal modifications in an endogenous CH3 sequence, wherein the E domain interacts with the K domain, and wherein neither the E domain nor the K domain significantly interacts with a CH3 domain lacking the orthogonal modification. In certain embodiments, the orthogonal modifications include, but are not limited to, engineered disulfide bridges, knob-in-hole mutations, and charge-pair mutations, as described in greater detail above in sections 6.3.14.1-6.3.14.3. In particular embodiments, orthogonal modifications include a combination of orthogonal modifications selected from, but not limited to, engineered disulfide bridges, knob-in-hole mutations, and charge-pair mutations. In particular embodiments, the orthogonal modifications can be combined with amino acid substitutions that reduce immunogenicity, such as isoallotype mutations.

6.3.16. Pairing of Domains I & M and Domains H & L

In a variety of embodiments, domain I has a CL sequence and domain M has a CH1 sequence. In a variety of embodiments, domain H has a VL sequence and domain L has a VH sequence. In a preferred embodiment, domain H has a VL amino acid sequence, domain I has a CL amino acid sequence, domain L has a VH amino acid sequence, and domain M has a CH1 amino acid sequence. In another preferred embodiment, domain H has a VL amino acid sequence, domain I has a CL amino acid sequence, domain L has a VH amino acid sequence, domain M has a CH1 amino acid sequence, and domain K has a CH3 amino acid sequence.

In a variety of embodiments, the amino acid sequences of the I domain and the M domain separately comprise respectively orthogonal modifications in an endogenous sequence, wherein the I domain interacts with the M domain, and wherein neither the I domain nor the M domain significantly interacts with a domain lacking the orthogonal modification. In a series of embodiments, the orthogonal mutations in the I domain are in a CL sequence and the orthogonal mutations in the M domain are in CH1 sequence. Orthogonal mutations are in CH1 and CL sequences are described in more detail above in Section 6.3.8.2.

In a variety of embodiments, the amino acid sequences of the H domain and the L domain separately comprise respectively orthogonal modifications in an endogenous sequence, wherein the H domain interacts with the L domain, and wherein neither the H domain nor the L domain significantly interacts with a domain lacking the orthogonal modification. In a series of embodiments, the orthogonal mutations in the H domain are in a VL sequence and the orthogonal mutations in the L domain are in VH sequence. In specific embodiments, the orthogonal mutations are charge-pair mutations at the VH/VL interface. In preferred embodiments, the charge-pair mutations at the VH/VL interface are a Q39E in VH with a corresponding Q38K in VL, or a Q39K in VH with a corresponding Q38E in VL, as described in greater detail in Igawa et al. (*Protein Eng. Des. Sel.* 2010, vol. 23, 667-677), herein incorporated by reference for all it teaches.

In certain embodiments, the interaction between the A domain and the F domain form a first antigen binding site specific for a first antigen, and the interaction between the H domain and the L domain form a second antigen binding site specific for a second antigen. In certain embodiments, the interaction between the A domain and the F domain form a first antigen binding site specific for a first antigen, and the interaction between the H domain and the L domain form a second antigen binding site specific for the first antigen.

6.3.17. Trivalent ROR Binding Molecules

In another series of embodiments, the ROR binding molecules have three antigen binding sites and are therefore termed "trivalent."

With reference to FIG. 21, in various trivalent embodiments the ROR binding molecules further comprise a fifth polypeptide chain, wherein (a) the first polypeptide chain further comprises a domain N and a domain O, wherein the domains are arranged, from N-terminus to C-terminus, in a N-O-A-B-D-E orientation, and wherein domain N has a VL amino acid sequence, domain O has a constant region amino acid sequence; (b) the ROR binding molecule further comprises a fifth polypeptide chain, comprising: a domain P and a domain Q, wherein the domains are arranged, from N-terminus to C-terminus, in a P-Q orientation, and wherein domain P has a VH amino acid sequence and domain Q has a constant amino acid sequence; and (c) the first and the fifth polypeptides are associated through an interaction between the N and the P domains and an interaction between the O and the Q domains to form the ROR binding molecule. As schematized in FIG. 2, these trivalent embodiments are termed "2×1" trivalent constructs.

With reference to FIG. 26, in a further series of trivalent embodiments, the ROR binding molecules further comprise a sixth polypeptide chain, wherein (a) the third polypeptide chain further comprises a domain R and a domain S, wherein the domains are arranged, from N-terminus to C-terminus, in a R-S-H-I-J-K orientation, and wherein domain R has a VL amino acid sequence and domain S has a constant domain amino acid sequence; (b) the ROR binding molecule further comprises a sixth polypeptide chain, comprising: a domain T and a domain U, wherein the domains are arranged, from N-terminus to C-terminus, in a T-U orientation, and wherein domain T has a VH amino acid sequence and domain U has a constant domain amino acid sequence; and (c) the third and the sixth polypeptides are associated through an interaction between the R and the T domains and an interaction between the S and the U domains to form the ROR binding molecule. As schematized in FIG. 2, these trivalent embodiments are termed "1×2" trivalent constructs.

In a variety of embodiments, the domain O is connected to domain A through a peptide linker. In a variety of embodiments, the domain S is connected to domain H through a peptide linker. In a preferred embodiment, the peptide linker connecting either domain O to domain A or connecting domain S to domain H is a 6 amino acid GSGSGS (SEQ ID NO:541) peptide sequence, as described in more detail in Section 6.3.19.6.

6.3.17.1. Trivalent 2×1 Bispecific Constructs [2(A-A)×1(B)]

With reference to FIG. 21, in a variety of embodiments the amino acid sequences of domain N and domain A are identical, the amino acid sequences of domain H is different from domains N and A, the amino acid sequences of domain O and domain B are identical, the amino acid sequences of domain I is different from domains O and B, the amino acid sequences of domain P and domain F are identical, the amino acid sequences of domain L is different from domains P and F, the amino acid sequences of domain Q and domain G are identical, the amino acid sequences of domain M is different from domains Q and G; and the interaction between the A domain and the F domain form a first antigen binding site specific for a first antigen, the interaction between the H domain and the L domain form a second antigen binding site specific for a second antigen, and the domain N and domain P form a third antigen binding site specific for the first antigen.

6.3.17.2. Trivalent 2×1 Bispecific Constructs [2(A-B)×1(A)]

With reference to FIG. 21, in a variety of embodiments the amino acid sequences of domain N and domain H are identical, the amino acid sequences of domain A is different from domains N and H, the amino acid sequences of domain O and domain I are identical, the amino acid sequences of domain B is different from domains O and I, the amino acid sequences of domain P and domain L are identical, the amino acid sequences of domain F is different from domains P and L, the amino acid sequences of domain Q and domain M are identical, the amino acid sequences of domain G is different from domains Q and M; and the interaction between the A domain and the F domain form a first antigen binding site specific for a first antigen, the interaction between the H domain and the L domain form a second antigen binding site specific for a second antigen, and the domain N and domain P form a third antigen binding site specific for the second antigen.

6.3.17.3. Trivalent 2×1 Trispecific Constructs [2(A-B)×1(C)]

With reference to FIG. 21, in a variety of embodiments, the amino acid sequences of domain N, domain A, and domain H are different, the amino acid sequences of domain O, domain B, and domain I are different, the amino acid sequences of domain P, domain F. and domain L are different, and the amino acid sequences of domain Q, domain G, and domain M are different; and the interaction between the A domain and the F domain form a first antigen binding site specific for a first antigen, the interaction between the H domain and the L domain form a second antigen binding site specific for a second antigen, and the domain N and domain P form a third antigen binding site specific for a third antigen.

In certain embodiments, domain O has a constant region sequence that is a CL from a kappa light chain and domain Q has a constant region sequence that is a CH1 from an IgG1 isotype, as discussed in more detail in Section 6.3.8.1. In a preferred embodiment, domain O and domain Q have CH3 sequences such that they specifically associate with each other, as discussed in more detail above in Section 6.3.14.

6.3.17.4. Trivalent 1×2 Bispecific Constructs [1(A)×2(B-A)]

With reference to FIG. 26, in a variety of embodiments, the amino acid sequences of domain R and domain A are identical, the amino acid sequences of domain H is different from domain R and A, the amino acid sequences of domain S and domain B are identical, the amino acid sequences of domain I is different from domain S and B, the amino acid sequences of domain T and domain F are identical, the amino acid sequences of domain L is different from domain T and F, the amino acid sequences of domain U and domain G are identical, the amino acid sequences of domain M is different from domain U and G and the interaction between the A domain and the F domain form a first antigen binding site specific for a first antigen, the interaction between the H domain and the L domain form a second antigen binding site specific for a second antigen, and the domain R and domain T form a third antigen binding site specific for the first antigen.

6.3.17.5. Trivalent 1×2 Bispecific Constructs [1(A)×2(B-B)]

In a variety of embodiments, the ROR binding molecule further comprises a second CH1 domain, or portion thereof. With reference to FIG. 26, in specific embodiments, the amino acid sequences of domain R and domain H are identical, the amino acid sequences of domain A is different from domain R and H, the amino acid sequences of domain S and domain I are identical, the amino acid sequences of domain B is different from domain S and I, the amino acid sequences of domain T and domain L are identical, the amino acid sequences of domain F is different from domain T and L, the amino acid sequences of domain U and domain M are identical, the amino acid sequences of domain G is different from domain U and M and the interaction between the A domain and the F domain form a first antigen binding site specific for a first antigen, the interaction between the H domain and the L domain form a second antigen binding site specific for a second antigen, and the domain R and domain T form a third antigen binding site specific for the second antigen.

In particular embodiments, the amino acid sequences of domain S and domain I are CH1 sequences. In particular embodiments, the amino acid sequences of domain U and domain M are CH1 sequences.

6.3.17.6. Trivalent 1×2 Trispecific Constructs [1(A)×2(B-C)]

With reference to FIG. 26, in a variety of embodiments, the amino acid sequences of domain R, domain A, and domain H are different, the amino acid sequences of domain S, domain B, and domain I are different, the amino acid sequences of domain T, domain F, and domain L are different, and the amino acid sequences of domain U, domain G, and domain M are different; and the interaction between the A domain and the F domain form a first antigen binding site specific for a first antigen, the interaction between the H domain and the L domain form a second antigen binding site specific for a second antigen, and the domain R and domain T form a third antigen binding site specific for a third antigen.

In particular embodiments, domain S has a constant region sequence that is a CL from a kappa light chain and domain U has a constant region sequence that is a CH1 from an IgG1 isotype, as discussed in more detail in Section 6.3.8.1. In a preferred embodiment, domain S and domain U have CH3 sequences such that they specifically associate with each other, as discussed in more detail above in Section 6.3.14.

In certain embodiments, the ROR binding molecule further comprises a second CH1 domain, or portion thereof. In particular embodiments, the amino acid sequences of domain S and domain I are CH1 sequences. In particular embodiments, the amino acid sequences of domain U and domain M are CH1 sequences.

6.3.18. Tetravalent 2×2 ROR binding molecules

In a variety of embodiments, the ROR binding molecules have 4 antigen binding sites and are therefore termed "tetravalent."

With reference to FIG. 34, in a further series of embodiments, the ROR binding molecules further comprise a fifth and a sixth polypeptide chain, wherein (a) the first polypeptide chain further comprises a domain N and a domain O, wherein the domains are arranged, from N-terminus to C-terminus, in a N-O-A-B-D-E orientation; (b) the third polypeptide chain further comprises a domain R and a domain S, wherein the domains are arranged, from N-terminus to C-terminus, in a R-S-H-I-J-K orientation; (c) the ROR binding molecule further comprises a fifth and a sixth polypeptide chain, wherein the fifth polypeptide chain comprises a domain P and a domain Q, wherein the domains are arranged, from N-terminus to C-terminus, in a P-Q orientation, and the sixth polypeptide chain comprises a domain T and a domain U, wherein the domains are arranged, from N-terminus to C-terminus, in a T-U orientation; and (d) the first and the fifth polypeptides are associated through an interaction between the N and the P domains and an interaction between the O and the Q domains, and the third and the sixth polypeptides are associated through an interaction between the R and the T domains and an interaction between the S and the U domains to form the ROR binding molecule.

In a variety of embodiments, the domain O is connected to domain A through a peptide linker and the domain S is connected to domain H through a peptide linker. In a preferred embodiment, the peptide linker connecting domain O to domain A and connecting domain S to domain H is a 6 amino acid GSGSGS (SEQ ID NO:541) peptide sequence, as described in more detail in Section 6.3.19.6.

6.3.18.1. Tetravalent 2×2 Bispecific Constructs

With reference to FIG. 34, in a series of tetravalent 2×2 bispecific ROR binding molecules, the amino acid sequences of domain N and domain A are identical, the amino acid sequences of domain H and domain R are identical, the amino acid sequences of domain O and domain B are identical, the amino acid sequences of domain I and domain S are identical, the amino acid sequences of domain P and domain F are identical, the amino acid sequences of domain L and domain T are identical, the amino acid sequences of domain Q and domain G are identical, the amino acid sequences of domain M and domain U are identical; and wherein the interaction between the A domain and the F domain form a first antigen binding site specific for a first antigen, the domain N and domain P form a second antigen binding site specific for the first antigen, the interaction between the H domain and the L domain form a third antigen binding site specific for a second antigen, and the interaction between the R domain and the T domain form a fourth antigen binding site specific for the second antigen.

With reference to FIG. 34, in another series of tetravalent 2×2 bispecific ROR binding molecules, the amino acid sequences of domain H and domain A are identical, the amino acid sequences of domain N and domain R are identical, the amino acid sequences of domain I and domain B are identical, the amino acid sequences of domain O and domain S are identical, the amino acid sequences of domain L and domain F are identical, the amino acid sequences of domain P and domain T are identical, the amino acid sequences of domain M and domain G are identical, the amino acid sequences of domain Q and domain U are identical; and wherein the interaction between the A domain and the F domain form a first antigen binding site specific for a first antigen, the domain N and domain P form a second antigen binding site specific for a second antigen, the interaction between the H domain and the L domain form a third antigen binding site specific for the first antigen, and the interaction between the R domain and the T domain form a fourth antigen binding site specific for the second antigen.

6.3.19. Domain Junctions

6.3.19.1. Junctions Connecting VL and CH3 Domains

In a variety of embodiments, the amino acid sequence that forms a junction between the C-terminus of a VL domain and the N-terminus of a CH3 domain is an engineered sequence. In certain embodiments, one or more amino acids are deleted or added in the C-terminus of the VL domain. In certain embodiments, the junction connecting the C-terminus of a VL domain and the N-terminus of a CH3 domain is one of the sequences described in Table 2 below in Section 6.13.7. In particular embodiments, A111 is deleted in the C-terminus of the VL domain. In certain embodiments, one or more amino acids are deleted or added in the N-terminus of the CH3 domain. In particular embodiments, P343 is deleted in the N-terminus of the CH3 domain. In particular embodiments, P343 and R344 are deleted in the N-terminus of the CH3 domain. In certain embodiments, one or more amino acids are deleted or added to both the C-terminus of the VL domain and the N-terminus of the CH3 domain. In particular embodiments, A111 is deleted in the C-terminus of the VL domain and P343 is deleted in the N-terminus of the CH3 domain. In a preferred embodiment, A111 and V110 are deleted in the C-terminus of the VL domain. In another preferred embodiment, A111 and V110 are deleted in the C-terminus of the VL domain and the N-terminus of the CH3 domain has a P343V mutation.

6.3.19.2. Junctions Connecting VH and CH3 Domains

In a variety of embodiments, the amino acid sequence that forms a junction between the C-terminus of a VH domain and the N-terminus of a CH3 domain is an engineered sequence. In certain embodiments, one or more amino acids are deleted or added in the C-terminus of the VH domain. In certain embodiments, the junction connecting the C-terminus of a VH domain and the N-terminus of the CH3 domain is one of the sequences described in Table 3 below in Section 6.13.7. In particular embodiments, K117 and G118 are deleted in the C-terminus of the VH domain. In certain embodiments, one or more amino acids are deleted or added in the N-terminus of the CH3 domain. In particular embodiments, P343 is deleted in the N-terminus of the CH3 domain. In particular embodiments, P343 and R344 are deleted in the N-terminus of the CH3 domain. In particular embodiments, P343, R344, and E345 are deleted in the N-terminus of the CH3 domain. In certain embodiments, one or more amino acids are deleted or added to both the C-terminus of the VH domain and the N-terminus of the CH3 domain. In a preferred embodiment, T116, K117, and G118 are deleted in the C-terminus of the VH domain.

6.3.19.3. Junctions Connecting CH3 C-Terminus to CH2 N-Terminus (Hinge)

In the ROR binding molecules described herein, the N-terminus of the CH2 domain has a "hinge" region amino acid sequence. As used herein, hinge regions are sequences of an antibody heavy chain that link the N-terminal variable domain-constant domain segment of an antibody and a CH2 domain of an antibody. In addition, the hinge region typically provides both flexibility between the N-terminal variable domain-constant domain segment and CH2 domain, as well as amino acid sequence motifs that form disulfide bridges between heavy chains (e.g. the first and the third polypeptide chains). As used herein, the hinge region amino acid sequence is SEQ ID NO: 56.

In a variety of embodiments, a CH3 amino acid sequence is extended at the C-terminus at the junction between the C-terminus of the CH3 domain and the N-terminus of a CH2 domain. In certain embodiments, a CH3 amino acid sequence is extended at the C-terminus at the junction between the C-terminus of the CH3 domain and a hinge region, which in turn is connected to the N-terminus of a CH2 domain. In a preferred embodiment, the CH3 amino acid sequence is extended by inserting a PGK tripeptide sequence followed by the DKTHT (SEQ ID NO:542) motif of an IgG1 hinge region.

In a particular embodiment, the extension at the C-terminus of the CH3 domain incorporates amino acid sequences that can form a disulfide bond with orthogonal C-terminal extension of another CH3 domain. In a preferred embodiment, the extension at the C-terminus of the CH3 domain incorporates a KSC tripeptide sequence that is followed by the DKTHT (SEQ ID NO:542) motif of an IgG1 hinge region that forms a disulfide bond with orthogonal C-terminal extension of another CH3 domain that incorporates a GEC motif of a kappa light chain.

6.3.19.4. Junctions Connecting CL C-Terminus and CH2 N-Terminus (Hinge)

In a variety of embodiments, a CL amino acid sequence is connected through its C-terminus to a hinge region, which in turn is connected to the N-terminus of a CH2 domain. Hinge region sequences are described in more detail above in Section 6.3.19.3. In a preferred embodiment, the hinge region amino acid sequence is SEQ ID NO:56.

6.3.19.5. Junctions Connecting CH2 C-terminus to Constant Region Domain

In a variety of embodiments, a CH2 amino acid sequence is connected through its C-terminus to the N-terminus of a constant region domain. Constant regions are described in more detail above in Section 6.3.4. In a preferred embodiment, the CH2 sequence is connected to a CH3 sequence via its endogenous sequence. In other embodiments, the CH2 sequence is connected to a CH1 or CL sequence. Examples discussing connecting a CH2 sequence to a CH1 or CL sequence are described in more detail in U.S. Pat. No. 8,242,247, which is hereby incorporated in its entirety.

6.3.19.6. Junctions Connecting Domain O to Domain A or Domain S to Domain H on Trivalent and Tetravalent Molecules In a variety of embodiments, heavy chains of antibodies (e.g. the first and third polypeptide chains) are extended at their N-terminus to include additional domains that provide additional ABSs. With reference to FIG. 21, FIG. 26, and FIG. 34, in certain embodiments, the C-terminus of the constant region domain amino acid sequence of a domain O and/or a domain S is connected to the N-terminus of the variable region domain amino acid sequence of a domain A and/or a domain H, respectively. In some preferred embodiments, the constant region domain is a CH3 amino acid sequence and the variable region domain is a VL amino acid sequence. In some preferred embodiments, the constant region domain is a CL amino acid sequence and the variable region domain is a VL amino acid sequence. In certain embodiments, the constant region domain is connected to the variable region domain through a peptide linker. In a preferred embodiment, the peptide linker is a 6 amino acid GSGSGS (SEQ ID NO:541) peptide sequence.

In a variety of embodiments, light chains of antibodies (e.g. the second and fourth polypeptide chains) are extended at their N-terminus to include additional variable domain-constant domain segments of an antibody. In certain embodiments, the constant region domain is a CH1 amino acid sequence and the variable region domain is a VH amino acid sequence.

6.4. Specific Bivalent ROR Binding Molecules

In a further aspect, bivalent ROR binding molecules are provided.

With reference to FIG. 3, in a series of embodiments the ROR binding molecules comprise a first, second, third, and fourth polypeptide chain, wherein (a) the first polypeptide chain comprises a domain A, a domain B, a domain D, and a domain E, wherein the domains are arranged, from N-terminus to C-terminus, in a A-B-D-E orientation, and domain A has a VL amino acid sequence, domain B has a CH3 amino acid sequence, domain D has a CH2 amino acid sequence, and domain E has a constant region domain amino acid sequence; (b) the second polypeptide chain comprises a domain F and a domain G, wherein the domains are arranged, from N-terminus to C-terminus, in a F-G orientation, and wherein domain F has a VH amino acid sequence and domain G has a CH3 amino acid sequence, (c) the third polypeptide chain comprises a domain H, a domain I, a domain J, and a domain K, wherein the domains are arranged, from N-terminus to C-terminus, in a H-I-J-K orientation, and wherein domain H has a variable region domain amino acid sequence, domain I has a constant region domain amino acid sequence, domain J has a CH2 amino acid sequence, and K has a constant region domain amino acid sequence; (d) the fourth polypeptide chain comprises a domain L and a domain M, wherein the domains are arranged, from N-terminus to C-terminus, in a L-M orientation, and wherein domain L has a variable region domain amino acid sequence and domain M has a constant region domain amino acid sequence; (e) the first and the second polypeptides are associated through an interaction between the A and the F domains and an interaction between the B and the G domains; (f) the third and the fourth polypeptides are associated through an interaction between the H and the L domains and an interaction between the I and the M domains; and (g) the first and the third polypeptides are associated through an interaction between the D and the J domains and an interaction between the E and the K domains to form the ROR binding molecule.

In a preferred embodiment, domain E has a CH3 amino acid sequence, domain H has a VL amino acid sequence, domain I has a CL amino acid sequence, domain K has a CH3 amino acid sequence, domain L has a VH amino acid sequence, and domain M has a CH1 amino acid sequence.

In certain embodiments, the interaction between the A domain and the F domain form a first antigen binding site specific for a first antigen, and the interaction between the H domain and the L domain form a second antigen binding site specific for a second antigen, and the ROR binding molecule is a bispecific bivalent ROR binding molecule. In certain embodiments, the interaction between the A domain and the F domain form a first antigen binding site specific for a first antigen, and the interaction between the H domain and the L domain form a second antigen binding site specific for the first antigen, and the ROR binding molecule is a monospecific bivalent ROR binding molecule.

6.4.1. Bivalent Bispecific B-Body "BC1"

With reference to FIG. 3 and FIG. 6, in a series of embodiments, the ROR binding molecule has a first, second, third, and fourth polypeptide chain, wherein (a) the first polypeptide chain comprises a domain A, a domain B, a domain D, and a domain E, wherein the domains are arranged, from N-terminus to C-terminus, in a A-B-D-E orientation, and domain A has a first VL amino acid sequence, domain B has a human IgG1 CH3 amino acid sequence with a T366K mutation and a C-terminal extension incorporating a KSC tripeptide sequence that is followed by the DKTHT (SEQ ID NO:542) motif of an IgG1 hinge region, domain D has a human IgG1 CH2 amino acid sequence, and domain E has human IgG1 CH3 amino acid with a S354C and T366W mutation; (b) the second polypeptide chain has a domain F and a domain G, wherein the domains are arranged, from N-terminus to C-terminus, in a F-G orientation, and wherein domain F has a first VH amino acid sequence and domain G has a human IgG1 CH3 amino acid sequence with a L351D mutation and a C-terminal extension incorporating a GEC amino acid disulfide motif; (c) the third polypeptide chain has a domain H, a domain I, a domain J, and a domain K, wherein the domains are arranged, from N-terminus to C-terminus, in a H-I-J-K orientation, and wherein domain H has a second VL amino acid sequence, domain I has a human CL kappa amino acid sequence, domain J has a human IgG1 CH2 amino acid sequence, and K has a human IgG1 CH3 amino acid sequence with a Y349C, a D356E, a L358M, a T366S, a L368A, and a Y407V mutation; (d) the fourth polypeptide chain has a domain L and a domain M, wherein the domains are arranged, from N-terminus to C-terminus, in a L-M orientation, and wherein domain L has a second VH amino acid sequence and domain M has a human IgG1 CH1 amino acid sequence; (e) the first and the second polypeptides are associated through an interaction between the A and the F domains and an interaction between the B and the G domains; (f) the third and the fourth polypeptides are associated through an interaction between the H and the L domains and an interaction between the I and the M domains: (g) the first and the third polypeptides are associated through an interaction between the D and the J domains and an interaction between the E and the K domains to form the ROR binding molecule; (h) domain A and domain F form a first antigen binding site specific for a first antigen; and (i) domain H and domain L form a second antigen binding site specific for a second antigen.

In preferred embodiments, the first polypeptide chain has the sequence SEQ ID NO:8, the second polypeptide chain has the sequence SEQ ID NO:9, the third polypeptide chain has the sequence SEQ ID NO:10, and the fourth polypeptide chain has the sequence SEQ ID NO:11.

6.4.2. Bivalent Bispecific B-Body "BC6"

With reference to FIG. 3 and FIG. 14, in a series of embodiments, the ROR binding molecule has a first, second, third, and fourth polypeptide chain, wherein (a) the first polypeptide chain comprises a domain A, a domain B, a domain D, and a domain E, wherein the domains are arranged, from N-terminus to C-terminus, in a A-B-D-E orientation, and domain A has a first VL amino acid sequence, domain B has a human IgG1 CH3 amino acid sequence with a C-terminal extension incorporating a KSC tripeptide sequence that is followed by the DKTHT (SEQ ID NO:542) motif of an IgG1 hinge region, domain D has a human IgG1 CH2 amino acid sequence, and domain E has human IgG1 CH3 amino acid with a S354C and a T366W mutation; (b) the second polypeptide chain has a domain F and a domain G, wherein the domains are arranged, from N-terminus to C-terminus, in a F-G orientation, and wherein domain F has a first VH amino acid sequence and domain G has a human IgG1 CH3 amino acid sequence with a C-terminal extension incorporating a GEC amino acid disulfide motif; (c) the third polypeptide chain has a domain H, a domain I, a domain J, and a domain K, wherein the domains are arranged, from N-terminus to C-terminus, in a H-I-J-K orientation, and wherein domain H has a second VL amino acid sequence, domain I has a human CL kappa amino acid sequence, domain J has a human IgG1 CH2 amino acid sequence, and K has a human IgG1 CH3 amino acid sequence with a Y349C, a D356E, a L358M, a T366S, a L368A, and a Y407V mutation; (d) the fourth polypeptide chain has a domain L and a domain M, wherein the domains are arranged, from N-terminus to C-terminus, in a L-M orientation, and wherein domain L has a second VH amino acid sequence and domain M has a human IgG1 amino acid sequence; (e) the first and the second polypeptides are associated through an interaction between the A and the F domains and an interaction between the B and the G domains: (f) the third and the fourth polypeptides are associated through an interaction between the H and the L domains and an interaction between the I and the M domains; (g) the first and the third polypeptides are associated through an interaction between the D and the J domains and an interaction between the E and the K domains to form the ROR binding molecule; (h) domain A and domain F form a first antigen binding site specific for a first antigen; and (i) domain H and domain L form a second antigen binding site specific for a second antigen.

6.43. Bivalent Bispecific B-Body "BC28"

With reference to FIG. 3 and FIG. 16, in a series of embodiments, the ROR binding molecule has a first, second, third, and fourth polypeptide chain, wherein (a) the first polypeptide chain comprises a domain A, a domain B, a domain D, and a domain E, wherein the domains are arranged, from N-terminus to C-terminus, in a A-B-D-E orientation, and domain A has a first VL amino acid sequence, domain B has a human IgG1 CH3 amino acid sequence with a Y349C mutation and a C-terminal extension incorporating a PGK tripeptide sequence that is followed by the DKTHT (SEQ ID NO:542) motif of an IgG1 hinge region, domain D has a human IgG1 CH2 amino acid sequence, and domain E has a human IgG1 CH3 amino acid with a S354C and a T366W mutation; (b) the second polypeptide chain has a domain F and a domain G, wherein the domains are arranged, from N-terminus to C-terminus, in a F-G orientation, and wherein domain F has a first VH amino acid sequence and domain G has a human IgG1 CH3 amino acid sequence with a S354C mutation and a C-terminal extension incorporating a PGK tripeptide sequence; (c) the third polypeptide chain has a domain H, a domain I, a domain J, and a domain K, wherein the domains are arranged, from N-terminus to C-terminus, in a H-I-J-K orientation, and wherein domain H has a second VL amino acid sequence, domain I has a human CL kappa amino acid sequence, domain J has a human IgG1 CH2 amino acid sequence, and K has a human IgG1 CH3 amino acid sequence with a Y349C, a D356E, a L358M, a T366S, a L368A, and a Y407V; (d) the fourth polypeptide chain has a domain L and a domain M, wherein the domains are arranged, from N-terminus to C-terminus, in a L-M orientation, and wherein domain L has a second VH amino acid sequence and domain M has a human IgG1 CH1 amino acid sequence; (e) the first and the second polypeptides are associated through an interaction between the A and the F domains and an interaction between the B and the G domains; (f) the third and the fourth polypeptides are associated through an interaction between the H and the L domains and an interaction between the I and the M domains; (g) the first and the third polypeptides are associated through an interaction between the D and the J domains and an interaction between the E and the K domains to form the ROR binding molecule; (h) domain A and domain F form a first antigen binding site specific for a first antigen; and (i) domain H and domain L form a second antigen binding site specific for a second antigen.

In preferred embodiments, the first polypeptide chain has the sequence SEQ ID NO:24, the second polypeptide chain has the sequence SEQ ID NO:25, the third polypeptide chain has the sequence SEQ ID NO:10, and the fourth polypeptide chain has the sequence SEQ ID NO:11.

6.4.4. Bivalent Bispecific B-Body "BC44"

With reference to FIG. 3 and FIG. 19, in a series of embodiments, the ROR binding molecule has a first, second, third, and fourth polypeptide chain, wherein (a) the first polypeptide chain comprises a domain A, a domain B, a domain D, and a domain E, wherein the domains are arranged, from N-terminus to C-terminus, in a A-B-D-E orientation, and domain A has a first VL amino acid sequence, domain B has a human IgG1 CH3 amino acid sequence with a Y349C mutation, a P343V mutation, and a C-terminal extension incorporating a PGK tripeptide sequence that is followed by the DKTHT (SEQ ID NO:542) motif of an IgG1 hinge region, domain D has a human IgG1 CH2 amino acid sequence, and domain E has human IgG1 CH3 amino acid with a S354C mutation and a T366W mutation; (b) the second polypeptide chain has a domain F and a domain G, wherein the domains are arranged, from N-terminus to C-terminus, in a F-G orientation, and wherein domain F has a first VH amino acid sequence and domain G has a human IgG1 CH3 amino acid sequence with a S354C mutation and a C-terminal extension incorporating a PGK tripeptide sequence; (c) the third polypeptide chain has a domain H, a domain I, a domain J, and a domain K, wherein the domains are arranged, from N-terminus to C-terminus, in a H-I-J-K orientation, and wherein domain H has a second VL amino acid sequence, domain I has a human CL kappa amino acid sequence, domain J has a human IgG1 CH2 amino acid sequence, and K has a human IgG1 CH3 amino acid sequence with a Y349C, T366S, L368A, and aY407V; (d) the fourth polypeptide chain has a domain L and a domain M, wherein the domains are arranged, from N-terminus to C-terminus, in a L-M orientation, and wherein domain L has a second VH amino acid sequence and domain M has a human IgG1 amino acid sequence; (e) the first and the second polypeptides are associated through an interaction between the A and the F domains and an interaction between the B and the G domains: (f) the third and the fourth polypeptides are associated through an interaction between the H and the L domains and an interaction between the I and the M domains; and (g) the first and the third polypeptides are associated through an interaction between the D and the J domains and an interaction between the E and the K domains to form the ROR binding molecule; (h) domain A and domain F form a first antigen binding site specific for a first antigen; and (i) domain H and domain L form a second antigen binding site specific for a second antigen.

In preferred embodiments, the first polypeptide chain has the sequence SEQ ID NO:32, the second polypeptide chain has the sequence SEQ ID NO:25, the third polypeptide chain has the sequence SEQ ID NO:10, and the fourth polypeptide chain has the sequence SEQ ID NO:11.

6.5. Specific Trivalent ROR Binding Molecules

6.5.1. Trivalent 1×2 Bispecific B-Body "BC28-1×2"

With reference to Section 6.4.3, and FIG. 26, in a series of embodiments, the ROR binding molecules further comprise a sixth polypeptide chain, wherein (a) the third polypeptide chain further comprises a domain R and a domain S, wherein the domains are arranged, from N-terminus to C-terminus, in a R-S-H-I-J-K orientation, and wherein domain R has the first VL amino acid sequence and domain S has a human IgG1 CH3 amino acid sequence with a Y349C mutation and a C-terminal extension incorporating a PGK tripeptide sequence that is followed by GSGSGS (SEQ ID NO:541) linker peptide connecting domain S to domain H; (b) the ROR binding molecule further comprises a sixth polypeptide chain, comprising: a domain T and a domain U, wherein the domains are arranged, from N-terminus to C-terminus, in a T-U orientation, and wherein domain T has the first VH amino acid sequence and domain U has a human IgG1 CH3 amino acid sequence with a S354C mutation and a C-terminal extension incorporating a PGK tripeptide sequence; (c) the third and the sixth polypeptides are associated through an interaction between the R and the T domains and an interaction between the S and the U domains to form the ROR binding molecule, and (d) domain R and domain T form a third antigen binding site specific for the first antigen.

In preferred embodiments, the first polypeptide chain has the sequence SEQ ID NO:24, the second polypeptide chain has the sequence SEQ ID NO:25, the third polypeptide chain has the sequence SEQ ID NO:37, the fourth polypeptide chain has the sequence SEQ ID NO:11, and the sixth polypeptide chain has the sequence SEQ ID NO:25.

6.5.2. Trivalent 1×2 Trispecific B-Body "BC28-1×1×1a"

With reference to Section 6.4.3, and FIG. 26 and FIG. 30, in a series of embodiments, the ROR binding molecules further comprise a sixth polypeptide chain, wherein (a) the third polypeptide chain further comprises a domain R and a domain S, wherein the domains are arranged, from N-terminus to C-terminus, in a R-S-H-I-J-K orientation, and wherein domain R has a third VL amino acid sequence and domain S has a human IgG1 CH3 amino acid sequence with a T366K mutation and a C-terminal extension incorporating a KSC tripeptide sequence that is followed by GSGSGS (SEQ ID NO:541) linker peptide connecting domain S to domain H; (b) the ROR binding molecule further comprises a sixth polypeptide chain, comprising: a domain T and a domain U, wherein the domains are arranged, from N-terminus to C-terminus, in a T-U orientation, and wherein domain T has a third VH amino acid sequence and domain U has a human IgG1 CH3 amino acid sequence with a L351D mutation and a C-terminal extension incorporating a GEC amino acid disulfide motif; and (c) the third and the sixth polypeptides are associated through an interaction between the R and the T domains and an interaction between the S and the U domains to form the ROR binding molecule, and (d) domain R and domain T form a third antigen binding site specific for a third antigen.

In preferred embodiments, the first polypeptide chain has the sequence SEQ ID NO:24, the second polypeptide chain has the sequence SEQ ID NO:25, the third polypeptide chain has the sequence SEQ ID NO:45, the fourth polypeptide chain has the sequence SEQ ID NO:11, and the sixth polypeptide chain has the sequence SEQ ID NO: 53.

6.6. Other ROR Binding Molecule Platforms

The various antibody platforms described above are not limiting. The antigen binding sites described herein, including specific CDR subsets, can be formatted into any binding molecule platform including, but not limited to, full-length antibodies, Fab fragments, Fvs, scFvs, tandem scFvs, Diabodies, scDiabodies, DARTs, tandAbs, minibodies, camelid VHH, and other antibody fragments or formats known to those skilled in the art. Exemplary antibody and antibody fragment formats are described in detail in Brinkmann et al. (*MABS*. 2017, Vol. 9, No. 2, 182-212), herein incorporated by reference for all that it teaches.

6.7. Antigen Specificities

Other antigens to which a ROR binding molecule as described herein can specifically bind, in addition to a ROR antigen, may be chosen from a wide variety of molecular targets. For example, an antigen binding site or sites may specifically bind E-Cad, CLDN7, FGFR2b, N-Cad, Cad-11, FGFR2c, ERBB2, ERBB3, FGFR1, FOLR1, IGF-Ira, GLPIR, PDGFRa, PDGFRb, EPHB6, ABCG2, CXCR4, CXCR7, Integrin-avb3, SPARC, VCAM, ICAM, Annexin, ROR1, ROR2, TNFα, CD137, angiopoietin 2, angiopoietin 3, BAFF, beta amyloid, C5, CA-125, CD147, CD125, CD147, CD152, CD19, CD20, CD22, CD23, CD24, CD25, CD274, CD28, CD3, CD30, CD33, CD37, CD4, CD40, CD44, CD44v4, CD44v6, CD44v7, CD50, CD51, CD52, CEA, CSF1R, CTLA-2, DLL4, EGFR, EPCAM, HER3, GD2 ganglioside. GDF-8, Her2/neu, CD2221, IL-17A, IL-12, IL-23, IL-13, IL-6, IL-23, an integrin, CD11a, MUC1, Notch, TAG-72, TGFβ, TRAIL-R2, VEGF-A, VEGFR-1, VEGFR2, VEGFc, hematopoietins (four-helix bundles) (such as EPO (erythropoietin), IL-2 (T-cell growth factor), IL-3 (multicolony CSF), IL-4 (BCGF-1, BSF-1), IL-5 (BCGF-2), IL-6 IL-4 (IFN-02, BSF-2, BCDF), IL-7, IL-8, IL-9, IL-11, IL-13 (P600), G-CSF, IL-15 (T-cell growth factor), GM-CSF (granulocyte macrophage colony stimulating factor), OSM (OM, oncostatin M), and LIF (leukemia inhibitory factor)); interferons (such as IFN-γ, IFN-α, and IFN-β); immunoglobin superfamily (such as B7.1 (CD80), and B7.2 (B70, CD86)); TNF family (such as TNF-α (cachectin), TNF-β (lymphotoxin, LT, LT-α), LT-β, Fas, CD27, CD30, and 4-1BBL); and those unassigned to a particular family (such as TGF-β, IL 1α, IL-1β, IL-1 RA, IL-10 (cytokine synthesis inhibitor F), IL-12 (NK cell stimulatory factor), MIF, IL-16, IL-17 (mCTLA-8), and/or IL-18 (IGIF, interferon-γ inducing factor)); in embodiments relating to bispecific antibodies, the antibody may for example bind two of these targets. Furthermore, the Fc portion of the heavy chain of an antibody may be used to target Fc receptor-expressing cells such as the use of the Fc portion of an IgE antibody to target mast cells and basophils.

Other antigens to which a ROR binding molecule as described herein can specifically bind, in addition to a ROR antigen, may be chosen that specifically binds the TNF family of receptors including, but not limited to, TNFR1 (also known as CD120a and TNFRSF1A), TNFR2 (also known as CD120b and TNFRSF1B), TNFRSF3 (also known as LTβR), TNFRSF4 (also known as OX40 and CD134), TNFRSF5 (also known as CD40), TNFRSF6 (also known as FAS and CD95), TNFRSF6B (also known as DCR3), TNFRSF7 (also known as CD27), TNFRSF8 (also known as CD30), TNFRSF9 (also known as 4-1BB), TNFRSF10A (also known as TRAILR1, DR4, and CD26), TNFRSF10B (also known as TRAILR2, DR5, and CD262), TNFRSF10C (also known as TRAILR3, DCR1, CD263), TNFRSF10D (also known as TRAILR4. DCR2, and CD264). TNFRSF11A (also known as RANK and CD265). TNFRSF11B (also known as OPG), TNFRSF12A (also known as FN14, TWEAKR, and CD266), TNFRSF13B (also known as TAC1 and CD267), TNFRSF13C (also known as BAFFR, BR3, and CD268), TNFRSF14 (also known as HVEM and CD270), TNFRSF16 (also known as NGFR, p75NTR, and CD271), or TNFRSF17 (also known as BCMA and CD269), TNFRSF18 (also known as GITR and CD357), TNFRSF19 (also known as TROY, TAJ, and TRADE), TNFRSF21 (also known as CD358), TNFRSF25 (also known as Apo-3, TRAMP, LARD, or WS-1), EDA2R (also known as XEDAR).

Other antigens to which a ROR binding molecule as described herein can specifically bind, in addition to a ROR antigen, may be chosen from immuno-oncology targets including, but not limited to, checkpoint inhibitor targets such as PD1, PDL1, CTLA-4, PDL2, B7-H3, B7-H4, BTLA, TIM3, GAL9, LAG3, VISTA, KIR, 2B4, BY55, and CGEN-15049.

6.8. Further Modifications

In a further series of embodiments, the ROR binding molecule has additional modifications.

6.8.1. Antibody-Drug Conjugates

In various embodiments, the ROR binding molecule is conjugated to a therapeutic agent (e.g., drug) to form a ROR binding molecule-drug conjugate. Therapeutic agents include, but are not limited to, chemotherapeutic agents, imaging agents (e.g., radioisotopes), immune modulators (e.g., cytokines, chemokines, or checkpoint inhibitors), and toxins (e.g., cytotoxic agents). In certain embodiments, the therapeutic agents are attached to the ROR binding molecule through a linker peptide, as discussed in more detail below in Section 6.8.3.

Methods of preparing antibody-drug conjugates (ADCs) that can be adapted to conjugate drugs to the ROR binding molecules disclosed herein are described. e.g., in U.S. Pat. No. 8,624,003 (pot method), U.S. Pat. No. 8,163,888 (one-step), U.S. Pat. No. 5,208,020 (two-step method), U.S. Pat. Nos. 8,337,856, 5,773,001, 7,829,531, 5,208,020, 7,745, 394, WO 2017/136623, WO 2017/015502, WO 2017/015496, WO 2017/015495, WO 2004/010957, WO 2005/077090, WO 2005/082023, WO 2006/065533, WO 2007/030642, WO 2007/103288, WO 2013/173337, WO 2015/057699, WO 2015/095755. WO 2015/123679. WO 2015/157286, WO 2017/165851, WO 2009/073445, WO 2010/068759, WO 2010/138719, WO 2012/171020, WO 2014/008375, WO 2014/093394, WO 2014/093640, WO 2014/160360, WO 2015/054659, WO 2015/195925, WO 2017/160754, Storz (MAbs. 2015 Nov-Dec; 7(6): 989-1009), Lambert el al. (*Adv Ther,* 2017 34: 1015), Diamantis et al. (*British Journal of Cancer,* 2016, 114, 362-367), Carrico et al. (*Nat Chem Biol.* 2007, 3: 321-2), We et al. (*Proc Natl Acad Sci USA,* 2009, 106: 3000-5), Rabuka et al. (*Curr Opin Chem Biol.,* 2011 14: 790-6), Hudak et al. (*Angew Chem Int Ed Engl.,* 2012: 4161-5), Rabuka et al. (*Nat Protoc.,* 2012 7:1052-67), Agarwal et al. (*Proc Natl Acad Sci USA.,* 2013, 110: 46-51), Agarwal et al. (*Bioconjugate Chem.,* 2013, 24: 846-851), Barfield et al. (*Drug Dev. and D.,* 2014, 14:34-41), Drake et al. (*Bioconjugate Chem.,* 2014, 25:1331-41), Liang et al. (*J Am Chem Soc.,* 2014, 136:10850-3), Drake et al. (*Curr Opin Chem Biol.,* 2015, 28:174-80), and York et al. (*BMC Biotechnology,* 2016, 16(1):23), each of which is hereby incorporated by reference in its entirety for all that it teaches.

6.8.2. Additional Binding Moieties

In various embodiments, the ROR binding molecule has modifications that comprise one or more additional binding moieties. In certain embodiments the binding moieties are antibody fragments or antibody formats including, but not limited to, full-length antibodies, Fab fragments, Fvs, scFvs, tandem scFvs, Diabodies, scDiabodies, DARTs, tandAbs, minibodies, camelid VHH, and other antibody fragments or formats known to those skilled in the art. Exemplary antibody and antibody fragment formats are described in detail in Brinkmann et al. (*MABS.* 2017, Vol. 9, No. 2, 182-212), herein incorporated by reference for all that it teaches.

In particular embodiments, the one or more additional binding moieties are attached to the C-terminus of the first or third polypeptide chain. In particular embodiments, the one or more additional binding moieties are attached to the C-terminus of both the first and third polypeptide chain. In particular embodiments, the one or more additional binding moieties are attached to the C-terminus of both the first and third polypeptide chains. In certain embodiments, individual portions of the one or more additional binding moieties are separately attached to the C-terminus of the first and third polypeptide chains such that the portions form the functional binding moiety.

In particular embodiments, the one or more additional binding moieties are attached to the N-terminus of any of the polypeptide chains (e.g. the first, second, third, fourth, fifth, or sixth polypeptide chains). In certain embodiments, individual portions of the additional binding moieties are separately attached to the N-terminus of different polypeptide chains such that the portions form the functional binding moiety.

In certain embodiments, the one or more additional binding moieties are specific for a different antigen or epitope of the ABSs within the ROR binding molecule. In certain embodiments, the one or more additional binding moieties are specific for the same antigen or epitope of the ABSs within the ROR binding molecule. In certain embodiments, wherein the modification is two or more additional binding moieties, the additional binding moieties are specific for the same antigen or epitope. In certain embodiments, wherein the modification is two or more additional binding moieties, the additional binding moieties are specific for different antigens or epitopes.

In certain embodiments, the one or more additional binding moieties are attached to the ROR binding molecule using in vitro methods including, but not limited to, reactive chemistry and affinity tagging systems, as discussed in more detail below in Section 6.8.3. In certain embodiments, the one or more additional binding moieties are attached to the ROR binding molecule through Fc-mediated binding (e.g. Protein A/G). In certain embodiments, the one or more additional binding moieties are attached to the ROR binding molecule using recombinant DNA techniques, such as encoding the nucleotide sequence of the fusion product between the ROR binding molecule and the additional binding moieties on the same expression vector (e.g. plasmid).

6.8.3. Functional/Reactive Groups

In various embodiments, the ROR binding molecule has modifications that comprise functional groups or chemically reactive groups that can be used in downstream processes, such as linking to additional moieties (e.g. drug conjugates and additional binding moieties, as discussed in more detail above in Sections 6.8.1, and 6.8.2) and downstream purification processes.

In certain embodiments, the modifications are chemically reactive groups including, but not limited to, reactive thiols (e.g. maleimide based reactive groups), reactive amines (e.g. N-hydroxysuccinimide based reactive groups), "click chemistry" groups (e.g. reactive alkyne groups), and aldehydes bearing formylglycine (FGly). In certain embodiments, the modifications are functional groups including, but not limited to, affinity peptide sequences (e.g. HA, HIS, FLAG, GST, MBP, and Strep systems etc.). In certain embodiments, the functional groups or chemically reactive groups have a cleavable peptide sequence. In particular embodiments, the cleavable peptide is cleaved by means including, but not limited to, photocleavage, chemical cleavage, protease cleavage, reducing conditions, and pH conditions. In particular embodiments, protease cleavage is carried out by intracellular proteases. In particular embodiments, protease cleavage is carried out by extracellular or membrane associated proteases. ADC therapies adopting protease cleavage are described in more detail in Choi et al. (*Theranostics*, 2012; 2(2): 156-178), the entirety of which is hereby incorporated by reference for all it teaches.

6.8.4. Reduced Effector Function

In certain embodiments, the ROR binding molecule has one or more engineered mutations in an amino acid sequence of an antibody domain that reduce the effector functions naturally associated with antibody binding. Effector functions include, but are not limited to, cellular functions that result from an Fc receptor binding to an Fc portion of an antibody, such as antibody-dependent cellular cytotoxicity (ADCC, also referred to as antibody-dependent cell-mediated cytotoxicity), complement fixation (e.g. C1q binding), antibody dependent cellular-mediated phagocytosis (ADCP), and opsonization. Engineered mutations that reduce the effector functions are described in more detail in U.S. Pub. No. 2017/0137530, Armour, et al. (Eur. J. Immunol. 29(8) (1999) 2613-2624), Shields, et al. (J. Biol. Chem. 276(9) (2001) 6591-6604), and Oganesyan, et al. (Acta Cristallographica D64 (2008) 700-704), each herein incorporated by reference in its entirety.

In specific embodiments, the ROR binding molecule has one or more engineered mutations in an amino acid sequence of an antibody domain that reduce binding of an Fc portion of the ROR binding molecule by FcR receptors. In some embodiments, the FcR receptors are FcRγ receptors. In particular embodiments, the FcR receptors are FcγRIIa and/or FcγRIIIA receptors.

In specific embodiments, the one or more engineered mutations that reduce effector function are mutations in a CH2 domain of an antibody. In various embodiments, the one or more engineered mutations are at position L234 and L235 of the CH2 domain. In particular embodiments, the one or more engineered mutations are L234A and L235A of the CH2 domain. In other embodiments, the one or more engineered mutations are at position L234, L235, and P329 of the CH2 domain. In particular embodiments, the one or more engineered mutations are L234A. L235A, and P329G of the CH2 domain. In preferred embodiments, the one or more engineered mutations are L234A. L235A, and P329K of the CH2 domain.

6.9. Methods of Purification

A method of purifying a ROR binding molecule comprising a B-body platform is provided herein.

In a series of embodiments, the method comprises the steps of: i) contacting a sample comprising the ROR binding molecule with a CH1 binding reagent, wherein the ROR binding molecule comprises at least a first, a second, a third, and a fourth polypeptide chain associated in a complex, wherein the complex comprises at least one CH1 domain, or portion thereof, and wherein the number of CH1 domains in the complex is at least one fewer than the valency of the complex, and wherein the contacting is performed under conditions sufficient for the CH1 binding reagent to bind the CH1 domain, or portion thereof; and ii) purifying the complex from one or more incomplete complexes, wherein the incomplete complexes do not comprise the first, the second, the third, and the fourth polypeptide chain.

In a typical, naturally occurring, antibody, two heavy chains are associated, each of which has a CH1 domain as the second domain, numbering from N-terminus to C-terminus. Thus, a typical antibody has two CH1 domains. CH1 domains are described in more detail in Section 6.3.8.1. In a variety of the ROR binding molecules described herein, the CH1 domain typically found in the protein has been substituted with another domain, such that the number of CH1 domains in the protein is effectively reduced. In a non-limiting illustrative example, the CH1 domain of a typical antibody can be substituted with a CH3 domain, generating an antigen-binding protein having only a single CH1 domain.

ROR binding molecules can also refer to molecules based on antibody architectures that have been engineered such that they no longer possess a typical antibody architecture. For example, an antibody can be extended at its N or C terminus to increase the valency (described in more detail in Section 6.3.13.1) of the antigen-binding protein, and in certain instances the number of CH1 domains is also increased beyond the typical two CH1 domains. Such molecules can also have one or more of their CH1 domains substituted, such that the number of CH1 domains in the protein is at least one fewer than the valency of the antigen-binding protein. In some embodiments, the number of CH1 domains that are substituted by other domains generates a ROR binding molecule having only a single CH1 domain. In other embodiments, the number of CH1 domains substituted by another domain generates a ROR binding molecule having two or more CH1 domains, but at least one fewer than the valency of the antigen-binding protein. In particular embodiments, where a ROR binding molecule has two or more CH1 domains, the multiple CH1 domains can all be in the same polypeptide chain. In other particular embodiments, where a ROR binding molecule has two or more CH1 domains, the multiple CH1 domains can be a single CH1 domain in multiple copies of the same polypeptide chain present in the complete complex.

6.9.1. CH1 Binding Reagents

In exemplary non-limiting methods of purifying ROR binding molecules, a sample comprising the ROR binding molecules is contacted with CH1 binding reagents. CH1 binding reagents, as described herein, can be any molecule that specifically binds a CH1 epitope. The various CH1 sequences that provide the CH1 epitope are described in more detail in Section 6.3.8.1, and specific binding is described in more detail in Section 6.3.13.1.

In some embodiments, CH1 binding reagents are derived from immunoglobulin proteins and have an antigen binding site (ABS) that specifically binds the CH1 epitope. In particular embodiments, the CH1 binding reagent is an antibody, also referred to as an "anti-CH1 antibody." The anti-CH1 antibody can be derived from a variety of species. In particular embodiments, the anti-CH1 antibody is a mammalian antibody, including, but not limited to mouse, rat, hamster, rabbit, camel, donkey, goat, and human antibodies. In specific embodiments, the anti-CH1 antibody is a single-domain antibody. Single-domain antibodies, as described herein, have a single variable domain that forms the ABS and specifically binds the CH1 epitope. Exemplary single-domain antibodies include, but are not limited to, heavy chain antibodies derived from camels and sharks, as described in more detail in international application WO 2009/011572, herein incorporated by reference for all it teaches. In a preferred embodiment, the anti-CH1 antibody is a camel derived antibody (also referred to as a "camelid antibody"). Exemplary camelid antibodies include, but are not limited to, human IgG-CH1 CaptureSelect™ (ThermoFisher, #194320010) and human IgA-CH1 (ThermoFisher, #194311010). In some embodiments, the anti-CH1 antibody is a monoclonal antibody. Monoclonal antibodies are typically produced from cultured antibody-producing cell lines. In other embodiments, the anti-CH1 antibody is a polyclonal antibody, i.e., a collection of different anti-CH1 antibodies that each recognize the CH1 epitope. Polyclonal antibodies are typically produced by collecting the antibody containing serum of an animal immunized with the antigen of interest, or fragment thereof, here CH1.

In some embodiments, CH1 binding reagents are molecules not derived from immunoglobulin proteins. Examples of such molecules include, but are not limited to, aptamers, peptoids, and affibodies, as described in more detail in Perret and Boschetti (*Biochimie*. Feb. 2018, Vol 145:98-112).

6.9.2. Solid Supports

In exemplary non-limiting methods of purifying ROR binding molecules, the CH1 binding reagent can be attached to a solid support in various embodiments of the invention. Solid supports, as described herein, refers to a material to which other entities can be attached or immobilized, e.g., the CH1 binding reagent. Solid supports, also referred to as "carriers," are described in more detail in international application WO 2009/011572.

In specific embodiments, the solid support comprises a bead or nanoparticle. Examples of beads and nanoparticles include, but are not limited to, agarose beads, polystyrene beads, magnetic nanoparticles (e.g., Dynabeads™, ThermoFisher), polymers (e.g., dextran), synthetic polymers (e.g., Sepharose™), or any other material suitable for attaching the CH1 binding reagent. In particular embodiments, the solid support is modified to enable attachment of the CH1 binding reagent. Example of solid support modifications include, but are not limited to, chemical modifications that form covalent bonds with proteins (e.g., activated aldehyde groups) and modifications that specifically pair with a cognate modification of a CH1 binding reagent (e.g., biotin-streptavidin pairs, disulfide linkages, polyhistidine-nickel, or "click-chemistry" modifications such as azido-alkynyl pairs).

In certain embodiments, the CH1 binding reagent is attached to the solid support prior to the CH1 binding reagent contacting the ROR binding molecules, herein also referred to as an "anti-CH1 resin." In some embodiments, anti-CH1 resins are dispersed in a solution. In other embodiments, anti-CH1 resins are "packed" into a column. The anti-CH1 resin is then contacted with the ROR binding molecules and the CH1 binding reagents specifically bind the ROR binding molecules.

In other embodiments, the CH1 binding reagent is attached to the solid support after the CH1 binding reagent contacts the ROR binding molecules. As a non-limiting illustration, a CH1 binding reagent with a biotin modification can be contacted with the ROR binding molecules, and subsequently the CH1 binding reagent/ROR binding molecule mixture can be contacted with streptavidin modified solid support to attach the CH1 binding reagent to the solid support, including CH1 binding reagents specifically bound to the ROR binding molecules.

In methods wherein the CH1 binding reagents are attached to solid supports, in a variety of embodiments, the bound ROR binding molecules are released, or "eluted," from the solid support forming an eluate having the ROR binding molecules. In some embodiments, the bound ROR binding molecules are released through reversing the paired modifications (e.g., reduction of the disulfide linkage), adding a reagent to compete off the ROR binding molecules (e.g., adding imidazole that competes with a polyhistidine for binding to nickel), cleaving off the ROR binding molecules (e.g., a cleavable moiety can be included in the modification), or otherwise interfering with the specific binding of the CH1 binding reagent for the ROR binding molecule. Methods that interfere with specific binding include, but are not limited to, contacting ROR binding molecules bound to CH1 binding reagents with a low-pH solution. In preferred embodiment, the low-pH solution comprises 0.1 M acetic acid pH 4.0. In other embodiments, the bound ROR binding molecules can be contacted with a range of low-pH solutions, i.e., a "gradient."

6.9.3. Further Purification

In some embodiments of the exemplary non-limiting methods, a single iteration of the method using the steps of contacting the ROR binding molecules with the CH1 binding reagents, followed by eluting the ROR binding molecules, is used to purify the ROR binding molecules from the one or more incomplete complexes. In particular embodiments, no other purifying step is performed. In other embodiments, one or more additional purification steps are performed to further purify the ROR binding molecules from the one or more incomplete complexes. The one or more additional purification steps include, but are not limited to, purifying the ROR binding molecules based on other protein characteristics, such as size (e.g., size exclusion chromatography), charge (e.g., ion exchange chromatography), or hydrophobicity (e.g., hydrophobicity interaction chromatography). In a preferred embodiment, an additional cation exchange chromatograph is performed. Additionally, the ROR binding molecules can be further purified repeating contacting the ROR binding molecules with the CH1 binding reagents as described above, as well as modifying the CH1 purification method between iterations, e.g., using a step elution for the first iteration and a gradient elution for a subsequent elution.

6.9.4. Assembly and Purity of Complexes

In the embodiments of the present invention, at least four distinct polypeptide chains associate together to form a complete complex, e.g., the ROR binding molecule. However, incomplete complexes can also form that do not contain the at least four distinct polypeptide chains. For example, incomplete complexes may form that only have one, two, or three of the polypeptide chains. In other examples, an incomplete complex may contain more than three polypeptide chains, but does not contain the at least four distinct polypeptide chains, e.g., the incomplete complex inappropriately associates with more than one copy of a distinct polypeptide chain. The method of the invention purifies the complex, e.g., the completely assembled ROR binding molecule, from incomplete complexes.

Methods to assess the efficacy and efficiency of the purification steps are well known to those skilled in the art and include, but are not limited to, SDS-PAGE analysis, ion exchange chromatography, size exclusion chromatography, and mass spectrometry. Purity can also be assessed according to a variety of criteria. Examples of criterion include, but are not limited to: 1) assessing the percentage of the total protein in an eluate that is provided by the completely assembled ROR binding molecule, 2) assessing the fold enrichment or percent increase of the method for purifying the desired products, e.g., comparing the total protein provided by the completely assembled ROR binding molecule in the eluate to that in a starting sample, 3) assessing the percentage of the total protein or the percent decrease of undesired products, e.g., the incomplete complexes described above, including determining the percent or the percent decrease of specific undesired products (e.g., unassociated single polypeptide chains, dimers of any combination of the polypeptide chains, or trimers of any combination of the polypeptide chains). Purity can be assessed after any combination of methods described herein. For example, purity can be assessed after a single iteration of using the anti-CH1 binding reagent, as described herein, or after additional purification steps, as described in more detail in Section 6.9.3. The efficacy and efficiency of the purification steps may also be used to compare the methods described using the anti-CH1 binding reagent to other purification methods known to those skilled in the art, such as Protein A purification.

6.10. Methods of Manufacturing

The ROR binding molecules described herein can readily be manufactured by expression using standard cell free translation, transient transfection, and stable transfection approaches currently used for antibody manufacture. In specific embodiments, Expi293 cells (ThermoFisher) can be used for production of the ROR binding molecules using protocols and reagents from ThermoFisher, such as Expi-Fectamine, or other reagents known to those skilled in the art, such as polyethylenimine as described in detail in Fang el al. (*Biological Procedures Online*, 2017, 19:11), herein incorporated by reference for all it teaches.

As further described in the Examples below, the expressed proteins can be readily separated from undesired proteins and protein complexes using a CH1 affinity resin, such as the CaptureSelect CH1 resin and provided protocol from ThermoFisher. Other purification strategies include, but are not limited to, use of Protein A, Protein G, or Protein A/G reagents. Further purification can be affected using ion exchange chromatography as is routinely used in the art.

6.11. Pharmaceutical Compositions

In another aspect, pharmaceutical compositions are provided that comprise a ROR binding molecule as described herein and a pharmaceutically acceptable carrier or diluent. In typical embodiments, the pharmaceutical composition is sterile.

In various embodiments, the pharmaceutical composition comprises the ROR binding molecule at a concentration of 0.1 mg/ml-100 mg/ml. In specific embodiments, the pharmaceutical composition comprises the ROR binding molecule at a concentration of 0.5 mg/ml, 1 mg/ml, 1.5 mg/ml, 2 mg/ml, 2.5 mg/ml, 5 mg/ml, 7.5 mg/ml, or 10 mg/ml. In some embodiments, the pharmaceutical composition comprises the ROR binding molecule at a concentration of more than 10 mg/ml. In certain embodiments, the ROR binding molecule is present at a concentration of 20 mg/ml, 25 mg/ml, 30 mg/ml, 35 mg/ml, 40 mg/ml, 45 mg/ml, or even 50 mg/ml or higher. In particular embodiments, the ROR binding molecule is present at a concentration of more than 50 mg/ml.

In various embodiments, the pharmaceutical compositions are described in more detail in U.S. Pat. Nos. 8,961,964, 8,945,865, 8,420,081, 6,685,940, 6,171,586, 8,821,865, 9,216,219, U.S. application Ser. No. 10/813,483, WO 2014/066468, WO 2011/104381, and WO 2016/180941, each of which is incorporated herein in its entirety.

6.12. Methods of Treatment

In another aspect, methods of treatment are provided, the methods comprising administering a ROR binding molecule (e.g., antibody) as described herein to a subject in an amount effective to treat the subject. Such ROR antigen binding molecules are useful in the treatment of ROR expressing cancers, including cancers that express an ROR1 antigen, cancers that express an ROR2 antigen, and/or cancers that express both an ROR1 antigen and an ROR2 antigen.

In some embodiments, an antibody of the present disclosure may be used to treat a variety of cancers. The cancer may be a cancer from the bladder, blood (myeloid leukemia [acute and chronic], acute lymphoblastic leukemia, chronic lymphocytic leukemia, myeloproliferative diseases, multiple myeloma, myelodysplastic syndrome), bone, bone marrow, brain (astrocytoma, medulloblastoma, glioma, ependymoma, germinoma [pinealoma], glioblastoma multiform, oligodendroglioma, schwannoma, retinoblastoma, congenital tumors), breast, colon, esophagus (squamous cell carcinoma, adenocarcinoma, leiomyosarcoma, lymphoma), gastrointestine, gum, head, kidney (adenocarcinoma. Wilm's tumor [nephroblastoma], lymphoma, leukemia, renal cell carcinoma), liver, lung, nasopharynx, neck, ovary, prostate (adenocarcinoma, sarcoma, castrate resistant prostate cancer), skin, stomach (carcinoma, lymphoma, leiomyosarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma), tongue, or uterus. In some embodiments, the cancer may be a neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma, pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma (angiosarcoma, fibrosarcoma, rhabdomyosarcoma, liposarcoma); fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant, choriocarcinoma; mesonephroma, malignant; hemangiosarcoma; hemangioendothelioma, malignant; kaposi's sarcoma; hemangiopencytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma (reticulum cell sarcoma); hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; hairy cell leukemia; myxoma; rhabdomyoma; fibroma; squamous cell carcinomas of the head and neck; laryngeal and hypopharyngeal cancer; nasal cavity and paranasal sinus cancer; nasopharyngeal cancer; salivary gland cancer; oral; orppharyngeal cancer; bronchogenic carcinoma (squamous cell, undifferentiated small cell, undifferentiated large cell, adenocarcinoma, non-small cell lung cancer); alveolar (bronchiolar) carcinoma; bronchial adenoma; chondromatous hamartoma; colorectal cancer; gastrointestinal stromal tumors; carcinoids; Turcot Syndrome; gastric cancer; gastroesophageal junction adenocarcinoma; pancreas (ductal adenocarcinoma, insulinoma, glucagonoma, gastrinoma, carcinoid tumors, vipoma); small bowel (adenocarcinoma, lymphoma, carcinoid tumors, Karposi's sarcoma, leiomyoma, hemangioma, lipoma, neurofibroma, fibroma); large bowel (adenocarcinoma, tubular adenoma, villous adenoma, hamartoma, leiomyoma); metastatic breast cancer; ductal carcinoma in situ; invasive ductal carcinoma; tubular carcinoma; mucinous carcinoma; lobular carcinoma in situ; triple negative breast cancer; bladder and urethra (squamous cell carcinoma, transitional cell carcinoma, adenocarcinoma, urothelial carcinoma); clear cell carcinoma; hepatoma (hepatocellular carcinoma); angiosarcoma; hepatocellular adenoma; hemangioma; osteogenic sarcoma (osteosarcoma); malignant fibrous histiocytoma; malignant giant cell tumor chordoma; osteochrondroma (osteocartilaginous exostoses), benign chondroma; chondromyxofibroma; osteoid osteoma; giant cell tumors; medullary thyroid cancer; differentiated thyroid cancer; papillary thyroid cancer; follicular thyroid cancer; hurthle cell cancer; anaplastic thyroid cancer; skull (osteoma, hemangioma, granuloma, xanthoma, osteitis deformans); meninges (meningioma, meningiosarcoma, gliomatosis); spinal cord (neurofibroma, meningioma, glioma, sarcoma); uterus (clear); cervix (cervical carcinoma, pre-tumor cervical dysplasia); ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma); vulva (squamous cell carcinoma, intraepithelial carcinoma, adenocarcinoma, fibrosarcoma, melanoma); vagina (clear cell carcinoma, squamous cell carcinoma); botryoid sarcoma (embryonal rhabdomyosarcoma); fallopian tubes (carcinoma); non-Hodgkin's lymphoma [malignant lymphoma]; Karposi's sarcoma; moles dysplastic nevi; angioma; dermatofibroma; keloids; psoriasis; neuroblastoma; adrenocortical carcinoma; pheochromocytomas; paragangliomas; merkel cell carcinoma; pancreatic neuroendocrine and carcinoid tumors; neuroendocrine tumors; carcinoid tumors; pancreatic cancers, gastroesophageal; clear cell renal cell carcinoma; and primary peritoneal cancer.

An antibody of the present disclosure may be administered to a subject per se or in the form of a pharmaceutical composition for the treatment of, e.g., cancer, autoimmunity, transplantation rejection, post-traumatic immune responses, graft-versus-host disease, ischemia, stroke, and infectious diseases (e.g., by targeting viral antigens, such as gp120 of HIV).

In another aspect, a ROR binding molecule (e.g., antibody) as described herein may be used in a method of treating a subject with cancer in combination with one or more additional therapies. The additional therapies that may be used in combination with an ROR antigen binding molecule (e.g., antibody) described herein include but are not limited to: (i) surgery; (ii) radiotherapy; (iii) endocrine therapy; (iv) immunotherapy (including adjuvant therapy and cell therapy such as CAR T-cell therapy); and (v) chemotherapy, including cytotoxic agents and chemotherapeutic agents.

Any therapy that has an activity against a cancer may be used in combination with an ROR antigen binding molecule (e.g., antibody) provided herein. Examples of such agents for A cancer treatment can be found, for instance, in publically available sources such as Cancer Principles and Practice of Oncology by V. T. Devita and S. Hellman (editors), 11$^{th}$ edition (2018), Lippincott Williams & Wilkins Publishers. A person of ordinary skill in the art would be able to discern which combinations of agents would be useful based on the particular characteristics of the drugs and the type of cancer involved.

In certain embodiments, the additional therapy is a radiotherapy including, for example, gamma radiation, neutron beam radiotherapy, electron beam radiotherapy, proton therapy, brachytherapy, and systemic radioactive isotopes. Radiotherapy may comprise radiation or associated administration of radiopharmaceuticals. The source of radiation may be either external or internal to the subject being treated (radiation treatment may, for example, be in the form of external beam radiation therapy (EBRT) or brachytherapy (BT)). Exemplary radioactive elements include, e.g., radium, cesium-137, iridium-192, americium-241, gold-198, cobalt-57, copper-67, technetium-99, iodide-123, iodide-131, and indium-111.

In certain embodiments, the additional therapy is an immunotherapy. Immunotherapy (also called biological response modifier therapy, biologic therapy, biotherapy, immune therapy, or biological therapy) is treatment that uses parts of the immune system to fight disease. Immunotherapy can help the immune system recognize cancer cells, or enhance a response against cancer cells. Immunotherapies include active and passive immunotherapies. Active immunotherapies, including immunotherapeutic agents, stimulate the body's own immune system (e.g., vaccines) while passive immunotherapies, including immunotherapeutic agents, generally use immune system components created outside of the body (e.g., antibodies), antibodies conjugated with drugs, toxins, or radionuclides, and targeted therapeutics.

Exemplary immunotherapeutic agents include immune checkpoint inhibitors. In some embodiments, the immune checkpoint inhibitor used in methods of treatment can totally or partially reduce, inhibit, interfere with, or modulate one or more checkpoint proteins which regulate T-cell activation or function. Numerous checkpoint proteins are known, such as CTLA-4 and its ligands CD80 and CD86; and PD-1 with its ligands PD-L1 and PD-L2 (Pardoll, Nature Reviews Cancer, 2012, 12, 252-264). Immune checkpoint inhibitors include antibodies or are derived from antibodies.

In certain embodiments, the checkpoint inhibitor is an OX40 (CD134) agonist. In some embodiments, the checkpoint inhibitor is an anti-OX40 antibody. In some embodiments, the anti-OX40 antibody is anti-OX-40. In some embodiments, the anti-OX40 antibody is MED16469.

In certain embodiments, the checkpoint inhibitor is a CD40 agonist. In some embodiments, the checkpoint inhibitor is an anti-CD40 antibody. In some embodiments, the anti-CD40 antibody is CF-870, 893.

In certain embodiments, the checkpoint inhibitor is a CTLA-4 inhibitor. In some embodiments, the CTLA-4 inhibitor is an anti-CTLA-4 antibody. Examples of anti CTLA 4 antibodies include, but are not limited to, those described in U.S. Pat. Nos. 5,811,097; 5,811,097; 5,855,887; 6,051,227; 6,207,157; 6,682,736; 6,984,720; and 7,605,238. In some embodiments, the anti-CTLA-4 antibody is tremelimumab (also known as ticilimumab or CP-675,206). In some embodiments, the anti-CTLA-4 antibody is ipilimumab (also known as MDX-010 or MDX-101). Ipilimumab is a fully human monoclonal IgG antibody that binds to CTLA-4. Ipilimumab is marketed under the trade name Yervoy™.

In certain embodiments, the checkpoint inhibitor is a PD-1/PD-LI inhibitor. Examples of PD-L/PD-L1 inhibitors include, but are not limited to, those described in U.S. Pat. Nos. 7,488,802; 7,943,743; 8,008,449; 8,168,757; 8,217, 149, and PCT Patent Application Publication Nos. WO2003042402, WO2008156712, WO2010089411, WO2010036959, WO2011066342, WO2011159877, WO2011082400, and WO2011161699.

In certain embodiments, the checkpoint inhibitor is a PD-1 inhibitor. In some embodiments, the PD-1 inhibitor is an anti-PD-1 antibody. In some embodiments, the anti-PD-1 antibody is BGB-A317, nivolumab (also known as ONO-4538, BMS-936558, or MDX1106) or pembrolizumab (also known as MK-3475, SCH 900475, or lambrolizumab). In some embodiments, the anti-PD-1 antibody is nivolumab. Nivolumab is a human IgG4 anti-PD-1 monoclonal antibody, and is marketed under the trade name Opdivo™. In some embodiments, the anti-PD-1 antibody is pembrolizumab. Pembrolizumab is a humanized monoclonal IgG4 antibody and is marketed under the trade name Keytruda™. In some embodiments, the anti-PD-1 antibody is CT-011, a humanized antibody. CT-011 administered alone has failed to show response in treating acute myeloid leukemia (AML) at relapse. In some embodiments, the anti-PD-1 antibody is AMP-224, a fusion protein. In some embodiments, the PD-1 antibody is BGB-A317. BGB-A317 is a monoclonal antibody in which the ability to bind Fc gamma receptor I is specifically engineered out, and which has a unique binding signature to PD-1 with high affinity and superior target specificity.

In certain embodiments, the checkpoint inhibitor is a PD-L1 inhibitor. In one embodiments, the PD-L1 inhibitor is an anti-PD-L1 antibody. In some embodiments, the anti-PD- L1 antibody is MEDI4736 (durvalumab). In some embodiments, the anti-PD-L1 antibody is BMS-936559 (also known as MDX-1105-01). In some embodiments, the PD-L1 inhibitor is atezolizumab (also known as MPDL3280A, and Tecentriq®).

In certain embodiments, the checkpoint inhibitor is a PD-L2 inhibitor. In some embodiments, the PD-L2 inhibitor is an anti-PD-L2 antibody. In some embodiments, the anti-PD-L2 antibody is rHIgM12B7A.

In certain embodiments, the checkpoint inhibitor is a lymphocyte activation gene-3 (LAG-3) inhibitor. In some embodiments, the LAG-3 inhibitor is IMP321, a soluble Ig fusion protein (Brignone et al., J. Immunol., 2007, 179, 4202-4211). In some embodiments, the LAG-3 inhibitor is BMS-986016.

In certain embodiments, the checkpoint inhibitor is a B7 inhibitor. In some embodiments, the B7 inhibitor is a B7-H3 inhibitor or a B7-H4 inhibitor. In some embodiments, the B7-H3 inhibitor is MGA271, an anti-B7-H3 antibody (Loo et al., Clin. Cancer Res., 2012, 3834).

In certain embodiments, the checkpoint inhibitor is a TIM3 (T-cell immunoglobulin domain and mucin domain 3) inhibitor (Fourcade et al., J. Exp. Med., 2010, 207, 2175-86; Sakuishi et al., J. Exp. Med., 2010, 207, 2187-94).

In certain embodiments, the checkpoint inhibitor is a GITR agonist. In some embodiments, the checkpoint inhibitor is an anti-GITR antibody. In some embodiments, the anti-GITR antibody is TRX518.

In certain embodiments, the checkpoint inhibitor is a CD137 agonist. In some embodiments, the checkpoint inhibitor is an anti-CD137 antibody. In some embodiments, the anti-CD137 antibody is urelumab. In some embodiments, the anti-CD137 antibody is PF-05082566.

In certain embodiments, the checkpoint inhibitor is recombinant human interleukin-15 (rhIL-15).

In certain embodiments, the checkpoint inhibitor is an IDO inhibitor. In some embodiments, the IDO inhibitor is INCB024360. In some embodiments, the IDO inhibitor is indoximod.

Other exemplary immunotherapies include adjuvant therapies, including immunotherapeutic agents such as cytokines, chemokines, interferons, interleukins, or lymphokines. Examples include cytokines, such as granulocyte-macrophage colony-stimulating factor (GM-CSF), granulocyte-colony stimulating factor (G-CSF), macrophage inflammatory protein (MIP)-1-alpha, interleukins (including IL-1, IL-2, IL-4, IL-6, IL-7, IL-12, IL-15, IL-18, IL-21, and IL-27), tumor necrosis factors (including TNF-alpha), and interferons (including IFN-alpha, IFN-beta, and IFN-gamma); aluminum hydroxide (alum); Bacille Calmette-Guerin (BCG); Keyhole limpet hemocyanin (KLH); Incomplete Freund's adjuvant (IFA); QS-21; DETOX; Levamisole; and Dinitrophenyl (DNP), and combinations thereof, such as, for example, combinations of, interleukins, for example, IL-2 with other cytokines, such as IFN-alpha.

Other exemplary immunotherapies include cell therapies, for example, a population of immune cells, such as leukocytes (nucleated white blood cells), comprising (e.g., expressing) a receptor that binds to an antigen of interest. A leukocyte of the present disclosure may be, for example, a neutrophil, eosinophil, basophil, lymphocyte or a monocyte. In some embodiments, a leukocyte is a lymphocyte. Examples of lymphocytes include T cells. B cells. Natural Killer (NK) cells or NKT cells. In some embodiments, a T-cell is a CD4+Th (T helper) cell, a CD8+ cytotoxic T cell, a γδT cell or a regulatory (suppressor) T cell. In some embodiments, an immune cell is a dendritic cell. In some embodiments, the cell therapies are CAR-T cell therapies. In some embodiments, a bispecific CAR is comprised of two distinct antigen recognition domains present in tandem on a single transgenic receptor (referred to as a TanCAR; see, e.g., Grada Z et al. Molecular Therapy Nucleic Acids 2013; 2:e105, incorporated herein by reference in its entirety). Thus, methods, in some embodiments, comprise delivering to a tumor a combination comprising a ROR antigen binding molecule (e.g., antibody) and an immunotherapeutic agent, wherein the immunotherapeutic agent is an engineered nucleic acid that encodes an antigen, or delivering to a tumor an engineered nucleic acid that induces expression of a self-antigen, and delivering to the tumor an immune cell expressing a bispecific CAR that binds to two antigens, one of which is encoded by the engineered nucleic acid.

Other exemplary immunotherapies include immunotherapeutic agents such as cancer vaccines, which can be used to illicit an immune response in a subject against a cancer antigen. An exemplary method involves administering to a subject a RNA vaccine comprising at least one RNA polynucleotide having an open reading frame encoding at least one antigenic polypeptide or an immunogenic fragment thereof, thereby inducing in the subject an immune response specific to the antigenic polypeptide or an immunogenic fragment thereof, in combination with administering a ROR antigen binding molecule (e.g., antibody) either in the same composition or a separate composition, administered at the same time, or sequentially dosed, wherein the anti-antigenic polypeptide antibody titer in the subject is increased following vaccination relative to anti-antigenic polypeptide antibody titer in a subject vaccinated with a prophylactically effective dose of a traditional vaccine against the cancer.

In certain embodiments, the additional therapies include chemotherapy such as one or more cytotoxic agents or one or more chemotherapeutic agents. An cytotoxic agent can inhibit or prevent a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

In certain embodiments, the additional therapy includes one or more chemotherapeutic agents. Chemotherapeutic agents include chemical compounds useful in the treatment of cancer. Chemotherapeutic agents include (i) anti-hormonal agents that act to regulate or inhibit hormone action on tumors such as anti-estrogens and selective estrogen receptor modulators; (ii) aromatase inhibitors that inhibit the enzyme aromatase, which regulates estrogen production in the adrenal glands; (iii) anti-androgens; (iv) protein kinase inhibitors; (v) lipid kinase inhibitors; (vi) antisense oligonucleotides, including those which inhibit expression of genes in signaling pathways implicated in aberrant cell proliferation; (viii) vaccines such as gene therapy vaccines. Chemotherapeutic agents can also include antibodies.

Exemplary kinase inhibitors include erlotinib (Tarceva®), gefitinib (Iressa®), dasatinib (Sprycel®), nilotinib (Tasigna®), crizotinib (Xalkori®), ruxolitinib (Jakafi®), vemurafenib (Zelboraf®), vandetanib (Caprelsa®), pazopanib (Votrient®), afatinib, alisertib, amuvatinib, axitinib, baricitinib, bosutinib, brivanib, canertinib, cabozantinib (Cabometyx®), cediranib, ceritinib, crenolanib, dabrafenib, dacomitinib, danusertib, dovitinib, foretinib, ganetespib, ibrutinib, idelalisib, imatinib, iniparib, lapatinib, lenvatinib, linifanib, linsitinib, masitinib, momelotinib, motesanib, neratinib, nintedanib, niraparib, oprozomib, olaparib, palbociclib, pictilisib, pirfenidone, ponatinib, quizartinib, regorafenib, rigosertib, rucaparib, saracatinib, saridegib, sorafenib, sunitinib, tandutinib, tasocitinib, telatinib, tivantinib, tivozanib, tofacitinib, trametinib, veliparib, vismodegib, volasertib, cobimetinib (Cotellic®), XL-147, XL-765, XL-499, XL-880, and others. In some embodiments, a ROR antigen binding molecule (e.g., antibody) can be used in combination with a HSP90 inhibitor (e.g., XL888), liver X receptor (LXR) modulators, retinoid-related orphan receptor gamma (RORy) modulators, a CK1 inhibitor, a CK1-α inhibitor, a Wnt pathway inhibitor (e.g., SST-215), or a mineralocorticoid receptor inhibitor, (e.g., esaxerenone or XL-550) for the treatment of cancer.

Kinase inhibitors can be tyrosine kinase inhibitors, such as the EGFR inhibitors; small molecule HER2 tyrosine kinase inhibitor such as Mubritonib (TAK165, Takeda); CP-724.714, (Axon Medchem BV, an oral selective inhibitor of the ErbB2 receptor tyrosine kinase); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PK1-166 (available from Novartis); pan-HER inhibitors such as canertinib (CI-1033: Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase 1 inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthalimide); tyrphostines containing nitrothiophene moieties; antisense molecules (e.g. those that bind to HER-encoding nucleic acid); quinoxalines (U.S. Pat. No. 5,804,396); tryphostins (U.S. Pat. No. 5,804, 396); Affinitac (ISIS 3521; Isis/Lilly); PKI166 (Novartis); Semaxinib (Pfizer); INC-1C11 (Imclone), rapamycin (sirolimus, RAPAMUNEX®); or as described in any of the following patent publications: U.S. Pat. No. 5,804,396: WO 1999/09016 (American Cyanamid); WO 1998/43960 (American Cyanamid); WO 1997/38983 (Warner Lambert); WO 1999/06378 (Warner Lambert), WO 1999/06396 (Warner Lambert); WO 1996/30347 (Pfizer, Inc); WO 1996/33978 (Zeneca); WO 1996/3397 (Zeneca) and WO 1996/33980 (Zeneca).

Combined treatment with the ROR antigen binding molecule (e.g., antibody) provided herein and the additional therapy, such as a therapeutic agent, may be simultaneous, separate or sequential, in any order. For combinations of therapeutic agents such as an ROR antigen binding providing molecule and another therapeutic agent such as an immunotherapeutic agent or a chemotherapeutic agent, simultaneous administration, the therapeutics agents may be administered as one composition or as separate compositions, as appropriate.

6.13. EXAMPLES

The following examples are provided by way of illustration, not limitation.

6.13.1. Methods

Non-limiting, illustrative methods for the purification of the various antigen-binding proteins and their use in various assays are described in more detail below.

6.13.1.1. Expi293 Expression

The various antigen-binding proteins tested were expressed using the Expi293 transient transfection system according to manufacturer's instructions. Briefly, four plasmids coding for four individual chains were mixed at 1:1:1:1 mass ratio, unless otherwise stated, and transfected with ExpiFectamine 293 transfection kit to Expi 293 cells. Cells were cultured at 37° C. with 8% CO2, 100% humidity and shaking at 125 rpm. Transfected cells were fed once after 16-18 hours of transfections. The cells were harvested at day 5 by centrifugation at 2000 g for 10 minutes. The supernatant was collected for affinity chromatography purification.

6.13.1.2. Protein A and Anti-CH1 Purification

Cleared supernatants containing the various antigen-binding proteins were separated using either a Protein A (ProtA) resin or an anti-CH1 resin on an AKTA Purifier FPLC. In examples where a head-to-head comparison was performed, supernatants containing the various antigen-binding proteins were split into two equal samples. For ProtA purification, a 1 mL Protein A column (GE Healthcare) was equilibrated with PBS (5 mM sodium potassium phosphate pH 7.4, 150 mM sodium chloride). The sample was loaded onto the column at 5 m/min. The sample was eluted using 0.1 M acetic acid pH 4.0. The elution was monitored by absorbance at 280 nm and the elution peaks were pooled for analysis. For anti-CH1 purification, a 1 mL CaptureSelect™ XL column (ThermoFisher) was equilibrated with PBS. The sample was loaded onto the column at 5 ml/min. The sample was eluted using 0.1 M acetic acid pH 4.0. The elution was monitored by absorbance at 280 nm and the elution peaks were pooled for analysis.

6.13.1.3. SDS-Page Analysis

Samples containing the various separated antigen-binding proteins were analyzed by reducing and non-reducing SDS-PAGE for the presence of complete product, incomplete product, and overall purity. 2 µg of each sample was added to 15 µL SDS loading buffer. Reducing samples were incubated in the presence of 10 mM reducing agent at 75° C. for 10 minutes. Non-reducing samples were incubated at 95° C. for 5 minutes without reducing agent. The reducing and non-reducing samples were loaded into a 4-15% gradient TGX gel (BioRad) with running buffer and run for 30 minutes at 250 volts. Upon completion of the run, the gel was washed with DI water and stained using GelCode Blue Safe Protein Stain (ThermoFisher). The gels were destained with DI water prior to analysis. Densitometry analysis of scanned images of the destained gels was performed using standard image analysis software to calculate the relative abundance of bands in each sample.

6.13.1.4. IEX Chromatography

Samples containing the various separated antigen-binding proteins were analyzed by cation exchange chromatography for the ratio of complete product to incomplete product and impurities. Cleared supernatants were analyzed with a 5-ml MonoS (GE Lifesciences) on an AKTA Purifier FPLC. The MonoS column was equilibrated with buffer A 10 mM MES pH 6.0. The samples were loaded onto the column at 2 ml/min. The sample was eluted using a 0-30% gradient with buffer B (10 mM MES pH 6.0, 1 M sodium chloride) over 6 CV. The elution was monitored by absorbance at 280 nm and the purity of the samples were calculated by peak integration to identify the abundance of the monomer peak and contaminants peaks. The monomer peak and contaminant peaks were separately pooled for analysis by SDS-PAGE as described above.

6.13.1.5. Analytical SEC Chromatography

Samples containing the various separated antigen-binding proteins were analyzed by analytical size exclusion chromatography for the ratio of monomer to high molecular weight product and impurities. Cleared supernatants were analyzed with an industry standard TSK G3000SW×1 column (Tosoh Bioscience) on an Agilent 1100 HPLC. The TSK column was equilibrated with PBS. 25 µL of each sample at 1 mg/mL was loaded onto the column at 1 mi/min. The sample was eluted using an isocratic flow of PBS for 1.5 CV. The elution was monitored by absorbance at 280 nm and the elution peaks were analyzed by peak integration.

6.13.1.6. Mass Spectrometry

Samples containing the various separated antigen-binding proteins were analyzed by mass spectrometry to confirm the correct species by molecular weight. All analysis was performed by a third-party research organization. Briefly, samples were treated with a cocktail of enzymes to remove glycosylation. Samples were both tested in the reduced format to specifically identify each chain by molecular weight. Samples were all tested under non-reducing conditions to identify the molecular weights of all complexes in the samples. Mass spec analysis was used to identify the number of unique products based on molecular weight.

6.13.1.7. Antibody Discovery by Phage Display

Phage display of human Fab libraries was carried out using standard protocols. Biotinylated extracellular domains of human ROR1 and ROR2 protein were purchased from Acro Biosystems and biotinylated with EZ-Link NHS biotin (Thermo Scientific Cat. No. 20217). Phage clones were screened for the ability to bind the extracellular domains of ROR1 (Acro Cat. No. RO1-H522y) and ROR2 (Acro Cat. No. R02-H52E5) by phage ELISA using standard protocols. Briefly. Fab-formatted phage libraries were constructed using expression vectors capable of replication and expression in phage (also referred to as a phagemid). Both the heavy chain and the light chain were encoded for in the same expression vector, where the heavy chain was fused to a truncated variant of the phage coat protein pIII. The light chain and heavy chain-pIII fusion are expressed as separate polypeptides and assemble in the bacterial periplasm, where the redox potential enables disulfide bond formation, to form the phage display antibody containing the candidate ABS.

The library was created using sequences derived from a specific human heavy chain variable domain (VH3-23) and a specific human light chain variable domain (Vk-1). Light chain variable domains within the screened library were generated with diversity was introduced into the VL CDR3 (L3) and where the light chain VL CDR1 (L1) and CDR2 (L2) remained the human germline sequence. For the screened library, all three CDRs of the VH domain were diversified to match the positional amino acid frequency by CDR length found in the human antibody repertoire. The phage display heavy chain (SEQ ID NO:74) and light chain (SEQ ID NO:75) scaffolds used in the library are listed below, where a lower case "x" represents CDR amino acids that were varied to create the library, and bold italic represents the CDR sequences that were constant.

Diversity was created through Kunkel mutagenesis using primers to introduce diversity into VL CDR3 and VH CDR1 (H1), CDR2 (H2) and CDR3 (H3) to mimic the diversity found in the natural antibody repertoire, as described in more detail in Kunkel, TA (*PNAS* Jan. 1, 1985, 82 (2) 488-492), herein incorporated by reference in its entirety.

Briefly, single-stranded DNA were prepared from isolated phage using standard procedures and Kunkel mutagenesis carried out. Chemically synthesized DNA was then electroporated into TG1 cells, followed by recovery. Recovered cells were sub-cultured and infected with M13K07 helper phage to produce the phage library.

Phage panning was performed using standard procedures. Briefly, the first round of phage panning was performed with target immobilized on streptavidin magnetic beads which were subjected to ~5×10$^{12}$ phages from the prepared library in a volume of 1 mL in PBST-2% BSA. After a one-hour incubation, the bead-bound phage were separated from the supernatant using a magnetic stand. Beads were washed three times to remove non-specifically bound phage and were then added to ER2738 cells (5 mL) at OD$_{600}$~0.6. After 20 minutes, infected cells were sub-cultured in 25 mL 2×YT+Ampicillin and M13K07 helper phage and allowed to grow overnight at 37° C. with vigorous shaking. The next day, phage were prepared using standard procedures by PEG precipitation. Pre-clearance of phage specific to SAV-coated beads was performed prior to panning. The second round of panning was performed using the KingFisher magnetic bead handler with 100 nM bead-immobilized antigen using standard procedures. In total, 3-4 rounds of phage panning were performed to enrich in phage displaying Fabs specific for the target antigen. Target-specific enrichment was confirmed using polyclonal and monoclonal phage ELISA. DNA sequencing was used to determine isolated Fab clones containing a candidate ABS.

To measure binding affinity in ROR binder discovery campaigns, the VL and VH domains identified in the phage screen described above were formatted into a bivalent monospecific native human full-length IgG1 architecture and immobilized to a biosensor on an Octet (Pall ForteBio) biolayer interferometer. Soluble ROR antigens, including the extracellular domains of ROR (Acro Cat. No. RO1-H522y) and ROR2 (Acro Cat. No. R02-H52E5), as well as the individual ROR Frizzled (Acro Cat. No. RO1-H5222), Ig-like (Acro Cat. No. RO1-H5221), and Kringle (Acro Cat. No. ROI-H5223) domains, were then added to the system and binding measured.

For experiments performed using the B-Body format, VL variable regions of individual clones were formatted into Domain A and/or H, and VH region into Domain F and/or L of a bivalent lxi B-Body "BC1" scaffold shown below and with reference to FIG. 3.

"BC1" Scaffold:
    1$^{st}$ polypeptide chain (SEQ ID NO:78)
        Domain A=Antigen 1 B-Body Domain A/H Scaffold
            (SEQ ID NO:76)

Domain B=CH3 (T366K; 445K, 446S, 447C tripeptide insertion)
Domain D=CH2
Domain E=CH3 (T366W, S354C)
2$^{nd}$ polypeptide chain (SEQ ID NO:79):
  Domain F=Antigen 1 B-Body Domain F/L Scaffold (SEQ ID NO:77)
  Domain G=CH3 (L351D; 445G, 446E, 447C tripeptide insertion)
3$^{rd}$ polypeptide chain (SEQ ID NO:80):
  Domain H=Antigen 2 B-Body Domain A/H Scaffold (SEQ ID NO:76)
  Domain I=CL (Kappa)
  Domain J=CH2
  Domain K=CH3 (Y349C, D356E, L358M, T366S, L368A, Y407V)
4$^{th}$ polypeptide chain (SEQ ID NO:81):
  Domain L=Antigen 2 B-Body Domain F/L Scaffold (SEQ ID NO:77)
  Domain M=CH1.

For ROR ABS candidates formatted into a bivalent bispecific 1×1 format with anti-CD3 SP34-89, domain H has the amino acid sequence of SEQ ID NO:69 and domain L has the amino acid sequence of SEQ ID NO:68, while domain A has the candidate ROR VL sequence and domain F had the candidate ROR VH sequence.

For BC1 1×2 formats, the variable domains were formatted into the 1(A)×2(B-A) format described in Section 6.3.17.4, which refers to FIG. 26. FIG. 26 presents a schematic of five polypeptide chains and their domains, with respective naming conventions, for the trivalent 1×2 antibody constructs described herein, wherein according to the naming convention, chain 5 is named "6$^{th}$ polypeptide chain" in the schematic. Unless otherwise specified, the ROR antigen binding site (ABS) is the bivalent binder (the "A" specificity) and CD3 the monovalent binder (the "B" specificity). The SP34-89 1×2 chain 3 scaffold has the sequence of SEQ ID NO:82, where the junction between domain S and domain H is a 10 amino acid linker having the sequence TASSGGSSSG (SEQ ID NO:83), unless otherwise stated. Polypeptide chain 2 and chain 5 are identical in the 1(A)×2(B-A) format (see, e.g., FIG. 26, wherein according to the naming convention chain 5 is named "6$^{th}$ polypeptide chain" in the schematic).

6.13.1.8. NFκB GFP Jurkat T Cell Stimulation Assay

The NFκB/Jurkat/GFP transcriptional reporter cell line was purchased from System Biosciences (Cat #TR850-1). The anti-CD28 antibody used for co-stimulation was purchased from BD Pharmingen (Cat 555725). The Solution C background suppression dye was purchased from Life Technologies (K1037). Briefly, the Jurkat cells (effector cells, E) were mixed with the tumor cells (T) at an E:T ratio of 2:1 to 4:1 in the presence of a dilution series of B-body™ antibodies and an anti-CD28 antibody at 1 ug/mL in a 96 well black walled clear bottom plate. The plate was incubated at 37° C./5% CO2 for 6 hours, following which a 6× solution of Solution C background suppressor was added to the plate and GFP fluorescence was read out on a plate reader. EC50 values, referring to the concentration of antibody that gives the half-maximal response, were determined from the dilution series.

6.13.1.9. Primary T Cell Cytotoxicity Assay

Cells expressing the target tumor antigen (T) and effector cells (E) were mixed at an E:T ratio ranging from 3:1 to 10:1. Effector cells used include PBMCs or isolated cytotoxic CD8+ T cells. The candidate redirecting T cell antibody was added in a dilution series to the cells. Controls included media only controls, tumor cell only controls, and untreated E:T cell controls. The mixed cells and control conditions were incubated at 37° C./5% CO2 for 40-50 hours. The Cytotoxicity Detection Kit Plus (LDH) was purchased from Sigma (Cat 4744934001) and the manufacturer's directions were followed. Briefly, lysis solution added to tumor cells served as the 100% cytotoxicity control and untreated E:T cells served as the 0% cytotoxicity control. The level of lactate dehydrogenase (LDH) in each sample was determined via absorbance at 490 nm and normalize to the 100% and 0% controls. EC50 values, referring to the concentration of antibody that gives the half-maximal response, were determined from the dilution series.

6.13.2. Example 1: Bivalent Monospecific Construct and Bivalent Bispecific Construct A bivalent monospecific B-Body recognizing TNFα was constructed with the following architecture (VL(Certolizumab)-CH3(Knob)-CH2-CH3/VH(Certolizumab)-CH3 (Hole)) using standard molecular biology procedures. In this construct,
  1$^{st}$ polypeptide chain (SEQ ID NO:1)
    Domain A=VL (certolizumab)
    Domain B=CH3 (IgG1) (knob: S354C+T366W)
    Domain D=CH2 (IgG1)
    Domain E=CH3 (IgG1)
  2$^{nd}$ polypeptide chain (SEQ ID NO:2)
    Domain F=VH (certolizumab)
    Domain G=CH3 (IgG1) (hole: Y349C. T366S, L368A, Y407V)
  3$^{nd}$ polypeptide chain:
    identical to the 1$^{st}$ polypeptide chain
  4$^{th}$ polypeptide chain:
    identical to the 2$^{nd}$ polypeptide chain.

Domain and polypeptide chain references are in accordance with FIG. 3. The overall construct architecture is illustrated in FIG. 4. The sequence of the first polypeptide chain, with domain A identified in shorthand as "(VL)", is provided in SEQ ID NO:1. The sequence of the second polypeptide chain, with domain F identified in shorthand as "(VH)", is provided in SEQ ID NO:2.

The full-length construct was expressed in an *E. coli* cell free protein synthesis expression system for ~18 hours at 26° C. with gentle agitation. Following expression, the cell-free extract was centrifuged to pellet insoluble material and the supernatant was diluted 2× with 10× Kinetic Buffer (Forte Bio) and used as analyte for biolayer interferometry.

Figure 5:
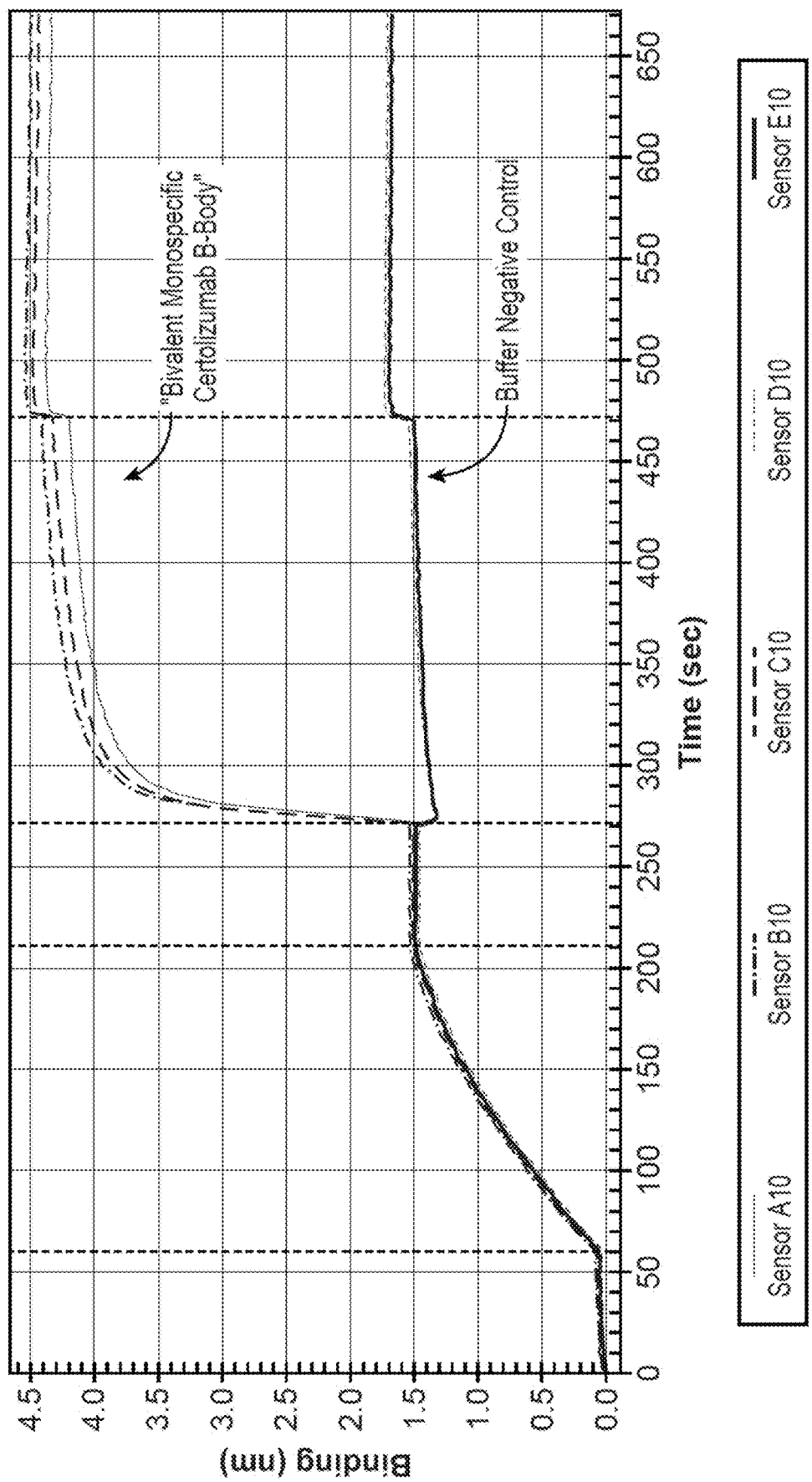

Biotinylated TNFα was immobilized on a streptavidin sensor to give a wave shift response of ~1.5 nm. After establishing a baseline with 10× kinetic buffer, the sensor was dipped into the antibody construct analyte solution. The construct gave a response of ~3 nm, comparable to the traditional IgG format of certolizumab, demonstrating the ability of the bivalent monospecific construct to assemble into a functional, full-length antibody. Results are shown in FIG. 5.

We also constructed a bivalent bispecific antibody with the following domain architecture:
  1$^{St}$ polypeptide chain: VL-CH3-CH2-CH3(Knob)
  2$^{nd}$ polypeptide chain: VH-CH3
  3$^{rd}$ polypeptide chain: VL-CL-CH2-CH3(Hole)
  4$^{th}$ polypeptide chain VH-CH1.

The sequences (except for the variable region sequences) are provided respectively in SEQ ID NO:3 (1st polypeptide chain), SEQ ID NO:4 (2nd polypeptide chain), SEQ ID NO:5 (3rd polypeptide chain), SEQ ID NO:6 (4$^{th}$ polypeptide chain).

6.13.3. Example 2: Bivalent Bispecific B-Body "BC1"

We constructed a bivalent bispecific construct, termed "BC1", specific for PD1 and a second antigen, "Antigen A"). Salient features of the "BC1" architecture are illustrated in FIG. 6.

In greater detail, with domain and polypeptide chain references in accordance with FIG. 3 and modifications from native sequence indicated in parentheses, the architecture was:

1$^{st}$ polypeptide chain (SEQ ID NO:8)
  Domain A=VL ("Antigen A")
  Domain B=CH3 (T366K; 445K, 446S, 447C tripeptide insertion)
  Domain D=CH2
  Domain E=CH3 (T366W. S354C)
2$^{nd}$ polypeptide chain (SEQ ID NO:9):
  Domain F=VH ("Antigen A")
  Domain G=CH3 (L351D; 445G, 446E, 447C tripeptide insertion)
3$^{rd}$ polypeptide chain (SEQ ID NO:10):
  Domain H=VL ("Nivo")
  Domain I=CL (Kappa)
  Domain J=CH2
  Domain K=CH3 (Y349C. D356E, L358M, T366S, L368A, Y407V)
4$^{th}$ polypeptide chain (SEQ ID NO: 11):
  Domain L=VH ("Nivo")
  Domain M=CH1.

The A domain (SEQ ID NO: 12) and F domain (SEQ ID NO: 16) form an antigen binding site (A:F) specific for "Antigen A". The H domain has the VH sequence from nivolumab and the L domain has the VL sequence from nivolumab; H and L associate to form an antigen binding site (H:L) specific for human PD1.

The B domain (SEQ ID NO:13) has the sequence of human IgG1 CH3 with several mutations: T366K, 445K, 446S, and 447C insertion. The T366K mutation is a charge pair cognate of the L351D residue in Domain G. The "447C" residue on domain B comes from the C-terminal KSC tripeptide insertion.

Domain D (SEQ ID NO: 14) has the sequence of human IgG1 CH2

Domain E (SEQ ID NO: 15) has the sequence of human IgG1 CH3 with the mutations T366W and S354C. The 366W is the "knob" mutation. The 354C introduces a cysteine that is able to form a disulfide bond with the cognate 349C mutation in Domain K.

Domain G (SEQ ID NO:17) has the sequence of human IgG1 CH3 with the following mutations: L351D, and 445G, 446E, 447C tripeptide insertion. The L351D mutation introduces a charge pair cognate to the Domain B T366K mutation. The "447C" residue on domain G comes from the C-terminal GEC tripeptide insertion.

Domain I (SEQ ID NO: 19) has the sequence of human C kappa light chain (Cκ)

Domain J [SEQ ID NO: 20] has the sequence of human IgG1 CH2 domain, and is identical to the sequence of domain D.

Domain K [SEQ ID NO: 21] has the sequence of human IgG1 CH3 with the following changes: Y349C, D356E, L358M, T366S, L368A, Y407V. The 349C mutation introduces a cysteine that is able to form a disulfide bond with the cognate 354C mutation in Domain E. The 356E and L358M introduce isoallotype amino acids that reduce immunogenicity. The 366S, 368A, and 407V are "hole" mutations.

Domain M [SEQ ID NO: 23] has the sequence of the human IgG1 CH1 region.

"BC1" could readily be expressed at high levels using mammalian expression at concentrations greater than 100 µg/ml.

We found that the bivalent bispecific "BC1" protein could easily be purified in a single step using a CH1-specific CaptureSelect™ affinity resin from ThermoFisher.

Figure 7A:
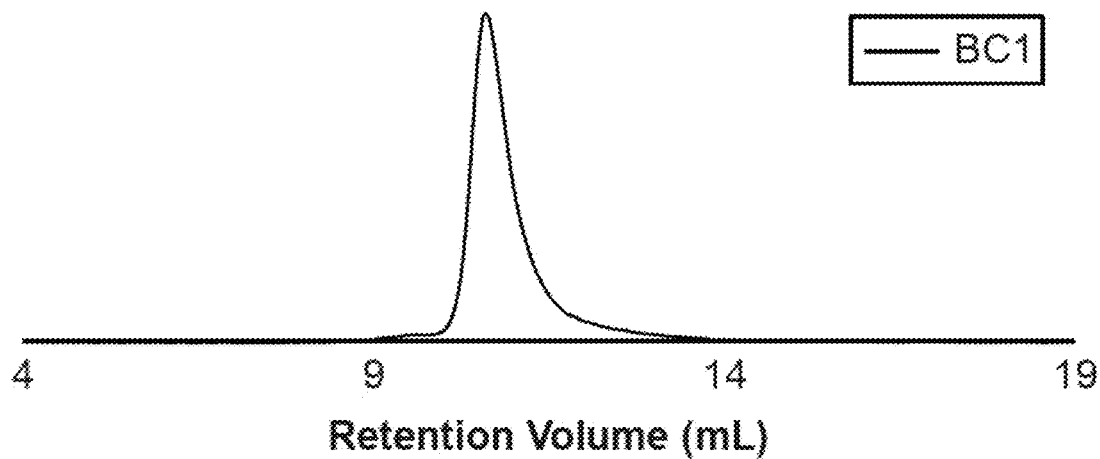
Figure 7B:
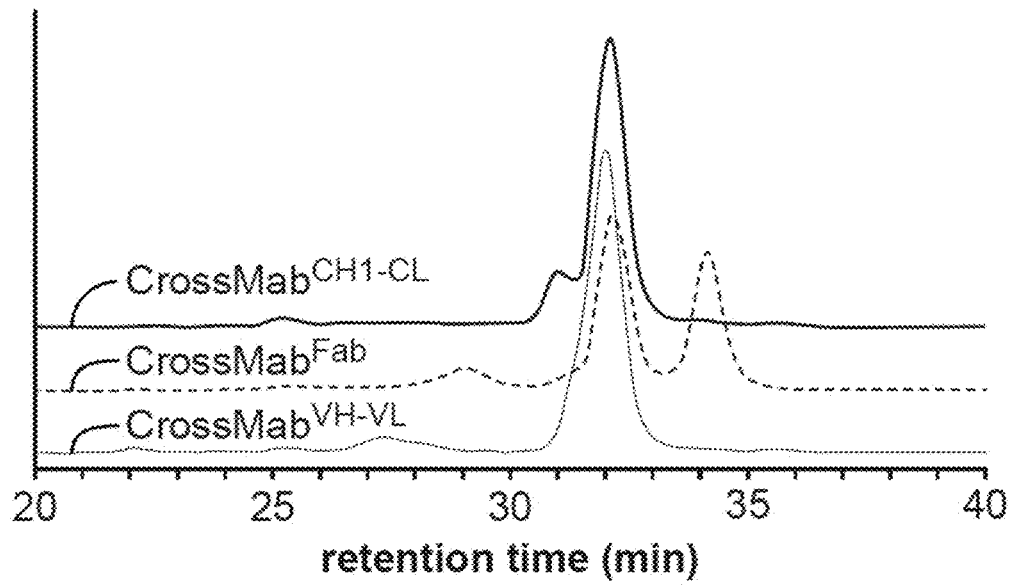

As shown in FIG. 7A. SEC analysis demonstrates that a single-step CH1 affinity purification step yields a single, monodisperse peak via gel filtration in which >98% is monomer. FIG. 7B shows comparative literature data of SEC analysis of a CrossMab bivalent antibody construct.

Figure 8A:
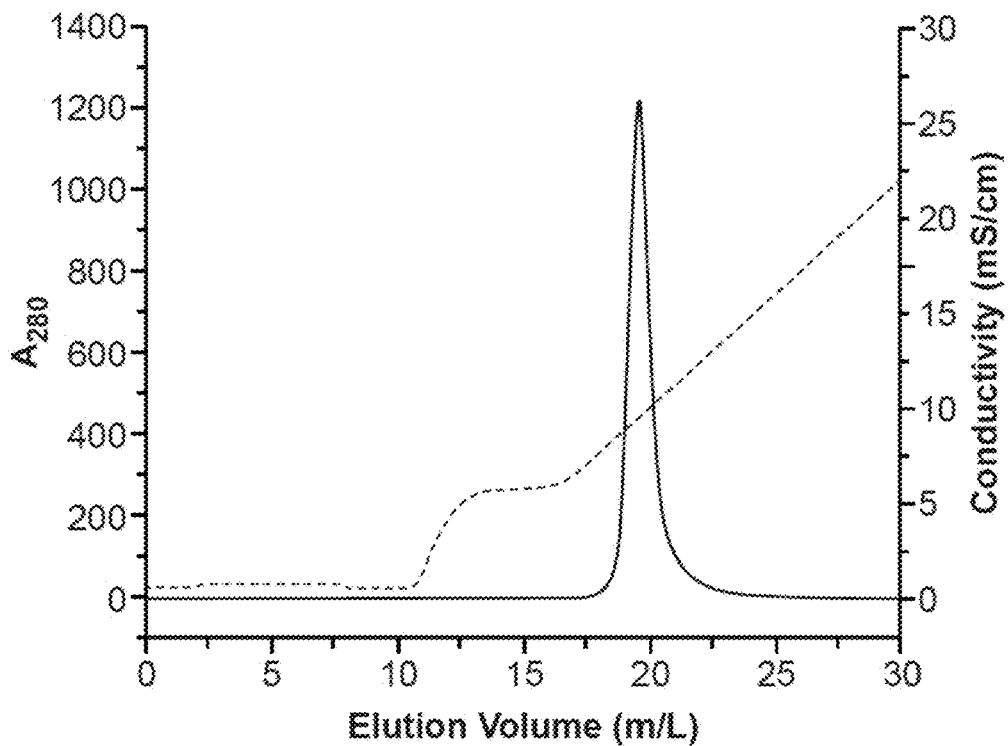
FIG. 8A is a cation exchange chromatography elution profile of "BC1" following one-step purification using the CaptureSelect™ CH1 affinity resin, showing a single tight peak.
Figure 8B:
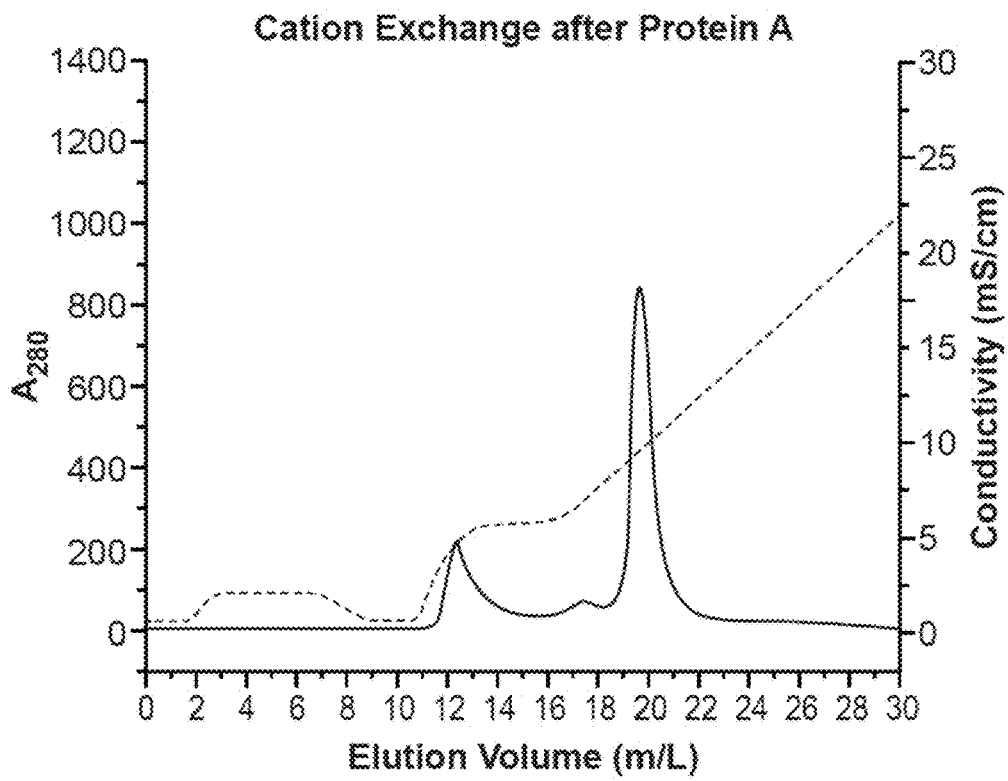
FIG. 8B is a cation exchange chromatography elution profile of "BC1" following purification using standard Protein A purification.

FIG. 8A is a cation exchange chromatography elution profile of "BC1" following one-step purification using the CaptureSelect™ CH1 affinity resin, showing a single tight peak. FIG. 8B is a cation exchange chromatography elution profile of "BC1" following purification using standard Protein A purification, showing additional elution peaks consistent with the co-purification of incomplete assembly products.

Figure 9:
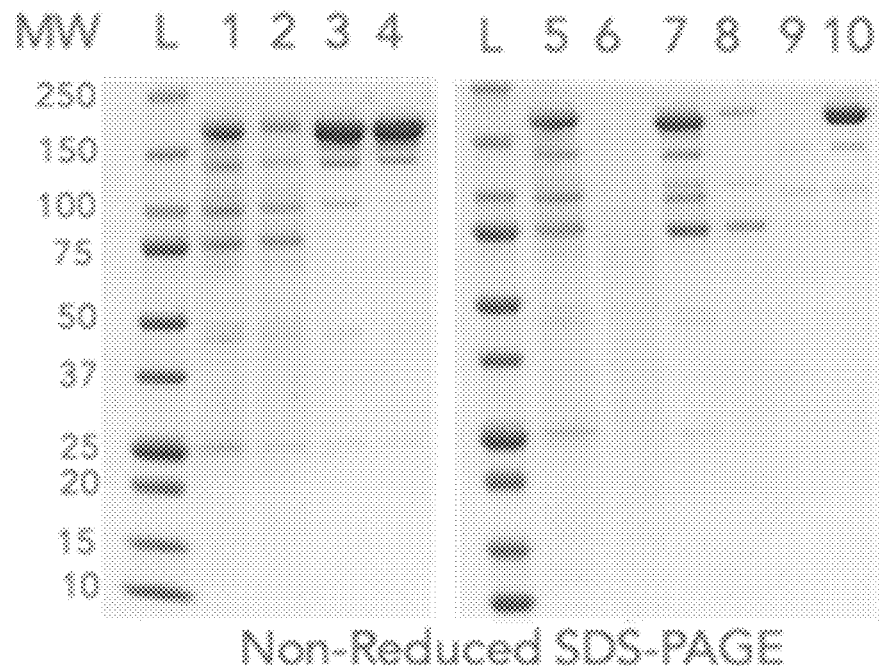
FIG. 9 shows nonreducing SDS-PAGE gels of "BC1" at various stages of purification.

FIG. 9 shows SDS-PAGE gels under non-reducing conditions. As seen in lane 3, single-step purification of "BC1" with CH1 affinity resin provides a nearly homogeneous single band, with lane 4 showing minimal additional purification with a subsequent cation exchange polishing step. Lane 7, by comparison, shows less substantial purification using standard Protein A purification, with lanes 8-10 demonstrating further purification of the Protein A purified material using cation exchange chromatography.

FIG. 10 compares SDS-PAGE gels of "BC1" after single-step CH1-affinity purification, under both non-reducing and reducing conditions (Panel A) with SDS-PAGE gels of a CrossMab bispecific antibody under non-reducing and reducing conditions as published in the referenced literature (Panel B).

Figure 11B:
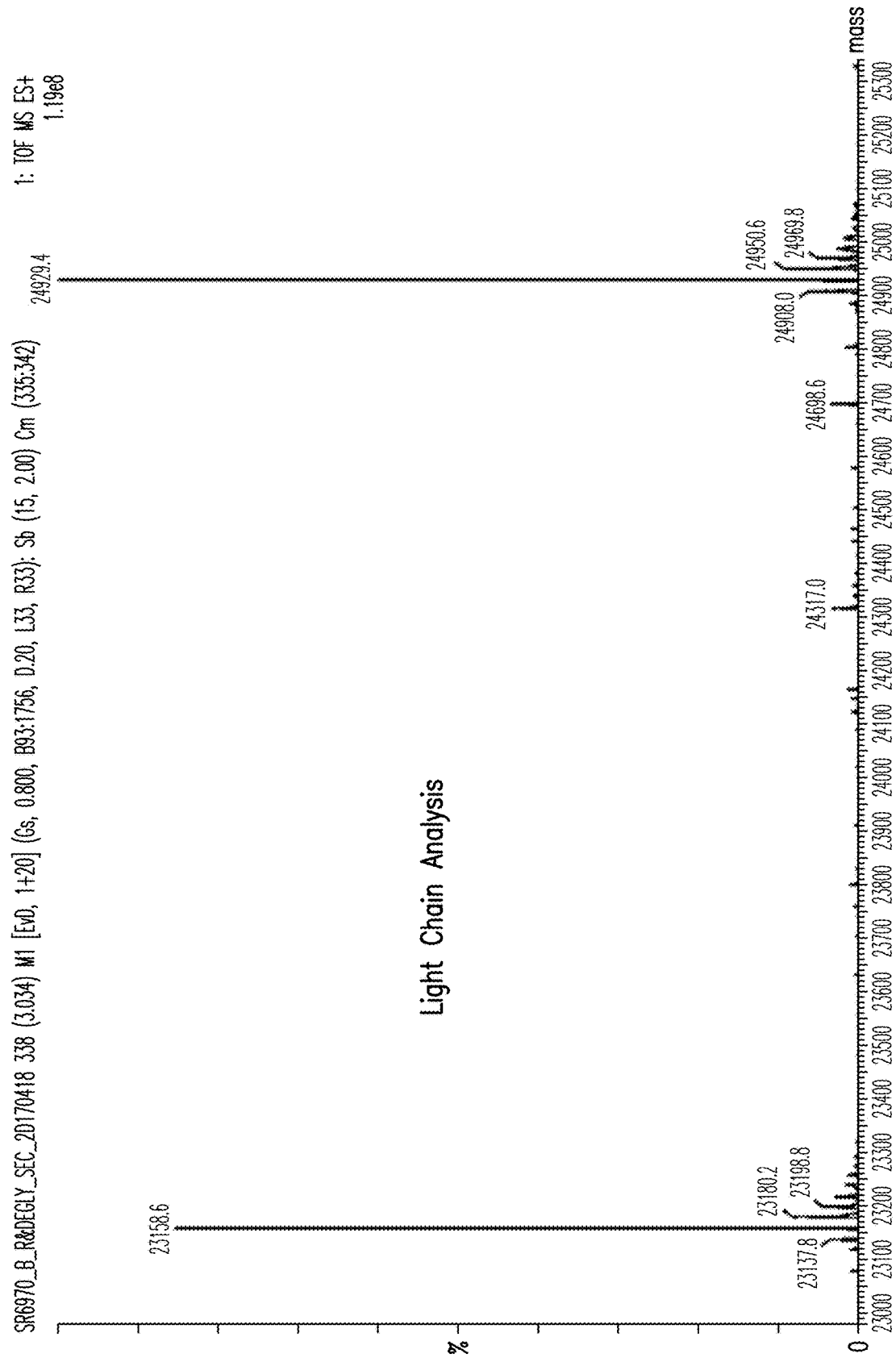

FIG. 11 shows mass spec analysis of "BC1", demonstrating two distinct heavy chains (FIG. 11A) and two distinct light chains (FIG. 11B) under reducing conditions. The mass spectrometry data in FIG. 12 confirms the absence of incomplete pairing after purification.

Accelerated stability testing was performed to evaluate the long-term stability of the "BC1" B-Body design. The purified B-Body was concentrated to 8.6 mg/ml in PBS buffer and incubated at 40° C. The structural integrity was measured weekly using analytical size exclusion chromatography (SEC) with a Shodex KW-803 column. The structural integrity was determined by measuring the percentage of intact monomer (% Monomer) in relation to the formation of aggregates. Data are shown in FIG. 13. The IgG Control 1 is a positive control with good stability properties. IgG Control 2 is a negative control that is known to aggregate under the incubation conditions. The "BC1" B-Body has been incubated for 8 weeks without any loss of structural integrity as determined by the analytical SEC.

We have also determined that "BC1" has high thermostability, with a TM of the bivalent construct of ~72° C.

Table 1 compares "BC1" to CrossMab in key developability characteristics:

TABLE 1

| Parameter | Unit | Roche CrossMab* | "BC1" |
|---|---|---|---|
| Purification yield after protein A/SEC | mg/L | 58.5 | 300 |
| Homogeneity After purification | % SEC Area | 50-85 | 98 |
| Denaturation Temp (Tm) | degrees C. | 69.2 | 72 |

*Data from Schaefer et al. (Proc Natl Acad Sci USA. 2011 Jul 5; 108(27): 11187-92)

6.13.4. Example 3: Bivalent Bispecific B-Body "BC6"

We constructed a bivalent bispecific B-Body, termed "BC6", that is identical to "BC1" but for retaining wild type residues in Domain B at residue 366 and Domain G at residue 351. "BC6" thus lacks the charge-pair cognates T366K and L351D that had been designed to facilitate correct pairing of domain B and domain G in "BC1". Salient features of the "BC6" architecture are illustrated in FIG. 14.

Notwithstanding the absence of the charge-pair residues present in "BC1", we found that a single step purification of "BC6" using CH1 affinity resin resulted in a highly homogeneous sample. FIG. 15A shows SEC analysis of "BC6" following one-step purification using the CaptureSelect™ CH1 affinity resin. The data demonstrate that the single step CH1 affinity purification yields a single monodisperse peak, similar to what we observed with "BC1", demonstrating that the disulfide bonds between polypeptide chains 1 and 2 and between polypeptide chains 3 and 4 are intact. The chromatogram also shows the absence of non-covalent aggregates.

FIG. 15B shows a SDS-PAGE gel under non-reducing conditions, with lane 1 loaded with a first lot of "BC6" after a single-step CH1 affinity purification, lane 2 loaded with a second lot of "BC6" after a single-step CH1 affinity purification. Lanes 3 and 4 demonstrate further purification can be achieved with ion exchange chromatography subsequent to CH1 affinity purification.

6.13.5. Example 4: Bivalent Bispecific B-Bodies "BC28", "BC29", "BC30", "BC31"

We constructed bivalent 1×1 bispecific B-Bodies "BC28", "BC29", "BC30" and "BC31" having an engineered disulfide within the CH3 interface in Domains B and G as an alternative S-S linkage to the C-terminal disulfide present in "BC1" and "BC6". Literature indicates that CH3 interface disulfide bonding is insufficient to enforce orthogonality in the context of Fc CH3 domains. The general architecture of these B-Body constructs is schematized in FIG. 16 with salient features of "BC28" summarized below:
  Polypeptide chain 1: "BC28" chain 1 (SEQ ID NO:24)
    Domain A=VL (Antigen "A")
    Domain B=CH3 (Y349C; 445P, 446G, 447K insertion)
    Domain D=CH2
    Domain E=CH3 (S354C, T366W)
  Polypeptide chain 2: "BC28" chain 2 (SEQ ID NO:25)
    Domain F=VH (Antigen "A")
    Domain G=CH3 (S354C; 445P, 446G, 447K insertion)
  Polypeptide chain 3: "BC1" chain 3 (SEQ ID NO:10)
    Domain H=VL ("Nivo")
    Domain I=CL (Kappa)
    Domain J=CH2
    Domain K=CH3 (Y349C, D356E, L358M, T366S, L368A, Y407V)
  Polypeptide chain 4: "BC1" chain 4 (SEQ ID NO:11)
    Domain L=VH ("Nivo")
    Domain M=CH1.

The "BC28" A:F antigen binding site is specific for "Antigen A". The "BC28" H:L antigen binding site is specific for PD1 (nivolumab sequences). "BC28" domain B has the following changes as compared to wild type CH3: Y349C; 445P, 446G, 447K insertion. "BC28" domain E has the following changes as compared to wild type CH3: S354C, T366W. "BC28" domain G has the following changes as compared to wild type: S354C; 445P, 446G, 447K insertion.

"BC28" thus has an engineered cysteine at residue 349C of Domain B and engineered cysteine at residue 354C of domain G ("349C-354C").

"BC29" has engineered cysteines at residue 351C of Domain B and 351C of Domain G ("351C-351C"). "BC30" has an engineered cysteine at residue 354C of Domain B and 349C of Domain G ("354C-349C"). BC31 has an engineered cysteine at residue 394C and engineered cysteine at 394C of Domain G ("394C-394C"). BC32 has engineered cysteines at residue 407C of Domain B and 407C of Domain G ("407C-407C").

FIG. 17 shows SDS-PAGE analysis under non-reducing conditions following one-step purification using the CaptureSelect™ CH1 affinity resin. Lanes 1 and 3 show high levels of expression and substantial homogeneity of intact "BC28" (lane 1) and "BC30" (lane 3). Lane 2 shows oligomerization of BC29. Lanes 4 and 5 show poor expression of BC31 and BC32, respectively, and insufficient linkage in BC32. Another construct, BC9, which had cysteines introduced at residue 392 in domain B and 399 in Domain G ("392C-399C"), a disulfide pairing reported by Genentech, demonstrated oligomerization on SDS PAGE (data not shown).

FIG. 18 shows SEC analysis of "BC28" and "BC30" following one-step purification using the CaptureSelect™ CH1 affinity resin. We have also demonstrated that "BC28" can readily be purified using a single step purification using Protein A resin (results not shown).

6.13.6. Example 5: Bivalent Bispecific B-Body "BC44"

FIG. 19 shows the general architecture of the bivalent bispecific 1×1 B-Body "BC44", our currently preferred bivalent bispecific 1×1 construct.
  first polypeptide chain ("BC44" chain 1) (SEQ ID NO:32)
    Domain A=VL (Antigen "A")
    Domain B=CH3 (P343V; Y349C; 445P, 446G, 447K insertion)
    Domain E=CH2
    Domain E=CH3 (S354C, T366W)
  second polypeptide chain (="BC28" polypeptide chain 2) (SEQ NO:25)
    Domain F=VH (Antigen "A")
    Domain G=CH3 (S354C; 445P, 446G, 447K insertion)
  third polypeptide chain (="BC1" polypeptide chain 3) (SEQ ID NO:10)
    Domain H=VL ("Nivo")
    Domain I=CL (Kappa)
    Domain J=CH2
    Domain K=CH3 (Y349C. D356E, L358M, T366S, L368A, Y407V)
  fourth polypeptide chain (="BC1" polypeptide chain 4) (SEQ ID NO:11)
    Domain L=VH ("Nivo")
    Domain M=CH1

6.13.7. Example 6: Variable-CH3 Junction Engineering

We produced a series of variants in which we mutated the VL-CH3 junction between Domains A and B and the VH-CH3 junction between domains F and G to assess the expression level, assembly and stability of bivalent lxi B-Body constructs. Although there are likely many solutions, to reduce introduction of T cell epitopes we chose to only use residues found naturally within the VL, VH and CH3 domains. Structural assessment of the domain architecture further limits desirable sequence combinations. Table 2 and Table 3 below show junctions for several junctional variants based on "BC1" and other bivalent constructs.

TABLE 2

Variants of Variable Domain/Constant Domain Junctions for 1st Polypeptide Chain

| | VL | | | | | | CH3 | | | | |
|---|---|---|---|---|---|---|---|---|---|---|---|
| Variant | 106 | 107 | 108 | 109 | 110 | 111 | 343 | 344 | 345 | 346 | Sequence |
| BC1 | I | K | R | T | | | P | R | E | P | IKRTPREP (SEQ ID NO: 57) |
| BC13 | I | K | R | T | | | P | R | E | P | IKRTPREP (SEQ ID NO: 57) |
| BC14 | I | K | R | T | | | P | R | E | P | IKRTPREP (SEQ ID NO: 57) |
| BC15 | I | K | R | T | V | | | R | E | P | IKRTVREP (SEQ ID NO: 58) |
| BC16 | I | K | R | T | | | | R | E | P | IKRTREP (SEQ ID NO: 59) |
| BC17 | I | K | R | T | V | | P | R | E | P | IKRTVPREP (SEQ ID NO: 60) |
| BC24 | I | K | R | T | | | P | R | E | P | IKRTPREP (SEQ ID NO: 57) |
| BC25 | I | K | R | T | | | P | R | E | P | IKRTPREP (SEQ ID NO: 57) |
| BC26 | I | K | R | T | V | A | | | E | P | IKRTVAEP (SEQ ID NO: 61) |
| BC27 | I | K | R | T | V | A | P | R | E | P | IKRTVAPREP (SEQ ID NO: 62) |
| BC44 | I | K | R | T | | | V | R | E | P | IKRTVREP (SEQ ID NO: 58) |
| BC45 | I | K | R | T | | | P | R | E | P | IKRTPREP (SEQ ID NO: 57) |
| BC5 | I | K | R | T | | | P | R | E | P | IKRTPREP (SEQ ID NO: 57) |
| BC6 | I | K | R | T | | | P | R | E | P | IKRTPREP (SEQ ID NO: 57) |
| BC28 | I | K | R | T | | | P | R | E | P | IKRTPREP (SEQ ID NO: 57) |
| BC30 | I | K | R | T | | | P | R | E | P | IKRTPREP (SEQ ID NO: 57) |

TABLE 3

Variants of Variable Domain/Constant Domain Junctions for 2nd Polypeptide Chain

| | VH | | | | | | | CH3 | | | | |
|---|---|---|---|---|---|---|---|---|---|---|---|---|
| Variant | 112 | 113 | 114 | 115 | 116 | 117 | 118 | 343 | 344 | 345 | 346 | Sequence |
| BC1 | S | S | A | S | | | | P | R | E | P | SSASPREP (SEQ ID NO: 63) |
| BC13 | S | S | A | S | T | | | | R | E | P | SSASTREP (SEQ ID NO: 64) |
| BC14 | S | S | A | S | T | | | P | R | E | P | SSASTPREP (SEQ ID NO: 65) |
| BC15 | S | S | A | S | | | | P | R | E | P | SSASPREP (SEQ ID NO: 63) |
| BC16 | S | S | A | S | | | | P | R | E | P | SSASPREP (SEQ ID NO: 63) |

TABLE 3-continued

Variants of Variable Domain/Constant Domain Junctions for 2nd Polypeptide Chain

| Variant | VH | | | | | | | CH3 | | | | Sequence |
|---|---|---|---|---|---|---|---|---|---|---|---|---|
| | 112 | 113 | 114 | 115 | 116 | 117 | 118 | 343 | 344 | 345 | 346 | |
| BC17 | S | S | A | S | | | | P | R | E | P | SSASPREP (SEQ ID NO: 63) |
| BC24 | S | S | A | S | T | K | G | | E | P | | SSASTKGEP (SEQ ID NO: 66) |
| BC25 | S | S | A | S | T | K | G | R | E | P | | SSASTKGREP (SEQ ID NO: 67) |
| BC26 | S | S | A | S | | | | P | R | E | P | SSASPREP (SEQ ID NO: 63) |
| BC27 | S | S | A | S | | | | P | R | E | P | SSASPREP (SEQ ID NO: 63) |
| BC44 | S | S | A | S | | | | P | R | E | P | SSASPREP (SEQ ID NO: 63) |
| BC45 | S | S | A | S | | | | P | R | E | P | SSASPREP (SEQ ID NO: 63) |
| BC5 | S | S | A | S | | | | P | R | E | P | SSASPREP (SEQ ID NO: 63) |
| BC6 | S | S | A | S | | | | P | R | E | P | SSASPREP (SEQ ID NO: 63) |
| BC28 | S | S | A | S | | | | P | R | E | P | SSASPREP (SEQ ID NO: 63) |
| BC30 | S | S | A | S | | | | P | R | E | P | SSASPREP (SEQ ID NO: 63) |

FIG. 20 shows size exclusion chromatography of "BC115" and "BC116" samples at the indicated week of an accelerated stability testing protocol at 40° C. "BC15" remained stable; "BC16" proved to be unstable over time.

6.13.8. Example 7: Trivalent 2×1 Bispecific B-Body Construct ("BC1-2×1")

We constructed a trivalent 2×1 bispecific B-Body "BC1-2×1" based on "BC1". Salient features of the architecture are illustrated in FIG. 22.

In greater detail, using the domain and polypeptide chain references summarized in FIG. 21,
1st polypeptide chain
   Domain N=V L ("Antigen A")
   Domain O=CH3 (T366K, 447C)
   Domain A=VL ("Antigen A")
   Domain B=CH3 (T366K, 447C)
   Domain D=CH2
   Domain E=CH3 (Knob, 354C)
5th polypeptide chain (="BC1" chain 2)
   Domain P=VH ("Antigen A")
   Domain Q=CH3 (L351D, 447C)
2nd polypeptide chain (="1BC1" chain 2)
   Domain F=VH ("Antigen A")
   Domain G=CH3 (L351D, 447C)
3rd polypeptide chain (="BC I" chain 3)
   Domain H=VL ("Nivo")
   Domain I=CL (Kappa)
   Domain J=CH2
   Domain K=CH3 (Hole, 349C)

4th polypeptide chain (="BC1" chain 4)
   Domain L=VH ("Nivo")
   Domain M=CH1.

FIG. 23 shows non-reducing SDS-PAGE of protein expressed using the ThermoFisher Expi293 transient transfection system.

Lane 1 shows the eluate of the trivalent 2×1 "BC1-2×1" protein following one-step purification using the CaptureSelect™ CH1 affinity resin. Lane 2 shows the lower molecular weight, faster migrating, bivalent "BC1" protein following one-step purification using the CaptureSelect™ CH1 affinity resin. Lanes 3-5 demonstrate purification of "BC1-2×1" using protein A. Lanes 6 and 7 show purification of "BC1-2×1" using CH1 affinity resin.

FIG. 24 compares the avidity of the bivalent "BC1" construct to the avidity of the trivalent 2×1 "BC1-2×1" construct using an Octet (Pall ForteBio) analysis. Biotinylated antigen "A" is immobilized on the surface, and the antibody constructs are passed over the surface for binding analysis.

6.13.9. Example 8: Trivalent 2×1 Trispecific B-Body Construct ("TB111")

We designed a trivalent 2×1 trispecific molecule, "TB111", having the architecture schematized in FIG. 25. With reference to the domain naming conventions set forth in FIG. 21, TB111 has the following architecture ("Ada" indicates a V region from adalimumab):

polypeptide chain 1
  Domain N: VH ("Ada")
  Domain O: CH3 (T366K, 394C)
  Domain A: VL ("Antigen A")
  Domain B: CH3 (T366K, 349C)
  Domain D: CH2
  Domain E: CH3 (Knob, 354C)
polypeptide chain 5
  Domain P: VL ("Ada")
  Domain Q: CH3 (L351 D, 394C)
polypeptide chain 2
  Domain F: VH ("Antigen A")
  Domain G: CH3 (L351D, 351C)
polypeptide chain 3
  Domain H: VL ("Nivo")
  Domain I: CL (kappa)
  Domain J: CH2
  Domain K: CH3 (Hole, 349C)
polypeptide chain 4 (="BC1" chain 4)
  Domain L: VH ("Nivo")
  Domain M: CH1

This construct did not express.

6.13.10. Example 9: Trivalent 1×2 Bispecific Construct ("BC28-1×2")

We constructed a trivalent 1×2 bispecific B-Body having the following domain and chain structure with reference to the domain and chain nomenclature set forth in FIG. 26:
1$^{st}$ polypeptide chain (="BC28" chain 1) (SEQ ID NO:24)
  Domain A=VL (Antigen "A")
  Domain B=CH3 (Y349C: 445P, 446G, 447K insertion)
  Domain D=CH2
  Domain E=CH3 (S354C, T366W)
2$^{nd}$ polypeptide chain (="BC28" chain 2) (SEQ ID NO:25)
  Domain F=VH (Antigen "A")
  Domain G=CH3 (S354C; 445P, 446G, 447K insertion)
3$^{rd}$ polypeptide chain (SEQ ID NO:37)
  Domain R=VL (Antigen "A")
  Domain S=CH3 (Y349C: 445P, 446G, 447K insertion)
  Linker=GSGSGS (SEQ ID NO:541)
  Domain H=VL ("Nivo")
  Domain I=CL
  Domain J=CH2
  Domain K=CH3 (Y349C, D356E, L358M, T366S, L368A, Y407V)
4$^{th}$ polypeptide chain (="BC1" chain 4) (SEQ ID NO:11):
  Domain L=VH ("Nivo")
  Domain M=CH1.
6$^{th}$ polypeptide chain (="BC28" chain 2) (SEQ ID NO:25)
  Domain T=VH (Antigen "A")
  Domain U=CH3 (S354C; 445P, 446G, 447K insertion)

The A:F antigen binding site is specific for "Antigen A", as is the H:L binding antigen binding site. The R:T antigen binding site is specific for PD. The specificity of this construct is thus Antigen "A"×(PD1-Antigen "A").

6.13.11. Example 10: Trivalent 1×2 Bispecific Construct ("CTLA4-4×Nivo×CTLA4-4")

We constructed a trivalent 1×2 bispecific molecule having the general structure schematized in FIG. 27 ("CTLA4-4× Nivo×CTLA4-4"). Domain nomenclature is set forth in FIG. 26.

FIG. 28 is a SDS-PAGE gel in which the lanes showing the "CTLA4-4×Nivo×CTLA4-4" construct under non-reducing and reducing conditions have been boxed.

FIG. 29 compares antigen binding of two antibodies: "CTLA4-4×OX40-8" and "CTLA4-4×Nivo×CTLA4-4". "CTLA4-4×OX40-8" binds to CTLA4 monovalently; while "CTLA4-4×Nivo×CTLA4-4" bind to CTLA4 bivalently.

6.13.12. Example 11: Trivalent 1×2 Trispecific Construct "BC28-1×1×1a"

We constructed a trivalent 1×2 trispecific molecule having the general structure schematized in FIG. 30. With reference to the domain and chain nomenclature set forth in FIG. 26,
1$^{st}$ polypeptide chain (="BC28" chain1) [SEQ ID NO:24]
  Domain A=VL (Antigen "A")
  Domain B=CH3 (Y349C: 445P, 446G, 447K insertion)
  Domain D=CH2
  Domain E=CH3 (S354C. T366W)
2$^{nd}$ polypeptide chain (="BC28" chain 2) (SEQ ID NO:25)
  Domain F=VH (Antigen "A")
  Domain G=CH3 (S354C: 445P, 446G, 447K insertion)
3$^{rd}$ polypeptide chain (SEQ ID NO:45)
  Domain R=VL (CTLA4-4)
  Domain S=CH3 (T366K: 445K, 446S, 447C insertion)
  Linker=GSGSGS (SEQ ID NO:541)
  Domain H=VL ("Nivo")
  Domain I=CL
  Domain J=CH2
  Domain K=CH3 (Y349C, D356E, L358M, T366S, L368A, Y407V)
4$^{th}$ polypeptide chain (="BC1" chain 4) (SEQ ID NO:11)
  Domain L=VH ("Nivo")
  Domain M=CH1
6$^{th}$ polypeptide chain (=hCTLA4-4 chain2) (SEQ ID NO:53)
  Domain T=VH (CTLA4)
  Domain U=CH3 (L351D, 445G, 446E, 447C insertion)

The antigen binding sites of this trispecific construct were:
  Antigen binding site A:F was specific for "Antigen A"
  Antigen binding site H:L was specific for PD1 (nivolumab sequence)
  Antigen binding site R:T was specific for CTLA4.

FIG. 31 shows size exclusion chromatography with "BC28-1×1×1a" following transient expression and one-step purification using the CaptureSelect™ CH1 affinity resin, demonstrating a single well-defined peak.

6.13.13. Example 12: SDS-PAGE Analysis of Bivalent and Trivalent Constructs

FIG. 32 shows a SDS-PAGE gel with various constructs, each after transient expression and one-step purification using the CaptureSelect™ CH1 affinity resin, under non-reducing and reducing conditions.

Lanes 1 (nonreducing conditions) and 2 (reducing conditions, +DTT) are the bivalent 1×1 bispecific construct "BC1". Lanes 3 (nonreducing) and 4 (reducing) are the trivalent bispecific 2×1 construct "BC1-2×1" (see Example 7). Lanes 5 (nonreducing) and 6 (reducing) are the trivalent 1×2 bispecific construct "CTLA4-4×Nivo×CTLA4-4" (see Example 10). Lanes 7 (nonreducing) and 8 (reducing) are the trivalent 1×2 trispecific "BC28-1×1×1α" construct described in Example 11.

The SDS-PAGE gel demonstrates the complete assembly of each construct, with the predominant band in the non-reducing gel appearing at the expected molecular weight for each construct.

6.13.14. Example 13: Binding Analysis

FIG. 33 shows Octet binding analyses to 3 antigens: PD1, Antigen "A", and CTLA-4. In each instance, the antigen is immobilized and the B-Body is the analyte. For reference, 1×1 bispecifics "BC1" and "CTLA4-4×OX40-8" were also compared to demonstrate 1×1 B-Bodies bind specifically only to antigens for which the antigen binding sites were selected.

FIG. 33A shows binding of "BC1" to PD1 and to Antigen "A", but not CTLA4. FIG. 33B shows binding of a bivalent bispecific 1×1 construct "CTLA4-4×OX40-8" to CTLA4, but not to Antigen "A" or PD1. FIG. 33C shows the binding of the trivalent trispecific 1×2 construct, "BC28-1×1×1α" to PD1, Antigen "A", and CTLA4.

6.13.15. Example 14: Tetravalent Constructs

FIG. 35 shows the overall architecture of a 2×2 tetravalent bispecific construct "BC22-2×2". The 2×2 tetravalent bispecific was constructed with "1BC1" scaffold by duplicating each variable domain-constant domain segment. Domain nomenclature is schematized in FIG. 34.

FIG. 36 is a SDS-PAGE gel. Lanes 7-9 show the "BC22-2×2" tetravalent construct respectively following one-step purification using the CaptureSelect™ CH1 affinity resin ("CH1 eluate"), and after an additional ion exchange chromatography purification (lane 8, "pk 1 after IEX"; lane 9, "pk 2 after IEX"). Lanes 1-3 are the trivalent 2×1 construct "BC21-2×1" after CH1 affinity purification (lane 1) and, in lanes 2 and 3, subsequent ion exchange chromatography. Lanes 4-6 are the 1×2 trivalent construct "BC12-1×2".

FIG. 37 shows the overall architecture of a 2×2 tetravalent construct.

FIGS. 39 and 40 schematize tetravalent constructs having alternative architectures. Domain nomenclature is presented in FIG. 38.

6.13.16. Example 15: Bispecific Antigen Engagement by B-Body

A tetravalent bispecific 2×2 B-Body "B-Body-IgG 2×2" was constructed. In greater detail, using the domain and polypeptide chain nomenclature references summarized in FIG. 38, $1^{st}$ polypeptide chain
 Domain A=VL (Certolizumab)
 Domain B=CH3 (IgG1, knob)
 Domain D=CH2 (IgG1)
 Domain E=CH3 (IgG1)
 Domain W=VH (Antigen "A")
 Domain X=CH1 (IgG1)
$3^{rd}$ polypeptide chain (identical to first polypeptide chain)
 Domain H=VL (Certolizumab)
 Domain I=CH3 (IgG1, knob)
 Domain J=CH2 (IgG1)
 Domain K=CH3 (IgG1)
 Domain WW=VH (Antigen "A")
 Domain XX=CH1 (IgG1)
$2^{nd}$ polypeptide chain
 Domain F=VH (Certolizumab)
 Domain G=CH3 (IgG1, hole)
$4^{th}$ polypeptide chain (identical to third polypeptide chain)
 Domain F=VH (Certolizumab)
 Domain G=CH3 (IgG1, hole)
$7^{th}$ polypeptide chain
 Domain Y=VH ("Antigen A")
 Domain Z=CL Kappa
$8^{th}$ polypeptide chain (identical to seventh polypeptide chain)
 Domain YY=VH ("Antigen A")
 Domain ZZ=CL Kappa.

This was cloned and expressed as described in Example 1. Here, the BLI experiment consisted of immobilization of biotinylated antigen "A" on a streptavidin sensor, followed by establishing baseline with 10× kinetic buffer. The sensor was then dipped in cell-free expressed "B-Body-IgG 2×2" followed by establishment of a new baseline. Finally, the sensor was dipped in 100 nM TNFα where a second binding event was observed, confirming the bispecific binding of both antigens by a single "B-Body-IgG 2×2" construct. Results are shown in FIG. 41.

6.13.17. Example 16: Antigen-Specific Cell Binding of "BB-IgG 2×2"

Expi-293 cells were either mock transfected or transiently transfected with Antigen "B" using the Expi-293 Transfection Kit (Life Technologies). Forty-eight hours after transfection, the Expi-293 cells were harvested and fixed in 4% paraformaldehyde for 15 minutes at room temperature. The cells were washed twice in PBS. 200,000 Antigen B or Mock transfected Expi-293 cells were placed in a V-bottom 96 well plate in 100 µL of PBS. The cells were incubated with the "B-Body-IgG 2×2" at a concentration of 3 ug/mL for 1.5 hours at room temperature. The cells were centrifuged at 300×G for 7 minutes, washed in PBS, and incubated with 100 µL of FITC labeled goat-anti human secondary antibody at a concentration of 8 µg/mL for 1 hour at room temperature. The cells were centrifuged at 300×G for 7 minutes, washed in PBS, and cell binding was confirmed by flow cytometry using a Guava easyCyte. Results are shown in FIG. 42.

6.13.18. Example 17: SDS-PAGE Analysis of Bivalent and Trivalent Constructs

FIG. 45 shows a SDS-PAGE gel with various constructs, each after transient expression and one-step purification using the CaptureSelect™ CH1 affinity resin, under non-reducing and reducing conditions.

Lanes 1 (nonreducing conditions) and 2 (reducing conditions, +DTT) are the bivalent 1×1 bispecific construct "BC I". Lanes 3 (nonreducing) and 4 (reducing) are the bivalent 1×1 bispecific construct "BC28" (see Example 4). Lanes 5 (nonreducing) and 6 (reducing) are the bivalent 1×1 bispecific construct "BC44" (see Example 5). Lanes 7 (nonreducing) and 8 (reducing) are the trivalent 1×2 bispecific "BC28-1×2" construct (see Example 9). Lanes 9 (nonreducing) and 10 (reducing) are the trivalent 1×2 trispecific "BC28-1×1×1a" construct described in Example 11.

The SDS-PAGE gel demonstrates the complete assembly of each construct, with the predominant band in the non-reducing gel appearing at the expected molecular weight for each construct.

6.13.19. Example 18: Stability Analysis of Variable-CH3 Junction Engineering Pairing stability between various junctional variant combinations was assessed. Differential scanning fluorimetry was performed to determine the melting temperature of various junctional variant pairings between VL-CH3 polypeptides from Chain 1 (domains A and B) and VH-CH3 polypeptides from 2 (domains F and G). Junctional variants "BC6jv", "BC28jv", "BC30jv", "BC44jv", and "BC45jv", each having the corresponding junctional sequences of "BC6", "BC28", "BC30", "BC44", and "BC45" found in Table 2 and Table 3 above, demonstrate increased pairing stability with Tm's in the 76-77 degree range (see Table 4). FIG. 46 shows differences in the thermal transitions for "BC24jv", "BC26jv", and "BC28jv", with "BC28jv" demonstrating the greatest stability of the three. The x-axis of the figure is temperature and the y-axis is the change in fluorescence divided by the change in temperature (−dFluor/dTemp). Experiments were performed as described in Niesen et al. (*Nature Protocols*, (2007) 2, 2212-2221), which is hereby incorporated by reference for all it teaches.

TABLE 4

Melting Temperatures of Junctional Variant Pairs

| JUNCTIONAL VARIANT PAIR | MELTING TEMP #1 (° C.) | MELTING TEMP #2 (° C.) |
|---|---|---|
| BC1jv | 69.7 | 55.6 |
| BC5jv | 71.6 | |
| BC6jv | 77 | |
| BC15jv | 68.2 | 54 |
| BC16jv | 65.9 | |
| BC17jv | 68 | |
| BC24jv | 69.7 | |
| BC26jv | 70.3 | |
| BC28jv | 76.7 | |
| BC30jv | 76.8 | |
| BC44jv | 76.2 | |
| BC45jv | 76 | |

6.13.20. Example 19: RORxCD3 Candidate Binding Molecules

Various RORxCD3 antibodies were constructed and tested as described below.

6.13.20.1. CD3 Binding Arm

A series of CD3 binding arm variants based on a humanized version of the SP34 anti-CD3 antibody (SP34-89, SEQ ID NOs:68 and 69) were engineered with point mutations in either the VH or VL amino acid sequences (SEQ ID Nos: 70-73). The various VH and VL sequences were paired together as described in Table 5.

TABLE 5

Anti-CD3 SP34 Binding Arm Variants

| VL/VH Variants | SP34-89 VL-WT (SEQ ID NO: 69) | SP34-89 VL-W57G (SEQ ID NO: 73) |
|---|---|---|
| SP34-89 VH-WT SEQ ID NO: 68 | SP34-89 VL-WT/ SP34-89 VH-WT | SP34-89 VL-W57G/ SP34-89 VH-WT |
| SP34-89 VH-N30S SEQ ID NO: 70 | SP34-89 VL-WT/ SP34-89 VH-N30S | SP34-89 VL-W57G/ SP34-89 VH-N30S |
| SP34-89 VH-G65D SEQ ID NO: 71 | SP34-89 VL-WT/ SP34-89 VH-G65D | SP34-89 VL-W57G/ SP34-89 VH-G65D |
| SP34-89 VH-S68T SEQ ID NO: 72 | SP34-89 VL-WT/ SP34-89 VH-S68T | SP34-89 VL-W57G/ SP34-89 VH-S68T |

The VL and VH variants were cloned into one arm of a 1×1 BC1 B-Body, while the other arm contained an irrelevant antigen binding site. FIG. 47 demonstrates binding affinity of the non-mutagenized SP34-89 monovalent B-Body as determined by Octet (Pall ForteBio) biolayer interferometry analysis. A two-fold serial dilution (200-12.5 nM) of the construct was used to determine a binding affinity of 23 nM for SP34-89 ($k_{on}$=3×10$^5$ M$^{-1}$s$^{-1}$, $k_{off}$=7.1×10$^{-3}$ s$^{-1}$), matching the affinity for other SP34 variants in the literature. The kinetic affinity also matched the equilibrium binding affinity.

6.13.20.2. ROR Binding Arm

A chemically synthetic Fab phage library with diversity introduced into the Fab CDRs was screened against ROR antigens using a monoclonal phage ELISA format where plate-immobilized ROR variants were assessed for binding to phage, as described above. Phage clones expressing Fabs that recognized antigens were sequenced. A first screening campaign for binding to ROR1 identified the antigen binding site (ABS) clones designated "12A" in Table 6, and a second screening campaign for binding to ROR2 identified the ABS clones designated "12C" in Table 6.

TABLE 6

ROR Antigen Binding Site Candidates

| ABS | CDR1 VH | CDR2 VH | CDR3 VH | CDR1 VL | CDR2 VL | CDR3 VL |
|---|---|---|---|---|---|---|
| I2A-1 | FSSYFI (SEQ ID NO: 153) | AIYPEGGYTY (SEQ ID NO: 154) | DYKYVGAL (SEQ ID NO: 155) | RASQSVSSAVA (SEQ ID NO: 156) | SASSLYS (SEQ ID NO: 157) | YYYFPG (SEQ ID NO: 158) |
| I2A-2 | FSYYGI (SEQ ID NO: 159) | FIYSRGGYTI (SEQ ID NO: 160) | YIGAGL (SEQ ID NO: 161) | RASQSVSSAVA (SEQ ID NO: 162) | SASSLYS (SEQ ID NO: 163) | YYWDPI (SEQ ID NO: 164) |
| I2A-3 | FTSYEI (SEQ ID NO: 165) | HIDPYGGYTQ (SEQ ID NO: 166) | RGVAVF (SEQ ID NO: 167) | RASQSVSSAVA (SEQ ID NO: 168) | SASSLYS (SEQ ID NO: 169) | WAYAPV (SEQ ID NO: 170) |
| I2A-4 | FYSYDI (SEQ ID NO: 171) | YISPYWGITT (SEQ ID NO: 172) | YIGSSYWDAL (SEQ ID NO: 173) | RASQSVSSAVA (SEQ ID NO: 174) | SASSLYS (SEQ ID NO: 175) | SDSSLV (SEQ ID NO: 176) |

TABLE 6-continued

ROR Antigen Binding Site Candidates

| ABS | CDR1 VH | CDR2 VH | CDR3 VH | CDR1 VL | CDR2 VL | CDR3 VL |
|---|---|---|---|---|---|---|
| I2A-5 | FSSYGI (SEQ ID NO: 177) | WISPTGSITI (SEQ ID NO: 178) | SYMIYGGL (SEQ ID NO: 179) | RASQSVSSAVA (SEQ ID NO: 180) | SASSLYS (SEQ ID NO: 181) | RVSSPW (SEQ ID NO: 182) |
| I2A-6 | FSLYAI (SEQ ID NO: 183) | EIDSWLGYTY (SEQ ID NO: 184) | RPVTEVYYSAL (SEQ ID NO: 185) | RASQSVSSAVA (SEQ ID NO: 186) | SASSLYS (SEQ ID NO: 187) | YDRSLH (SEQ ID NO: 188) |
| I2A-7 | FSRYYI (SEQ ID NO: 189) | DIDSYGGFTY (SEQ ID NO: 190) | AHRFLQGGYVL (SEQ ID NO: 191) | RASQSVSSAVA (SEQ ID NO: 192) | SASSLYS (SEQ ID NO: 193) | YSWGLW (SEQ ID NO: 194) |
| I2A-8 | FYGYYI (SEQ ID NO: 195) | GIRPGGTYTY (SEQ ID NO: 196) | YRYPAF (SEQ ID NO: 197) | RASQSVSSAVA (SEQ ID NO: 198) | SASSLYS (SEQ ID NO: 199) | RRQHLW (SEQ ID NO: 200) |
| I2A-9 | FSSYTI (SEQ ID NO: 201) | AIDSGWSYTD (SEQ ID NO: 202) | AYGGVM (SEQ ID NO: 203) | RASQSVSSAVA (SEQ ID NO: 204) | SASSLYS (SEQ ID NO: 205) | YWWPG (SEQ ID NO: 206) |
| I2A-10 | FSSYFI (SEQ ID NO: 207) | GIYPSDGYTS (SEQ ID NO: 208) | YYVSGM (SEQ ID NO: 209) | RASQSVSSAVA (SEQ ID NO: 210) | SASSLYS (SEQ ID NO: 211) | YYYYPG (SEQ ID NO: 212) |
| I2A-10 D54E Y55Q | FSSYFI (SEQ ID NO: 213) | GIYPSEGYTS (SEQ ID NO: 214) | YYVSGM (SEQ ID NO: 215) | RASQSVSSAVA (SEQ ID NO: 216) | SASSLQS (SEQ ID NO: 217) | YYYYPG (SEQ ID NO: 218) |
| I2A-11 | FSSYVI (SEQ ID NO: 219) | AIYPYTSSTQ (SEQ ID NO: 220) | SYGTGGF (SEQ ID NO: 221) | RASQSVSSAVA (SEQ ID NO: 222) | SASSLYS (SEQ ID NO: 223) | WYSYPL (SEQ ID NO: 224) |
| I2A-12 | FTTYYI (SEQ ID NO: 225) | YISPEDGYTS (SEQ ID NO: 226) | AYYSAVM (SEQ ID NO: 227) | RASQSVSSAVA (SEQ ID NO: 228) | SASSLYS (SEQ ID NO: 229) | SWSPAT (SEQ ID NO: 230) |
| I2A-13 | FSYYFI (SEQ ID NO: 231) | VIYPDGGYTL (SEQ ID NO: 232) | IYYPSGAM (SEQ ID NO: 233) | RASQSVSSAVA (SEQ ID NO: 234) | SASSLYS (SEQ ID NO: 235) | TYWYPG (SEQ ID NO: 236) |
| I2A-14 | FDSYVI (SEQ ID NO: 237) | YIFSFGGYTY (SEQ ID NO: 238) | SPYGTFAL (SEQ ID NO: 239) | RASQSVSSAVA (SEQ ID NO: 240) | SASSLYS (SEQ ID NO: 241) | YYYTPG (SEQ ID NO: 242) |
| I2A-15 | FWGYVI (SEQ ID NO: 243) | AIDSWDGDTD (SEQ ID NO: 244) | SFYYIYVM (SEQ ID NO: 245) | RASQSVSSAVA (SEQ ID NO: 246) | SASSLYS (SEQ ID NO: 247) | LYSTLV (SEQ ID NO: 248) |
| I2A-16 | FSGYFI (SEQ ID NO: 249) | AIFPYRGGTS (SEQ ID NO: 250) | GGVSPGGF (SEQ ID NO: 251) | RASQSVSSAVA (SEQ ID NO: 252) | SASSLYS (SEQ ID NO: 253) | YYLYPG (SEQ ID NO: 254) |
| I2A-17 | FESYDI (SEQ ID NO: 255) | AIFSYGGYTT (SEQ ID NO: 256) | GSYGDGRGM (SEQ ID NO: 257) | RASQSVSSAVA (SEQ ID NO: 258) | SASSLYS (SEQ ID NO: 259) | YYYWPG (SEQ ID NO: 260) |
| I2A-18 | FSSYFI (SEQ ID NO: 261) | AIHPAFSFTY (SEQ ID NO: 262) | PRLSSAVVL (SEQ ID NO: 263) | RASQSVSSAVA (SEQ ID NO: 264) | SASSLYS (SEQ ID NO: 265) | * |
| I2A-19 | FSSYFI (SEQ ID NO: 266) | WIYPSGSYTY (SEQ ID NO: 267) | EMDRVGYSGM (SEQ ID NO: 268) | RASQSVSSAVA (SEQ ID NO: 269) | SASSLYS (SEQ ID NO: 270) | YRTPLG (SEQ ID NO: 271) |
| I2A-20 | FSDYGI (SEQ ID NO: 272) | EIDSWLGYTY (SEQ ID NO: 273) | SPYHYLYYGL (SEQ ID NO: 274) | RASQSVSSAVA (SEQ ID NO: 275) | SASSLYS (SEQ ID NO: 276) | LSSSLG (SEQ ID NO: 277) |
| I2A-21 | FSGYFI (SEQ ID NO: 278) | GISPWAGYTS (SEQ ID NO: 279) | GGGRAF (SEQ ID NO: 280) | RASQSVSSAVA (SEQ ID NO: 281) | SASSLYS (SEQ ID NO: 282) | YYWYPG (SEQ ID NO: 283) |

TABLE 6-continued

ROR Antigen Binding Site Candidates

| ABS | CDR1 VH | CDR2 VH | CDR3 VH | CDR1 VL | CDR2 VL | CDR3 VL |
|---|---|---|---|---|---|---|
| I2A-22 | FSSYFI (SEQ ID NO: 284) | AIYPSGWYTS (SEQ ID NO: 285) | VQAGVF (SEQ ID NO: 286) | RASQSVSSAVA (SEQ ID NO: 287) | SASSLYS (SEQ ID NO: 288) | YYYYPG (SEQ ID NO: 289) |
| I2A-23 | FDDYFI (SEQ ID NO: 290) | AISSEGGYTD (SEQ ID NO: 291) | AYRGVF (SEQ ID NO: 292) | RASQSVSSAVA (SEQ ID NO: 293) | SASSLYS (SEQ ID NO: 294) | YYYFPG (SEQ ID NO: 295) |
| I2A-24 | FSTYGI (SEQ ID NO: 296) | AIYPGTSYTG (SEQ ID NO: 297) | EYFMGM (SEQ ID NO: 298) | RASQSVSSAVA (SEQ ID NO: 299) | SASSLYS (SEQ ID NO: 300) | YYYWPG (SEQ ID NO: 301) |
| I2A-25 | FYGYTI (SEQ ID NO: 302) | AIYPYTDSTR (SEQ ID NO: 303) | DYRRAL (SEQ ID NO: 304) | RASQSVSSAVA (SEQ ID NO: 305) | SASSLYS (SEQ ID NO: 306) | YTDFPW (SEQ ID NO: 307) |
| I2A-26 | FQSYDI (SEQ ID NO: 308) | AIDPTGRSTA (SEQ ID NO: 309) | DYGVF (SEQ ID NO: 310) | RASQSVSSAVA (SEQ ID NO: 311) | SASSLYS (SEQ ID NO: 312) | FYRSPA (SEQ ID NO: 313) |
| I2A-27 | FKGYYI (SEQ ID NO: 314) | AIYPYGGSTD (SEQ ID NO: 315) | VYIYGVF (SEQ ID NO: 316) | RASQSVSSAVA (SEQ ID NO: 317) | SASSLYS (SEQ ID NO: 318) | YYSSPR (SEQ ID NO: 319) |
| I2A-28 | FSSYWI (SEQ ID NO: 320) | WIYPGTRYTE (SEQ ID NO: 321) | DYVWPYGF (SEQ ID NO: 322) | RASQSVSSAVA (SEQ ID NO: 323) | SASSLYS (SEQ ID NO: 324) | ASWSPV (SEQ ID NO: 325) |
| I2A-29 | FSSYWI (SEQ ID NO: 326) | WIYSSGGYTF (SEQ ID NO: 327) | EYFLYTGF (SEQ ID NO: 328) | RASQSVSSAVA (SEQ ID NO: 329) | SASSLYS (SEQ ID NO: 330) | YSSGPV (SEQ ID NO: 331) |
| I2A-30 | FDSYFI (SEQ ID NO: 332) | YIYSWGSYTH (SEQ ID NO: 333) | GHRRYFAL (SEQ ID NO: 334) | RASQSVSSAVA (SEQ ID NO: 335) | SASSLYS (SEQ ID NO: 336) | VYFTPG (SEQ ID NO: 337) |
| I2A-31 | FSSYWI (SEQ ID NO: 338) | FIGPSGGYTY (SEQ ID NO: 339) | ETDSYTGF (SEQ ID NO: 340) | RASQSVSSAVA (SEQ ID NO: 341) | SASSLYS (SEQ ID NO: 342) | YYSWLG (SEQ ID NO: 343) |
| I2A-32 | FQSYVI (SEQ ID NO: 344) | AIYPYSSSTI (SEQ ID NO: 345) | SWSVYLGM (SEQ ID NO: 346) | RASQSVSSAVA (SEQ ID NO: 347) | SASSLYS (SEQ ID NO: 348) | SYDSPR (SEQ ID NO: 349) |
| I2A-33 | FDDYYI (SEQ ID NO: 350) | WIDSYGGYTS (SEQ ID NO: 351) | SSYYYPGGF (SEQ ID NO: 352) | RASQSVSSAVA (SEQ ID NO: 353) | SASSLYS (SEQ ID NO: 354) | WDSTLY (SEQ ID NO: 355) |
| I2A-34 | FSWYVI (SEQ ID NO: 356) | YIAPYTGSTY (SEQ ID NO: 357) | AFFGIRLGL (SEQ ID NO: 358) | RASQSVSSAVA (SEQ ID NO: 359) | SASSLYS (SEQ ID NO: 360) | AISSPY (SEQ ID NO: 361) |
| I2A-35 | FSAYDI (SEQ ID NO: 362) | WIDPYGGDTD (SEQ ID NO: 363) | SPSYMQYGGL (SEQ ID NO: 364) | RASQSVSSAVA (SEQ ID NO: 365) | SASSLYS (SEQ ID NO: 366) | YYSSLL (SEQ ID NO: 367) |
| I2A-36 | FSQYWI (SEQ ID NO: 368) | AIYSSTKYTI (SEQ ID NO: 369) | ESMYFYSYGL (SEQ ID NO: 370) | RASQSVSSAVA (SEQ ID NO: 371) | SASSLYS (SEQ ID NO: 372) | LPSTPL (SEQ ID NO: 373) |
| I2A-37 | FSWYGI (SEQ ID NO: 374) | YIDSYTSSTY (SEQ ID NO: 375) | SHFGHYDYVM (SEQ ID NO: 376) | RASQSVSSAVA (SEQ ID NO: 377) | SASSLYS (SEQ ID NO: 378) | AYDQLY (SEQ ID NO: 379) |
| I2A-38 | FDWYRI (SEQ ID NO: 380) | WIDSYGSWTG (SEQ ID NO: 381) | SYFGPYGYVL (SEQ ID NO: 382) | RASQSVSSAVA (SEQ ID NO: 383) | SASSLYS (SEQ ID NO: 384) | * |
| I2C-1 | FTSYGI (SEQ ID NO: 385) | AIYPHSGFTS (SEQ ID NO: 386) | TSYRGF (SEQ ID NO: 387) | RASQSVSSAVA (SEQ ID NO: 388) | SASSLYS (SEQ ID NO: 389) | YYWYPG (SEQ ID NO: 390) |

TABLE 6-continued

ROR Antigen Binding Site Candidates

| ABS | CDR1 VH | CDR2 VH | CDR3 VH | CDR1 VL | CDR2 VL | CDR3 VL |
|---|---|---|---|---|---|---|
| I2C-2 | FSDYFI (SEQ ID NO: 391) | GIYPYSGYTK (SEQ ID NO: 392) | DHSPVL (SEQ ID NO: 393) | RASQSVSSAVA (SEQ ID NO: 394) | SASSLYS (SEQ ID NO: 395) | WYYWPG (SEQ ID NO: 396) |
| I2C-3 | FSHYWI (SEQ ID NO: 397) | LIAPGGDYTS (SEQ ID NO: 398) | SGLPGF (SEQ ID NO: 399) | RASQSVSSAVA (SEQ ID NO: 400) | SASSLYS (SEQ ID NO: 401) | YKSSPL (SEQ ID NO: 402) |
| I2C-4 | FWSYFI (SEQ ID NO: 403) | YIHPSSSYTD (SEQ ID NO: 404) | TSRDGAM (SEQ ID NO: 405) | RASQSVSSAVA (SEQ ID NO: 406) | SASSLYS (SEQ ID NO: 407) | WYSPPE (SEQ ID NO: 408) |
| I2C-5 | FSSYDI (SEQ ID NO: 409) | WIYPYWGYTI (SEQ ID NO: 410) | GTYAPAL (SEQ ID NO: 411) | RASQSVSSAVA (SEQ ID NO: 412) | SASSLYS (SEQ ID NO: 413) | FYSYLS (SEQ ID NO: 414) |
| I2C-6 | FSWYFI (SEQ ID NO: 415) | RIYSTGGYTE (SEQ ID NO: 416) | SAFFGAL (SEQ ID NO: 417) | RASQSVSSAVA (SEQ ID NO: 418) | SASSLYS (SEQ ID NO: 419) | YPSGPE (SEQ ID NO: 420) |
| I2C-7 | FDSYYI (SEQ ID NO: 421) | WIDPYGLDTK (SEQ ID NO: 422) | EPGDYGM (SEQ ID NO: 423) | RASQSVSSAVA (SEQ ID NO: 424) | SASSLYS (SEQ ID NO: 425) | AYGSLL (SEQ ID NO: 426) |
| I2C-8 | FSGYFI (SEQ ID NO: 427) | AIFPYRGGTS (SEQ ID NO: 428) | GGVSPGGF (SEQ ID NO: 429) | RASQSVSSAVA (SEQ ID NO: 430) | SASSLYS (SEQ ID NO: 431) | YYLYPG (SEQ ID NO: 432) |
| I2C-9 | FTDYDI (SEQ ID NO: 433) | RIWPHGSYTF (SEQ ID NO: 434) | SLTHSYGF (SEQ ID NO: 435) | RASQSVSSAVA (SEQ ID NO: 436) | SASSLYS (SEQ ID NO: 437) | YYTWLI (SEQ ID NO: 438) |
| I2C-10 | FSSYFI (SEQ ID NO: 439) | TIHSYFDGTS (SEQ ID NO: 440) | TRPTGGAF (SEQ ID NO: 441) | RASQSVSSAVA (SEQ ID NO: 442) | SASSLYS (SEQ ID NO: 443) | AYWSPA (SEQ ID NO: 444) |
| I2C-11 | FGSYFI (SEQ ID NO: 445) | AIFPAGGYTY (SEQ ID NO: 446) | YGSMGGAF (SEQ ID NO: 447) | RASQSVSSAVA (SEQ ID NO: 448) | SASSLYS (SEQ ID NO: 449) | YYWFPG (SEQ ID NO: 450) |
| I2C-12 | FSSYFI (SEQ ID NO: 451) | AIHPAFSFTY (SEQ ID NO: 452) | PRLSSAVVL (SEQ ID NO: 453) | RASQSVSSAVA (SEQ ID NO: 454) | SASSLYS (SEQ ID NO: 455) | GYYFPG (SEQ ID NO: 456) |
| I2C-13 | FSSYGI (SEQ ID NO: 457) | YIHSGIGYTI (SEQ ID NO: 458) | TSSTSTSVM (SEQ ID NO: 459) | RASQSVSSAVA (SEQ ID NO: 460) | SASSLYS (SEQ ID NO: 461) | TYWSPG (SEQ ID NO: 462) |
| I2C-14 | FESYDI (SEQ ID NO: 463) | AIFSYGGYTT (SEQ ID NO: 464) | GSYGDGRGM (SEQ ID NO: 465) | RASQSVSSAVA (SEQ ID NO: 466) | SASSLYS (SEQ ID NO: 467) | YYYWPG (SEQ ID NO: 468) |
| I2C-15 | FSSYFI (SEQ ID NO: 469) | LIYPDTDDTY (SEQ ID NO: 470) | YGYLGVGAF (SEQ ID NO: 471) | RASQSVSSAVA (SEQ ID NO: 472) | SASSLYS (SEQ ID NO: 473) | LYWTPG (SEQ ID NO: 474) |
| I2C-16 | FSSYWI (SEQ ID NO: 475) | AIHPSGSYTY (SEQ ID NO: 476) | VGLLVTSVM (SEQ ID NO: 477) | RASQSVSSAVA (SEQ ID NO: 478) | SASSLYS (SEQ ID NO: 479) | YYYFPG (SEQ ID NO: 480) |
| I2C-17 | FSDYFI (SEQ ID NO: 481) | YIYPASGGTC (SEQ ID NO: 482) | GYIPHMAAL (SEQ ID NO: 483) | RASQSVSSAVA (SEQ ID NO: 484) | SASSLYS (SEQ ID NO: 485) | YYWWPG (SEQ ID NO: 486) |
| I2C-18 | FAGYPI (SEQ ID NO: 487) | AIDPDGGYTY (SEQ ID NO: 488) | HTGFHRYRGM (SEQ ID NO: 489) | RASQSVSSAVA (SEQ ID NO: 490) | SASSLYS (SEQ ID NO: 491) | YYWFPP (SEQ ID NO: 492) |
| I2C-19 | FTSYDI (SEQ ID NO: 493) | WIDPGLSYTS (SEQ ID NO: 494) | ASIGGGVPVM (SEQ ID NO: 495) | RASQSVSSAVA (SEQ ID NO: 496) | SASSLYS (SEQ ID NO: 497) | YVTGPY (SEQ ID NO: 498) |
| I2C-20 | FSSYYI (SEQ ID NO: 499) | IIIPYSGYTY (SEQ ID NO: 500) | RGYFSLGTAM (SEQ ID NO: 501) | RASQSVSSAVA (SEQ ID NO: 502) | SASSLYS (SEQ ID NO: 503) | VYWWPG (SEQ ID NO: 504) |

TABLE 6-continued

ROR Antigen Binding Site Candidates

| ABS | CDR1 VH | CDR2 VH | CDR3 VH | CDR1 VL | CDR2 VL | CDR3 VL |
|---|---|---|---|---|---|---|
| I2C-21 | FSSYYI (SEQ ID NO: 505) | WIDPYISYTY (SEQ ID NO: 506) | DSELVSGYAM (SEQ ID NO: 507) | RASQSVSSAVA (SEQ ID NO: 508) | SASSLYS (SEQ ID NO: 509) | GDSSLV (SEQ ID NO: 510) |
| I2C-22 | FSSYSI (SEQ ID NO: 511) | AIYPYWGTTE (SEQ ID NO: 512) | PSGVTYGYAL (SEQ ID NO: 513) | RASQSVSSAVA (SEQ ID NO: 514) | SASSLYS (SEQ ID NO: 515) | YYYSPW (SEQ ID NO: 516) |
| I2C-23 | FSSYEI (SEQ ID NO: 517) | SIYPFSGDTY (SEQ ID NO: 518) | PGRAIYYAVM (SEQ ID NO: 519) | RASQSVSSAVA (SEQ ID NO: 520) | SASSLYS (SEQ ID NO: 521) | AGSHLF (SEQ ID NO: 522) |
| I2C-24 | FSRYYI (SEQ ID NO: 523) | DIDSYGGFTY (SEQ ID NO: 524) | AHRFLQGGYVL (SEQ ID NO: 525) | RASQSVSSAVA (SEQ ID NO: 526) | SASSLYS (SEQ ID NO: 527) | YSWGLW (SEQ ID NO: 528) |
| I2C-25 | FSDYYI (SEQ ID NO: 529) | YIAPYGGFTY (SEQ ID NO: 530) | DSYRRGYVSGF (SEQ ID NO: 531) | RASQSVSSAVA (SEQ ID NO: 532) | SASSLYS (SEQ ID NO: 533) | RYSSPS (SEQ ID NO: 534) |
| I2C-26 | FSDYYI (SEQ ID NO: 535) | DIDSYGGFTY (SEQ ID NO: 536) | DPHFLDDVYVL (SEQ ID NO: 537) | RASQSVSSAVA (SEQ ID NO: 538) | SASSLYS (SEQ ID NO: 539) | YSWGLW (SEQ ID NO: 540) |

"I2A" screened against ROR1;
"I2C" screened against ROR2;
* denotes no sequence determined;
bold denotes potential isomerization sites (see below)

The VH and VL sequences above were formatted into a bivalent monospecific native human full-length IgG1 architecture. FIGS. 48A-48B demonstrate Octet (Pall ForteBio) biolayer interferometry analysis of a two-fold serial dilution (200-12.5 nM) for two ROR binding candidates (FIG. 48A clone 12-A10; FIG. 48B clone 12-A27). Binding affinities and kinetics were determined from the serial dilutions and are shown in Table 7.

TABLE 7

Binding Kinetics of ROR ABS Candidates

| Candidate | KD (nM) | $K_{on}$ (1/Ms) | $K_{dis}$ (1/s) | RMax |
|---|---|---|---|---|
| I2-A10 | 0.82 | $5.38 \times 10^5$ | $3.8 \times 10^{-4}$ | 0.4159 |
| I2-A27 | 4.1 | $5.11 \times 10^5$ | $1.85 \times 10^{-3}$ | 0.5668 |

ROR binding candidates, formatted in the bivalent monospecific native human full-length IgG1 architecture, were further characterized for binding to ROR1 and/or ROR2. Table 8 presents candidates that bound specifically to ROR only, bound specifically to ROR2 only, and were cross-reactive for both ROR1 and ROR2. ROR binding candidates were also characterized for their binding to specific ROR1 domains. Table 9 presents candidates that bound specifically to Frizzled, Ig-like, and Kringle domains.

TABLE 8

ROR Binding Candidate Specificity

| ROR1 Specific | ROR2 Specific | ROR1/ROR2 Cross Reactive |
|---|---|---|
| I2A-3 | I2C-3 | I2A-1 |
| I2A-4 | I2C-5 | I2A-10 |
| I2A-6 | I2C-7 | I2A-10 D54E Y55Q |
| I2-A8 | I2C-19 | I2A-11 |
| I2-A12 | I2C-21 | I2A-13 |

TABLE 8-continued

ROR Binding Candidate Specificity

| ROR1 Specific | ROR2 Specific | ROR1/ROR2 Cross Reactive |
|---|---|---|
| I2A-20 | I2C-25 | I2A-14 |
| I2-A25 | I2C-26 | I2A-16 |
| I2A-26 | | I2-A18 |
| I2A-27 | | I2A-19 |
| I2-A30 | | I2A-22 |
| I2-A32 | | I2A-24 |
| I2-A33 | | I2-A26 |
| I2-A37 | | I2-A34 |
| | | I2-A36 |
| | | I2C-1 |
| | | I2C-2 |
| | | I2C-4 |
| | | I2C-6 |
| | | I2C-8 |
| | | I2C-9 |
| | | I2C-10 |
| | | I2C-11 |
| | | I2C-12 |
| | | I2C-13 |
| | | I2C-14 |
| | | I2C-15 |
| | | I2C-16 |
| | | I2C-17 |
| | | I2C-18 |
| | | I2C-20 |
| | | I2C-22 |
| | | I2C-23 |
| | | I2C-24 |

TABLE 9

Domain Mapping

| Clone | Domain of ROR1 |
|---|---|
| I2A-11 | Frizzled |
| I2A-19 | Frizzled |

TABLE 9-continued

Domain Mapping

| Clone | Domain of ROR1 |
|---|---|
| I2C-23 | Frizzled |
| I2C-6 | Frizzled |
| I2A-32 | Frizzled |
| I2A-34 | Frizzled |
| I2A-26 | Frizzled |
| I2A-25 | Frizzled |
| I2A-26 | Frizzled |
| I2-A12 | Frizzled |
| I2A-1 | Ig-like |
| I2A-10 | Ig-like |
| I2A-10 D54E Y55Q | Ig-like |
| I2A-14 | Ig-like |
| I2A-16 | Ig-like |
| I2A-20 | Ig-like |
| I2A-22 | Ig-like |
| I2A-3 | Ig-like |
| I2A-35 | Ig-like |
| I2A-4 | Ig-like |
| I2-A6 | Ig-like |
| I2-A13 | Ig-like |
| I2-A18 | Ig-like |
| I2-A30 | Ig-like |
| I2-A33 | Ig-like |
| I2-A37 | Ig-like |
| I2C-1 | Ig-like |
| I2C-10 | Ig-like |
| I2C-11 | Ig-like |
| I2C-12 | Ig-like |
| I2C-13 | Ig-like |
| I2C-14 | Ig-like |
| I2C-15 | Ig-like |
| I2C-16 | Ig-like |
| I2C-17 | Ig-like |
| I2C-2 | Ig-like |
| I2C-20 | Ig-like |
| I2C-24 | Ig-like |
| I2C-4 | Ig-like |
| I2C-8 | Ig-like |
| I2C-9 | Ig-like |
| I2A-27 | Kringle |

Select ROR binding candidates were further analyzed for sequence motifs that could adversely affect antibody properties that are relevant to clinical development, such as stability, mutability, and immunogenicity. Computational analysis was performed according to Kumar and Singh (*Developability of biotherapeutics: computational approaches*. Boca Raton: CRC Press, Taylor & Francis Group, 2016). Analysis results are presented in Table 10, and demonstrate a limited number of adverse sequence motifs are present in the listed clones illustrating the potential for further clinical development.

TABLE 10

Number of Potential Adverse Sequence Motifs

| ABS | Deamidation Sites (NG, NS, NA, NH, ND) | Isomerization Sites (DG, DP, DS) | N-linked Glycosylation Sites (NXS/T) | Cys in CDR | Other Sites (LLQG, HPQ, FHENSP, LPRWG, HHH) | # T-cell Epitopes* |
|---|---|---|---|---|---|---|
| I2A-27 | 0 | 1 | 0 | 0 | 0 | 2 |
| I2A-3 | 0 | 1 | 0 | 0 | 0 | 0 |
| I2A-10 | 0 | 2 | 0 | 0 | 0 | 0 |
| I2A-11 | 0 | 1 | 0 | 0 | 0 | 0 |
| I2A-19 | 0 | 1 | 0 | 0 | 0 | 0 |

*Predicted T-cell epitope found in herceptin is present in these molecules

6.13.21. Example 20: ROR×CD3 Bispecific B-Body Efficacy In Vitro

Candidate ROR and CD3 antigen binding sites were formatted into B-Body BC1 1×1 and 1×2 formats and tested in a series of tumor efficacy models.

6.13.21.1. Bispecific B-Body Format Comparison

ROR antigen binding site (ABS) candidate 12A-3 and CD3 ABS candidate SP34-89 were formatted into bispecific B-Body "BC1" 1×1 and 1×2 formats. With reference to FIG. 3 and FIG. 26, the ROR ABS candidate forms the A:F and the R:T binding sites, while the CD3 ABS candidate forms the H:L binding site. Two 1×2 formats were constructed with either a 10 amino acid junction or 16 amino acid junction between the S domain and the H domain, with reference to FIG. 26. The different constructs were tested in the NFκB GFP Jurkat T cell stimulation assay described herein. Briefly, reporter T cells (effector cells) were mixed with either the non-small cell lung cancer target tumor cell line HOP-92, which expresses the ROR1 antigen, or the B16 melanoma target tumor cell line, which does not express ROR1. A dilution series of the different B-body constructs were then incubated with the effector:target mixture.

As shown in FIG. 49 and presented in Table 11, the ROR×CD3 bispecific 1×1 and 1×2 B-bodies resulted in activation of the reporter T cells when mixed with ROR1 expressing tumor lines (HOP-92), but no activation was observed when the ROR×CD3 bispecific 1×1 and 1×2 B-bodies were mixed with tumor lines that do not express ROR1 (B16). In addition, the 1×2 B-body format possessing bivalent specificity for ROR1 was more potent than the 1×1 B-body format, and varying the junction length resulted in minimal differences in potency.

TABLE 11

B-body bispecific format comparison

| Cell Line/Antibody | EC50(pM) |
|---|---|
| HOP-92 1x1 | 634 |
| HOP-92 1x2 16 aa linker | 47 |
| HOP-92 1x2 10 aa linker | 37 |

6.13.21.2. CD3 Binding Alone does not Activate T Cells

ROR ABS candidate 12A-10 and CD3 ABS candidate SP34-89 was formatted into a bispecific B-Body "BC1" 1×2 format ("12-A10 1×2"). In a separate construct, a control arm to a tumor antigen other than ROR1 was also formatted with CD3 ABS candidate SP34-89 into a bispecific B-Body "BC1" 1×2 format ("Neg Ctrl"). With reference to FIG. 3 and FIG. 26, the ROR candidate ABS and "Neg Ctrl" arm ABS forms the A:F and the R:T binding sites, while the CD3 ABS candidate forms the H:L binding site. The different constructs were tested in a T cell cytotoxicity assay. Briefly, isolated CD8+ T cells (effector cells) were mixed with the triple negative breast cancer tumor cell line MDA-MD-231, which expresses the ROR1 antigen (target cells). A dilution series of the different B-body constructs were then incubated with the effector:target mixture.

As shown in FIG. 50, the ROR×CD3 trivalent bispecific 1×2 B-body resulted in cytotoxic T cell mediated killing when mixed with ROR1 expressing tumor lines (MDA-MD-231), but did not result in cytotoxicity when a CD3 bispecific B-body having an irrelevant tumor ABS (e.g., a tumor antigen not expressed in MDA-MD-231) was added to the mixture.

6.13.21.3. ROR×CD3 Bispecific B-body Efficacy in Multiple Tumor Models

ROR ABS candidate 12A-3 and CD3 ABS candidate SP34-89 were formatted into bispecific B-Body "BC1" 1×1 and 1×2 formats, as described above, with the 1×2 format having a 10 amino acid junction between the S and the H domains. The different constructs were tested in the NFκB GFP Jurkat T cell stimulation assay described herein. Briefly, reporter T cells (effector cells) were mixed with ROR1 expressing tumor cell lines HOP-92 (non-small cell lung cancer 1), A549 (non-small cell lung cancer 2), MDA-MD-231 (triple negative breast cancer), JeKo-1 (mantle cell lymphoma), and RPMI-8226 (multiple myeloma). The constructs were also mixed with the B16 melanoma tumor cell line that does not express ROR1 (target cells). A dilution series of the different B-body constructs were then incubated with the effector:target mixture.

As shown in FIGS. 51A-51E and presented in Table 12, the ROR×CD3 bispecific 1×1 and 1×2 B-bodies resulted in activation of the reporter T cells when mixed with ROR1 expressing tumor lines HOP-92 (FIG. 51A), A549 (FIG. 51B), MDA-MD-231 (FIG. 51C), JeKo-1 (FIG. 51D), and RPMI-8226 (FIG. 51E), but there was no activation when these constructs were mixed with tumor lines that do not express ROR1 (B16). The 1×2 B-body format possessing bivalent specificity for ROR1 was more potent than the 1×1 B-body format in all tumor lines tested. Thus, the ROR×CD3 bispecific 1×1 and 1×2 B-bodies demonstrated efficacy across a range of tumor models.

TABLE 12

| B-body bispecific efficacy in multiple tumor models | |
|---|---|
| Cell Line/Antibody | EC50 (pM) |
| HOP-92 1x1 | 634 |
| HOP-92 1x2 | 37 |
| MDA-MB-231 1x1 | 510 |
| MDA-MB-231 1x2 | 31 |
| A549 1x1 | 678 |
| A549 1x2 | 70 |
| JeKo-1 1x1 | 342 |
| JeKo-1 1x2 | 41 |
| RPMI-8226 | 29 |

6.13.21.4. ROR ABS Candidate Screening for T Cell Activation

ROR ABS candidates 12A-1, 12A-3, 12A-10, 12A-14, 12A-16, 12A-20, 12A-22, and 12A-27 were formatted with CD3 ABS candidate SP34-89 into a bispecific B-Body "BC1" 1×2 format, as described above, with the 1×2 format having a 10 amino acid junction between the S and the H domains. The different constructs were tested in the T cell cytotoxicity assay described above. Briefly, isolated CD8+ T cells (effector cells) were mixed with the triple negative breast cancer tumor cell line MDA-MD-231, which expresses the ROR1 antigen (target cells) at an E:T ratio of 6:1. A dilution series of the different B-body constructs were then incubated with the effector:target mixture.

As shown in FIG. 52 and presented in Table 13, the ROR×CD3 bispecific 1×2 B-bodies 12A-1, 12A-3, 12A-10, 12A-14, 12A-22, and 12A-27 resulted in cytotoxic T cell mediated killing when mixed with ROR1 expressing tumor lines (MDA-MD-231), but 1×2 B-bodies 12A-16 and 12A-20 did not result in potent cytotoxicity. In addition, 12A-22 resulted in an irregular dose response curve. Thus, ROR ABS candidates 12A-1, 12A-3, 12A-10, 12A-14, and 12A-17 resulted in effective T cell mediated killing.

TABLE 13

| ROR ABS Candidate T cell Mediated Killing | |
|---|---|
| ABS | EC50 (pM) |
| I2-A1 | 5.3 |
| I3-A3 | 23 |
| I2-A10 | 13 |
| I2-A14 | 21 |
| I2-A16 | ND |
| I2-A20 | ND |
| I2-A22 | ND |
| I2-A27 | 8.2 |

6.13.21.5. Cytotoxic Killing Correlates with ROR Expression

ROR ABS candidate 12A-10 and CD3 ABS candidate SP34-89 were formatted into a bispecific B-Body "BC1" 1×2 format, as described above, with the 1×2 format having a 10 amino acid junction between the S and the H domains. The 12A-10 candidate was tested in the T cell cytotoxicity assay described. Briefly, isolated CD8+ T cells (effector cells) were mixed with ROR1 expressing tumor cell lines MDA-MD-231 (triple negative breast cancer) and RPMI-8226 (multiple myeloma) at an E:T ratio of 4:1. A dilution series of the candidate incubated with the effector:target mixture.

FIG. 53A illustrates published ROR1 expression data for the MDA-MD-231 and RPMI-8226 tumor lines. FIG. 53B and FIG. 53C demonstrate that the cytotoxicity efficacy observed in our experiments correlates with ROR1 in MDA-MD-231 and RPMI-8226 tumor cell lines.

6.13.21.6. Primary T Cell Activation with ROR ABS Candidates 12A-10 and 12A-27

ROR ABS candidates 12A-10 and 12A-27 were formatted with CD3 ABS candidate SP34-89 into a bispecific B-body "BC1" 1×2 format, as described above, with the 1×2 format having a 10 amino acid junction between the S and the H domains. The amino acid sequences for the four polypeptide chains that form the 12A-10 BC1 1×2 B-body are listed in SEQ ID NOs:84, 85, 87, and 88. The amino acid sequences for the four polypeptide chains that form the 12A-27 BC1 1×2 are listed in SEQ ID NOs:89, 90, 92, and 93.

The different constructs were tested in the T cell activation assay, as quantified by flow cytometry. Briefly, isolated peripheral blood mononuclear cells (PBMCs, effector cells) were mixed with the triple negative breast cancer tumor cell line MDA-MD-231 and the pancreatic carcinoma tumor cell line PANC1 (target cells), each expresses the ROR1 antigen, at an E:T ratio of 7:1. A dilution series of the different B-body constructs were then incubated with the effector:target mixture and incubated together for 44 hours. Cells were then stained for T cell markers CD3, CD4, and CD8, as well as activation markers CD25 and CD69 and analyzed by flow cytometry.

As shown in FIGS. 54A-54F, 12A-10 and 12A-27 B-bodies activated CD8+ T cells in the PBMC population as determined by expression of CD25 (FIG. 54A), CD69 (FIG. 54C), both CD25 and CD69 (FIG. 54E), and activated CD4+ T cells in the PBMC population as determined by CD25 (FIG. 54B), CD69 (FIG. 54D), both CD25 and CD69 (FIG. 54F). Thus, ROR ABS candidates are capable of activating primary T cells.

6.13.21.7. Internalization of ROR ABS Candidates 12A-10 and 12A-27

ROR ABS candidates 12A-10 and 12A-27 were formatted with CD3 ABS candidate SP34-89 into a bispecific B-body "BC1" 1×2 format, as described above, with the 1×2 format having a 10 amino acid junction between the S and the H domains. The different constructs were tested for internalization by tumor cell lines, as quantified by flow cytometry. Briefly, MDA-MB-231 cells were incubated for 2 hours at 37° C. or 4° C. with 12-A10, 12-A27, or an isotype control. After 2 hours, a labeled secondary antibody was added at 4° C. for 30 min and then analyzed by flow cytometry. Percent internalization was calculated by normalizing between the isotype control (0%) and the 4° C. control (100%) based upon Mean Fluorescence Intensity (MFI).

As shown in FIG. 55, 26% and 36% of candidates 12A-10 (top panel) and 12A-27 (bottom panel) were internalized following a 2 hour incubation with MDA-MB-231 cells, respectively. Internalization by tumor cells makes possible various antibody-drug conjugate strategies for killing tumor cells expression a ROR antigen.

6.13.22. Example 21: ROR×CD3 Bispecific B-Body Single Step Purification

ROR ABS candidates 12A-10 and 12A-27 were formatted with CD3 ABS candidate SP34-89 into a bispecific B-body "BC1" trivalent 1×2 format, as described above, with the 1×2 format having a 10 amino acid junction between the S and the H domains. The constructs were purified using a one-step purification using the CaptureSelect™ CH1 affinity resin.

FIG. 56 shows size exclusion chromatography (SEC) analysis, demonstrating that a single-step CH1 affinity purification step yields single, monodisperse peaks via gel filtration in which >98% is unaggregated protein for 1×2 B-body candidates 12A-10 (top panel) and 12A-27 (bottom panel).

FIG. 57A shows non-reducing SDS-PAGE gels of 1×2 B-body candidates 12A-10 (left panel) and 12A-27 (right panel), demonstrating a major band of fully assembled constructs (high-migrating 250 kDa band). FIG. 57B shows Bioanalyzer (Agilent) analysis of non-reduced samples for 1×2 B-body candidates 12A-10 and 12A-27 demonstrating a major band of fully assembled constructs.

Anti-CH1 purification efficiency of bispecific antibodies was also tested for ROR binding molecules having only standard knob-hole orthogonal mutations introduced into CH3 domains found in their native positions within the Fc portion of the bispecific antibody, with no other domain modifications. Therefore, the two antibodies tested, KL27-6 and KL27-7, each contained two CH1 domains, one on each arm of the antibody. As described in more detail in Section 6.13.1, each bispecific antibody was expressed, purified from undesired protein products on an anti-CH1 column, and run on an SDS-PAGE gel. As shown in FIG. 58, a significant band at 75 kDa representing an incomplete bispecific antibody was present, interpreted as a complex containing only (i) a first and second or (ii) third and fourth polypeptide chains with reference to FIG. 3. Thus, methods using anti-CH1 to purify complete bispecific molecules that have a CH1 domain in each arm resulted in background contamination due to incomplete antibody complexes.

6.13.23. Example 22: Fc Mutations Reducing Effector Function

A series of engineered Fc variants were generated in the monoclonal IgG1 antibody trastuzumab (Herceptin, "WT-IgG1") with mutations at positions L234, L235, and P329 of the CH2 domain. The specific mutations for the variants tested are described in Table 14 below and include sFc1 (PALALA), sFc7 (PGLALA), and sFc10 (PKLALA). All variants displayed similar stability as determined by melting temperatures (Table 14 TM1 and TM2).

WT-IgG1 and the Fc variants were immobilized to the Octet biosensor and soluble FcγRIa was added to the system to determine binding. FIGS. 59A-59B shows Octet (Pall ForteBio) biolayer interferometry analysis demonstrating FcγRIa binding to trastuzumab (FIG. 59A "WT IgG1"), but not sFc10 (FIG. 59B). Upon addition of FcγRIa, an increase in signal was seen for trastuzumab, but no observable signal increase was detected for sFc10 demonstrating FcγRIa no longer binds the antibody with the engineered mutations. Binding summaries for the variants tested presented in Table 14. In addition, all variants retained strong binding to HER2 (not shown).

TABLE 14

Fc Variant Comparison

| Variant | L234 | L235 | P329 | TM1 (° C.) | TM2 (° C.) | FcγRIa Binding |
|---|---|---|---|---|---|---|
| sFc1 | A | A | P | 68.1 | 81.8 | Yes (weak) |
| sFc7 | A | A | G | 65.7 | 81.8 | No |
| sFc10 | A | A | K | 65.3 | 81.1 | No |
| WT IgG1 | L | L | P | 66.2 | 81.1 | Yes (strong) |

WT-IgG1 and the Fc variants were tested in an antibody dependent cellular cytotoxicity (ADCC) assay as another measure of FcγR binding, specifically FcγRIIIa. As shown in FIG. 60, trastuzumab (Herceptin, "WT-IgG1") demonstrated killing, while neither sFc7 nor sFc10 resulted in detectable levels of killing. WT-IgG1 and the Fc variants were also tested for complement component C1q binding by ELISA. As shown in FIG. 61, trastuzumab (Herceptin, "WT-IgG1") demonstrated C1q binding, while neither sFc1, sFc7, nor sFc10 resulted in detectable C1q binding. Thus, the results demonstrate that the Fc variants tested have reduced levels of Fc effector function.

6.13.24. Example 23: RORxCD3 Bispecific B-Body Efficacy In Vivo

In vivo efficacy was measured using xenograft studies in humanized mice. Briefly, $5 \times 10^6$ MDA-MB-231 tumor cells were engrafted subcutaneously into the hind flank of NOD Scid Gamma (NSG) mice (Jackson Labs) and grown to approximately 120-150 mm3. The mice were then humanized through the intravenous (IV) injection of $1 \times 10^7$ human PBMCs from a single donor. The humanized NSG mice were randomized into three groups of eight and dosed IV with PBS, 0.5 mg/Kg ROR ABS candidate 12-A10 formatted with CD3 ABS candidate SP34-89 into a 1×2 B-body architecture ("12-A10"), or 0.5 mg/Kg ROR ABS candidate 12-A27 formatted with CD3 ABS candidate SP34-89 into a 1×2 B-body architecture ("12-A27") three days following PBMC engraftment. Dosing continued twice a week for three weeks. Animals were monitored for tumor growth, body weight, and general health. Upon completion of the study, the animals were sacrificed for analysis. Flow cytometric analysis was performed using standard techniques to determine the humanization status of the NSG mice.

Tumors are collected and analyzed using standard immunohistochemistry techniques to monitor the infiltration of human T-cells into the tumors in response to treatment. IHC is carried out using standard techniques. Briefly. FFPE samples are deparaffinized and rehydrated by baking at 60° C., placing in 100% xylene solution, and then rehydrated through a series of ethanol washes (100% ethanol, 95% ethanol, 70% ethanol, 50% ethanol, PBS). Antigen retrieval is carried out by incubating the slides for 10 minutes in a 10 mM NaCitrate+0.05% Tween 20, pH 6.0 buffer at 95° C. The AbCam Mouse on Mouse IHC kit (Cat. Ab127055) is used according to manufacturer's directions for staining. Briefly, endogenous peroxidase activity is blocked with a hydrogen peroxide solution and endogenous non-specific interactions are blocked with a Rodent Block solution. The slides are incubated with the primary antibodies according to the manufacturer's recommendations (generally 2 hr. at room temperature or overnight at 4° C.) and then stained with the mouse on mouse HRP polymer from the AbCam kit. DAB chromagen staining with hemotoxylin counterstaining are used for visualization.

6.13.24.1. RORxCD3 Trivalent Bispecific B-Body Results in Tumor Growth Reduction As shown in FIGS. 62A-62C, tumor volume was monitored for mice engrafted with tumor cells, humanized with PBMCs (left solid arrow), then subsequently treated IV (right dashed arrow) with PBS (FIG. 62A), 1×2 B-body candidate 12-A10 (FIG. 62B), or 1×2 B-body candidate 12-A27 (FIG. 62C). FIG. 63 shows tumor volume at the conclusion of the study for each of the mice, with mean and standard deviation for each group shown. The open square for the 12-A27 group was removed from the analysis due to probable non-humanization by PMBCs. The results demonstrate that the 12-A27 treatment resulted in a significant reduction in tumor growth of approximately 40%.

Humanization status of the NSG mice in the study was confirmed through flow cytometric analysis. As shown in Table 15, all mice analyzed were successfully humanized with human lymphocytes, as determined by staining for human CD45 (% hu CD45+). Sample 03_B10 (b) was not analyzed. The humanized lymphocyte populations in all mice analyzed also had human T cells, including CD4 and CD8 positive T cells, as determined by staining for human CD3 (% CD3 gated on huCD45+ lymphocytes, and % CD4+/CD8+ gated on human CD3+ T cells).

Immunohistochemistry is performed on the tumor samples and confirms infiltration of human T-cells into the tumors in response to treatment.

TABLE 15

Humanization of NSG Mice

| | | Non-doublet gate | | huCD45+ gate | human CD3+ gate | |
|---|---|---|---|---|---|---|
| Sample ID | Condition | % ms CD45+ | % hu CD45+ | % CD3+ | % CD4+ | % CD8+ |
| 01_A01 | PBS | 48.1 | 50.8 | 99.6 | 44.5 | 46.1 |
| 01_A02 | PBS | 60.1 | 39.0 | 98.5 | 76.6 | 13.7 |
| 01_A07 | PBS | 56.0 | 43.8 | 99.1 | 23.5 | 64.1 |
| 01_B06 | PBS | 42.6 | 56.4 | 99.8 | 80.6 | 9.8 |
| 01_C04 | PBS | 51.0 | 47.7 | 99.2 | 64.6 | 23.8 |
| 01_C05 | PBS | 22.1 | 77.0 | 98.5 | 77.9 | 14.1 |
| 01_C09 | PBS | 67.8 | 31.8 | 99.4 | 27.7 | 64.6 |
| 01_D05 | PBS | 37.0 | 62.0 | 98.7 | 77.2 | 18.0 |
| 02_B01 | I2-A10 1x2 | 44.8 | 53.5 | 99.0 | 83.3 | 10.4 |
| 02_B07 | I2-A10 1x2 | 50.4 | 47.8 | 98.3 | 78.6 | 16.5 |
| 02_C02 | I2-A10 1x2 | 6.9 | 92.8 | 98.5 | 81.5 | 11.9 |
| 02_C03 | I2-A10 1x2 | 32.6 | 65.2 | 99.5 | 81.6 | 9.2 |
| 02_C06 (a) | I2-A10 1x2 | 2.9 | 94.4 | 95.0 | 60.2 | 30.9 |
| 02_C08 (a) | I2-A10 1x2 | 31.3 | 65.2 | 98.7 | 53.0 | 39.6 |
| 02_D04 (a) | I2-A10 1x2 | 29.9 | 66.5 | 99.3 | 33.9 | 61.1 |
| 03_A03 | I2-A27 1x2 | 32.4 | 66.4 | 93.0 | 84.7 | 3.8 |
| 03_A04 | I2-A27 1x2 | 30.5 | 66.9 | 98.9 | 84.9 | 6.2 |
| 03_A10 | I2-A27 1x2 | 58.6 | 40.2 | 98.9 | 92.5 | 4.2 |
| 03_B02 | I2-A27 1x2 | 20.5 | 78.2 | 99.2 | 86.6 | 7.6 |
| 03_B10 (b) | I2-A27 1x2 | — | — | — | — | — |
| 03_C10 | I2-A27 1x2 | 34.2 | 64.2 | 98.8 | 91.7 | 4.8 |
| 03_D03 | I2-A27 1x2 | 60.9 | 38.5 | 99.4 | 49.8 | 43.2 |

6.13.25. Example 24: ROR1×CD3 Bispecific B-body™ Efficacy

Additional ROR antigen binding molecules comprising the six CDRs of 12A-27 as shown in Table 6 were prepared and experiments were performed to test their efficacy as trivalent bispecific constructs in a ROR1×CD3 bispecific B-body™ format.

6.13.25.1. Generation of Additional ROR1×CD3 1×2 B-Body™ Bispecific Antibody Based on 12-A27

ROR ABS candidate 12A-27 was formatted with CD3 ABS candidate SP34-89 into a bispecific B-body "BC1" 1×2 format, as described above, with the 1×2 format having a 10 amino acid junction between the S and the H domains (see, e.g., FIG. 26 for schematic of domains). The amino acid sequences for the five polypeptide chains that form an exemplary 12A-27 BC1 1×2 trivalent bispecific ROR antigen binding molecule are listed as SEQ ID NO:96 (Chain 1), SEQ ID NO:97 (Chain 2), SEQ ID NO:98 (Chain 3), SEQ ID NO:99 (Chain 4), and SEQ ID NO:97 (Chain 5).

In the following description in this Example, the term "12-A27 1×2 B-body™" or "12-A27" or "A27" refers to this ROR1×CD3 1×2 B-body™ having a Chain 1 of SEQ ID NO:96, a Chain 2 of SEQ ID NO:97, a Chain 3 of SEQ ID NO:98, a Chain 4 of SEQ ID NO:99, and a Chain 5 of SEQ ID NO:97.

6.13.25.2. Binding of ROR1×CD3 1×2 B-Body™ Bispecific Antibody to CD3 and ROR1

As described in Example 19 above. SP34-89 showed a monovalent Kd of 23 nM to human CD3 delta and epsilon heterodimer (see FIG. 47).

In this Example, the binding to human and cynomolgus CD3 was further characterized by assessing cell binding to Jurkat T cells, a Jurkat CD3 knock-out cell line, or a cynomolgus T cell line. Specifically, binding of the SP34-89 humanized antibody to human Jurkat and cynomolgus T cells was determined by flow cytometry. SP34-89 was incubated with the indicated cell lines at the indicated concentrations followed by labeling with a fluorescently labeled secondary antibody. The mean fluorescence intensity was plotted versus the concentration of SP34-89. As shown in FIG. 64A, SP34-89 exhibited strong binding to both the Jurkat and cynomolgus T cells but did not show significant binding to the Jurkat CD3 knock-out cell line, verifying that the human and cynomolgus cross reactivity and cell binding was maintained.

In addition, the binding affinity of the resulting 12-A27 1×2 B-body™ bispecific antibody as described in section 6.13.25.1 to cynomolgus CD3 delta and epsilon heterodimer was determined by bio-layer interferometry (BLI) binding assessment.

More specifically, monovalent binding affinity analysis was performed using the Octet$^{QK}$ 384 (ForteBio) using Fc biosensors. Unlabeled B-body™ is first bound to the Fc biosensor at a concentration to yield approximately 1 nm response (typically 10 to 50 nM protein). The biosensors are then equilibrated in 10× Kinetic Buffer (ForteBio) to establish a baseline. The untagged monomer of each antigen is contacted with the antibody-coated sensors at concentrations ranging from 50 nm to 0.75 nM. The association response and dissociation were monitored and recorded. The resulting $K_{on}$ and $K_{off}$ was fit using the Octet analysis software. As shown in FIG. 64B, the bispecific antibody exhibited a monovalent Kd of 3 nM to cynomolgus CD3 delta and epsilon heterodimer.

Next, the binding to ROR1 was assessed. Consistent with the data described in 6.13.20.2 above (see, e.g., FIG. 48B), when the VH and VL sequences were formatted into a bivalent monospecific IgG architecture, the 12-A27 IgG antibody showed monovalent binding of 2.8 nM to ROR1 and minimal binding to ROR2 (FIG. 65A and FIG. 65B).

Then, the monovalent and bivalent binding of the 12-A27 1×2 B-body™ bispecific antibody to ROR1 and ROR2 was analyzed using BLI.

Monovalent binding analysis was performed as described above and the antibody was captured with an Fc sensor and contacted with the indicated antigen for the association phase followed by a dissociation phase in buffer only.

Bivalent binding analysis was performed using the Octet$^{QK}$ 384 (ForteBio) using streptavidin biosensors. Biotinylated antigen was first bound to the streptavidin biosensor at a concentration to yield approximately 1 nm response (typically 10 to 50 nM biotinylated protein). The biosensors were then equilibrated in 10× Kinetic Buffer (ForteBio) to establish a baseline. The 1×2 B-body™ was contacted with the antigen-coated sensors at concentrations ranging from 50 nm to 0.75 nM. The association response and dissociation were monitored and recorded. The resulting $K_{on}$ and $K_{off}$ was fit using the Octet analysis software.

As shown in FIGS. 65C, 65D, and 65E, the 12-A27 1×2 B-body™ format showed monovalent binding of 3.8 nM and bivalent binding of 0.71 nM to ROR1 and minimal binding to ROR2.

6.13.25.3. Further Characterization of ROR1×CD3 1×2 B-Body™ Bispecific Antibody An 12-A27 1×2 B-body™ bispecific antibody as described in section 6.13.25.1 was produced through transient transfection of DNA encoding polypeptide chains 1-4 (polypeptide chain 5 is the same as polypeptide chain 2) in Expi-CHO cells. The five chain antibody was purified with a CH1 affinity resin and buffer exchanged into PBS, pH 7.4.

The assembly and purity of the resulting B-body™ was assessed through non-reducing and reducing SDS-PAGE.

Non-reducing SDS-PAGE was performed using 2 μg of antibody ranging from ~0.2 to 1 mg/mL. Sample, up to 10 μL, was mixed with 4 μL 2× Laemmli Sample Buffer (Bio-Rad) in 200 μL PCR tubes. To a separate tube was added 4 μL molecular weight ladder (Precision Plus Protein Dual Color Standards, Bio-Rad). PCR tubes were incubated at 55° C. for 10 mm and cooled to 4° C. using a thermocycler. Tubes were centrifuged and the entire volume of each tube was loaded into individual wells of a 4-15% Bis-Tris Gel (Mini-PROTEAN TGX, Bio-Rad). Samples were electrophoresed over 30 min using a Bio-Rad Mini-PROTEAN Tetra System with Tris/Glycine/SDS running buffer (diluted from 10× to 1×) operated at constant voltage (220 V) using an external power supply. Gels were washed with deionized water and stained with coomassie dye (GelCode Blue Safe Protein Stain, ThermoFisher Scientific) for a minimum of 15 min. Gels were subsequently destained with deionized water for a minimum of 30 min and imaged.

Reducing SDS-PAGE was performed using 3 μg of antibody ranging from ~0.3 to 1.5 mg/mL. Sample, up to 10 μL, was mixed with 4 μL 2× Laemmli Sample Buffer (Bio-Rad) in 200 μL PCR tubes and 5 μL of 5 M dithiothreitol. To a separate tube was added 4 μL molecular weight ladder (Precision Plus Protein Dual Color Standards, Bio-Rad).

PCR tubes were incubated at room temperature for 30 min. Samples were then incubated at 55° C. for 10 min and cooled to 4° C. using a thermocycler. Tubes were centrifuged and up to 14 µL of sample was loaded into individual wells of a 4-15% Bis-Tris Gel (Mini-PROTEAN TGX, Bio-Rad). Samples were electrophoresed over 30 min using a Bio-Rad Mini-PROTEAN Tetra System with Tris/Glycine/SDS running buffer (diluted from 10× to 1×) operated at constant voltage (220 V) using an external power supply. Gels were washed with deionized water and stained with coomassie dye (GelCode Blue Safe Protein Stain, ThermoFisher Scientific) for a minimum of 15 min. Gels were subsequently destained with deionized water for a minimum of 30 min and imaged.

The 1×2 B-body™ ran near the expected molecular weight of 200 kD in a non-reduced format (data not shown here) In a reduced format, the expected 3 bands were resolved (one chain at 75 kD, one chain at 50 kD, and 2 chains at 25 kD) (data not shown here).

The protein was subsequently analyzed by capillary electrophoresis in a reduced and non-reduced format.

Capillary electrophoresis was run on the Agilent 2100 Bioanalyzer following the manufacturer's instructions. Briefly, the samples were incubated with labeling dye in labeling buffer on ice in the dark for 30 min. Ethanolamine was then and the samples were incubated for 10 min on ice in the dark to quench unincorporated dye. For reduced samples, 1 M DTT was added to the sample buffer. Samples were incubated at 98° C. for 5 min to denature the samples prior to loading in the NanoFluidic chip. The percent purity was calculated from the three major bands in the reduced sample to be 95.54% (data not shown here).

The antibody protein was then analyzed via a set of columns to assess the homogeneity with size-exclusion chromatography (SEC), the propensity towards aggregation with standup monolayer adsorption chromatography (SMAC), and the hydrophobicity with hydrophobic interaction chromatography (HIC).

SEC analysis was performed using a 7.8 mm ID×30 cm TSKgel G3000SWXL column (Tosoh Bioscience LLC, PN 08541) on an Agilent 1100 HPLC. Antibodies were normalized to 1 mg/mL concentration in dPBS (pH 7.4) and clarified via centrifugation to pellet particulates. The mobile phase buffer was dPBS (pH 7.4, without calcium and magnesium). For each sample, 10 µL was loaded and isocratically eluted at 1.0 mL/min over 20 min. Absorbance was monitored at 280 nm. Chromatographic peaks were integrated to determine % homogeneity and retention time.

SMAC analysis was performed using a 4.6 mm ID×300 mm Zenix SEC 300 column (Sepax Technologies, PN 213300P-4630) on an Agilent 1100 HPLC. Antibodies were normalized to 1 mg/mL concentration in dPBS (pH 7.4) and clarified via centrifugation to pellet particulates. The mobile phase buffer was dPBS (pH 7.4, without calcium and magnesium). For each sample, 10 µL was loaded and isocratically eluted at 0.25 mL/min over 32 min. Absorbance was monitored at 280 nm. Sample retention time was calculated and compared to a set of standard controls to identify antibodies with increased retention time (increased propensity to form aggregates).

HIC analysis was performed using a 4.6 mm ID×3.5 cm TSKgel Butyl-NPR column (Tosoh Bioscience LLC, PN 14947) on an Agilent 1100 HPLC. Antibodies were normalized to 2 mg/mL concentration in dPBS (pH 7.4) and then diluted with an equal volume of mobile phase buffer B to a final protein concentration of 1 mg/mL. The column was equilibrated with 100% mobile phase Buffer B (2 M ammonium sulfate/20 mM sodium phosphate, pH 7.0) at a flow rate of 1 mL/min. For each sample, 10 µL was loaded and eluted using a gradient from 100% mobile phase buffer B to 100% mobile phase buffer A (20 mM sodium phosphate, pH 7.0) at 1.0 mL/min over 15 min, held at 100% A for 3 min to wash the column, and returned 100% B for 2 min for equilibration. Absorbance was monitored at 280 nm. Sample retention time was calculated and compared to a set of standard controls to identify antibodies with increased retention time (increased hydrophobicity).

The results of these analysis are shown in FIGS. 66A, 66B and 66C. As shown, the protein appeared >99% homogeneous by SEC and resulted in a single peak with both SMAC and HIC that fell within the range observed for other developable antibodies suggesting an acceptable aggregation and hydrophobicity profile.

The protein was next analyzed with the UNcle analytic instrument which is capable of measuring the Tm, PDl, and hydrodynamic diameter using dynamic light scattering (DLS), static light scattering (SLS), and fluorescence. Antibodies were normalized to 1 mg/mL concentration in dPBS (pH 7.4) and clarified via centrifugation to pellet particulates. Samples were aliquoted into UNcle's 9 µL quartz capillary cuvette device (Uni) and sealed. PD1 and hydrodynamic diameter were measured by DLS at 15° C. The temperature was ramped from 15° C. to 95° C. at 0.5° C./min during which Tm was measured by intrinsic fluorescence. Data were analyzed using UNcle Analysis Software v 3.1.

The protein showed melting temperatures of 67.4° C. and 73.7° C. The median PD1 from three measurements was 0.19 which is indicative of a monodisperse sample (PD1<0.25 is considered monodisperse) with a hydrodynamic diameter of 14.4 nm (see Table 16 below).

TABLE 16

Results for melting temperature, polydispersity index, and hydrodynamic diameter from the UNcle analytical instrument

| | Tm1 (° C.) | Tm2 (° C.) | PDI | Diameter (nm) |
|---|---|---|---|---|
| I2-A27 1×2 B-body ™ | 67.4 | 73.7 | 0.19 | 14.4 |

6.13.25.4. In Vitro Functional Assessment of ROR1×CD3 1×2 B-Body™ Bispecific Antibody The functional capability of an 12-A27 B-body™ in cellular co-culture assays of T cells and ROR1 expressing cancer cells was analyzed. Cancer cell lines that expressed ROR1 and/or ROR2 were assessed.

MDA-MB-231, RPMI-8226, and K562 were assessed for the number of copies of surface expressed ROR1 and the closely related ROR2 protein via flow cytometry using a ROR1 specific antibody (12-A27) and a ROR2 specific antibody (12-C21). Specificity of the antibodies used for copy number assessment was determined by BLI and it was confirmed that 12-A27 selectively binds to ROR1 and 12-C21 selectively binds to ROR2. The MDA-MB-231 cell line was determined to primarily express ROR1, the RPMI-8226 cell line was determined to express both ROR and ROR2, and the K562 cell line was determined to express primarily ROR2 as shown in Table 17.

TABLE 17

Surface protein copy number of ROR1 and ROR2 on MDA-MB-231, RPMI-8226, and K562 cells

|  | ROR1 Copy Number | ROR2 Copy Number |
| --- | --- | --- |
| MDA-MB-231 | 114,000 | <7,000 |
| RPMI-8226 | 110,000 | 72,000 |
| K562 | <7,000 | 68,000 |

To assess whether the 12-A27 B-body™ could activate T cells in the presence of ROR1 or ROR2 expressing cancer cells, an NFκB Jurkat co-culture reporter gene assay was utilized. Activation of the Jurkat T cells leads to activation of the NFκB response element and production of eGFP. Specifically, RPMI-8226 or K562 cells were plated the day of the assay (35,000 cells/well) or MDA-MB-231 cells were plated the day before the assay (25,000 cells/well) in a half area, black-walled, clear-bottom 96 well plate. The day of the assay, dilutions of the antibody at the concentrations indicated were added in the presence of 1 µg/mL anti-CD28 antibody. NFκB-GFP Jurkat reporter cells were added to the well at 75,000 cells/well. The plate was incubated for 6 hours at 37° C./5% CO2. A background suppression dye was added and a Safire plate reader was used to determine the fluorescence at 520 nm.

As shown in FIGS. 67A, 67B, 67C and 67D, the 12-A27 1×2 B-body™ bispecific antibody was shown to be able to activate the Jurkat reporter cell line in the pM range in the presence of MDA-MB-231 (ROR1 expressing) or RPMI-8226 (ROR1 and ROR2 expressing) cells but not in the presence of K562 (ROR2 expressing) cells or in the absence of a target cell line.

Next, the function of the 12-A27 1×2 B-body™ bispecific antibody to activate primary CD8+ T cells was studied in the presence of ROR1 expressing cell lines as assessed by increased expression levels of the early T cell activation marker, CD69, and the late T cell activation marker, CD25. Specifically, the 12-A27 1×2 B-body™ bispecific antibody, CD8+ T cells, with or without MDA-MB-231 cells or RPMI-8226 cells at a 6:1 E:T ratio, were incubated for 48-hours. Then, cells were labeled with PE-Cy7 CD69 antibody (BD Biosciences 561928) and a BB515 CD25 antibody (BD Biosciences 564467) for 1 hr at 4° C. After labeling, samples were centrifuged at 300×g and resuspended in live cell imaging solution (Thermo Fisher) prior to analysis by flow cytometry on the IntelliCyt IQue screener.

As shown in FIGS. 68A-68D, the 12-A27 1×2 B-body® bispecific antibody led to a dose dependent increase in expression of CD69 and CD25 when in the presence of ROR1 expressing cells (MDA-MB-231 or RPMI-8226) but not in the absence of these cells.

Whether the activated T cells could subsequently kill the ROR1 expressing cell lines was assessed by LDH release from the target cells and secretion of Granzyme B, TNFα, and IFNγ by the CD8+ effector cells.

LDH release from the target cells was analyzed as follows: RPMI-8226 cells were plated the day of the assay or MDA-MB-231 cells were plated the day before the assay in half area, black walled, clear-bottom 96-well plates. CD8+ cells were added at an effector to target cell ratio of 6:1. Assay media was RPMI+2% heat inactivated FBS. Cells were incubated for two days at 37° C./5% CO2. A lactate dehydrogenase (LDH) release assay (Roche) was performed following the manufacturer's protocol using the assay media from each well. Data was normalized to a no CD8+ control (0% Cytotoxicity) and a detergent killed control (100% Cytotoxicity).

As shown in FIGS. 69A and 69B, the 12-A27 1×2 B-body™ bispecific antibody led to dose dependent cytotoxicity of ROR1 expressing cells in the presence of CD8+ T cells, but not in the absence of CD8+ T cells.

Secretion of Granzyme B, TNFα, and IFNγ by the CD8+ effector cells was analyzed as follows: MultiCyt QBeads PlexScreen Secreted Protein Assay Kit (IntelliCyt) was used to determine the level of secreted TNFα, IFNγ, and Granzyme B following the Manufacturer's protocol. Briefly, capture beads for each analyte are provided as a 50× concentrate. The beads are combined together and diluted to a 2× concentrate prior to use. 10 µL of supernatant is transferred to a V bottom plate, 10 µL of prepared beads are added to the samples, the plate is mixed on a plate shaker, and the plate is incubated at room temperature for 1 hr. Following the incubation, 10 µL of detection reagent is added to each well, the plate is mixed on a plate shaker, and the plate is incubated at room temperature for 2 hr. Following the incubation, 50 µL of wash buffer is added to each well, the plate is centrifuged for 5 min at 1100×g, the supernatants are aspirated and the samples are resuspended by adding 10 µL of wash buffer to each well. The data is acquired on the IntelliCyt IQue Screener flow cytometer.

A dose dependent increase in Granzyme B, TNFα, and IFNγ released by the CD8+ T cells was observed in the presence of 12-A27 and ROR1 expressing cells; no such increase was observed in the absence of ROR1 expressing cells, as shown in FIGS. 70A-70F.

6.13.25.5. Serum Stability Assessment of ROR1×CD3 1×2 B-Body™ Bispecific Antibody Serum stability of an 12-A27 1×2 B-body™ bispecific antibody was analyzed. The 12-A27 1×2 B-body™ bispecific antibody was diluted from 2.5 mg/mL in PBS to 170 µg/mL in human serum (~93% final serum concentration) or PBS. Samples were then incubated at 37° C. or 4° C. for 1 week. Following the week-long incubation, the Jurkat activity assay was carried out on the samples stored in human serum or the PBS control. It was found that there was no loss in activity for samples that were stored in human serum at 4° C. or 37° C. for 1 week (see FIG. 71A). If material had aggregated during the week-long incubation in serum, the B-body™ may be expected to lead to an increase in signal in the absence of ROR1 expressing cells due to direct activation of the CD3 receptor. No increase in activity was detected when the assay was run in the absence of ROR1 expressing cells (see FIG. 71B).

The stability of the 12-A27 1×2 B-body™ bispecific antibody was then assessed by storing the antibody at 4° C. or 40° C. at 2.5 mg/mL in PBS and assessing the homogeneity of the samples by SEC and PD1 weekly. For accelerated stability assays, the antibody was stored at 2.5 mg/mL in PBS at 40° C. for up to four weeks. The antibody appeared to be stable under the accelerated stability conditions (see FIG. 72). For real time assays, the antibody was stored at 2.5 mg/mL in PBS at 4° C. for up to twelve weeks. The antibody also appeared to be stable under the real time conditions (see FIG. 73).

The PD1 and Z-ave Diameter for each accelerated and real time stability sample was determined using the UNcle analytical instrument, and results are shown in Table 18 below.

TABLE 18

The PDI and Z-ave Diameter for each accelerated and real time stability sample as determined using the UNcle analytical instrument

| I2-A27 Batch 18-007-44 | PDI | Z-Ave Diameter (nm) |
|---|---|---|
| 1 W, 4 C. | 0.10 | 12.16 |
| 2 W, 4 C. | 0.10 | 11.82 |
| 3 W, 4 C. | N/D | N/D |
| 4 W, 4 C. | 0.16 | 11.72 |
| 5 W, 4 C. | 0.17 | 11.57 |
| 6 W, 4 C. | | |
| 8 W, 4 C. | | |
| 10 W, 4 C. | | |
| 12 W, 4 C. | | |
| 1 W, 40 C. | 0.22 | 12.41 |
| 2 W, 40 C. | 0.14 | 12.41 |
| 3 W, 40 C. | 0.10 | 12.28 |

Next the stability of the antibody in acid was assessed. The B-body™ was subjected to the purification procedure as outlined above by binding to a CH1 affinity resin with elution using 100 mM sodium acetate, pH 3.5. The B-body™ was left in the acid for 0, 30, 60, or 120 min prior to neutralization with Tris-HCl buffer. The protein was then buffer exchanged into PBS prior to being analyzed by SEC. As shown in FIG. 74, the 12-A27 1×2 B-body™ bispecific antibody was stable in acid for up to 2 hours.

6.13.25.6. In Vivo Efficacy Study of ROR1×CD3 1×2 B-Body™ Bispecific Antibody The in vivo efficacy of an exemplary ROR1×CD3 bispecific B-body™, the 12-A27 1×2 B-body™, was studied in a PBMC-humanized NSGT™ mouse model of breast cancer.

More specifically, NSM™ (Jackson Laboratory, Stock No. 005557, also known as NOD-scid IL2 Rgamma$^{null}$, NOD-scid L2Rg$^{null}$, NSG, NOD scid gamma) female mice aged six- to eight-weeks old were inoculated orthotopically in the mammary fat pad with 5×10$^6$ MDA-MB-231 resuspended in 1:1 mixture of Matrigel with PBS or serum free media. Body weights and clinical observations were recorded once to twice weekly. Digital caliper measurements were initiated to determine tumor volume once to twice weekly when tumors become palpable. Mice were randomized based on tumor volumes when the tumor volumes reach ~60-80 mm$^3$ (Study Day −1 or Study Day 0). Mice were injected with PBMCs on Study Day 0. Following injection of PBMCs, dosing began based on the results of the phase I validation. Mice were dosed at 0.5 mg/kg, 2.5 mg/kg, and 10 mg/kg. Body weights, clinical observations and digital caliper measurements were recorded twice weekly post dose initiation. Animals that reached a body condition score of ≤2, a body weight loss of ≥20% or a tumor volume >2000 mm$^3$ were euthanized before study terminus. Animals with ulcerated tumors were euthanized before study terminus. Tissues were not collected from animals that were found dead. On Study Day 30, all animals were euthanized by CO2 asphyxiation and tissues collected. Tumors were then collected and separated into fragments. One fragment was placed in media for flow cytometry analysis. The following markers were examined: CD45, CD3, CD8, CD4, and 7AAD. One fragment was fixed in 10% neutral buffered formalin (NBF) for paraffin embedding (FFPE). One fragment was flash frozen. Whole blood was collected at the end of study. About 50 μL whole blood was obtained for flow cytometry analysis. The following markers were examined: CD45, CD3, CD8, CD4, and 7AAD.

The results are shown in FIG. 87 (upper panel) and FIG. 88. As shown, the 12-A27 1×2 B-body™ demonstrated in vivo efficacy in reducing tumor growth at dose 0.5 mg/kg and 2.5 mg/kg.

6.13.26. Example 25: ROR1/ROR2×CD3 Bispecific B-body™ Efficacy

Additional ROR antigen binding molecules comprising the six CDRs of 12-A10 as shown in Table 6 and various CDR mutants were prepared and experiments were performed to test their efficacy as trivalent bispecific constructs in a ROR1×CD3 bispecific B-body™ format.

6.13.26.1. Generation of Additional ROR1/ROR2×CD3 1×2 B-Body™ Bispecific Antibodies Based on 12-A10

Selective mutations in the CDR regions of an 12-A10 antibody and antibody constructs in the IgG, 1×1 B-body™, and 1×2 B-body™ formats were made and tested.

For example, ROR ABS candidate designated 12A-10 was formatted with CD3 ABS candidate SP34-89 into a bispecific B-body "BC1" 1×2 format, as described above, with the 1×2 format having a 10 amino acid junction between the S and the H domains (see, e.g., FIG. 26 for schematic of domains). The amino acid sequences for the five polypeptide chains that form an exemplary 12-A10 BC1 1×2 trivalent bispecific ROR antigen binding molecule are listed as SEQ ID NO:114 (Chain 1), SEQ ID NO:115 (Chain 2), SEQ ID NO:116 (Chain 3), SEQ ID NO:117 (Chain 4), and SEQ ID NO:115 (Chain 5).

In the following description in this Example, the term "12-A10 1×2 B-body™" or "12-A10" or "A10" refers to this ROR1/ROR2×CD3 1×2 B-body™ having a Chain 1 of SEQ ID NO: 114, a Chain 2 of SEQ ID NO:115, a Chain 3 of SEQ ID NO:116, a Chain 4 of SEQ ID NO:117, and a Chain 5 of SEQ ID NO: 115.

The 12-A10 antibody constructs with mutations included 12-A10 R66G, 12-A10 R66K, 12-A1 P D54G, 12-A10 D54E, 12-Ai Y55E, 12-A10 Y55Q, 12-Y56S12-A Y93SY94S, and 12-A10 A32Y.

Expression titer and yield of these antibody constructs were analyzed as shown in Table 19.

TABLE 19

| | Expression Titer and Yield | | | | | |
|---|---|---|---|---|---|---|
| | IgG | | 1x1 B-Body | | 1x2 B-Body | |
| | Pre Yield (μg/mL) | Post Yield (μg/mL) | Pre Yield (μg/mL) | Post Yield (μg/mL) | Pre Yield (μg/mL) | Post Yield (μg/mL) |
| I2-A10 | 140 | 114 | 450 | 144 | 125 | 22 (47) |
| I2-A27 | 140 | 98 | 525 | 174 | 135 | 20 (62) |

TABLE 19-continued

Expression Titer and Yield

| | IgG | | 1x1 B-Body | | 1x2 B-Body | |
|---|---|---|---|---|---|---|
| | Pre Yield (µg/mL) | Post Yield (µg/mL) | Pre Yield (µg/mL) | Post Yield (µg/mL) | Pre Yield (µg/mL) | Post Yield (µg/mL) |
| I2-A10 R66G | N/D | N/D | 215 | 48 | 224 | 12 (63) |
| I2-A10 R66K | N/D | N/D | 245 | 68 | 225 | 45 (84) |
| I2-A10 D54G | N/D | N/D | 235 | 72 | 226 | 11 (67) |
| I2-A10 D54E | N/D | N/D | 61 | 24 | 213 | 47 |
| I2-A10 Y55E | N/D | N/D | 122 | 52 | 252 | 84 |
| I2-A10 Y55Q | N/D | N/D | 119 | 58 | 233 | 64 |
| I2-A10 Y56S | N/D | N/D | 148 | 38 | 230 | 64 |
| I2-A10 Y93SY94S | N/D | N/D | 98 | 66 | 217 | 62 |
| I2-A10 A32Y | N/D | N/D | 116 | 54 | 245 | 68 |

The binding to ROR1 of these antibody constructs was then tested and each showed positive binding, except the A32Y and Y93/94S constructs which showed poor binding.

These antibody constructs were then tested in the Jurkat functional assay described herein (see. e.g., 6.13.1.8). The results are shown in Table 20.

TABLE 20

Jurkat Functional Assay for I2-A10 Constructs with Mutations

| Ab | MDAEC50 (pM) 1x1 | MDAEC50 (pM) 1x2 | K562 EC50 (pM) 1x1 | K562 EC50 (pM) 1x2 | RPMI EC50 (pM) 1x1 | RPMI EC50 (pM) 1x2 |
|---|---|---|---|---|---|---|
| A27 | 378 | 58 | N/A | N/A | 351 | 19 |
| A10 | 102 | 33 | 33 | 3.2 | 36 | 12 |
| R66G | 314 | 30 | 91 | 3.5 | N/D | 218 |
| R66K | 121 | 20 | 24 | 1.2 | 49 | 7.7 |
| D54G | 51 | 19 | 20 | 0.2 | 23 | 5.9 |
| D54E | 43 | 9 | 26 | 0.3 | 16 | 6.7 |
| Y55E | 552 | 36 | 322 | 4.7 | 512 | 16 |
| Y55Q | 256 | 49 | 68 | 0.8 | 192 | 8.8 |
| Y56S | 480 | 49 | 85 | 13 | 235 | 12 |

These variants were also tested in the cell killing assay. The results are shown in Table 21.

TABLE 21

Cell Killing Assay for I2-A10 Variants

| Ab | LDH pM | Max % Act |
|---|---|---|
| I2-A10 | 5.4 | 36 |
| I2-A27 | 0.3 | 46 |
| I2-A10 R66G | 47.3 | 35 |
| I2-A10 R66K | 5.8 | 31 |
| I2-A10 D54G | 3.6 | 58 |
| I2-A10 Y55E | 10.2 | 29 |
| I2-A10 Y55Q | 6.1 | 39 |
| I2-A10 Y56S | 15.1 | 35 |
| I2-A10 D54E | 2.5 | 48 |

Then, the antibody constructs were analyzed to assess the homogeneity with SEC, the propensity towards aggregation with SMAC, and the hydrophobicity with HIC. SEC, SMAC and HIC assays were preformed as described in Example 24. D54G was not acceptable according to the SEC assay. Y55Q (and Y55E) showed improved HIC values over the 12-A10 parent. Differential scanning fluorimetry (DSF) was also used to test the antibody constructs.

Based on the above described assays and analyses, the D54E and Y55Q mutations were selected for the preparation of a novel A10-related antibody designated 12-A10 D54E Y55Q. The D54E mutation which corrects a potential isomerization site unexpectedly resulted in an antibody with better activity (in vitro functional assays) than the activity of the 12-A10 parent antibody. The Y55Q mutation which reverts a rare residue to germline unexpectedly resulted in an antibody with improved HIC values as compared to the 12-A10 parent antibody.

An additional ROR1/ROR2xCD3 1x2 B-body™ was then generated incorporating the D54E and Y55Q mutations. Y55Q is a mutation in the CDR2 region of the VL of the antigen binding site for ROR1 and ROR2 as shown in Table 6, and was introduced into chain 1 and chain 3 as shown below. D54E is a mutation in the CDR2 region of the VH of the antigen binding site for ROR1 and ROR2 as shown in Table 6, and was introduced into chain 2 and chain 5 as shown below. In addition, mutations to generate a knob-and-hole configuration were included in the second CH3 domains in chain 1 (hole) and chain 3 (knob).

ROR ABS candidate designated 12A-10 D54E Y55Q was formatted with CD3 ABS candidate SP34-89 into a bispecific B-body "BC1" 1x2 format, as described above, with the 1x2 format having a 10 amino acid junction between the S and the H domains (see. e.g., FIG. 26 for schematic of domains). The amino acid sequences for the five polypeptide chains that form an exemplary 12A-10 D54E Y55Q BC1 1x2 trivalent bispecific ROR antigen binding molecule are listed as SEQ ID NO:132 (Chain 1), SEQ ID NO:133 (Chain 2), SEQ ID NO:134 (Chain 3), SEQ ID NO:135 (Chain 4), and SEQ ID NO:133 (Chain 5).

In the following description in this Example, the term 12-A10 D54E Y55Q 1x2 B-body™ or "12-A10 D54E Y55Q" refers to this ROR1/ROR2xCD3 1x2 B-body™ having a Chain 1 of SEQ ID NO:132, a Chain 2 of SEQ ID NO:133, a Chain 3 of SEQ ID NO:134, a Chain 4 of SEQ ID NO:135, and a Chain 5 of SEQ ID NO:133.

6.13.26.2. Binding of ROR1/ROR2xCD3 1x2 B-Body™ Bispecific Antibody to CD3 and ROR1

The binding affinity of an 12-A10 D54E Y55Q 1x2 B-body™ to cynomolgus CD3 delta and epsilon heterodimer was determined by the monovalent BLI binding assessment described in Example 24 above. As shown in FIG. 75, the bispecific antibody exhibited a monovalent Kd of 3.5 nM to cynomolgus CD3 delta and epsilon heterodimer.

Next, the binding of the antibody to ROR1 and ROR2 was assessed using the monovalent and bivalent BLI binding assessments as described in Example 24. As shown in FIGS.

76A-76B, 12-A10 D54E Y55Q IgG antibody showed monovalent binding of 0.7 nM to ROR1 and less than 1 pM to ROR2. The 12-A10 D54E Y55Q 1×2 B-body™ showed a monovalent binding of 0.46 nM to ROR1 and less than 1 pM to ROR2 and bivalent binding of 21 pM to ROR1 and 3 pM to ROR2 (see FIGS. 76C-76F).

Binding of 12-A10 D54E Y55Q IgG to Ig-like, Frizzled, and Kringle domains was then determined by BLI. As shown in FIG. 77, 12-A10 D54E Y55Q IgG binds to the Ig-like domain of ROR1.

6.13.26.3. Further Characterization of ROR1/ROR2×CD3 1×2 B-Body™

An 12-A10 D54E Y55Q 1×2 B-body™ was produced through transient transfection of DNA encoding polypeptide chains 1-4 (polypeptide chain 5 is the same as polypeptide chain 2) in Expi-CHO cells. The five chain antibody was purified with a CH1 affinity resin and buffer exchanged into PBS, pH 7.4.

The assembly and purity of the resulting B-body™ was assessed through non-reducing and reducing SDS-PAGE as described in Example 24. The 2×1 B-body™ ran near the expected molecular weight of 200 kD in a non-reduced format. In a reduced format, the expected 3 bands were resolved (one chain at 75 kD, one chain at 50 kD, and 2 chains at 25 kD) (data not shown here). The protein was subsequently analyzed by capillary electrophoresis in a reduced and non-reduced format as described in Example 24 and the percent purity was calculated from the three major bands in the reduced sample to be 96.25%.

The antibody protein was then analyzed via a set of columns to assess the homogeneity with SEC, the propensity towards aggregation with SMAC, and the hydrophobicity with HIC. SEC, SMAC and HIC assays were performed as described in Example 24.

The results of these analyses are shown in FIGS. 78A-78C. As shown, the protein appeared >99% homogeneous by SEC and resulted in a single peak with both SMAC and HIC that fell within the range observed for other developable antibodies suggesting an acceptable aggregation and hydrophobicity profile.

The protein was next analyzed with the UNcle analytic instrument as described in Example 24. The antibody showed melting temperatures of 68.5° C. and 77.4° C. The median PD1 from three measurements was 0.21 which is indicative of a monodisperse sample (PD1<0.25 is considered monodisperse) with a hydrodynamic diameter of 12.6 nm (see Table 22 below).

TABLE 22

Results for melting temperature, polydispersity index, and hydrodynamic diameter from the UNcle analytical instrument

|  | Tm1 (° C.) | Tm2 (° C.) | PDI | Diameter (nm) |
| --- | --- | --- | --- | --- |
| I2-A10 D54E Y55Q 1x2 B-body ™ | 68.5 | 77.4 | 0.21 | 12.6 |

6.13.26.4. In Vitro Functional Assessment of ROR1/ROR2×CD3×2 B-body™

The functional capability of an 12-A10 D54E Y55Q 1×2 B-body™ in cellular co-culture assays of T cells and ROR1 expressing cancer cells was analyzed. Cancer cell lines that expressed ROR1 and/or ROR2 were assessed.

MDA-MB-231, RPMI-8226, and K562 cells were used in this study, and as shown in Example 24, the MDA-MB-231 cell line was determined to primarily express ROR1, the RPMI-8226 cell line was determined to express both ROR1 and ROR2, and the K562 cell line was determined to express primarily ROR2.

To assess whether the 12-A10 D54E Y55Q 1×2 B-body™ could activate T cells in the presence of ROR1 or ROR2 expressing cancer cells, an NFκB Jurkat co-culture reporter gene assay as described in Example 24 was utilized. Activation of the Jurkat T cells leads to activation of the NFκB response element and production of eGFP. As shown in FIGS. 79A-79D, the 12-A10 D54E Y55Q 1×2 B-body™ was able to activate the Jurkat reporter cell line in the pM range in the presence of MDA-MB-231 (ROR1 expressing), RPMI-8226 (ROR1 and ROR2 expressing), and K562 (ROR2 expressing) cells but not in the absence of a ROR1 or ROR2 expressing cell line.

Next, the function of the 12-A10 D54E Y55Q 1×2 B-body™ to activate primary CD8+ T cells was studied. This functional assay is as described in Example 24 above, in the presence of ROR1 expressing cell lines as assessed by increased expression levels of the early T cell activation marker, CD69, and the late T cell activation marker, CD25.

As shown in FIGS. 80A-80D, the 12-A10 D54E Y55Q 1×2 B-body™ led to a dose dependent increase in expression of CD69 and CD25 when in the presence of ROR1 expressing cells (MDA-MB-231 or RPMI-8226) but not in the absence of these cells.

Whether the activated T cells could subsequently kill the ROR1 expressing cell lines was assessed by LDH release from the target cells and secretion of Granzyme B. TNFα, and IFNγ by the CD8+ effector cells.

LDH release from the target cells was analyzed as described in Example 24. As shown in FIGS. 81A and 81B, the 12-A10 D54E Y55Q 1×2 B-body™ led to dose dependent cytotoxicity of ROR1 expressing cells in the presence of CD8+ T cells, but not in the absence of CD8+ T cells.

Secretion of Granzyme B, TNFα, and IFNγ by the CD8+ effector cells was analyzed as described in Example 24. A dose dependent increase in Granzyme B, TNFα, and IFNγ released by the CD8+ T cells was observed in the presence of the 12-A10 D54E Y55Q 1×2 B-body™ and ROR1 expressing cells; no such increase was observed in the absence of ROR1 expressing cells, as shown in FIGS. 82A-82F.

6.13.26.5. Serum Stability Assessment of ROR1×CD3 1×2 B-Body™ Bispecific Antibody Serum stability of the 12-A10 D54E Y55Q 1×2 B-body™ was analyzed. The bispecific antibody was diluted from 2.5 mg/mL in PBS to 170 μg/mL in human serum (~93% final serum concentration) or PBS. Samples were then incubated at 37° C. or 4° C. for 1 week. Following the week-long incubation, the Jurkat activity assay was carried out on the samples stored in human serum or the PBS control. It was found that there was no loss in activity for samples that were stored in human serum at 4° C. or 37° C. for 1 week (see FIG. 83A). If material had aggregated during the week-long incubation in serum, the B-body™ may be expected to lead to an increase in signal in the absence of ROR1 expressing cells due to direct activation of the CD3 receptor. No increase in activity was detected when the assay was run in the absence of ROR1 expressing cells (see FIG. 83B).

The stability of the 12-A10 D54E Y55Q 1×2 B-body™ was then assessed by storing the antibody at 4° C. or 40° C.

at 2.5 mg/mL in PBS and assessing the homogeneity of the samples by SEC and PD1 weekly. For accelerated stability assays, the antibody was stored at 2.5 mg/mL in PBS at 40° C. for up to four weeks. The antibody appeared to be stable under the accelerated stability conditions (see FIG. 84). For real time assays, the antibody was stored at 2.5 mg/mL in PBS at 4° C. for up to twelve weeks. The antibody also appeared to be stable under the real time conditions (see FIG. 85).

The PD1 and Z-ave Diameter for each accelerated and real time stability sample was determined using the UNcle analytical instrument, and results are shown in Table 23.

TABLE 23

The PDI and Z-ave Diameter for each accelerated and real time stability sample as determined using the UNcle analytical instrument

| I2-A10 D54E Y55Q Batch 18-007-45 | PDI | Z-Ave Diameter (nm) |
| --- | --- | --- |
| 1 W, 4 C. | 0.13 | 12.24 |
| 2 W, 4 C. | 0.14 | 11.68 |
| 3 W, 4 C. | 0.21 | 12.17 |
| 4 W, 4 C. | 0.12 | 11.68 |
| 5 W, 4 C. | 0.25 | 11.33 |
| 6 W, 4 C. | | |
| 8 W, 4 C. | | |
| 10 W, 4 C. | | |
| 12 W, 4 C. | | |
| 1 W, 40 C. | 0.184 | 12.15 |
| 2 W, 40 C. | 0.139 | 12.01 |
| 3 W, 40 C. | 0.058 | 14.72 |

Next the stability of the antibody in acid was assessed. The 12-A10 D54E Y55Q 1×2 B-body™ was subjected to the purification procedure as outlined above by binding to a CH1 affinity resin with elution using 100 mM sodium acetate, pH 3.5. The bispecific antibody was left in the acid for 0, 30, 60, or 120 min prior to neutralization with Tris-HCl buffer. The protein was then buffer exchanged into PBS prior to being analyzed by SEC. As shown in FIG. 86, the 12-A10 D54E Y55Q 1×2 B-body™ was stable in acid for up to 2 hours.

6.13.26.6. In Vivo Efficacy Study of ROR1/ROR2×CD3 1×2 B-Body™ Bispecific Antibody The in vivo efficacy of an exemplary ROR1/ROR2×CD3 bispecific B-body™, 12-A10 D54E Y55Q 1×2 B-body™, was studied in a PBMC-humanized NSG™ mouse model of breast cancer. The study was performed as described in Example 24 above.

The results are shown in FIG. 87 (lower panel) and FIG. 88. As shown, the 12-A10 D54E Y55Q 1×2 B-body™ demonstrated in vivo efficacy in reducing tumor growth at dose 0.5 mg/kg, 2.5 mg/kg, and 10 mg/kg.

```
6.14. Sequences
>Example 1, bivalent monospecific construct
CHAIN 1 [SEQ ID NO: 1]
(VL)~VEIKRTPREPQVYTLPPCRDELTKNQVSLWCLVKGFYPSDIAVEWESNGQPEN

NYKTTPPVLDSDGSFFLYSKLTVDKSRWQQGNVFSCSVMHEALHNHYTQKSLSLSPGK

DKTHTCPPCPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAPIEKTI

SKAKGQPREPQVYTLPPCRDELTKNQVSLWCLVKGFYPSDIAVEWESNGQPENNYKTT

PPVLDSDGSFFLYSKLTVDKSRWQQGNVFSCSVMHEALHNHYTQKSLSLSPGK

>Example 1, bivalent monospecific construct
CHAIN 2 [SEQ ID NO: 2]
(VH)~VTVSSASPREPQVYTLPPCRDELTKNQVSLWCLVKGFYPSDIAVEWESNGQPE

NNYKTTPPVLDSDGSFFLYSKLTVDKSRWQQGNVFSCSVMHEALHNHYTQKSLSLSPG

K

>Example 1, bivalent, bispecific construct
CHAIN 1 [SEQ ID NO: 3]
(VL)~VEIKRTPREPQVYTLPPCRDELTKNQVSLWCLVKGFYPSDIAVEWESNGQPEN

NYKTTPPVLDSDGSFFLYSKLTVDKSRWQQGNVFSCSVMHEALHNHYTQKSLSLSPGK

DKTHTCPPCPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAPIEKTI

SKAKGQPREPQVYTLPPCRDELTKNQVSLWCLVKGFYPSDIAVEWESNGQPENNYKT

TPPVLDSDGSFFLYSKLTVDKSRWQQGNVFSCSVMHEALHNHYTQKSLSLSPGK

VL-  CH3-  Hinge-  CH2-  CH3(knob)
```

-continued

```
>Example 1, bivalent, bispecific construct
CHAIN 2 [SEQ ID NO: 4]
(VH)~VTVSSASPREPQVYTLPPCRDELTKNQVSLWCLVKGFYPSDIAVEWESNGQPE

NNYKTTPPVLDSDGSFFLYSKLTVDKSRWQQGNVFSCSVMHEALHNHYTQKSLSLSPG

K

VH- CH3

>Example 1, bivalent, bispecific construct
CHAIN 3_ [SEQ ID NO: 5]
(VL)~VEIKRTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVTKSFNRGEC

DKTHTCPPCPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAPIEKTI

SKAKGQPREPQVCTLPPSREEMTKNQVSLSCAVKGFYPSDIAVEWESNGQPENNYKTT

PPVLDSDGSFFLVSKLTVDKSRWQQGNVFSCSVMHEALHNHYTQKSLSLSPGK

VL- CL- Hinge- CH2- CH3(hole)

>Example 1, bivalent, bispecific construct
CHAIN 4 [SEQ ID NO: 6]
(VH)~VTVSSASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKKVEPPKSC

VH- CH1

>Fc Fragment of Human IgG1 [SEQ ID NO: 7]
GQPREPQVYTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSP

>BC1 chain 1 [SEQ ID NO: 8]
DIQMTQSPSSLSASVGDRVTITCRASQDVNTAVAWYQQKPGKAPKLLIYSASFLYSGV

PSRFSGSRSGTDFTLTISSLQPEDFATYYCQQHYTTPPTFGQGTKVEIKRTPREPQVY

TLPPSRDELTKNQVSLKCLVKGFYPSDIAVEWESNGQPENNYKTTPPVLDSDGSFFLY

SKLTVDKSRWQQGNVFSCSVMHEALHNHYTQKSLSLSKSCDKTHTCPPCPAPELLGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPC

RDELTKNQVSLWCLVKGFYPSDIAVEWESNGQPENNYKTTPPVLDSDGSFFLYSKLTV

DKSRWQQGNVFSCSVMHEALHNHYTQKSLSLSPGK

Domain arrangement:
A- B- Hinge- D- E

VL- CH3- Hinge- CH2- CH3(knob)

Mutations in first CH3 (Domain B):
T366K; 445K, 446S, 447C insertion

Mutations in second CH3 (Domain E):
S354C, T366W

>BC1 chain 2 [SEQ ID NO: 9]
EVQLVESGGGLVQPGGSLRLSCAASGFTFSDYDIHWVRQAPGKGLEWVGDITPYDGTT

NYADSVKGRFTISADTSKNTAYLQMNSLRAEDTAVYYCARLVGEIATGFDYWGQGTLV

TVSSASPREPQVYTDPPSRDELTKNQVSLTCLVKGFYPSDIAVEWESNGQPENNYKTT

PPVLDSDGSFFLYSKLTVDKSRWQQGNVFSCSVMHEALHNHYTQKSLSLSGEC
```

-continued

Domain arrangement:
F- G

VH- CH3

Mutations in CH3 (Domain G):
L351D; 445G, 446E, 447C insertion

>BC1 chain 3 [SEQ ID NO: 10]
EIVLTQSPATLSLSPGERATLSCRASQSVSSYLAWYQQKPGQAPRLLIYDASNRATGI

PARFSGSGSGTDFTLTISSLEPEDFAVYYCQQSSNWPRTFGQGTKVEIKRTVAAPSVF

IFPPSDEQLKSGTASVVCLLNNFYPREAKVQWKVDNALQSGNSQESVTEQDSKDSTYS

LSSTLTLSKADYEKHKVYACEVTHQGLSSPVTKSFNRGEC*DKTHTCPPCP*APELLGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAK*GQPREPQVCTLPPS*

*REEMTKNQVSLSCAVKGFYPSDIAVEWESNGQPENNYKTTPPVLDSDGSFFLVSKLTV*

*DKSRWQQGNFFSCSVMHEALHNHYTQKSLSLSPGK*

Domain arrangement:
H- I- Hinge- J- K

VL- CL- *Hinge*- CH2- *CH3(hole)*

Mutations in CH3 (domain K):
Y349C, D356E, L358M, T366S, L368A, Y407V

>BC1 chain 4 [SEQ ID NO: 11]
QVQLVESGGGVVQPGRSLRLDCKASGITFSNSGMHWVRQAPGKGLEWVAVIWYDGSKR

YYADSVKGRFTISRDNSKNTLFLQMNSLRAEDTAVYYCATNDDYWGQGTLVTVSSAST

KGPSVFPLAPSSKSTSGGTAALGCLVKDYFPEPVTVSWNSGALTSGVHTFPAVLQSSG

LYSLSSVVTVPSSSLGTQTYICNVNHKPSNTKVDKKVEPPKSC

Domain arrangement:
L- M

VH- CH1

>BC1 Domain A [SEQ ID NO: 12]
DIQMTQSPSSLSASVGDRVTITCRASQDVNTAVAWYQQKPGKAPKLLIYSASFLYSGV

PSRFSGSRSGTDFTLTISSLQPEDFATYYCQQHYTTPPTFGQGTKVEIKRT

>BC1 Domain B [SEQ ID NO: 13]
PREPQVYTLPPSRDELTKNQVSLKCLVKGFYPSDIAVEWESNGQPENNYKTTPPVLDS

DGSFFLYSKLTVDKSRWQQGNVFSCSVMHEALHNHYTQKSLSLSKSC

>BC1 Domain D [SEQ ID NO: 14]
APELLGGPSVFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISKAK

>BC1 Domain E [SEQ ID NO: 15]
GQPREPQVYTLPPCRDELTKNQVSLWCLVKGFYPSDIAVEWESNGQPENNYKTTPPVL

DSDGSFFLYSKLTVDKSRWQQGNVFSCSVMHEALHNHYTQKSLSLSPGK

>BC1 Domain F [SEQ ID NO: 16]
EVQLVESGGGLVQPGGSLRLSCAASGFTFSDYDIHWVRQAPGKGLEWVGDITPYDGTT

NYADSVKGRFTISADTSKNTAYLQMNSLRAEDTAVYYCARLVGEIATGFDYWGQGTLV

TVSSAS

>BC1 Domain G [SEQ ID NO: 17]
PREPQVYTDPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSGEC

```
>BC1 Domain H [SEQ ID NO: 18]
EIVLTQSPATLSLSPGERATLSCRASQSVSSYLAWYQQKPGQAPRLLIYDASNRATGI

PARFSGSGSGTDFTLTISSLEPEDFAVYYCQQSSNWPRTFGQGTKVEIK

>BC1 Domain I [SEQ ID NO: 19]
RTVAAPSVFIFPPSDEQLKSGTASVVCLLNNFYPREAKVQWKVDNALQSGNSQESVTE

QDSKDSTYSLSSTLTLSKADYEKHKVYACEVTHQGLSSPVTKSFNRGEC

>BC1 Domain J [SEQ ID NO: 20]
APELLGGPSVFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISKAK

>BC1 Domain K [SEQ ID NO: 21]
GQPREPQVCTLPPSREEMTKNQVSLSCAVKGFYPSDIAVEWESNGQPENNYKTTPPVL

DSDGSFFLVSKLTVDKSRWQQGNVFSCSVMHEALHNHYTQKSLSLSPGK

>BC1 Domain L [SEQ ID NO: 22]
QVQLVESGGGVVQPGRSLRLDCKASGITFSNSGMHWVRQAPGKGLEWVAVIWYDGSKR

YYADSVKGRFTISRDNSKNTLFLQMNSLRAEDTAVYYCATNDDYWGQGTLVTVSS

>BC1 Domain M [SEQ ID NO: 23]
ASTKGPSVFPLAPSSKSTSGGTAALGCLVKDYFPEPVTVSWNSGALTSGVHTFPAVLQ

SSGLYSLSSVVTVPSSSLGTQTYICNVNHKPSNTKVDKKVEPPKSC

>BC28 chain 1 [SEQ ID NO: 24]
DIQMTQSPSSLSASVGDRVTITCRASQDVNTAVAWYQQKPGKAPKLLIYSASFLYSGV

PSRFSGSRSGTDFTLTISSLQPEDFATYYCQQHYTTPPTFGQGTKVEIKRT PREPQVC

TLPPSRDELTKNQVSLTCLVKGFYPSDIAVEWESNGQPENNYKTTPPVLDSDGSFFLY

SKLTVDKSRWQQGNVFSCSVMHEALHNHYTQKSLSLSPGK DKTHTCPPCP APELLGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAK GQPREPQVYTLPPC

RDELTKNQVSLWCLVKGFYPSDIAVEWESNGQPENNYKTTPPVLDSDGSFFLYSKLTV

DKSRWQQGNVFSCSVMHEALHNHYTQKSLSLSPGK

Domain arrangement:
A-  B-  Hinge-  D-    E

VL- CH3- Hinge- CH2- CH3(knob)

Mutations in domain B:
Y349C; 445P, 446G, 447K insertion

Mutations in domain E:
S354C, T366W

>BC28 chain 2 [SEQ ID NO: 25]
EVQLVESGGGLVQPGGSLRLSCAASGFTFSDYDIHWVRQAPGKGLEWVGDITPYDGTT

NYADSVKGRFTISADTSKNTAYLQMNSLRAEDTAVYYCARLVGEIATGFDYWGQGTLV

TVSSAS PREPQVYTLPPCRDELTKNQVSLTCLVKGFYPSDIAVEWESNGQPENNYKTT

PPVLDSDGSFFLYSKLTVDKSRWQQGNVFSCSVMHEALHNHYTQKSLSLSPGK

Domain arrangement:
F-  G

VH- CH3

Mutations in domain G:
S354C; 445P, 446G, 447K insertion

>BC28 domain A [SEQ ID NO: 26]
DIQMTQSPSSLSASVGDRVTITCRASQDVNTAVAWYQQKPGKAPKLLIYSASFLYSGV

PSRFSGSRSGTDFTLTISSLQPEDFATYYCQQHYTTPPTFGQGTKVEIKRT
```

-continued

>BC28 domain B [SEQ ID NO: 27]
PREPQVCTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK

>BC28 domain D [SEQ ID NO: 28]
APELLGGPSVFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISKAK

>BC28 domain E [SEQ ID NO: 29]
GQPREPQVYTLPPCRDELTKNQVSLWCLVKGFYPSDIAVEWESNGQPENNYKTTPPVL

DSDGSFFLYSKLTVDKSRWQQGNVFSCSVMHEALHNHYTQKSLSLSPGK

>BC28 domain F [SEQ ID NO: 30]
EVQLVESGGGLVQPGGSLRLSCAASGFTFSDYDIHWVRQAPGKGLEWVGDITPYDGTT

NYADSVKGRFTISADTSKNTAYLQMNSLRAEDTAVYYCARLVGEIATGFDYWGQGTLV

TVSSAS

>BC28 domain G [SEQ ID NO: 31]
PREPQVYTLPPCRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK

>BC44 chain 1 [SEQ ID NO: 32]
DIQMTQSPSSLSASVGDRVTITCRASQDVNTAVAWYQQKPGKAPKLLIYSASFLYSGV

PSRFSGSRSGTDFTLTISSLQPEDFATYYCQQHYTTPPTFGQGTKVEIKRTVREPQVC

TLPPSRDELTKNQVSLTCLVKGFYPSDIAVEWESNGQPENNYKTTPPVLDSDGSFFLY

SKLTVDKSRWQQGNVFSCSVMHEALHNHYTQKSLSLSPGKDKTHTCPPCPAPELLGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPC

RDELTKNQVSLWCLVKGFYPSDIAVEWESNGQPENNYKTTPPVLDSDGSFFLYSKLTV

DKSRWQQGNVFSCSVMHEALHNHYTQKSLSLSPGK

Domain arrangement:
A-  B-  Hinge-  D-  E

VL-  CH3-  Hinge-  CH2-  CH3(knob)

Mutations in domain B:
P343V; Y349C; 445P, 446G, 447K insertion

Mutations in domain E:
S354C, T366W

>BC44 Domain A [SEQ ID NO: 33]
DIQMTQSPSSLSASVGDRVTITCRASQDVNTAVAWYQQKPGKAPKLLIYSASFLYSGV

PSRFSGSRSGTDFTLTISSLQPEDFATYYCQQHYTTPPTFGQGTKVEIKRT

>BC44 Domain B [SEQ ID NO: 34]
VREPQVCTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK

>BC44 Domain D [SEQ ID NO: 35]
APELLGGPSVFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISKAK

-continued

>BC44 Domain E [SEQ ID NO: 36]
GQPREPQVYTLPPCRDELTKNQVSLWCLVKGFYPSDIAVEWESNGQPENNYKTTPPVL

DSDGSFFLYSKLTVDKSRWQQGNVFSCSVMHEALHNHYTQKSLSLSPGK

>BC28 bivalent chain 3 equivalent to SEQ ID NO: 10

>BC28 bivalent chain 4 equivalent to SEQ ID NO: 11

>BC28 1x2 chain 3 [SEQ ID NO: 37]
DIQMTQSPSSLSASVGDRVTITCRASQDVNTAVAWYQQKPGKAPKLLIYSASF

LYSGVPSRFSGSRSGTDFTLTISSLQPEDFATYYCQQHYTTPPTFGQGTKVEI

KRTPREPQVCTLPPSRDELTKNQVSLTCLVKGFYPSDIAVEWESNGQPENNYK

TTPPVLDSDGSFFLYSKLTVDKSRWQQGNVFSCSVMHEALHNHYTQKSLSLSP

GK*GSGSGSEIVLTQSPATLSLSPGERATLSCRASQSVSSYLAWYQQKPGQAPRL*

*LIYDASNRATGIPARFSGSGSGTDFTLTISSLEPEDFAVYYCQQSSNWPRTFGQ*

*GTKVEIKRTVAAPSVFIFPPSDEQLKSGTASVVCLLNNFYPREAKVQWKVD*

NALQSGNSQESVTEQDSKDSTYSLSSTLTLSKADYEKHKVYACEVTHQGLSSP

VTKSFNRGEC*DKTHTCPPCP*APELLGGPSVFLFPPKPKDTLMISRTPEVTCVV

VDVSHEDPEVKFNWYVDGVEVHNAKTKPREEQYNSTYRVVSVLTVLHQDWLNG

KEYKCKVSNKALPAPIEKTISKAK*GQPREPQVCTLPPSREEMTKNQVSLSCAV*

*KGFYPSDIAVEWESNGQPENNYKTTPPVLDSDGSFFLVSKLTVDKSRWQQGNV*

*FSCSVMHEALHNHYTQKSLSLSPGK*

Domain arrangement:
R-  S-    linker-  H-   I-   Hinge-  J-  K-

VL- CH3- *linker*- VL- CL- Hinge- CH2- *CH3(hole)*

Mutations in domain S:
Y349C; 445P, 446G, 447K insertion

Six amino acids linker insertion: GSGSGS (SEQ ID NO: 541)

Mutations in domain K:
Y349C, D356E, L358M, T366S, L368A, Y407V

>BC28 1x2 domain R [SEQ ID NO: 38]
DIQMTQSPSSLSASVGDRVTITCRASQDVNTAVAWYQQKPGKAPKLLIYSASFLYSGV

PSRFSGSRSGTDFTLTISSLQPEDFATYYCQQHYTTPPTFGQGTKVEIKRT

>BC28 1x2 domain S [SEQ ID NO: 39]
PREPQVCTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK

>BC28 1x2 linker [SEQ ID NO: 40]
GSGSGS

>BC28 1x2 domain H [SEQ ID NO: 41]
EIVLTQSPATLSLSPGERATLSCRASQSVSSYLAWYQQKPGQAPRLLIYDASNRATGI

PARFSGSGSGTDFTLTISSLEPEDFAVYYCQQSSNWPRTFGQGTKVEIK

>BC28 1x2 domain I [SEQ ID NO: 42]
RTVAAPSVFIFPPSDEQLKSGTASVVCLLNNFYPREAKVQWKVDNALQSGNSQESVTE

QDSKDSTYSLSSTLTLSKADYEKHKVYACEVTHQGLSSPVTKSFNRGEC

>BC28 1x2 domain J [SEQ ID NO: 43]
APELLGGPSVFLEPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISKAK

>BC28 1x2 domain K [SEQ ID NO: 44]
GQPREPQVCTLPPSREEMTKNQVSLSCAVKGFYPSDIAVEWESNGQPENNYKTTPPVL

DSDGSFFLVSKLTVDKSRWQQGNVFSCSVMHEALHNHYTQKSLSLSPGK

-continued

```
>BC28-1x1x1a chain 3 [SEQ ID NO: 45]
DIQMTQSPSSLSASVGDRVTITCRASQSVSSAVAWYQQKPGKAPKLLIYSASS

LYSGVPSRFSGSRSGTDFTLTISSLQPEDFATYYCQQRDSYLWTFGQGTKVEI

KRTPREPQVYTLPPSRDELTKNQVSLKCLVKGFYPSDIAVEWESNGQPENNYK

TTPPVLDSDGSFFLYSKLTVDKSRWQQGNVFSCSVMHEALHNHYTQKSLSLSK

SCGSGSGSEIVLTQSPATLSLSPGERATLSCRASQSVSSYLAWYQQKPGQAPRL

LIYDASNRATGIPARFSGSGSGTDFTLTISSLEPEDFAVYYCQQSSNWPRTFGQ

GTKVEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGLSSP

VTKSFNRGECDKTHTCPPCPAPELLGGPSVFLFPPKPKDTLMISRTPEVTCVV

VDVSHEDPEVKFNWYVDGVEVHNAKTKPREEQYNSTYRVVSVLTVLHQDWLNG

KEYKCKVSNKALPAPIEKTISKAKGQPREPQVCTLPPSREEMTKNQVSLSCAV

KGFYPSDIAVEWESNGQPENNYKTTPPVLDSDGSFFLVSKLTVDKSRWQQGN

VFSCSVMHEALHNHYTQKSLSLSPGK

Domain arrangement:
R-  S-   linker- H-  I-  Hinge- J- K-

VL- CH3- linker- VL- CL- Hinge- CH2- CH3(hole)

Mutations in domain S:
T366K; 445K, 446S, 447C insertion

Six amino acids linker insertion: GSGSGS (SEQ ID NO: 541)

Mutations in domain K:
Y349C, D356E, L358M, T366S, L368A, Y407V

>BC28-1x1x1a domain R [SEQ ID NO: 46]
DIQMTQSPSSLSASVGDRVTITCRASQSVSSAVAWYQQKPGKAPKLLIYSASSLYSGV

PSRFSGSRSGTDFTLTISSLQPEDFATYYCQQRDSYLWTFGQGTKVEIKRT

>BC28-1x1x1a domain S [SEQ ID NO: 47]
PREPQVYTLPPSRDELTKNQVSLKCLVKGFYPSDIAVEWESNGQPENNYKTTPPVLDS

DGSFFLYSKLTVDKSRWQQGNVFSCSVMHEALHNHYTQKSLSLSKSC

>BC28-1x1x1a linker [SEQ ID NO: 48]
GSGSGS

>BC28-1x1x1a domain H [SEQ ID NO: 49]
EIVLTQSPATLSLSPGERATLSCRASQSVSSYLAWYQQKPGQAPRLLIYDASNRATGI

PARFSGSGSGTDFTLTISSLEPEDFAVYYCQQSSNWPRTFGQGTKVEIK

>BC28-1x1x1a domain I [SEQ ID NO: 50]
RTVAAPSVFIFPPSDEQLKSGTASVVCLLNNFYPREAKVQWKVDNALQSGNSQESVTE

QDSKDSTYSLSSTLTLSKADYEKHKVYACEVTHQGLSSPVTKSFNRGEC

>BC28-1x1x1a domain J [SEQ ID NO: 51]
APELLGGPSVFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISKAK

>BC28-1x1x1a domain K [SEQ ID NO: 52]
GQPREPQVCTLPPSREEMTKNQVSLSCAVKGFYPSDIAVEWESNGQPENNYKTTPPVL

DSDGSFFLVSKLTVDKSRWQQGNVFSCSVMHEALHNHYTQKSLSLSPGK
```

```
-continued
>hCTLA4-4.chain 2 [SEQ ID NO: 53]
EVQLVESGGGLVQPGGSLRLSCAASGFTFSTYYIHWVRQAPGKGLEWVAVIYPYTGFT

YYADSVKGRFTISADTSKNTAYLQMNSLRAEDTAVYYCARGEYTVLDYWGQGTLVTVS

SASPREPQVYTDPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSGEC

Domain arrangement:
F- G

VH- CH3

Mutations in domain G
L351D, 445G, 446E, 447C insertion

>hCTLA4-4 domain F [SEQ ID NO: 54]
EVQLVESGGGLVQPGGSLRLSCAASGFTFSTYYIHWVRQAPGKGLEWVAVIYPYTGFT

YYADSVKGRFTISADTSKNTAYLQMNSLRAEDTAVYYCARGEYTVLDYWGQGTLVTVS

SAS

>hCTLA4-4 domain G [SEQ ID NO: 55]
PREPQVYTDPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSGEC

Other Sequences:
>Hinge: DKTHTCPPCP [SEQ ID NO: 56]

>BC1-Polypeptide 1 Domain Junction: IKRTPREP [SEQ ID NO: 57]

>BC15-Polypeptide 1 Domain Junction: IKRTVREP [SEQ ID NO: 58]

>BC16-Polypeptide 1 Domain Junction: IKRTREP [SEQ ID NO: 59]

>BC17-Polypeptide 1 Domain Junction: IKRTVPREP [SEQ ID NO: 60]

>BC26-Polypeptide 1 Domain Junction: IKRTVAEP [SEQ ID NO: 61]

>BC27-Polypeptide 1 Domain Junction: IKRTVAPREP [SEQ ID NO: 62]

>BC1-Polypeptide 2 Domain Junction: SSASPREP [SEQ ID NO: 63]

>BC13-Polypeptide 2 Domain Junction: SSASTREP [SEQ ID NO: 64]

>BC14-Polypeptide 2 Domain Junction: SSASTPREP [SEQ ID NO: 65]

>BC24-Polypeptide 2 Domain Junction: SSASTKGEP [SEQ ID NO: 66]

>BC25-Polypeptide 2 Domain Junction: SSASTKGREP [SEQ ID NO: 67]

>SP34-89 VH [SEQ ID NO: 68]
EVQLVESGGGLVQPGGSLRLSCAASGFTFNTYAMNWVRQAPGKGLEWVARIRSKYNNY

ATYYADSVKGRFSISRDDSKNTAYLQMNSLRAEDTAVYYCVRHGNFGNSYVSWFAYWG

QGTLVTV

>SP34-89 VL [SEQ ID NO: 69]
QAVVTQEPSLTVSPGGTVTLTCRSSTGAVTTSNYANWVQQKPGQAPRGLIGGTNKRAP

WTPARFSGSLLGGKAALTITGAQAEDEADYYCALWYSNLWVFGGGTKLTVL

>SP34-89 VH-N30S VH [SEQ ID NO: 70] lower case
denotes mutation
EVQLVESGGGLVQPGGSLRLSCAASGFTFsTYAMNWVRQAPGKGLEWVARIRSKYNNY

ATYYADSVKGRFSISRDDSKNTAYLQMNSLRAEDTAVYYCVRHGNFGNSYVSWFAYWG

QGTLVTV

>SP34-89 VH-G65D VH [SEQ ID NO: 71] lower case
denotes mutation
EVQLVESGGGLVQPGGSLRLSCAASGFTFNTYAMNWVRQAPGKGLEWVARIRSKYNNY ATYYADSVKdRFSISRDDSKNTAYLQMNSLRAEDTAVYYCVRHGNFGNSYVSWFAYWG

QGTLVTV
```

-continued

>SP34-89 VH-S68T VH [SEQ ID NO: 72] lower case
denotes mutation
EVQLVESGGGLVQPGGSLRLSCAASGFTFNTYAMNWVRQAPGKGLEWVARIRSKYNNY ATYYADSVKGRFtISRDDSKNTAYLQMNSLRAEDTAVYYCVRHGNFGNSYVSWFAYWG

QGTLVTV

>SP34-89 VL-W57G VL [SEQ ID NO: 73] lower case
denotes mutation
QAVVTQEPSLTVSPGGTVTLTCRSSTGAVTTSNYANWVQQKPGQAPRGLIGGTNKRAP gTPARFSGSLLGGKAALTITGAQAEDEADYYCALWYSNLWVFGGGTKLTVL >Phage display heavy chain [SEQ ID NO: 74]:
EVQLVESGGGLVQPGGSLRLSCAASGFTExxxx*IH*WVRQAPGKGLEWVAxxxx xxxxxxx*YADSVKG*RFTISADTSKNTAYLQMNSLRAEDTAVYYCARxxxxxxxxxx xxx*DY*WGQGTLVTVSSASTKGPSVFPLAPSSKSTSGGTAALGCLVKDYFPEPV

TVSWNSGALTSGVHTFPAVLQSSGLYSLSSVVTVPSSSLGTQTYICNVNHKPS

NTKVDKKVEPKSCDKTHTCPPCPAPELLGGPSVFLFPPKPKDTLMISRTPEVT

CVVVDVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQVSLT

CLVKGFYPSDIAVEWESNGQPENNYKTTPPVLDSDGSFFLYSKLTVDKSRWQQ

GNVFSCSVMHEALHNHYTQKSLSLSPGK

>Phage display light chain [SEQ ID NO: 75]:
DIQMTQSPSSLSASVGDRVTITC*RASQSVSSA*VAWYQQKPGKAPKLLIY*SASSL*

*YS*GVPSRFSGSRSGTDFTLTISSLQPEDFATYYC*QQ*xxxxxx*TF*GQGTKVEIKRT

VAAPSVFIFPPSDSQLKSGTASVVCLLNNFYPREAKVQWKVDNALQSGNSQES

VTEQDSKDSTYSLSSTLTLSKADYEKHKVYACEVTHQGLSSPVTKSFNRGEC

>B-Body Domain A/H Scaffold [SEQ ID NO: 76]:
DIQMTQSPSSLSASVGDRVTITC*RASQSVSSA*VAWYQQKPGKAPKLLIY*SASSL*

*YS*GVPSRFSGSRSGTDFTLTISSLQPEDFATYYC*QQ*xxxxxx*TF*GQGTKVEIKRT

>B-Body Domain F/L Scaffold [SEQ ID NO: 77]:
EVQLVESGGGLVQPGGSLRLSCAASGFTFxxxx*IH*WVRQAPGKGLEWVAxxxx xxxxxxx*YADSVKG*RFTISADTSKNTAYLQMNSLRAEDTAVYYCARxxxxxxxxxx xxx*DY*WGQGTLVTVSSAS >BC1 Chain 1 Scaffold [SEQ ID NO: 78]
DIQMTQSPSSLSASVGDRVTITC*RASQSVSSA*VAWYQQKPGKAPKLLIY*SASSL*

*YS*GVPSRFSGSRSGTDFTLTISSLQPEDFATYYC*QQ*xxxxxx*TF*GQGTKVEIKRT<u>P</u>

<u>REPQVYTLPPSRDELTKNQVSLKCLVKGFYPSDIAVEWESNGQPENNYKTTPP</u>

<u>VLDSDGSFFLYSKLTVDKSRWQQGNVFSCSVMHEALHNHYTQKSLSLSKSC</u>DK

THTCPPCPAPELLGGPSVFLFPPKPKDTLMISRTPEVTCVVVDVSHEDPEVKF

NWYVDGVEVHNAKTKPREEQYNSTYRVVSVLTVLHQDWLNGKEYKCKVSNKAL

PAPIEKTISKAK*GQPREPQVYTLPPCRDELTKNQVSLWCLVKGFYPSDIAVEW*

*ESNGQPENNYKTTPPVLDSDGSFFLYSKLTVDKSRWQQGNVFSCSVMHEALHN*

*HYTQKSLSLSPGK*

"x" represents CDR amino acids that were varied to create the
library, and bold italic represents the CDR sequences that
were constant -continued Domain arrangement:
A- B- Hinge- D- E VL- CH3- Hinge- CH2- CH3(knob)

Mutations in first CH3 (Domain B):
T366K; 445K, 446S, 447C insertion

Mutations in second CH3 (Domain E):
S354C, T366W

>BC1 Chain 2 Scaffold [SEQ ID NO: 79]
EVQLVESGGGLVQPGGSLRLSCAASGFTFxxxx*IH*WVRQAPGKGLEWVAxxxx xxxxxxx*YADSVKG*RFTISADTSKNTAYLQMNSLRAEDTAVYYCARxxxxxxxxxx xxx*DY*WGQGTLVTVSSASPREPQVYTDPPSRDELTKNQVSLTCLVKGFYPSDIA

VEWESNGQPENNYKTTPPVLDSDGSFFLYSKLTVDKSRWQQGNVFSCSVMHEAL

HNHYTQKSLSLSGEC

"x" represents CDR amino acids that were varied to create the
library, and bold italic represents the CDR sequences that
were constant Domain arrangement:
F- G

VH- CH3

Mutations in CH3 (Domain G):
L351D; 445G, 446E, 447C insertion

>BC1 Chain 3 Scaffold [SEQ ID NO: 80]
DIQMTQSPSSLSASVGDRVTITC*RASQSVSSA*VAWYQQKPGKAPKLLIY*SASSL*

*YS*GVPSRFSGSRSGTDFTLTISSLQPEDFATYYC*QQ*xxxxxx*TF*GQGTKVEIKRT

VAAPSVFIFPPSDEQLKSGTASVVCLLNNFYPREAKVQWKVDNALQSGNSQES

VTEQDSKDSTYSLSSTLTLSKADYEKHKVYACEVTHQGLSSPVTKSFNRGEC*D*

*KTHTCPPCP*APELLGGPSVFLFPPKPKDTLMISRTPEVTCVVVDVSHEDPEVK

FNWYVDGVEVHNAKTKPREEQYNSTYRVVSVLTVLHQDWLNGKEYKCKVSNKA

LPAPIEKTISKAK*GQPREPQVCTLPPSREEMTKNQVSLSCAVKGFYPSDIAVE*

*WESNGQPENNYKTTPPVLDSDGSFFLVSKLTVDKSRWQQGNVFSCSVMHEALH*

*NHYTQKSLSLSPGK*

"x" represents CDR amino acids that were varied to create the
library, and bold italic represents the CDR sequences that
were constant Domain arrangement:
H- I- Hinge- J- K VL- CL- Hinge- CH2- CH3(hole)

Mutations in CH3 (domain K):
Y349C, D356E, L358M, T366S, L368A, Y407V

>BC1 Chain 4 Scaffold [SEQ ID NO: 81]
EVQLVESGGGLVQPGGSLRLSCAASGFTFxxxx*IH*WVRQAPGKGLEWVAxxxx xxxxxxx*YADSVKG*RFTISADTSKNTAYLQMNSLRAEDTAVYYCARxxxxxxxxxx xxx*DY*WGQGTLVTVSSASTKGPSVFPLAPSSKSTSGGTAALGCLVKDYFPEPV

TVSWNSGALTSGVHTFPAVLQSSGLYSLSSVVTVPSSSLGTQTYICNVNHKPS

NTKVDKKVEPPKSC

"x" represents CDR amino acids that were varied to create the
library, and bold italic represents the CDR sequences that
were constant -continued Domain arrangement:
L- M

VH- CH1

>BC1 Chain 3 1(A)x2(B-A) SP34-89 Scaffold [SEQ ID NO: 82]
DIQMTQSPSSLSASVGDRVTITC*RASQSVSSA*VAWYQQKPGKAPKLLIY*SASSL*

*YS*GVPSRFSGSRSGTDFTLTISSLQPEDFATYYC*QQ*xxxxxx*TF*GQGTKVEIKRTP

REPQVYTLPPSRDELTKNQVSLKCLVKGFYPSDIAVEWESNGQPENNYKTTPP

VLDSDGSFFLYSKLTVDKSRWQQGNVFSCSVMHEALHNHYTQKSLSLSKSCT

*ASSGGSSSG*QAVVTQEPSLTVSPGGTVTLTCRSSTGAVTTSNYANWVQQKPGQ

APRGLIGGTNKRAPWTPARFSGSLLGGKAALTITGAQAEDEADYYCALWYSNL

WVFGGGTKLTVLGRTVAAPSVFIFPPSDEQLKSGTASVVCLLNNFYPREAKVQ

WKVDNALQSGNSQESVTEQDSKDSTYSLSSTLTLSKADYEKHKVYACEVTHQG

LSSPVTKSFNRGECDKTHTCPPCPAPEAAGGPSVFLFPPKPKDTLMISRTPEV

TCVVVDVSHEDPEVKFNWYVDGVEVHNAKTKPREEQYNSTYRVVSVLTVLHQD

WLNGKEYKCKVSNKALKAPIEKTISKAK*GQPREPQVCTLPPSREEMTKNQVSL*

*SCAVKGFYPSDIAVEWESNGQPENNYKTTPPVLDSDGSFFLVSKLTVDKSRWQ*

*QGNVFSCSVMHEALHNHYTQKSLSLSPGK*

"x" represents CDR amino acids that were varied to create the
library, and bold italic represents the CDR sequences that
were constant Domain arrangement:
R- S- linker- H- I- Hinge- J- K VL- CH3- *linker*- SP34- CL- Hinge- CH2- *CH3(hole)*

Mutations in domain S:
T366K; 445K, 446S, 447C insertion

Ten amino acids linker insertion: TASSGGSSSG (SEQ ID NO: 83)

Mutations in Domain J:
L234A, L235A, and P329K

Mutations in domain K:
Y349C, D356E, L358M, T366S, L368A, Y407V

>BC1 Chain 3 1(A)x2(B-A) SP34-89 S-H Junction [SEQ ID NO: 83]
TASSGGSSSG

>I2A-10 Chain 1 BC1 1x1 [SEQ ID NO: 84]
DIQMTQSPSSLSASVGDRVTITCRASQSVSSAVAWYQQKPGKAPKLLIYSASSLYSGV

PSRFSGSRSGTDFTLTISSLQPEDFATYYCQQYYYYPGTFGQGTKVEIKRTPREPQVY

TLPPSRDELTKNQVSLKCLVKGFYPSDIAVEWESNGQPENNYKTTPPVLDSDGSFFLY

SKLTVDKSRWQQGNVFSCSVMHEALHNHYTQKSLSLSKSCDKTHTCPPCPAPEAAGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALKAPIEKTISKAKGQPREPQVYTLPPC

RDELTKNQVSLWCLVKGFYPSDIAVEWESNGQPENNYKTTPPVLDSDGSFFLYSKLTV

DKSRWQQGNVFSCSVMHEALHNHYTQKSLSLSPGK

>I2A-10 Chain 2 BC1 1x1 [SEQ ID NO: 85]
EVQLVESGGGLVQPGGSLRLSCAASGFTFSSYFIHWVRQAPGKGLEWVAGIYPSDGYT

SYADSVKGRFTISADTSKNTAYLQMNSLRAEDTAVYYCARYYSGMDYWGQGTLVTVSS

ASPREPQVYTDPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSGEC

>I2A-10 Chain 3 BC1 1x1 [SEQ ID NO: 86]
QAVVTQEPSLTVSPGGTVTLTCRSSTGAVTTSNYANWVQQKPGQAPRGLIGGTNKRAP

WTPARFSGSLLGGKAALTITGAQAEDEADYYCALWYSNLWVFGGGTKLTVLGRTVAAP

SVFIFPPPSDEQLKSGTASVVCLLNNFYPREAKVQWKVDNALQSGNSQESVTEQDSKDS

TYSLSSTLTLSKADYEKHKVYACEVTHQGLSSPVTKSFNRGECDKTHTCPPCPAPEAA

GGPSVFLFPPKPKDTLMISRTPEVTCVVVDVSHEDPEVKFNWYVDGVEVHNAKTKPRE

EQYNSTYRVVSVLTVLHQDWLNGKEYKCKVSNKALKAPIEKTISKAKGQPREPQVCTL

PPSREEMTKNQVSLSCAVKGFYPSDIAVEWESNGQPENNYKTTPPVLDSDGSFFLVSK

LTVDKSRWQQGNVFSCSVMHEALHNHYTQKSLSLSPGK

>I2A-10 Chain 4 BC1 1x1 [SEQ ID NO: 87]
EVQLVESGGGLVQPGGSLRLSCAASGFTFNTYAMNWVRQAPGKGLEWVARIRSKYNNY

ATYYADSVKGRFSISRDDSKNTAYLQMNSLRAEDTAVYYCVRHGNFGNSYVSWFAYWG

QGTLVTVSSASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKVEPPKSC

>I2A-10 Chain 3 BC1 1x2 [SEQ ID NO: 88]
DIQMTQSPSSLSASVGDRVTITCRASQSVSSAVAWYQQKPGKAPKLLIYSASSLYSGV

PSRFSGSRSGTDFTLTISSLQPEDFATYYCQQYYYYPGTFGQGTKVEIKRTPREPQVY

TLPPSRDELTKNQVSLKCLVKGFYPSDIAVEWESNGQPENNYKTTPPVLDSDGSFFLY

SKLTVDKSRWQQGNVFSCSVMHEALHNHYTQKSLSLSKSCTASSGGSSSGQAVVTQEP

SLTVSPGGTVTLTCRSSTGAVTTSNYANWVQQKPGQAPRGLIGGTNKRAPWTPARFSG

SLLGGKAALTITGAQAEDEADYYCALWYSNLWVFGGGTKLTVLGRTVAAPSVFIFPPS

DEQLKSGTASVVCLLNNFYPREAKVQWKVDNALQSGNSQESVTEQDSKDSTYSLSSTL

TLSKADYEKHKVYACEVTHQGLSSPVTKSFNRGECDKTHTCPPCPAPEAAGGPSVFLF

PPKPKDTLMISRTPEVTCVVVDVSHEDPEVKFNWYVDGVEVHNAKTKPREEQYNSTYR

VVSVLTVLHQDWLNGKEYKCKVSNKALKAPIEKTISKAKGQPREPQVCTLPPSREEMT

KNQVSLSCAVKGFYPSDIAVEWESNGQPENNYKTTPPVLDSDGSFFLVSKLTVDKSRW

QQGNVFSCSVMHEALHNHYTQKSLSLSPGK

>I2A-27 Chain 1 BC1 1x1 [SEQ ID NO: 89]
DIQMTQSPSSLSASVGDRVTITCRASQSVSSAVAWYQQKPGKAPKLLIYSASSLYSGV

PSRFSGSRSGTDFTLTISSLQPEDFATYYCQQYYSSPRTFGQGTKVEIKRTPREPQVY

TLPPSRDELTKNQVSLKCLVKGFYPSDIAVEWESNGQPENNYKTTPPVLDSDGSFFLY

SKLTVDKSRWQQGNVFSCSVMHEALHNHYTQKSLSLSKSCDKTHTCPPCPAPEAAGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALKAPIEKTISKAKGQPREPQVYTLPPC

RDELTKNQVSLWCLVKGFYPSDIAVEWESNGQPENNYKTTPPVLDSDGSFFLYSKLTV

DKSRWQQGNVFSCSVMHEALHNHYTQKSLSLSPGK

>I2A-27 Chain 2 BC1 1x1 [SEQ ID NO: 90]
EVQLVESGGGLVQPGGSLRLSCAASGFTFKGYYIHWVRQAPGKGLEWVAAIYPYGGST

DYADSVKGRFTISADTSKNTAYLQMNSLRAEDTAVYYCARVYIYGVFDYWGQGTLVTV

SSASPREPQVYTDPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSGEC

>I2A-27 Chain 3 BC1 1x1 [SEQ ID NO: 91]
QAVVTQEPSLTVSPGGTVTLTCRSSTGAVTTSNYANWVQQKPGQAPRGLIGGTNKRAP

WTPARFSGSLLGGKAALTITGAQAEDEADYYCALWYSNLWVFGGGTKLTVLGRTVAAP

-continued

SVFIFPPSDEQLKSGTASVVCLLNNFYPREAKVQWKVDNALQSGNSQESVTEQDSKDS

TYSLSSTLTLSKADYEKHKVYACEVTHQGLSSPVTKSFNRGECDKTHTCPPCPAPEAA

GGPSVFLFPPKPKDTLMISRTPEVTCVVVDVSHEDPEVKFNWYVDGVEVHNAKTKPRE

EQYNSTYRVVSVLTVLHQDWLNGKEYKCKVSNKALKAPIEKTISKAKGQPREPQVCTL

PPSREEMTKNQVSLSCAVKGFYPSDIAVEWESNGQPENNYKTTPPVLDSDGSFFLVSK

LTVDKSRWQQGNVFSCSVMHEALHNHYTQKSLSLSPGK

>I2A-27 Chain 4 BC1 1x1 [SEQ ID NO: 92]
EVQLVESGGGLVQPGGSLRLSCAASGFTFNTYAMNWVRQAPGKGLEWVARIRSKYNNY

ATYYADSVKGRFSISRDDSKNTAYLQMNSLRAEDTAVYYCVRHGNFGNSYVSWFAYWG

QGTLVTVSSASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKVEPPKSC

>I2A-27 Chain 3 BC1 1x2 [SEQ ID NO: 93]
DIQMTQSPSSLSASVGDRVTITCRASQSVSSAVAWYQQKPGKAPKLLIYSASSLYSGV

PSRFSGSRSGTDFTLTISSLQPEDFATYYCQQYSSPRTFGQGTKVEIKRTPREPQVY

TLPPSRDELTKNQVSLKCLVKGFYPSDIAVEWESNGQPENNYKTTPPVLDSDGSFFLY

SKLTVDKSRWQQGNVFSCSVMHEALHNHYTQKSLSLSKSCTASSGGSSSGQAVVTQEP

SLTVSPGGTVTLTCRSSTGAVTTSNYANWVQQKPGQAPRGLIGGTNKRAPWTPARFSG

SLLGGKAALTITGAQAEDEADYYCALWYSNLWVFGGGTKLTVLGRTVAAPSVFIFPPS

DEQLKSGTASVVCLLNNFYPREAKVQWKVDNALQSGNSQESVTEQDSKDSTYSLSSTL

TLSKADYEKHKVYACEVTHQGLSSPVTKSFNRGECDKTHTCPPCPAPEAAGGPSVFLF

PPKPKDTLMISRTPEVTCVVVDVSHEDPEVKFNWYVDGVEVHNAKTKPREEQYNSTYR

VVSVLTVLHQDWLNGKEYKCKVSNKALKAPIEKTISKAKGQPREPQVCTLPPSREEMT

KNQVSLSCAVKGFYPSDIAVEWESNGQPENNYKTTPPVLDSDGSFFLVSKLTVDKSRW

QQGNVFSCSVMHEALHNHYTQKSLSLSPGK

>Human ROR1 (UniProt accession #Q01973) [SEQ ID NO: 94]
MHRPRRRGTRPPLLALLAALLLAARGAAAQETELSVSAELVPTSSWNISSELNKDSYL

TLDEPMNNITTSLGQTAELHCKVSGNPPPTIRWFKNDAPVVQEPRRLSFRSTIYGSRL

RIRNLDTTDTGYFQCVATNGKEVVSSTGVLFVKFGPPPTASPGYSDEYEEDGFCQPYR

GIACARFIGNRTVYMESLHMQGEIENQITAAFTMIGTSSHLSDKCSQFAIPSLCHYAF

PYCDETSSVPKPRDLCRDECEILENVLCQTEYIFARSNPMILMRLKLPNCEDLPQPES

PEAANCIRIGIPMADPINKNHKCYNSTGVDYRGTVSVTKSGRQCQPWNSQYPHTHTFT

ALRFPELNGGHSYCRNPGNQKEAPWCFTLDENFKSDLCDIPACDSKDSKEKNKMEILY

ILVPSVAIPLAIALLFFFICVCRNNQKSSSAPVQRQPKHVRGQNVEMSMLNAYKPKSK

AKELPLSAVRFMEELGECAFGKIYKGHLYLPGMDHAQLVAIKTLKDYNNPQQWTEFQQ

EASLMAELHHPNIVCLLGAVTQEQPVCMLFEYINQGDLHEFLIMRSPHSDVGCSSDED

GTVKSSLDHGDFLHIAIQIAAGMEYLSSHFFVHKDLAARNILIGEQLHVKISDLGLSR

EIYSADYYRVQSKSLLPIRWMPPEAIMYGKFSSDSDIWSFGVVLWEIFSFGLQPYYGF

SNQEVIEMVRKRQLLPCSEDCPPRMYSLMTECWNEIPSRRPRFKDIHVRLRSWEGLSS

HTSSTTPSGGNATTQTTSLSASPVSNLSNPRYPNYMFPSQGITPQGQIAGFIGPPIPQ

NQRFIPINGYPIPPGYAAFPAAHYQPTGPPRVIQHCPPPKSRSPSSASGSTSTGHVTS

LPSSGSNQEANIPLLPHMSIPNHPGGMGITVFGNKSQKPYKIDSKQASLLGDANIHGH

TESMISAEL

```
>Human ROR2 (UniProt accession #Q01974) [SEQ ID NO: 95]
MARGSALPRRPLLCIPAVWAAAALLLSVSRTSGEVEVLDPNDPLGPLDGQDGPIPTLK

GYFLNFLEPVNNITIVQGQTAILHCKVAGNPPPNVRWLKNDAPVVQEPRRIIIRKTEY

GSRLRIQDLDTTDTGYYQCVATNGMKTITATGVLFVRLGPTHSPNHNFQDDYHEDGFC

QPYRGIACARFIGNRTIYVDSLQMQGEIENRITAAFTMIGTSTHLSDQCSQFAIPSFC

HFVFPLCDARSRTPKPRELCRDECEVLESDLCRQEYTIARSNPLILMRLQLPKCEALP

MPESPDAANCMRIGIPAERLGRYHQCYNGSGMDYRGTASTTKSGHQCQPWALQHPHSH

HLSSTDFPELGGGHAYCRNPGGQMEGPWCFTQNKNVRMELCDVPSCSPRDSSKMGILY

ILVPSIAIPLVIACLFFLVCMCRNKQKASASTPQRRQLMASPSQDMEMPLINQHKQAK

LKEISLSAVRFMEELGEDRFGKVYKGHLFGPAPGEQTQAVAIKTLKDKAEGPLREEFR

HEAMLRARLQHPNVVCLLGVVTKDQPLSMIFSYCSHGDLHEFLVMRSPHSDVGSTDDD

RTVKSALEPPDFVHLVAQIAAGMEYLSSHHVVHKDLATRNVLVYDKLNVKISDLGLFR

EVYAADYYKLLGNSLLPIRWMAPEAIMYGKFSIDSDIWSYGVVLWEVFSYGLQPYCGY

SNQDVVEMIRNRQVLPCPDDCPAWVYALMIECWNEFPSRRPRFKDIHSRLRAWGNLSN

YNSSAQTSGASNTTQTSSLSTSPVSNVSNARYVGPKQKAPPFPQPQFIPMKGQIRPMV

PPPQLYVPVNGYQPVPAYGAYLPNFYPVQIPMQMAPQQVPPQMVPKPSSHHSGSGSTS

TGYVTTAPSNTSMADRAALLSEGADDTQNAPEDGAQSTVQEAEEEEEGSVPETELLGD

CDTLQVDEAQVQLEA

I2A-27 Chain 1 [SEQ ID NO: 96]
DIQMTQSPSSLSASVGDRVTITCRASQSVSSAVAWYQQKPGKAPKLLIYSASSLYSGV

PSRFSGSRSGTDFTLTISSLQPEDFATYYCQQYYSSPRTFGQGTKVEIKRTPREPQVY

TLPPSRDELTKNQVSLKCLVKGFYPSDIAVEWESNGQPENNYKTTPPVLDSDGSFFLY

SKLTVDKSRWQQGNVFSCSVMHEALHNHYTQKSLSLSKSCDKTHTCPPCPAPEAAGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALKAPIEKTISKAKGQPREPQVCTLPPS

REEMTKNQVSLSCAVKGFYPSDIAVEWESNGQPENNYKTTPPVLDSDGSFFLVSKLTV

DKSRWQQGNVFSCSVMHEALHNHYTQKSLSLSPGK

Domain arrangement:
A-  B-  Hinge- D-  E

VL- CH3- Hinge- CH2- CH3(hole)

Mutations in first CH3 (Domain B):
T366K; 445K, 446S, 447C insertion

Hinge sequence: DKTHTCPPCP (SEQ ID NO: 56)

Mutations in second CH3 (Domain E):
Y349C, D356E, L358M, T366S, L368A, Y407V

Exemplary signal sequence for Chain 1:
MGWSLILLFLVAVATRVLS (SEQ ID NO: 150)

>I2A-27 Chain 2 [SEQ ID NO: 97]
EVQLVESGGGLVQPGGSLRLSCAASGFTFKGYYIHWVRQAPGKGLEWVAAIYPYGGST

DYADSVKGRFTISADTSKNTAYLQMNSLRAEDTAVYYCARVYIYGVFDYWGQGTLVTV

SSASPREPQVYTDPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSGEC
```

-continued

Domain arrangement:
F-  G

VH- CH3

Mutations in CH3 (Domain G):
L351D; 445G, 446E, 447C insertion

Exemplary signal sequence for Chain 2:
MDFQVQIISFLLISASVIMSRG (SEQ ID NO: 151)

>I2A-27 Chain 3 [SEQ ID NO: 98]
DIQMTQSPSSLSASVGDRVTITCRASQSVSSAVAWYQQKPGKAPKLLIYSASS

LYSGVPSRFSGSRSGTDFTLTISSLQPEDFATYYCQQYYSSPRTFGQGTKVEI

KRTPREPQVYTLPPSRDELTKNQVSLKCLVKGFYPSDIAVEWESNGQPENNYK

TTPPVLDSDGSFFLYSKLTVDKSRWQQGNVFSCSVMHEALHNHYTQKSLSLSK

SCTASSGGSSSGQAVVTQEPSLTVSPGGTVTLTCRSSTGAVTTSNYANWVQQKP

GQAPRGLIGGTNKRAPWTPARFSGSLLGGKAALTITGAQAEDEADYYCALWY

SNLWVFGGGTKLTVLGRTVAAPSVFIFPPSDEQLKSGTASVVCLLNNFYPRE

AKVQWKVDNALQSGNSQESVTEQDSKDSTYSLSSTLTLSKADYEKHKVYACEV

THQGLSSPVTKSFNRGECDKTHTCPPCPAPEAAGGPSVFLFPPKPKDTLMISR

TPEVTCVVVDVSHEDPEVKFNWYVDGVEVHNAKTKPREEQYNSTYRVVSVLTV

LHQDWLNGKEYKCKVSNKALKAPIEKTISKAKGQPREPQVYTLPPCRDELTKN

QVSLWCLVKGFYPSDIAVEWESNGQPENNYKTTPPVLDSDGSFFLYSKLTVDK

SRWQQGNVFSCSVMHEALHNHYTQKSLSLSPGK

Domain arrangement:
R-  S-   linker-  H-  I-  Hinge-  J-  K

VL- CH3- linker- VL- CL- Hinge- CH2- CH3(knob)

Mutations in first CH3 (Domain S):
T366K; 445K, 446S, 447C insertion

Ten amino acid linker insertion: TASSGGSSSG (SEQ ID NO: 83)

Hinge sequence: DKTHTCPPCP (SEQ ID NO: 56)

Mutations in second CH3 (Domain K):
S354C, K366W

Exemplary signal sequence for Chain 3:
MDFQVQIISFLLISASVIMSRGS (SEQ ID NO: 152)

>I2A-27 Chain 4 [SEQ ID NO: 99]
EVQLVESGGGLVQPGGSLRLSCAASGFTFNTYAMNWVRQAPGKGLEWVARIRSKYNNY

ATYYADSVKGRFSISRDDSKNTAYLQMNSLRAEDTAVYYCVRHGNFGNSYVSWFAYWG

QGTLVTVSSASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKVEPPKSC

Domain arrangement:
L-  M

VH- CH1

Exemplary signal sequence for Chain 4:
MDFQVQIISFLLISASVIMSRG (SEQ ID NO: 151)

>I2A-27 Chain 5 [SEQ ID NO: 97]
EVQLVESGGGLVQPGGSLRLSCAASGFTFKGYYIHWVRQAPGKGLEWVAAIYPYGGST

DYADSVKGRFTISADTSKNTAYLQMNSLRAEDTAVYYCARVYIYGVFDYWGQGTLVTV

SSASPREPQVYTDPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSGEC

```
Domain arrangement:
T- U

VH- CH3

Mutations in CH3 (Domain U):
L351D; 445G, 446E, 447C insertion

Exemplary signal sequence for Chain 5:
MDFQVQIISFLLISASVIMSRG (SEQ ID NO: 151)

>I2A-27 Domain A [SEQ ID NO: 100]
DIQMTQSPSSLSASVGDRVTITCRASQSVSSAVAWYQQKPGKAPKLLIYSASSLYSGV

PSRFSGSRSGTDFTLTISSLQPEDFATYYCQQYYSSPRTFGQGTKVEIKRT

>I2A-27 Domain B [SEQ ID NO: 101]
PREPQVYTLPPSRDELTKNQVSLKCLVKGFYPSDIAVEWESNGQPENNYKTTPPVLDS

DGSFFLYSKLTVDKSRWQQGNVFSCSVMHEALHNHYTQKSLSLSKSC

>I2A-27 Domain D [SEQ ID NO: 102]
APEAAGGPSVFLFPPKPKDTLMISRTPEVTCVVVDVSHEDPEVKFNWYVDGVEVHNAK

TKPREEQYNSTYRVVSVLTVLHQDWLNGKEYKCKVSNKALKAPIEKTISKAK

>I2A-27 Domain E [SEQ ID NO: 103]
GQPREPQVCTLPPSREEMTKNQVSLSCAVKGFYPSDIAVEWESNGQPENNYKTTPPVL

DSDGSFFLVSKLTVDKSRWQQGNVFSCSVMHEALHNHYTQKSLSLSPGK

>I2A-27 Domain F [SEQ ID NO: 104]
EVQLVESGGGLVQPGGSLRLSCAASGFTFKGYYIHWVRQAPGKGLEWVAAIYPYGGST

DYADSVKGRFTISADTSKNTAYLQMNSLRAEDTAVYYCARVYIYGVFDYWGQGTLVTV

SSAS

>I2A-27 Domain G [SEQ ID NO: 105]
PREPQVYTDPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSGEC

>I2A-27 Domain R [SEQ ID NO: 106]
DIQMTQSPSSLSASVGDRVTITCRASQSVSSAVAWYQQKPGKAPKLLIYSASSLYSGV

PSRFSGSRSGTDFTLTISSLQPEDFATYYCQQYYSSPRTFGQGTKVEIKRT

>I2A-27 Domain S [SEQ ID NO: 107]
PREPQVYTLPPSRDELTKNQVSLKCLVKGFYPSDIAVEWESNGQPENNYKTTPPVLDS

DGSFFLYSKLTVDKSRWQQGNVFSCSVMHEALHNHYTQKSLSLSKSC

>I2A-27 Domain H [SEQ ID NO: 108]
QAVVTQEPSLTVSPGGTVTLTCRSSTGAVTTSNYANWVQQKPGQAPRGLIGGTNKRAP

WTPARFSGSLLGGKAALTITGAQAEDEADYYCALWYSNLWVFGGGTKLTVLGRTV

>I2A-27 Domain I [SEQ ID NO: 109]
AAPSVFIFPPSDEQLKSGTASVVCLLNNFYPREAKVQWKVDNALQSGNSQESVTEQDS

KDSTYSLSSTLTLSKADYEKHKVYACEVTHQGLSSPVTKSFNRGEC

>I2A-27 Domain J [SEQ ID NO: 110]
APEAAGGPSVFLFPPKPKDTLMISRTPEVTCVVVDVSHEDPEVKFNWYVDGVEVHNAK

TKPREEQYNSTYRVVSVLTVLHQDWLNGKEYKCKVSNKALKAPIEKTISKAK

>I2A-27 Domain K [SEQ ID NO: 111]
GQPREPQVYTLPPCRDELTKNQVSLWCLVKGFYPSDIAVEWESNGQPENNYKTTPPVL

DSDGSFFLYSKLTVDKSRWQQGNVFSCSVMHEALHNHYTQKSLSLSPGK

>I2A-27 Domain L [SEQ ID NO: 112]
EVQLVESGGGLVQPGGSLRLSCAASGFTFNTYAMNWVRQAPGKGLEWVARIRSKYNNY

ATYYADSVKGRFSISRDDSKNTAYLQMNSLRAEDTAVYYCVRHGNFGNSYVSWFAYWG

QGTLVTVSSAS
```

```
>I2A-27 Domain M [SEQ ID NO: 113]
TKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPPKSC

>I2A-27 Domain T [SEQ ID NO: 104]
EVQLVESGGGLVQPGGSLRLSCAASGFTFKGYYIHWVRQAPGKGLEWVAAIYPYGGST

DYADSVKGRFTISADTSKNTAYLQMNSLRAEDTAVYYCARVYIYGVFDYWGQGTLVTV

SSAS

>I2A-27 Domain U [SEQ ID NO: 105]
PREPQVYTDPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSGEC

>I2A-10 Chain 1 [SEQ ID NO: 114]
DIQMTQSPSSLSASVGDRVTITCRASQSVSSAVAWYQQKPGKAPKLLIYSASSLYSGV

PSRFSGSRSGTDFTLTISSLQPEDFATYYCQQYYYYPGTFGQGTKVEIKRTPREPQVY

TLPPSRDELTKNQVSLKCLVKGFYPSDIAVEWESNGQPENNYKTTPPVLDSDGSFFLY

SKLTVDKSRWQQGNVFSCSVMHEALHNHYTQKSLSLSKSCDKTHTCPPCPAPEAAGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALKAPIEKTISKAKGQPREPQVCTLPPS

REEMTKNQVSLSCAVKGFYPSDIAVEWESNGQPENNYKTTPPVLDSDGSFFLVSKLTV

DKSRWQQGNVFSCSVMHEALHNHYTQKSLSLSPGK

Domain arrangement:
A-  B-  Hinge- D-    E

VL- CH3- Hinge- CH2- CH3(hole)

Mutations in first CH3 (Domain B):
T366K; 445K, 446S, 447C insertion

Hinge sequence: DKTHTCPPCP (SEQ ID NO: 56)

Mutations in second CH3 (Domain E):
Y349C, D356E, L358M, T366S, L368A, Y407V

Exemplary signal sequence for Chain 1:
MGWSLILLFLVAVATRVLS (SEQ ID NO: 150)

>I2A-10 Chain 2 [SEQ ID NO: 115]
EVQLVESGGGLVQPGGSLRLSCAASGFTFSSYFIHWVRQAPGKGLEWVAGIYPSDGYT

SYADSVKGRFTISADTSKNTAYLQMNSLRAEDTAVYYCARYYVSGMDYWGQGTLVTVS

SASPREPQVYTDPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSGEC

Domain arrangement:
F-  G

VH- CH3

Mutations in CH3 (Domain G):
L351D; 445G, 446E, 447C insertion

Exemplary signal sequence for Chain 2:
MDFQVQIISFLLISASVIMSRG (SEQ ID NO: 151)

>I2A-10 Chain 3 [SEQ ID NO: 116]
DIQMTQSPSSLSASVGDRVTITCRASQSVSSAVAWYQQKPGKAPKLLIYSASS

LYSGVPSRFSGSRSGTDFTLTISSLQPEDFATYYCQQYYYYPGTFGQGTKVEI

KRTPREPQVYTLPPSRDELTKNQVSLKCLVKGFYPSDIAVEWESNGQPENNYK

TTPPVLDSDGSFFLYSKLTVDKSRWQQGNVFSCSVMHEALHNHYTQKSLSLSK

SCTASSGGSSSGQAVVTQEPSLTVSPGGTVTLTCRSSTGAVTTSNYANWVQQKP
```

-continued

*GQAPRGLIGGTNKRAPWTPARFSGSLLGGKAALTITGAQAEDEADYYCALWY*

*SNLWVFGGGTKLTVLGRT*VAAPSVFIFPPSDEQLKSGTASVVCLLNNFYPRE

AKVQWKVDNALQSGNSQESVTEQDSKDSTYSLSSTLTLSKADYEKHKVYACEV

THQGLSSPVTKSFNRGECDKTHTCPPCPAPEAAGGPSVFLFPPKPKDTLMISR

TPEVTCVVVDVSHEDPEVKFNWYVDGVEVHNAKTKPREEQYNSTYRVVSVLTV

LHQDWLNGKEYKCKVSNKALKAPIEKTISKAK*GQPREPQVYTLPPCRDELTKN*

*QVSLWCLVKGFYPSDIAVEWESNGQPENNYKTTPPVLDSDGSFFLYSKLTVDK*

*SRWQQGNVFSCSVMHEALHNHYTQKSLSLSPGK*

Domain arrangement:
R- S- linker- H- I- Hinge- J- K

VL- CH3- linker- VL- CL- Hinge- CH2- CH3(knob)

Mutations in first CH3 (Domain S):
T366K; 445K, 446S, 447C insertion

Ten amino acid linker insertion: TASSGGSSSG (SEQ ID NO: 83)

Hinge sequence: DKTHTCPPCP (SEQ ID NO: 56)

Mutations in second CH3 (Domain K):
S354C, K366W

Exemplary signal sequence for Chain 3:
MDFQVQIISFLLISASVIMSRGS (SEQ ID NO: 152)

>I2A-10 Chain 4 [SEQ ID NO: 117]
EVQLVESGGGLVQPGGSLRLSCAASGFTFNTYAMNWVRQAPGKGLEWVARIRSKYNNY

ATYYADSVKGRFSISRDDSKNTAYLQMNSLRAEDTAVYYCVRHGNFGNSYVSWFAYWG

QGTLVTVSSASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKVEPPKSC

Domain arrangement:
L- M
VH- CH1

Exemplary signal sequence for Chain 4:
MDFQVQIISFLLISASVIMSRG (SEQ ID NO: 151)

>I2A-10 Chain 5 [SEQ ID NO: 115]
EVQLVESGGGLVQPGGSLRLSCAASGFTFSSYFIHWVRQAPGKGLEWVAGIYPSDGYT

SYADSVKGRFTISADTSKNTAYLQMNSLRAEDTAVYYCARYYVSGMDYWGQGTLVTVS

SASPREPQVYTDPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSGEC

Domain arrangement:
T- U

VH- CH3

Mutations in CH3 (Domain U):
L351D; 445G, 446E, 447C insertion

Exemplary signal sequence for Chain 5:
MDFQVQIISFLLISASVIMSRG (SEQ ID NO: 151)

>I2A-10 Domain A [SEQ ID NO: 118]
DIQMTQSPSSLSASVGDRVTITCRASQSVSSAVAWYQQKPGKAPKLLIYSASSLYSGV

PSRFSGSRSGTDFTLTISSLQPEDFATYYCQQYYYYPGTFGQGTKVEIKRT

>I2A-10 Domain B [SEQ ID NO: 119]
PREPQVYTLPPSRDELTKNQVSLKCLVKGFYPSDIAVEWESNGQPENNYKTTPPVLDS

DGSFFLYSKLTVDKSRWQQGNVFSCSVMHEALHNHYTQKSLSLSKSC

-continued

>I2A-10 Domain D [SEQ ID NO: 120]
APEAAGGPSVFLFPPKPKDTLMISRTPEVTCVVVDVSHEDPEVKFNWYVDGVEVHNAK

TKPREEQYNSTYRVVSVLTVLHQDWLNGKEYKCKVSNKALKAPIEKTISKAK

>I2A-10 Domain E [SEQ ID NO: 121]
GQPREPQVCTLPPSREEMTKNQVSLSCAVKGFYPSDIAVEWESNGQPENNYKTTPPVL

DSDGSFFLVSKLTVDKSRWQQGNVFSCSVMHEALHNHYTQKSLSLSPGK

>I2A-10 Domain F [SEQ ID NO: 122]
EVQLVESGGGLVQPGGSLRLSCAASGFTFSSYFIHWVRQAPGKGLEWVAGIYPSDGYT

SYADSVKGRFTISADTSKNTAYLQMNSLRAEDTAVYYCARYYVSGMDYWGQGTLVTVS

SAS

>I2A-10 Domain G [SEQ ID NO: 123]
PREPQVYTDPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSGEC

>I2A-10 Domain R [SEQ ID NO: 124]
DIQMTQSPSSLSASVGDRVTITCRASQSVSSAVAWYQQKPGKAPKLLIYSASSLYSGV

PSRFSGSRSGTDFTLTISSLQPEDFATYYCQQYYYYPGTFGQGTKVEIKRT

>I2A-10 Domain S [SEQ ID NO: 125]
PREPQVYTLPPSRDELTKNQVSLKCLVKGFYPSDIAVEWESNGQPENNYKTTPPVLDS

DGSFFLYSKLTVDKSRWQQGNVFSCSVMHEALHNHYTQKSLSLSKSC

>I2A-10 Domain H [SEQ ID NO: 126]
QAVVTQEPSLTVSPGGTVTLTCRSSTGAVTTSNYANWVQQKPGQAPRGLIGGTNKRAP

WTPARFSGSLLGGKAALTITGAQAEDEADYYCALWYSNLWVFGGGTKLTVLGRTV

>I2A-10 Domain I [SEQ ID NO: 127]
AAPSVFIFPPSDEQLKSGTASVVCLLNNFYPREAKVQWKVDNALQSGNSQESVTEQDS

KDSTYSLSSTLTLSKADYEKHKVYACEVTHQGLSSPVTKSFNRGEC

>I2A-10 Domain J [SEQ ID NO: 128]
APEAAGGPSVFLFPPKPKDTLMISRTPEVTCVVVDVSHEDPEVKFNWYVDGVEVHNAK

TKPREEQYNSTYRVVSVLTVLHQDWLNGKEYKCKVSNKALKAPIEKTISKAK

>I2A-10 Domain K [SEQ ID NO: 129]
GQPREPQVYTLPPCRDELTKNQVSLWCLVKGFYPSDIAVEWESNGQPENNYKTTPPVL

DSDGSFFLYSKLTVDKSRWQQGNVFSCSVMHEALHNHYTQKSLSLSPGK

>I2A-10 Domain L [SEQ ID NO: 130]
EVQLVESGGGLVQPGGSLRLSCAASGFTFNTYAMNWVRQAPGKGLEWVARIRSKYNNY

ATYYADSVKGRFSISRDDSKNTAYLQMNSLRAEDTAVYYCVRHGNFGNSYVSWFAYWG

QGTLVTVSSAS

>I2A-10 Domain M [SEQ ID NO: 131]
TKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPPKSC

>I2A-10 Domain T [SEQ ID NO: 122]
EVQLVESGGGLVQPGGSLRLSCAASGFTFSSYFIHWVRQAPGKGLEWVAGIYPSDGYT

SYADSVKGRFTISADTSKNTAYLQMNSLRAEDTAVYYCARYYVSGMDYWGQGTLVTVS

SAS

>I2A-10 Domain U [SEQ ID NO: 123]
PREPQVYTDPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSGEC

>I2A-10 D54E Y55Q Chain 1 [SEQ ID NO: 132]
DIQMTQSPSSLSASVGDRVTITCRASQSVSSAVAWYQQKPGKAPKLLIYSASSLQSGV

PSRFSGSRSGTDFTLTISSLQPEDFATYYCQQYYYYPGTFGQGTKVEIKRTPREPQVY

-continued

TLPPSRDELTKNQVSLKCLVKGFYPSDIAVEWESNGQPENNYKTTPPVLDSDGSFFLY

SKLTVDKSRWQQGNVFSCSVMHEALHNHYTQKSLSLSKSCDKTHTCPPCPAPEAAGGP

SVFLFPPKPKDTLMISRTPEVTCVVVDVSHEDPEVKFNWYVDGVEVHNAKTKPREEQY

NSTYRVVSVLTVLHQDWLNGKEYKCKVSNKALKAPIEKTISKAK_GQPREPQVCTLPPS_

_REEMTKNQVSLSCAVKGFYPSDIAVEWESNGQPENNYKTTPPVLDSDGSFFLVSKLTV_

_DKSRWQQGNVFSCSVMHEALHNHYTQKSLSLSPGK_

Domain arrangement:
A-  B-   Hinge-  D-    E

VL-  CH3-  _Hinge_-  CH2-  _CH3(hole)_

Mutations in first CH3 (Domain B):
T366K; 445K, 446S, 447C insertion

Hinge sequence: DKTHTCPPCP (SEQ ID NO: 56)

Mutations in second CH3 (Domain E):
Y349C, D356E, L358M, T366S, L368A, Y407V

Exemplary signal sequence for Chain 1:
MGWSLILLFLVAVATRVLS (SEQ ID NO: 150)

>I2A-10 D54E Y55Q Chain 2 [SEQ ID NO: 133]
EVQLVESGGGLVQPGGSLRLSCAASGFTFSSYFIHWVRQAPGKGLEWVAGIYPSEGYT

SYADSVKGRFTISADTSKNTAYLQMNSLRAEDTAVYYCARYYVSGMDYWGQGTLVTVS

SASPREPQVYTDPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSGEC

Domain arrangement:
F-  G

VH-  CH3

Mutations in CH3 (Domain G):
L351D; 445G, 446E, 447C insertion

Exemplary signal sequence for Chain 2:
MDFQVQIISFLLISASVIMSRG (SEQ ID NO: 151)

>I2A-10 D54E Y55Q Chain 3 [SEQ ID NO: 134]
DIQMTQSPSSLSASVGDRVTITCRASQSVSSAVAWYQQKPGKAPKLLIYSASS

LQSGVPSRFSGSRSGTDFTLTISSLQPEDFATYYCQQYYYYPGTFGQGTKVEI

KRTPREPQVYTLPPSRDELTKNQVSLKCLVKGFYPSDIAVEWESNGQPENNYK

TTPPVLDSDGSFFLYSKLTVDKSRWQQGNVFSCSVMHEALHNHYTQKSLSLSK

_SCTA_SSGGGSSSG_QAVVTQEPSLTVSPGGTVTLTCRSSTGAVTTSNYANWVQQKP_

_GQAPRGLIGGTNKRAPWTPARFSGSLLGGKAALTITGAQAEDEADYYCALWY_

_SNLWVFGGGTKLTVLGRTV_AAPSVFIFPPSDEQLKSGTASVVCLLNNFYPRE

AKVQWKVDNALQSGNSQESVTEQDSKDSTYSLSSTLTLSKADYEKHKVYACEV

THQGLSSPVTKSFNRGEC_DKTHTCPPCP_APEAAGGPSVFLFPPKPKDTLMISR

TPEVTCVVVDVSHEDPEVKFNWYVDGVEVHNAKTKPREEQYNSTYRVVSVLTV

LHQDWLNGKEYKCKVSNKALKAPIEKTISKAK_GQPREPQVYTLPPCRDELTKN_

_QVSLWCLVKGFYPSDIAVEWESNGQPENNYKTTPPVLDSDGSFFLYSKLTVDK_

_SRWQQGNVFSCSVMHEALHNHYTQKSLSLSPGK_

Domain arrangement:
R-  S-   linker-  H-   I-  Hinge-  J-    K

VL-  CH3-  _linker_-  VL-  CL-  _Hinge_-  CH2-  _CH3(knob)_

-continued

Mutations in first CH3 (Domain S):
T366K; 445K, 446S, 447C insertion

Ten amino acid linker insertion: TASSGGSSSG (SEQ ID NO: 83)

Hinge sequence: DKTHTCPPCP (SEQ ID NO: 56)

Mutations in second CH3 (Domain K):
S354C, K366W

Exemplary signal sequence for Chain 3:
MDFQVQIISFLLISASVIMSRGS (SEQ ID NO: 152)

>I2A-10 D54E Y55Q Chain 4 [SEQ ID NO: 135]
EVQLVESGGGLVQPGGSLRLSCAASGFTFNTYAMNWVRQAPGKGLEWVARIRSKYNNY

ATYYADSVKGRFSISRDDSKNTAYLQMNSLRAEDTAVYYCVRHGNFGNSYVSWFAYWG

QGTLVTVSSASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKVEPPKSC

Domain arrangement:
L- M

VH- CH1

Exemplary signal sequence for Chain 4:
MDFQVQIISFLLISASVIMSRG (SEQ ID NO: 151)

>I2A-10 D54E Y55Q Chain 5 [SEQ ID NO: 133]
EVQLVESGGGLVQPGGSLRLSCAASGFTFSSYFIHWVRQAPGKGLEWVAGIYPSEGYT

SYADSVKGRFTISADTSKNTAYLQMNSLRAEDTAVYYCARYYVSGMDYWGQGTLVTVS

SASPREPQVYTDPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSGEC

Domain arrangement:
T- U

VH- CH3

Mutations in CH3 (Domain U):
L351D; 445G, 446E, 447C insertion

Exemplary signal sequence for Chain 5:
MDFQVQIISFLLISASVIMSRG (SEQ ID NO: 151)

>I2A-10 D54E Y55Q Domain A [SEQ ID NO: 136]
DIQMTQSPSSLSASVGDRVTITCRASQSVSSAVAWYQQKPGKAPKLLIYSASSLQSGV

PSRFSGSRSGTDFTLTISSLQPEDFATYYCQQYYYYPGTFGQGTKVEIKRT

>I2A-10 D54E Y55Q Domain B [SEQ ID NO: 137]
PREPQVYTLPPSRDELTKNQVSLKCLVKGFYPSDIAVEWESNGQPENNYKTTPPVLDS

DGSFFLYSKLTVDKSRWQQGNVFSCSVMHEALHNHYTQKSLSLSKSC

>I2A-10 D54E Y55Q Domain D [SEQ ID NO: 138]
APEAAGGPSVFLFPPKPKDTLMISRTPEVTCVVVDVSHEDPEVKFNWYVDGVEVHNAK

TKPREEQYNSTYRVVSVLTVLHQDWLNGKEYKCKVSNKALKAPIEKTISKAK

>I2A-10 D54E Y55Q Domain E [SEQ ID NO: 139]
GQPREPQVCTLPPSREEMTKNQVSLSCAVKGFYPSDIAVEWESNGQPENNYKTTPPVL

DSDGSFFLVSKLTVDKSRWQQGNVFSCSVMHEALHNHYTQKSLSLSPGK

>I2A-10 D54E Y55Q Domain F [SEQ ID NO: 140]
EVQLVESGGGLVQPGGSLRLSCAASGFTFSSYFIHWVRQAPGKGLEWVAGIYPSEGYT

SYADSVKGRFTISADTSKNTAYLQMNSLRAEDTAVYYCARYYVSGMDYWGQGTLVTVS

SAS

>I2A-10 D54E Y55Q Domain G [SEQ ID NO: 141]
PREPQVYTDPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSGEC

-continued

>I2A-10 D54E Y55Q Domain R [SEQ ID NO: 142]
DIQMTQSPSSLSASVGDRVTITCRASQSVSSAVAWYQQKPGKAPKLLIYSASSLQSGV

PSRFSGSRSGTDFTLTISSLQPEDFATYYCQQYYYPGTFGQGTKVEIKRT

>I2A-10 D54E Y55Q Domain S [SEQ ID NO: 143]
PREPQVYTLPPSRDELTKNQVSLKCLVKGFYPSDIAVEWESNGQPENNYKTTPPVLDS

DGSFFLYSKLTVDKSRWQQGNVFSCSVMHEALHNHYTQKSLSLSKSC

>I2A-10 D54E Y55Q Domain H [SEQ ID NO: 144]
QAVVTQEPSLTVSPGGTVTLTCRSSTGAVTTSNYANWVQQKPGQAPRGLIGGTNKRAP

WTPARFSGSLLGGKAALTITGAQAEDEADYYCALWYSNLWVFGGGTKLTVLGRTV

>I2A-10 D54E Y55Q Domain I [SEQ ID NO: 145]
AAPSVFIFPPSDEQLKSGTASVVCLLNNFYPREAKVQWKVDNALQSGNSQESVTEQDS

KDSTYSLSSTLTLSKADYEKHKVYACEVTHQGLSSPVTKSFNRGEC

>I2A-10 D54E Y55Q Domain J [SEQ ID NO: 146]
APEAAGGPSVFLFPPKPKDTLMISRTPEVTCVVVDVSHEDPEVKFNWYVDGVEVHNAK

TKPREEQYNSTYRVVSVLTVLHQDWLNGKEYKCKVSNKALKAPIEKTISKAK

>I2A-10 D54E Y55Q Domain K [SEQ ID NO: 147]
GQPREPQVYTLPPCRDELTKNQVSLWCLVKGFYPSDIAVEWESNGQPENNYKTTPPVL

DSDGSFFLYSKLTVDKSRWQQGNVFSCSVMHEALHNHYTQKSLSLSPGK

>I2A-10 D54E Y55Q Domain L [SEQ ID NO: 148]
EVQLVESGGGLVQPGGSLRLSCAASGFTFNTYAMNWVRQAPGKGLEWVARIRSKYNNY

ATYYADSVKGRFSISRDDSKNTAYLQMNSLRAEDTAVYYCVRHGNFGNSYVSWFAYWG

QGTLVTVSSAS

>I2A-10 D54E Y55Q Domain M [SEQ ID NO: 149]
TKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPPKSC

>I2A-10 D54E Y55Q Domain T [SEQ ID NO: 140]
EVQLVESGGGLVQPGGSLRLSCAASGFTFSSYFIHWVRQAPGKGLEWVAGIYPSEGYT

SYADSVKGRFTISADTSKNTAYLQMNSLRAEDTAVYYCARYYVSGMDYWGQGTLVTVS

SAS

>I2A-10 D54E Y55Q Domain U [SEQ ID NO: 141]
PREPQVYTDPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSGEC

7. Incorporation by Reference

All publications, patents, patent applications and other documents cited in this application are hereby incorporated by reference in their entireties for all purposes to the same extent as if each individual publication, patent, patent application or other document were individually indicated to be incorporated by reference for all purposes.

8. Equivalents

While various specific embodiments have been illustrated and described, the above specification is not restrictive. It will be appreciated that various changes can be made without departing from the spirit and scope of the invention(s). Many variations will become apparent to those skilled in the art upon review of this specification.

What is claimed is:

1. A tyrosine-protein kinase transmembrane receptor (ROR) binding molecule, the ROR antigen binding molecule comprising
a first antigen binding site specific for a ROR antigen, wherein the first antigen binding site comprises an antibody heavy chain variable (VH) region, and an antibody light chain variable (VL) region, wherein the VH region comprises a VH CDR1, a VH CDR2, and a VH CDR3 as set forth in the amino acid sequence of SEQ ID NO: 140, and the VL region comprises a VL CDR1, a VL CDR2, and a VL CDR3 as set forth in the amino acid sequence of SEQ ID NO: 136,
wherein the first antigen binding site is specific for ROR1 and ROR2.

2. The ROR antigen binding molecule of claim 1, wherein the ROR antigen is a ROR1 Ig-like domain or a ROR2 Ig-like domain.

3. The ROR antigen binding molecule of claim 1, wherein the ROR antigen comprises a human ROR antigen.

4. The ROR antigen binding molecule of claim 1, wherein the ROR antigen binding molecule further comprises a second antigen binding site.

5. The ROR antigen binding molecule of claim 4, wherein the second antigen binding site is the same as the first antigen binding site.

6. The ROR antigen binding molecule of claim 4, wherein the second antigen binding site comprises:

(1) a heavy chain CDR1 comprising the amino acid sequence of SEQ ID NO: 213, a heavy chain CDR2 comprising the amino acid sequence of SEQ ID NO: 214, a heavy chain CDR3 comprising the amino acid sequence of SEQ ID NO: 215, a light chain CDR1 comprising the amino acid sequence of SEQ ID NO: 216, a light chain CDR2 comprising the amino acid sequence of SEQ ID NO: 217, and a light chain CDR3 comprising the amino acid sequence of SEQ ID NO: 218, (2) a heavy chain CDR1 comprising the amino acid sequence of SEQ ID NO: 207, a heavy chain CDR2 comprising the amino acid sequence of SEQ ID NO: 208, a heavy chain CDR3 comprising the amino acid sequence of SEQ ID NO: 209, a light chain CDR1 comprising the amino acid sequence of SEQ ID NO: 210, a light chain CDR2 comprising the amino acid sequence of SEQ ID NO: 211, and a light chain CDR3 comprising the amino acid sequence of SEQ ID NO: 212;

(3) a heavy chain CDR1 comprising the amino acid sequence of SEQ ID NO: 153, a heavy chain CDR2 comprising the amino acid sequence of SEQ ID NO: 154, a heavy chain CDR3 comprising the amino acid sequence of SEQ ID NO: 155, a light chain CDR1 comprising the amino acid sequence of SEQ ID NO: 156, a light chain CDR2 comprising the amino acid sequence of SEQ ID NO: 157, and a light chain CDR3 comprising the amino acid sequence of SEQ ID NO: 158, a heavy chain CDR1 comprising the amino acid sequence of SEQ ID NO: 219, a heavy chain CDR2 comprising the amino acid sequence of SEQ ID NO: 220, a heavy chain CDR3 comprising the amino acid sequence of SEQ ID NO: 221, a light chain CDR1 comprising the amino acid sequence of SEQ ID NO: 222, (4) a light chain CDR2 comprising the amino acid sequence of SEQ ID NO: 223, and a light chain CDR3 comprising the amino acid sequence of SEQ ID NO: 224, (5) a heavy chain CDR1 comprising the amino acid sequence of SEQ ID NO: 231, a heavy chain CDR2 comprising the amino acid sequence of SEQ ID NO: 232, a heavy chain CDR3 comprising the amino acid sequence of SEQ ID NO: 233, a light chain CDR1 comprising the amino acid sequence of SEQ ID NO: 234, a light chain CDR2 comprising the amino acid sequence of SEQ ID NO: 235, and a light chain CDR3 comprising the amino acid sequence of SEQ ID NO: 236, (6) a heavy chain CDR1 comprising the amino acid sequence of SEQ ID NO: 237, a heavy chain CDR2 comprising the amino acid sequence of SEQ ID NO: 238, a heavy chain CDR3 comprising the amino acid sequence of SEQ ID NO: 239, a light chain CDR1 comprising the amino acid sequence of SEQ ID NO: 240, a light chain CDR2 comprising the amino acid sequence of SEQ ID NO: 241, and a light chain CDR3 comprising the amino acid sequence of SEQ ID NO: 242, (7) a heavy chain CDR1 comprising the amino acid sequence of SEQ ID NO: 249, a heavy chain CDR2 comprising the amino acid sequence of SEQ ID NO: 250, a heavy chain CDR3 comprising the amino acid sequence of SEQ ID NO: 251, a light chain CDR1 comprising the amino acid sequence of SEQ ID NO: 252, a light chain CDR2 comprising the amino acid sequence of SEQ ID NO: 253, and a light chain CDR3 comprising the amino acid sequence of SEQ ID NO: 254, (8) a heavy chain CDR1 comprising the amino acid sequence of SEQ ID NO: 261, a heavy chain CDR2 comprising the amino acid sequence of SEQ ID NO: 262, a heavy chain CDR3 comprising the amino acid sequence of SEQ ID NO: 263, a light chain CDR1 comprising the amino acid sequence of SEQ ID NO: 264, and a light chain CDR2 comprising the amino acid sequence of SEQ ID NO: 265, (9) a heavy chain CDR1 comprising the amino acid sequence of SEQ ID NO: 266, a heavy chain CDR2 comprising the amino acid sequence of SEQ ID NO: 267, a heavy chain CDR3 comprising the amino acid sequence of SEQ ID NO: 268, a light chain CDR1 comprising the amino acid sequence of SEQ ID NO: 269, a light chain CDR2 comprising the amino acid sequence of SEQ ID NO: 270, and a light chain CDR3 comprising the amino acid sequence of SEQ ID NO: 271,

(10) a heavy chain CDR1 comprising the amino acid sequence of SEQ ID NO: 284, a heavy chain CDR2 comprising the amino acid sequence of SEQ ID NO: 285, a heavy chain CDR3 comprising the amino acid sequence of SEQ ID NO: 286, a light chain CDR1 comprising the amino acid sequence of SEQ ID NO: 287, a light chain CDR2 comprising the amino acid sequence of SEQ ID NO: 288, and a light chain CDR3 comprising the amino acid sequence of SEQ ID NO: 289,

(11) a heavy chain CDR1 comprising the amino acid sequence of SEQ ID NO: 296, a heavy chain CDR2 comprising the amino acid sequence of SEQ ID NO: 297, a heavy chain CDR3 comprising the amino acid sequence of SEQ ID NO: 298, a light chain CDR1 comprising the amino acid sequence of SEQ ID NO: 299, a light chain CDR2 comprising the amino acid sequence of SEQ ID NO: 300, and a light chain CDR3 comprising the amino acid sequence of SEQ ID NO: 301,

(12) a heavy chain CDR1 comprising the amino acid sequence of SEQ ID NO: 308, a heavy chain CDR2 comprising the amino acid sequence of SEQ ID NO: 309, a heavy chain CDR3 comprising the amino acid sequence of SEQ ID NO: 310, a light chain CDR1 comprising the amino acid sequence of SEQ ID NO: 311, a light chain CDR2 comprising the amino acid sequence of SEQ ID NO: 312, and a light chain CDR3 comprising the amino acid sequence of SEQ ID NO: 313,

(13) a heavy chain CDR1 comprising the amino acid sequence of SEQ ID NO: 356, a heavy chain CDR2 comprising the amino acid sequence of SEQ ID NO: 357, a heavy chain CDR3 comprising the amino acid sequence of SEQ ID NO: 358, a light chain CDR1 comprising the amino acid sequence of SEQ ID NO: 359, a light chain CDR2 comprising the amino acid sequence of SEQ ID NO: 360, and a light chain CDR3 comprising the amino acid sequence of SEQ ID NO: 361,

(14) a heavy chain CDR1 comprising the amino acid sequence of SEQ ID NO: 368, a heavy chain CDR2 comprising the amino acid sequence of SEQ ID NO: 369, a heavy chain CDR3 comprising the amino acid sequence of SEQ ID NO: 370, a light chain CDR1 comprising the amino acid sequence of SEQ ID NO: 371, a light chain CDR2 comprising the amino acid sequence of SEQ ID NO: 372, and a light chain CDR3 comprising the amino acid sequence of SEQ ID NO: 373,

(15) a heavy chain CDR1 comprising the amino acid sequence of SEQ ID NO: 385, a heavy chain CDR2 comprising the amino acid sequence of SEQ ID NO: 386, a heavy chain CDR3 comprising the amino acid sequence of SEQ ID NO: 387, a light chain CDR1 comprising the amino acid sequence of SEQ ID NO: 388, a light chain CDR2 comprising the amino acid sequence of SEQ ID NO: 389, and a light chain CDR3 comprising the amino acid sequence of SEQ ID NO: 390,

(16) a heavy chain CDR1 comprising the amino acid sequence of SEQ ID NO: 391, a heavy chain CDR2 comprising the amino acid sequence of SEQ ID NO: 392, a heavy chain CDR3 comprising the amino acid sequence of SEQ ID NO: 393, a light chain CDR1 comprising the amino acid sequence of SEQ ID NO: 394, a light chain CDR2 comprising the amino acid sequence of SEQ ID NO: 395, and a light chain CDR3 comprising the amino acid sequence of SEQ ID NO: 396,

(17) a heavy chain CDR1 comprising the amino acid sequence of SEQ ID NO: 403, a heavy chain CDR2 comprising the amino acid sequence of SEQ ID NO: 404, a heavy chain CDR3 comprising the amino acid sequence of SEQ ID NO: 405, a light chain CDR1 comprising the amino acid sequence of SEQ ID NO: 406, a light chain CDR2 comprising the amino acid sequence of SEQ ID NO: 407, and a light chain CDR3 comprising the amino acid sequence of SEQ ID NO: 408,

(18) a heavy chain CDR1 comprising the amino acid sequence of SEQ ID NO: 415, a heavy chain CDR2 comprising the amino acid sequence of SEQ ID NO: 416, a heavy chain CDR3 comprising the amino acid sequence of SEQ ID NO: 417, a light chain CDR1 comprising the amino acid sequence of SEQ ID NO: 418, a light chain CDR2 comprising the amino acid sequence of SEQ ID NO: 419, and a light chain CDR3 comprising the amino acid sequence of SEQ ID NO: 420,

(19) a heavy chain CDR1 comprising the amino acid sequence of SEQ ID NO: 427, a heavy chain CDR2 comprising the amino acid sequence of SEQ ID NO: 428, a heavy chain CDR3 comprising the amino acid sequence of SEQ ID NO: 429, a light chain CDR1 comprising the amino acid sequence of SEQ ID NO: 430, a light chain CDR2 comprising the amino acid sequence of SEQ ID NO: 431, and a light chain CDR3 comprising the amino acid sequence of SEQ ID NO: 432,

(20) a heavy chain CDR1 comprising the amino acid sequence of SEQ ID NO: 433, a heavy chain CDR2 comprising the amino acid sequence of SEQ ID NO: 434, a heavy chain CDR3 comprising the amino acid sequence of SEQ ID NO: 435, a light chain CDR1 comprising the amino acid sequence of SEQ ID NO: 436, a light chain CDR2 comprising the amino acid sequence of SEQ ID NO: 437, and a light chain CDR3 comprising the amino acid sequence of SEQ ID NO: 438,

(21) a heavy chain CDR1 comprising the amino acid sequence of SEQ ID NO: 439, a heavy chain CDR2 comprising the amino acid sequence of SEQ ID NO: 440, a heavy chain CDR3 comprising the amino acid sequence of SEQ ID NO: 441, a light chain CDR1 comprising the amino acid sequence of SEQ ID NO: 442, a light chain CDR2 comprising the amino acid sequence of SEQ ID NO: 443, and a light chain CDR3 comprising the amino acid sequence of SEQ ID NO: 444,

(22) a heavy chain CDR1 comprising the amino acid sequence of SEQ ID NO: 445, a heavy chain CDR2 comprising the amino acid sequence of SEQ ID NO: 446, a heavy chain CDR3 comprising the amino acid sequence of SEQ ID NO: 447, a light chain CDR1 comprising the amino acid sequence of SEQ ID NO: 448, a light chain CDR2 comprising the amino acid sequence of SEQ ID NO: 449, and a light chain CDR3 comprising the amino acid sequence of SEQ ID NO: 450,

(23) a heavy chain CDR1 comprising the amino acid sequence of SEQ ID NO: 451, a heavy chain CDR2 comprising the amino acid sequence of SEQ ID NO: 452, a heavy chain CDR3 comprising the amino acid sequence of SEQ ID NO: 453, a light chain CDR1 comprising the amino acid sequence of SEQ ID NO: 454, a light chain CDR2 comprising the amino acid sequence of SEQ ID NO: 455, and a light chain CDR3 comprising the amino acid sequence of SEQ ID NO: 456,

(24) a heavy chain CDR1 comprising the amino acid sequence of SEQ ID NO: 457, a heavy chain CDR2 comprising the amino acid sequence of SEQ ID NO: 458, a heavy chain CDR3 comprising the amino acid sequence of SEQ ID NO: 459, a light chain CDR1 comprising the amino acid sequence of SEQ ID NO: 460, a light chain CDR2 comprising the amino acid sequence of SEQ ID NO: 461, and a light chain CDR3 comprising the amino acid sequence of SEQ ID NO: 462,

(25) a heavy chain CDR1 comprising the amino acid sequence of SEQ ID NO: 463, a heavy chain CDR2 comprising the amino acid sequence of SEQ ID NO: 464, a heavy chain CDR3 comprising the amino acid sequence of SEQ ID NO: 465, a light chain CDR1 comprising the amino acid sequence of SEQ ID NO: 466, a light chain CDR2 comprising the amino acid sequence of SEQ ID NO: 467, and a light chain CDR3 comprising the amino acid sequence of SEQ ID NO: 468,

(26) a heavy chain CDR1 comprising the amino acid sequence of SEQ ID NO: 469, a heavy chain CDR2 comprising the amino acid sequence of SEQ ID NO: 470, a heavy chain CDR3 comprising the amino acid sequence of SEQ ID NO: 471, a light chain CDR1 comprising the amino acid sequence of SEQ ID NO: 472, a light chain CDR2 comprising the amino acid sequence of SEQ ID NO: 473, and a light chain CDR3 comprising the amino acid sequence of SEQ ID NO: 474,

(27) a heavy chain CDR1 comprising the amino acid sequence of SEQ ID NO: 475, a heavy chain CDR2 comprising the amino acid sequence of SEQ ID NO: 476, a heavy chain CDR3 comprising the amino acid sequence of SEQ ID NO: 477, a light chain CDR1 comprising the amino acid sequence of SEQ ID NO: 478, a light chain CDR2 comprising the amino acid sequence of SEQ ID NO: 479, and a light chain CDR3 comprising the amino acid sequence of SEQ ID NO: 480,

(28) a heavy chain CDR1 comprising the amino acid sequence of SEQ ID NO: 481, a heavy chain CDR2 comprising the amino acid sequence of SEQ ID NO: 482, a heavy chain CDR3 comprising the amino acid sequence of SEQ ID NO: 483, a light chain CDR1 comprising the amino acid sequence of SEQ ID NO: 484, a light chain CDR2 comprising the amino acid sequence of SEQ ID NO: 485, and a light chain CDR3 comprising the amino acid sequence of SEQ ID NO: 486,

(29) a heavy chain CDR1 comprising the amino acid sequence of SEQ ID NO: 487, a heavy chain CDR2 comprising the amino acid sequence of SEQ ID NO: 488, a heavy chain CDR3 comprising the amino acid sequence of SEQ ID NO: 489, a light chain CDR1 comprising the amino acid sequence of SEQ ID NO: 490, a light chain CDR2 comprising the amino acid sequence of SEQ ID NO: 491, and a light chain CDR3 comprising the amino acid sequence of SEQ ID NO: 492,

(30) a heavy chain CDR1 comprising the amino acid sequence of SEQ ID NO: 499, a heavy chain CDR2 comprising the amino acid sequence of SEQ ID NO: 500, a heavy chain CDR3 comprising the amino acid sequence of SEQ ID NO: 501, a light chain CDR1 comprising the amino acid sequence of SEQ ID NO: 502, a light chain CDR2 comprising the amino acid sequence of SEQ ID NO: 503, and a light chain CDR3 comprising the amino acid sequence of SEQ ID NO: 504,

(31) a heavy chain CDR1 comprising the amino acid sequence of SEQ ID NO: 511, a heavy chain CDR2 comprising the amino acid sequence of SEQ ID NO: 512, a heavy chain CDR3 comprising the amino acid sequence of SEQ ID NO: 513, a light chain CDR1 comprising the amino acid sequence of SEQ ID NO: 514, a light chain CDR2 comprising the amino acid sequence of SEQ ID NO: 515, and a light chain CDR3 comprising the amino acid sequence of SEQ ID NO: 516,

(32) a heavy chain CDR1 comprising the amino acid sequence of SEQ ID NO: 517, a heavy chain CDR2 comprising the amino acid sequence of SEQ ID NO: 518, a heavy chain CDR3 comprising the amino acid sequence of SEQ ID NO: 519, a light chain CDR1 comprising the amino acid sequence of SEQ ID NO: 520, a light chain CDR2 comprising the amino acid sequence of SEQ ID NO: 521, and a light chain CDR3 comprising the amino acid sequence of SEQ ID NO: 522, or

(33) a heavy chain CDR1 comprising the amino acid sequence of SEQ ID NO: 523, a heavy chain CDR2 comprising the amino acid sequence of SEQ ID NO: 524, a heavy chain CDR3 comprising the amino acid sequence of SEQ ID NO: 525, a light chain CDR1 comprising the amino acid sequence of SEQ ID NO: 526, a light chain CDR2 comprising the amino acid sequence of SEQ ID NO: 527, and a light chain CDR3 comprising the amino acid sequence of SEQ ID NO: 528.

7. The ROR antigen binding molecule of claim 4, wherein the second antigen binding site comprises:
(1) a heavy chain CDR1 comprising the amino acid sequence of SEQ ID NO: 314, a heavy chain CDR2 comprising the amino acid sequence of SEQ ID NO: 315, a heavy chain CDR3 comprising the amino acid sequence of SEQ ID NO: 316, a light chain CDR1 comprising the amino acid sequence of SEQ ID NO: 317, a light chain CDR2 comprising the amino acid sequence of SEQ ID NO: 318, and a light chain CDR3 comprising the amino acid sequence of SEQ ID NO: 319;
(2) a heavy chain CDR1 comprising the amino acid sequence of SEQ ID NO: 165, a heavy chain CDR2 comprising the amino acid sequence of SEQ ID NO: 166, a heavy chain CDR3 comprising the amino acid sequence of SEQ ID NO: 167, a light chain CDR1 comprising the amino acid sequence of SEQ ID NO: 168, a light chain CDR2 comprising the amino acid sequence of SEQ ID NO: 169, and a light chain CDR3 comprising the amino acid sequence of SEQ ID NO: 170;
(3) a heavy chain CDR1 comprising the amino acid sequence of SEQ ID NO: 171, a heavy chain CDR2 comprising the amino acid sequence of SEQ ID NO: 172, a heavy chain CDR3 comprising the amino acid sequence of SEQ ID NO: 173, a light chain CDR1 comprising the amino acid sequence of SEQ ID NO: 174, a light chain CDR2 comprising the amino acid sequence of SEQ ID NO: 175, and a light chain CDR3 comprising the amino acid sequence of SEQ ID NO: 176;
(4) a heavy chain CDR1 comprising the amino acid sequence of SEQ ID NO: 183, a heavy chain CDR2 comprising the amino acid sequence of SEQ ID NO: 184, a heavy chain CDR3 comprising the amino acid sequence of SEQ ID NO: 185, a light chain CDR1 comprising the amino acid sequence of SEQ ID NO: 186, a light chain CDR2 comprising the amino acid sequence of SEQ ID NO: 187, and a light chain CDR3 comprising the amino acid sequence of SEQ ID NO: 188;
(5) a heavy chain CDR1 comprising the amino acid sequence of SEQ ID NO: 195, a heavy chain CDR2 comprising the amino acid sequence of SEQ ID NO: 196, a heavy chain CDR3 comprising the amino acid sequence of SEQ ID NO: 197, a light chain CDR1 comprising the amino acid sequence of SEQ ID NO: 198, a light chain CDR2 comprising the amino acid sequence of SEQ ID NO: 199, and a light chain CDR3 comprising the amino acid sequence of SEQ ID NO: 200;
(6) a heavy chain CDR1 comprising the amino acid sequence of SEQ ID NO: 225, a heavy chain CDR2 comprising the amino acid sequence of SEQ ID NO: 226, a heavy chain CDR3 comprising the amino acid sequence of SEQ ID NO: 227, a light chain CDR1 comprising the amino acid sequence of SEQ ID NO: 228, a light chain CDR2 comprising the amino acid sequence of SEQ ID NO: 229, and a light chain CDR3 comprising the amino acid sequence of SEQ ID NO: 230;
(7) a heavy chain CDR1 comprising the amino acid sequence of SEQ ID NO: 272, a heavy chain CDR2 comprising the amino acid sequence of SEQ ID NO: 273, a heavy chain CDR3 comprising the amino acid sequence of SEQ ID NO: 274, a light chain CDR1 comprising the amino acid sequence of SEQ ID NO: 275, a light chain CDR2 comprising the amino acid sequence of SEQ ID NO: 276, and a light chain CDR3 comprising the amino acid sequence of SEQ ID NO: 277;
(8) a heavy chain CDR1 comprising the amino acid sequence of SEQ ID NO: 302, a heavy chain CDR2 comprising the amino acid sequence of SEQ ID NO: 303, a heavy chain CDR3 comprising the amino acid sequence of SEQ ID NO: 304, a light chain CDR1 comprising the amino acid sequence of SEQ ID NO: 305, a light chain CDR2 comprising the amino acid sequence of SEQ ID NO: 306, and a light chain CDR3 comprising the amino acid sequence of SEQ ID NO: 307;
(9) a heavy chain CDR1 comprising the amino acid sequence of SEQ ID NO: 308, a heavy chain CDR2 comprising the amino acid sequence of SEQ ID NO: 309, a heavy chain CDR3 comprising the amino acid sequence of SEQ ID NO: 310, a light chain CDR1 comprising the amino acid sequence of SEQ ID NO: 311, a light chain CDR2 comprising the amino acid sequence of SEQ ID NO: 312, and a light chain CDR3 comprising the amino acid sequence of SEQ ID NO: 313;
(10) a heavy chain CDR1 comprising the amino acid sequence of SEQ ID NO: 332, a heavy chain CDR2 comprising the amino acid sequence of SEQ ID NO: 333, a heavy chain CDR3 comprising the amino acid sequence of SEQ ID NO: 334, a light chain CDR1 comprising the amino acid sequence of SEQ ID NO: 335, a light chain CDR2 comprising the amino acid sequence of SEQ ID NO: 336, and a light chain CDR3 comprising the amino acid sequence of SEQ ID NO: 337;
(11) a heavy chain CDR1 comprising the amino acid sequence of SEQ ID NO: 344, a heavy chain CDR2 comprising the amino acid sequence of SEQ ID NO: 345, a heavy chain CDR3 comprising the amino acid sequence of SEQ ID NO: 346, a light chain CDR1 comprising the amino acid sequence of SEQ ID NO: 347, a light chain CDR2 comprising the amino acid sequence of SEQ ID NO: 348, and a light chain CDR3 comprising the amino acid sequence of SEQ ID NO: 349;
(12) a heavy chain CDR1 comprising the amino acid sequence of SEQ ID NO: 350, a heavy chain CDR2 comprising the amino acid sequence of SEQ ID NO: 351, a heavy chain CDR3 comprising the amino acid sequence of SEQ ID NO: 352, a light chain CDR1 comprising the amino acid sequence of SEQ ID NO: 353, a light chain CDR2 comprising the amino acid sequence of SEQ ID NO: 354, and a light chain CDR3 comprising the amino acid sequence of SEQ ID NO: 355; or
(13) a heavy chain CDR1 comprising the amino acid sequence of SEQ ID NO: 374, a heavy chain CDR2 comprising the amino acid sequence of SEQ ID NO: 375, a heavy chain CDR3 comprising the amino acid sequence of SEQ ID NO: 376, a light chain CDR1 comprising the amino acid sequence of SEQ ID NO: 377, a light chain CDR2 comprising the amino acid sequence of SEQ ID NO: 378, and a light chain CDR3 comprising the amino acid sequence of SEQ ID NO: 379.

8. The ROR antigen binding molecule of claim 4, wherein the second antigen binding site comprises:
(1) a heavy chain CDR1 comprising the amino acid sequence of SEQ ID NO: 505, a heavy chain CDR2 comprising the amino acid sequence of SEQ ID NO: 506, a heavy chain CDR3 comprising the amino acid sequence of SEQ ID NO: 507, a light chain CDR1 comprising the amino acid sequence of SEQ ID NO: 508, a light chain CDR2 comprising the amino acid sequence of SEQ ID NO: 509, and a light chain CDR3 comprising the amino acid sequence of SEQ ID NO: 510;
(2) a heavy chain CDR1 comprising the amino acid sequence of SEQ ID NO: 397, a heavy chain CDR2 comprising the amino acid sequence of SEQ ID NO: 398, a heavy chain CDR3 comprising the amino acid sequence of SEQ ID NO: 399, a light chain CDR1 comprising the amino acid sequence of SEQ ID NO: 400, a light chain CDR2 comprising the amino acid sequence of SEQ ID NO: 401, and a light chain CDR3 comprising the amino acid sequence of SEQ ID NO: 402;
(3) a heavy chain CDR1 comprising the amino acid sequence of SEQ ID NO: 409, a heavy chain CDR2 comprising the amino acid sequence of SEQ ID NO: 410, a heavy chain CDR3 comprising the amino acid sequence of SEQ ID NO: 411, a light chain CDR1 comprising the amino acid sequence of SEQ ID NO: 412, a light chain CDR2 comprising the amino acid sequence of SEQ ID NO: 413, and a light chain CDR3 comprising the amino acid sequence of SEQ ID NO: 414;
(4) a heavy chain CDR1 comprising the amino acid sequence of SEQ ID NO: 421, a heavy chain CDR2 comprising the amino acid sequence of SEQ ID NO: 422, a heavy chain CDR3 comprising the amino acid sequence of SEQ ID NO: 423, a light chain CDR1 comprising the amino acid sequence of SEQ ID NO: 424, a light chain CDR2 comprising the amino acid sequence of SEQ ID NO: 425, and a light chain CDR3 comprising the amino acid sequence of SEQ ID NO: 426;
(5) a heavy chain CDR1 comprising the amino acid sequence of SEQ ID NO: 493, a heavy chain CDR2 comprising the amino acid sequence of SEQ ID NO: 494, a heavy chain CDR3 comprising the amino acid sequence of SEQ ID NO: 495, a light chain CDR1 comprising the amino acid sequence of SEQ ID NO: 496, a light chain CDR2 comprising the amino acid sequence of SEQ ID NO: 497, and a light chain CDR3 comprising the amino acid sequence of SEQ ID NO: 498;
(6) a heavy chain CDR1 comprising the amino acid sequence of SEQ ID NO: 529, a heavy chain CDR2 comprising the amino acid sequence of SEQ ID NO: 530, a heavy chain CDR3 comprising the amino acid sequence of SEQ ID NO: 531, a light chain CDR1 comprising the amino acid sequence of SEQ ID NO: 532, a light chain CDR2 comprising the amino acid sequence of SEQ ID NO: 533, and a light chain CDR3 comprising the amino acid sequence of SEQ ID NO: 534; or
(7) a heavy chain CDR1 comprising the amino acid sequence of SEQ ID NO: 535, a heavy chain CDR2 comprising the amino acid sequence of SEQ ID NO: 536, a heavy chain CDR3 comprising the amino acid sequence of SEQ ID NO: 537, a light chain CDR1 comprising the amino acid sequence of SEQ ID NO: 538, a light chain CDR2 comprising the amino acid sequence of SEQ ID NO: 539, and a light chain CDR3 comprising the amino acid sequence of SEQ ID NO: 540.

9. The ROR antigen binding molecule of claim 4, wherein the second antigen binding site is specific for a second antigen different from the ROR antigen.

10. The ROR antigen binding molecule of claim 9, wherein the second antigen is a CD3 antigen.

11. The ROR antigen binding molecule of claim 1, wherein the ROR antigen binding molecule comprises an antibody format selected from the group consisting of: full-length antibodies, Fab fragments, Fvs, scFvs, tandem scFvs, Diabodies, scDiabodies, DARTs, tandAbs, and minibodies.

12. The ROR antigen binding molecule of claim 1, wherein the molecule comprises a sequence of one or more constant regions.

13. The ROR antigen binding molecule of claim 12, wherein the constant region is a CH1, CH2, CH3 and/or CL constant region.

14. The ROR antigen binding molecule of claim 1, wherein the ROR antigen binding molecule further comprises a third antigen binding site.

15. The ROR antigen binding molecule of claim 14, wherein the third antigen binding site is specific for ROR1 and ROR2, ROR1, or ROR2.

16. The ROR antigen binding molecule of claim 15, wherein the third antigen binding site is the same as the first antigen binding site.

17. The ROR antigen binding molecule of claim 15, wherein the third antigen binding site comprises:
(1) a heavy chain CDR1 comprising the amino acid sequence of SEQ ID NO: 213, a heavy chain CDR2 comprising the amino acid sequence of SEQ ID NO: 214, a heavy chain CDR3 comprising the amino acid sequence of SEQ ID NO: 215, a light chain CDR1 comprising the amino acid sequence of SEQ ID NO: 216, a light chain CDR2 comprising the amino acid sequence of SEQ ID NO: 217, and a light chain CDR3 comprising the amino acid sequence of SEQ ID NO: 218,
(2) a heavy chain CDR1 comprising the amino acid sequence of SEQ ID NO: 207, a heavy chain CDR2 comprising the amino acid sequence of SEQ ID NO: 208, a heavy chain CDR3 comprising the amino acid sequence of SEQ ID NO: 209, a light chain CDR1 comprising the amino acid sequence of SEQ ID NO: 210, a light chain CDR2 comprising the amino acid sequence of SEQ ID NO: 211, and a light chain CDR3 comprising the amino acid sequence of SEQ ID NO: 212;
(3) a heavy chain CDR1 comprising the amino acid sequence of SEQ ID NO: 153, a heavy chain CDR2 comprising the amino acid sequence of SEQ ID NO: 154, a heavy chain CDR3 comprising the amino acid sequence of SEQ ID NO: 155, a light chain CDR1 comprising the amino acid sequence of SEQ ID NO:

156, a light chain CDR2 comprising the amino acid sequence of SEQ ID NO: 157, and a light chain CDR3 comprising the amino acid sequence of SEQ ID NO: 158, (4) a heavy chain CDR1 comprising the amino acid sequence of SEQ ID NO: 219, a heavy chain CDR2 comprising the amino acid sequence of SEQ ID NO: 220, a heavy chain CDR3 comprising the amino acid sequence of SEQ ID NO: 221, a light chain CDR1 comprising the amino acid sequence of SEQ ID NO: 222, a light chain CDR2 comprising the amino acid sequence of SEQ ID NO: 223, and a light chain CDR3 comprising the amino acid sequence of SEQ ID NO: 224, (5) a heavy chain CDR1 comprising the amino acid sequence of SEQ ID NO: 231, a heavy chain CDR2 comprising the amino acid sequence of SEQ ID NO: 232, a heavy chain CDR3 comprising the amino acid sequence of SEQ ID NO: 233, a light chain CDR1 comprising the amino acid sequence of SEQ ID NO: 234, a light chain CDR2 comprising the amino acid sequence of SEQ ID NO: 235, and a light chain CDR3 comprising the amino acid sequence of SEQ ID NO: 236, (6) a heavy chain CDR1 comprising the amino acid sequence of SEQ ID NO: 237, a heavy chain CDR2 comprising the amino acid sequence of SEQ ID NO: 238, a heavy chain CDR3 comprising the amino acid sequence of SEQ ID NO: 239, a light chain CDR1 comprising the amino acid sequence of SEQ ID NO: 240, a light chain CDR2 comprising the amino acid sequence of SEQ ID NO: 241, and a light chain CDR3 comprising the amino acid sequence of SEQ ID NO: 242, (7) a heavy chain CDR1 comprising the amino acid sequence of SEQ ID NO: 249, a heavy chain CDR2 comprising the amino acid sequence of SEQ ID NO: 250, a heavy chain CDR3 comprising the amino acid sequence of SEQ ID NO: 251, a light chain CDR1 comprising the amino acid sequence of SEQ ID NO: 252, a light chain CDR2 comprising the amino acid sequence of SEQ ID NO: 253, and a light chain CDR3 comprising the amino acid sequence of SEQ ID NO: 254, (8) a heavy chain CDR1 comprising the amino acid sequence of SEQ ID NO: 261, a heavy chain CDR2 comprising the amino acid sequence of SEQ ID NO: 262, a heavy chain CDR3 comprising the amino acid sequence of SEQ ID NO: 263, a light chain CDR1 comprising the amino acid sequence of SEQ ID NO: 264, and a light chain CDR2 comprising the amino acid sequence of SEQ ID NO: 265, (9) a heavy chain CDR1 comprising the amino acid sequence of SEQ ID NO: 266, a heavy chain CDR2 comprising the amino acid sequence of SEQ ID NO: 267, a heavy chain CDR3 comprising the amino acid sequence of SEQ ID NO: 268, a light chain CDR1 comprising the amino acid sequence of SEQ ID NO: 269, a light chain CDR2 comprising the amino acid sequence of SEQ ID NO: 270, and a light chain CDR3 comprising the amino acid sequence of SEQ ID NO: 271,

(10) a heavy chain CDR1 comprising the amino acid sequence of SEQ ID NO: 284, a heavy chain CDR2 comprising the amino acid sequence of SEQ ID NO: 285, a heavy chain CDR3 comprising the amino acid sequence of SEQ ID NO: 286, a light chain CDR1 comprising the amino acid sequence of SEQ ID NO: 287, a light chain CDR2 comprising the amino acid sequence of SEQ ID NO: 288, and a light chain CDR3 comprising the amino acid sequence of SEQ ID NO: 289,

(11) a heavy chain CDR1 comprising the amino acid sequence of SEQ ID NO: 296, a heavy chain CDR2 comprising the amino acid sequence of SEQ ID NO: 297, a heavy chain CDR3 comprising the amino acid sequence of SEQ ID NO: 298, a light chain CDR1 comprising the amino acid sequence of SEQ ID NO: 299, a light chain CDR2 comprising the amino acid sequence of SEQ ID NO: 300, and a light chain CDR3 comprising the amino acid sequence of SEQ ID NO: 301,

(12) a heavy chain CDR1 comprising the amino acid sequence of SEQ ID NO: 308, a heavy chain CDR2 comprising the amino acid sequence of SEQ ID NO: 309, a heavy chain CDR3 comprising the amino acid sequence of SEQ ID NO: 310, a light chain CDR1 comprising the amino acid sequence of SEQ ID NO: 311, a light chain CDR2 comprising the amino acid sequence of SEQ ID NO: 312, and a light chain CDR3 comprising the amino acid sequence of SEQ ID NO: 313,

(13) a heavy chain CDR1 comprising the amino acid sequence of SEQ ID NO: 356, a heavy chain CDR2 comprising the amino acid sequence of SEQ ID NO: 357, a heavy chain CDR3 comprising the amino acid sequence of SEQ ID NO: 358, a light chain CDR1 comprising the amino acid sequence of SEQ ID NO: 359, a light chain CDR2 comprising the amino acid sequence of SEQ ID NO: 360, and a light chain CDR3 comprising the amino acid sequence of SEQ ID NO: 361,

(14) a heavy chain CDR1 comprising the amino acid sequence of SEQ ID NO: 368, a heavy chain CDR2 comprising the amino acid sequence of SEQ ID NO: 369, a heavy chain CDR3 comprising the amino acid sequence of SEQ ID NO: 370, a light chain CDR1 comprising the amino acid sequence of SEQ ID NO: 371, a light chain CDR2 comprising the amino acid sequence of SEQ ID NO: 372, and a light chain CDR3 comprising the amino acid sequence of SEQ ID NO: 373,

(15) a heavy chain CDR1 comprising the amino acid sequence of SEQ ID NO: 385, a heavy chain CDR2 comprising the amino acid sequence of SEQ ID NO: 386, a heavy chain CDR3 comprising the amino acid sequence of SEQ ID NO: 387, a light chain CDR1 comprising the amino acid sequence of SEQ ID NO: 388, a light chain CDR2 comprising the amino acid sequence of SEQ ID NO: 389, and a light chain CDR3 comprising the amino acid sequence of SEQ ID NO: 390,

(16) a heavy chain CDR1 comprising the amino acid sequence of SEQ ID NO: 391, a heavy chain CDR2 comprising the amino acid sequence of SEQ ID NO: 392, a heavy chain CDR3 comprising the amino acid sequence of SEQ ID NO: 393, a light chain CDR1 comprising the amino acid sequence of SEQ ID NO: 394, a light chain CDR2 comprising the amino acid sequence of SEQ ID NO: 395, and a light chain CDR3 comprising the amino acid sequence of SEQ ID NO: 396,

(17) a heavy chain CDR1 comprising the amino acid sequence of SEQ ID NO: 403, a heavy chain CDR2 comprising the amino acid sequence of SEQ ID NO: 404, a heavy chain CDR3 comprising the amino acid sequence of SEQ ID NO: 405, a light chain CDR1 comprising the amino acid sequence of SEQ ID NO: 406, a light chain CDR2 comprising the amino acid sequence of SEQ ID NO: 407, and a light chain CDR3 comprising the amino acid sequence of SEQ ID NO: 408,

(18) a heavy chain CDR1 comprising the amino acid sequence of SEQ ID NO: 415, a heavy chain CDR2 comprising the amino acid sequence of SEQ ID NO: 416, a heavy chain CDR3 comprising the amino acid sequence of SEQ ID NO: 417, a light chain CDR1 comprising the amino acid sequence of SEQ ID NO: 418, a light chain CDR2 comprising the amino acid sequence of SEQ ID NO: 419, and a light chain CDR3 comprising the amino acid sequence of SEQ ID NO: 420,

(19) a heavy chain CDR1 comprising the amino acid sequence of SEQ ID NO: 427, a heavy chain CDR2 comprising the amino acid sequence of SEQ ID NO: 428, a heavy chain CDR3 comprising the amino acid sequence of SEQ ID NO: 429, a light chain CDR1 comprising the amino acid sequence of SEQ ID NO: 430, a light chain CDR2 comprising the amino acid sequence of SEQ ID NO: 431, and a light chain CDR3 comprising the amino acid sequence of SEQ ID NO: 432,

(20) a heavy chain CDR1 comprising the amino acid sequence of SEQ ID NO: 433, a heavy chain CDR2 comprising the amino acid sequence of SEQ ID NO: 434, a heavy chain CDR3 comprising the amino acid sequence of SEQ ID NO: 435, a light chain CDR1 comprising the amino acid sequence of SEQ ID NO: 436, a light chain CDR2 comprising the amino acid sequence of SEQ ID NO: 437, and a light chain CDR3 comprising the amino acid sequence of SEQ ID NO: 438,

(21) a heavy chain CDR1 comprising the amino acid sequence of SEQ ID NO: 439, a heavy chain CDR2 comprising the amino acid sequence of SEQ ID NO: 440, a heavy chain CDR3 comprising the amino acid sequence of SEQ ID NO: 441, a light chain CDR1 comprising the amino acid sequence of SEQ ID NO: 442, a light chain CDR2 comprising the amino acid sequence of SEQ ID NO: 443, and a light chain CDR3 comprising the amino acid sequence of SEQ ID NO: 444,

(22) a heavy chain CDR1 comprising the amino acid sequence of SEQ ID NO: 445, a heavy chain CDR2 comprising the amino acid sequence of SEQ ID NO: 446, a heavy chain CDR3 comprising the amino acid sequence of SEQ ID NO: 447, a light chain CDR1 comprising the amino acid sequence of SEQ ID NO: 448, a light chain CDR2 comprising the amino acid sequence of SEQ ID NO: 449, and a light chain CDR3 comprising the amino acid sequence of SEQ ID NO: 450,

(23) a heavy chain CDR1 comprising the amino acid sequence of SEQ ID NO: 451, a heavy chain CDR2 comprising the amino acid sequence of SEQ ID NO: 452, a heavy chain CDR3 comprising the amino acid sequence of SEQ ID NO: 453, a light chain CDR1 comprising the amino acid sequence of SEQ ID NO: 454, a light chain CDR2 comprising the amino acid sequence of SEQ ID NO: 455, and a light chain CDR3 comprising the amino acid sequence of SEQ ID NO: 456,

(24) a heavy chain CDR1 comprising the amino acid sequence of SEQ ID NO: 457, a heavy chain CDR2 comprising the amino acid sequence of SEQ ID NO: 458, a heavy chain CDR3 comprising the amino acid sequence of SEQ ID NO: 459, a light chain CDR1 comprising the amino acid sequence of SEQ ID NO: 460, a light chain CDR2 comprising the amino acid sequence of SEQ ID NO: 461, and a light chain CDR3 comprising the amino acid sequence of SEQ ID NO: 462,

(25) a heavy chain CDR1 comprising the amino acid sequence of SEQ ID NO: 463, a heavy chain CDR2 comprising the amino acid sequence of SEQ ID NO: 464, a heavy chain CDR3 comprising the amino acid sequence of SEQ ID NO: 465, a light chain CDR1 comprising the amino acid sequence of SEQ ID NO: 466, a light chain CDR2 comprising the amino acid sequence of SEQ ID NO: 467, and a light chain CDR3 comprising the amino acid sequence of SEQ ID NO: 468,

(26) a heavy chain CDR1 comprising the amino acid sequence of SEQ ID NO: 469, a heavy chain CDR2 comprising the amino acid sequence of SEQ ID NO: 470, a heavy chain CDR3 comprising the amino acid sequence of SEQ ID NO: 471, a light chain CDR1 comprising the amino acid sequence of SEQ ID NO: 472, a light chain CDR2 comprising the amino acid sequence of SEQ ID NO: 473, and a light chain CDR3 comprising the amino acid sequence of SEQ ID NO: 474,

(27) a heavy chain CDR1 comprising the amino acid sequence of SEQ ID NO: 475, a heavy chain CDR2 comprising the amino acid sequence of SEQ ID NO: 476, a heavy chain CDR3 comprising the amino acid sequence of SEQ ID NO: 477, a light chain CDR1 comprising the amino acid sequence of SEQ ID NO: 478, a light chain CDR2 comprising the amino acid sequence of SEQ ID NO: 479, and a light chain CDR3 comprising the amino acid sequence of SEQ ID NO: 480,

(28) a heavy chain CDR1 comprising the amino acid sequence of SEQ ID NO: 481, a heavy chain CDR2 comprising the amino acid sequence of SEQ ID NO: 482, a heavy chain CDR3 comprising the amino acid sequence of SEQ ID NO: 483, a light chain CDR1 comprising the amino acid sequence of SEQ ID NO: 484, a light chain CDR2 comprising the amino acid sequence of SEQ ID NO: 485, and a light chain CDR3 comprising the amino acid sequence of SEQ ID NO: 486,

(29) a heavy chain CDR1 comprising the amino acid sequence of SEQ ID NO: 487, a heavy chain CDR2 comprising the amino acid sequence of SEQ ID NO: 488, a heavy chain CDR3 comprising the amino acid sequence of SEQ ID NO: 489, a light chain CDR1 comprising the amino acid sequence of SEQ ID NO: 490, a light chain CDR2 comprising the amino acid sequence of SEQ ID NO: 491, and a light chain CDR3 comprising the amino acid sequence of SEQ ID NO: 492,

(30) a heavy chain CDR1 comprising the amino acid sequence of SEQ ID NO: 499, a heavy chain CDR2 comprising the amino acid sequence of SEQ ID NO: 500, a heavy chain CDR3 comprising the amino acid sequence of SEQ ID NO: 501, a light chain CDR1 comprising the amino acid sequence of SEQ ID NO: 502, a light chain CDR2 comprising the amino acid sequence of SEQ ID NO: 503, and a light chain CDR3 comprising the amino acid sequence of SEQ ID NO: 504,

(31) a heavy chain CDR1 comprising the amino acid sequence of SEQ ID NO: 511, a heavy chain CDR2 comprising the amino acid sequence of SEQ ID NO: 512, a heavy chain CDR3 comprising the amino acid sequence of SEQ ID NO: 513, a light chain CDR1 comprising the amino acid sequence of SEQ ID NO: 514, a light chain CDR2 comprising the amino acid sequence of SEQ ID NO: 515, and a light chain CDR3 comprising the amino acid sequence of SEQ ID NO: 516,

(32) a heavy chain CDR1 comprising the amino acid sequence of SEQ ID NO: 517, a heavy chain CDR2 comprising the amino acid sequence of SEQ ID NO: 518, a heavy chain CDR3 comprising the amino acid sequence of SEQ ID NO: 519, a light chain CDR1 comprising the amino acid sequence of SEQ ID NO: 520, a light chain CDR2 comprising the amino acid sequence of SEQ ID NO: 521, and a light chain CDR3 comprising the amino acid sequence of SEQ ID NO: 522, or

(33) a heavy chain CDR1 comprising the amino acid sequence of SEQ ID NO: 523, a heavy chain CDR2 comprising the amino acid sequence of SEQ ID NO: 524, a heavy chain CDR3 comprising the amino acid sequence of SEQ ID NO: 525, a light chain CDR1 comprising the amino acid sequence of SEQ ID NO: 526, a light chain CDR2 comprising the amino acid sequence of SEQ ID NO: 527, and a light chain CDR3 comprising the amino acid sequence of SEQ ID NO: 528.

18. The ROR antigen binding molecule of claim 15, wherein the third antigen binding site comprises:

(1) a heavy chain CDR1 comprising the amino acid sequence of SEQ ID NO: 314, a heavy chain CDR2 comprising the amino acid sequence of SEQ ID NO: 315, a heavy chain CDR3 comprising the amino acid sequence of SEQ ID NO: 316, a light chain CDR1 comprising the amino acid sequence of SEQ ID NO: 317, a light chain CDR2 comprising the amino acid sequence of SEQ ID NO: 318, and a light chain CDR3 comprising the amino acid sequence of SEQ ID NO: 319;

(2) a heavy chain CDR1 comprising the amino acid sequence of SEQ ID NO: 165, a heavy chain CDR2 comprising the amino acid sequence of SEQ ID NO: 166, a heavy chain CDR3 comprising the amino acid sequence of SEQ ID NO: 167, a light chain CDR1 comprising the amino acid sequence of SEQ ID NO: 168, a light chain CDR2 comprising the amino acid sequence of SEQ ID NO: 169, and a light chain CDR3 comprising the amino acid sequence of SEQ ID NO: 170;

(3) a heavy chain CDR1 comprising the amino acid sequence of SEQ ID NO: 171, a heavy chain CDR2 comprising the amino acid sequence of SEQ ID NO: 172, a heavy chain CDR3 comprising the amino acid sequence of SEQ ID NO: 173, a light chain CDR1 comprising the amino acid sequence of SEQ ID NO: 174, a light chain CDR2 comprising the amino acid sequence of SEQ ID NO: 175, and a light chain CDR3 comprising the amino acid sequence of SEQ ID NO: 176;

(4) a heavy chain CDR1 comprising the amino acid sequence of SEQ ID NO: 183, a heavy chain CDR2 comprising the amino acid sequence of SEQ ID NO: 184, a heavy chain CDR3 comprising the amino acid sequence of SEQ ID NO: 185, a light chain CDR1 comprising the amino acid sequence of SEQ ID NO: 186, a light chain CDR2 comprising the amino acid sequence of SEQ ID NO: 187, and a light chain CDR3 comprising the amino acid sequence of SEQ ID NO: 188;

(5) a heavy chain CDR1 comprising the amino acid sequence of SEQ ID NO: 195, a heavy chain CDR2 comprising the amino acid sequence of SEQ ID NO: 196, a heavy chain CDR3 comprising the amino acid sequence of SEQ ID NO: 197, a light chain CDR1 comprising the amino acid sequence of SEQ ID NO: 198, a light chain CDR2 comprising the amino acid sequence of SEQ ID NO: 199, and a light chain CDR3 comprising the amino acid sequence of SEQ ID NO: 200;

(6) a heavy chain CDR1 comprising the amino acid sequence of SEQ ID NO: 225, a heavy chain CDR2 comprising the amino acid sequence of SEQ ID NO: 226, a heavy chain CDR3 comprising the amino acid sequence of SEQ ID NO: 227, a light chain CDR1 comprising the amino acid sequence of SEQ ID NO: 228, a light chain CDR2 comprising the amino acid sequence of SEQ ID NO: 229, and a light chain CDR3 comprising the amino acid sequence of SEQ ID NO: 230;

(7) a heavy chain CDR1 comprising the amino acid sequence of SEQ ID NO: 272, a heavy chain CDR2 comprising the amino acid sequence of SEQ ID NO: 273, a heavy chain CDR3 comprising the amino acid sequence of SEQ ID NO: 274, a light chain CDR1 comprising the amino acid sequence of SEQ ID NO: 275, a light chain CDR2 comprising the amino acid sequence of SEQ ID NO: 276, and a light chain CDR3 comprising the amino acid sequence of SEQ ID NO: 277;

(8) a heavy chain CDR1 comprising the amino acid sequence of SEQ ID NO: 302, a heavy chain CDR2 comprising the amino acid sequence of SEQ ID NO: 303, a heavy chain CDR3 comprising the amino acid sequence of SEQ ID NO: 304, a light chain CDR1 comprising the amino acid sequence of SEQ ID NO: 305, a light chain CDR2 comprising the amino acid sequence of SEQ ID NO: 306, and a light chain CDR3 comprising the amino acid sequence of SEQ ID NO: 307;

(9) a heavy chain CDR1 comprising the amino acid sequence of SEQ ID NO: 308, a heavy chain CDR2 comprising the amino acid sequence of SEQ ID NO: 309, a heavy chain CDR3 comprising the amino acid sequence of SEQ ID NO: 310, a light chain CDR1 comprising the amino acid sequence of SEQ ID NO: 311, a light chain CDR2 comprising the amino acid sequence of SEQ ID NO: 312, and a light chain CDR3 comprising the amino acid sequence of SEQ ID NO: 313;

(10) a heavy chain CDR1 comprising the amino acid sequence of SEQ ID NO: 332, a heavy chain CDR2 comprising the amino acid sequence of SEQ ID NO: 333, a heavy chain CDR3 comprising the amino acid sequence of SEQ ID NO: 334, a light chain CDR1 comprising the amino acid sequence of SEQ ID NO: 335, a light chain CDR2 comprising the amino acid sequence of SEQ ID NO: 336, and a light chain CDR3 comprising the amino acid sequence of SEQ ID NO: 337;

(11) a heavy chain CDR1 comprising the amino acid sequence of SEQ ID NO: 344, a heavy chain CDR2 comprising the amino acid sequence of SEQ ID NO: 345, a heavy chain CDR3 comprising the amino acid sequence of SEQ ID NO: 346, a light chain CDR1 comprising the amino acid sequence of SEQ ID NO: 347, a light chain CDR2 comprising the amino acid sequence of SEQ ID NO: 348, and a light chain CDR3 comprising the amino acid sequence of SEQ ID NO: 349;

(12) a heavy chain CDR1 comprising the amino acid sequence of SEQ ID NO: 350, a heavy chain CDR2 comprising the amino acid sequence of SEQ ID NO: 351, a heavy chain CDR3 comprising the amino acid sequence of SEQ ID NO: 352, a light chain CDR1 comprising the amino acid sequence of SEQ ID NO: 353, a light chain CDR2 comprising the amino acid sequence of SEQ ID NO: 354, and a light chain CDR3 comprising the amino acid sequence of SEQ ID NO: 355; or

(13) a heavy chain CDR1 comprising the amino acid sequence of SEQ ID NO: 374, a heavy chain CDR2 comprising the amino acid sequence of SEQ ID NO: 375, a heavy chain CDR3 comprising the amino acid sequence of SEQ ID NO: 376, a light chain CDR1 comprising the amino acid sequence of SEQ ID NO: 377, a light chain CDR2 comprising the amino acid sequence of SEQ ID NO: 378, and a light chain CDR3 comprising the amino acid sequence of SEQ ID NO: 379.

19. The ROR antigen binding molecule of claim 15, wherein the third antigen binding site comprises:

(1) a heavy chain CDR1 comprising the amino acid sequence of SEQ ID NO: 505, a heavy chain CDR2 comprising the amino acid sequence of SEQ ID NO: 506, a heavy chain CDR3 comprising the amino acid sequence of SEQ ID NO: 507, a light chain CDR1 comprising the amino acid sequence of SEQ ID NO: 508, a light chain CDR2 comprising the amino acid sequence of SEQ ID NO: 509, and a light chain CDR3 comprising the amino acid sequence of SEQ ID NO: 510;

(2) a heavy chain CDR1 comprising the amino acid sequence of SEQ ID NO: 397, a heavy chain CDR2 comprising the amino acid sequence of SEQ ID NO: 398, a heavy chain CDR3 comprising the amino acid sequence of SEQ ID NO: 399, a light chain CDR1 comprising the amino acid sequence of SEQ ID NO: 400, a light chain CDR2 comprising the amino acid sequence of SEQ ID NO: 401, and a light chain CDR3 comprising the amino acid sequence of SEQ ID NO: 402;

(3) a heavy chain CDR1 comprising the amino acid sequence of SEQ ID NO: 409, a heavy chain CDR2 comprising the amino acid sequence of SEQ ID NO: 410, a heavy chain CDR3 comprising the amino acid sequence of SEQ ID NO: 411, a light chain CDR1 comprising the amino acid sequence of SEQ ID NO: 412, a light chain CDR2 comprising the amino acid sequence of SEQ ID NO: 413, and a light chain CDR3 comprising the amino acid sequence of SEQ ID NO: 414;

(4) a heavy chain CDR1 comprising the amino acid sequence of SEQ ID NO: 421, a heavy chain CDR2 comprising the amino acid sequence of SEQ ID NO: 422, a heavy chain CDR3 comprising the amino acid sequence of SEQ ID NO: 423, a light chain CDR1 comprising the amino acid sequence of SEQ ID NO: 424, a light chain CDR2 comprising the amino acid sequence of SEQ ID NO: 425, and a light chain CDR3 comprising the amino acid sequence of SEQ ID NO: 426;

(5) a heavy chain CDR1 comprising the amino acid sequence of SEQ ID NO: 493, a heavy chain CDR2 comprising the amino acid sequence of SEQ ID NO: 494, a heavy chain CDR3 comprising the amino acid sequence of SEQ ID NO: 495, a light chain CDR1 comprising the amino acid sequence of SEQ ID NO: 496, a light chain CDR2 comprising the amino acid sequence of SEQ ID NO: 497, and a light chain CDR3 comprising the amino acid sequence of SEQ ID NO: 498;

(6) a heavy chain CDR1 comprising the amino acid sequence of SEQ ID NO: 529, a heavy chain CDR2 comprising the amino acid sequence of SEQ ID NO: 530, a heavy chain CDR3 comprising the amino acid sequence of SEQ ID NO: 531, a light chain CDR1 comprising the amino acid sequence of SEQ ID NO: 532, a light chain CDR2 comprising the amino acid sequence of SEQ ID NO: 533, and a light chain CDR3 comprising the amino acid sequence of SEQ ID NO: 534; or (7) a heavy chain CDR1 comprising the amino acid sequence of SEQ ID NO: 535, a heavy chain CDR2 comprising the amino acid sequence of SEQ ID NO: 536, a heavy chain CDR3 comprising the amino acid sequence of SEQ ID NO: 537, a light chain CDR1 comprising the amino acid sequence of SEQ ID NO: 538, a light chain CDR2 comprising the amino acid sequence of SEQ ID NO: 539, and a light chain CDR3 comprising the amino acid sequence of SEQ ID NO: 540.

20. A pharmaceutical composition comprising the ROR antigen binding molecule of claim 1 and a pharmaceutically acceptable diluent.

21. A method for treating a subject with cancer, the method comprising administering a therapeutically effective amount of the pharmaceutical composition of claim 20 to the subject.

22. The method of claim 21, wherein the cancer is an ROR antigen expressing cancer.

23. The method of claim 22, wherein the cancer expresses an ROR1 antigen.

24. The method of claim 22, wherein the cancer expresses an ROR2 antigen.

25. The method of claim 22, wherein the cancer expresses an ROR1 antigen and an ROR2 antigen.

26. The method of claim 21, wherein the cancer is selected from the group consisting of: pancreatic cancer, ovarian cancer, breast cancer, lung cancer, gastric cancer, melanoma, Ewing sarcoma, chronic lymphocytic leukemia, mantle cell lymphoma, B-ALL, hematological cancer, prostate cancer, colon cancer, renal cancer, thyroid cancer, liver cancer, urothelial carcinoma, melanoma, endometrial cancer, clear cell renal cell carcinoma, clear cell carcinoma, and uterine cancer.

27. The method of claim 21, wherein the pharmaceutical composition is administered in combination with an additional therapy.

28. The method of claim 27, wherein the additional therapy is surgery, radiotherapy, endocrine therapy, immunotherapy, or chemotherapy.

29. The method of claim 28, wherein the immunotherapy is an immunotherapeutic agent.

30. The method of claim 29, wherein the immunotherapeutic agent is an immune checkpoint inhibitor.

31. The method of claim 29, wherein the immunotherapeutic agent is a vaccine.

32. The method of claim 28, wherein the chemotherapy is a cytotoxic agent or a chemotherapeutic agent.

33. The ROR antigen binding molecule of claim 1, wherein the first antigen binding site comprises:
   a heavy chain CDR1 comprising SEQ ID NO: 213,
   a heavy chain CDR2 comprising SEQ ID NO: 214,
   a heavy chain CDR3 comprising SEQ ID NO: 215,
   a light chain CDR1 comprising SEQ ID NO: 216,
   a light chain CDR2 comprising SEQ ID NO: 217, and
   a light chain CDR3 comprising SEQ ID NO: 218.

34. The ROR antigen binding molecule of claim 1, wherein the VH region of the first antigen binding site comprises the amino acid sequence of SEQ ID NO: 140 and the VL region of the first antigen binding site comprises the amino acid sequence of SEQ ID NO: 136.

\* \* \* \* \*

SEQUENCE LISTING

```
<160> NUMBER OF SEQ ID NOS: 542

<210> SEQ ID NO 1
<211> LENGTH: 338
<212> TYPE: PRT
<213> ORGANISM: Artificial Sequence
<220> FEATURE:
<223> OTHER INFORMATION: Example 1, bivalent monospecific construct
      CHAIN 1, VL
```

```
<400> SEQUENCE: 1

Val Glu Ile Lys Arg Thr Pro Arg Glu Pro Gln Val Tyr Thr Leu Pro
1               5                   10                  15

Pro Cys Arg Asp Glu Leu Thr Lys Asn Gln Val Ser Leu Trp Cys Leu
            20                  25                  30

Val Lys Gly Phe Tyr Pro Ser Asp Ile Ala Val Glu Trp Glu Ser Asn
        35                  40                  45

Gly Gln Pro Glu Asn Asn Tyr Lys Thr Thr Pro Val Leu Asp Ser
    50                  55                  60

Asp Gly Ser Phe Phe Leu Tyr Ser Lys Leu Thr Val Asp Lys Ser Arg
65                  70                  75                  80

Trp Gln Gln Gly Asn Val Phe Ser Cys Ser Val Met His Glu Ala Leu
                85                  90                  95

His Asn His Tyr Thr Gln Lys Ser Leu Ser Leu Ser Pro Gly Lys Asp
            100                 105                 110

Lys Thr His Thr Cys Pro Pro Cys Pro Ala Pro Glu Leu Leu Gly Gly
            115                 120                 125

Pro Ser Val Phe Leu Phe Pro Pro Lys Pro Lys Asp Thr Leu Met Ile
    130                 135                 140

Ser Arg Thr Pro Glu Val Thr Cys Val Val Val Asp Val Ser His Glu
145                 150                 155                 160

Asp Pro Glu Val Lys Phe Asn Trp Tyr Val Asp Gly Val Glu Val His
                165                 170                 175

Asn Ala Lys Thr Lys Pro Arg Glu Glu Gln Tyr Asn Ser Thr Tyr Arg
            180                 185                 190

Val Val Ser Val Leu Thr Val Leu His Gln Asp Trp Leu Asn Gly Lys
        195                 200                 205

Glu Tyr Lys Cys Lys Val Ser Asn Lys Ala Leu Pro Ala Pro Ile Glu
210                 215                 220

Lys Thr Ile Ser Lys Ala Lys Gly Gln Pro Arg Glu Pro Gln Val Tyr
225                 230                 235                 240

Thr Leu Pro Pro Cys Arg Asp Glu Leu Thr Lys Asn Gln Val Ser Leu
                245                 250                 255

Trp Cys Leu Val Lys Gly Phe Tyr Pro Ser Asp Ile Ala Val Glu Trp
            260                 265                 270

Glu Ser Asn Gly Gln Pro Glu Asn Asn Tyr Lys Thr Thr Pro Pro Val
        275                 280                 285

Leu Asp Ser Asp Gly Ser Phe Phe Leu Tyr Ser Lys Leu Thr Val Asp
    290                 295                 300

Lys Ser Arg Trp Gln Gln Gly Asn Val Phe Ser Cys Ser Val Met His
305                 310                 315                 320

Glu Ala Leu His Asn His Tyr Thr Gln Lys Ser Leu Ser Leu Ser Pro
                325                 330                 335

Gly Lys

<210> SEQ ID NO 2
<211> LENGTH: 112
<212> TYPE: PRT
<213> ORGANISM: Artificial Sequence
<220> FEATURE:
<223> OTHER INFORMATION: Example 1, bivalent monospecific construct
      CHAIN 2, VH

<400> SEQUENCE: 2

Val Thr Val Ser Ser Ala Ser Pro Arg Glu Pro Gln Val Tyr Thr Leu
```

```
                1               5                      10                      15
            Pro Pro Cys Arg Asp Glu Leu Thr Lys Asn Gln Val Ser Leu Trp Cys
                            20                      25                      30

Leu Val Lys Gly Phe Tyr Pro Ser Asp Ile Ala Val Glu Trp Glu Ser
                            35                      40                      45

Asn Gly Gln Pro Glu Asn Asn Tyr Lys Thr Thr Pro Pro Val Leu Asp
                            50                      55                      60

Ser Asp Gly Ser Phe Phe Leu Tyr Ser Lys Leu Thr Val Asp Lys Ser
            65                          70                      75                      80

Arg Trp Gln Gln Gly Asn Val Phe Ser Cys Ser Val Met His Glu Ala
                            85                      90                      95

Leu His Asn His Tyr Thr Gln Lys Ser Leu Ser Leu Ser Pro Gly Lys
                            100                     105                     110

<210> SEQ ID NO 3
<211> LENGTH: 338
<212> TYPE: PRT
<213> ORGANISM: Artificial Sequence
<220> FEATURE:
<223> OTHER INFORMATION: Example 1, bivalent, bispecific construct
      CHAIN 1, VL

<400> SEQUENCE: 3

Val Glu Ile Lys Arg Thr Pro Arg Glu Pro Gln Val Tyr Thr Leu Pro
            1               5                      10                      15

Pro Cys Arg Asp Glu Leu Thr Lys Asn Gln Val Ser Leu Trp Cys Leu
                            20                      25                      30

Val Lys Gly Phe Tyr Pro Ser Asp Ile Ala Val Glu Trp Glu Ser Asn
                            35                      40                      45

Gly Gln Pro Glu Asn Asn Tyr Lys Thr Thr Pro Pro Val Leu Asp Ser
                            50                      55                      60

Asp Gly Ser Phe Phe Leu Tyr Ser Lys Leu Thr Val Asp Lys Ser Arg
            65                          70                      75                      80

Trp Gln Gln Gly Asn Val Phe Ser Cys Ser Val Met His Glu Ala Leu
                            85                      90                      95

His Asn His Tyr Thr Gln Lys Ser Leu Ser Leu Ser Pro Gly Lys Asp
                            100                     105                     110

Lys Thr His Thr Cys Pro Pro Cys Pro Ala Pro Glu Leu Leu Gly Gly
                            115                     120                     125

Pro Ser Val Phe Leu Phe Pro Pro Lys Pro Lys Asp Thr Leu Met Ile
                            130                     135                     140

Ser Arg Thr Pro Glu Val Thr Cys Val Val Val Asp Val Ser His Glu
            145                         150                     155                     160

Asp Pro Glu Val Lys Phe Asn Trp Tyr Val Asp Gly Val Glu Val His
                            165                     170                     175

Asn Ala Lys Thr Lys Pro Arg Glu Glu Gln Tyr Asn Ser Thr Tyr Arg
                            180                     185                     190

Val Val Ser Val Leu Thr Val Leu His Gln Asp Trp Leu Asn Gly Lys
                            195                     200                     205

Glu Tyr Lys Cys Lys Val Ser Asn Lys Ala Leu Pro Ala Pro Ile Glu
                            210                     215                     220

Lys Thr Ile Ser Lys Ala Lys Gly Gln Pro Arg Glu Pro Gln Val Tyr
            225                         230                     235                     240

Thr Leu Pro Pro Cys Arg Asp Glu Leu Thr Lys Asn Gln Val Ser Leu
                            245                     250                     255
```

```
Trp Cys Leu Val Lys Gly Phe Tyr Pro Ser Asp Ile Ala Val Glu Trp
            260                 265                 270

Glu Ser Asn Gly Gln Pro Glu Asn Asn Tyr Lys Thr Thr Pro Pro Val
        275                 280                 285

Leu Asp Ser Asp Gly Ser Phe Phe Leu Tyr Ser Lys Leu Thr Val Asp
    290                 295                 300

Lys Ser Arg Trp Gln Gln Gly Asn Val Phe Ser Cys Ser Val Met His
305                 310                 315                 320

Glu Ala Leu His Asn His Tyr Thr Gln Lys Ser Leu Ser Leu Ser Pro
                325                 330                 335

Gly Lys

<210> SEQ ID NO 4
<211> LENGTH: 112
<212> TYPE: PRT
<213> ORGANISM: Artificial Sequence
<220> FEATURE:
<223> OTHER INFORMATION: Example 1, bivalent, bispecific construct
      CHAIN 2, VH

<400> SEQUENCE: 4

Val Thr Val Ser Ser Ala Ser Pro Arg Glu Pro Gln Val Tyr Thr Leu
1               5                   10                  15

Pro Pro Cys Arg Asp Glu Leu Thr Lys Asn Gln Val Ser Leu Trp Cys
            20                  25                  30

Leu Val Lys Gly Phe Tyr Pro Ser Asp Ile Ala Val Glu Trp Glu Ser
        35                  40                  45

Asn Gly Gln Pro Glu Asn Asn Tyr Lys Thr Thr Pro Pro Val Leu Asp
    50                  55                  60

Ser Asp Gly Ser Phe Phe Leu Tyr Ser Lys Leu Thr Val Asp Lys Ser
65                  70                  75                  80

Arg Trp Gln Gln Gly Asn Val Phe Ser Cys Ser Val Met His Glu Ala
                85                  90                  95

Leu His Asn His Tyr Thr Gln Lys Ser Leu Ser Leu Ser Pro Gly Lys
            100                 105                 110

<210> SEQ ID NO 5
<211> LENGTH: 338
<212> TYPE: PRT
<213> ORGANISM: Artificial Sequence
<220> FEATURE:
<223> OTHER INFORMATION: Example 1, bivalent, bispecific construct
      CHAIN 3, VL

<400> SEQUENCE: 5

Val Glu Ile Lys Arg Thr Val Ala Ala Pro Ser Val Phe Ile Phe Pro
1               5                   10                  15

Pro Ser Asp Glu Gln Leu Lys Ser Gly Thr Ala Ser Val Val Cys Leu
            20                  25                  30

Leu Asn Asn Phe Tyr Pro Arg Glu Ala Lys Val Gln Trp Lys Val Asp
        35                  40                  45

Asn Ala Leu Gln Ser Gly Asn Ser Gln Glu Ser Val Thr Glu Gln Asp
    50                  55                  60

Ser Lys Asp Ser Thr Tyr Ser Leu Ser Ser Thr Leu Thr Leu Ser Lys
65                  70                  75                  80

Ala Asp Tyr Glu Lys His Lys Val Tyr Ala Cys Glu Val Thr His Gln
                85                  90                  95

Gly Leu Ser Ser Pro Val Thr Lys Ser Phe Asn Arg Gly Glu Cys Asp
```

```
                    100                 105                 110
Lys Thr His Thr Cys Pro Pro Cys Pro Ala Pro Glu Leu Leu Gly Gly
                115                 120                 125

Pro Ser Val Phe Leu Phe Pro Lys Pro Lys Asp Thr Leu Met Ile
            130                 135                 140

Ser Arg Thr Pro Glu Val Thr Cys Val Val Asp Val Ser His Glu
145                 150                 155                 160

Asp Pro Glu Val Lys Phe Asn Trp Tyr Val Asp Gly Val Glu Val His
                165                 170                 175

Asn Ala Lys Thr Lys Pro Arg Glu Glu Gln Tyr Asn Ser Thr Tyr Arg
            180                 185                 190

Val Val Ser Val Leu Thr Val Leu His Gln Asp Trp Leu Asn Gly Lys
        195                 200                 205

Glu Tyr Lys Cys Lys Val Ser Asn Lys Ala Leu Pro Ala Pro Ile Glu
    210                 215                 220

Lys Thr Ile Ser Lys Ala Lys Gly Gln Pro Arg Glu Pro Gln Val Cys
225                 230                 235                 240

Thr Leu Pro Pro Ser Arg Glu Glu Met Thr Lys Asn Gln Val Ser Leu
                245                 250                 255

Ser Cys Ala Val Lys Gly Phe Tyr Pro Ser Asp Ile Ala Val Glu Trp
            260                 265                 270

Glu Ser Asn Gly Gln Pro Glu Asn Asn Tyr Lys Thr Thr Pro Pro Val
        275                 280                 285

Leu Asp Ser Asp Gly Ser Phe Phe Leu Val Ser Lys Leu Thr Val Asp
    290                 295                 300

Lys Ser Arg Trp Gln Gln Gly Asn Val Phe Ser Cys Ser Val Met His
305                 310                 315                 320

Glu Ala Leu His Asn His Tyr Thr Gln Lys Ser Leu Ser Leu Ser Pro
                325                 330                 335

Gly Lys

<210> SEQ ID NO 6
<211> LENGTH: 109
<212> TYPE: PRT
<213> ORGANISM: Artificial Sequence
<220> FEATURE:
<223> OTHER INFORMATION: Example 1, bivalent, bispecific construct
      CHAIN 4, VH

<400> SEQUENCE: 6

Val Thr Val Ser Ser Ala Ser Thr Lys Gly Pro Ser Val Phe Pro Leu
1               5                   10                  15

Ala Pro Ser Ser Lys Ser Thr Ser Gly Gly Thr Ala Ala Leu Gly Cys
            20                  25                  30

Leu Val Lys Asp Tyr Phe Pro Glu Pro Val Thr Val Ser Trp Asn Ser
        35                  40                  45

Gly Ala Leu Thr Ser Gly Val His Thr Phe Pro Ala Val Leu Gln Ser
    50                  55                  60

Ser Gly Leu Tyr Ser Leu Ser Ser Val Val Thr Val Pro Ser Ser Ser
65                  70                  75                  80

Leu Gly Thr Gln Thr Tyr Ile Cys Asn Val Asn His Lys Pro Ser Asn
                85                  90                  95

Thr Lys Val Asp Lys Lys Val Glu Pro Pro Lys Ser Cys
            100                 105
```

```
<210> SEQ ID NO 7
<211> LENGTH: 105
<212> TYPE: PRT
<213> ORGANISM: Artificial Sequence
<220> FEATURE:
<223> OTHER INFORMATION: Fc Fragment of Human IgG1

<400> SEQUENCE: 7

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro
            100                 105

<210> SEQ ID NO 8
<211> LENGTH: 441
<212> TYPE: PRT
<213> ORGANISM: Artificial Sequence
<220> FEATURE:
<223> OTHER INFORMATION: BC1 chain 1

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Pro Arg Glu
            100                 105                 110

Pro Gln Val Tyr Thr Leu Pro Pro Ser Arg Asp Glu Leu Thr Lys Asn
        115                 120                 125

Gln Val Ser Leu Lys Cys Leu Val Lys Gly Phe Tyr Pro Ser Asp Ile
    130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
                165                 170                 175

Leu Thr Val Asp Lys Ser Arg Trp Gln Gln Gly Asn Val Phe Ser Cys
            180                 185                 190

Ser Val Met His Glu Ala Leu His Asn His Tyr Thr Gln Lys Ser Leu
        195                 200                 205
```

```
Ser Leu Ser Lys Ser Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
                260                 265                 270

Val Asp Gly Val Glu Val His Asn Ala Lys Thr Lys Pro Arg Glu Glu
            275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Cys Arg Asp Glu Leu
                340                 345                 350

Thr Lys Asn Gln Val Ser Leu Trp Cys Leu Val Lys Gly Phe Tyr Pro
            355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
                420                 425                 430

Lys Ser Leu Ser Leu Ser Pro Gly Lys
            435                 440

<210> SEQ ID NO 9
<211> LENGTH: 227
<212> TYPE: PRT
<213> ORGANISM: Artificial Sequence
<220> FEATURE:
<223> OTHER INFORMATION: BC1 chain 2

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Ile His Trp Val Arg Gln Ala Pro Gly Lys Gly Leu Glu Trp Val
        35                  40                  45

Gly Asp Ile Thr Pro Tyr Asp Gly Thr Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Leu Val Gly Glu Ile Ala Thr Gly Phe Asp Tyr Trp Gly Gln
            100                 105                 110

Gly Thr Leu Val Thr Val Ser Ser Ala Ser Pro Arg Glu Pro Gln Val
        115                 120                 125
```

```
Tyr Thr Asp Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Gly Glu Cys
225

<210> SEQ ID NO 10
<211> LENGTH: 441
<212> TYPE: PRT
<213> ORGANISM: Artificial Sequence
<220> FEATURE:
<223> OTHER INFORMATION: BC1 chain 3 and BC28 bivalent chain 3

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Asp Lys Thr His Thr Cys Pro Pro Cys Pro
210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255
```

```
Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Cys Thr Leu Pro Pro Ser Arg Glu Glu Met
            340                 345                 350

Thr Lys Asn Gln Val Ser Leu Ser Cys Ala Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Val Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
            435                 440

<210> SEQ ID NO 11
<211> LENGTH: 217
<212> TYPE: PRT
<213> ORGANISM: Artificial Sequence
<220> FEATURE:
<223> OTHER INFORMATION: BC1 chain 4 and BC28 bivalent chain 4

<400> SEQUENCE: 11

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175
```

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys
    210                 215

<210> SEQ ID NO 12
<211> LENGTH: 109
<212> TYPE: PRT
<213> ORGANISM: Artificial Sequence
<220> FEATURE:
<223> OTHER INFORMATION: BC1 Domain A

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr
            100                 105

<210> SEQ ID NO 13
<211> LENGTH: 105
<212> TYPE: PRT
<213> ORGANISM: Artificial Sequence
<220> FEATURE:
<223> OTHER INFORMATION: BC1 Domain B

<400> SEQUENCE: 13

Pro Arg Glu Pro Gln Val Tyr Thr Leu Pro Pro Ser Arg Asp Glu Leu
1               5                   10                  15

Thr Lys Asn Gln Val Ser Leu Lys Cys Leu Val Lys Gly Phe Tyr Pro
            20                  25                  30

Ser Asp Ile Ala Val Glu Trp Glu Ser Asn Gly Gln Pro Glu Asn Asn
        35                  40                  45

Tyr Lys Thr Thr Pro Pro Val Leu Asp Ser Asp Gly Ser Phe Phe Leu
    50                  55                  60

Tyr Ser Lys Leu Thr Val Asp Lys Ser Arg Trp Gln Gln Gly Asn Val
65                  70                  75                  80

Phe Ser Cys Ser Val Met His Glu Ala Leu His Asn His Tyr Thr Gln
                85                  90                  95

Lys Ser Leu Ser Leu Ser Lys Ser Cys
            100                 105

<210> SEQ ID NO 14
<211> LENGTH: 110
<212> TYPE: PRT
<213> ORGANISM: Artificial Sequence
<220> FEATURE:
<223> OTHER INFORMATION: BC1 Domain D

```
<400> SEQUENCE: 14

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 15
<211> LENGTH: 107
<212> TYPE: PRT
<213> ORGANISM: Artificial Sequence
<220> FEATURE:
<223> OTHER INFORMATION: BC1 Domain E

<400> SEQUENCE: 15

Gly Gln Pro Arg Glu Pro Gln Val Tyr Thr Leu Pro Pro Cys Arg Asp
1               5                   10                  15

Glu Leu Thr Lys Asn Gln Val Ser Leu Trp Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 16
<211> LENGTH: 122
<212> TYPE: PRT
<213> ORGANISM: Artificial Sequence
<220> FEATURE:
<223> OTHER INFORMATION: BC1 Domain F

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Ile His Trp Val Arg Gln Ala Pro Gly Lys Gly Leu Glu Trp Val
        35                  40                  45

Gly Asp Ile Thr Pro Tyr Asp Gly Thr Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80
```

```
Leu Gln Met Asn Ser Leu Arg Ala Glu Asp Thr Ala Val Tyr Tyr Cys
                85                  90                  95

Ala Arg Leu Val Gly Glu Ile Ala Thr Gly Phe Asp Tyr Trp Gly Gln
            100                 105                 110

Gly Thr Leu Val Thr Val Ser Ser Ala Ser
        115                 120
```

<210> SEQ ID NO 17
<211> LENGTH: 105
<212> TYPE: PRT
<213> ORGANISM: Artificial Sequence
<220> FEATURE:
<223> OTHER INFORMATION: BC1 Domain G

<400> SEQUENCE: 17

```
Pro Arg Glu Pro Gln Val Tyr Thr Asp Pro Pro Ser Arg Asp Glu Leu
1               5                   10                  15

Thr Lys Asn Gln Val Ser Leu Thr Cys Leu Val Lys Gly Phe Tyr Pro
            20                  25                  30

Ser Asp Ile Ala Val Glu Trp Glu Ser Asn Gly Gln Pro Glu Asn Asn
        35                  40                  45

Tyr Lys Thr Thr Pro Pro Val Leu Asp Ser Asp Gly Ser Phe Phe Leu
    50                  55                  60

Tyr Ser Lys Leu Thr Val Asp Lys Ser Arg Trp Gln Gln Gly Asn Val
65                  70                  75                  80

Phe Ser Cys Ser Val Met His Glu Ala Leu His Asn His Tyr Thr Gln
                85                  90                  95

Lys Ser Leu Ser Leu Ser Gly Glu Cys
            100                 105
```

<210> SEQ ID NO 18
<211> LENGTH: 107
<212> TYPE: PRT
<213> ORGANISM: Artificial Sequence
<220> FEATURE:
<223> OTHER INFORMATION: BC1 Domain H

<400> SEQUENCE: 18

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105
```

<210> SEQ ID NO 19
<211> LENGTH: 107
<212> TYPE: PRT
<213> ORGANISM: Artificial Sequence
<220> FEATURE:
<223> OTHER INFORMATION: BC1 Domain I

<400> SEQUENCE: 19

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 20
<211> LENGTH: 110
<212> TYPE: PRT
<213> ORGANISM: Artificial Sequence
<220> FEATURE:
<223> OTHER INFORMATION: BC1 Domain J

<400> SEQUENCE: 20

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 21
<211> LENGTH: 107
<212> TYPE: PRT
<213> ORGANISM: Artificial Sequence
<220> FEATURE:
<223> OTHER INFORMATION: BC1 Domain K

<400> SEQUENCE: 21

Gly Gln Pro Arg Glu Pro Gln Val Cys Thr Leu Pro Pro Ser Arg Glu
1               5                   10                  15

Glu Met Thr Lys Asn Gln Val Ser Leu Ser Cys Ala Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Val Ser Lys Leu Thr Val Asp Lys Ser Arg Trp Gln Gln Gly
65                  70                  75                  80

-continued

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 22
<211> LENGTH: 113
<212> TYPE: PRT
<213> ORGANISM: Artificial Sequence
<220> FEATURE:
<223> OTHER INFORMATION: BC1 Domain L

<400> SEQUENCE: 22

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 23
<211> LENGTH: 104
<212> TYPE: PRT
<213> ORGANISM: Artificial Sequence
<220> FEATURE:
<223> OTHER INFORMATION: BC1 Domain M

<400> SEQUENCE: 23

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Pro Lys Ser Cys
            100

<210> SEQ ID NO 24
<211> LENGTH: 441
<212> TYPE: PRT
<213> ORGANISM: Artificial Sequence
<220> FEATURE:
<223> OTHER INFORMATION: BC28 chain 1

<400> SEQUENCE: 24

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Pro Arg Glu
            100                 105                 110

Pro Gln Val Cys Thr Leu Pro Pro Ser Arg Asp Glu Leu Thr Lys Asn
        115                 120                 125

Gln Val Ser Leu Thr Cys Leu Val Lys Gly Phe Tyr Pro Ser Asp Ile
    130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
                165                 170                 175

Leu Thr Val Asp Lys Ser Arg Trp Gln Gln Gly Asn Val Phe Ser Cys
            180                 185                 190

Ser Val Met His Glu Ala Leu His Asn His Tyr Thr Gln Lys Ser Leu
        195                 200                 205

Ser Leu Ser Pro Gly Lys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Cys Arg Asp Glu Leu
            340                 345                 350

Thr Lys Asn Gln Val Ser Leu Trp Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415
```

```
Phe Ser Cys Ser Val Met His Glu Ala Leu His Asn His Tyr Thr Gln
            420                 425                 430
Lys Ser Leu Ser Leu Ser Pro Gly Lys
        435                 440

<210> SEQ ID NO 25
<211> LENGTH: 227
<212> TYPE: PRT
<213> ORGANISM: Artificial Sequence
<220> FEATURE:
<223> OTHER INFORMATION: BC28 chain 2

<400> SEQUENCE: 25

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asp Tyr
            20                  25                  30
Asp Ile His Trp Val Arg Gln Ala Pro Gly Lys Gly Leu Glu Trp Val
        35                  40                  45
Gly Asp Ile Thr Pro Tyr Asp Gly Thr Thr Asn Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Leu Val Gly Glu Ile Ala Thr Gly Phe Asp Tyr Trp Gly Gln
            100                 105                 110
Gly Thr Leu Val Thr Val Ser Ser Ala Ser Pro Arg Glu Pro Gln Val
        115                 120                 125
Tyr Thr Leu Pro Pro Cys Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Lys
225

<210> SEQ ID NO 26
<211> LENGTH: 109
<212> TYPE: PRT
<213> ORGANISM: Artificial Sequence
<220> FEATURE:
<223> OTHER INFORMATION: BC28 domain A

<400> SEQUENCE: 26

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Asn Thr Ala
            20                  25                  30
Val Ala Trp Tyr Gln Gln Lys Pro Gly Lys Ala Pro Lys Leu Leu Ile
        35                  40                  45
```

```
Tyr Ser Ala Ser Phe Leu Tyr Ser Gly Val Pro Ser Arg Phe Ser Gly
            50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                    85                  90                  95

Thr Phe Gly Gln Gly Thr Lys Val Glu Ile Lys Arg Thr
                100                 105

<210> SEQ ID NO 27
<211> LENGTH: 105
<212> TYPE: PRT
<213> ORGANISM: Artificial Sequence
<220> FEATURE:
<223> OTHER INFORMATION: BC28 domain B

<400> SEQUENCE: 27

Pro Arg Glu Pro Gln Val Cys Thr Leu Pro Pro Ser Arg Asp Glu Leu
 1               5                  10                  15

Thr Lys Asn Gln Val Ser Leu Thr Cys Leu Val Lys Gly Phe Tyr Pro
                20                  25                  30

Ser Asp Ile Ala Val Glu Trp Glu Ser Asn Gly Gln Pro Glu Asn Asn
                35                  40                  45

Tyr Lys Thr Thr Pro Pro Val Leu Asp Ser Asp Gly Ser Phe Phe Leu
            50                  55                  60

Tyr Ser Lys Leu Thr Val Asp Lys Ser Arg Trp Gln Gln Gly Asn Val
 65                  70                  75                  80

Phe Ser Cys Ser Val Met His Glu Ala Leu His Asn His Tyr Thr Gln
                85                  90                  95

Lys Ser Leu Ser Leu Ser Pro Gly Lys
                100                 105

<210> SEQ ID NO 28
<211> LENGTH: 110
<212> TYPE: PRT
<213> ORGANISM: Artificial Sequence
<220> FEATURE:
<223> OTHER INFORMATION: BC28 domain D

<400> SEQUENCE: 28

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
                35                  40                  45

Val Asp Gly Val Glu Val His Asn Ala Lys Thr Lys Pro Arg Glu Glu
            50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
                100                 105                 110

<210> SEQ ID NO 29
<211> LENGTH: 107
<212> TYPE: PRT
```

```
<213> ORGANISM: Artificial Sequence
<220> FEATURE:
<223> OTHER INFORMATION: BC28 domain E

<400> SEQUENCE: 29

Gly Gln Pro Arg Glu Pro Gln Val Tyr Thr Leu Pro Pro Cys Arg Asp
1               5                   10                  15

Glu Leu Thr Lys Asn Gln Val Ser Leu Trp Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 30
<211> LENGTH: 122
<212> TYPE: PRT
<213> ORGANISM: Artificial Sequence
<220> FEATURE:
<223> OTHER INFORMATION: BC28 domain F

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Ile His Trp Val Arg Gln Ala Pro Gly Lys Gly Leu Glu Trp Val
        35                  40                  45

Gly Asp Ile Thr Pro Tyr Asp Gly Thr Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Leu Val Gly Glu Ile Ala Thr Gly Phe Asp Tyr Trp Gly Gln
            100                 105                 110

Gly Thr Leu Val Thr Val Ser Ser Ala Ser
            115                 120

<210> SEQ ID NO 31
<211> LENGTH: 105
<212> TYPE: PRT
<213> ORGANISM: Artificial Sequence
<220> FEATURE:
<223> OTHER INFORMATION: BC28 domain G

<400> SEQUENCE: 31

Pro Arg Glu Pro Gln Val Tyr Thr Leu Pro Pro Cys Arg Asp Glu Leu
1               5                   10                  15

Thr Lys Asn Gln Val Ser Leu Thr Cys Leu Val Lys Gly Phe Tyr Pro
            20                  25                  30

Ser Asp Ile Ala Val Glu Trp Glu Ser Asn Gly Gln Pro Glu Asn Asn
        35                  40                  45
```

```
Tyr Lys Thr Thr Pro Pro Val Leu Asp Ser Asp Gly Ser Phe Phe Leu
     50                  55                  60

Tyr Ser Lys Leu Thr Val Asp Lys Ser Arg Trp Gln Gln Gly Asn Val
 65                  70                  75                  80

Phe Ser Cys Ser Val Met His Glu Ala Leu His Asn His Tyr Thr Gln
                 85                  90                  95

Lys Ser Leu Ser Leu Ser Pro Gly Lys
                100                 105

<210> SEQ ID NO 32
<211> LENGTH: 441
<212> TYPE: PRT
<213> ORGANISM: Artificial Sequence
<220> FEATURE:
<223> OTHER INFORMATION: BC44 chain 1

<400> SEQUENCE: 32

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
                 20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Arg Glu
                100                 105                 110

Pro Gln Val Cys Thr Leu Pro Pro Ser Arg Asp Glu Leu Thr Lys Asn
                115                 120                 125

Gln Val Ser Leu Thr Cys Leu Val Lys Gly Phe Tyr Pro Ser Asp Ile
            130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
                165                 170                 175

Leu Thr Val Asp Lys Ser Arg Trp Gln Gln Gly Asn Val Phe Ser Cys
            180                 185                 190

Ser Val Met His Glu Ala Leu His Asn His Tyr Thr Gln Lys Ser Leu
        195                 200                 205

Ser Leu Ser Pro Gly Lys Asp Lys Thr His Thr Cys Pro Pro Cys Pro
210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
290                 295                 300
```

-continued

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
            325                 330                 335

Pro Arg Glu Pro Gln Val Tyr Thr Leu Pro Pro Cys Arg Asp Glu Leu
        340                 345                 350

Thr Lys Asn Gln Val Ser Leu Trp Cys Leu Val Lys Gly Phe Tyr Pro
    355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
            405                 410                 415

Phe Ser Cys Ser Val Met His Glu Ala Leu His Asn His Tyr Thr Gln
        420                 425                 430

Lys Ser Leu Ser Leu Ser Pro Gly Lys
            435                 440

<210> SEQ ID NO 33
<211> LENGTH: 109
<212> TYPE: PRT
<213> ORGANISM: Artificial Sequence
<220> FEATURE:
<223> OTHER INFORMATION: BC44 Domain A

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr
            100                 105

<210> SEQ ID NO 34
<211> LENGTH: 105
<212> TYPE: PRT
<213> ORGANISM: Artificial Sequence
<220> FEATURE:
<223> OTHER INFORMATION: BC44 Domain B

<400> SEQUENCE: 34

Val Arg Glu Pro Gln Val Cys Thr Leu Pro Pro Ser Arg Asp Glu Leu
1               5                   10                  15

Thr Lys Asn Gln Val Ser Leu Thr Cys Leu Val Lys Gly Phe Tyr Pro
            20                  25                  30

Ser Asp Ile Ala Val Glu Trp Glu Ser Asn Gly Gln Pro Glu Asn Asn
        35                  40                  45

Tyr Lys Thr Thr Pro Pro Val Leu Asp Ser Asp Gly Ser Phe Phe Leu

```
                 50                  55                  60

Tyr Ser Lys Leu Thr Val Asp Lys Ser Arg Trp Gln Gln Gly Asn Val
 65                  70                  75                  80

Phe Ser Cys Ser Val Met His Glu Ala Leu His Asn His Tyr Thr Gln
                 85                  90                  95

Lys Ser Leu Ser Leu Ser Pro Gly Lys
            100                 105

<210> SEQ ID NO 35
<211> LENGTH: 110
<212> TYPE: PRT
<213> ORGANISM: Artificial Sequence
<220> FEATURE:
<223> OTHER INFORMATION: BC44 Domain D

<400> SEQUENCE: 35

Ala Pro Glu Leu Leu Gly Gly Pro Ser Val Phe Leu Phe Pro Pro Lys
  1               5                  10                  15

Pro Lys Asp Thr Leu Met Ile Ser Arg Thr Pro Glu Val Thr Cys Val
                 20                  25                  30

Val Val Asp Val Ser His Glu Asp Pro Glu Val Lys Phe Asn Trp Tyr
             35                  40                  45

Val Asp Gly Val Glu Val His Asn Ala Lys Thr Lys Pro Arg Glu Glu
         50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys
            100                 105                 110

<210> SEQ ID NO 36
<211> LENGTH: 107
<212> TYPE: PRT
<213> ORGANISM: Artificial Sequence
<220> FEATURE:
<223> OTHER INFORMATION: BC44 Domain E

<400> SEQUENCE: 36

Gly Gln Pro Arg Glu Pro Gln Val Tyr Thr Leu Pro Pro Cys Arg Asp
  1               5                  10                  15

Glu Leu Thr Lys Asn Gln Val Ser Leu Trp Cys Leu Val Lys Gly Phe
                 20                  25                  30

Tyr Pro Ser Asp Ile Ala Val Glu Trp Glu Ser Asn Gly Gln Pro Glu
             35                  40                  45

Asn Asn Tyr Lys Thr Thr Pro Pro Val Leu Asp Ser Asp Gly Ser Phe
         50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 37
<211> LENGTH: 661
<212> TYPE: PRT
<213> ORGANISM: Artificial Sequence
<220> FEATURE:
```

<223> OTHER INFORMATION: BC28 1x2 chain 3

<400> SEQUENCE: 37

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Pro Arg Glu
            100                 105                 110

Pro Gln Val Cys Thr Leu Pro Pro Ser Arg Asp Glu Leu Thr Lys Asn
        115                 120                 125

Gln Val Ser Leu Thr Cys Leu Val Lys Gly Phe Tyr Pro Ser Asp Ile
130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
                165                 170                 175

Leu Thr Val Asp Lys Ser Arg Trp Gln Gln Gly Asn Val Phe Ser Cys
            180                 185                 190

Ser Val Met His Glu Ala Leu His Asn His Tyr Thr Gln Lys Ser Leu
        195                 200                 205

Ser Leu Ser Pro Gly Lys Gly Ser Gly Ser Gly Ser Glu Ile Val Leu
    210                 215                 220

Thr Gln Ser Pro Ala Thr Leu Ser Leu Ser Pro Gly Glu Arg Ala Thr
225                 230                 235                 240

Leu Ser Cys Arg Ala Ser Gln Ser Val Ser Ser Tyr Leu Ala Trp Tyr
                245                 250                 255

Gln Gln Lys Pro Gly Gln Ala Pro Arg Leu Leu Ile Tyr Asp Ala Ser
            260                 265                 270

Asn Arg Ala Thr Gly Ile Pro Ala Arg Phe Ser Gly Ser Gly Ser Gly
        275                 280                 285

Thr Asp Phe Thr Leu Thr Ile Ser Ser Leu Glu Pro Glu Asp Phe Ala
    290                 295                 300

Val Tyr Tyr Cys Gln Gln Ser Ser Asn Trp Pro Arg Thr Phe Gly Gln
305                 310                 315                 320

Gly Thr Lys Val Glu Ile Lys Arg Thr Val Ala Ala Pro Ser Val Phe
                325                 330                 335

Ile Phe Pro Pro Ser Asp Glu Gln Leu Lys Ser Gly Thr Ala Ser Val
            340                 345                 350

Val Cys Leu Leu Asn Asn Phe Tyr Pro Arg Glu Ala Lys Val Gln Trp
        355                 360                 365

Lys Val Asp Asn Ala Leu Gln Ser Gly Asn Ser Gln Glu Ser Val Thr
    370                 375                 380

Glu Gln Asp Ser Lys Asp Ser Thr Tyr Ser Leu Ser Ser Thr Leu Thr
385                 390                 395                 400
```

```
Leu Ser Lys Ala Asp Tyr Glu Lys His Lys Val Tyr Ala Cys Glu Val
                405                 410                 415
Thr His Gln Gly Leu Ser Ser Pro Val Thr Lys Ser Phe Asn Arg Gly
            420                 425                 430
Glu Cys Asp Lys Thr His Thr Cys Pro Pro Cys Pro Ala Pro Glu Leu
        435                 440                 445
Leu Gly Gly Pro Ser Val Phe Leu Phe Pro Pro Lys Pro Lys Asp Thr
    450                 455                 460
Leu Met Ile Ser Arg Thr Pro Glu Val Thr Cys Val Val Val Asp Val
465                 470                 475                 480
Ser His Glu Asp Pro Glu Val Lys Phe Asn Trp Tyr Val Asp Gly Val
                485                 490                 495
Glu Val His Asn Ala Lys Thr Lys Pro Arg Glu Glu Gln Tyr Asn Ser
            500                 505                 510
Thr Tyr Arg Val Val Ser Val Leu Thr Val Leu His Gln Asp Trp Leu
        515                 520                 525
Asn Gly Lys Glu Tyr Lys Cys Lys Val Ser Asn Lys Ala Leu Pro Ala
    530                 535                 540
Pro Ile Glu Lys Thr Ile Ser Lys Ala Lys Gly Gln Pro Arg Glu Pro
545                 550                 555                 560
Gln Val Cys Thr Leu Pro Pro Ser Arg Glu Glu Met Thr Lys Asn Gln
                565                 570                 575
Val Ser Leu Ser Cys Ala Val Lys Gly Phe Tyr Pro Ser Asp Ile Ala
            580                 585                 590
Val Glu Trp Glu Ser Asn Gly Gln Pro Glu Asn Asn Tyr Lys Thr Thr
        595                 600                 605
Pro Pro Val Leu Asp Ser Asp Gly Ser Phe Phe Leu Val Ser Lys Leu
    610                 615                 620
Thr Val Asp Lys Ser Arg Trp Gln Gln Gly Asn Val Phe Ser Cys Ser
625                 630                 635                 640
Val Met His Glu Ala Leu His Asn His Tyr Thr Gln Lys Ser Leu Ser
                645                 650                 655
Leu Ser Pro Gly Lys
            660

<210> SEQ ID NO 38
<211> LENGTH: 109
<212> TYPE: PRT
<213> ORGANISM: Artificial Sequence
<220> FEATURE:
<223> OTHER INFORMATION: BC28 1x2 domain R

<400> SEQUENCE: 38

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Asn Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Thr Thr Pro Pro
                85                  90                  95
```

-continued

Thr Phe Gly Gln Gly Thr Lys Val Glu Ile Lys Arg Thr
            100                 105

<210> SEQ ID NO 39
<211> LENGTH: 105
<212> TYPE: PRT
<213> ORGANISM: Artificial Sequence
<220> FEATURE:
<223> OTHER INFORMATION: BC28 1x2 domain S

<400> SEQUENCE: 39

Pro Arg Glu Pro Gln Val Cys Thr Leu Pro Pro Ser Arg Asp Glu Leu
1               5                   10                  15

Thr Lys Asn Gln Val Ser Leu Thr Cys Leu Val Lys Gly Phe Tyr Pro
            20                  25                  30

Ser Asp Ile Ala Val Glu Trp Glu Ser Asn Gly Gln Pro Glu Asn Asn
        35                  40                  45

Tyr Lys Thr Thr Pro Pro Val Leu Asp Ser Asp Gly Ser Phe Phe Leu
    50                  55                  60

Tyr Ser Lys Leu Thr Val Asp Lys Ser Arg Trp Gln Gln Gly Asn Val
65                  70                  75                  80

Phe Ser Cys Ser Val Met His Glu Ala Leu His Asn His Tyr Thr Gln
                85                  90                  95

Lys Ser Leu Ser Leu Ser Pro Gly Lys
            100                 105

<210> SEQ ID NO 40
<211> LENGTH: 6
<212> TYPE: PRT
<213> ORGANISM: Artificial Sequence
<220> FEATURE:
<223> OTHER INFORMATION: BC28 1x2 linker

<400> SEQUENCE: 40

Gly Ser Gly Ser Gly Ser
1               5

<210> SEQ ID NO 41
<211> LENGTH: 107
<212> TYPE: PRT
<213> ORGANISM: Artificial Sequence
<220> FEATURE:
<223> OTHER INFORMATION: BC28 1x2 domain H

<400> SEQUENCE: 41

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

```
<210> SEQ ID NO 42
<211> LENGTH: 107
<212> TYPE: PRT
<213> ORGANISM: Artificial Sequence
<220> FEATURE:
<223> OTHER INFORMATION: BC28 1x2 domain I

<400> SEQUENCE: 42

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 43
<211> LENGTH: 110
<212> TYPE: PRT
<213> ORGANISM: Artificial Sequence
<220> FEATURE:
<223> OTHER INFORMATION: BC28 1x2 domain J

<400> SEQUENCE: 43

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 44
<211> LENGTH: 107
<212> TYPE: PRT
<213> ORGANISM: Artificial Sequence
<220> FEATURE:
<223> OTHER INFORMATION: BC28 1x2 domain K

<400> SEQUENCE: 44

Gly Gln Pro Arg Glu Pro Gln Val Cys Thr Leu Pro Pro Ser Arg Glu
1               5                   10                  15

Glu Met Thr Lys Asn Gln Val Ser Leu Ser Cys Ala Val Lys Gly Phe
            20                  25                  30

Tyr Pro Ser Asp Ile Ala Val Glu Trp Glu Ser Asn Gly Gln Pro Glu
        35                  40                  45
```

```
Asn Asn Tyr Lys Thr Thr Pro Pro Val Leu Asp Ser Asp Gly Ser Phe
            50                  55                  60

Phe Leu Val Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 45
<211> LENGTH: 661
<212> TYPE: PRT
<213> ORGANISM: Artificial Sequence
<220> FEATURE:
<223> OTHER INFORMATION: BC28-1x1x1a chain 3

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Asp Ser Tyr Leu Trp
                85                  90                  95

Thr Phe Gly Gln Gly Thr Lys Val Glu Ile Lys Arg Thr Pro Arg Glu
            100                 105                 110

Pro Gln Val Tyr Thr Leu Pro Pro Ser Arg Asp Glu Leu Thr Lys Asn
        115                 120                 125

Gln Val Ser Leu Lys Cys Leu Val Lys Gly Phe Tyr Pro Ser Asp Ile
    130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
                165                 170                 175

Leu Thr Val Asp Lys Ser Arg Trp Gln Gln Gly Asn Val Phe Ser Cys
            180                 185                 190

Ser Val Met His Glu Ala Leu His Asn His Tyr Thr Gln Lys Ser Leu
        195                 200                 205

Ser Leu Ser Lys Ser Cys Gly Ser Gly Ser Gly Glu Ile Val Leu
    210                 215                 220

Thr Gln Ser Pro Ala Thr Leu Ser Leu Ser Pro Gly Glu Arg Ala Thr
225                 230                 235                 240

Leu Ser Cys Arg Ala Ser Gln Ser Val Ser Ser Tyr Leu Ala Trp Tyr
                245                 250                 255

Gln Gln Lys Pro Gly Gln Ala Pro Arg Leu Leu Ile Tyr Asp Ala Ser
            260                 265                 270

Asn Arg Ala Thr Gly Ile Pro Ala Arg Phe Ser Gly Ser Gly Ser Gly
        275                 280                 285

Thr Asp Phe Thr Leu Thr Ile Ser Ser Leu Glu Pro Glu Asp Phe Ala
    290                 295                 300
```

Val Tyr Tyr Cys Gln Gln Ser Ser Asn Trp Pro Arg Thr Phe Gly Gln
305                 310                 315                 320

Gly Thr Lys Val Glu Ile Lys Arg Thr Val Ala Ala Pro Ser Val Phe
            325                 330                 335

Ile Phe Pro Pro Ser Asp Glu Gln Leu Lys Ser Gly Thr Ala Ser Val
        340                 345                 350

Val Cys Leu Leu Asn Asn Phe Tyr Pro Arg Glu Ala Lys Val Gln Trp
    355                 360                 365

Lys Val Asp Asn Ala Leu Gln Ser Gly Asn Ser Gln Glu Ser Val Thr
370                 375                 380

Glu Gln Asp Ser Lys Asp Ser Thr Tyr Ser Leu Ser Ser Thr Leu Thr
385                 390                 395                 400

Leu Ser Lys Ala Asp Tyr Glu Lys His Lys Val Tyr Ala Cys Glu Val
            405                 410                 415

Thr His Gln Gly Leu Ser Ser Pro Val Thr Lys Ser Phe Asn Arg Gly
        420                 425                 430

Glu Cys Asp Lys Thr His Thr Cys Pro Pro Cys Pro Ala Pro Glu Leu
    435                 440                 445

Leu Gly Gly Pro Ser Val Phe Leu Phe Pro Pro Lys Pro Lys Asp Thr
450                 455                 460

Leu Met Ile Ser Arg Thr Pro Glu Val Thr Cys Val Val Val Asp Val
465                 470                 475                 480

Ser His Glu Asp Pro Glu Val Lys Phe Asn Trp Tyr Val Asp Gly Val
            485                 490                 495

Glu Val His Asn Ala Lys Thr Lys Pro Arg Glu Glu Gln Tyr Asn Ser
        500                 505                 510

Thr Tyr Arg Val Val Ser Val Leu Thr Val Leu His Gln Asp Trp Leu
    515                 520                 525

Asn Gly Lys Glu Tyr Lys Cys Lys Val Ser Asn Lys Ala Leu Pro Ala
530                 535                 540

Pro Ile Glu Lys Thr Ile Ser Lys Ala Lys Gly Gln Pro Arg Glu Pro
545                 550                 555                 560

Gln Val Cys Thr Leu Pro Pro Ser Arg Glu Glu Met Thr Lys Asn Gln
            565                 570                 575

Val Ser Leu Ser Cys Ala Val Lys Gly Phe Tyr Pro Ser Asp Ile Ala
        580                 585                 590

Val Glu Trp Glu Ser Asn Gly Gln Pro Glu Asn Asn Tyr Lys Thr Thr
    595                 600                 605

Pro Pro Val Leu Asp Ser Asp Gly Ser Phe Phe Leu Val Ser Lys Leu
610                 615                 620

Thr Val Asp Lys Ser Arg Trp Gln Gln Gly Asn Val Phe Ser Cys Ser
625                 630                 635                 640

Val Met His Glu Ala Leu His Asn His Tyr Thr Gln Lys Ser Leu Ser
            645                 650                 655

Leu Ser Pro Gly Lys
            660

<210> SEQ ID NO 46
<211> LENGTH: 109
<212> TYPE: PRT
<213> ORGANISM: Artificial Sequence
<220> FEATURE:
<223> OTHER INFORMATION: BC28-1x1x1a domain R

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Asp Ser Tyr Leu Trp
                85                  90                  95

Thr Phe Gly Gln Gly Thr Lys Val Glu Ile Lys Arg Thr
            100                 105

<210> SEQ ID NO 47
<211> LENGTH: 105
<212> TYPE: PRT
<213> ORGANISM: Artificial Sequence
<220> FEATURE:
<223> OTHER INFORMATION: BC28-1x1x1a domain S

<400> SEQUENCE: 47

Pro Arg Glu Pro Gln Val Tyr Thr Leu Pro Pro Ser Arg Asp Glu Leu
1               5                   10                  15

Thr Lys Asn Gln Val Ser Leu Lys Cys Leu Val Lys Gly Phe Tyr Pro
            20                  25                  30

Ser Asp Ile Ala Val Glu Trp Glu Ser Asn Gly Gln Pro Glu Asn Asn
        35                  40                  45

Tyr Lys Thr Thr Pro Pro Val Leu Asp Ser Asp Gly Ser Phe Phe Leu
    50                  55                  60

Tyr Ser Lys Leu Thr Val Asp Lys Ser Arg Trp Gln Gln Gly Asn Val
65                  70                  75                  80

Phe Ser Cys Ser Val Met His Glu Ala Leu His Asn His Tyr Thr Gln
                85                  90                  95

Lys Ser Leu Ser Leu Ser Lys Ser Cys
            100                 105

<210> SEQ ID NO 48
<211> LENGTH: 6
<212> TYPE: PRT
<213> ORGANISM: Artificial Sequence
<220> FEATURE:
<223> OTHER INFORMATION: BC28-1x1x1a linker

<400> SEQUENCE: 48

Gly Ser Gly Ser Gly Ser
1               5

<210> SEQ ID NO 49
<211> LENGTH: 107
<212> TYPE: PRT
<213> ORGANISM: Artificial Sequence
<220> FEATURE:
<223> OTHER INFORMATION: BC28-1x1x1a domain H

<400> SEQUENCE: 49

Glu Ile Val Leu Thr Gln Ser Pro Ala Thr Leu Ser Leu Ser Pro Gly
1               5                   10                  15

-continued

Glu Arg Ala Thr Leu Ser Cys Arg Ala Ser Gln Ser Val Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 50
<211> LENGTH: 107
<212> TYPE: PRT
<213> ORGANISM: Artificial Sequence
<220> FEATURE:
<223> OTHER INFORMATION: BC28-1x1x1a domain I

<400> SEQUENCE: 50

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 51
<211> LENGTH: 110
<212> TYPE: PRT
<213> ORGANISM: Artificial Sequence
<220> FEATURE:
<223> OTHER INFORMATION: BC28-1x1x1a domain J

<400> SEQUENCE: 51

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 52
<211> LENGTH: 107
<212> TYPE: PRT
<213> ORGANISM: Artificial Sequence
<220> FEATURE:
<223> OTHER INFORMATION: BC28-1x1x1a domain K

<400> SEQUENCE: 52

Gly Gln Pro Arg Glu Pro Gln Val Cys Thr Leu Pro Pro Ser Arg Glu
1               5                   10                  15

Glu Met Thr Lys Asn Gln Val Ser Leu Ser Cys Ala Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Val Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 53
<211> LENGTH: 224
<212> TYPE: PRT
<213> ORGANISM: Artificial Sequence
<220> FEATURE:
<223> OTHER INFORMATION: hCTLA4-4.chain 2

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Tyr Ile His Trp Val Arg Gln Ala Pro Gly Lys Gly Leu Glu Trp Val
        35                  40                  45

Ala Val Ile Tyr Pro Tyr Thr Gly Phe Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Glu Tyr Thr Val Leu Asp Tyr Trp Gly Gln Gly Thr Leu
            100                 105                 110

Val Thr Val Ser Ser Ala Ser Pro Arg Glu Pro Gln Val Tyr Thr Asp
        115                 120                 125

Pro Pro Ser Arg Asp Glu Leu Thr Lys Asn Gln Val Ser Leu Thr Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala 195                 200                 205
Leu His Asn His Tyr Thr Gln Lys Ser Leu Ser Leu Ser Gly Glu Cys
    210                 215                 220

<210> SEQ ID NO 54
<211> LENGTH: 119
<212> TYPE: PRT
<213> ORGANISM: Artificial Sequence
<220> FEATURE:
<223> OTHER INFORMATION: hCTLA4-4 domain F

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Tyr Ile His Trp Val Arg Gln Ala Pro Gly Lys Gly Leu Glu Trp Val
        35                  40                  45

Ala Val Ile Tyr Pro Tyr Thr Gly Phe Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Glu Tyr Thr Val Leu Asp Tyr Trp Gly Gln Gly Thr Leu
            100                 105                 110

Val Thr Val Ser Ser Ala Ser
        115

<210> SEQ ID NO 55
<211> LENGTH: 105
<212> TYPE: PRT
<213> ORGANISM: Artificial Sequence
<220> FEATURE:
<223> OTHER INFORMATION: hCTLA4-4 domain G

<400> SEQUENCE: 55

Pro Arg Glu Pro Gln Val Tyr Thr Asp Pro Pro Ser Arg Asp Glu Leu
1               5                   10                  15

Thr Lys Asn Gln Val Ser Leu Thr Cys Leu Val Lys Gly Phe Tyr Pro
            20                  25                  30

Ser Asp Ile Ala Val Glu Trp Glu Ser Asn Gly Gln Pro Glu Asn Asn
        35                  40                  45

Tyr Lys Thr Thr Pro Pro Val Leu Asp Ser Asp Gly Ser Phe Phe Leu
    50                  55                  60

Tyr Ser Lys Leu Thr Val Asp Lys Ser Arg Trp Gln Gln Gly Asn Val
65                  70                  75                  80

Phe Ser Cys Ser Val Met His Glu Ala Leu His Asn His Tyr Thr Gln
                85                  90                  95

Lys Ser Leu Ser Leu Ser Gly Glu Cys
            100                 105

<210> SEQ ID NO 56
<211> LENGTH: 10
<212> TYPE: PRT
<213> ORGANISM: Artificial Sequence
<220> FEATURE:
<223> OTHER INFORMATION: Hinge

<400> SEQUENCE: 56

Asp Lys Thr His Thr Cys Pro Pro Cys Pro
1               5                   10

<210> SEQ ID NO 57
<211> LENGTH: 8
<212> TYPE: PRT
<213> ORGANISM: Artificial Sequence
<220> FEATURE:
<223> OTHER INFORMATION: BC1, BC5, BC6, BC13, BC14, BC24, BC25, BC28,
      BC30, and BC45, Polypeptide 1 Domain Junction

<400> SEQUENCE: 57

Ile Lys Arg Thr Pro Arg Glu Pro
1               5

<210> SEQ ID NO 58
<211> LENGTH: 8
<212> TYPE: PRT
<213> ORGANISM: Artificial Sequence
<220> FEATURE:
<223> OTHER INFORMATION: BC15 and BC44 Polypeptide 1 Domain Junction

<400> SEQUENCE: 58

Ile Lys Arg Thr Val Arg Glu Pro
1               5

<210> SEQ ID NO 59
<211> LENGTH: 7
<212> TYPE: PRT
<213> ORGANISM: Artificial Sequence
<220> FEATURE:
<223> OTHER INFORMATION: BC16-Polypeptide 1 Domain Junction

<400> SEQUENCE: 59

Ile Lys Arg Thr Arg Glu Pro
1               5

<210> SEQ ID NO 60
<211> LENGTH: 9
<212> TYPE: PRT
<213> ORGANISM: Artificial Sequence
<220> FEATURE:
<223> OTHER INFORMATION: BC17-Polypeptide 1 Domain Junction

<400> SEQUENCE: 60

Ile Lys Arg Thr Val Pro Arg Glu Pro
1               5

<210> SEQ ID NO 61
<211> LENGTH: 8
<212> TYPE: PRT
<213> ORGANISM: Artificial Sequence
<220> FEATURE:
<223> OTHER INFORMATION: BC26-Polypeptide 1 Domain Junction

<400> SEQUENCE: 61

Ile Lys Arg Thr Val Ala Glu Pro
1               5

<210> SEQ ID NO 62
<211> LENGTH: 10
<212> TYPE: PRT
<213> ORGANISM: Artificial Sequence
<220> FEATURE:
<223> OTHER INFORMATION: BC27-Polypeptide 1 Domain Junction

<400> SEQUENCE: 62

```
Ile Lys Arg Thr Val Ala Pro Arg Glu Pro
1               5                   10

<210> SEQ ID NO 63
<211> LENGTH: 8
<212> TYPE: PRT
<213> ORGANISM: Artificial Sequence
<220> FEATURE:
<223> OTHER INFORMATION: BC1, BC5, BC6, BC15, BC16, BC17, BC26, BC27,
      BC28, BC30, BC44, and BC45, Polypeptide 2 Domain Junction

<400> SEQUENCE: 63

Ser Ser Ala Ser Pro Arg Glu Pro
1               5

<210> SEQ ID NO 64
<211> LENGTH: 8
<212> TYPE: PRT
<213> ORGANISM: Artificial Sequence
<220> FEATURE:
<223> OTHER INFORMATION: BC13-Polypeptide 2 Domain Junction

<400> SEQUENCE: 64

Ser Ser Ala Ser Thr Arg Glu Pro
1               5

<210> SEQ ID NO 65
<211> LENGTH: 9
<212> TYPE: PRT
<213> ORGANISM: Artificial Sequence
<220> FEATURE:
<223> OTHER INFORMATION: BC14-Polypeptide 2 Domain Junction

<400> SEQUENCE: 65

Ser Ser Ala Ser Thr Pro Arg Glu Pro
1               5

<210> SEQ ID NO 66
<211> LENGTH: 9
<212> TYPE: PRT
<213> ORGANISM: Artificial Sequence
<220> FEATURE:
<223> OTHER INFORMATION: BC24-Polypeptide 2 Domain Junction

<400> SEQUENCE: 66

Ser Ser Ala Ser Thr Lys Gly Glu Pro
1               5

<210> SEQ ID NO 67
<211> LENGTH: 10
<212> TYPE: PRT
<213> ORGANISM: Artificial Sequence
<220> FEATURE:
<223> OTHER INFORMATION: BC25-Polypeptide 2 Domain Junction

<400> SEQUENCE: 67

Ser Ser Ala Ser Thr Lys Gly Arg Glu Pro
1               5                   10

<210> SEQ ID NO 68
<211> LENGTH: 123
<212> TYPE: PRT
<213> ORGANISM: Artificial Sequence
<220> FEATURE:
<223> OTHER INFORMATION: SP34-89 VH

<400> SEQUENCE: 68
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Ser Ile Ser Arg Asp Asp Ser Lys Asn Thr
65                  70                  75                  80

Ala Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val
            115                 120

<210> SEQ ID NO 69
<211> LENGTH: 109
<212> TYPE: PRT
<213> ORGANISM: Artificial Sequence
<220> FEATURE:
<223> OTHER INFORMATION: SP34-89 VL

<400> SEQUENCE: 69

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 70
<211> LENGTH: 123
<212> TYPE: PRT
<213> ORGANISM: Artificial Sequence
<220> FEATURE:
<223> OTHER INFORMATION: SP34-89 VH-N30S VH, lower case denotes mutation

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Ser Ile Ser Arg Asp Asp Ser Lys Asn Thr

```
                65                  70                  75                  80
Ala Tyr Leu Gln Met Asn Ser Leu Arg Ala Glu Asp Thr Ala Val Tyr
                    85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val
            115                 120
```

<210> SEQ ID NO 71
<211> LENGTH: 123
<212> TYPE: PRT
<213> ORGANISM: Artificial Sequence
<220> FEATURE:
<223> OTHER INFORMATION: SP34-89 VH-G65D VH, lower case denotes mutation

<400> SEQUENCE: 71

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
                35                  40                  45

Ala Arg Ile Arg Ser Lys Tyr Asn Asn Tyr Ala Thr Tyr Tyr Ala Asp
        50                  55                  60

Ser Val Lys Asp Arg Phe Ser Ile Ser Arg Asp Asp Ser Lys Asn Thr
65                  70                  75                  80

Ala Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val
            115                 120
```

<210> SEQ ID NO 72
<211> LENGTH: 123
<212> TYPE: PRT
<213> ORGANISM: Artificial Sequence
<220> FEATURE:
<223> OTHER INFORMATION: SP34-89 VH-S68T VH, lower case denotes mutation

<400> SEQUENCE: 72

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
                35                  40                  45

Ala Arg Ile Arg Ser Lys Tyr Asn Asn Tyr Ala Thr Tyr Tyr Ala Asp
        50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val
            115                 120
```

```
<210> SEQ ID NO 73
<211> LENGTH: 109
<212> TYPE: PRT
<213> ORGANISM: Artificial Sequence
<220> FEATURE:
<223> OTHER INFORMATION: SP34-89 VL-W57G VL, lower case denotes mutation

<400> SEQUENCE: 73

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 74
<211> LENGTH: 455
<212> TYPE: PRT
<213> ORGANISM: Artificial Sequence
<220> FEATURE:
<223> OTHER INFORMATION: Phage display heavy chain
<220> FEATURE:
<221> NAME/KEY: misc_feature
<222> LOCATION: (30)..(33)
<223> OTHER INFORMATION: Xaa can be any naturally occurring amino acid
<220> FEATURE:
<221> NAME/KEY: MISC_FEATURE
<222> LOCATION: (34)..(35)
<223> OTHER INFORMATION: CDR sequences that were constant
<220> FEATURE:
<221> NAME/KEY: misc_feature
<222> LOCATION: (50)..(60)
<223> OTHER INFORMATION: Xaa can be any naturally occurring amino acid
<220> FEATURE:
<221> NAME/KEY: MISC_FEATURE
<222> LOCATION: (61)..(67)
<223> OTHER INFORMATION: CDR sequences that were constant
<220> FEATURE:
<221> NAME/KEY: misc_feature
<222> LOCATION: (100)..(112)
<223> OTHER INFORMATION: Xaa can be any naturally occurring amino acid
<220> FEATURE:
<221> NAME/KEY: MISC_FEATURE
<222> LOCATION: (113)..(114)
<223> OTHER INFORMATION: CDR sequences that were constant

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Xaa Xaa
            20                  25                  30

Xaa His Trp Val Arg Gln Ala Pro Gly Lys Gly Leu Glu Trp Val
        35                  40                  45

Ala Xaa Xaa Xaa Xaa Xaa Xaa Xaa Xaa Xaa Xaa Xaa Tyr Ala Asp Ser
    50                  55                  60

Val Lys Gly Arg Phe Thr Ile Ser Ala Asp Thr Ser Lys Asn Thr Ala
65                  70                  75                  80
```

-continued

Tyr Leu Gln Met Asn Ser Leu Arg Ala Glu Asp Thr Ala Val Tyr Tyr
            85                  90                  95

Cys Ala Arg Xaa Xaa Xaa Xaa Xaa Xaa Xaa Xaa Xaa Xaa
            100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
450                 455

<210> SEQ ID NO 75
<211> LENGTH: 214
<212> TYPE: PRT
<213> ORGANISM: Artificial Sequence
<220> FEATURE:

<223> OTHER INFORMATION: Phage display light chain
<220> FEATURE:
<221> NAME/KEY: MISC_FEATURE
<222> LOCATION: (24)..(32)
<223> OTHER INFORMATION: CDR sequences that were constant
<220> FEATURE:
<221> NAME/KEY: MISC_FEATURE
<222> LOCATION: (50)..(56)
<223> OTHER INFORMATION: CDR sequences that were constant
<220> FEATURE:
<221> NAME/KEY: MISC_FEATURE
<222> LOCATION: (89)..(90)
<223> OTHER INFORMATION: CDR sequences that were constant
<220> FEATURE:
<221> NAME/KEY: misc_feature
<222> LOCATION: (91)..(96)
<223> OTHER INFORMATION: Xaa can be any naturally occurring amino acid
<220> FEATURE:
<221> NAME/KEY: MISC_FEATURE
<222> LOCATION: (97)..(98)
<223> OTHER INFORMATION: CDR sequences that were constant

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Xaa Xaa Xaa Xaa Xaa Xaa
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Ser Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 76
<211> LENGTH: 109
<212> TYPE: PRT
<213> ORGANISM: Artificial Sequence
<220> FEATURE:
<223> OTHER INFORMATION: B-Body Domain A/H Scaffold
<220> FEATURE:
<221> NAME/KEY: MISC_FEATURE
<222> LOCATION: (24)..(32)
<223> OTHER INFORMATION: CDR sequences that were constant
<220> FEATURE:
<221> NAME/KEY: MISC_FEATURE

```
<222> LOCATION: (50)..(56)
<223> OTHER INFORMATION: CDR sequences that were constant
<220> FEATURE:
<221> NAME/KEY: MISC_FEATURE
<222> LOCATION: (89)..(90)
<223> OTHER INFORMATION: CDR sequences that were constant
<220> FEATURE:
<221> NAME/KEY: misc_feature
<222> LOCATION: (91)..(96)
<223> OTHER INFORMATION: Xaa can be any naturally occurring amino acid
<220> FEATURE:
<221> NAME/KEY: MISC_FEATURE
<222> LOCATION: (97)..(98)
<223> OTHER INFORMATION: CDR sequences that were constant

<400> SEQUENCE: 76

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Xaa Xaa Xaa Xaa Xaa Xaa
                85                  90                  95

Thr Phe Gly Gln Gly Thr Lys Val Glu Ile Lys Arg Thr
            100                 105

<210> SEQ ID NO 77
<211> LENGTH: 127
<212> TYPE: PRT
<213> ORGANISM: Artificial Sequence
<220> FEATURE:
<223> OTHER INFORMATION: B-Body Domain F/L Scaffold
<220> FEATURE:
<221> NAME/KEY: misc_feature
<222> LOCATION: (30)..(33)
<223> OTHER INFORMATION: Xaa can be any naturally occurring amino acid
<220> FEATURE:
<221> NAME/KEY: MISC_FEATURE
<222> LOCATION: (34)..(35)
<223> OTHER INFORMATION: CDR sequences that were constant
<220> FEATURE:
<221> NAME/KEY: misc_feature
<222> LOCATION: (50)..(60)
<223> OTHER INFORMATION: Xaa can be any naturally occurring amino acid
<220> FEATURE:
<221> NAME/KEY: MISC_FEATURE
<222> LOCATION: (61)..(67)
<223> OTHER INFORMATION: CDR sequences that were constant
<220> FEATURE:
<221> NAME/KEY: misc_feature
<222> LOCATION: (100)..(112)
<223> OTHER INFORMATION: Xaa can be any naturally occurring amino acid
<220> FEATURE:
<221> NAME/KEY: MISC_FEATURE
<222> LOCATION: (113)..(114)
<223> OTHER INFORMATION: CDR sequences that were constant

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Xaa Xaa
            20                  25                  30

Xaa Ile His Trp Val Arg Gln Ala Pro Gly Lys Gly Leu Glu Trp Val
```

```
                 35                  40                  45

Ala Xaa Xaa Xaa Xaa Xaa Xaa Xaa Xaa Xaa Tyr Ala Asp Ser
    50                  55                  60

Val Lys Gly Arg Phe Thr Ile Ser Ala Asp Thr Ser Lys Asn Thr Ala
65                  70                  75                  80

Tyr Leu Gln Met Asn Ser Leu Arg Ala Glu Asp Thr Ala Val Tyr Tyr
                85                  90                  95

Cys Ala Arg Xaa Xaa Xaa Xaa Xaa Xaa Xaa Xaa Xaa Xaa Xaa
            100                 105                 110

Asp Tyr Trp Gly Gln Gly Thr Leu Val Thr Val Ser Ser Ala Ser
        115                 120                 125

<210> SEQ ID NO 78
<211> LENGTH: 441
<212> TYPE: PRT
<213> ORGANISM: Artificial Sequence
<220> FEATURE:
<223> OTHER INFORMATION: BC1 Chain 1 Scaffold
<220> FEATURE:
<221> NAME/KEY: MISC_FEATURE
<222> LOCATION: (24)..(32)
<223> OTHER INFORMATION: CDR sequences that were constant
<220> FEATURE:
<221> NAME/KEY: MISC_FEATURE
<222> LOCATION: (50)..(56)
<223> OTHER INFORMATION: CDR sequences that were constant
<220> FEATURE:
<221> NAME/KEY: MISC_FEATURE
<222> LOCATION: (89)..(90)
<223> OTHER INFORMATION: CDR sequences that were constant
<220> FEATURE:
<221> NAME/KEY: misc_feature
<222> LOCATION: (91)..(96)
<223> OTHER INFORMATION: Xaa can be any naturally occurring amino acid
<220> FEATURE:
<221> NAME/KEY: MISC_FEATURE
<222> LOCATION: (97)..(98)
<223> OTHER INFORMATION: CDR sequences that were constant

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
                20                  25                  30

Val Ala Trp Tyr Gln Gln Lys Pro Gly Lys Ala Pro Lys Leu Leu Ile
            35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Xaa Xaa Xaa Xaa Xaa Xaa
                85                  90                  95

Thr Phe Gly Gln Gly Thr Lys Val Glu Ile Lys Arg Thr Pro Arg Glu
            100                 105                 110

Pro Gln Val Tyr Thr Leu Pro Pro Ser Arg Asp Glu Leu Thr Lys Asn
        115                 120                 125

Gln Val Ser Leu Lys Cys Leu Val Lys Gly Phe Tyr Pro Ser Asp Ile
    130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
                165                 170                 175
```

Leu Thr Val Asp Lys Ser Arg Trp Gln Gln Gly Asn Val Phe Ser Cys
                180                 185                 190

Ser Val Met His Glu Ala Leu His Asn His Tyr Thr Gln Lys Ser Leu
            195                 200                 205

Ser Leu Ser Lys Ser Cys Asp Lys Thr His Thr Cys Pro Pro Cys Pro
        210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Cys Arg Asp Glu Leu
            340                 345                 350

Thr Lys Asn Gln Val Ser Leu Trp Cys Leu Val Lys Gly Phe Tyr Pro
        355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440

<210> SEQ ID NO 79
<211> LENGTH: 232
<212> TYPE: PRT
<213> ORGANISM: Artificial Sequence
<220> FEATURE:
<223> OTHER INFORMATION: BC1 Chain 2 Scaffold
<220> FEATURE:
<221> NAME/KEY: misc_feature
<222> LOCATION: (30)..(33)
<223> OTHER INFORMATION: Xaa can be any naturally occurring amino acid
<220> FEATURE:
<221> NAME/KEY: MISC_FEATURE
<222> LOCATION: (34)..(35)
<223> OTHER INFORMATION: CDR sequences that were constant
<220> FEATURE:
<221> NAME/KEY: misc_feature
<222> LOCATION: (50)..(60)
<223> OTHER INFORMATION: Xaa can be any naturally occurring amino acid
<220> FEATURE:
<221> NAME/KEY: MISC_FEATURE
<222> LOCATION: (61)..(67)
<223> OTHER INFORMATION: CDR sequences that were constant
<220> FEATURE:
<221> NAME/KEY: misc_feature
<222> LOCATION: (100)..(112)
<223> OTHER INFORMATION: Xaa can be any naturally occurring amino acid
<220> FEATURE:
<221> NAME/KEY: MISC_FEATURE
<222> LOCATION: (113)..(114)
<223> OTHER INFORMATION: CDR sequences that were constant

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Xaa Xaa
            20                  25                  30

Xaa Ile His Trp Val Arg Gln Ala Pro Gly Lys Gly Leu Glu Trp Val
        35                  40                  45

Ala Xaa Xaa Xaa Xaa Xaa Xaa Xaa Xaa Xaa Xaa Tyr Ala Asp Ser
    50                  55                  60

Val Lys Gly Arg Phe Thr Ile Ser Ala Asp Thr Ser Lys Asn Thr Ala
65                  70                  75                  80

Tyr Leu Gln Met Asn Ser Leu Arg Ala Glu Asp Thr Ala Val Tyr Tyr
                85                  90                  95

Cys Ala Arg Xaa Xaa Xaa Xaa Xaa Xaa Xaa Xaa Xaa Xaa Xaa
            100                 105                 110

Asp Tyr Trp Gly Gln Gly Thr Leu Val Thr Val Ser Ser Ala Ser Pro
    115                 120                 125

Arg Glu Pro Gln Val Tyr Thr Asp Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Gly Glu Cys
225                 230

<210> SEQ ID NO 80
<211> LENGTH: 441
<212> TYPE: PRT
<213> ORGANISM: Artificial Sequence
<220> FEATURE:
<223> OTHER INFORMATION: BC1 Chain 3 Scaffold
<220> FEATURE:
<221> NAME/KEY: MISC_FEATURE
<222> LOCATION: (24)..(32)
<223> OTHER INFORMATION: CDR sequences that were constant
<220> FEATURE:
<221> NAME/KEY: MISC_FEATURE
<222> LOCATION: (50)..(56)
<223> OTHER INFORMATION: CDR sequences that were constant
<220> FEATURE:
<221> NAME/KEY: MISC_FEATURE
<222> LOCATION: (89)..(90)
<223> OTHER INFORMATION: CDR sequences that were constant
<220> FEATURE:
<221> NAME/KEY: misc_feature
<222> LOCATION: (91)..(96)
<223> OTHER INFORMATION: Xaa can be any naturally occurring amino acid
<220> FEATURE:
<221> NAME/KEY: MISC_FEATURE
<222> LOCATION: (97)..(98)
<223> OTHER INFORMATION: CDR sequences that were constant

```
<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Xaa Xaa Xaa Xaa Xaa
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Cys Thr Leu Pro Pro Ser Arg Glu Glu Met
            340                 345                 350

Thr Lys Asn Gln Val Ser Leu Ser Cys Ala Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Val Ser Lys Leu Thr Val Asp Lys Ser Arg Trp Gln Gln Gly Asn Val
```

```
                    405                 410                 415
Phe Ser Cys Ser Val Met His Glu Ala Leu His Asn His Tyr Thr Gln
            420                 425                 430

Lys Ser Leu Ser Leu Ser Pro Gly Lys
        435                 440

<210> SEQ ID NO 81
<211> LENGTH: 229
<212> TYPE: PRT
<213> ORGANISM: Artificial Sequence
<220> FEATURE:
<223> OTHER INFORMATION: BC1 Chain 4 Scaffold
<220> FEATURE:
<221> NAME/KEY: misc_feature
<222> LOCATION: (30)..(33)
<223> OTHER INFORMATION: Xaa can be any naturally occurring amino acid
<220> FEATURE:
<221> NAME/KEY: MISC_FEATURE
<222> LOCATION: (34)..(35)
<223> OTHER INFORMATION: CDR sequences that were constant
<220> FEATURE:
<221> NAME/KEY: misc_feature
<222> LOCATION: (50)..(60)
<223> OTHER INFORMATION: Xaa can be any naturally occurring amino acid
<220> FEATURE:
<221> NAME/KEY: MISC_FEATURE
<222> LOCATION: (61)..(67)
<223> OTHER INFORMATION: CDR sequences that were constant
<220> FEATURE:
<221> NAME/KEY: misc_feature
<222> LOCATION: (100)..(112)
<223> OTHER INFORMATION: Xaa can be any naturally occurring amino acid
<220> FEATURE:
<221> NAME/KEY: MISC_FEATURE
<222> LOCATION: (113)..(114)
<223> OTHER INFORMATION: CDR sequences that were constant

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Xaa Xaa
            20                  25                  30

Xaa Ile His Trp Val Arg Gln Ala Pro Gly Lys Gly Leu Glu Trp Val
        35                  40                  45

Ala Xaa Xaa Xaa Xaa Xaa Xaa Xaa Xaa Xaa Xaa Tyr Ala Asp Ser
    50                  55                  60

Val Lys Gly Arg Phe Thr Ile Ser Ala Asp Thr Ser Lys Asn Thr Ala
65                  70                  75                  80

Tyr Leu Gln Met Asn Ser Leu Arg Ala Glu Asp Thr Ala Val Tyr Tyr
                85                  90                  95

Cys Ala Arg Xaa Xaa Xaa Xaa Xaa Xaa Xaa Xaa Xaa Xaa Xaa
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
```

```
                195                 200                 205
Asn Val Asn His Lys Pro Ser Asn Thr Lys Val Asp Lys Lys Val Glu
    210                 215                 220

Pro Pro Lys Ser Cys
225

<210> SEQ ID NO 82
<211> LENGTH: 668
<212> TYPE: PRT
<213> ORGANISM: Artificial Sequence
<220> FEATURE:
<223> OTHER INFORMATION: BC1 Chain 3 1(A)x2(B-A) SP34-89 Scaffold
<220> FEATURE:
<221> NAME/KEY: MISC_FEATURE
<222> LOCATION: (24)..(32)
<223> OTHER INFORMATION: CDR sequences that were constant
<220> FEATURE:
<221> NAME/KEY: MISC_FEATURE
<222> LOCATION: (50)..(56)
<223> OTHER INFORMATION: CDR sequences that were constant
<220> FEATURE:
<221> NAME/KEY: MISC_FEATURE
<222> LOCATION: (89)..(90)
<223> OTHER INFORMATION: CDR sequences that were constant
<220> FEATURE:
<221> NAME/KEY: misc_feature
<222> LOCATION: (91)..(96)
<223> OTHER INFORMATION: Xaa can be any naturally occurring amino acid
<220> FEATURE:
<221> NAME/KEY: MISC_FEATURE
<222> LOCATION: (97)..(98)
<223> OTHER INFORMATION: CDR sequences that were constant

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Xaa Xaa Xaa Xaa Xaa Xaa
                85                  90                  95

Thr Phe Gly Gln Gly Thr Lys Val Glu Ile Lys Arg Thr Pro Arg Glu
            100                 105                 110

Pro Gln Val Tyr Thr Leu Pro Pro Ser Arg Asp Glu Leu Thr Lys Asn
        115                 120                 125

Gln Val Ser Leu Lys Cys Leu Val Lys Gly Phe Tyr Pro Ser Asp Ile
    130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
                165                 170                 175

Leu Thr Val Asp Lys Ser Arg Trp Gln Gln Gly Asn Val Phe Ser Cys
            180                 185                 190

Ser Val Met His Glu Ala Leu His Asn His Tyr Thr Gln Lys Ser Leu
        195                 200                 205

Ser Leu Ser Lys Ser Cys Thr Ala Ser Ser Gly Gly Ser Ser Ser Gly
    210                 215                 220
```

```
Gln Ala Val Val Thr Gln Glu Pro Ser Leu Thr Val Ser Pro Gly Gly
225                 230                 235                 240

Thr Val Thr Leu Thr Cys Arg Ser Ser Thr Gly Ala Val Thr Thr Ser
                245                 250                 255

Asn Tyr Ala Asn Trp Val Gln Gln Lys Pro Gly Gln Ala Pro Arg Gly
            260                 265                 270

Leu Ile Gly Gly Thr Asn Lys Arg Ala Pro Trp Thr Pro Ala Arg Phe
        275                 280                 285

Ser Gly Ser Leu Leu Gly Gly Lys Ala Ala Leu Thr Ile Thr Gly Ala
    290                 295                 300

Gln Ala Glu Asp Glu Ala Asp Tyr Tyr Cys Ala Leu Trp Tyr Ser Asn
305                 310                 315                 320

Leu Trp Val Phe Gly Gly Gly Thr Lys Leu Thr Val Leu Gly Arg Thr
                325                 330                 335

Val Ala Ala Pro Ser Val Phe Ile Phe Pro Pro Ser Asp Glu Gln Leu
            340                 345                 350

Lys Ser Gly Thr Ala Ser Val Val Cys Leu Leu Asn Asn Phe Tyr Pro
        355                 360                 365

Arg Glu Ala Lys Val Gln Trp Lys Val Asp Asn Ala Leu Gln Ser Gly
    370                 375                 380

Asn Ser Gln Glu Ser Val Thr Glu Gln Asp Ser Lys Asp Ser Thr Tyr
385                 390                 395                 400

Ser Leu Ser Ser Thr Leu Thr Leu Ser Lys Ala Asp Tyr Glu Lys His
                405                 410                 415

Lys Val Tyr Ala Cys Glu Val Thr His Gln Gly Leu Ser Ser Pro Val
            420                 425                 430

Thr Lys Ser Phe Asn Arg Gly Glu Cys Asp Lys Thr His Thr Cys Pro
        435                 440                 445

Pro Cys Pro Ala Pro Glu Ala Ala Gly Gly Pro Ser Val Phe Leu Phe
    450                 455                 460

Pro Pro Lys Pro Lys Asp Thr Leu Met Ile Ser Arg Thr Pro Glu Val
465                 470                 475                 480

Thr Cys Val Val Val Asp Val Ser His Glu Asp Pro Glu Val Lys Phe
                485                 490                 495

Asn Trp Tyr Val Asp Gly Val Glu Val His Asn Ala Lys Thr Lys Pro
            500                 505                 510

Arg Glu Glu Gln Tyr Asn Ser Thr Tyr Arg Val Val Ser Val Leu Thr
        515                 520                 525

Val Leu His Gln Asp Trp Leu Asn Gly Lys Glu Tyr Lys Cys Lys Val
    530                 535                 540

Ser Asn Lys Ala Leu Lys Ala Pro Ile Glu Lys Thr Ile Ser Lys Ala
545                 550                 555                 560

Lys Gly Gln Pro Arg Glu Pro Gln Val Cys Thr Leu Pro Pro Ser Arg
                565                 570                 575

Glu Glu Met Thr Lys Asn Gln Val Ser Leu Ser Cys Ala Val Lys Gly
            580                 585                 590

Phe Tyr Pro Ser Asp Ile Ala Val Glu Trp Glu Ser Asn Gly Gln Pro
        595                 600                 605

Glu Asn Asn Tyr Lys Thr Thr Pro Pro Val Leu Asp Ser Asp Gly Ser
    610                 615                 620

Phe Phe Leu Val Ser Lys Leu Thr Val Asp Lys Ser Arg Trp Gln Gln
625                 630                 635                 640
```

-continued

Gly Asn Val Phe Ser Cys Ser Val Met His Glu Ala Leu His Asn His
                    645                 650                 655

Tyr Thr Gln Lys Ser Leu Ser Leu Ser Pro Gly Lys
            660                 665

<210> SEQ ID NO 83
<211> LENGTH: 10
<212> TYPE: PRT
<213> ORGANISM: Artificial Sequence
<220> FEATURE:
<223> OTHER INFORMATION: BC1 Chain 3 1(A)x2(B-A) SP34-89 S-H Junction

<400> SEQUENCE: 83

Thr Ala Ser Ser Gly Gly Ser Ser Ser Gly
1               5                   10

<210> SEQ ID NO 84
<211> LENGTH: 441
<212> TYPE: PRT
<213> ORGANISM: Artificial Sequence
<220> FEATURE:
<223> OTHER INFORMATION: I2A-10 Chain 1 BC1 1x1

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Tyr Tyr Pro Gly
                85                  90                  95

Thr Phe Gly Gln Gly Thr Lys Val Glu Ile Lys Arg Thr Pro Arg Glu
            100                 105                 110

Pro Gln Val Tyr Thr Leu Pro Pro Ser Arg Asp Glu Leu Thr Lys Asn
        115                 120                 125

Gln Val Ser Leu Lys Cys Leu Val Lys Gly Phe Tyr Pro Ser Asp Ile
    130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
                165                 170                 175

Leu Thr Val Asp Lys Ser Arg Trp Gln Gln Gly Asn Val Phe Ser Cys
            180                 185                 190

Ser Val Met His Glu Ala Leu His Asn His Tyr Thr Gln Lys Ser Leu
        195                 200                 205

Ser Leu Ser Lys Ser Cys Asp Lys Thr His Thr Cys Pro Pro Cys Pro
    210                 215                 220

Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

```
Val Asp Gly Val Glu Val His Asn Ala Lys Thr Lys Pro Arg Glu Glu
            275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Lys Ala Pro Ile Glu Lys Thr Ile Ser Lys Ala Lys Gly Gln
                325                 330                 335

Pro Arg Glu Pro Gln Val Tyr Thr Leu Pro Pro Cys Arg Asp Glu Leu
            340                 345                 350

Thr Lys Asn Gln Val Ser Leu Trp Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440

<210> SEQ ID NO 85
<211> LENGTH: 223
<212> TYPE: PRT
<213> ORGANISM: Artificial Sequence
<220> FEATURE:
<223> OTHER INFORMATION: I2A-10 Chain 2 BC1 1x1

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Phe Ile His Trp Val Arg Gln Ala Pro Gly Lys Gly Leu Glu Trp Val
        35                  40                  45

Ala Gly Ile Tyr Pro Ser Asp Gly Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Ser Gly Met Asp Tyr Trp Gly Gln Gly Thr Leu Val
            100                 105                 110

Thr Val Ser Ser Ala Ser Pro Arg Glu Pro Gln Val Tyr Thr Asp Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190
```

```
Trp Gln Gln Gly Asn Val Phe Ser Cys Ser Val Met His Glu Ala Leu
        195                 200                 205

His Asn His Tyr Thr Gln Lys Ser Leu Ser Leu Ser Gly Glu Cys
    210                 215                 220

<210> SEQ ID NO 86
<211> LENGTH: 444
<212> TYPE: PRT
<213> ORGANISM: Artificial Sequence
<220> FEATURE:
<223> OTHER INFORMATION: I2A-10 Chain 3 BC1 1x1

<400> SEQUENCE: 86

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys Asp Lys Thr His Thr Cys Pro
    210                 215                 220

Pro Cys Pro Ala Pro Glu Ala Ala Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Lys Ala Pro Ile Glu Lys Thr Ile Ser Lys Ala
                325                 330                 335
```

```
Lys Gly Gln Pro Arg Glu Pro Gln Val Cys Thr Leu Pro Ser Arg
            340                 345                 350

Glu Glu Met Thr Lys Asn Gln Val Ser Leu Ser Cys Ala Val Lys Gly
                355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Val Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
            435                 440
```

<210> SEQ ID NO 87
<211> LENGTH: 229
<212> TYPE: PRT
<213> ORGANISM: Artificial Sequence
<220> FEATURE:
<223> OTHER INFORMATION: I2A-10 Chain 4 BC1 1x1

<400> SEQUENCE: 87

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Ser Ile Ser Arg Asp Asp Ser Lys Asn Thr
65                  70                  75                  80

Ala Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Pro Lys Ser Cys
225
```

<210> SEQ ID NO 88

```
<211> LENGTH: 668
<212> TYPE: PRT
<213> ORGANISM: Artificial Sequence
<220> FEATURE:
<223> OTHER INFORMATION: I2A-10 Chain 3 BC1 1x2

<400> SEQUENCE: 88
```

| | | | | | | | | | | | | | | |
|---|---|---|---|---|---|---|---|---|---|---|---|---|---|---|
|Asp|Ile|Gln|Met|Thr|Gln|Ser|Pro|Ser|Ser|Leu|Ser|Ala|Ser|Val|Gly|
|1| | | |5| | | | |10| | | | |15|

| | | | | | | | | | | | | |
|---|---|---|---|---|---|---|---|---|---|---|---|---|
|Asp|Arg|Val|Thr|Ile|Thr|Cys|Arg|Ala|Ser|Gln|Ser|Val|Ser|Ala|
| | | | |20| | | | |25| | | | |30|

Val Ala Trp Tyr Gln Gln Lys Pro Gly Lys Ala Pro Lys Leu Leu Ile
                35                  40                  45

Tyr Ser Ala Ser Ser Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Tyr Pro Gly
                85                  90                  95

Thr Phe Gly Gln Gly Thr Lys Val Glu Ile Lys Arg Thr Pro Arg Glu
                100                 105                 110

Pro Gln Val Tyr Thr Leu Pro Pro Ser Arg Asp Glu Leu Thr Lys Asn
                115                 120                 125

Gln Val Ser Leu Lys Cys Leu Val Lys Gly Phe Tyr Pro Ser Asp Ile
        130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
                165                 170                 175

Leu Thr Val Asp Lys Ser Arg Trp Gln Gln Gly Asn Val Phe Ser Cys
                180                 185                 190

Ser Val Met His Glu Ala Leu His Asn His Tyr Thr Gln Lys Ser Leu
                195                 200                 205

Ser Leu Ser Lys Ser Cys Thr Ala Ser Ser Gly Gly Ser Ser Ser Gly
        210                 215                 220

Gln Ala Val Val Thr Gln Glu Pro Ser Leu Thr Val Ser Pro Gly Gly
225                 230                 235                 240

Thr Val Thr Leu Thr Cys Arg Ser Ser Thr Gly Ala Val Thr Thr Ser
                245                 250                 255

Asn Tyr Ala Asn Trp Val Gln Gln Lys Pro Gly Gln Ala Pro Arg Gly
                260                 265                 270

Leu Ile Gly Gly Thr Asn Lys Arg Ala Pro Trp Thr Pro Ala Arg Phe
                275                 280                 285

Ser Gly Ser Leu Leu Gly Gly Lys Ala Ala Leu Thr Ile Thr Gly Ala
        290                 295                 300

Gln Ala Glu Asp Glu Ala Asp Tyr Tyr Cys Ala Leu Trp Tyr Ser Asn
305                 310                 315                 320

Leu Trp Val Phe Gly Gly Gly Thr Lys Leu Thr Val Leu Gly Arg Thr
                325                 330                 335

Val Ala Ala Pro Ser Val Phe Ile Phe Pro Pro Ser Asp Glu Gln Leu
                340                 345                 350

Lys Ser Gly Thr Ala Ser Val Val Cys Leu Leu Asn Asn Phe Tyr Pro
        355                 360                 365

Arg Glu Ala Lys Val Gln Trp Lys Val Asp Asn Ala Leu Gln Ser Gly
                370                 375                 380

```
Asn Ser Gln Glu Ser Val Thr Glu Gln Asp Ser Lys Asp Ser Thr Tyr
385                 390                 395                 400

Ser Leu Ser Ser Thr Leu Thr Leu Ser Lys Ala Asp Tyr Glu Lys His
            405                 410                 415

Lys Val Tyr Ala Cys Glu Val Thr His Gln Gly Leu Ser Ser Pro Val
        420                 425                 430

Thr Lys Ser Phe Asn Arg Gly Glu Cys Asp Lys Thr His Thr Cys Pro
    435                 440                 445

Pro Cys Pro Ala Pro Glu Ala Ala Gly Gly Pro Ser Val Phe Leu Phe
450                 455                 460

Pro Pro Lys Pro Lys Asp Thr Leu Met Ile Ser Arg Thr Pro Glu Val
465                 470                 475                 480

Thr Cys Val Val Val Asp Val Ser His Glu Asp Pro Glu Val Lys Phe
                485                 490                 495

Asn Trp Tyr Val Asp Gly Val Glu Val His Asn Ala Lys Thr Lys Pro
                500                 505                 510

Arg Glu Glu Gln Tyr Asn Ser Thr Tyr Arg Val Val Ser Val Leu Thr
            515                 520                 525

Val Leu His Gln Asp Trp Leu Asn Gly Lys Glu Tyr Lys Cys Lys Val
        530                 535                 540

Ser Asn Lys Ala Leu Lys Ala Pro Ile Glu Lys Thr Ile Ser Lys Ala
545                 550                 555                 560

Lys Gly Gln Pro Arg Glu Pro Gln Val Cys Thr Leu Pro Pro Ser Arg
                565                 570                 575

Glu Glu Met Thr Lys Asn Gln Val Ser Leu Ser Cys Ala Val Lys Gly
                580                 585                 590

Phe Tyr Pro Ser Asp Ile Ala Val Glu Trp Glu Ser Asn Gly Gln Pro
            595                 600                 605

Glu Asn Asn Tyr Lys Thr Thr Pro Pro Val Leu Asp Ser Asp Gly Ser
        610                 615                 620

Phe Phe Leu Val Ser Lys Leu Thr Val Asp Lys Ser Arg Trp Gln Gln
625                 630                 635                 640

Gly Asn Val Phe Ser Cys Ser Val Met His Glu Ala Leu His Asn His
                645                 650                 655

Tyr Thr Gln Lys Ser Leu Ser Leu Ser Pro Gly Lys
            660                 665

<210> SEQ ID NO 89
<211> LENGTH: 441
<212> TYPE: PRT
<213> ORGANISM: Artificial Sequence
<220> FEATURE:
<223> OTHER INFORMATION: I2A-27 Chain 1 BC1 1x1

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80
```

Glu Asp Phe Ala Thr Tyr Tyr Cys Gln Gln Tyr Tyr Ser Ser Pro Arg
                85                  90                  95

Thr Phe Gly Gln Gly Thr Lys Val Glu Ile Lys Arg Thr Pro Arg Glu
            100                 105                 110

Pro Gln Val Tyr Thr Leu Pro Pro Ser Arg Asp Glu Leu Thr Lys Asn
        115                 120                 125

Gln Val Ser Leu Lys Cys Leu Val Lys Gly Phe Tyr Pro Ser Asp Ile
130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
                165                 170                 175

Leu Thr Val Asp Lys Ser Arg Trp Gln Gln Gly Asn Val Phe Ser Cys
            180                 185                 190

Ser Val Met His Glu Ala Leu His Asn His Tyr Thr Gln Lys Ser Leu
        195                 200                 205

Ser Leu Ser Lys Ser Cys Asp Lys Thr His Thr Cys Pro Pro Cys Pro
210                 215                 220

Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
290                 295                 300

Gln Asp Trp Leu Asn Gly Lys Glu Tyr Lys Cys Lys Val Ser Asn Lys
305                 310                 315                 320

Ala Leu Lys Ala Pro Ile Glu Lys Thr Ile Ser Lys Ala Lys Gly Gln
                325                 330                 335

Pro Arg Glu Pro Gln Val Tyr Thr Leu Pro Pro Cys Arg Asp Glu Leu
            340                 345                 350

Thr Lys Asn Gln Val Ser Leu Trp Cys Leu Val Lys Gly Phe Tyr Pro
        355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440

<210> SEQ ID NO 90
<211> LENGTH: 225
<212> TYPE: PRT
<213> ORGANISM: Artificial Sequence
<220> FEATURE:
<223> OTHER INFORMATION: I2A-27 Chain 2 BC1 1x1

<400> SEQUENCE: 90

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Lys Gly Tyr
            20                  25                  30

Tyr Ile His Trp Val Arg Gln Ala Pro Gly Lys Gly Leu Glu Trp Val
        35                  40                  45

Ala Ala Ile Tyr Pro Tyr Gly Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Val Tyr Ile Tyr Gly Val Phe Asp Tyr Trp Gly Gln Gly Thr
            100                 105                 110

Leu Val Thr Val Ser Ser Ala Ser Pro Arg Glu Pro Gln Val Tyr Thr
        115                 120                 125

Asp Pro Pro Ser Arg Asp Glu Leu Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Gly Glu
    210                 215                 220

Cys
225

<210> SEQ ID NO 91
<211> LENGTH: 444
<212> TYPE: PRT
<213> ORGANISM: Artificial Sequence
<220> FEATURE:
<223> OTHER INFORMATION: I2A-27 Chain 3 BC1 1x1

<400> SEQUENCE: 91

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Arg Thr
            100                 105                 110

Val Ala Ala Pro Ser Val Phe Ile Phe Pro Pro Ser Asp Glu Gln Leu
        115                 120                 125
```

-continued

```
Lys Ser Gly Thr Ala Ser Val Cys Leu Leu Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys Asp Lys Thr His Thr Cys Pro
    210                 215                 220

Pro Cys Pro Ala Pro Glu Ala Ala Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Lys Ala Pro Ile Glu Lys Thr Ile Ser Lys Ala
                325                 330                 335

Lys Gly Gln Pro Arg Glu Pro Gln Val Cys Thr Leu Pro Pro Ser Arg
            340                 345                 350

Glu Glu Met Thr Lys Asn Gln Val Ser Leu Ser Cys Ala Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Val Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 92
<211> LENGTH: 229
<212> TYPE: PRT
<213> ORGANISM: Artificial Sequence
<220> FEATURE:
<223> OTHER INFORMATION: I2A-27 Chain 4 BC1 1x1

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45
```

```
Ala Arg Ile Arg Ser Lys Tyr Asn Asn Tyr Ala Thr Tyr Tyr Ala Asp
        50                  55                  60

Ser Val Lys Gly Arg Phe Ser Ile Ser Arg Asp Asp Ser Lys Asn Thr
65                  70                  75                  80

Ala Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Leu Gly Thr Gln Thr Tyr Ile Cys
                195                 200                 205

Asn Val Asn His Lys Pro Ser Asn Thr Lys Val Asp Lys Lys Val Glu
    210                 215                 220

Pro Pro Lys Ser Cys
225

<210> SEQ ID NO 93
<211> LENGTH: 668
<212> TYPE: PRT
<213> ORGANISM: Artificial Sequence
<220> FEATURE:
<223> OTHER INFORMATION: I2A-27 Chain 3 BC1 1x2

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Ser Pro Arg
                85                  90                  95

Thr Phe Gly Gln Gly Thr Lys Val Glu Ile Lys Arg Thr Pro Arg Glu
                100                 105                 110

Pro Gln Val Tyr Thr Leu Pro Pro Ser Arg Asp Glu Leu Thr Lys Asn
            115                 120                 125

Gln Val Ser Leu Lys Cys Leu Val Lys Gly Phe Tyr Pro Ser Asp Ile
    130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
                165                 170                 175
```

```
Leu Thr Val Asp Lys Ser Arg Trp Gln Gln Gly Asn Val Phe Ser Cys
            180                 185                 190

Ser Val Met His Glu Ala Leu His Asn His Tyr Thr Gln Lys Ser Leu
        195                 200                 205

Ser Leu Ser Lys Ser Cys Thr Ala Ser Ser Gly Gly Ser Ser Ser Gly
    210                 215                 220

Gln Ala Val Val Thr Gln Glu Pro Ser Leu Thr Val Ser Pro Gly Gly
225                 230                 235                 240

Thr Val Thr Leu Thr Cys Arg Ser Ser Thr Gly Ala Val Thr Thr Ser
                245                 250                 255

Asn Tyr Ala Asn Trp Val Gln Gln Lys Pro Gly Gln Ala Pro Arg Gly
            260                 265                 270

Leu Ile Gly Gly Thr Asn Lys Arg Ala Pro Trp Thr Pro Ala Arg Phe
        275                 280                 285

Ser Gly Ser Leu Leu Gly Gly Lys Ala Ala Leu Thr Ile Thr Gly Ala
    290                 295                 300

Gln Ala Glu Asp Glu Ala Asp Tyr Tyr Cys Ala Leu Trp Tyr Ser Asn
305                 310                 315                 320

Leu Trp Val Phe Gly Gly Gly Thr Lys Leu Thr Val Leu Gly Arg Thr
                325                 330                 335

Val Ala Ala Pro Ser Val Phe Ile Phe Pro Pro Ser Asp Glu Gln Leu
            340                 345                 350

Lys Ser Gly Thr Ala Ser Val Val Cys Leu Leu Asn Asn Phe Tyr Pro
        355                 360                 365

Arg Glu Ala Lys Val Gln Trp Lys Val Asp Asn Ala Leu Gln Ser Gly
    370                 375                 380

Asn Ser Gln Glu Ser Val Thr Glu Gln Asp Ser Lys Asp Ser Thr Tyr
385                 390                 395                 400

Ser Leu Ser Ser Thr Leu Thr Leu Ser Lys Ala Asp Tyr Glu Lys His
                405                 410                 415

Lys Val Tyr Ala Cys Glu Val Thr His Gln Gly Leu Ser Ser Pro Val
            420                 425                 430

Thr Lys Ser Phe Asn Arg Gly Glu Cys Asp Lys Thr His Thr Cys Pro
        435                 440                 445

Pro Cys Pro Ala Pro Glu Ala Ala Gly Gly Pro Ser Val Phe Leu Phe
    450                 455                 460

Pro Pro Lys Pro Lys Asp Thr Leu Met Ile Ser Arg Thr Pro Glu Val
465                 470                 475                 480

Thr Cys Val Val Val Asp Val Ser His Glu Asp Pro Glu Val Lys Phe
                485                 490                 495

Asn Trp Tyr Val Asp Gly Val Glu Val His Asn Ala Lys Thr Lys Pro
            500                 505                 510

Arg Glu Glu Gln Tyr Asn Ser Thr Tyr Arg Val Val Ser Val Leu Thr
        515                 520                 525

Val Leu His Gln Asp Trp Leu Asn Gly Lys Glu Tyr Lys Cys Lys Val
    530                 535                 540

Ser Asn Lys Ala Leu Lys Ala Pro Ile Glu Lys Thr Ile Ser Lys Ala
545                 550                 555                 560

Lys Gly Gln Pro Arg Glu Pro Gln Val Cys Thr Leu Pro Pro Ser Arg
                565                 570                 575

Glu Glu Met Thr Lys Asn Gln Val Ser Leu Ser Cys Ala Val Lys Gly
            580                 585                 590
```

```
Phe Tyr Pro Ser Asp Ile Ala Val Glu Trp Glu Ser Asn Gly Gln Pro
            595                 600                 605

Glu Asn Asn Tyr Lys Thr Thr Pro Pro Val Leu Asp Ser Asp Gly Ser
    610                 615                 620

Phe Phe Leu Val Ser Lys Leu Thr Val Asp Lys Ser Arg Trp Gln Gln
625                 630                 635                 640

Gly Asn Val Phe Ser Cys Ser Val Met His Glu Ala Leu His Asn His
                645                 650                 655

Tyr Thr Gln Lys Ser Leu Ser Leu Ser Pro Gly Lys
            660                 665
```

<210> SEQ ID NO 94
<211> LENGTH: 937
<212> TYPE: PRT
<213> ORGANISM: Homo sapiens
<220> FEATURE:
<223> OTHER INFORMATION: Human ROR1 (UniProt accession #Q01973)

<400> SEQUENCE: 94

```
Met His Arg Pro Arg Arg Arg Gly Thr Arg Pro Pro Leu Leu Ala Leu
1               5                   10                  15

Leu Ala Leu Leu Leu Ala Ala Arg Gly Ala Ala Ala Gln Glu Thr
            20                  25                  30

Glu Leu Ser Val Ser Ala Glu Leu Val Pro Thr Ser Ser Trp Asn Ile
        35                  40                  45

Ser Ser Glu Leu Asn Lys Asp Ser Tyr Leu Thr Leu Asp Glu Pro Met
    50                  55                  60

Asn Asn Ile Thr Thr Ser Leu Gly Gln Thr Ala Glu Leu His Cys Lys
65                  70                  75                  80

Val Ser Gly Asn Pro Pro Pro Thr Ile Arg Trp Phe Lys Asn Asp Ala
                85                  90                  95

Pro Val Val Gln Glu Pro Arg Arg Leu Ser Phe Arg Ser Thr Ile Tyr
            100                 105                 110

Gly Ser Arg Leu Arg Ile Arg Asn Leu Asp Thr Thr Asp Thr Gly Tyr
        115                 120                 125

Phe Gln Cys Val Ala Thr Asn Gly Lys Glu Val Val Ser Ser Thr Gly
    130                 135                 140

Val Leu Phe Val Lys Phe Gly Pro Pro Thr Ala Ser Pro Gly Tyr
145                 150                 155                 160

Ser Asp Glu Tyr Glu Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
            180                 185                 190

His Met Gln Gly Glu Ile Glu Asn Gln Ile Thr Ala Ala Phe Thr Met
        195                 200                 205

Ile Gly Thr Ser Ser His Leu Ser Asp Lys Cys Ser Gln Phe Ala Ile
    210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Ile Leu Glu
                245                 250                 255

Asn Val Leu Cys Gln Thr Glu Tyr Ile Phe Ala Arg Ser Asn Pro Met
            260                 265                 270

Ile Leu Met Arg Leu Lys Leu Pro Asn Cys Glu Asp Leu Pro Gln Pro
        275                 280                 285
```

```
Glu Ser Pro Glu Ala Ala Asn Cys Ile Arg Ile Gly Ile Pro Met Ala
290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
                325                 330                 335

Trp Asn Ser Gln Tyr Pro His Thr His Thr Phe Thr Ala Leu Arg Phe
                340                 345                 350

Pro Glu Leu Asn Gly Gly His Ser Tyr Cys Arg Asn Pro Gly Asn Gln
                355                 360                 365

Lys Glu Ala Pro Trp Cys Phe Thr Leu Asp Glu Asn Phe Lys Ser Asp
370                 375                 380

Leu Cys Asp Ile Pro Ala Cys Asp Ser Lys Asp Ser Lys Glu Lys Asn
385                 390                 395                 400

Lys Met Glu Ile Leu Tyr Ile Leu Val Pro Ser Val Ala Ile Pro Leu
                405                 410                 415

Ala Ile Ala Leu Leu Phe Phe Phe Ile Cys Val Cys Arg Asn Asn Gln
                420                 425                 430

Lys Ser Ser Ser Ala Pro Val Gln Arg Gln Pro Lys His Val Arg Gly
                435                 440                 445

Gln Asn Val Glu Met Ser Met Leu Asn Ala Tyr Lys Pro Lys Ser Lys
450                 455                 460

Ala Lys Glu Leu Pro Leu Ser Ala Val Arg Phe Met Glu Glu Leu Gly
465                 470                 475                 480

Glu Cys Ala Phe Gly Lys Ile Tyr Lys Gly His Leu Tyr Leu Pro Gly
                485                 490                 495

Met Asp His Ala Gln Leu Val Ala Ile Lys Thr Leu Lys Asp Tyr Asn
                500                 505                 510

Asn Pro Gln Gln Trp Thr Glu Phe Gln Gln Glu Ala Ser Leu Met Ala
                515                 520                 525

Glu Leu His His Pro Asn Ile Val Cys Leu Leu Gly Ala Val Thr Gln
530                 535                 540

Glu Gln Pro Val Cys Met Leu Phe Glu Tyr Ile Asn Gln Gly Asp Leu
545                 550                 555                 560

His Glu Phe Leu Ile Met Arg Ser Pro His Ser Asp Val Gly Cys Ser
                565                 570                 575

Ser Asp Glu Asp Gly Thr Val Lys Ser Ser Leu Asp His Gly Asp Phe
                580                 585                 590

Leu His Ile Ala Ile Gln Ile Ala Ala Gly Met Glu Tyr Leu Ser Ser
                595                 600                 605

His Phe Phe Val His Lys Asp Leu Ala Ala Arg Asn Ile Leu Ile Gly
                610                 615                 620

Glu Gln Leu His Val Lys Ile Ser Asp Leu Gly Leu Ser Arg Glu Ile
625                 630                 635                 640

Tyr Ser Ala Asp Tyr Tyr Arg Val Gln Ser Lys Ser Leu Leu Pro Ile
                645                 650                 655

Arg Trp Met Pro Pro Glu Ala Ile Met Tyr Gly Lys Phe Ser Ser Asp
                660                 665                 670

Ser Asp Ile Trp Ser Phe Gly Val Leu Trp Glu Ile Phe Ser Phe
                675                 680                 685

Gly Leu Gln Pro Tyr Tyr Gly Phe Ser Asn Gln Glu Val Ile Glu Met
690                 695                 700

Val Arg Lys Arg Gln Leu Leu Pro Cys Ser Glu Asp Cys Pro Pro Arg
```

```
                705                 710                 715                 720
         Met Tyr Ser Leu Met Thr Glu Cys Trp Asn Glu Ile Pro Ser Arg Arg
                         725                 730                 735

Pro Arg Phe Lys Asp Ile His Val Arg Leu Arg Ser Trp Glu Gly Leu
                     740                 745                 750

Ser Ser His Thr Ser Ser Thr Thr Pro Ser Gly Gly Asn Ala Thr Thr
                     755                 760                 765

Gln Thr Thr Ser Leu Ser Ala Ser Pro Val Ser Asn Leu Ser Asn Pro
                 770                 775                 780

Arg Tyr Pro Asn Tyr Met Phe Pro Ser Gln Gly Ile Thr Pro Gln Gly
         785                 790                 795                 800

Gln Ile Ala Gly Phe Ile Gly Pro Pro Ile Pro Gln Asn Gln Arg Phe
                         805                 810                 815

Ile Pro Ile Asn Gly Tyr Pro Ile Pro Pro Gly Tyr Ala Ala Phe Pro
                     820                 825                 830

Ala Ala His Tyr Gln Pro Thr Gly Pro Pro Arg Val Ile Gln His Cys
                     835                 840                 845

Pro Pro Pro Lys Ser Arg Ser Pro Ser Ser Ala Ser Gly Ser Thr Ser
                 850                 855                 860

Thr Gly His Val Thr Ser Leu Pro Ser Ser Gly Ser Asn Gln Glu Ala
         865                 870                 875                 880

Asn Ile Pro Leu Leu Pro His Met Ser Ile Pro Asn His Pro Gly Gly
                         885                 890                 895

Met Gly Ile Thr Val Phe Gly Asn Lys Ser Gln Lys Pro Tyr Lys Ile
                     900                 905                 910

Asp Ser Lys Gln Ala Ser Leu Leu Gly Asp Ala Asn Ile His Gly His
                     915                 920                 925

Thr Glu Ser Met Ile Ser Ala Glu Leu
                 930                 935

<210> SEQ ID NO 95
<211> LENGTH: 943
<212> TYPE: PRT
<213> ORGANISM: Homo sapiens
<220> FEATURE:
<223> OTHER INFORMATION: Human ROR2 (UniProt accession #Q01974)

<400> SEQUENCE: 95

Met Ala Arg Gly Ser Ala Leu Pro Arg Arg Pro Leu Leu Cys Ile Pro
         1               5                   10                  15

Ala Val Trp Ala Ala Ala Leu Leu Leu Ser Val Ser Arg Thr Ser
                         20                  25                  30

Gly Glu Val Glu Val Leu Asp Pro Asn Asp Pro Leu Gly Pro Leu Asp
                     35                  40                  45

Gly Gln Asp Gly Pro Ile Pro Thr Leu Lys Gly Tyr Phe Leu Asn Phe
                 50                  55                  60

Leu Glu Pro Val Asn Asn Ile Thr Ile Val Gln Gly Gln Thr Ala Ile
         65                  70                  75                  80

Leu His Cys Lys Val Ala Gly Asn Pro Pro Asn Val Arg Trp Leu
                         85                  90                  95

Lys Asn Asp Ala Pro Val Val Gln Glu Pro Arg Arg Ile Ile Ile Arg
                     100                 105                 110

Lys Thr Glu Tyr Gly Ser Arg Leu Arg Ile Gln Asp Leu Asp Thr Thr
                     115                 120                 125

Asp Thr Gly Tyr Tyr Gln Cys Val Ala Thr Asn Gly Met Lys Thr Ile
```

```
                130                 135                 140
Thr Ala Thr Gly Val Leu Phe Val Arg Leu Gly Pro Thr His Ser Pro
145                 150                 155                 160

Asn His Asn Phe Gln Asp Asp Tyr His Glu Asp Gly Phe Cys Gln Pro
                165                 170                 175

Tyr Arg Gly Ile Ala Cys Ala Arg Phe Ile Gly Asn Arg Thr Ile Tyr
            180                 185                 190

Val Asp Ser Leu Gln Met Gln Gly Glu Ile Glu Asn Arg Ile Thr Ala
        195                 200                 205

Ala Phe Thr Met Ile Gly Thr Ser Thr His Leu Ser Asp Gln Cys Ser
    210                 215                 220

Gln Phe Ala Ile Pro Ser Phe Cys His Phe Val Phe Pro Leu Cys Asp
225                 230                 235                 240

Ala Arg Ser Arg Thr Pro Lys Pro Arg Glu Leu Cys Arg Asp Glu Cys
                245                 250                 255

Glu Val Leu Glu Ser Asp Leu Cys Arg Gln Glu Tyr Thr Ile Ala Arg
            260                 265                 270

Ser Asn Pro Leu Ile Leu Met Arg Leu Gln Leu Pro Lys Cys Glu Ala
        275                 280                 285

Leu Pro Met Pro Glu Ser Pro Asp Ala Ala Asn Cys Met Arg Ile Gly
    290                 295                 300

Ile Pro Ala Glu Arg Leu Gly Arg Tyr His Gln Cys Tyr Asn Gly Ser
305                 310                 315                 320

Gly Met Asp Tyr Arg Gly Thr Ala Ser Thr Thr Lys Ser Gly His Gln
                325                 330                 335

Cys Gln Pro Trp Ala Leu Gln His Pro His Ser His His Leu Ser Ser
            340                 345                 350

Thr Asp Phe Pro Glu Leu Gly Gly Gly His Ala Tyr Cys Arg Asn Pro
        355                 360                 365

Gly Gly Gln Met Glu Gly Pro Trp Cys Phe Thr Gln Asn Lys Asn Val
    370                 375                 380

Arg Met Glu Leu Cys Asp Val Pro Ser Cys Ser Pro Arg Asp Ser Ser
385                 390                 395                 400

Lys Met Gly Ile Leu Tyr Ile Leu Val Pro Ser Ile Ala Ile Pro Leu
                405                 410                 415

Val Ile Ala Cys Leu Phe Phe Leu Val Cys Met Cys Arg Asn Lys Gln
            420                 425                 430

Lys Ala Ser Ala Ser Thr Pro Gln Arg Arg Gln Leu Met Ala Ser Pro
        435                 440                 445

Ser Gln Asp Met Glu Met Pro Leu Ile Asn Gln His Lys Gln Ala Lys
    450                 455                 460

Leu Lys Glu Ile Ser Leu Ser Ala Val Arg Phe Met Glu Glu Leu Gly
465                 470                 475                 480

Glu Asp Arg Phe Gly Lys Val Tyr Lys Gly His Leu Phe Gly Pro Ala
                485                 490                 495

Pro Gly Glu Gln Thr Gln Ala Val Ala Ile Lys Thr Leu Lys Asp Lys
            500                 505                 510

Ala Glu Gly Pro Leu Arg Glu Glu Phe Arg His Glu Ala Met Leu Arg
        515                 520                 525

Ala Arg Leu Gln His Pro Asn Val Val Cys Leu Leu Gly Val Val Thr
    530                 535                 540

Lys Asp Gln Pro Leu Ser Met Ile Phe Ser Tyr Cys Ser His Gly Asp
545                 550                 555                 560
```

Leu His Glu Phe Leu Val Met Arg Ser Pro His Ser Asp Val Gly Ser
                565                 570                 575

Thr Asp Asp Arg Thr Val Lys Ser Ala Leu Glu Pro Pro Asp Phe
            580                 585                 590

Val His Leu Val Ala Gln Ile Ala Ala Gly Met Glu Tyr Leu Ser Ser
        595                 600                 605

His His Val Val His Lys Asp Leu Ala Thr Arg Asn Val Leu Val Tyr
610                 615                 620

Asp Lys Leu Asn Val Lys Ile Ser Asp Leu Gly Leu Phe Arg Glu Val
625                 630                 635                 640

Tyr Ala Ala Asp Tyr Tyr Lys Leu Leu Gly Asn Ser Leu Leu Pro Ile
                645                 650                 655

Arg Trp Met Ala Pro Glu Ala Ile Met Tyr Gly Lys Phe Ser Ile Asp
            660                 665                 670

Ser Asp Ile Trp Ser Tyr Gly Val Val Leu Trp Glu Val Phe Ser Tyr
        675                 680                 685

Gly Leu Gln Pro Tyr Cys Gly Tyr Ser Asn Gln Asp Val Val Glu Met
    690                 695                 700

Ile Arg Asn Arg Gln Val Leu Pro Cys Pro Asp Asp Cys Pro Ala Trp
705                 710                 715                 720

Val Tyr Ala Leu Met Ile Glu Cys Trp Asn Glu Phe Pro Ser Arg Arg
                725                 730                 735

Pro Arg Phe Lys Asp Ile His Ser Arg Leu Arg Ala Trp Gly Asn Leu
            740                 745                 750

Ser Asn Tyr Asn Ser Ser Ala Gln Thr Ser Gly Ala Ser Asn Thr Thr
        755                 760                 765

Gln Thr Ser Ser Leu Ser Thr Ser Pro Val Ser Asn Val Ser Asn Ala
    770                 775                 780

Arg Tyr Val Gly Pro Lys Gln Lys Ala Pro Pro Phe Pro Gln Pro Gln
785                 790                 795                 800

Phe Ile Pro Met Lys Gly Gln Ile Arg Pro Met Val Pro Pro Pro Gln
                805                 810                 815

Leu Tyr Val Pro Val Asn Gly Tyr Gln Pro Val Pro Ala Tyr Gly Ala
            820                 825                 830

Tyr Leu Pro Asn Phe Tyr Pro Val Gln Ile Pro Met Gln Met Ala Pro
        835                 840                 845

Gln Gln Val Pro Pro Gln Met Val Pro Lys Pro Ser Ser His His Ser
    850                 855                 860

Gly Ser Gly Ser Thr Ser Thr Gly Tyr Val Thr Thr Ala Pro Ser Asn
865                 870                 875                 880

Thr Ser Met Ala Asp Arg Ala Ala Leu Leu Ser Glu Gly Ala Asp Asp
                885                 890                 895

Thr Gln Asn Ala Pro Glu Asp Gly Ala Gln Ser Thr Val Gln Glu Ala
            900                 905                 910

Glu Glu Glu Glu Glu Gly Ser Val Pro Glu Thr Glu Leu Leu Gly Asp
        915                 920                 925

Cys Asp Thr Leu Gln Val Asp Glu Ala Gln Val Gln Leu Glu Ala
    930                 935                 940

<210> SEQ ID NO 96
<211> LENGTH: 441
<212> TYPE: PRT
<213> ORGANISM: Artificial Sequence
<220> FEATURE:

<223> OTHER INFORMATION: I2A-27 Chain 1

<400> SEQUENCE: 96

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Ser Pro Arg
                85                  90                  95

Thr Phe Gly Gln Gly Thr Lys Val Glu Ile Lys Arg Thr Pro Arg Glu
            100                 105                 110

Pro Gln Val Tyr Thr Leu Pro Pro Ser Arg Asp Glu Leu Thr Lys Asn
        115                 120                 125

Gln Val Ser Leu Lys Cys Leu Val Lys Gly Phe Tyr Pro Ser Asp Ile
    130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
                165                 170                 175

Leu Thr Val Asp Lys Ser Arg Trp Gln Gln Gly Asn Val Phe Ser Cys
            180                 185                 190

Ser Val Met His Glu Ala Leu His Asn His Tyr Thr Gln Lys Ser Leu
        195                 200                 205

Ser Leu Ser Lys Ser Cys Asp Lys Thr His Thr Cys Pro Pro Cys Pro
    210                 215                 220

Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Lys Ala Pro Ile Glu Lys Thr Ile Ser Lys Ala Lys Gly Gln
                325                 330                 335

Pro Arg Glu Pro Gln Val Cys Thr Leu Pro Pro Ser Arg Glu Glu Met
            340                 345                 350

Thr Lys Asn Gln Val Ser Leu Ser Cys Ala Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400
```

Val Ser Lys Leu Thr Val Asp Lys Ser Arg Trp Gln Gln Gly Asn Val
            405                 410                 415

Phe Ser Cys Ser Val Met His Glu Ala Leu His Asn His Tyr Thr Gln
        420                 425                 430

Lys Ser Leu Ser Leu Ser Pro Gly Lys
        435                 440

<210> SEQ ID NO 97
<211> LENGTH: 225
<212> TYPE: PRT
<213> ORGANISM: Artificial Sequence
<220> FEATURE:
<223> OTHER INFORMATION: I2A-27 Chain 2 or Chain 5

<400> SEQUENCE: 97

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Lys Gly Tyr
            20                  25                  30

Tyr Ile His Trp Val Arg Gln Ala Pro Gly Lys Gly Leu Glu Trp Val
        35                  40                  45

Ala Ala Ile Tyr Pro Tyr Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Val Tyr Ile Tyr Gly Val Phe Asp Tyr Trp Gly Gln Gly Thr
            100                 105                 110

Leu Val Thr Val Ser Ser Ala Ser Pro Arg Glu Pro Gln Val Tyr Thr
        115                 120                 125

Asp Pro Pro Ser Arg Asp Glu Leu Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Gly Glu
    210                 215                 220

Cys
225

<210> SEQ ID NO 98
<211> LENGTH: 668
<212> TYPE: PRT
<213> ORGANISM: Artificial Sequence
<220> FEATURE:
<223> OTHER INFORMATION: I2A-27 Chain 3

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

```
Val Ala Trp Tyr Gln Gln Lys Pro Gly Lys Ala Pro Lys Leu Leu Ile
             35                  40                  45

Tyr Ser Ala Ser Ser Leu Tyr Ser Gly Val Pro Ser Arg Phe Ser Gly
         50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ser Ser Pro Arg
                 85                  90                  95

Thr Phe Gly Gln Gly Thr Lys Val Glu Ile Lys Arg Thr Pro Arg Glu
                100                 105                 110

Pro Gln Val Tyr Thr Leu Pro Pro Ser Arg Asp Glu Leu Thr Lys Asn
            115                 120                 125

Gln Val Ser Leu Lys Cys Leu Val Lys Gly Phe Tyr Pro Ser Asp Ile
        130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
                165                 170                 175

Leu Thr Val Asp Lys Ser Arg Trp Gln Gln Gly Asn Val Phe Ser Cys
                180                 185                 190

Ser Val Met His Glu Ala Leu His Asn His Tyr Thr Gln Lys Ser Leu
            195                 200                 205

Ser Leu Ser Lys Ser Cys Thr Ala Ser Ser Gly Ser Ser Ser Gly
        210                 215                 220

Gln Ala Val Val Thr Gln Glu Pro Ser Leu Thr Val Ser Pro Gly Gly
225                 230                 235                 240

Thr Val Thr Leu Thr Cys Arg Ser Ser Thr Gly Ala Val Thr Thr Ser
                245                 250                 255

Asn Tyr Ala Asn Trp Val Gln Gln Lys Pro Gly Gln Ala Pro Arg Gly
            260                 265                 270

Leu Ile Gly Gly Thr Asn Lys Arg Ala Pro Trp Thr Pro Ala Arg Phe
        275                 280                 285

Ser Gly Ser Leu Leu Gly Gly Lys Ala Ala Leu Thr Ile Thr Gly Ala
290                 295                 300

Gln Ala Glu Asp Glu Ala Asp Tyr Tyr Cys Ala Leu Trp Tyr Ser Asn
305                 310                 315                 320

Leu Trp Val Phe Gly Gly Gly Thr Lys Leu Thr Val Leu Gly Arg Thr
                325                 330                 335

Val Ala Ala Pro Ser Val Phe Ile Phe Pro Pro Ser Asp Glu Gln Leu
            340                 345                 350

Lys Ser Gly Thr Ala Ser Val Val Cys Leu Leu Asn Asn Phe Tyr Pro
        355                 360                 365

Arg Glu Ala Lys Val Gln Trp Lys Val Asp Asn Ala Leu Gln Ser Gly
    370                 375                 380

Asn Ser Gln Glu Ser Val Thr Glu Gln Asp Ser Lys Asp Ser Thr Tyr
385                 390                 395                 400

Ser Leu Ser Ser Thr Leu Thr Leu Ser Lys Ala Asp Tyr Glu Lys His
                405                 410                 415

Lys Val Tyr Ala Cys Glu Val Thr His Gln Gly Leu Ser Ser Pro Val
            420                 425                 430

Thr Lys Ser Phe Asn Arg Gly Glu Cys Asp Lys Thr His Thr Cys Pro
        435                 440                 445
```

```
Pro Cys Pro Ala Pro Glu Ala Ala Gly Gly Pro Ser Val Phe Leu Phe
    450                 455                 460

Pro Pro Lys Pro Lys Asp Thr Leu Met Ile Ser Arg Thr Pro Glu Val
465                 470                 475                 480

Thr Cys Val Val Val Asp Val Ser His Glu Asp Pro Glu Val Lys Phe
                485                 490                 495

Asn Trp Tyr Val Asp Gly Val Glu Val His Asn Ala Lys Thr Lys Pro
            500                 505                 510

Arg Glu Glu Gln Tyr Asn Ser Thr Tyr Arg Val Val Ser Val Leu Thr
                515                 520                 525

Val Leu His Gln Asp Trp Leu Asn Gly Lys Glu Tyr Lys Cys Lys Val
    530                 535                 540

Ser Asn Lys Ala Leu Lys Ala Pro Ile Glu Lys Thr Ile Ser Lys Ala
545                 550                 555                 560

Lys Gly Gln Pro Arg Glu Pro Gln Val Tyr Thr Leu Pro Pro Cys Arg
                565                 570                 575

Asp Glu Leu Thr Lys Asn Gln Val Ser Leu Trp Cys Leu Val Lys Gly
            580                 585                 590

Phe Tyr Pro Ser Asp Ile Ala Val Glu Trp Glu Ser Asn Gly Gln Pro
            595                 600                 605

Glu Asn Asn Tyr Lys Thr Thr Pro Pro Val Leu Asp Ser Asp Gly Ser
    610                 615                 620

Phe Phe Leu Tyr Ser Lys Leu Thr Val Asp Lys Ser Arg Trp Gln Gln
625                 630                 635                 640

Gly Asn Val Phe Ser Cys Ser Val Met His Glu Ala Leu His Asn His
                645                 650                 655

Tyr Thr Gln Lys Ser Leu Ser Leu Ser Pro Gly Lys
            660                 665

<210> SEQ ID NO 99
<211> LENGTH: 229
<212> TYPE: PRT
<213> ORGANISM: Artificial Sequence
<220> FEATURE:
<223> OTHER INFORMATION: I2A-27 Chain 4

<400> SEQUENCE: 99

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Ser Ile Ser Arg Asp Asp Ser Lys Asn Thr
65                  70                  75                  80

Ala Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140
```

```
Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
            210                 215                 220

Pro Pro Lys Ser Cys
225

<210> SEQ ID NO 100
<211> LENGTH: 109
<212> TYPE: PRT
<213> ORGANISM: Artificial Sequence
<220> FEATURE:
<223> OTHER INFORMATION: I2A-27 Domain A

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Ser Pro Arg
                85                  90                  95

Thr Phe Gly Gln Gly Thr Lys Val Glu Ile Lys Arg Thr
            100                 105

<210> SEQ ID NO 101
<211> LENGTH: 105
<212> TYPE: PRT
<213> ORGANISM: Artificial Sequence
<220> FEATURE:
<223> OTHER INFORMATION: I2A-27 Domain B

<400> SEQUENCE: 101

Pro Arg Glu Pro Gln Val Tyr Thr Leu Pro Pro Ser Arg Asp Glu Leu
1               5                   10                  15

Thr Lys Asn Gln Val Ser Leu Lys Cys Leu Val Lys Gly Phe Tyr Pro
            20                  25                  30

Ser Asp Ile Ala Val Glu Trp Glu Ser Asn Gly Gln Pro Glu Asn Asn
        35                  40                  45

Tyr Lys Thr Thr Pro Pro Val Leu Asp Ser Asp Gly Ser Phe Phe Leu
50                  55                  60

Tyr Ser Lys Leu Thr Val Asp Lys Ser Arg Trp Gln Gln Gly Asn Val
65                  70                  75                  80

Phe Ser Cys Ser Val Met His Glu Ala Leu His Asn His Tyr Thr Gln
                85                  90                  95

Lys Ser Leu Ser Leu Ser Lys Ser Cys
            100                 105
```

<210> SEQ ID NO 102
<211> LENGTH: 110
<212> TYPE: PRT
<213> ORGANISM: Artificial Sequence
<220> FEATURE:
<223> OTHER INFORMATION: I2A-27 Domain D

<400> SEQUENCE: 102

Ala Pro Glu Ala Ala Gly Gly Pro Ser Val Phe Leu Phe Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Lys Ala Pro Ile Glu Lys Thr Ile Ser Lys Ala Lys
            100                 105                 110

<210> SEQ ID NO 103
<211> LENGTH: 107
<212> TYPE: PRT
<213> ORGANISM: Artificial Sequence
<220> FEATURE:
<223> OTHER INFORMATION: I2A-27 Domain E

<400> SEQUENCE: 103

Gly Gln Pro Arg Glu Pro Gln Val Cys Thr Leu Pro Pro Ser Arg Glu
1               5                   10                  15

Glu Met Thr Lys Asn Gln Val Ser Leu Ser Cys Ala Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Val Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 104
<211> LENGTH: 120
<212> TYPE: PRT
<213> ORGANISM: Artificial Sequence
<220> FEATURE:
<223> OTHER INFORMATION: I2A-27 Domain F or Domain T

<400> SEQUENCE: 104

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Lys Gly Tyr
                20                  25                  30

```
Tyr Ile His Trp Val Arg Gln Ala Pro Gly Lys Gly Leu Glu Trp Val
         35                  40                  45

Ala Ala Ile Tyr Pro Tyr Gly Gly Ser Thr Asp Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Val Tyr Ile Tyr Gly Val Phe Asp Tyr Trp Gly Gln Gly Thr
             100                 105                 110

Leu Val Thr Val Ser Ser Ala Ser
         115                 120

<210> SEQ ID NO 105
<211> LENGTH: 105
<212> TYPE: PRT
<213> ORGANISM: Artificial Sequence
<220> FEATURE:
<223> OTHER INFORMATION: I2A-27 Domain G or Domain U

<400> SEQUENCE: 105

Pro Arg Glu Pro Gln Val Tyr Thr Asp Pro Pro Ser Arg Asp Glu Leu
 1               5                  10                  15

Thr Lys Asn Gln Val Ser Leu Thr Cys Leu Val Lys Gly Phe Tyr Pro
             20                  25                  30

Ser Asp Ile Ala Val Glu Trp Glu Ser Asn Gly Gln Pro Glu Asn Asn
         35                  40                  45

Tyr Lys Thr Thr Pro Pro Val Leu Asp Ser Asp Gly Ser Phe Phe Leu
 50                  55                  60

Tyr Ser Lys Leu Thr Val Asp Lys Ser Arg Trp Gln Gln Gly Asn Val
 65                  70                  75                  80

Phe Ser Cys Ser Val Met His Glu Ala Leu His Asn His Tyr Thr Gln
                 85                  90                  95

Lys Ser Leu Ser Leu Ser Gly Glu Cys
             100                 105

<210> SEQ ID NO 106
<211> LENGTH: 109
<212> TYPE: PRT
<213> ORGANISM: Artificial Sequence
<220> FEATURE:
<223> OTHER INFORMATION: I2A-27 Domain R

<400> SEQUENCE: 106

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
             20                  25                  30

Val Ala Trp Tyr Gln Gln Lys Pro Gly Lys Ala Pro Lys Leu Leu Ile
         35                  40                  45

Tyr Ser Ala Ser Ser Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ser Ser Pro Arg
                 85                  90                  95

Thr Phe Gly Gln Gly Thr Lys Val Glu Ile Lys Arg Thr
             100                 105
```

<210> SEQ ID NO 107
<211> LENGTH: 105
<212> TYPE: PRT
<213> ORGANISM: Artificial Sequence
<220> FEATURE:
<223> OTHER INFORMATION: I2A-27 Domain S

<400> SEQUENCE: 107

Pro Arg Glu Pro Gln Val Tyr Thr Leu Pro Pro Ser Arg Asp Glu Leu
1               5                   10                  15

Thr Lys Asn Gln Val Ser Leu Lys Cys Leu Val Lys Gly Phe Tyr Pro
            20                  25                  30

Ser Asp Ile Ala Val Glu Trp Glu Ser Asn Gly Gln Pro Glu Asn Asn
        35                  40                  45

Tyr Lys Thr Thr Pro Pro Val Leu Asp Ser Asp Gly Ser Phe Phe Leu
    50                  55                  60

Tyr Ser Lys Leu Thr Val Asp Lys Ser Arg Trp Gln Gln Gly Asn Val
65                  70                  75                  80

Phe Ser Cys Ser Val Met His Glu Ala Leu His Asn His Tyr Thr Gln
                85                  90                  95

Lys Ser Leu Ser Leu Ser Lys Ser Cys
            100                 105

<210> SEQ ID NO 108
<211> LENGTH: 113
<212> TYPE: PRT
<213> ORGANISM: Artificial Sequence
<220> FEATURE:
<223> OTHER INFORMATION: I2A-27 Domain H

<400> SEQUENCE: 108

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Arg Thr
            100                 105                 110

Val

<210> SEQ ID NO 109
<211> LENGTH: 104
<212> TYPE: PRT
<213> ORGANISM: Artificial Sequence
<220> FEATURE:
<223> OTHER INFORMATION: I2A-27 Domain I

<400> SEQUENCE: 109

Ala Ala Pro Ser Val Phe Ile Phe Pro Pro Ser Asp Glu Gln Leu Lys
1               5                   10                  15

Ser Gly Thr Ala Ser Val Val Cys Leu Leu Asn Asn Phe Tyr Pro Arg

```
                    20                  25                  30

Glu Ala Lys Val Gln Trp Lys Val Asp Asn Ala Leu Gln Ser Gly Asn
                35                  40                  45

Ser Gln Glu Ser Val Thr Glu Gln Asp Ser Lys Asp Ser Thr Tyr Ser
 50                  55                  60

Leu Ser Ser Thr Leu Thr Leu Ser Lys Ala Asp Tyr Glu Lys His Lys
 65                  70                  75                  80

Val Tyr Ala Cys Glu Val Thr His Gln Gly Leu Ser Ser Pro Val Thr
                85                  90                  95

Lys Ser Phe Asn Arg Gly Glu Cys
                100

<210> SEQ ID NO 110
<211> LENGTH: 110
<212> TYPE: PRT
<213> ORGANISM: Artificial Sequence
<220> FEATURE:
<223> OTHER INFORMATION: I2A-27 Domain J

<400> SEQUENCE: 110

Ala Pro Glu Ala Ala Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
                35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                85                  90                  95

Ala Leu Lys Ala Pro Ile Glu Lys Thr Ile Ser Lys Ala Lys
                100                 105                 110

<210> SEQ ID NO 111
<211> LENGTH: 107
<212> TYPE: PRT
<213> ORGANISM: Artificial Sequence
<220> FEATURE:
<223> OTHER INFORMATION: I2A-27 Domain K

<400> SEQUENCE: 111

Gly Gln Pro Arg Glu Pro Gln Val Tyr Thr Leu Pro Pro Cys Arg Asp
 1               5                  10                  15

Glu Leu Thr Lys Asn Gln Val Ser Leu Trp Cys Leu Val Lys Gly Phe
                20                  25                  30

Tyr Pro Ser Asp Ile Ala Val Glu Trp Glu Ser Asn Gly Gln Pro Glu
                35                  40                  45

Asn Asn Tyr Lys Thr Thr Pro Pro Val Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
                100                 105
```

<210> SEQ ID NO 112
<211> LENGTH: 127
<212> TYPE: PRT
<213> ORGANISM: Artificial Sequence
<220> FEATURE:
<223> OTHER INFORMATION: I2A-27 Domain L

<400> SEQUENCE: 112

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Ser Ile Ser Arg Asp Asp Ser Lys Asn Thr
65                  70                  75                  80

Ala Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala Ser
        115                 120                 125
```

<210> SEQ ID NO 113
<211> LENGTH: 102
<212> TYPE: PRT
<213> ORGANISM: Artificial Sequence
<220> FEATURE:
<223> OTHER INFORMATION: I2A-27 Domain M

<400> SEQUENCE: 113

```
Thr Lys Gly Pro Ser Val Phe Pro Leu Ala Pro Ser Ser Lys Ser Thr
1               5                   10                  15

Ser Gly Gly Thr Ala Ala Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Phe Pro Ala Val Leu Gln Ser Ser Gly Leu Tyr Ser Leu Ser
    50                  55                  60

Ser Val Val Thr Val Pro Ser Ser Ser Leu Gly Thr Gln Thr Tyr Ile
65                  70                  75                  80

Cys Asn Val Asn His Lys Pro Ser Asn Thr Lys Val Asp Lys Lys Val
                85                  90                  95

Glu Pro Pro Lys Ser Cys
            100
```

<210> SEQ ID NO 114
<211> LENGTH: 441
<212> TYPE: PRT
<213> ORGANISM: Artificial Sequence
<220> FEATURE:
<223> OTHER INFORMATION: I2A-10 Chain 1

<400> SEQUENCE: 114

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
```

-continued

```
                20                  25                  30
Val Ala Trp Tyr Gln Gln Lys Pro Gly Lys Ala Pro Lys Leu Leu Ile
            35                  40                  45
Tyr Ser Ala Ser Ser Leu Tyr Ser Gly Val Pro Ser Arg Phe Ser Gly
50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Tyr Tyr Pro Gly
                85                  90                  95
Thr Phe Gly Gln Gly Thr Lys Val Glu Ile Lys Arg Thr Pro Arg Glu
            100                 105                 110
Pro Gln Val Tyr Thr Leu Pro Pro Ser Arg Asp Glu Leu Thr Lys Asn
            115                 120                 125
Gln Val Ser Leu Lys Cys Leu Val Lys Gly Phe Tyr Pro Ser Asp Ile
            130                 135                 140
Ala Val Glu Trp Glu Ser Asn Gly Gln Pro Glu Asn Asn Tyr Lys Thr
145                 150                 155                 160
Thr Pro Pro Val Leu Asp Ser Asp Gly Ser Phe Phe Leu Tyr Ser Lys
            165                 170                 175
Leu Thr Val Asp Lys Ser Arg Trp Gln Gln Gly Asn Val Phe Ser Cys
            180                 185                 190
Ser Val Met His Glu Ala Leu His Asn His Tyr Thr Gln Lys Ser Leu
            195                 200                 205
Ser Leu Ser Lys Ser Cys Asp Lys Thr His Thr Cys Pro Pro Cys Pro
            210                 215                 220
Ala Pro Glu Ala Ala Gly Gly Pro Ser Val Phe Leu Phe Pro Pro Lys
225                 230                 235                 240
Pro Lys Asp Thr Leu Met Ile Ser Arg Thr Pro Glu Val Thr Cys Val
            245                 250                 255
Val Val Asp Val Ser His Glu Asp Pro Glu Val Lys Phe Asn Trp Tyr
            260                 265                 270
Val Asp Gly Val Glu Val His Asn Ala Lys Thr Lys Pro Arg Glu Glu
            275                 280                 285
Gln Tyr Asn Ser Thr Tyr Arg Val Val Ser Val Leu Thr Val Leu His
            290                 295                 300
Gln Asp Trp Leu Asn Gly Lys Glu Tyr Lys Cys Lys Val Ser Asn Lys
305                 310                 315                 320
Ala Leu Lys Ala Pro Ile Glu Lys Thr Ile Ser Lys Ala Lys Gly Gln
            325                 330                 335
Pro Arg Glu Pro Gln Val Cys Thr Leu Pro Pro Ser Arg Glu Glu Met
            340                 345                 350
Thr Lys Asn Gln Val Ser Leu Ser Cys Ala Val Lys Gly Phe Tyr Pro
            355                 360                 365
Ser Asp Ile Ala Val Glu Trp Glu Ser Asn Gly Gln Pro Glu Asn Asn
            370                 375                 380
Tyr Lys Thr Thr Pro Pro Val Leu Asp Ser Asp Gly Ser Phe Phe Leu
385                 390                 395                 400
Val Ser Lys Leu Thr Val Asp Lys Ser Arg Trp Gln Gln Gly Asn Val
            405                 410                 415
Phe Ser Cys Ser Val Met His Glu Ala Leu His Asn His Tyr Thr Gln
            420                 425                 430
Lys Ser Leu Ser Leu Ser Pro Gly Lys
            435                 440
```

<210> SEQ ID NO 115
<211> LENGTH: 224
<212> TYPE: PRT
<213> ORGANISM: Artificial Sequence
<220> FEATURE:
<223> OTHER INFORMATION: I2A-10 Chain 2 or Chain 5

<400> SEQUENCE: 115

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Phe Ile His Trp Val Arg Gln Ala Pro Gly Lys Gly Leu Glu Trp Val
        35                  40                  45

Ala Gly Ile Tyr Pro Ser Asp Gly Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Val Ser Gly Met Asp Tyr Trp Gly Gln Gly Thr Leu
            100                 105                 110

Val Thr Val Ser Ser Ala Ser Pro Arg Glu Pro Gln Val Tyr Thr Asp
        115                 120                 125

Pro Pro Ser Arg Asp Glu Leu Thr Lys Asn Gln Val Ser Leu Thr Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Gly Glu Cys
    210                 215                 220

<210> SEQ ID NO 116
<211> LENGTH: 668
<212> TYPE: PRT
<213> ORGANISM: Artificial Sequence
<220> FEATURE:
<223> OTHER INFORMATION: I2A-10 Chain 3

<400> SEQUENCE: 116

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Tyr Tyr Pro Gly

```
                    85                  90                  95
Thr Phe Gly Gln Gly Thr Lys Val Glu Ile Lys Arg Thr Pro Arg Glu
                100                 105                 110

Pro Gln Val Tyr Thr Leu Pro Pro Ser Arg Asp Glu Leu Thr Lys Asn
                115                 120                 125

Gln Val Ser Leu Lys Cys Leu Val Lys Gly Phe Tyr Pro Ser Asp Ile
130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
                165                 170                 175

Leu Thr Val Asp Lys Ser Arg Trp Gln Gln Gly Asn Val Phe Ser Cys
                180                 185                 190

Ser Val Met His Glu Ala Leu His Asn His Tyr Thr Gln Lys Ser Leu
                195                 200                 205

Ser Leu Ser Lys Ser Cys Thr Ala Ser Ser Gly Gly Ser Ser Ser Gly
210                 215                 220

Gln Ala Val Val Thr Gln Glu Pro Ser Leu Thr Val Ser Pro Gly Gly
225                 230                 235                 240

Thr Val Thr Leu Thr Cys Arg Ser Ser Thr Gly Ala Val Thr Thr Ser
                245                 250                 255

Asn Tyr Ala Asn Trp Val Gln Gln Lys Pro Gly Gln Ala Pro Arg Gly
                260                 265                 270

Leu Ile Gly Gly Thr Asn Lys Arg Ala Pro Trp Thr Pro Ala Arg Phe
                275                 280                 285

Ser Gly Ser Leu Leu Gly Gly Lys Ala Ala Leu Thr Ile Thr Gly Ala
                290                 295                 300

Gln Ala Glu Asp Glu Ala Asp Tyr Tyr Cys Ala Leu Trp Tyr Ser Asn
305                 310                 315                 320

Leu Trp Val Phe Gly Gly Gly Thr Lys Leu Thr Val Leu Gly Arg Thr
                325                 330                 335

Val Ala Ala Pro Ser Val Phe Ile Phe Pro Pro Ser Asp Glu Gln Leu
                340                 345                 350

Lys Ser Gly Thr Ala Ser Val Val Cys Leu Leu Asn Asn Phe Tyr Pro
                355                 360                 365

Arg Glu Ala Lys Val Gln Trp Lys Val Asp Asn Ala Leu Gln Ser Gly
                370                 375                 380

Asn Ser Gln Glu Ser Val Thr Glu Gln Asp Ser Lys Asp Ser Thr Tyr
385                 390                 395                 400

Ser Leu Ser Ser Thr Leu Thr Leu Ser Lys Ala Asp Tyr Glu Lys His
                405                 410                 415

Lys Val Tyr Ala Cys Glu Val Thr His Gln Gly Leu Ser Ser Pro Val
                420                 425                 430

Thr Lys Ser Phe Asn Arg Gly Glu Cys Asp Lys Thr His Thr Cys Pro
                435                 440                 445

Pro Cys Pro Ala Pro Glu Ala Ala Gly Gly Pro Ser Val Phe Leu Phe
                450                 455                 460

Pro Pro Lys Pro Lys Asp Thr Leu Met Ile Ser Arg Thr Pro Glu Val
465                 470                 475                 480

Thr Cys Val Val Val Asp Val Ser His Glu Asp Pro Glu Val Lys Phe
                485                 490                 495

Asn Trp Tyr Val Asp Gly Val Glu Val His Asn Ala Lys Thr Lys Pro
                500                 505                 510
```

```
Arg Glu Glu Gln Tyr Asn Ser Thr Tyr Arg Val Val Ser Val Leu Thr
            515                 520                 525

Val Leu His Gln Asp Trp Leu Asn Gly Lys Glu Tyr Lys Cys Lys Val
        530                 535                 540

Ser Asn Lys Ala Leu Lys Ala Pro Ile Glu Lys Thr Ile Ser Lys Ala
545                 550                 555                 560

Lys Gly Gln Pro Arg Glu Pro Gln Val Tyr Thr Leu Pro Pro Cys Arg
                565                 570                 575

Asp Glu Leu Thr Lys Asn Gln Val Ser Leu Trp Cys Leu Val Lys Gly
            580                 585                 590

Phe Tyr Pro Ser Asp Ile Ala Val Glu Trp Glu Ser Asn Gly Gln Pro
        595                 600                 605

Glu Asn Asn Tyr Lys Thr Thr Pro Pro Val Leu Asp Ser Asp Gly Ser
    610                 615                 620

Phe Phe Leu Tyr Ser Lys Leu Thr Val Asp Lys Ser Arg Trp Gln Gln
625                 630                 635                 640

Gly Asn Val Phe Ser Cys Ser Val Met His Glu Ala Leu His Asn His
                645                 650                 655

Tyr Thr Gln Lys Ser Leu Ser Leu Ser Pro Gly Lys
            660                 665

<210> SEQ ID NO 117
<211> LENGTH: 229
<212> TYPE: PRT
<213> ORGANISM: Artificial Sequence
<220> FEATURE:
<223> OTHER INFORMATION: I2A-10 Chain 4

<400> SEQUENCE: 117

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Ser Ile Ser Arg Asp Asp Ser Lys Asn Thr
65                  70                  75                  80

Ala Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205
```

Asn Val Asn His Lys Pro Ser Asn Thr Lys Val Asp Lys Lys Val Glu
210                215                220

Pro Pro Lys Ser Cys
225

<210> SEQ ID NO 118
<211> LENGTH: 109
<212> TYPE: PRT
<213> ORGANISM: Artificial Sequence
<220> FEATURE:
<223> OTHER INFORMATION: I2A-10 Domain A

<400> SEQUENCE: 118

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Tyr Pro Gly
                85                  90                  95

Thr Phe Gly Gln Gly Thr Lys Val Glu Ile Lys Arg Thr
            100                 105

<210> SEQ ID NO 119
<211> LENGTH: 105
<212> TYPE: PRT
<213> ORGANISM: Artificial Sequence
<220> FEATURE:
<223> OTHER INFORMATION: I2A-10 Domain B

<400> SEQUENCE: 119

Pro Arg Glu Pro Gln Val Tyr Thr Leu Pro Pro Ser Arg Asp Glu Leu
1               5                   10                  15

Thr Lys Asn Gln Val Ser Leu Lys Cys Leu Val Lys Gly Phe Tyr Pro
            20                  25                  30

Ser Asp Ile Ala Val Glu Trp Glu Ser Asn Gly Gln Pro Glu Asn Asn
        35                  40                  45

Tyr Lys Thr Thr Pro Pro Val Leu Asp Ser Asp Gly Ser Phe Phe Leu
    50                  55                  60

Tyr Ser Lys Leu Thr Val Asp Lys Ser Arg Trp Gln Gln Gly Asn Val
65                  70                  75                  80

Phe Ser Cys Ser Val Met His Glu Ala Leu His Asn His Tyr Thr Gln
                85                  90                  95

Lys Ser Leu Ser Leu Ser Lys Cys
            100                 105

<210> SEQ ID NO 120
<211> LENGTH: 110
<212> TYPE: PRT
<213> ORGANISM: Artificial Sequence
<220> FEATURE:
<223> OTHER INFORMATION: I2A-10 Domain D

<400> SEQUENCE: 120

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Lys Ala Pro Ile Glu Lys Thr Ile Ser Lys Ala Lys
            100                 105                 110

<210> SEQ ID NO 121
<211> LENGTH: 107
<212> TYPE: PRT
<213> ORGANISM: Artificial Sequence
<220> FEATURE:
<223> OTHER INFORMATION: I2A-10 Domain E

<400> SEQUENCE: 121

Gly Gln Pro Arg Glu Pro Gln Val Cys Thr Leu Pro Pro Ser Arg Glu
1               5                   10                  15

Glu Met Thr Lys Asn Gln Val Ser Leu Ser Cys Ala Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Val Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 122
<211> LENGTH: 119
<212> TYPE: PRT
<213> ORGANISM: Artificial Sequence
<220> FEATURE:
<223> OTHER INFORMATION: I2A-10 Domain F or Domain T

<400> SEQUENCE: 122

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Phe Ile His Trp Val Arg Gln Ala Pro Gly Lys Gly Leu Glu Trp Val
        35                  40                  45

Ala Gly Ile Tyr Pro Ser Asp Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

```
Ala Arg Tyr Tyr Val Ser Gly Met Asp Tyr Trp Gly Gln Gly Thr Leu
            100                 105                 110

Val Thr Val Ser Ser Ala Ser
            115

<210> SEQ ID NO 123
<211> LENGTH: 105
<212> TYPE: PRT
<213> ORGANISM: Artificial Sequence
<220> FEATURE:
<223> OTHER INFORMATION: I2A-10 Domain G or Domain U

<400> SEQUENCE: 123

Pro Arg Glu Pro Gln Val Tyr Thr Asp Pro Pro Ser Arg Asp Glu Leu
1               5                   10                  15

Thr Lys Asn Gln Val Ser Leu Thr Cys Leu Val Lys Gly Phe Tyr Pro
            20                  25                  30

Ser Asp Ile Ala Val Glu Trp Glu Ser Asn Gly Gln Pro Glu Asn Asn
        35                  40                  45

Tyr Lys Thr Thr Pro Pro Val Leu Asp Ser Asp Gly Ser Phe Phe Leu
    50                  55                  60

Tyr Ser Lys Leu Thr Val Asp Lys Ser Arg Trp Gln Gln Gly Asn Val
65                  70                  75                  80

Phe Ser Cys Ser Val Met His Glu Ala Leu His Asn His Tyr Thr Gln
                85                  90                  95

Lys Ser Leu Ser Leu Ser Gly Glu Cys
            100                 105

<210> SEQ ID NO 124
<211> LENGTH: 109
<212> TYPE: PRT
<213> ORGANISM: Artificial Sequence
<220> FEATURE:
<223> OTHER INFORMATION: I2A-10 Domain R

<400> SEQUENCE: 124

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Tyr Pro Gly
                85                  90                  95

Thr Phe Gly Gln Gly Thr Lys Val Glu Ile Lys Arg Thr
            100                 105

<210> SEQ ID NO 125
<211> LENGTH: 105
<212> TYPE: PRT
<213> ORGANISM: Artificial Sequence
<220> FEATURE:
<223> OTHER INFORMATION: I2A-10 Domain S

<400> SEQUENCE: 125
```

```
Pro Arg Glu Pro Gln Val Tyr Thr Leu Pro Pro Ser Arg Asp Glu Leu
1               5                   10                  15

Thr Lys Asn Gln Val Ser Leu Lys Cys Leu Val Lys Gly Phe Tyr Pro
            20                  25                  30

Ser Asp Ile Ala Val Glu Trp Glu Ser Asn Gly Gln Pro Glu Asn Asn
            35                  40                  45

Tyr Lys Thr Thr Pro Pro Val Leu Asp Ser Asp Gly Ser Phe Phe Leu
50                  55                  60

Tyr Ser Lys Leu Thr Val Asp Lys Ser Arg Trp Gln Gln Gly Asn Val
65                  70                  75                  80

Phe Ser Cys Ser Val Met His Glu Ala Leu His Asn His Tyr Thr Gln
                85                  90                  95

Lys Ser Leu Ser Leu Ser Leu Lys Ser Cys
                100                 105
```

<210> SEQ ID NO 126
<211> LENGTH: 113
<212> TYPE: PRT
<213> ORGANISM: Artificial Sequence
<220> FEATURE:
<223> OTHER INFORMATION: I2A-10 Domain H

<400> SEQUENCE: 126

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Lys Pro Gly Gln Ala Pro Arg Gly
            35                  40                  45

Leu Ile Gly Gly Thr Asn Lys Arg Ala Pro Trp Thr Pro Ala Arg Phe
50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Arg Thr
                100                 105                 110

Val
```

<210> SEQ ID NO 127
<211> LENGTH: 104
<212> TYPE: PRT
<213> ORGANISM: Artificial Sequence
<220> FEATURE:
<223> OTHER INFORMATION: I2A-10 Domain I

<400> SEQUENCE: 127

```
Ala Ala Pro Ser Val Phe Ile Phe Pro Pro Ser Asp Glu Gln Leu Lys
1               5                   10                  15

Ser Gly Thr Ala Ser Val Val Cys Leu Leu Asn Asn Phe Tyr Pro Arg
            20                  25                  30

Glu Ala Lys Val Gln Trp Lys Val Asp Asn Ala Leu Gln Ser Gly Asn
            35                  40                  45

Ser Gln Glu Ser Val Thr Glu Gln Asp Ser Lys Asp Ser Thr Tyr Ser
50                  55                  60

Leu Ser Ser Thr Leu Thr Leu Ser Lys Ala Asp Tyr Glu Lys His Lys
65                  70                  75                  80
```

-continued

Val Tyr Ala Cys Glu Val Thr His Gln Gly Leu Ser Ser Pro Val Thr
                85                  90                  95

Lys Ser Phe Asn Arg Gly Glu Cys
            100

<210> SEQ ID NO 128
<211> LENGTH: 110
<212> TYPE: PRT
<213> ORGANISM: Artificial Sequence
<220> FEATURE:
<223> OTHER INFORMATION: I2A-10 Domain J

<400> SEQUENCE: 128

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Lys Ala Pro Ile Glu Lys Thr Ile Ser Lys Ala Lys
            100                 105                 110

<210> SEQ ID NO 129
<211> LENGTH: 107
<212> TYPE: PRT
<213> ORGANISM: Artificial Sequence
<220> FEATURE:
<223> OTHER INFORMATION: I2A-10 Domain K

<400> SEQUENCE: 129

Gly Gln Pro Arg Glu Pro Gln Val Tyr Thr Leu Pro Pro Cys Arg Asp
1               5                   10                  15

Glu Leu Thr Lys Asn Gln Val Ser Leu Trp Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 130
<211> LENGTH: 127
<212> TYPE: PRT
<213> ORGANISM: Artificial Sequence
<220> FEATURE:
<223> OTHER INFORMATION: I2A-10 Domain L

<400> SEQUENCE: 130

Glu Val Gln Leu Val Glu Ser Gly Gly Gly Leu Val Gln Pro Gly Gly

```
                1               5                  10                 15
            Ser Leu Arg Leu Ser Cys Ala Ala Ser Gly Phe Thr Phe Asn Thr Tyr
                           20                  25                 30
            Ala Met Asn Trp Val Arg Gln Ala Pro Gly Lys Gly Leu Glu Trp Val
                           35                  40                 45
            Ala Arg Ile Arg Ser Lys Tyr Asn Asn Tyr Ala Thr Tyr Tyr Ala Asp
                           50                  55                 60
            Ser Val Lys Gly Arg Phe Ser Ile Ser Arg Asp Asp Ser Lys Asn Thr
             65                 70                  75                 80
            Ala Tyr Leu Gln Met Asn Ser Leu Arg Ala Glu Asp Thr Ala Val Tyr
                           85                  90                 95
            Tyr Cys Val Arg His Gly Asn Phe Gly Asn Ser Tyr Val Ser Trp Phe
                           100                 105                110
            Ala Tyr Trp Gly Gln Gly Thr Leu Val Thr Val Ser Ser Ala Ser
                           115                 120                125

<210> SEQ ID NO 131
<211> LENGTH: 102
<212> TYPE: PRT
<213> ORGANISM: Artificial Sequence
<220> FEATURE:
<223> OTHER INFORMATION: I2A-10 Domain M

<400> SEQUENCE: 131

Thr Lys Gly Pro Ser Val Phe Pro Leu Ala Pro Ser Ser Lys Ser Thr
             1              5                  10                 15
            Ser Gly Gly Thr Ala Ala Leu Gly Cys Leu Val Lys Asp Tyr Phe Pro
                           20                  25                 30
            Glu Pro Val Thr Val Ser Trp Asn Ser Gly Ala Leu Thr Ser Gly Val
                           35                  40                 45
            His Thr Phe Pro Ala Val Leu Gln Ser Ser Gly Leu Tyr Ser Leu Ser
                           50                  55                 60
            Ser Val Val Thr Val Pro Ser Ser Ser Leu Gly Thr Gln Thr Tyr Ile
             65                 70                  75                 80
            Cys Asn Val Asn His Lys Pro Ser Asn Thr Lys Val Asp Lys Lys Val
                           85                  90                 95
            Glu Pro Pro Lys Ser Cys
                           100

<210> SEQ ID NO 132
<211> LENGTH: 441
<212> TYPE: PRT
<213> ORGANISM: Artificial Sequence
<220> FEATURE:
<223> OTHER INFORMATION: I2A-10 D54E Y55Q Chain 1

<400> SEQUENCE: 132

Asp Ile Gln Met Thr Gln Ser Pro Ser Ser Leu Ser Ala Ser Val Gly
             1              5                  10                 15
            Asp Arg Val Thr Ile Thr Cys Arg Ala Ser Gln Ser Val Ser Ser Ala
                           20                  25                 30
            Val Ala Trp Tyr Gln Gln Lys Pro Gly Lys Ala Pro Lys Leu Leu Ile
                           35                  40                 45
            Tyr Ser Ala Ser Ser Leu Gln Ser Gly Val Pro Ser Arg Phe Ser Gly
                           50                  55                 60
            Ser Arg Ser Gly Thr Asp Phe Thr Leu Thr Ile Ser Ser Leu Gln Pro
             65                 70                  75                 80
```

Glu Asp Phe Ala Thr Tyr Tyr Cys Gln Gln Tyr Tyr Tyr Pro Gly
                85                  90                  95

Thr Phe Gly Gln Gly Thr Lys Val Glu Ile Lys Arg Thr Pro Arg Glu
            100                 105                 110

Pro Gln Val Tyr Thr Leu Pro Pro Ser Arg Asp Glu Leu Thr Lys Asn
            115                 120                 125

Gln Val Ser Leu Lys Cys Leu Val Lys Gly Phe Tyr Pro Ser Asp Ile
130             135                 140

Ala Val Glu Trp Glu Ser Asn Gly Gln Pro Glu Asn Asn Tyr Lys Thr
145             150                 155                 160

Thr Pro Pro Val Leu Asp Ser Asp Gly Ser Phe Phe Leu Tyr Ser Lys
                165                 170                 175

Leu Thr Val Asp Lys Ser Arg Trp Gln Gln Gly Asn Val Phe Ser Cys
                180                 185                 190

Ser Val Met His Glu Ala Leu His Asn His Tyr Thr Gln Lys Ser Leu
                195                 200                 205

Ser Leu Ser Lys Ser Cys Asp Lys Thr His Thr Cys Pro Pro Cys Pro
            210                 215                 220

Ala Pro Glu Ala Ala Gly Gly Pro Ser Val Phe Leu Phe Pro Pro Lys
225             230                 235                 240

Pro Lys Asp Thr Leu Met Ile Ser Arg Thr Pro Glu Val Thr Cys Val
            245                 250                 255

Val Val Asp Val Ser His Glu Asp Pro Glu Val Lys Phe Asn Trp Tyr
                260                 265                 270

Val Asp Gly Val Glu Val His Asn Ala Lys Thr Lys Pro Arg Glu Glu
                275                 280                 285

Gln Tyr Asn Ser Thr Tyr Arg Val Val Ser Val Leu Thr Val Leu His
290             295                 300

Gln Asp Trp Leu Asn Gly Lys Glu Tyr Lys Cys Lys Val Ser Asn Lys
305             310                 315                 320

Ala Leu Lys Ala Pro Ile Glu Lys Thr Ile Ser Lys Ala Lys Gly Gln
                325                 330                 335

Pro Arg Glu Pro Gln Val Cys Thr Leu Pro Pro Ser Arg Glu Glu Met
            340                 345                 350

Thr Lys Asn Gln Val Ser Leu Ser Cys Ala Val Lys Gly Phe Tyr Pro
            355                 360                 365

Ser Asp Ile Ala Val Glu Trp Glu Ser Asn Gly Gln Pro Glu Asn Asn
            370                 375                 380

Tyr Lys Thr Thr Pro Pro Val Leu Asp Ser Asp Gly Ser Phe Phe Leu
385                 390                 395                 400

Val Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
                420                 425                 430

Lys Ser Leu Ser Leu Ser Pro Gly Lys
                435                 440

<210> SEQ ID NO 133
<211> LENGTH: 224
<212> TYPE: PRT
<213> ORGANISM: Artificial Sequence
<220> FEATURE:
<223> OTHER INFORMATION: I2A-10 D54E Y55Q Chain 2 or Chain 5

<400> SEQUENCE: 133

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Phe Ile His Trp Val Arg Gln Ala Pro Gly Lys Gly Leu Glu Trp Val
        35                  40                  45

Ala Gly Ile Tyr Pro Ser Glu Gly Tyr Thr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Val Ser Gly Met Asp Tyr Trp Gly Gln Gly Thr Leu
            100                 105                 110

Val Thr Val Ser Ser Ala Ser Pro Arg Glu Pro Gln Val Tyr Thr Asp
            115                 120                 125

Pro Pro Ser Arg Asp Glu Leu Thr Lys Asn Gln Val Ser Leu Thr Cys
        130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Gly Glu Cys
210                 215                 220

<210> SEQ ID NO 134
<211> LENGTH: 668
<212> TYPE: PRT
<213> ORGANISM: Artificial Sequence
<220> FEATURE:
<223> OTHER INFORMATION: I2A-10 D54E Y55Q Chain 3

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Gln Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Tyr Pro Gly
                85                  90                  95

Thr Phe Gly Gln Gly Thr Lys Val Glu Ile Lys Arg Thr Pro Arg Glu
            100                 105                 110

Pro Gln Val Tyr Thr Leu Pro Pro Ser Arg Asp Glu Leu Thr Lys Asn
        115                 120                 125

Gln Val Ser Leu Lys Cys Leu Val Lys Gly Phe Tyr Pro Ser Asp Ile
        130                 135                 140

```
Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
            165                 170                 175

Leu Thr Val Asp Lys Ser Arg Trp Gln Gln Gly Asn Val Phe Ser Cys
            180                 185                 190

Ser Val Met His Glu Ala Leu His Asn His Tyr Thr Gln Lys Ser Leu
        195                 200                 205

Ser Leu Ser Lys Ser Cys Thr Ala Ser Ser Gly Gly Ser Ser Ser Gly
    210                 215                 220

Gln Ala Val Val Thr Gln Glu Pro Ser Leu Thr Val Ser Pro Gly Gly
225                 230                 235                 240

Thr Val Thr Leu Thr Cys Arg Ser Ser Thr Gly Ala Val Thr Thr Ser
            245                 250                 255

Asn Tyr Ala Asn Trp Val Gln Gln Lys Pro Gly Gln Ala Pro Arg Gly
            260                 265                 270

Leu Ile Gly Gly Thr Asn Lys Arg Ala Pro Trp Thr Pro Ala Arg Phe
        275                 280                 285

Ser Gly Ser Leu Leu Gly Gly Lys Ala Ala Leu Thr Ile Thr Gly Ala
    290                 295                 300

Gln Ala Glu Asp Glu Ala Asp Tyr Tyr Cys Ala Leu Trp Tyr Ser Asn
305                 310                 315                 320

Leu Trp Val Phe Gly Gly Gly Thr Lys Leu Thr Val Leu Gly Arg Thr
            325                 330                 335

Val Ala Ala Pro Ser Val Phe Ile Phe Pro Pro Ser Asp Glu Gln Leu
            340                 345                 350

Lys Ser Gly Thr Ala Ser Val Val Cys Leu Leu Asn Asn Phe Tyr Pro
        355                 360                 365

Arg Glu Ala Lys Val Gln Trp Lys Val Asp Asn Ala Leu Gln Ser Gly
    370                 375                 380

Asn Ser Gln Glu Ser Val Thr Glu Gln Asp Ser Lys Asp Ser Thr Tyr
385                 390                 395                 400

Ser Leu Ser Ser Thr Leu Thr Leu Ser Lys Ala Asp Tyr Glu Lys His
            405                 410                 415

Lys Val Tyr Ala Cys Glu Val Thr His Gln Gly Leu Ser Ser Pro Val
            420                 425                 430

Thr Lys Ser Phe Asn Arg Gly Glu Cys Asp Lys Thr His Thr Cys Pro
        435                 440                 445

Pro Cys Pro Ala Pro Glu Ala Ala Gly Gly Pro Ser Val Phe Leu Phe
    450                 455                 460

Pro Pro Lys Pro Lys Asp Thr Leu Met Ile Ser Arg Thr Pro Glu Val
465                 470                 475                 480

Thr Cys Val Val Val Asp Val Ser His Glu Asp Pro Glu Val Lys Phe
            485                 490                 495

Asn Trp Tyr Val Asp Gly Val Glu Val His Asn Ala Lys Thr Lys Pro
            500                 505                 510

Arg Glu Glu Gln Tyr Asn Ser Thr Tyr Arg Val Val Ser Val Leu Thr
        515                 520                 525

Val Leu His Gln Asp Trp Leu Asn Gly Lys Glu Tyr Lys Cys Lys Val
    530                 535                 540

Ser Asn Lys Ala Leu Lys Ala Pro Ile Glu Lys Thr Ile Ser Lys Ala
545                 550                 555                 560

Lys Gly Gln Pro Arg Glu Pro Gln Val Tyr Thr Leu Pro Pro Cys Arg
```

```
            565                 570                 575
Asp Glu Leu Thr Lys Asn Gln Val Ser Leu Trp Cys Leu Val Lys Gly
            580                 585                 590

Phe Tyr Pro Ser Asp Ile Ala Val Glu Trp Glu Ser Asn Gly Gln Pro
            595                 600                 605

Glu Asn Asn Tyr Lys Thr Thr Pro Pro Val Leu Asp Ser Asp Gly Ser
610                 615                 620

Phe Phe Leu Tyr Ser Lys Leu Thr Val Asp Lys Ser Arg Trp Gln Gln
625                 630                 635                 640

Gly Asn Val Phe Ser Cys Ser Val Met His Glu Ala Leu His Asn His
                645                 650                 655

Tyr Thr Gln Lys Ser Leu Ser Leu Ser Pro Gly Lys
            660                 665

<210> SEQ ID NO 135
<211> LENGTH: 229
<212> TYPE: PRT
<213> ORGANISM: Artificial Sequence
<220> FEATURE:
<223> OTHER INFORMATION: I2A-10 D54E Y55Q Chain 4

<400> SEQUENCE: 135

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Ser Ile Ser Arg Asp Asp Ser Lys Asn Thr
65                  70                  75                  80

Ala Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Pro Lys Ser Cys
225

<210> SEQ ID NO 136
<211> LENGTH: 109
<212> TYPE: PRT
```

```
<213> ORGANISM: Artificial Sequence
<220> FEATURE:
<223> OTHER INFORMATION: I2A-10 D54E Y55Q Domain A

<400> SEQUENCE: 136
```

Asp Ile Gln Met Thr Gln Ser Pro Ser Leu Ser Ala Ser Val Gly
1               5                   10                  15

Asp Arg Val Thr Ile Thr Cys Arg Ala Ser Gln Ser Val Ser Ser Ala
                20                  25                  30

Val Ala Trp Tyr Gln Gln Lys Pro Gly Lys Ala Pro Lys Leu Leu Ile
            35                  40                  45

Tyr Ser Ala Ser Ser Leu Gln Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Tyr Tyr Pro Gly
                85                  90                  95

Thr Phe Gly Gln Gly Thr Lys Val Glu Ile Lys Arg Thr
            100                 105

```
<210> SEQ ID NO 137
<211> LENGTH: 105
<212> TYPE: PRT
<213> ORGANISM: Artificial Sequence
<220> FEATURE:
<223> OTHER INFORMATION: I2A-10 D54E Y55Q Domain B

<400> SEQUENCE: 137
```

Pro Arg Glu Pro Gln Val Tyr Thr Leu Pro Pro Ser Arg Asp Glu Leu
1               5                   10                  15

Thr Lys Asn Gln Val Ser Leu Lys Cys Leu Val Lys Gly Phe Tyr Pro
                20                  25                  30

Ser Asp Ile Ala Val Glu Trp Glu Ser Asn Gly Gln Pro Glu Asn Asn
            35                  40                  45

Tyr Lys Thr Thr Pro Pro Val Leu Asp Ser Asp Gly Ser Phe Phe Leu
    50                  55                  60

Tyr Ser Lys Leu Thr Val Asp Lys Ser Arg Trp Gln Gln Gly Asn Val
65                  70                  75                  80

Phe Ser Cys Ser Val Met His Glu Ala Leu His Asn His Tyr Thr Gln
                85                  90                  95

Lys Ser Leu Ser Leu Ser Lys Ser Cys
            100                 105

```
<210> SEQ ID NO 138
<211> LENGTH: 110
<212> TYPE: PRT
<213> ORGANISM: Artificial Sequence
<220> FEATURE:
<223> OTHER INFORMATION: I2A-10 D54E Y55Q Domain D

<400> SEQUENCE: 138
```

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Lys Ala Pro Ile Glu Lys Thr Ile Ser Lys Ala Lys
            100                 105                 110

<210> SEQ ID NO 139
<211> LENGTH: 107
<212> TYPE: PRT
<213> ORGANISM: Artificial Sequence
<220> FEATURE:
<223> OTHER INFORMATION: I2A-10 D54E Y55Q Domain E

<400> SEQUENCE: 139

Gly Gln Pro Arg Glu Pro Gln Val Cys Thr Leu Pro Pro Ser Arg Glu
1               5                   10                  15

Glu Met Thr Lys Asn Gln Val Ser Leu Ser Cys Ala Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
50                  55                  60

Phe Leu Val Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 140
<211> LENGTH: 119
<212> TYPE: PRT
<213> ORGANISM: Artificial Sequence
<220> FEATURE:
<223> OTHER INFORMATION: I2A-10 D54E Y55Q Domain F or Domain T

<400> SEQUENCE: 140

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Phe Ile His Trp Val Arg Gln Ala Pro Gly Lys Gly Leu Glu Trp Val
        35                  40                  45

Ala Gly Ile Tyr Pro Ser Glu Gly Tyr Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Val Ser Gly Met Asp Tyr Trp Gly Gln Gly Thr Leu
            100                 105                 110

Val Thr Val Ser Ser Ala Ser
        115

<210> SEQ ID NO 141
<211> LENGTH: 105
<212> TYPE: PRT

<213> ORGANISM: Artificial Sequence
<220> FEATURE:
<223> OTHER INFORMATION: I2A-10 D54E Y55Q Domain G or Domain U

<400> SEQUENCE: 141

```
Pro Arg Glu Pro Gln Val Tyr Thr Asp Pro Pro Ser Arg Asp Glu Leu
1               5                   10                  15

Thr Lys Asn Gln Val Ser Leu Thr Cys Leu Val Lys Gly Phe Tyr Pro
            20                  25                  30

Ser Asp Ile Ala Val Glu Trp Glu Ser Asn Gly Gln Pro Glu Asn Asn
        35                  40                  45

Tyr Lys Thr Thr Pro Pro Val Leu Asp Ser Asp Gly Ser Phe Phe Leu
    50                  55                  60

Tyr Ser Lys Leu Thr Val Asp Lys Ser Arg Trp Gln Gln Gly Asn Val
65                  70                  75                  80

Phe Ser Cys Ser Val Met His Glu Ala Leu His Asn His Tyr Thr Gln
                85                  90                  95

Lys Ser Leu Ser Leu Ser Gly Glu Cys
            100                 105
```

<210> SEQ ID NO 142
<211> LENGTH: 109
<212> TYPE: PRT
<213> ORGANISM: Artificial Sequence
<220> FEATURE:
<223> OTHER INFORMATION: I2A-10 D54E Y55Q Domain R

<400> SEQUENCE: 142

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Gln Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Tyr Pro Gly
                85                  90                  95

Thr Phe Gly Gln Gly Thr Lys Val Glu Ile Lys Arg Thr
            100                 105
```

<210> SEQ ID NO 143
<211> LENGTH: 105
<212> TYPE: PRT
<213> ORGANISM: Artificial Sequence
<220> FEATURE:
<223> OTHER INFORMATION: I2A-10 D54E Y55Q Domain S

<400> SEQUENCE: 143

```
Pro Arg Glu Pro Gln Val Tyr Thr Leu Pro Pro Ser Arg Asp Glu Leu
1               5                   10                  15

Thr Lys Asn Gln Val Ser Leu Lys Cys Leu Val Lys Gly Phe Tyr Pro
            20                  25                  30

Ser Asp Ile Ala Val Glu Trp Glu Ser Asn Gly Gln Pro Glu Asn Asn
        35                  40                  45

Tyr Lys Thr Thr Pro Pro Val Leu Asp Ser Asp Gly Ser Phe Phe Leu
    50                  55                  60
```

Tyr Ser Lys Leu Thr Val Asp Lys Ser Arg Trp Gln Gln Gly Asn Val
65                  70                  75                  80

Phe Ser Cys Ser Val Met His Glu Ala Leu His Asn His Tyr Thr Gln
                85                  90                  95

Lys Ser Leu Ser Leu Ser Lys Ser Cys
            100                 105

<210> SEQ ID NO 144
<211> LENGTH: 113
<212> TYPE: PRT
<213> ORGANISM: Artificial Sequence
<220> FEATURE:
<223> OTHER INFORMATION: I2A-10 D54E Y55Q Domain H

<400> SEQUENCE: 144

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Arg Thr
            100                 105                 110

Val

<210> SEQ ID NO 145
<211> LENGTH: 104
<212> TYPE: PRT
<213> ORGANISM: Artificial Sequence
<220> FEATURE:
<223> OTHER INFORMATION: I2A-10 D54E Y55Q Domain I

<400> SEQUENCE: 145

Ala Ala Pro Ser Val Phe Ile Phe Pro Pro Ser Asp Glu Gln Leu Lys
1               5                   10                  15

Ser Gly Thr Ala Ser Val Val Cys Leu Leu Asn Asn Phe Tyr Pro Arg
            20                  25                  30

Glu Ala Lys Val Gln Trp Lys Val Asp Asn Ala Leu Gln Ser Gly Asn
        35                  40                  45

Ser Gln Glu Ser Val Thr Glu Gln Asp Ser Lys Asp Ser Thr Tyr Ser
    50                  55                  60

Leu Ser Ser Thr Leu Thr Leu Ser Lys Ala Asp Tyr Glu Lys His Lys
65                  70                  75                  80

Val Tyr Ala Cys Glu Val Thr His Gln Gly Leu Ser Ser Pro Val Thr
                85                  90                  95

Lys Ser Phe Asn Arg Gly Glu Cys
            100

<210> SEQ ID NO 146
<211> LENGTH: 110
<212> TYPE: PRT
<213> ORGANISM: Artificial Sequence
<220> FEATURE:
<223> OTHER INFORMATION: I2A-10 D54E Y55Q Domain J

<400> SEQUENCE: 146

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Lys Ala Pro Ile Glu Lys Thr Ile Ser Lys Ala Lys
            100                 105                 110

<210> SEQ ID NO 147
<211> LENGTH: 107
<212> TYPE: PRT
<213> ORGANISM: Artificial Sequence
<220> FEATURE:
<223> OTHER INFORMATION: I2A-10 D54E Y55Q Domain K

<400> SEQUENCE: 147

Gly Gln Pro Arg Glu Pro Gln Val Tyr Thr Leu Pro Pro Cys Arg Asp
1               5                   10                  15

Glu Leu Thr Lys Asn Gln Val Ser Leu Trp Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 148
<211> LENGTH: 127
<212> TYPE: PRT
<213> ORGANISM: Artificial Sequence
<220> FEATURE:
<223> OTHER INFORMATION: I2A-10 D54E Y55Q Domain L

<400> SEQUENCE: 148

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Ser Ile Ser Arg Asp Asp Ser Lys Asn Thr
65                  70                  75                  80

Ala Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser
            115                 120                 125

<210> SEQ ID NO 149
<211> LENGTH: 102
<212> TYPE: PRT
<213> ORGANISM: Artificial Sequence
<220> FEATURE:
<223> OTHER INFORMATION: I2A-10 D54E Y55Q Domain M

<400> SEQUENCE: 149

Thr Lys Gly Pro Ser Val Phe Pro Leu Ala Pro Ser Ser Lys Ser Thr
1               5                   10                  15

Ser Gly Gly Thr Ala Ala Leu Gly Cys Leu Val Lys Asp Tyr Phe Pro
            20                  25                  30

Glu Pro Val Thr Val Ser Trp Asn Ser Gly Ala Leu Thr Ser Gly Val
            35                  40                  45

His Thr Phe Pro Ala Val Leu Gln Ser Ser Gly Leu Tyr Ser Leu Ser
        50                  55                  60

Ser Val Val Thr Val Pro Ser Ser Ser Leu Gly Thr Gln Thr Tyr Ile
65                  70                  75                  80

Cys Asn Val Asn His Lys Pro Ser Asn Thr Lys Val Asp Lys Lys Val
                85                  90                  95

Glu Pro Pro Lys Ser Cys
            100

<210> SEQ ID NO 150
<211> LENGTH: 19
<212> TYPE: PRT
<213> ORGANISM: Artificial Sequence
<220> FEATURE:
<223> OTHER INFORMATION: Exemplary signal sequence for I2A-27, I2A-10
      and I2A-10 D54E Y55Q, e.g., Chain 1

<400> SEQUENCE: 150

Met Gly Trp Ser Leu Ile Leu Leu Phe Leu Val Ala Val Ala Thr Arg
1               5                   10                  15

Val Leu Ser

<210> SEQ ID NO 151
<211> LENGTH: 22
<212> TYPE: PRT
<213> ORGANISM: Artificial Sequence
<220> FEATURE:
<223> OTHER INFORMATION: Exemplary signal sequence for I2A-27, I2A-10
      and I2A-10 D54E Y55Q, e.g., Chain 2, 3, 4 or 5

<400> SEQUENCE: 151

Met Asp Phe Gln Val Gln Ile Ile Ser Phe Leu Leu Ile Ser Ala Ser
1               5                   10                  15

Val Ile Met Ser Arg Gly
            20

<210> SEQ ID NO 152
<211> LENGTH: 23

```
<212> TYPE: PRT
<213> ORGANISM: Artificial Sequence
<220> FEATURE:
<223> OTHER INFORMATION: Exemplary signal sequence for I2A-27, I2A-10
      and I2A-10 D54E Y55Q, e.g., Chain 3

<400> SEQUENCE: 152

Met Asp Phe Gln Val Gln Ile Ile Ser Phe Leu Leu Ile Ser Ala Ser
1               5                   10                  15

Val Ile Met Ser Arg Gly Ser
            20

<210> SEQ ID NO 153
<211> LENGTH: 6
<212> TYPE: PRT
<213> ORGANISM: Artificial Sequence
<220> FEATURE:
<223> OTHER INFORMATION: CDR1 VH of I2A-1

<400> SEQUENCE: 153

Phe Ser Ser Tyr Phe Ile
1               5

<210> SEQ ID NO 154
<211> LENGTH: 10
<212> TYPE: PRT
<213> ORGANISM: Artificial Sequence
<220> FEATURE:
<223> OTHER INFORMATION: CDR2 VH of I2A-1

<400> SEQUENCE: 154

Ala Ile Tyr Pro Glu Gly Gly Tyr Thr Tyr
1               5                   10

<210> SEQ ID NO 155
<211> LENGTH: 8
<212> TYPE: PRT
<213> ORGANISM: Artificial Sequence
<220> FEATURE:
<223> OTHER INFORMATION: CDR3 VH of I2A-1

<400> SEQUENCE: 155

Asp Tyr Lys Tyr Val Gly Ala Leu
1               5

<210> SEQ ID NO 156
<211> LENGTH: 11
<212> TYPE: PRT
<213> ORGANISM: Artificial Sequence
<220> FEATURE:
<223> OTHER INFORMATION: CDR1 VL of I2A-1

<400> SEQUENCE: 156

Arg Ala Ser Gln Ser Val Ser Ser Ala Val Ala
1               5                   10

<210> SEQ ID NO 157
<211> LENGTH: 7
<212> TYPE: PRT
<213> ORGANISM: Artificial Sequence
<220> FEATURE:
<223> OTHER INFORMATION: CDR2 VL of I2A-1

<400> SEQUENCE: 157

Ser Ala Ser Ser Leu Tyr Ser
1               5
```

```
<210> SEQ ID NO 158
<211> LENGTH: 6
<212> TYPE: PRT
<213> ORGANISM: Artificial Sequence
<220> FEATURE:
<223> OTHER INFORMATION: CDR3 VL of I2A-1

<400> SEQUENCE: 158

Tyr Tyr Tyr Phe Pro Gly
1               5

<210> SEQ ID NO 159
<211> LENGTH: 6
<212> TYPE: PRT
<213> ORGANISM: Artificial Sequence
<220> FEATURE:
<223> OTHER INFORMATION: CDR1 VH of I2A-2

<400> SEQUENCE: 159

Phe Ser Tyr Tyr Gly Ile
1               5

<210> SEQ ID NO 160
<211> LENGTH: 10
<212> TYPE: PRT
<213> ORGANISM: Artificial Sequence
<220> FEATURE:
<223> OTHER INFORMATION: CDR2 VH of I2A-2

<400> SEQUENCE: 160

Phe Ile Tyr Ser Arg Gly Gly Tyr Thr Ile
1               5                   10

<210> SEQ ID NO 161
<211> LENGTH: 6
<212> TYPE: PRT
<213> ORGANISM: Artificial Sequence
<220> FEATURE:
<223> OTHER INFORMATION: CDR3 VH of I2A-2

<400> SEQUENCE: 161

Tyr Ile Gly Ala Gly Leu
1               5

<210> SEQ ID NO 162
<211> LENGTH: 11
<212> TYPE: PRT
<213> ORGANISM: Artificial Sequence
<220> FEATURE:
<223> OTHER INFORMATION: CDR1 VL of I2A-2

<400> SEQUENCE: 162

Arg Ala Ser Gln Ser Val Ser Ser Ala Val Ala
1               5                   10

<210> SEQ ID NO 163
<211> LENGTH: 7
<212> TYPE: PRT
<213> ORGANISM: Artificial Sequence
<220> FEATURE:
<223> OTHER INFORMATION: CDR2 VL of I2A-2

<400> SEQUENCE: 163

Ser Ala Ser Ser Leu Tyr Ser
1               5
```

```
<210> SEQ ID NO 164
<211> LENGTH: 6
<212> TYPE: PRT
<213> ORGANISM: Artificial Sequence
<220> FEATURE:
<223> OTHER INFORMATION: CDR3 VL of I2A-2

<400> SEQUENCE: 164

Tyr Tyr Trp Asp Pro Ile
1               5

<210> SEQ ID NO 165
<211> LENGTH: 6
<212> TYPE: PRT
<213> ORGANISM: Artificial Sequence
<220> FEATURE:
<223> OTHER INFORMATION: CDR1 VH of I2A-3

<400> SEQUENCE: 165

Phe Thr Ser Tyr Glu Ile
1               5

<210> SEQ ID NO 166
<211> LENGTH: 10
<212> TYPE: PRT
<213> ORGANISM: Artificial Sequence
<220> FEATURE:
<223> OTHER INFORMATION: CDR2 VH of I2A-3

<400> SEQUENCE: 166

His Ile Asp Pro Tyr Gly Gly Tyr Thr Gln
1               5                   10

<210> SEQ ID NO 167
<211> LENGTH: 6
<212> TYPE: PRT
<213> ORGANISM: Artificial Sequence
<220> FEATURE:
<223> OTHER INFORMATION: CDR3 VH of I2A-3

<400> SEQUENCE: 167

Arg Gly Val Ala Val Phe
1               5

<210> SEQ ID NO 168
<211> LENGTH: 11
<212> TYPE: PRT
<213> ORGANISM: Artificial Sequence
<220> FEATURE:
<223> OTHER INFORMATION: CDR1 VL of I2A-3

<400> SEQUENCE: 168

Arg Ala Ser Gln Ser Val Ser Ser Ala Val Ala
1               5                   10

<210> SEQ ID NO 169
<211> LENGTH: 7
<212> TYPE: PRT
<213> ORGANISM: Artificial Sequence
<220> FEATURE:
<223> OTHER INFORMATION: CDR2 VL of I2A-3

<400> SEQUENCE: 169

Ser Ala Ser Ser Leu Tyr Ser
1               5

<210> SEQ ID NO 170
```

<211> LENGTH: 6
<212> TYPE: PRT
<213> ORGANISM: Artificial Sequence
<220> FEATURE:
<223> OTHER INFORMATION: CDR3 VL of I2A-3

<400> SEQUENCE: 170

Trp Ala Tyr Ala Pro Val
1               5

<210> SEQ ID NO 171
<211> LENGTH: 6
<212> TYPE: PRT
<213> ORGANISM: Artificial Sequence
<220> FEATURE:
<223> OTHER INFORMATION: CDR1 VH of I2A-4

<400> SEQUENCE: 171

Phe Tyr Ser Tyr Asp Ile
1               5

<210> SEQ ID NO 172
<211> LENGTH: 10
<212> TYPE: PRT
<213> ORGANISM: Artificial Sequence
<220> FEATURE:
<223> OTHER INFORMATION: CDR2 VH of I2A-4

<400> SEQUENCE: 172

Tyr Ile Ser Pro Tyr Trp Gly Ile Thr Thr
1               5                   10

<210> SEQ ID NO 173
<211> LENGTH: 10
<212> TYPE: PRT
<213> ORGANISM: Artificial Sequence
<220> FEATURE:
<223> OTHER INFORMATION: CDR3 VH of I2A-4

<400> SEQUENCE: 173

Tyr Ile Gly Ser Ser Tyr Trp Asp Ala Leu
1               5                   10

<210> SEQ ID NO 174
<211> LENGTH: 11
<212> TYPE: PRT
<213> ORGANISM: Artificial Sequence
<220> FEATURE:
<223> OTHER INFORMATION: CDR1 VL of I2A-4

<400> SEQUENCE: 174

Arg Ala Ser Gln Ser Val Ser Ser Ala Val Ala
1               5                   10

<210> SEQ ID NO 175
<211> LENGTH: 7
<212> TYPE: PRT
<213> ORGANISM: Artificial Sequence
<220> FEATURE:
<223> OTHER INFORMATION: CDR2 VL of I2A-4

<400> SEQUENCE: 175

Ser Ala Ser Ser Leu Tyr Ser
1               5

<210> SEQ ID NO 176
<211> LENGTH: 6

-continued

```
<212> TYPE: PRT
<213> ORGANISM: Artificial Sequence
<220> FEATURE:
<223> OTHER INFORMATION: CDR3 VL of I2A-4

<400> SEQUENCE: 176

Ser Asp Ser Ser Leu Val
1               5

<210> SEQ ID NO 177
<211> LENGTH: 6
<212> TYPE: PRT
<213> ORGANISM: Artificial Sequence
<220> FEATURE:
<223> OTHER INFORMATION: CDR1 VH of I2A-5

<400> SEQUENCE: 177

Phe Ser Ser Tyr Gly Ile
1               5

<210> SEQ ID NO 178
<211> LENGTH: 10
<212> TYPE: PRT
<213> ORGANISM: Artificial Sequence
<220> FEATURE:
<223> OTHER INFORMATION: CDR2 VH of I2A-5

<400> SEQUENCE: 178

Trp Ile Ser Pro Thr Gly Ser Ile Thr Ile
1               5                   10

<210> SEQ ID NO 179
<211> LENGTH: 8
<212> TYPE: PRT
<213> ORGANISM: Artificial Sequence
<220> FEATURE:
<223> OTHER INFORMATION: CDR3 VH of I2A-5

<400> SEQUENCE: 179

Ser Tyr Met Ile Tyr Gly Gly Leu
1               5

<210> SEQ ID NO 180
<211> LENGTH: 11
<212> TYPE: PRT
<213> ORGANISM: Artificial Sequence
<220> FEATURE:
<223> OTHER INFORMATION: CDR1 VL of I2A-5

<400> SEQUENCE: 180

Arg Ala Ser Gln Ser Val Ser Ser Ala Val Ala
1               5                   10

<210> SEQ ID NO 181
<211> LENGTH: 7
<212> TYPE: PRT
<213> ORGANISM: Artificial Sequence
<220> FEATURE:
<223> OTHER INFORMATION: CDR2 VL of I2A-5

<400> SEQUENCE: 181

Ser Ala Ser Ser Leu Tyr Ser
1               5

<210> SEQ ID NO 182
<211> LENGTH: 6
<212> TYPE: PRT
```

```
<213> ORGANISM: Artificial Sequence
<220> FEATURE:
<223> OTHER INFORMATION: CDR3 VL of I2A-5

<400> SEQUENCE: 182

Arg Val Ser Ser Pro Trp
1               5

<210> SEQ ID NO 183
<211> LENGTH: 6
<212> TYPE: PRT
<213> ORGANISM: Artificial Sequence
<220> FEATURE:
<223> OTHER INFORMATION: CDR1 VH of I2A-6

<400> SEQUENCE: 183

Phe Ser Leu Tyr Ala Ile
1               5

<210> SEQ ID NO 184
<211> LENGTH: 10
<212> TYPE: PRT
<213> ORGANISM: Artificial Sequence
<220> FEATURE:
<223> OTHER INFORMATION: CDR2 VH of I2A-6

<400> SEQUENCE: 184

Glu Ile Asp Ser Trp Leu Gly Tyr Thr Tyr
1               5                   10

<210> SEQ ID NO 185
<211> LENGTH: 11
<212> TYPE: PRT
<213> ORGANISM: Artificial Sequence
<220> FEATURE:
<223> OTHER INFORMATION: CDR3 VH of I2A-6

<400> SEQUENCE: 185

Arg Pro Val Thr Glu Val Tyr Tyr Ser Ala Leu
1               5                   10

<210> SEQ ID NO 186
<211> LENGTH: 11
<212> TYPE: PRT
<213> ORGANISM: Artificial Sequence
<220> FEATURE:
<223> OTHER INFORMATION: CDR1 VL of I2A-6

<400> SEQUENCE: 186

Arg Ala Ser Gln Ser Val Ser Ser Ala Val Ala
1               5                   10

<210> SEQ ID NO 187
<211> LENGTH: 7
<212> TYPE: PRT
<213> ORGANISM: Artificial Sequence
<220> FEATURE:
<223> OTHER INFORMATION: CDR2 VL of I2A-6

<400> SEQUENCE: 187

Ser Ala Ser Ser Leu Tyr Ser
1               5

<210> SEQ ID NO 188
<211> LENGTH: 6
<212> TYPE: PRT
<213> ORGANISM: Artificial Sequence
```

```
<220> FEATURE:
<223> OTHER INFORMATION: CDR3 VL of I2A-6

<400> SEQUENCE: 188

Tyr Asp Arg Ser Leu His
1               5

<210> SEQ ID NO 189
<211> LENGTH: 6
<212> TYPE: PRT
<213> ORGANISM: Artificial Sequence
<220> FEATURE:
<223> OTHER INFORMATION: CDR1 VH of I2A-7

<400> SEQUENCE: 189

Phe Ser Arg Tyr Tyr Ile
1               5

<210> SEQ ID NO 190
<211> LENGTH: 10
<212> TYPE: PRT
<213> ORGANISM: Artificial Sequence
<220> FEATURE:
<223> OTHER INFORMATION: CDR2 VH of I2A-7

<400> SEQUENCE: 190

Asp Ile Asp Ser Tyr Gly Gly Phe Thr Tyr
1               5                   10

<210> SEQ ID NO 191
<211> LENGTH: 11
<212> TYPE: PRT
<213> ORGANISM: Artificial Sequence
<220> FEATURE:
<223> OTHER INFORMATION: CDR3 VH of I2A-7

<400> SEQUENCE: 191

Ala His Arg Phe Leu Gln Gly Gly Tyr Val Leu
1               5                   10

<210> SEQ ID NO 192
<211> LENGTH: 11
<212> TYPE: PRT
<213> ORGANISM: Artificial Sequence
<220> FEATURE:
<223> OTHER INFORMATION: CDR1 VL of I2A-7

<400> SEQUENCE: 192

Arg Ala Ser Gln Ser Val Ser Ser Ala Val Ala
1               5                   10

<210> SEQ ID NO 193
<211> LENGTH: 7
<212> TYPE: PRT
<213> ORGANISM: Artificial Sequence
<220> FEATURE:
<223> OTHER INFORMATION: CDR2 VL of I2A-7

<400> SEQUENCE: 193

Ser Ala Ser Ser Leu Tyr Ser
1               5

<210> SEQ ID NO 194
<211> LENGTH: 6
<212> TYPE: PRT
<213> ORGANISM: Artificial Sequence
<220> FEATURE:
```

<223> OTHER INFORMATION: CDR3 VL of I2A-7

<400> SEQUENCE: 194

Tyr Ser Trp Gly Leu Trp
1               5

<210> SEQ ID NO 195
<211> LENGTH: 6
<212> TYPE: PRT
<213> ORGANISM: Artificial Sequence
<220> FEATURE:
<223> OTHER INFORMATION: CDR1 VH of I2A-8

<400> SEQUENCE: 195

Phe Tyr Gly Tyr Tyr Ile
1               5

<210> SEQ ID NO 196
<211> LENGTH: 10
<212> TYPE: PRT
<213> ORGANISM: Artificial Sequence
<220> FEATURE:
<223> OTHER INFORMATION: CDR2 VH of I2A-8

<400> SEQUENCE: 196

Gly Ile Arg Pro Gly Gly Thr Tyr Thr Tyr
1               5                   10

<210> SEQ ID NO 197
<211> LENGTH: 6
<212> TYPE: PRT
<213> ORGANISM: Artificial Sequence
<220> FEATURE:
<223> OTHER INFORMATION: CDR3 VH of I2A-8

<400> SEQUENCE: 197

Tyr Arg Tyr Pro Ala Phe
1               5

<210> SEQ ID NO 198
<211> LENGTH: 11
<212> TYPE: PRT
<213> ORGANISM: Artificial Sequence
<220> FEATURE:
<223> OTHER INFORMATION: CDR1 VL of I2A-8

<400> SEQUENCE: 198

Arg Ala Ser Gln Ser Val Ser Ser Ala Val Ala
1               5                   10

<210> SEQ ID NO 199
<211> LENGTH: 7
<212> TYPE: PRT
<213> ORGANISM: Artificial Sequence
<220> FEATURE:
<223> OTHER INFORMATION: CDR2 VL of I2A-8

<400> SEQUENCE: 199

Ser Ala Ser Ser Leu Tyr Ser
1               5

<210> SEQ ID NO 200
<211> LENGTH: 6
<212> TYPE: PRT
<213> ORGANISM: Artificial Sequence
<220> FEATURE:
<223> OTHER INFORMATION: CDR3 VL of I2A-8

-continued

<400> SEQUENCE: 200

Arg Arg Gln His Leu Trp
1               5

<210> SEQ ID NO 201
<211> LENGTH: 6
<212> TYPE: PRT
<213> ORGANISM: Artificial Sequence
<220> FEATURE:
<223> OTHER INFORMATION: CDR1 VH of I2A-9

<400> SEQUENCE: 201

Phe Ser Ser Tyr Thr Ile
1               5

<210> SEQ ID NO 202
<211> LENGTH: 10
<212> TYPE: PRT
<213> ORGANISM: Artificial Sequence
<220> FEATURE:
<223> OTHER INFORMATION: CDR2 VH of I2A-9

<400> SEQUENCE: 202

Ala Ile Asp Ser Gly Trp Ser Tyr Thr Asp
1               5                   10

<210> SEQ ID NO 203
<211> LENGTH: 6
<212> TYPE: PRT
<213> ORGANISM: Artificial Sequence
<220> FEATURE:
<223> OTHER INFORMATION: CDR3 VH of I2A-9

<400> SEQUENCE: 203

Ala Tyr Gly Gly Val Met
1               5

<210> SEQ ID NO 204
<211> LENGTH: 11
<212> TYPE: PRT
<213> ORGANISM: Artificial Sequence
<220> FEATURE:
<223> OTHER INFORMATION: CDR1 VL of I2A-9

<400> SEQUENCE: 204

Arg Ala Ser Gln Ser Val Ser Ser Ala Val Ala
1               5                   10

<210> SEQ ID NO 205
<211> LENGTH: 7
<212> TYPE: PRT
<213> ORGANISM: Artificial Sequence
<220> FEATURE:
<223> OTHER INFORMATION: CDR2 VL of I2A-9

<400> SEQUENCE: 205

Ser Ala Ser Ser Leu Tyr Ser
1               5

<210> SEQ ID NO 206
<211> LENGTH: 5
<212> TYPE: PRT
<213> ORGANISM: Artificial Sequence
<220> FEATURE:
<223> OTHER INFORMATION: CDR3 VL of I2A-9

```
<400> SEQUENCE: 206

Tyr Trp Trp Pro Gly
1               5

<210> SEQ ID NO 207
<211> LENGTH: 6
<212> TYPE: PRT
<213> ORGANISM: Artificial Sequence
<220> FEATURE:
<223> OTHER INFORMATION: CDR1 VH of I2A-10

<400> SEQUENCE: 207

Phe Ser Ser Tyr Phe Ile
1               5

<210> SEQ ID NO 208
<211> LENGTH: 10
<212> TYPE: PRT
<213> ORGANISM: Artificial Sequence
<220> FEATURE:
<223> OTHER INFORMATION: CDR2 VH of I2A-10

<400> SEQUENCE: 208

Gly Ile Tyr Pro Ser Asp Gly Tyr Thr Ser
1               5                   10

<210> SEQ ID NO 209
<211> LENGTH: 6
<212> TYPE: PRT
<213> ORGANISM: Artificial Sequence
<220> FEATURE:
<223> OTHER INFORMATION: CDR3 VH of I2A-10

<400> SEQUENCE: 209

Tyr Tyr Val Ser Gly Met
1               5

<210> SEQ ID NO 210
<211> LENGTH: 11
<212> TYPE: PRT
<213> ORGANISM: Artificial Sequence
<220> FEATURE:
<223> OTHER INFORMATION: CDR1 VL of I2A-10

<400> SEQUENCE: 210

Arg Ala Ser Gln Ser Val Ser Ser Ala Val Ala
1               5                   10

<210> SEQ ID NO 211
<211> LENGTH: 7
<212> TYPE: PRT
<213> ORGANISM: Artificial Sequence
<220> FEATURE:
<223> OTHER INFORMATION: CDR2 VL of I2A-10

<400> SEQUENCE: 211

Ser Ala Ser Ser Leu Tyr Ser
1               5

<210> SEQ ID NO 212
<211> LENGTH: 6
<212> TYPE: PRT
<213> ORGANISM: Artificial Sequence
<220> FEATURE:
<223> OTHER INFORMATION: CDR3 VL of I2A-10

<400> SEQUENCE: 212
```

```
Tyr Tyr Tyr Tyr Pro Gly
1               5

<210> SEQ ID NO 213
<211> LENGTH: 6
<212> TYPE: PRT
<213> ORGANISM: Artificial Sequence
<220> FEATURE:
<223> OTHER INFORMATION: CDR1 VH of I2A-10 D54E Y55Q

<400> SEQUENCE: 213

Phe Ser Ser Tyr Phe Ile
1               5

<210> SEQ ID NO 214
<211> LENGTH: 10
<212> TYPE: PRT
<213> ORGANISM: Artificial Sequence
<220> FEATURE:
<223> OTHER INFORMATION: CDR2 VH of I2A-10 D54E Y55Q

<400> SEQUENCE: 214

Gly Ile Tyr Pro Ser Glu Gly Tyr Thr Ser
1               5                   10

<210> SEQ ID NO 215
<211> LENGTH: 6
<212> TYPE: PRT
<213> ORGANISM: Artificial Sequence
<220> FEATURE:
<223> OTHER INFORMATION: CDR3 VH of I2A-10 D54E Y55Q

<400> SEQUENCE: 215

Tyr Tyr Val Ser Gly Met
1               5

<210> SEQ ID NO 216
<211> LENGTH: 11
<212> TYPE: PRT
<213> ORGANISM: Artificial Sequence
<220> FEATURE:
<223> OTHER INFORMATION: CDR1 VL of I2A-10 D54E Y55Q

<400> SEQUENCE: 216

Arg Ala Ser Gln Ser Val Ser Ser Ala Val Ala
1               5                   10

<210> SEQ ID NO 217
<211> LENGTH: 7
<212> TYPE: PRT
<213> ORGANISM: Artificial Sequence
<220> FEATURE:
<223> OTHER INFORMATION: CDR2 VL of I2A-10 D54E Y55Q

<400> SEQUENCE: 217

Ser Ala Ser Ser Leu Gln Ser
1               5

<210> SEQ ID NO 218
<211> LENGTH: 6
<212> TYPE: PRT
<213> ORGANISM: Artificial Sequence
<220> FEATURE:
<223> OTHER INFORMATION: CDR3 VL of I2A-10 D54E Y55Q

<400> SEQUENCE: 218
```

```
Tyr Tyr Tyr Tyr Pro Gly
1               5

<210> SEQ ID NO 219
<211> LENGTH: 6
<212> TYPE: PRT
<213> ORGANISM: Artificial Sequence
<220> FEATURE:
<223> OTHER INFORMATION: CDR1 VH of I2A-11

<400> SEQUENCE: 219

Phe Ser Ser Tyr Val Ile
1               5

<210> SEQ ID NO 220
<211> LENGTH: 10
<212> TYPE: PRT
<213> ORGANISM: Artificial Sequence
<220> FEATURE:
<223> OTHER INFORMATION: CDR2 VH of I2A-11

<400> SEQUENCE: 220

Ala Ile Tyr Pro Tyr Thr Ser Ser Thr Gln
1               5                   10

<210> SEQ ID NO 221
<211> LENGTH: 7
<212> TYPE: PRT
<213> ORGANISM: Artificial Sequence
<220> FEATURE:
<223> OTHER INFORMATION: CDR3 VH of I2A-11

<400> SEQUENCE: 221

Ser Tyr Gly Thr Gly Gly Phe
1               5

<210> SEQ ID NO 222
<211> LENGTH: 11
<212> TYPE: PRT
<213> ORGANISM: Artificial Sequence
<220> FEATURE:
<223> OTHER INFORMATION: CDR1 VL of I2A-11

<400> SEQUENCE: 222

Arg Ala Ser Gln Ser Val Ser Ser Ala Val Ala
1               5                   10

<210> SEQ ID NO 223
<211> LENGTH: 7
<212> TYPE: PRT
<213> ORGANISM: Artificial Sequence
<220> FEATURE:
<223> OTHER INFORMATION: CDR2 VL of I2A-11

<400> SEQUENCE: 223

Ser Ala Ser Ser Leu Tyr Ser
1               5

<210> SEQ ID NO 224
<211> LENGTH: 6
<212> TYPE: PRT
<213> ORGANISM: Artificial Sequence
<220> FEATURE:
<223> OTHER INFORMATION: CDR3 VL of I2A-11

<400> SEQUENCE: 224

Trp Tyr Ser Tyr Pro Leu
```

```
1               5

<210> SEQ ID NO 225
<211> LENGTH: 6
<212> TYPE: PRT
<213> ORGANISM: Artificial Sequence
<220> FEATURE:
<223> OTHER INFORMATION: CDR1 VH of I2A-12

<400> SEQUENCE: 225

Phe Thr Thr Tyr Tyr Ile
1               5

<210> SEQ ID NO 226
<211> LENGTH: 10
<212> TYPE: PRT
<213> ORGANISM: Artificial Sequence
<220> FEATURE:
<223> OTHER INFORMATION: CDR2 VH of I2A-12

<400> SEQUENCE: 226

Tyr Ile Ser Pro Glu Asp Gly Tyr Thr Ser
1               5                   10

<210> SEQ ID NO 227
<211> LENGTH: 7
<212> TYPE: PRT
<213> ORGANISM: Artificial Sequence
<220> FEATURE:
<223> OTHER INFORMATION: CDR3 VH of I2A-12

<400> SEQUENCE: 227

Ala Tyr Tyr Ser Ala Val Met
1               5

<210> SEQ ID NO 228
<211> LENGTH: 11
<212> TYPE: PRT
<213> ORGANISM: Artificial Sequence
<220> FEATURE:
<223> OTHER INFORMATION: CDR1 VL of I2A-12

<400> SEQUENCE: 228

Arg Ala Ser Gln Ser Val Ser Ser Ala Val Ala
1               5                   10

<210> SEQ ID NO 229
<211> LENGTH: 7
<212> TYPE: PRT
<213> ORGANISM: Artificial Sequence
<220> FEATURE:
<223> OTHER INFORMATION: CDR2 VL of I2A-12

<400> SEQUENCE: 229

Ser Ala Ser Ser Leu Tyr Ser
1               5

<210> SEQ ID NO 230
<211> LENGTH: 6
<212> TYPE: PRT
<213> ORGANISM: Artificial Sequence
<220> FEATURE:
<223> OTHER INFORMATION: CDR3 VL of I2A-12

<400> SEQUENCE: 230

Ser Trp Ser Pro Ala Thr
1               5
```

```
<210> SEQ ID NO 231
<211> LENGTH: 6
<212> TYPE: PRT
<213> ORGANISM: Artificial Sequence
<220> FEATURE:
<223> OTHER INFORMATION: CDR1 VH of I2A-13

<400> SEQUENCE: 231

Phe Ser Tyr Tyr Phe Ile
1               5

<210> SEQ ID NO 232
<211> LENGTH: 10
<212> TYPE: PRT
<213> ORGANISM: Artificial Sequence
<220> FEATURE:
<223> OTHER INFORMATION: CDR2 VH of I2A-13

<400> SEQUENCE: 232

Val Ile Tyr Pro Asp Gly Gly Tyr Thr Leu
1               5                   10

<210> SEQ ID NO 233
<211> LENGTH: 8
<212> TYPE: PRT
<213> ORGANISM: Artificial Sequence
<220> FEATURE:
<223> OTHER INFORMATION: CDR3 VH of I2A-13

<400> SEQUENCE: 233

Ile Tyr Tyr Pro Ser Gly Ala Met
1               5

<210> SEQ ID NO 234
<211> LENGTH: 11
<212> TYPE: PRT
<213> ORGANISM: Artificial Sequence
<220> FEATURE:
<223> OTHER INFORMATION: CDR1 VL of I2A-13

<400> SEQUENCE: 234

Arg Ala Ser Gln Ser Val Ser Ser Ala Val Ala
1               5                   10

<210> SEQ ID NO 235
<211> LENGTH: 7
<212> TYPE: PRT
<213> ORGANISM: Artificial Sequence
<220> FEATURE:
<223> OTHER INFORMATION: CDR2 VL of I2A-13

<400> SEQUENCE: 235

Ser Ala Ser Ser Leu Tyr Ser
1               5

<210> SEQ ID NO 236
<211> LENGTH: 6
<212> TYPE: PRT
<213> ORGANISM: Artificial Sequence
<220> FEATURE:
<223> OTHER INFORMATION: CDR3 VL of I2A-13

<400> SEQUENCE: 236

Thr Tyr Trp Tyr Pro Gly
1               5
```

<210> SEQ ID NO 237
<211> LENGTH: 6
<212> TYPE: PRT
<213> ORGANISM: Artificial Sequence
<220> FEATURE:
<223> OTHER INFORMATION: CDR1 VH of I2A-14

<400> SEQUENCE: 237

Phe Asp Ser Tyr Val Ile
1               5

<210> SEQ ID NO 238
<211> LENGTH: 10
<212> TYPE: PRT
<213> ORGANISM: Artificial Sequence
<220> FEATURE:
<223> OTHER INFORMATION: CDR2 VH of I2A-14

<400> SEQUENCE: 238

Tyr Ile Phe Ser Phe Gly Gly Tyr Thr Tyr
1               5                   10

<210> SEQ ID NO 239
<211> LENGTH: 8
<212> TYPE: PRT
<213> ORGANISM: Artificial Sequence
<220> FEATURE:
<223> OTHER INFORMATION: CDR3 VH of I2A-14

<400> SEQUENCE: 239

Ser Pro Tyr Gly Thr Phe Ala Leu
1               5

<210> SEQ ID NO 240
<211> LENGTH: 11
<212> TYPE: PRT
<213> ORGANISM: Artificial Sequence
<220> FEATURE:
<223> OTHER INFORMATION: CDR1 VL of I2A-14

<400> SEQUENCE: 240

Arg Ala Ser Gln Ser Val Ser Ser Ala Val Ala
1               5                   10

<210> SEQ ID NO 241
<211> LENGTH: 7
<212> TYPE: PRT
<213> ORGANISM: Artificial Sequence
<220> FEATURE:
<223> OTHER INFORMATION: CDR2 VL of I2A-14

<400> SEQUENCE: 241

Ser Ala Ser Ser Leu Tyr Ser
1               5

<210> SEQ ID NO 242
<211> LENGTH: 6
<212> TYPE: PRT
<213> ORGANISM: Artificial Sequence
<220> FEATURE:
<223> OTHER INFORMATION: CDR3 VL of I2A-14

<400> SEQUENCE: 242

Tyr Tyr Tyr Thr Pro Gly
1               5

```
<210> SEQ ID NO 243
<211> LENGTH: 6
<212> TYPE: PRT
<213> ORGANISM: Artificial Sequence
<220> FEATURE:
<223> OTHER INFORMATION: CDR1 VH of I2A-15

<400> SEQUENCE: 243

Phe Trp Gly Tyr Val Ile
1               5

<210> SEQ ID NO 244
<211> LENGTH: 10
<212> TYPE: PRT
<213> ORGANISM: Artificial Sequence
<220> FEATURE:
<223> OTHER INFORMATION: CDR2 VH of I2A-15

<400> SEQUENCE: 244

Ala Ile Asp Ser Trp Asp Gly Asp Thr Asp
1               5                   10

<210> SEQ ID NO 245
<211> LENGTH: 8
<212> TYPE: PRT
<213> ORGANISM: Artificial Sequence
<220> FEATURE:
<223> OTHER INFORMATION: CDR3 VH of I2A-15

<400> SEQUENCE: 245

Ser Phe Tyr Tyr Ile Tyr Val Met
1               5

<210> SEQ ID NO 246
<211> LENGTH: 11
<212> TYPE: PRT
<213> ORGANISM: Artificial Sequence
<220> FEATURE:
<223> OTHER INFORMATION: CDR1 VL of I2A-15

<400> SEQUENCE: 246

Arg Ala Ser Gln Ser Val Ser Ser Ala Val Ala
1               5                   10

<210> SEQ ID NO 247
<211> LENGTH: 7
<212> TYPE: PRT
<213> ORGANISM: Artificial Sequence
<220> FEATURE:
<223> OTHER INFORMATION: CDR2 VL of I2A-15

<400> SEQUENCE: 247

Ser Ala Ser Ser Leu Tyr Ser
1               5

<210> SEQ ID NO 248
<211> LENGTH: 6
<212> TYPE: PRT
<213> ORGANISM: Artificial Sequence
<220> FEATURE:
<223> OTHER INFORMATION: CDR3 VL of I2A-15

<400> SEQUENCE: 248

Leu Tyr Ser Thr Leu Val
1               5

<210> SEQ ID NO 249
```

```
<211> LENGTH: 6
<212> TYPE: PRT
<213> ORGANISM: Artificial Sequence
<220> FEATURE:
<223> OTHER INFORMATION: CDR1 VH of I2A-16

<400> SEQUENCE: 249

Phe Ser Gly Tyr Phe Ile
1               5

<210> SEQ ID NO 250
<211> LENGTH: 10
<212> TYPE: PRT
<213> ORGANISM: Artificial Sequence
<220> FEATURE:
<223> OTHER INFORMATION: CDR2 VH of I2A-16

<400> SEQUENCE: 250

Ala Ile Phe Pro Tyr Arg Gly Gly Thr Ser
1               5                   10

<210> SEQ ID NO 251
<211> LENGTH: 8
<212> TYPE: PRT
<213> ORGANISM: Artificial Sequence
<220> FEATURE:
<223> OTHER INFORMATION: CDR3 VH of I2A-16

<400> SEQUENCE: 251

Gly Gly Val Ser Pro Gly Gly Phe
1               5

<210> SEQ ID NO 252
<211> LENGTH: 11
<212> TYPE: PRT
<213> ORGANISM: Artificial Sequence
<220> FEATURE:
<223> OTHER INFORMATION: CDR1 VL of I2A-16

<400> SEQUENCE: 252

Arg Ala Ser Gln Ser Val Ser Ser Ala Val Ala
1               5                   10

<210> SEQ ID NO 253
<211> LENGTH: 7
<212> TYPE: PRT
<213> ORGANISM: Artificial Sequence
<220> FEATURE:
<223> OTHER INFORMATION: CDR2 VL of I2A-16

<400> SEQUENCE: 253

Ser Ala Ser Ser Leu Tyr Ser
1               5

<210> SEQ ID NO 254
<211> LENGTH: 6
<212> TYPE: PRT
<213> ORGANISM: Artificial Sequence
<220> FEATURE:
<223> OTHER INFORMATION: CDR3 VL of I2A-16

<400> SEQUENCE: 254

Tyr Tyr Leu Tyr Pro Gly
1               5

<210> SEQ ID NO 255
<211> LENGTH: 6
```

```
<212> TYPE: PRT
<213> ORGANISM: Artificial Sequence
<220> FEATURE:
<223> OTHER INFORMATION: CDR1 VH of I2A-17

<400> SEQUENCE: 255

Phe Glu Ser Tyr Asp Ile
1               5

<210> SEQ ID NO 256
<211> LENGTH: 10
<212> TYPE: PRT
<213> ORGANISM: Artificial Sequence
<220> FEATURE:
<223> OTHER INFORMATION: CDR2 VH of I2A-17

<400> SEQUENCE: 256

Ala Ile Phe Ser Tyr Gly Gly Tyr Thr Thr
1               5                   10

<210> SEQ ID NO 257
<211> LENGTH: 9
<212> TYPE: PRT
<213> ORGANISM: Artificial Sequence
<220> FEATURE:
<223> OTHER INFORMATION: CDR3 VH of I2A-17

<400> SEQUENCE: 257

Gly Ser Tyr Gly Asp Gly Arg Gly Met
1               5

<210> SEQ ID NO 258
<211> LENGTH: 11
<212> TYPE: PRT
<213> ORGANISM: Artificial Sequence
<220> FEATURE:
<223> OTHER INFORMATION: CDR1 VL of I2A-17

<400> SEQUENCE: 258

Arg Ala Ser Gln Ser Val Ser Ser Ala Val Ala
1               5                   10

<210> SEQ ID NO 259
<211> LENGTH: 7
<212> TYPE: PRT
<213> ORGANISM: Artificial Sequence
<220> FEATURE:
<223> OTHER INFORMATION: CDR2 VL of I2A-17

<400> SEQUENCE: 259

Ser Ala Ser Ser Leu Tyr Ser
1               5

<210> SEQ ID NO 260
<211> LENGTH: 6
<212> TYPE: PRT
<213> ORGANISM: Artificial Sequence
<220> FEATURE:
<223> OTHER INFORMATION: CDR3 VL of I2A-17

<400> SEQUENCE: 260

Tyr Tyr Tyr Trp Pro Gly
1               5

<210> SEQ ID NO 261
<211> LENGTH: 6
<212> TYPE: PRT
```

```
<213> ORGANISM: Artificial Sequence
<220> FEATURE:
<223> OTHER INFORMATION: CDR1 VH of I2A-18

<400> SEQUENCE: 261

Phe Ser Ser Tyr Phe Ile
1               5

<210> SEQ ID NO 262
<211> LENGTH: 10
<212> TYPE: PRT
<213> ORGANISM: Artificial Sequence
<220> FEATURE:
<223> OTHER INFORMATION: CDR2 VH of I2A-18

<400> SEQUENCE: 262

Ala Ile His Pro Ala Phe Ser Phe Thr Tyr
1               5                   10

<210> SEQ ID NO 263
<211> LENGTH: 9
<212> TYPE: PRT
<213> ORGANISM: Artificial Sequence
<220> FEATURE:
<223> OTHER INFORMATION: CDR3 VH of I2A-18

<400> SEQUENCE: 263

Pro Arg Leu Ser Ser Ala Val Val Leu
1               5

<210> SEQ ID NO 264
<211> LENGTH: 11
<212> TYPE: PRT
<213> ORGANISM: Artificial Sequence
<220> FEATURE:
<223> OTHER INFORMATION: CDR1 VL of I2A-18

<400> SEQUENCE: 264

Arg Ala Ser Gln Ser Val Ser Ser Ala Val Ala
1               5                   10

<210> SEQ ID NO 265
<211> LENGTH: 7
<212> TYPE: PRT
<213> ORGANISM: Artificial Sequence
<220> FEATURE:
<223> OTHER INFORMATION: CDR2 VL of I2A-18

<400> SEQUENCE: 265

Ser Ala Ser Ser Leu Tyr Ser
1               5

<210> SEQ ID NO 266
<211> LENGTH: 6
<212> TYPE: PRT
<213> ORGANISM: Artificial Sequence
<220> FEATURE:
<223> OTHER INFORMATION: CDR1 VH of I2A-19

<400> SEQUENCE: 266

Phe Ser Ser Tyr Phe Ile
1               5

<210> SEQ ID NO 267
<211> LENGTH: 10
<212> TYPE: PRT
<213> ORGANISM: Artificial Sequence
```

```
<220> FEATURE:
<223> OTHER INFORMATION: CDR2 VH of I2A-19

<400> SEQUENCE: 267

Trp Ile Tyr Pro Ser Gly Ser Tyr Thr Tyr
1               5                   10

<210> SEQ ID NO 268
<211> LENGTH: 10
<212> TYPE: PRT
<213> ORGANISM: Artificial Sequence
<220> FEATURE:
<223> OTHER INFORMATION: CDR3 VH of I2A-19

<400> SEQUENCE: 268

Glu Met Asp Arg Val Gly Tyr Ser Gly Met
1               5                   10

<210> SEQ ID NO 269
<211> LENGTH: 11
<212> TYPE: PRT
<213> ORGANISM: Artificial Sequence
<220> FEATURE:
<223> OTHER INFORMATION: CDR1 VL of I2A-19

<400> SEQUENCE: 269

Arg Ala Ser Gln Ser Val Ser Ser Ala Val Ala
1               5                   10

<210> SEQ ID NO 270
<211> LENGTH: 7
<212> TYPE: PRT
<213> ORGANISM: Artificial Sequence
<220> FEATURE:
<223> OTHER INFORMATION: CDR2 VL of I2A-19

<400> SEQUENCE: 270

Ser Ala Ser Ser Leu Tyr Ser
1               5

<210> SEQ ID NO 271
<211> LENGTH: 6
<212> TYPE: PRT
<213> ORGANISM: Artificial Sequence
<220> FEATURE:
<223> OTHER INFORMATION: CDR3 VL of I2A-19

<400> SEQUENCE: 271

Tyr Arg Thr Pro Leu Gly
1               5

<210> SEQ ID NO 272
<211> LENGTH: 6
<212> TYPE: PRT
<213> ORGANISM: Artificial Sequence
<220> FEATURE:
<223> OTHER INFORMATION: CDR1 VH of I2A-20

<400> SEQUENCE: 272

Phe Ser Asp Tyr Gly Ile
1               5

<210> SEQ ID NO 273
<211> LENGTH: 10
<212> TYPE: PRT
<213> ORGANISM: Artificial Sequence
<220> FEATURE:
```

<223> OTHER INFORMATION: CDR2 VH of I2A-20

<400> SEQUENCE: 273

Glu Ile Asp Ser Trp Leu Gly Tyr Thr Tyr
1               5                   10

<210> SEQ ID NO 274
<211> LENGTH: 10
<212> TYPE: PRT
<213> ORGANISM: Artificial Sequence
<220> FEATURE:
<223> OTHER INFORMATION: CDR3 VH of I2A-20

<400> SEQUENCE: 274

Ser Pro Tyr His Tyr Leu Tyr Tyr Gly Leu
1               5                   10

<210> SEQ ID NO 275
<211> LENGTH: 11
<212> TYPE: PRT
<213> ORGANISM: Artificial Sequence
<220> FEATURE:
<223> OTHER INFORMATION: CDR1 VL of I2A-20

<400> SEQUENCE: 275

Arg Ala Ser Gln Ser Val Ser Ser Ala Val Ala
1               5                   10

<210> SEQ ID NO 276
<211> LENGTH: 7
<212> TYPE: PRT
<213> ORGANISM: Artificial Sequence
<220> FEATURE:
<223> OTHER INFORMATION: CDR2 VL of I2A-20

<400> SEQUENCE: 276

Ser Ala Ser Ser Leu Tyr Ser
1               5

<210> SEQ ID NO 277
<211> LENGTH: 6
<212> TYPE: PRT
<213> ORGANISM: Artificial Sequence
<220> FEATURE:
<223> OTHER INFORMATION: CDR3 VL of I2A-20

<400> SEQUENCE: 277

Leu Ser Ser Ser Leu Gly
1               5

<210> SEQ ID NO 278
<211> LENGTH: 6
<212> TYPE: PRT
<213> ORGANISM: Artificial Sequence
<220> FEATURE:
<223> OTHER INFORMATION: CDR1 VH of I2A-21

<400> SEQUENCE: 278

Phe Ser Gly Tyr Phe Ile
1               5

<210> SEQ ID NO 279
<211> LENGTH: 10
<212> TYPE: PRT
<213> ORGANISM: Artificial Sequence
<220> FEATURE:
<223> OTHER INFORMATION: CDR2 VH of I2A-21

```
<400> SEQUENCE: 279

Gly Ile Ser Pro Trp Ala Gly Tyr Thr Ser
 1               5                  10

<210> SEQ ID NO 280
<211> LENGTH: 6
<212> TYPE: PRT
<213> ORGANISM: Artificial Sequence
<220> FEATURE:
<223> OTHER INFORMATION: CDR3 VH of I2A-21

<400> SEQUENCE: 280

Gly Gly Gly Arg Ala Phe
 1               5

<210> SEQ ID NO 281
<211> LENGTH: 11
<212> TYPE: PRT
<213> ORGANISM: Artificial Sequence
<220> FEATURE:
<223> OTHER INFORMATION: CDR1 VL of I2A-21

<400> SEQUENCE: 281

Arg Ala Ser Gln Ser Val Ser Ser Ala Val Ala
 1               5                  10

<210> SEQ ID NO 282
<211> LENGTH: 7
<212> TYPE: PRT
<213> ORGANISM: Artificial Sequence
<220> FEATURE:
<223> OTHER INFORMATION: CDR2 VL of I2A-21

<400> SEQUENCE: 282

Ser Ala Ser Ser Leu Tyr Ser
 1               5

<210> SEQ ID NO 283
<211> LENGTH: 6
<212> TYPE: PRT
<213> ORGANISM: Artificial Sequence
<220> FEATURE:
<223> OTHER INFORMATION: CDR3 VL of I2A-21

<400> SEQUENCE: 283

Tyr Tyr Trp Tyr Pro Gly
 1               5

<210> SEQ ID NO 284
<211> LENGTH: 6
<212> TYPE: PRT
<213> ORGANISM: Artificial Sequence
<220> FEATURE:
<223> OTHER INFORMATION: CDR1 VH of I2A-22

<400> SEQUENCE: 284

Phe Ser Ser Tyr Phe Ile
 1               5

<210> SEQ ID NO 285
<211> LENGTH: 10
<212> TYPE: PRT
<213> ORGANISM: Artificial Sequence
<220> FEATURE:
<223> OTHER INFORMATION: CDR2 VH of I2A-22
```

<400> SEQUENCE: 285

Ala Ile Tyr Pro Ser Gly Trp Tyr Thr Ser
1               5                   10

<210> SEQ ID NO 286
<211> LENGTH: 6
<212> TYPE: PRT
<213> ORGANISM: Artificial Sequence
<220> FEATURE:
<223> OTHER INFORMATION: CDR3 VH of I2A-22

<400> SEQUENCE: 286

Val Gln Ala Gly Val Phe
1               5

<210> SEQ ID NO 287
<211> LENGTH: 11
<212> TYPE: PRT
<213> ORGANISM: Artificial Sequence
<220> FEATURE:
<223> OTHER INFORMATION: CDR1 VL of I2A-22

<400> SEQUENCE: 287

Arg Ala Ser Gln Ser Val Ser Ser Ala Val Ala
1               5                   10

<210> SEQ ID NO 288
<211> LENGTH: 7
<212> TYPE: PRT
<213> ORGANISM: Artificial Sequence
<220> FEATURE:
<223> OTHER INFORMATION: CDR2 VL of I2A-22

<400> SEQUENCE: 288

Ser Ala Ser Ser Leu Tyr Ser
1               5

<210> SEQ ID NO 289
<211> LENGTH: 6
<212> TYPE: PRT
<213> ORGANISM: Artificial Sequence
<220> FEATURE:
<223> OTHER INFORMATION: CDR3 VL of I2A-22

<400> SEQUENCE: 289

Tyr Tyr Tyr Tyr Pro Gly
1               5

<210> SEQ ID NO 290
<211> LENGTH: 6
<212> TYPE: PRT
<213> ORGANISM: Artificial Sequence
<220> FEATURE:
<223> OTHER INFORMATION: CDR1 VH of I2A-23

<400> SEQUENCE: 290

Phe Asp Asp Tyr Phe Ile
1               5

<210> SEQ ID NO 291
<211> LENGTH: 10
<212> TYPE: PRT
<213> ORGANISM: Artificial Sequence
<220> FEATURE:
<223> OTHER INFORMATION: CDR2 VH of I2A-23

<400> SEQUENCE: 291

```
Ala Ile Ser Ser Glu Gly Gly Tyr Thr Asp
1               5                   10

<210> SEQ ID NO 292
<211> LENGTH: 6
<212> TYPE: PRT
<213> ORGANISM: Artificial Sequence
<220> FEATURE:
<223> OTHER INFORMATION: CDR3 VH of I2A-23

<400> SEQUENCE: 292

Ala Tyr Arg Gly Val Phe
1               5

<210> SEQ ID NO 293
<211> LENGTH: 11
<212> TYPE: PRT
<213> ORGANISM: Artificial Sequence
<220> FEATURE:
<223> OTHER INFORMATION: CDR1 VL of I2A-23

<400> SEQUENCE: 293

Arg Ala Ser Gln Ser Val Ser Ser Ala Val Ala
1               5                   10

<210> SEQ ID NO 294
<211> LENGTH: 7
<212> TYPE: PRT
<213> ORGANISM: Artificial Sequence
<220> FEATURE:
<223> OTHER INFORMATION: CDR2 VL of I2A-23

<400> SEQUENCE: 294

Ser Ala Ser Ser Leu Tyr Ser
1               5

<210> SEQ ID NO 295
<211> LENGTH: 6
<212> TYPE: PRT
<213> ORGANISM: Artificial Sequence
<220> FEATURE:
<223> OTHER INFORMATION: CDR3 VL of I2A-23

<400> SEQUENCE: 295

Tyr Tyr Tyr Phe Pro Gly
1               5

<210> SEQ ID NO 296
<211> LENGTH: 6
<212> TYPE: PRT
<213> ORGANISM: Artificial Sequence
<220> FEATURE:
<223> OTHER INFORMATION: CDR1 VH of I2A-24

<400> SEQUENCE: 296

Phe Ser Thr Tyr Gly Ile
1               5

<210> SEQ ID NO 297
<211> LENGTH: 10
<212> TYPE: PRT
<213> ORGANISM: Artificial Sequence
<220> FEATURE:
<223> OTHER INFORMATION: CDR2 VH of I2A-24

<400> SEQUENCE: 297
```

```
Ala Ile Tyr Pro Gly Thr Ser Tyr Thr Gly
1               5                   10

<210> SEQ ID NO 298
<211> LENGTH: 6
<212> TYPE: PRT
<213> ORGANISM: Artificial Sequence
<220> FEATURE:
<223> OTHER INFORMATION: CDR3 VH of I2A-24

<400> SEQUENCE: 298

Glu Tyr Phe Met Gly Met
1               5

<210> SEQ ID NO 299
<211> LENGTH: 11
<212> TYPE: PRT
<213> ORGANISM: Artificial Sequence
<220> FEATURE:
<223> OTHER INFORMATION: CDR1 VL of I2A-24

<400> SEQUENCE: 299

Arg Ala Ser Gln Ser Val Ser Ser Ala Val Ala
1               5                   10

<210> SEQ ID NO 300
<211> LENGTH: 7
<212> TYPE: PRT
<213> ORGANISM: Artificial Sequence
<220> FEATURE:
<223> OTHER INFORMATION: CDR2 VL of I2A-24

<400> SEQUENCE: 300

Ser Ala Ser Ser Leu Tyr Ser
1               5

<210> SEQ ID NO 301
<211> LENGTH: 6
<212> TYPE: PRT
<213> ORGANISM: Artificial Sequence
<220> FEATURE:
<223> OTHER INFORMATION: CDR3 VL of I2A-24

<400> SEQUENCE: 301

Tyr Tyr Tyr Trp Pro Gly
1               5

<210> SEQ ID NO 302
<211> LENGTH: 6
<212> TYPE: PRT
<213> ORGANISM: Artificial Sequence
<220> FEATURE:
<223> OTHER INFORMATION: CDR1 VH of I2A-25

<400> SEQUENCE: 302

Phe Tyr Gly Tyr Thr Ile
1               5

<210> SEQ ID NO 303
<211> LENGTH: 10
<212> TYPE: PRT
<213> ORGANISM: Artificial Sequence
<220> FEATURE:
<223> OTHER INFORMATION: CDR2 VH of I2A-25

<400> SEQUENCE: 303

Ala Ile Tyr Pro Tyr Thr Asp Ser Thr Arg
```

<210> SEQ ID NO 304
<211> LENGTH: 6
<212> TYPE: PRT
<213> ORGANISM: Artificial Sequence
<220> FEATURE:
<223> OTHER INFORMATION: CDR3 VH of I2A-25

<400> SEQUENCE: 304

Asp Tyr Arg Arg Ala Leu
1               5

<210> SEQ ID NO 305
<211> LENGTH: 11
<212> TYPE: PRT
<213> ORGANISM: Artificial Sequence
<220> FEATURE:
<223> OTHER INFORMATION: CDR1 VL of I2A-25

<400> SEQUENCE: 305

Arg Ala Ser Gln Ser Val Ser Ser Ala Val Ala
1               5                   10

<210> SEQ ID NO 306
<211> LENGTH: 7
<212> TYPE: PRT
<213> ORGANISM: Artificial Sequence
<220> FEATURE:
<223> OTHER INFORMATION: CDR2 VL of I2A-25

<400> SEQUENCE: 306

Ser Ala Ser Ser Leu Tyr Ser
1               5

<210> SEQ ID NO 307
<211> LENGTH: 6
<212> TYPE: PRT
<213> ORGANISM: Artificial Sequence
<220> FEATURE:
<223> OTHER INFORMATION: CDR3 VL of I2A-25

<400> SEQUENCE: 307

Tyr Thr Asp Phe Pro Trp
1               5

<210> SEQ ID NO 308
<211> LENGTH: 6
<212> TYPE: PRT
<213> ORGANISM: Artificial Sequence
<220> FEATURE:
<223> OTHER INFORMATION: CDR1 VH of I2A-26

<400> SEQUENCE: 308

Phe Gln Ser Tyr Asp Ile
1               5

<210> SEQ ID NO 309
<211> LENGTH: 10
<212> TYPE: PRT
<213> ORGANISM: Artificial Sequence
<220> FEATURE:
<223> OTHER INFORMATION: CDR2 VH of I2A-26

<400> SEQUENCE: 309

Ala Ile Asp Pro Thr Gly Arg Ser Thr Ala
1               5                   10

```
<210> SEQ ID NO 310
<211> LENGTH: 5
<212> TYPE: PRT
<213> ORGANISM: Artificial Sequence
<220> FEATURE:
<223> OTHER INFORMATION: CDR3 VH of I2A-26

<400> SEQUENCE: 310

Asp Tyr Gly Val Phe
1               5

<210> SEQ ID NO 311
<211> LENGTH: 11
<212> TYPE: PRT
<213> ORGANISM: Artificial Sequence
<220> FEATURE:
<223> OTHER INFORMATION: CDR1 VL of I2A-26

<400> SEQUENCE: 311

Arg Ala Ser Gln Ser Val Ser Ser Ala Val Ala
1               5                   10

<210> SEQ ID NO 312
<211> LENGTH: 7
<212> TYPE: PRT
<213> ORGANISM: Artificial Sequence
<220> FEATURE:
<223> OTHER INFORMATION: CDR2 VL of I2A-26

<400> SEQUENCE: 312

Ser Ala Ser Ser Leu Tyr Ser
1               5

<210> SEQ ID NO 313
<211> LENGTH: 6
<212> TYPE: PRT
<213> ORGANISM: Artificial Sequence
<220> FEATURE:
<223> OTHER INFORMATION: CDR3 VL of I2A-26

<400> SEQUENCE: 313

Phe Tyr Arg Ser Pro Ala
1               5

<210> SEQ ID NO 314
<211> LENGTH: 6
<212> TYPE: PRT
<213> ORGANISM: Artificial Sequence
<220> FEATURE:
<223> OTHER INFORMATION: CDR1 VH of I2A-27

<400> SEQUENCE: 314

Phe Lys Gly Tyr Tyr Ile
1               5

<210> SEQ ID NO 315
<211> LENGTH: 10
<212> TYPE: PRT
<213> ORGANISM: Artificial Sequence
<220> FEATURE:
<223> OTHER INFORMATION: CDR2 VH of I2A-27

<400> SEQUENCE: 315

Ala Ile Tyr Pro Tyr Gly Gly Ser Thr Asp
1               5                   10
```

<210> SEQ ID NO 316
<211> LENGTH: 7
<212> TYPE: PRT
<213> ORGANISM: Artificial Sequence
<220> FEATURE:
<223> OTHER INFORMATION: CDR3 VH of I2A-27

<400> SEQUENCE: 316

Val Tyr Ile Tyr Gly Val Phe
1               5

<210> SEQ ID NO 317
<211> LENGTH: 11
<212> TYPE: PRT
<213> ORGANISM: Artificial Sequence
<220> FEATURE:
<223> OTHER INFORMATION: CDR1 VL of I2A-27

<400> SEQUENCE: 317

Arg Ala Ser Gln Ser Val Ser Ser Ala Val Ala
1               5                   10

<210> SEQ ID NO 318
<211> LENGTH: 7
<212> TYPE: PRT
<213> ORGANISM: Artificial Sequence
<220> FEATURE:
<223> OTHER INFORMATION: CDR2 VL of I2A-27

<400> SEQUENCE: 318

Ser Ala Ser Ser Leu Tyr Ser
1               5

<210> SEQ ID NO 319
<211> LENGTH: 6
<212> TYPE: PRT
<213> ORGANISM: Artificial Sequence
<220> FEATURE:
<223> OTHER INFORMATION: CDR3 VL of I2A-27

<400> SEQUENCE: 319

Tyr Tyr Ser Ser Pro Arg
1               5

<210> SEQ ID NO 320
<211> LENGTH: 6
<212> TYPE: PRT
<213> ORGANISM: Artificial Sequence
<220> FEATURE:
<223> OTHER INFORMATION: CDR1 VH of I2A-28

<400> SEQUENCE: 320

Phe Ser Ser Tyr Trp Ile
1               5

<210> SEQ ID NO 321
<211> LENGTH: 10
<212> TYPE: PRT
<213> ORGANISM: Artificial Sequence
<220> FEATURE:
<223> OTHER INFORMATION: CDR2 VH of I2A-28

<400> SEQUENCE: 321

Trp Ile Tyr Pro Gly Thr Arg Tyr Thr Glu
1               5                   10

```
<210> SEQ ID NO 322
<211> LENGTH: 8
<212> TYPE: PRT
<213> ORGANISM: Artificial Sequence
<220> FEATURE:
<223> OTHER INFORMATION: CDR3 VH of I2A-28

<400> SEQUENCE: 322

Asp Tyr Val Trp Pro Tyr Gly Phe
1               5

<210> SEQ ID NO 323
<211> LENGTH: 11
<212> TYPE: PRT
<213> ORGANISM: Artificial Sequence
<220> FEATURE:
<223> OTHER INFORMATION: CDR1 VL of I2A-28

<400> SEQUENCE: 323

Arg Ala Ser Gln Ser Val Ser Ser Ala Val Ala
1               5                   10

<210> SEQ ID NO 324
<211> LENGTH: 7
<212> TYPE: PRT
<213> ORGANISM: Artificial Sequence
<220> FEATURE:
<223> OTHER INFORMATION: CDR2 VL of I2A-28

<400> SEQUENCE: 324

Ser Ala Ser Ser Leu Tyr Ser
1               5

<210> SEQ ID NO 325
<211> LENGTH: 6
<212> TYPE: PRT
<213> ORGANISM: Artificial Sequence
<220> FEATURE:
<223> OTHER INFORMATION: CDR3 VL of I2A-28

<400> SEQUENCE: 325

Ala Ser Trp Ser Pro Val
1               5

<210> SEQ ID NO 326
<211> LENGTH: 6
<212> TYPE: PRT
<213> ORGANISM: Artificial Sequence
<220> FEATURE:
<223> OTHER INFORMATION: CDR1 VH of I2A-29

<400> SEQUENCE: 326

Phe Ser Ser Tyr Trp Ile
1               5

<210> SEQ ID NO 327
<211> LENGTH: 10
<212> TYPE: PRT
<213> ORGANISM: Artificial Sequence
<220> FEATURE:
<223> OTHER INFORMATION: CDR2 VH of I2A-29

<400> SEQUENCE: 327

Trp Ile Tyr Ser Ser Gly Gly Tyr Thr Phe
1               5                   10

<210> SEQ ID NO 328
```

```
<211> LENGTH: 8
<212> TYPE: PRT
<213> ORGANISM: Artificial Sequence
<220> FEATURE:
<223> OTHER INFORMATION: CDR3 VH of I2A-29

<400> SEQUENCE: 328

Glu Tyr Phe Leu Tyr Thr Gly Phe
1               5

<210> SEQ ID NO 329
<211> LENGTH: 11
<212> TYPE: PRT
<213> ORGANISM: Artificial Sequence
<220> FEATURE:
<223> OTHER INFORMATION: CDR1 VL of I2A-29

<400> SEQUENCE: 329

Arg Ala Ser Gln Ser Val Ser Ser Ala Val Ala
1               5                   10

<210> SEQ ID NO 330
<211> LENGTH: 7
<212> TYPE: PRT
<213> ORGANISM: Artificial Sequence
<220> FEATURE:
<223> OTHER INFORMATION: CDR2 VL of I2A-29

<400> SEQUENCE: 330

Ser Ala Ser Ser Leu Tyr Ser
1               5

<210> SEQ ID NO 331
<211> LENGTH: 6
<212> TYPE: PRT
<213> ORGANISM: Artificial Sequence
<220> FEATURE:
<223> OTHER INFORMATION: CDR3 VL of I2A-29

<400> SEQUENCE: 331

Tyr Ser Ser Gly Pro Val
1               5

<210> SEQ ID NO 332
<211> LENGTH: 6
<212> TYPE: PRT
<213> ORGANISM: Artificial Sequence
<220> FEATURE:
<223> OTHER INFORMATION: CDR1 VH of I2A-30

<400> SEQUENCE: 332

Phe Asp Ser Tyr Phe Ile
1               5

<210> SEQ ID NO 333
<211> LENGTH: 10
<212> TYPE: PRT
<213> ORGANISM: Artificial Sequence
<220> FEATURE:
<223> OTHER INFORMATION: CDR2 VH of I2A-30

<400> SEQUENCE: 333

Tyr Ile Tyr Ser Trp Gly Ser Tyr Thr His
1               5                   10

<210> SEQ ID NO 334
<211> LENGTH: 8
```

```
<212> TYPE: PRT
<213> ORGANISM: Artificial Sequence
<220> FEATURE:
<223> OTHER INFORMATION: CDR3 VH of I2A-30

<400> SEQUENCE: 334

Gly His Arg Arg Tyr Phe Ala Leu
1               5

<210> SEQ ID NO 335
<211> LENGTH: 11
<212> TYPE: PRT
<213> ORGANISM: Artificial Sequence
<220> FEATURE:
<223> OTHER INFORMATION: CDR1 VL of I2A-30

<400> SEQUENCE: 335

Arg Ala Ser Gln Ser Val Ser Ser Ala Val Ala
1               5                   10

<210> SEQ ID NO 336
<211> LENGTH: 7
<212> TYPE: PRT
<213> ORGANISM: Artificial Sequence
<220> FEATURE:
<223> OTHER INFORMATION: CDR2 VL of I2A-30

<400> SEQUENCE: 336

Ser Ala Ser Ser Leu Tyr Ser
1               5

<210> SEQ ID NO 337
<211> LENGTH: 6
<212> TYPE: PRT
<213> ORGANISM: Artificial Sequence
<220> FEATURE:
<223> OTHER INFORMATION: CDR3 VL of I2A-30

<400> SEQUENCE: 337

Val Tyr Phe Thr Pro Gly
1               5

<210> SEQ ID NO 338
<211> LENGTH: 6
<212> TYPE: PRT
<213> ORGANISM: Artificial Sequence
<220> FEATURE:
<223> OTHER INFORMATION: CDR1 VH of I2A-31

<400> SEQUENCE: 338

Phe Ser Ser Tyr Trp Ile
1               5

<210> SEQ ID NO 339
<211> LENGTH: 10
<212> TYPE: PRT
<213> ORGANISM: Artificial Sequence
<220> FEATURE:
<223> OTHER INFORMATION: CDR2 VH of I2A-31

<400> SEQUENCE: 339

Phe Ile Gly Pro Ser Gly Gly Tyr Thr Tyr
1               5                   10

<210> SEQ ID NO 340
<211> LENGTH: 8
<212> TYPE: PRT
```

```
<213> ORGANISM: Artificial Sequence
<220> FEATURE:
<223> OTHER INFORMATION: CDR3 VH of I2A-31

<400> SEQUENCE: 340

Glu Thr Asp Ser Tyr Thr Gly Phe
1               5

<210> SEQ ID NO 341
<211> LENGTH: 11
<212> TYPE: PRT
<213> ORGANISM: Artificial Sequence
<220> FEATURE:
<223> OTHER INFORMATION: CDR1 VL of I2A-31

<400> SEQUENCE: 341

Arg Ala Ser Gln Ser Val Ser Ser Ala Val Ala
1               5                   10

<210> SEQ ID NO 342
<211> LENGTH: 7
<212> TYPE: PRT
<213> ORGANISM: Artificial Sequence
<220> FEATURE:
<223> OTHER INFORMATION: CDR2 VL of I2A-31

<400> SEQUENCE: 342

Ser Ala Ser Ser Leu Tyr Ser
1               5

<210> SEQ ID NO 343
<211> LENGTH: 6
<212> TYPE: PRT
<213> ORGANISM: Artificial Sequence
<220> FEATURE:
<223> OTHER INFORMATION: CDR3 VL of I2A-31

<400> SEQUENCE: 343

Tyr Tyr Ser Trp Leu Gly
1               5

<210> SEQ ID NO 344
<211> LENGTH: 6
<212> TYPE: PRT
<213> ORGANISM: Artificial Sequence
<220> FEATURE:
<223> OTHER INFORMATION: CDR1 VH of I2A-32

<400> SEQUENCE: 344

Phe Gln Ser Tyr Val Ile
1               5

<210> SEQ ID NO 345
<211> LENGTH: 10
<212> TYPE: PRT
<213> ORGANISM: Artificial Sequence
<220> FEATURE:
<223> OTHER INFORMATION: CDR2 VH of I2A-32

<400> SEQUENCE: 345

Ala Ile Tyr Pro Tyr Ser Ser Ser Thr Ile
1               5                   10

<210> SEQ ID NO 346
<211> LENGTH: 8
<212> TYPE: PRT
<213> ORGANISM: Artificial Sequence
```

```
<220> FEATURE:
<223> OTHER INFORMATION: CDR3 VH of I2A-32

<400> SEQUENCE: 346

Ser Trp Ser Val Tyr Leu Gly Met
1               5

<210> SEQ ID NO 347
<211> LENGTH: 11
<212> TYPE: PRT
<213> ORGANISM: Artificial Sequence
<220> FEATURE:
<223> OTHER INFORMATION: CDR1 VL of I2A-32

<400> SEQUENCE: 347

Arg Ala Ser Gln Ser Val Ser Ser Ala Val Ala
1               5                   10

<210> SEQ ID NO 348
<211> LENGTH: 7
<212> TYPE: PRT
<213> ORGANISM: Artificial Sequence
<220> FEATURE:
<223> OTHER INFORMATION: CDR2 VL of I2A-32

<400> SEQUENCE: 348

Ser Ala Ser Ser Leu Tyr Ser
1               5

<210> SEQ ID NO 349
<211> LENGTH: 6
<212> TYPE: PRT
<213> ORGANISM: Artificial Sequence
<220> FEATURE:
<223> OTHER INFORMATION: CDR3 VL of I2A-32

<400> SEQUENCE: 349

Ser Tyr Asp Ser Pro Arg
1               5

<210> SEQ ID NO 350
<211> LENGTH: 6
<212> TYPE: PRT
<213> ORGANISM: Artificial Sequence
<220> FEATURE:
<223> OTHER INFORMATION: CDR1 VH of I2A-33

<400> SEQUENCE: 350

Phe Asp Asp Tyr Tyr Ile
1               5

<210> SEQ ID NO 351
<211> LENGTH: 10
<212> TYPE: PRT
<213> ORGANISM: Artificial Sequence
<220> FEATURE:
<223> OTHER INFORMATION: CDR2 VH of I2A-33

<400> SEQUENCE: 351

Trp Ile Asp Ser Tyr Gly Gly Tyr Thr Ser
1               5                   10

<210> SEQ ID NO 352
<211> LENGTH: 9
<212> TYPE: PRT
<213> ORGANISM: Artificial Sequence
<220> FEATURE:
```

```
<223> OTHER INFORMATION: CDR3 VH of I2A-33

<400> SEQUENCE: 352

Ser Ser Tyr Tyr Tyr Pro Gly Gly Phe
1               5

<210> SEQ ID NO 353
<211> LENGTH: 11
<212> TYPE: PRT
<213> ORGANISM: Artificial Sequence
<220> FEATURE:
<223> OTHER INFORMATION: CDR1 VL of I2A-33

<400> SEQUENCE: 353

Arg Ala Ser Gln Ser Val Ser Ser Ala Val Ala
1               5                   10

<210> SEQ ID NO 354
<211> LENGTH: 7
<212> TYPE: PRT
<213> ORGANISM: Artificial Sequence
<220> FEATURE:
<223> OTHER INFORMATION: CDR2 VL of I2A-33

<400> SEQUENCE: 354

Ser Ala Ser Ser Leu Tyr Ser
1               5

<210> SEQ ID NO 355
<211> LENGTH: 6
<212> TYPE: PRT
<213> ORGANISM: Artificial Sequence
<220> FEATURE:
<223> OTHER INFORMATION: CDR3 VL of I2A-33

<400> SEQUENCE: 355

Trp Asp Ser Thr Leu Tyr
1               5

<210> SEQ ID NO 356
<211> LENGTH: 6
<212> TYPE: PRT
<213> ORGANISM: Artificial Sequence
<220> FEATURE:
<223> OTHER INFORMATION: CDR1 VH of I2A-34

<400> SEQUENCE: 356

Phe Ser Trp Tyr Val Ile
1               5

<210> SEQ ID NO 357
<211> LENGTH: 10
<212> TYPE: PRT
<213> ORGANISM: Artificial Sequence
<220> FEATURE:
<223> OTHER INFORMATION: CDR2 VH of I2A-34

<400> SEQUENCE: 357

Tyr Ile Ala Pro Tyr Thr Gly Ser Thr Tyr
1               5                   10

<210> SEQ ID NO 358
<211> LENGTH: 9
<212> TYPE: PRT
<213> ORGANISM: Artificial Sequence
<220> FEATURE:
<223> OTHER INFORMATION: CDR3 VH of I2A-34
```

<400> SEQUENCE: 358

Ala Phe Phe Gly Ile Arg Leu Gly Leu
1               5

<210> SEQ ID NO 359
<211> LENGTH: 11
<212> TYPE: PRT
<213> ORGANISM: Artificial Sequence
<220> FEATURE:
<223> OTHER INFORMATION: CDR1 VL of I2A-34

<400> SEQUENCE: 359

Arg Ala Ser Gln Ser Val Ser Ser Ala Val Ala
1               5                   10

<210> SEQ ID NO 360
<211> LENGTH: 7
<212> TYPE: PRT
<213> ORGANISM: Artificial Sequence
<220> FEATURE:
<223> OTHER INFORMATION: CDR2 VL of I2A-34

<400> SEQUENCE: 360

Ser Ala Ser Ser Leu Tyr Ser
1               5

<210> SEQ ID NO 361
<211> LENGTH: 6
<212> TYPE: PRT
<213> ORGANISM: Artificial Sequence
<220> FEATURE:
<223> OTHER INFORMATION: CDR3 VL of I2A-34

<400> SEQUENCE: 361

Ala Ile Ser Ser Pro Tyr
1               5

<210> SEQ ID NO 362
<211> LENGTH: 6
<212> TYPE: PRT
<213> ORGANISM: Artificial Sequence
<220> FEATURE:
<223> OTHER INFORMATION: CDR1 VH of I2A-35

<400> SEQUENCE: 362

Phe Ser Ala Tyr Asp Ile
1               5

<210> SEQ ID NO 363
<211> LENGTH: 10
<212> TYPE: PRT
<213> ORGANISM: Artificial Sequence
<220> FEATURE:
<223> OTHER INFORMATION: CDR2 VH of I2A-35

<400> SEQUENCE: 363

Trp Ile Asp Pro Tyr Gly Gly Asp Thr Asp
1               5                   10

<210> SEQ ID NO 364
<211> LENGTH: 10
<212> TYPE: PRT
<213> ORGANISM: Artificial Sequence
<220> FEATURE:
<223> OTHER INFORMATION: CDR3 VH of I2A-35

```
<400> SEQUENCE: 364

Ser Pro Ser Tyr Met Gln Tyr Gly Gly Leu
1               5                   10

<210> SEQ ID NO 365
<211> LENGTH: 11
<212> TYPE: PRT
<213> ORGANISM: Artificial Sequence
<220> FEATURE:
<223> OTHER INFORMATION: CDR1 VL of I2A-35

<400> SEQUENCE: 365

Arg Ala Ser Gln Ser Val Ser Ser Ala Val Ala
1               5                   10

<210> SEQ ID NO 366
<211> LENGTH: 7
<212> TYPE: PRT
<213> ORGANISM: Artificial Sequence
<220> FEATURE:
<223> OTHER INFORMATION: CDR2 VL of I2A-35

<400> SEQUENCE: 366

Ser Ala Ser Ser Leu Tyr Ser
1               5

<210> SEQ ID NO 367
<211> LENGTH: 6
<212> TYPE: PRT
<213> ORGANISM: Artificial Sequence
<220> FEATURE:
<223> OTHER INFORMATION: CDR3 VL of I2A-35

<400> SEQUENCE: 367

Tyr Tyr Ser Ser Leu Leu
1               5

<210> SEQ ID NO 368
<211> LENGTH: 6
<212> TYPE: PRT
<213> ORGANISM: Artificial Sequence
<220> FEATURE:
<223> OTHER INFORMATION: CDR1 VH of I2A-36

<400> SEQUENCE: 368

Phe Ser Gln Tyr Trp Ile
1               5

<210> SEQ ID NO 369
<211> LENGTH: 10
<212> TYPE: PRT
<213> ORGANISM: Artificial Sequence
<220> FEATURE:
<223> OTHER INFORMATION: CDR2 VH of I2A-36

<400> SEQUENCE: 369

Ala Ile Tyr Ser Ser Thr Lys Tyr Thr Ile
1               5                   10

<210> SEQ ID NO 370
<211> LENGTH: 10
<212> TYPE: PRT
<213> ORGANISM: Artificial Sequence
<220> FEATURE:
<223> OTHER INFORMATION: CDR3 VH of I2A-36

<400> SEQUENCE: 370
```

```
Glu Ser Met Tyr Phe Tyr Ser Tyr Gly Leu
1               5                   10

<210> SEQ ID NO 371
<211> LENGTH: 11
<212> TYPE: PRT
<213> ORGANISM: Artificial Sequence
<220> FEATURE:
<223> OTHER INFORMATION: CDR1 VL of I2A-36

<400> SEQUENCE: 371

Arg Ala Ser Gln Ser Val Ser Ser Ala Val Ala
1               5                   10

<210> SEQ ID NO 372
<211> LENGTH: 7
<212> TYPE: PRT
<213> ORGANISM: Artificial Sequence
<220> FEATURE:
<223> OTHER INFORMATION: CDR2 VL of I2A-36

<400> SEQUENCE: 372

Ser Ala Ser Ser Leu Tyr Ser
1               5

<210> SEQ ID NO 373
<211> LENGTH: 6
<212> TYPE: PRT
<213> ORGANISM: Artificial Sequence
<220> FEATURE:
<223> OTHER INFORMATION: CDR3 VL of I2A-36

<400> SEQUENCE: 373

Leu Pro Ser Thr Pro Leu
1               5

<210> SEQ ID NO 374
<211> LENGTH: 6
<212> TYPE: PRT
<213> ORGANISM: Artificial Sequence
<220> FEATURE:
<223> OTHER INFORMATION: CDR1 VH of I2A-37

<400> SEQUENCE: 374

Phe Ser Trp Tyr Gly Ile
1               5

<210> SEQ ID NO 375
<211> LENGTH: 10
<212> TYPE: PRT
<213> ORGANISM: Artificial Sequence
<220> FEATURE:
<223> OTHER INFORMATION: CDR2 VH of I2A-37

<400> SEQUENCE: 375

Tyr Ile Asp Ser Tyr Thr Ser Ser Thr Tyr
1               5                   10

<210> SEQ ID NO 376
<211> LENGTH: 10
<212> TYPE: PRT
<213> ORGANISM: Artificial Sequence
<220> FEATURE:
<223> OTHER INFORMATION: CDR3 VH of I2A-37

<400> SEQUENCE: 376
```

```
Ser His Phe Gly His Tyr Asp Tyr Val Met
1               5                   10

<210> SEQ ID NO 377
<211> LENGTH: 11
<212> TYPE: PRT
<213> ORGANISM: Artificial Sequence
<220> FEATURE:
<223> OTHER INFORMATION: CDR1 VL of I2A-37

<400> SEQUENCE: 377

Arg Ala Ser Gln Ser Val Ser Ser Ala Val Ala
1               5                   10

<210> SEQ ID NO 378
<211> LENGTH: 7
<212> TYPE: PRT
<213> ORGANISM: Artificial Sequence
<220> FEATURE:
<223> OTHER INFORMATION: CDR2 VL of I2A-37

<400> SEQUENCE: 378

Ser Ala Ser Ser Leu Tyr Ser
1               5

<210> SEQ ID NO 379
<211> LENGTH: 6
<212> TYPE: PRT
<213> ORGANISM: Artificial Sequence
<220> FEATURE:
<223> OTHER INFORMATION: CDR3 VL of I2A-37

<400> SEQUENCE: 379

Ala Tyr Asp Gln Leu Tyr
1               5

<210> SEQ ID NO 380
<211> LENGTH: 6
<212> TYPE: PRT
<213> ORGANISM: Artificial Sequence
<220> FEATURE:
<223> OTHER INFORMATION: CDR1 VH of I2A-38

<400> SEQUENCE: 380

Phe Asp Trp Tyr Arg Ile
1               5

<210> SEQ ID NO 381
<211> LENGTH: 10
<212> TYPE: PRT
<213> ORGANISM: Artificial Sequence
<220> FEATURE:
<223> OTHER INFORMATION: CDR2 VH of I2A-38

<400> SEQUENCE: 381

Trp Ile Asp Ser Tyr Gly Ser Trp Thr Gly
1               5                   10

<210> SEQ ID NO 382
<211> LENGTH: 10
<212> TYPE: PRT
<213> ORGANISM: Artificial Sequence
<220> FEATURE:
<223> OTHER INFORMATION: CDR3 VH of I2A-38

<400> SEQUENCE: 382

Ser Tyr Phe Gly Pro Tyr Gly Tyr Val Leu
```

```
1               5                   10

<210> SEQ ID NO 383
<211> LENGTH: 11
<212> TYPE: PRT
<213> ORGANISM: Artificial Sequence
<220> FEATURE:
<223> OTHER INFORMATION: CDR1 VL of I2A-38

<400> SEQUENCE: 383

Arg Ala Ser Gln Ser Val Ser Ser Ala Val Ala
1               5                   10

<210> SEQ ID NO 384
<211> LENGTH: 7
<212> TYPE: PRT
<213> ORGANISM: Artificial Sequence
<220> FEATURE:
<223> OTHER INFORMATION: CDR2 VL of I2A-38

<400> SEQUENCE: 384

Ser Ala Ser Ser Leu Tyr Ser
1               5

<210> SEQ ID NO 385
<211> LENGTH: 6
<212> TYPE: PRT
<213> ORGANISM: Artificial Sequence
<220> FEATURE:
<223> OTHER INFORMATION: CDR1 VH of I2C-1

<400> SEQUENCE: 385

Phe Thr Ser Tyr Gly Ile
1               5

<210> SEQ ID NO 386
<211> LENGTH: 10
<212> TYPE: PRT
<213> ORGANISM: Artificial Sequence
<220> FEATURE:
<223> OTHER INFORMATION: CDR2 VH of I2C-1

<400> SEQUENCE: 386

Ala Ile Tyr Pro His Ser Gly Phe Thr Ser
1               5                   10

<210> SEQ ID NO 387
<211> LENGTH: 6
<212> TYPE: PRT
<213> ORGANISM: Artificial Sequence
<220> FEATURE:
<223> OTHER INFORMATION: CDR3 VH of I2C-1

<400> SEQUENCE: 387

Thr Ser Tyr Arg Gly Phe
1               5

<210> SEQ ID NO 388
<211> LENGTH: 11
<212> TYPE: PRT
<213> ORGANISM: Artificial Sequence
<220> FEATURE:
<223> OTHER INFORMATION: CDR1 VL of I2C-1

<400> SEQUENCE: 388

Arg Ala Ser Gln Ser Val Ser Ser Ala Val Ala
1               5                   10
```

```
<210> SEQ ID NO 389
<211> LENGTH: 7
<212> TYPE: PRT
<213> ORGANISM: Artificial Sequence
<220> FEATURE:
<223> OTHER INFORMATION: CDR2 VL of I2C-1

<400> SEQUENCE: 389

Ser Ala Ser Ser Leu Tyr Ser
1               5

<210> SEQ ID NO 390
<211> LENGTH: 6
<212> TYPE: PRT
<213> ORGANISM: Artificial Sequence
<220> FEATURE:
<223> OTHER INFORMATION: CDR3 VL of I2C-1

<400> SEQUENCE: 390

Tyr Tyr Trp Tyr Pro Gly
1               5

<210> SEQ ID NO 391
<211> LENGTH: 6
<212> TYPE: PRT
<213> ORGANISM: Artificial Sequence
<220> FEATURE:
<223> OTHER INFORMATION: CDR1 VH of I2C-2

<400> SEQUENCE: 391

Phe Ser Asp Tyr Phe Ile
1               5

<210> SEQ ID NO 392
<211> LENGTH: 10
<212> TYPE: PRT
<213> ORGANISM: Artificial Sequence
<220> FEATURE:
<223> OTHER INFORMATION: CDR2 VH of I2C-2

<400> SEQUENCE: 392

Gly Ile Tyr Pro Tyr Ser Gly Tyr Thr Lys
1               5                   10

<210> SEQ ID NO 393
<211> LENGTH: 6
<212> TYPE: PRT
<213> ORGANISM: Artificial Sequence
<220> FEATURE:
<223> OTHER INFORMATION: CDR3 VH of I2C-2

<400> SEQUENCE: 393

Asp His Ser Pro Val Leu
1               5

<210> SEQ ID NO 394
<211> LENGTH: 11
<212> TYPE: PRT
<213> ORGANISM: Artificial Sequence
<220> FEATURE:
<223> OTHER INFORMATION: CDR1 VL of I2C-2

<400> SEQUENCE: 394

Arg Ala Ser Gln Ser Val Ser Ser Ala Val Ala
1               5                   10
```

```
<210> SEQ ID NO 395
<211> LENGTH: 7
<212> TYPE: PRT
<213> ORGANISM: Artificial Sequence
<220> FEATURE:
<223> OTHER INFORMATION: CDR2 VL of I2C-2

<400> SEQUENCE: 395

Ser Ala Ser Ser Leu Tyr Ser
1               5

<210> SEQ ID NO 396
<211> LENGTH: 6
<212> TYPE: PRT
<213> ORGANISM: Artificial Sequence
<220> FEATURE:
<223> OTHER INFORMATION: CDR3 VL of I2C-2

<400> SEQUENCE: 396

Trp Tyr Tyr Trp Pro Gly
1               5

<210> SEQ ID NO 397
<211> LENGTH: 6
<212> TYPE: PRT
<213> ORGANISM: Artificial Sequence
<220> FEATURE:
<223> OTHER INFORMATION: CDR1 VH of I2C-3

<400> SEQUENCE: 397

Phe Ser His Tyr Trp Ile
1               5

<210> SEQ ID NO 398
<211> LENGTH: 10
<212> TYPE: PRT
<213> ORGANISM: Artificial Sequence
<220> FEATURE:
<223> OTHER INFORMATION: CDR2 VH of I2C-3

<400> SEQUENCE: 398

Leu Ile Ala Pro Gly Gly Asp Tyr Thr Ser
1               5                   10

<210> SEQ ID NO 399
<211> LENGTH: 6
<212> TYPE: PRT
<213> ORGANISM: Artificial Sequence
<220> FEATURE:
<223> OTHER INFORMATION: CDR3 VH of I2C-3

<400> SEQUENCE: 399

Ser Gly Leu Pro Gly Phe
1               5

<210> SEQ ID NO 400
<211> LENGTH: 11
<212> TYPE: PRT
<213> ORGANISM: Artificial Sequence
<220> FEATURE:
<223> OTHER INFORMATION: CDR1 VL of I2C-3

<400> SEQUENCE: 400

Arg Ala Ser Gln Ser Val Ser Ser Ala Val Ala
1               5                   10
```

```
<210> SEQ ID NO 401
<211> LENGTH: 7
<212> TYPE: PRT
<213> ORGANISM: Artificial Sequence
<220> FEATURE:
<223> OTHER INFORMATION: CDR2 VL of I2C-3

<400> SEQUENCE: 401

Ser Ala Ser Ser Leu Tyr Ser
1               5

<210> SEQ ID NO 402
<211> LENGTH: 6
<212> TYPE: PRT
<213> ORGANISM: Artificial Sequence
<220> FEATURE:
<223> OTHER INFORMATION: CDR3 VL of I2C-3

<400> SEQUENCE: 402

Tyr Lys Ser Ser Pro Leu
1               5

<210> SEQ ID NO 403
<211> LENGTH: 6
<212> TYPE: PRT
<213> ORGANISM: Artificial Sequence
<220> FEATURE:
<223> OTHER INFORMATION: CDR1 VH of I2C-4

<400> SEQUENCE: 403

Phe Trp Ser Tyr Phe Ile
1               5

<210> SEQ ID NO 404
<211> LENGTH: 10
<212> TYPE: PRT
<213> ORGANISM: Artificial Sequence
<220> FEATURE:
<223> OTHER INFORMATION: CDR2 VH of I2C-4

<400> SEQUENCE: 404

Tyr Ile His Pro Ser Ser Ser Tyr Thr Asp
1               5                   10

<210> SEQ ID NO 405
<211> LENGTH: 7
<212> TYPE: PRT
<213> ORGANISM: Artificial Sequence
<220> FEATURE:
<223> OTHER INFORMATION: CDR3 VH of I2C-4

<400> SEQUENCE: 405

Thr Ser Arg Asp Gly Ala Met
1               5

<210> SEQ ID NO 406
<211> LENGTH: 11
<212> TYPE: PRT
<213> ORGANISM: Artificial Sequence
<220> FEATURE:
<223> OTHER INFORMATION: CDR1 VL of I2C-4

<400> SEQUENCE: 406

Arg Ala Ser Gln Ser Val Ser Ser Ala Val Ala
1               5                   10

<210> SEQ ID NO 407
```

```
<211> LENGTH: 7
<212> TYPE: PRT
<213> ORGANISM: Artificial Sequence
<220> FEATURE:
<223> OTHER INFORMATION: CDR2 VL of I2C-4

<400> SEQUENCE: 407

Ser Ala Ser Ser Leu Tyr Ser
1               5

<210> SEQ ID NO 408
<211> LENGTH: 6
<212> TYPE: PRT
<213> ORGANISM: Artificial Sequence
<220> FEATURE:
<223> OTHER INFORMATION: CDR3 VL of I2C-4

<400> SEQUENCE: 408

Trp Tyr Ser Pro Pro Glu
1               5

<210> SEQ ID NO 409
<211> LENGTH: 6
<212> TYPE: PRT
<213> ORGANISM: Artificial Sequence
<220> FEATURE:
<223> OTHER INFORMATION: CDR1 VH of I2C-5

<400> SEQUENCE: 409

Phe Ser Ser Tyr Asp Ile
1               5

<210> SEQ ID NO 410
<211> LENGTH: 10
<212> TYPE: PRT
<213> ORGANISM: Artificial Sequence
<220> FEATURE:
<223> OTHER INFORMATION: CDR2 VH of I2C-5

<400> SEQUENCE: 410

Trp Ile Tyr Pro Tyr Trp Gly Tyr Thr Ile
1               5                   10

<210> SEQ ID NO 411
<211> LENGTH: 7
<212> TYPE: PRT
<213> ORGANISM: Artificial Sequence
<220> FEATURE:
<223> OTHER INFORMATION: CDR3 VH of I2C-5

<400> SEQUENCE: 411

Gly Thr Tyr Ala Pro Ala Leu
1               5

<210> SEQ ID NO 412
<211> LENGTH: 11
<212> TYPE: PRT
<213> ORGANISM: Artificial Sequence
<220> FEATURE:
<223> OTHER INFORMATION: CDR1 VL of I2C-5

<400> SEQUENCE: 412

Arg Ala Ser Gln Ser Val Ser Ser Ala Val Ala
1               5                   10

<210> SEQ ID NO 413
<211> LENGTH: 7
```

```
<212> TYPE: PRT
<213> ORGANISM: Artificial Sequence
<220> FEATURE:
<223> OTHER INFORMATION: CDR2 VL of I2C-5

<400> SEQUENCE: 413

Ser Ala Ser Ser Leu Tyr Ser
1               5

<210> SEQ ID NO 414
<211> LENGTH: 6
<212> TYPE: PRT
<213> ORGANISM: Artificial Sequence
<220> FEATURE:
<223> OTHER INFORMATION: CDR3 VL of I2C-5

<400> SEQUENCE: 414

Phe Tyr Ser Tyr Leu Ser
1               5

<210> SEQ ID NO 415
<211> LENGTH: 6
<212> TYPE: PRT
<213> ORGANISM: Artificial Sequence
<220> FEATURE:
<223> OTHER INFORMATION: CDR1 VH of I2C-6

<400> SEQUENCE: 415

Phe Ser Trp Tyr Phe Ile
1               5

<210> SEQ ID NO 416
<211> LENGTH: 10
<212> TYPE: PRT
<213> ORGANISM: Artificial Sequence
<220> FEATURE:
<223> OTHER INFORMATION: CDR2 VH of I2C-6

<400> SEQUENCE: 416

Arg Ile Tyr Ser Thr Gly Gly Tyr Thr Glu
1               5                   10

<210> SEQ ID NO 417
<211> LENGTH: 7
<212> TYPE: PRT
<213> ORGANISM: Artificial Sequence
<220> FEATURE:
<223> OTHER INFORMATION: CDR3 VH of I2C-6

<400> SEQUENCE: 417

Ser Ala Phe Phe Gly Ala Leu
1               5

<210> SEQ ID NO 418
<211> LENGTH: 11
<212> TYPE: PRT
<213> ORGANISM: Artificial Sequence
<220> FEATURE:
<223> OTHER INFORMATION: CDR1 VL of I2C-6

<400> SEQUENCE: 418

Arg Ala Ser Gln Ser Val Ser Ser Ala Val Ala
1               5                   10

<210> SEQ ID NO 419
<211> LENGTH: 7
<212> TYPE: PRT
```

-continued

```
<213> ORGANISM: Artificial Sequence
<220> FEATURE:
<223> OTHER INFORMATION: CDR2 VL of I2C-6

<400> SEQUENCE: 419

Ser Ala Ser Ser Leu Tyr Ser
1               5

<210> SEQ ID NO 420
<211> LENGTH: 6
<212> TYPE: PRT
<213> ORGANISM: Artificial Sequence
<220> FEATURE:
<223> OTHER INFORMATION: CDR3 VL of I2C-6

<400> SEQUENCE: 420

Tyr Pro Ser Gly Pro Glu
1               5

<210> SEQ ID NO 421
<211> LENGTH: 6
<212> TYPE: PRT
<213> ORGANISM: Artificial Sequence
<220> FEATURE:
<223> OTHER INFORMATION: CDR1 VH of I2C-7

<400> SEQUENCE: 421

Phe Asp Ser Tyr Tyr Ile
1               5

<210> SEQ ID NO 422
<211> LENGTH: 10
<212> TYPE: PRT
<213> ORGANISM: Artificial Sequence
<220> FEATURE:
<223> OTHER INFORMATION: CDR2 VH of I2C-7

<400> SEQUENCE: 422

Trp Ile Asp Pro Tyr Gly Leu Asp Thr Lys
1               5                   10

<210> SEQ ID NO 423
<211> LENGTH: 7
<212> TYPE: PRT
<213> ORGANISM: Artificial Sequence
<220> FEATURE:
<223> OTHER INFORMATION: CDR3 VH of I2C-7

<400> SEQUENCE: 423

Glu Pro Gly Asp Tyr Gly Met
1               5

<210> SEQ ID NO 424
<211> LENGTH: 11
<212> TYPE: PRT
<213> ORGANISM: Artificial Sequence
<220> FEATURE:
<223> OTHER INFORMATION: CDR1 VL of I2C-7

<400> SEQUENCE: 424

Arg Ala Ser Gln Ser Val Ser Ser Ala Val Ala
1               5                   10

<210> SEQ ID NO 425
<211> LENGTH: 7
<212> TYPE: PRT
<213> ORGANISM: Artificial Sequence
```

```
<220> FEATURE:
<223> OTHER INFORMATION: CDR2 VL of I2C-7

<400> SEQUENCE: 425

Ser Ala Ser Ser Leu Tyr Ser
1               5

<210> SEQ ID NO 426
<211> LENGTH: 6
<212> TYPE: PRT
<213> ORGANISM: Artificial Sequence
<220> FEATURE:
<223> OTHER INFORMATION: CDR3 VL of I2C-7

<400> SEQUENCE: 426

Ala Tyr Gly Ser Leu Leu
1               5

<210> SEQ ID NO 427
<211> LENGTH: 6
<212> TYPE: PRT
<213> ORGANISM: Artificial Sequence
<220> FEATURE:
<223> OTHER INFORMATION: CDR1 VH of I2C-8

<400> SEQUENCE: 427

Phe Ser Gly Tyr Phe Ile
1               5

<210> SEQ ID NO 428
<211> LENGTH: 10
<212> TYPE: PRT
<213> ORGANISM: Artificial Sequence
<220> FEATURE:
<223> OTHER INFORMATION: CDR2 VH of I2C-8

<400> SEQUENCE: 428

Ala Ile Phe Pro Tyr Arg Gly Gly Thr Ser
1               5                   10

<210> SEQ ID NO 429
<211> LENGTH: 8
<212> TYPE: PRT
<213> ORGANISM: Artificial Sequence
<220> FEATURE:
<223> OTHER INFORMATION: CDR3 VH of I2C-8

<400> SEQUENCE: 429

Gly Gly Val Ser Pro Gly Gly Phe
1               5

<210> SEQ ID NO 430
<211> LENGTH: 11
<212> TYPE: PRT
<213> ORGANISM: Artificial Sequence
<220> FEATURE:
<223> OTHER INFORMATION: CDR1 VL of I2C-8

<400> SEQUENCE: 430

Arg Ala Ser Gln Ser Val Ser Ser Ala Val Ala
1               5                   10

<210> SEQ ID NO 431
<211> LENGTH: 7
<212> TYPE: PRT
<213> ORGANISM: Artificial Sequence
<220> FEATURE:
```

```
<223> OTHER INFORMATION: CDR2 VL of I2C-8

<400> SEQUENCE: 431

Ser Ala Ser Ser Leu Tyr Ser
1               5

<210> SEQ ID NO 432
<211> LENGTH: 6
<212> TYPE: PRT
<213> ORGANISM: Artificial Sequence
<220> FEATURE:
<223> OTHER INFORMATION: CDR3 VL of I2C-8

<400> SEQUENCE: 432

Tyr Tyr Leu Tyr Pro Gly
1               5

<210> SEQ ID NO 433
<211> LENGTH: 6
<212> TYPE: PRT
<213> ORGANISM: Artificial Sequence
<220> FEATURE:
<223> OTHER INFORMATION: CDR1 VH of I2C-9

<400> SEQUENCE: 433

Phe Thr Asp Tyr Asp Ile
1               5

<210> SEQ ID NO 434
<211> LENGTH: 10
<212> TYPE: PRT
<213> ORGANISM: Artificial Sequence
<220> FEATURE:
<223> OTHER INFORMATION: CDR2 VH of I2C-9

<400> SEQUENCE: 434

Arg Ile Trp Pro His Gly Ser Tyr Thr Phe
1               5                   10

<210> SEQ ID NO 435
<211> LENGTH: 8
<212> TYPE: PRT
<213> ORGANISM: Artificial Sequence
<220> FEATURE:
<223> OTHER INFORMATION: CDR3 VH of I2C-9

<400> SEQUENCE: 435

Ser Leu Thr His Ser Tyr Gly Phe
1               5

<210> SEQ ID NO 436
<211> LENGTH: 11
<212> TYPE: PRT
<213> ORGANISM: Artificial Sequence
<220> FEATURE:
<223> OTHER INFORMATION: CDR1 VL of I2C-9

<400> SEQUENCE: 436

Arg Ala Ser Gln Ser Val Ser Ser Ala Val Ala
1               5                   10

<210> SEQ ID NO 437
<211> LENGTH: 7
<212> TYPE: PRT
<213> ORGANISM: Artificial Sequence
<220> FEATURE:
<223> OTHER INFORMATION: CDR2 VL of I2C-9
```

```
<400> SEQUENCE: 437

Ser Ala Ser Ser Leu Tyr Ser
1               5

<210> SEQ ID NO 438
<211> LENGTH: 6
<212> TYPE: PRT
<213> ORGANISM: Artificial Sequence
<220> FEATURE:
<223> OTHER INFORMATION: CDR3 VL of I2C-9

<400> SEQUENCE: 438

Tyr Tyr Thr Trp Leu Ile
1               5

<210> SEQ ID NO 439
<211> LENGTH: 6
<212> TYPE: PRT
<213> ORGANISM: Artificial Sequence
<220> FEATURE:
<223> OTHER INFORMATION: CDR1 VH of I2C-10

<400> SEQUENCE: 439

Phe Ser Ser Tyr Phe Ile
1               5

<210> SEQ ID NO 440
<211> LENGTH: 10
<212> TYPE: PRT
<213> ORGANISM: Artificial Sequence
<220> FEATURE:
<223> OTHER INFORMATION: CDR2 VH of I2C-10

<400> SEQUENCE: 440

Thr Ile His Ser Tyr Phe Asp Gly Thr Ser
1               5                   10

<210> SEQ ID NO 441
<211> LENGTH: 8
<212> TYPE: PRT
<213> ORGANISM: Artificial Sequence
<220> FEATURE:
<223> OTHER INFORMATION: CDR3 VH of I2C-10

<400> SEQUENCE: 441

Thr Arg Pro Thr Gly Gly Ala Phe
1               5

<210> SEQ ID NO 442
<211> LENGTH: 11
<212> TYPE: PRT
<213> ORGANISM: Artificial Sequence
<220> FEATURE:
<223> OTHER INFORMATION: CDR1 VL of I2C-10

<400> SEQUENCE: 442

Arg Ala Ser Gln Ser Val Ser Ser Ala Val Ala
1               5                   10

<210> SEQ ID NO 443
<211> LENGTH: 7
<212> TYPE: PRT
<213> ORGANISM: Artificial Sequence
<220> FEATURE:
<223> OTHER INFORMATION: CDR2 VL of I2C-10
```

```
<400> SEQUENCE: 443

Ser Ala Ser Ser Leu Tyr Ser
1               5

<210> SEQ ID NO 444
<211> LENGTH: 6
<212> TYPE: PRT
<213> ORGANISM: Artificial Sequence
<220> FEATURE:
<223> OTHER INFORMATION: CDR3 VL of I2C-10

<400> SEQUENCE: 444

Ala Tyr Trp Ser Pro Ala
1               5

<210> SEQ ID NO 445
<211> LENGTH: 6
<212> TYPE: PRT
<213> ORGANISM: Artificial Sequence
<220> FEATURE:
<223> OTHER INFORMATION: CDR1 VH of I2C-11

<400> SEQUENCE: 445

Phe Gly Ser Tyr Phe Ile
1               5

<210> SEQ ID NO 446
<211> LENGTH: 10
<212> TYPE: PRT
<213> ORGANISM: Artificial Sequence
<220> FEATURE:
<223> OTHER INFORMATION: CDR2 VH of I2C-11

<400> SEQUENCE: 446

Ala Ile Phe Pro Ala Gly Gly Tyr Thr Tyr
1               5                   10

<210> SEQ ID NO 447
<211> LENGTH: 8
<212> TYPE: PRT
<213> ORGANISM: Artificial Sequence
<220> FEATURE:
<223> OTHER INFORMATION: CDR3 VH of I2C-11

<400> SEQUENCE: 447

Tyr Gly Ser Met Gly Gly Ala Phe
1               5

<210> SEQ ID NO 448
<211> LENGTH: 11
<212> TYPE: PRT
<213> ORGANISM: Artificial Sequence
<220> FEATURE:
<223> OTHER INFORMATION: CDR1 VL of I2C-11

<400> SEQUENCE: 448

Arg Ala Ser Gln Ser Val Ser Ser Ala Val Ala
1               5                   10

<210> SEQ ID NO 449
<211> LENGTH: 7
<212> TYPE: PRT
<213> ORGANISM: Artificial Sequence
<220> FEATURE:
<223> OTHER INFORMATION: CDR2 VL of I2C-11

<400> SEQUENCE: 449
```

```
Ser Ala Ser Ser Leu Tyr Ser
1               5

<210> SEQ ID NO 450
<211> LENGTH: 6
<212> TYPE: PRT
<213> ORGANISM: Artificial Sequence
<220> FEATURE:
<223> OTHER INFORMATION: CDR3 VL of I2C-11

<400> SEQUENCE: 450

Tyr Tyr Trp Phe Pro Gly
1               5

<210> SEQ ID NO 451
<211> LENGTH: 6
<212> TYPE: PRT
<213> ORGANISM: Artificial Sequence
<220> FEATURE:
<223> OTHER INFORMATION: CDR1 VH of I2C-12

<400> SEQUENCE: 451

Phe Ser Ser Tyr Phe Ile
1               5

<210> SEQ ID NO 452
<211> LENGTH: 10
<212> TYPE: PRT
<213> ORGANISM: Artificial Sequence
<220> FEATURE:
<223> OTHER INFORMATION: CDR2 VH of I2C-12

<400> SEQUENCE: 452

Ala Ile His Pro Ala Phe Ser Phe Thr Tyr
1               5                   10

<210> SEQ ID NO 453
<211> LENGTH: 9
<212> TYPE: PRT
<213> ORGANISM: Artificial Sequence
<220> FEATURE:
<223> OTHER INFORMATION: CDR3 VH of I2C-12

<400> SEQUENCE: 453

Pro Arg Leu Ser Ser Ala Val Val Leu
1               5

<210> SEQ ID NO 454
<211> LENGTH: 11
<212> TYPE: PRT
<213> ORGANISM: Artificial Sequence
<220> FEATURE:
<223> OTHER INFORMATION: CDR1 VL of I2C-12

<400> SEQUENCE: 454

Arg Ala Ser Gln Ser Val Ser Ser Ala Val Ala
1               5                   10

<210> SEQ ID NO 455
<211> LENGTH: 7
<212> TYPE: PRT
<213> ORGANISM: Artificial Sequence
<220> FEATURE:
<223> OTHER INFORMATION: CDR2 VL of I2C-12

<400> SEQUENCE: 455
```

Ser Ala Ser Ser Leu Tyr Ser
1               5

<210> SEQ ID NO 456
<211> LENGTH: 6
<212> TYPE: PRT
<213> ORGANISM: Artificial Sequence
<220> FEATURE:
<223> OTHER INFORMATION: CDR3 VL of I2C-12

<400> SEQUENCE: 456

Gly Tyr Tyr Phe Pro Gly
1               5

<210> SEQ ID NO 457
<211> LENGTH: 6
<212> TYPE: PRT
<213> ORGANISM: Artificial Sequence
<220> FEATURE:
<223> OTHER INFORMATION: CDR1 VH of I2C-13

<400> SEQUENCE: 457

Phe Ser Ser Tyr Gly Ile
1               5

<210> SEQ ID NO 458
<211> LENGTH: 10
<212> TYPE: PRT
<213> ORGANISM: Artificial Sequence
<220> FEATURE:
<223> OTHER INFORMATION: CDR2 VH of I2C-13

<400> SEQUENCE: 458

Tyr Ile His Ser Gly Ile Gly Tyr Thr Ile
1               5                   10

<210> SEQ ID NO 459
<211> LENGTH: 9
<212> TYPE: PRT
<213> ORGANISM: Artificial Sequence
<220> FEATURE:
<223> OTHER INFORMATION: CDR3 VH of I2C-13

<400> SEQUENCE: 459

Thr Ser Ser Thr Ser Thr Ser Val Met
1               5

<210> SEQ ID NO 460
<211> LENGTH: 11
<212> TYPE: PRT
<213> ORGANISM: Artificial Sequence
<220> FEATURE:
<223> OTHER INFORMATION: CDR1 VL of I2C-13

<400> SEQUENCE: 460

Arg Ala Ser Gln Ser Val Ser Ser Ala Val Ala
1               5                   10

<210> SEQ ID NO 461
<211> LENGTH: 7
<212> TYPE: PRT
<213> ORGANISM: Artificial Sequence
<220> FEATURE:
<223> OTHER INFORMATION: CDR2 VL of I2C-13

<400> SEQUENCE: 461

Ser Ala Ser Ser Leu Tyr Ser

```
1               5

<210> SEQ ID NO 462
<211> LENGTH: 6
<212> TYPE: PRT
<213> ORGANISM: Artificial Sequence
<220> FEATURE:
<223> OTHER INFORMATION: CDR3 VL of I2C-13

<400> SEQUENCE: 462

Thr Tyr Trp Ser Pro Gly
1               5

<210> SEQ ID NO 463
<211> LENGTH: 6
<212> TYPE: PRT
<213> ORGANISM: Artificial Sequence
<220> FEATURE:
<223> OTHER INFORMATION: CDR1 VH of I2C-14

<400> SEQUENCE: 463

Phe Glu Ser Tyr Asp Ile
1               5

<210> SEQ ID NO 464
<211> LENGTH: 10
<212> TYPE: PRT
<213> ORGANISM: Artificial Sequence
<220> FEATURE:
<223> OTHER INFORMATION: CDR2 VH of I2C-14

<400> SEQUENCE: 464

Ala Ile Phe Ser Tyr Gly Gly Tyr Thr Thr
1               5                   10

<210> SEQ ID NO 465
<211> LENGTH: 9
<212> TYPE: PRT
<213> ORGANISM: Artificial Sequence
<220> FEATURE:
<223> OTHER INFORMATION: CDR3 VH of I2C-14

<400> SEQUENCE: 465

Gly Ser Tyr Gly Asp Gly Arg Gly Met
1               5

<210> SEQ ID NO 466
<211> LENGTH: 11
<212> TYPE: PRT
<213> ORGANISM: Artificial Sequence
<220> FEATURE:
<223> OTHER INFORMATION: CDR1 VL of I2C-14

<400> SEQUENCE: 466

Arg Ala Ser Gln Ser Val Ser Ser Ala Val Ala
1               5                   10

<210> SEQ ID NO 467
<211> LENGTH: 7
<212> TYPE: PRT
<213> ORGANISM: Artificial Sequence
<220> FEATURE:
<223> OTHER INFORMATION: CDR2 VL of I2C-14

<400> SEQUENCE: 467

Ser Ala Ser Ser Leu Tyr Ser
1               5
```

```
<210> SEQ ID NO 468
<211> LENGTH: 6
<212> TYPE: PRT
<213> ORGANISM: Artificial Sequence
<220> FEATURE:
<223> OTHER INFORMATION: CDR3 VL of I2C-14

<400> SEQUENCE: 468

Tyr Tyr Tyr Trp Pro Gly
1               5

<210> SEQ ID NO 469
<211> LENGTH: 6
<212> TYPE: PRT
<213> ORGANISM: Artificial Sequence
<220> FEATURE:
<223> OTHER INFORMATION: CDR1 VH of I2C-15

<400> SEQUENCE: 469

Phe Ser Ser Tyr Phe Ile
1               5

<210> SEQ ID NO 470
<211> LENGTH: 10
<212> TYPE: PRT
<213> ORGANISM: Artificial Sequence
<220> FEATURE:
<223> OTHER INFORMATION: CDR2 VH of I2C-15

<400> SEQUENCE: 470

Leu Ile Tyr Pro Asp Thr Asp Asp Thr Tyr
1               5                   10

<210> SEQ ID NO 471
<211> LENGTH: 9
<212> TYPE: PRT
<213> ORGANISM: Artificial Sequence
<220> FEATURE:
<223> OTHER INFORMATION: CDR3 VH of I2C-15

<400> SEQUENCE: 471

Tyr Gly Tyr Leu Gly Val Gly Ala Phe
1               5

<210> SEQ ID NO 472
<211> LENGTH: 11
<212> TYPE: PRT
<213> ORGANISM: Artificial Sequence
<220> FEATURE:
<223> OTHER INFORMATION: CDR1 VL of I2C-15

<400> SEQUENCE: 472

Arg Ala Ser Gln Ser Val Ser Ala Val Ala
1               5                   10

<210> SEQ ID NO 473
<211> LENGTH: 7
<212> TYPE: PRT
<213> ORGANISM: Artificial Sequence
<220> FEATURE:
<223> OTHER INFORMATION: CDR2 VL of I2C-15

<400> SEQUENCE: 473

Ser Ala Ser Ser Leu Tyr Ser
1               5
```

```
<210> SEQ ID NO 474
<211> LENGTH: 6
<212> TYPE: PRT
<213> ORGANISM: Artificial Sequence
<220> FEATURE:
<223> OTHER INFORMATION: CDR3 VL of I2C-15

<400> SEQUENCE: 474

Leu Tyr Trp Thr Pro Gly
1               5

<210> SEQ ID NO 475
<211> LENGTH: 6
<212> TYPE: PRT
<213> ORGANISM: Artificial Sequence
<220> FEATURE:
<223> OTHER INFORMATION: CDR1 VH of I2C-16

<400> SEQUENCE: 475

Phe Ser Ser Tyr Trp Ile
1               5

<210> SEQ ID NO 476
<211> LENGTH: 10
<212> TYPE: PRT
<213> ORGANISM: Artificial Sequence
<220> FEATURE:
<223> OTHER INFORMATION: CDR2 VH of I2C-16

<400> SEQUENCE: 476

Ala Ile His Pro Ser Gly Ser Tyr Thr Tyr
1               5                   10

<210> SEQ ID NO 477
<211> LENGTH: 9
<212> TYPE: PRT
<213> ORGANISM: Artificial Sequence
<220> FEATURE:
<223> OTHER INFORMATION: CDR3 VH of I2C-16

<400> SEQUENCE: 477

Val Gly Leu Leu Val Thr Ser Val Met
1               5

<210> SEQ ID NO 478
<211> LENGTH: 11
<212> TYPE: PRT
<213> ORGANISM: Artificial Sequence
<220> FEATURE:
<223> OTHER INFORMATION: CDR1 VL of I2C-16

<400> SEQUENCE: 478

Arg Ala Ser Gln Ser Val Ser Ser Ala Val Ala
1               5                   10

<210> SEQ ID NO 479
<211> LENGTH: 7
<212> TYPE: PRT
<213> ORGANISM: Artificial Sequence
<220> FEATURE:
<223> OTHER INFORMATION: CDR2 VL of I2C-16

<400> SEQUENCE: 479

Ser Ala Ser Ser Leu Tyr Ser
1               5
```

```
<210> SEQ ID NO 480
<211> LENGTH: 6
<212> TYPE: PRT
<213> ORGANISM: Artificial Sequence
<220> FEATURE:
<223> OTHER INFORMATION: CDR3 VL of I2C-16

<400> SEQUENCE: 480

Tyr Tyr Tyr Phe Pro Gly
1               5

<210> SEQ ID NO 481
<211> LENGTH: 6
<212> TYPE: PRT
<213> ORGANISM: Artificial Sequence
<220> FEATURE:
<223> OTHER INFORMATION: CDR1 VH of I2C-17

<400> SEQUENCE: 481

Phe Ser Asp Tyr Phe Ile
1               5

<210> SEQ ID NO 482
<211> LENGTH: 10
<212> TYPE: PRT
<213> ORGANISM: Artificial Sequence
<220> FEATURE:
<223> OTHER INFORMATION: CDR2 VH of I2C-17

<400> SEQUENCE: 482

Tyr Ile Tyr Pro Ala Ser Gly Gly Thr Cys
1               5                   10

<210> SEQ ID NO 483
<211> LENGTH: 9
<212> TYPE: PRT
<213> ORGANISM: Artificial Sequence
<220> FEATURE:
<223> OTHER INFORMATION: CDR3 VH of I2C-17

<400> SEQUENCE: 483

Gly Tyr Ile Pro His Met Ala Ala Leu
1               5

<210> SEQ ID NO 484
<211> LENGTH: 11
<212> TYPE: PRT
<213> ORGANISM: Artificial Sequence
<220> FEATURE:
<223> OTHER INFORMATION: CDR1 VL of I2C-17

<400> SEQUENCE: 484

Arg Ala Ser Gln Ser Val Ser Ser Ala Val Ala
1               5                   10

<210> SEQ ID NO 485
<211> LENGTH: 7
<212> TYPE: PRT
<213> ORGANISM: Artificial Sequence
<220> FEATURE:
<223> OTHER INFORMATION: CDR2 VL of I2C-17

<400> SEQUENCE: 485

Ser Ala Ser Ser Leu Tyr Ser
1               5

<210> SEQ ID NO 486
```

```
<211> LENGTH: 6
<212> TYPE: PRT
<213> ORGANISM: Artificial Sequence
<220> FEATURE:
<223> OTHER INFORMATION: CDR3 VL of I2C-17

<400> SEQUENCE: 486

Tyr Tyr Trp Trp Pro Gly
1               5

<210> SEQ ID NO 487
<211> LENGTH: 6
<212> TYPE: PRT
<213> ORGANISM: Artificial Sequence
<220> FEATURE:
<223> OTHER INFORMATION: CDR1 VH of I2C-18

<400> SEQUENCE: 487

Phe Ala Gly Tyr Pro Ile
1               5

<210> SEQ ID NO 488
<211> LENGTH: 10
<212> TYPE: PRT
<213> ORGANISM: Artificial Sequence
<220> FEATURE:
<223> OTHER INFORMATION: CDR2 VH of I2C-18

<400> SEQUENCE: 488

Ala Ile Asp Pro Asp Gly Gly Tyr Thr Tyr
1               5                   10

<210> SEQ ID NO 489
<211> LENGTH: 10
<212> TYPE: PRT
<213> ORGANISM: Artificial Sequence
<220> FEATURE:
<223> OTHER INFORMATION: CDR3 VH of I2C-18

<400> SEQUENCE: 489

His Thr Gly Phe His Arg Tyr Arg Gly Met
1               5                   10

<210> SEQ ID NO 490
<211> LENGTH: 11
<212> TYPE: PRT
<213> ORGANISM: Artificial Sequence
<220> FEATURE:
<223> OTHER INFORMATION: CDR1 VL of I2C-18

<400> SEQUENCE: 490

Arg Ala Ser Gln Ser Val Ser Ser Ala Val Ala
1               5                   10

<210> SEQ ID NO 491
<211> LENGTH: 7
<212> TYPE: PRT
<213> ORGANISM: Artificial Sequence
<220> FEATURE:
<223> OTHER INFORMATION: CDR2 VL of I2C-18

<400> SEQUENCE: 491

Ser Ala Ser Ser Leu Tyr Ser
1               5

<210> SEQ ID NO 492
<211> LENGTH: 6
```

```
<212> TYPE: PRT
<213> ORGANISM: Artificial Sequence
<220> FEATURE:
<223> OTHER INFORMATION: CDR3 VL of I2C-18

<400> SEQUENCE: 492

Tyr Tyr Trp Phe Pro Pro
1               5

<210> SEQ ID NO 493
<211> LENGTH: 6
<212> TYPE: PRT
<213> ORGANISM: Artificial Sequence
<220> FEATURE:
<223> OTHER INFORMATION: CDR1 VH of I2C-19

<400> SEQUENCE: 493

Phe Thr Ser Tyr Asp Ile
1               5

<210> SEQ ID NO 494
<211> LENGTH: 10
<212> TYPE: PRT
<213> ORGANISM: Artificial Sequence
<220> FEATURE:
<223> OTHER INFORMATION: CDR2 VH of I2C-19

<400> SEQUENCE: 494

Trp Ile Asp Pro Gly Leu Ser Tyr Thr Ser
1               5                   10

<210> SEQ ID NO 495
<211> LENGTH: 10
<212> TYPE: PRT
<213> ORGANISM: Artificial Sequence
<220> FEATURE:
<223> OTHER INFORMATION: CDR3 VH of I2C-19

<400> SEQUENCE: 495

Ala Ser Ile Gly Gly Gly Val Pro Val Met
1               5                   10

<210> SEQ ID NO 496
<211> LENGTH: 11
<212> TYPE: PRT
<213> ORGANISM: Artificial Sequence
<220> FEATURE:
<223> OTHER INFORMATION: CDR1 VL of I2C-19

<400> SEQUENCE: 496

Arg Ala Ser Gln Ser Val Ser Ser Ala Val Ala
1               5                   10

<210> SEQ ID NO 497
<211> LENGTH: 7
<212> TYPE: PRT
<213> ORGANISM: Artificial Sequence
<220> FEATURE:
<223> OTHER INFORMATION: CDR2 VL of I2C-19

<400> SEQUENCE: 497

Ser Ala Ser Ser Leu Tyr Ser
1               5

<210> SEQ ID NO 498
<211> LENGTH: 6
<212> TYPE: PRT
```

```
<213> ORGANISM: Artificial Sequence
<220> FEATURE:
<223> OTHER INFORMATION: CDR3 VL of I2C-19

<400> SEQUENCE: 498

Tyr Val Thr Gly Pro Tyr
1               5

<210> SEQ ID NO 499
<211> LENGTH: 6
<212> TYPE: PRT
<213> ORGANISM: Artificial Sequence
<220> FEATURE:
<223> OTHER INFORMATION: CDR1 VH of I2C-20

<400> SEQUENCE: 499

Phe Ser Ser Tyr Tyr Ile
1               5

<210> SEQ ID NO 500
<211> LENGTH: 10
<212> TYPE: PRT
<213> ORGANISM: Artificial Sequence
<220> FEATURE:
<223> OTHER INFORMATION: CDR2 VH of I2C-20

<400> SEQUENCE: 500

Ile Ile Ile Pro Tyr Ser Gly Tyr Thr Tyr
1               5                   10

<210> SEQ ID NO 501
<211> LENGTH: 10
<212> TYPE: PRT
<213> ORGANISM: Artificial Sequence
<220> FEATURE:
<223> OTHER INFORMATION: CDR3 VH of I2C-20

<400> SEQUENCE: 501

Arg Gly Tyr Phe Ser Leu Gly Thr Ala Met
1               5                   10

<210> SEQ ID NO 502
<211> LENGTH: 11
<212> TYPE: PRT
<213> ORGANISM: Artificial Sequence
<220> FEATURE:
<223> OTHER INFORMATION: CDR1 VL of I2C-20

<400> SEQUENCE: 502

Arg Ala Ser Gln Ser Val Ser Ser Ala Val Ala
1               5                   10

<210> SEQ ID NO 503
<211> LENGTH: 7
<212> TYPE: PRT
<213> ORGANISM: Artificial Sequence
<220> FEATURE:
<223> OTHER INFORMATION: CDR2 VL of I2C-20

<400> SEQUENCE: 503

Ser Ala Ser Ser Leu Tyr Ser
1               5

<210> SEQ ID NO 504
<211> LENGTH: 6
<212> TYPE: PRT
<213> ORGANISM: Artificial Sequence
```

-continued

<220> FEATURE:
<223> OTHER INFORMATION: CDR3 VL of I2C-20

<400> SEQUENCE: 504

Val Tyr Trp Trp Pro Gly
1               5

<210> SEQ ID NO 505
<211> LENGTH: 6
<212> TYPE: PRT
<213> ORGANISM: Artificial Sequence
<220> FEATURE:
<223> OTHER INFORMATION: CDR1 VH of I2C-21

<400> SEQUENCE: 505

Phe Ser Ser Tyr Tyr Ile
1               5

<210> SEQ ID NO 506
<211> LENGTH: 10
<212> TYPE: PRT
<213> ORGANISM: Artificial Sequence
<220> FEATURE:
<223> OTHER INFORMATION: CDR2 VH of I2C-21

<400> SEQUENCE: 506

Trp Ile Asp Pro Tyr Ile Ser Tyr Thr Tyr
1               5                   10

<210> SEQ ID NO 507
<211> LENGTH: 10
<212> TYPE: PRT
<213> ORGANISM: Artificial Sequence
<220> FEATURE:
<223> OTHER INFORMATION: CDR3 VH of I2C-21

<400> SEQUENCE: 507

Asp Ser Glu Leu Val Ser Gly Tyr Ala Met
1               5                   10

<210> SEQ ID NO 508
<211> LENGTH: 11
<212> TYPE: PRT
<213> ORGANISM: Artificial Sequence
<220> FEATURE:
<223> OTHER INFORMATION: CDR1 VL of I2C-21

<400> SEQUENCE: 508

Arg Ala Ser Gln Ser Val Ser Ser Ala Val Ala
1               5                   10

<210> SEQ ID NO 509
<211> LENGTH: 7
<212> TYPE: PRT
<213> ORGANISM: Artificial Sequence
<220> FEATURE:
<223> OTHER INFORMATION: CDR2 VL of I2C-21

<400> SEQUENCE: 509

Ser Ala Ser Ser Leu Tyr Ser
1               5

<210> SEQ ID NO 510
<211> LENGTH: 6
<212> TYPE: PRT
<213> ORGANISM: Artificial Sequence
<220> FEATURE:

```
<223> OTHER INFORMATION: CDR3 VL of I2C-21

<400> SEQUENCE: 510

Gly Asp Ser Ser Leu Val
1               5

<210> SEQ ID NO 511
<211> LENGTH: 6
<212> TYPE: PRT
<213> ORGANISM: Artificial Sequence
<220> FEATURE:
<223> OTHER INFORMATION: CDR1 VH of I2C-22

<400> SEQUENCE: 511

Phe Ser Ser Tyr Ser Ile
1               5

<210> SEQ ID NO 512
<211> LENGTH: 10
<212> TYPE: PRT
<213> ORGANISM: Artificial Sequence
<220> FEATURE:
<223> OTHER INFORMATION: CDR2 VH of I2C-22

<400> SEQUENCE: 512

Ala Ile Tyr Pro Tyr Trp Gly Thr Thr Glu
1               5                   10

<210> SEQ ID NO 513
<211> LENGTH: 10
<212> TYPE: PRT
<213> ORGANISM: Artificial Sequence
<220> FEATURE:
<223> OTHER INFORMATION: CDR3 VH of I2C-22

<400> SEQUENCE: 513

Pro Ser Gly Val Thr Tyr Gly Tyr Ala Leu
1               5                   10

<210> SEQ ID NO 514
<211> LENGTH: 11
<212> TYPE: PRT
<213> ORGANISM: Artificial Sequence
<220> FEATURE:
<223> OTHER INFORMATION: CDR1 VL of I2C-22

<400> SEQUENCE: 514

Arg Ala Ser Gln Ser Val Ser Ser Ala Val Ala
1               5                   10

<210> SEQ ID NO 515
<211> LENGTH: 7
<212> TYPE: PRT
<213> ORGANISM: Artificial Sequence
<220> FEATURE:
<223> OTHER INFORMATION: CDR2 VL of I2C-22

<400> SEQUENCE: 515

Ser Ala Ser Ser Leu Tyr Ser
1               5

<210> SEQ ID NO 516
<211> LENGTH: 6
<212> TYPE: PRT
<213> ORGANISM: Artificial Sequence
<220> FEATURE:
<223> OTHER INFORMATION: CDR3 VL of I2C-22
```

<400> SEQUENCE: 516

Tyr Tyr Tyr Ser Pro Trp
1               5

<210> SEQ ID NO 517
<211> LENGTH: 6
<212> TYPE: PRT
<213> ORGANISM: Artificial Sequence
<220> FEATURE:
<223> OTHER INFORMATION: CDR1 VH of I2C-23

<400> SEQUENCE: 517

Phe Ser Ser Tyr Glu Ile
1               5

<210> SEQ ID NO 518
<211> LENGTH: 10
<212> TYPE: PRT
<213> ORGANISM: Artificial Sequence
<220> FEATURE:
<223> OTHER INFORMATION: CDR2 VH of I2C-23

<400> SEQUENCE: 518

Ser Ile Tyr Pro Phe Ser Gly Asp Thr Tyr
1               5                   10

<210> SEQ ID NO 519
<211> LENGTH: 10
<212> TYPE: PRT
<213> ORGANISM: Artificial Sequence
<220> FEATURE:
<223> OTHER INFORMATION: CDR3 VH of I2C-23

<400> SEQUENCE: 519

Pro Gly Arg Ala Ile Tyr Tyr Ala Val Met
1               5                   10

<210> SEQ ID NO 520
<211> LENGTH: 11
<212> TYPE: PRT
<213> ORGANISM: Artificial Sequence
<220> FEATURE:
<223> OTHER INFORMATION: CDR1 VL of I2C-23

<400> SEQUENCE: 520

Arg Ala Ser Gln Ser Val Ser Ser Ala Val Ala
1               5                   10

<210> SEQ ID NO 521
<211> LENGTH: 7
<212> TYPE: PRT
<213> ORGANISM: Artificial Sequence
<220> FEATURE:
<223> OTHER INFORMATION: CDR2 VL of I2C-23

<400> SEQUENCE: 521

Ser Ala Ser Ser Leu Tyr Ser
1               5

<210> SEQ ID NO 522
<211> LENGTH: 6
<212> TYPE: PRT
<213> ORGANISM: Artificial Sequence
<220> FEATURE:
<223> OTHER INFORMATION: CDR3 VL of I2C-23

```
<400> SEQUENCE: 522

Ala Gly Ser His Leu Phe
1               5

<210> SEQ ID NO 523
<211> LENGTH: 6
<212> TYPE: PRT
<213> ORGANISM: Artificial Sequence
<220> FEATURE:
<223> OTHER INFORMATION: CDR1 VH of I2C-24

<400> SEQUENCE: 523

Phe Ser Arg Tyr Tyr Ile
1               5

<210> SEQ ID NO 524
<211> LENGTH: 10
<212> TYPE: PRT
<213> ORGANISM: Artificial Sequence
<220> FEATURE:
<223> OTHER INFORMATION: CDR2 VH of I2C-24

<400> SEQUENCE: 524

Asp Ile Asp Ser Tyr Gly Gly Phe Thr Tyr
1               5                   10

<210> SEQ ID NO 525
<211> LENGTH: 11
<212> TYPE: PRT
<213> ORGANISM: Artificial Sequence
<220> FEATURE:
<223> OTHER INFORMATION: CDR3 VH of I2C-24

<400> SEQUENCE: 525

Ala His Arg Phe Leu Gln Gly Gly Tyr Val Leu
1               5                   10

<210> SEQ ID NO 526
<211> LENGTH: 11
<212> TYPE: PRT
<213> ORGANISM: Artificial Sequence
<220> FEATURE:
<223> OTHER INFORMATION: CDR1 VL of I2C-24

<400> SEQUENCE: 526

Arg Ala Ser Gln Ser Val Ser Ser Ala Val Ala
1               5                   10

<210> SEQ ID NO 527
<211> LENGTH: 7
<212> TYPE: PRT
<213> ORGANISM: Artificial Sequence
<220> FEATURE:
<223> OTHER INFORMATION: CDR2 VL of I2C-24

<400> SEQUENCE: 527

Ser Ala Ser Ser Leu Tyr Ser
1               5

<210> SEQ ID NO 528
<211> LENGTH: 6
<212> TYPE: PRT
<213> ORGANISM: Artificial Sequence
<220> FEATURE:
<223> OTHER INFORMATION: CDR3 VL of I2C-24

<400> SEQUENCE: 528
```

```
Tyr Ser Trp Gly Leu Trp
1               5

<210> SEQ ID NO 529
<211> LENGTH: 6
<212> TYPE: PRT
<213> ORGANISM: Artificial Sequence
<220> FEATURE:
<223> OTHER INFORMATION: CDR1 VH of I2C-25

<400> SEQUENCE: 529

Phe Ser Asp Tyr Tyr Ile
1               5

<210> SEQ ID NO 530
<211> LENGTH: 10
<212> TYPE: PRT
<213> ORGANISM: Artificial Sequence
<220> FEATURE:
<223> OTHER INFORMATION: CDR2 VH of I2C-25

<400> SEQUENCE: 530

Tyr Ile Ala Pro Tyr Gly Gly Phe Thr Tyr
1               5                   10

<210> SEQ ID NO 531
<211> LENGTH: 11
<212> TYPE: PRT
<213> ORGANISM: Artificial Sequence
<220> FEATURE:
<223> OTHER INFORMATION: CDR3 VH of I2C-25

<400> SEQUENCE: 531

Asp Ser Tyr Arg Arg Gly Tyr Val Ser Gly Phe
1               5                   10

<210> SEQ ID NO 532
<211> LENGTH: 11
<212> TYPE: PRT
<213> ORGANISM: Artificial Sequence
<220> FEATURE:
<223> OTHER INFORMATION: CDR1 VL of I2C-25

<400> SEQUENCE: 532

Arg Ala Ser Gln Ser Val Ser Ser Ala Val Ala
1               5                   10

<210> SEQ ID NO 533
<211> LENGTH: 7
<212> TYPE: PRT
<213> ORGANISM: Artificial Sequence
<220> FEATURE:
<223> OTHER INFORMATION: CDR2 VL of I2C-25

<400> SEQUENCE: 533

Ser Ala Ser Ser Leu Tyr Ser
1               5

<210> SEQ ID NO 534
<211> LENGTH: 6
<212> TYPE: PRT
<213> ORGANISM: Artificial Sequence
<220> FEATURE:
<223> OTHER INFORMATION: CDR3 VL of I2C-25

<400> SEQUENCE: 534
```

Arg Tyr Ser Ser Pro Ser
1               5

<210> SEQ ID NO 535
<211> LENGTH: 6
<212> TYPE: PRT
<213> ORGANISM: Artificial Sequence
<220> FEATURE:
<223> OTHER INFORMATION: CDR1 VH of I2C-26

<400> SEQUENCE: 535

Phe Ser Asp Tyr Tyr Ile
1               5

<210> SEQ ID NO 536
<211> LENGTH: 10
<212> TYPE: PRT
<213> ORGANISM: Artificial Sequence
<220> FEATURE:
<223> OTHER INFORMATION: CDR2 VH of I2C-26

<400> SEQUENCE: 536

Asp Ile Asp Ser Tyr Gly Gly Phe Thr Tyr
1               5                   10

<210> SEQ ID NO 537
<211> LENGTH: 11
<212> TYPE: PRT
<213> ORGANISM: Artificial Sequence
<220> FEATURE:
<223> OTHER INFORMATION: CDR3 VH of I2C-26

<400> SEQUENCE: 537

Asp Pro His Phe Leu Asp Asp Val Tyr Val Leu
1               5                   10

<210> SEQ ID NO 538
<211> LENGTH: 11
<212> TYPE: PRT
<213> ORGANISM: Artificial Sequence
<220> FEATURE:
<223> OTHER INFORMATION: CDR1 VL of I2C-26

<400> SEQUENCE: 538

Arg Ala Ser Gln Ser Val Ser Ser Ala Val Ala
1               5                   10

<210> SEQ ID NO 539
<211> LENGTH: 7
<212> TYPE: PRT
<213> ORGANISM: Artificial Sequence
<220> FEATURE:
<223> OTHER INFORMATION: CDR2 VL of I2C-26

<400> SEQUENCE: 539

Ser Ala Ser Ser Leu Tyr Ser
1               5

<210> SEQ ID NO 540
<211> LENGTH: 6
<212> TYPE: PRT
<213> ORGANISM: Artificial Sequence
<220> FEATURE:
<223> OTHER INFORMATION: CDR3 VL of I2C-26

<400> SEQUENCE: 540

Tyr Ser Trp Gly Leu Trp

```
<210> SEQ ID NO 541
<211> LENGTH: 6
<212> TYPE: PRT
<213> ORGANISM: Artificial Sequence
<220> FEATURE:
<223> OTHER INFORMATION: Peptide linker

<400> SEQUENCE: 541

Gly Ser Gly Ser Gly Ser
1               5

<210> SEQ ID NO 542
<211> LENGTH: 5
<212> TYPE: PRT
<213> ORGANISM: Artificial Sequence
<220> FEATURE:
<223> OTHER INFORMATION: Hinge

<400> SEQUENCE: 542

Asp Lys Thr His Thr
1               5
```